(12) United States Patent
Lander et al.

(10) Patent No.: US 6,692,909 B1
(45) Date of Patent: Feb. 17, 2004

(54) CODING SEQUENCE POLYMORPHISMS IN VASCULAR PATHOLOGY GENES

(75) Inventors: Eric S. Lander, Cambridge, MA (US); George Q. Daley, Weston, MA (US); Michele Cargill, Cambridge, MA (US); James S. Ireland, Somerville, MA (US); Steven G. Rozen, Somerville, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 09/054,272

(22) Filed: Apr. 1, 1998

(51) Int. Cl.[7] .................................................. C12Q 1/68
(52) U.S. Cl. .......................... 435/6; 536/23.1; 536/23.5
(58) Field of Search ............................. 435/6; 536/23.1, 536/23.2, 23.5, 23.51–23.53

(56) References Cited

U.S. PATENT DOCUMENTS 6,451,526 B1 * 9/2002 Song et al. .................... 435/6

FOREIGN PATENT DOCUMENTS

| WO | 95/11995 | 5/1995 |
| WO | 95/12607 | 5/1995 |
| WO | WO-9512607 A1 * | 5/1995 |
| WO | WO-9630546 A1 * | 10/1996 |
| WO | 98/20165 | 5/1998 |

OTHER PUBLICATIONS

Dürr, C., et al., "Genetic studies of antithrombin III with IEF and ASO hybridization," *Hum Genet* 90:457–459 (1992).

Okajima, K., et al., "Antithrombin III Nagasaki (Ser116–Pro): A Heterozygous Variant With Defective Heparin Binding Associated With Thrombosis," *Blood* 81(5):1300–1305 (1993).

Ueyama, H., et al., "Antithrombin III Kumamoto: Identification of a Point Mutation and Genotype Analysis of the Family," *Thrombosis and Haemostasis* 63(2):231–234 (1990).

Zee, R.Y.L., et al., "Association and linkage analyses of restriction fragment length polymorphisms for the human renin and antithrombin III genes in essential hypertension," *Journal of Hypertension* 9:825–830 (1991).

Bock, S.C., et al., "Antithrombin III Utah: Proline–407 to Leucine Mutation in a Highly Conserved Region near the Inhibitor Reactive Site," *Biochemistry* 27:6171–6178 (1988).

Belgrader, P., et al., "A Multiplex PCR–Ligase Detection Reaction Assay for Human Identity Testing," *Genome Science & Technology* 1(2):77–87 (1996).

Syvänen, A.-C., et al., "Identification of Individuals by Analysis of Biallelic DNA Markers, Using PCR and Solid-Phase Minisequencing," *Am. J. Hum. Genet.* 52:46–59 (1993).

Wang, D., et al., "Toward a third generation genetic map of the human genome based on bi-allelic polymorphisms," *American Journal of Human Genetics* 59(4): A03 Abstract (1996).

Daley, G.Q., et al., "High Throughput Polymorphism Discovery in Genes Related to Thrombosis: A Paradigm for Linking Common Variants to Common Disease," *Blood* 92(10/1): 1953 Abstract (1998).

Cargill, M., et al., "Characterization of single-nucleotide polymorphisms in coding regions of human genes," *Nature Genetics* 22:231–238 (1999).

Hiller, L., et al., "The WashU–Merck EST Project," *Database EMBL* [Online] European Molecular Biology Laboratory AT3 precursor (*AC: H94189*), Abstract (1995).

Hiller, L., et al., "The WashU–Merck EST Project," *Database EMBL* [Online] European Molecular Biology Laboratory AT3 precursor (*AC: T73852*), Abstract (1995).

* cited by examiner

Primary Examiner—James Martinell
(74) Attorney, Agent, or Firm—Hamilton, Brook, Smith & Reynolds, P.C

(57) ABSTRACT

The invention provides nucleic acid segments of the human genome, particularly necleic acid segments from the coding region of a gene, including polymorphic sites. Allele-specific primers and probes hybridizing to regions flanking or containing these sites are also provided. The nucleic acids, primers and probes are used in applications such as phenotype correlations, forensics, paternity testing, medicine and genetic analysis.

12 Claims, 112 Drawing Sheets

FIG. 1A

| Polymorphism ID | Gene | Codon No. | SILENT POLYMORPHISMS ||| MISSENSE POLYMORPHISMS ||| NONSENSE POLYMORPHISMS ||| ALLELE FREQUENCIES ||||
|---|---|---|---|---|---|---|---|---|---|---|---|---|---|---|---|
| | | | Ref codon | Var codon | AA change | Ref codon | Var codon | AA change | Ref codon | Var codon | AA change | Ref allele | Freq | Var allele | Freq |
| AT3u3 | AT3 | 438 | | | | AGG | GGG | R to G | | | | A | 0.99 | G | 0.01 |
| CETPu1 | CETP | 390 | | | | GCC | CCC | A to P | | | | G | 0.95 | C | 0.05 |
| CETPu8 | CETP | 455 | | | | GTG | ATG | V to M | | | | G | 0.99 | A | 0.01 |
| CETPu9 | CETP | 486 | | | | GTG | ATG | V to M | | | | G | 0.99 | A | 0.01 |
| CLanalogu3 | CLanalog | 111 | | | | GTG | ATG | V to M | | | | G | 0.99 | A | 0.01 |
| CLanalogu4 | CLanalog | 135 | | | | GTC | ATC | V to I | | | | G | 0.99 | A | 0.01 |
| F2Ru1 | F2R | 91 | | | | GAT | GGT | D to G | | | | A | 0.99 | G | 0.01 |
| F2Ru2 | F2R | 129 | | | | CTG | CGG | L to R | | | | T | 0.98 | G | 0.02 |
| F2Ru3 | F2R | 147 | | | | GCA | GAA | A to E | | | | C | 0.91 | A | 0.09 |
| F2Ru4 | F2R | 166 | | | | AGT | GGT | S to G | | | | A | 0.99 | G | 0.01 |
| F2Ru6 | F2R | 61 | | | | AAA | CAA | K to Q | | | | A | 0.93 | C | 0.07 |
| F2u1 | F2 | 165 | | | | ACG | ATG | T to M | | | | C | 0.97 | T | 0.03 |
| F2u2 | F2 | 386 | | | | CCC | ACC | P to T | | | | C | 0.99 | A | 0.01 |
| F3u1 | F3 | 163 | | | | CGG | TGG | R to W | | | | C | 0.99 | T | 0.01 |
| F5u4 | F5 | 413 | | | | ATG | ACG | N to T | | | | T | 0.94 | C | 0.06 |
| HCF2u3 | HCF2 | 442 | | | | ACG | ATG | T to M | | | | C | 0.99 | T | 0.01 |
| HCF2u4 | HCF2 | 7 | | | | GCA | ACA | A to T | | | | G | 0.98 | A | 0.02 |

FIG. 1B

| Polymorphism ID | Gene | Codon No. | SILENT POLYMORPHISMS | | | MISSENSE POLYMORPHISMS | | | NONSENSE POLYMORPHISMS | | | ALLELE FREQUENCIES | | | |
|---|---|---|---|---|---|---|---|---|---|---|---|---|---|---|---|
| | | | Ref codon | Var codon | AA change | Ref codon | Var codon | AA change | Ref codon | Var codon | AA change | Ref allele | Freq | Var allele | Freq |
| HCF2u6 | HCF2 | 208 | | | | CGC | CAC | R to H | | | | G | 0.99 | A | 0.01 |
| HMGCRu1 | HMGCR | 638 | | | | ATA | GTA | I to V | | | | A | 0.99 | G | 0.01 |
| ITGA2Bu2 | ITGA2B | 874 | | | | ATC | AGC | I to S | | | | T | 0.79 | G | 0.21 |
| ITGA2Bu5 | ITGA2B | 968 | | | | TAT | AAT | Y to N | | | | T | 0.99 | A | 0.01 |
| ITGA2Bu6 | ITGA2B | 40 | | | | ACC | ATC | T to I | | | | C | 0.97 | T | 0.03 |
| ITGA2Bu7 | ITGA2B | 766 | | | | ATT | AGT | I to S | | | | T | 0.99 | G | 0.01 |
| ITGB3u1 | ITGB3 | 169 | | | | CGA | CAA | R to Q | | | | G | 0.99 | A | 0.01 |
| ITGB3u8 | ITGB3 | 453 | | | | GTC | ATC | V to I | | | | G | 0.99 | A | 0.01 |
| LCATu2 | LCAT | 232 | | | | TCT | ACT | S to T | | | | T | 0.98 | A | 0.02 |
| LDLRu14 | LDLR | 814 | | | | CGG | CAG | R to Q | | | | G | 0.99 | A | 0.01 |
| LDLRu7 | LDLR | 2 | | | | GGG | CGG | G to R | | | | G | 0.99 | C | 0.01 |
| LDLRu8 | LDLR | 468 | | | | GTC | ATC | V to I | | | | G | 0.99 | A | 0.01 |
| LPLu2 | LPL | 427 | | | | GCC | ACC | A to T | | | | G | 0.99 | A | 0.01 |
| PROCu4 | PROC | 283 | | | | AAG | AGG | K to R | | | | A | 0.99 | G | 0.01 |
| PTAFRu3 | PTAFR | 224 | | | | GCT | GAT | A to D | | | | C | 0.99 | A | 0.01 |
| PTAFRu4 | PTAFR | 28 | | | | CTC | TTC | L to F | | | | C | 0.99 | T | 0.01 |
| PTAFRu5 | PTAFR | 338 | | | | AAT | AGT | N to S | | | | A | 0.98 | G | 0.02 |
| TFPIu1 | TFPI | 292 | | | | GTG | ATG | V to M | | | | G | 0.99 | A | 0.01 |

FIG. 1C

| Polymorphism ID | Gene | Codon No. | SILENT POLYMORPHISMS ||| MISSENSE POLYMORPHISMS ||| NONSENSE POLYMORPHISMS ||| ALLELE FREQUENCIES ||||
|---|---|---|---|---|---|---|---|---|---|---|---|---|---|---|---|
| | | | Ref codon | Var codon | AA change | Ref codon | Var codon | AA change | Ref codon | Var codon | AA change | Ref allele | Freq | Var allele | Freq |
| CETPu4 | CETP | 22 | ACC | ACA | T to T | | | | | | | C | 0.99 | A | 0.01 |
| LDLRu13 | LDLR | 27 | TGT | TGC | C to C | | | | | | | T | 0.62 | C | 0.38 |
| HCF2u2 | HCF2 | 77 | GAC | GAT | D to D | | | | | | | C | 0.97 | T | 0.03 |
| CETPu5 | CETP | 86 | ATC | ATT | I to I | | | | | | | C | 0.99 | T | 0.01 |
| HCF2u5 | HCF2 | 95 | ATC | ATT | I to I | | | | | | | C | 0.99 | T | 0.01 |
| ITGB3u7 | ITGB3 | 114 | ATT | ATC | I to I | | | | | | | T | 0.97 | C | 0.03 |
| F2Ru7 | F2R | 129 | CTG | TTG | L to L | | | | | | | C | 0.98 | T | 0.02 |
| PROCu2 | PROC | 141 | TCT | TCG | S to S | | | | | | | C | 0.46 | G | 0.54 |
| CLanalogu2 | CLanalog | 167 | GGC | GGT | G to G | | | | | | | C | 0.88 | T | 0.12 |
| F2Ru5 | F2R | 172 | TCT | TCG | S to S | | | | | | | T | 0.99 | G | 0.01 |
| LCATu1 | LCAT | 199 | GTC | GTT | V to V | | | | | | | C | 0.99 | T | 0.01 |
| CETPu6 | CETP | 212 | GCC | GCT | A to A | | | | | | | C | 0.98 | T | 0.02 |
| PROCu3 | PROC | 256 | GAT | GAC | D to D | | | | | | | T | 0.98 | C | 0.02 |
| F2u4 | F2 | 271 | GGC | GGT | G to G | | | | | | | C | 0.98 | T | 0.02 |
| ITGB3u3 | ITGB3 | 294 | CCT | CCC | P to P | | | | | | | T | 0.87 | C | 0.13 |
| PROCu1 | PROC | 297 | GAC | GAT | D to D | | | | | | | C | 0.99 | T | 0.01 |
| LCATu4 | LCAT | 300 | CGT | CGC | R to R | | | | | | | T | 0.99 | C | 0.01 |
| CLanalogu5 | CLanalog | 301 | TTC | TTT | F to F | | | | | | | C | 0.95 | T | 0.05 |

| Polymorphism ID | Gene | Codon No. | SILENT POLYMORPHISMS ||| MISSENSE POLYMORPHISMS ||| NONSENSE POLYMORPHISMS ||| ALLELE FREQUENCIES ||||
|---|---|---|---|---|---|---|---|---|---|---|---|---|---|---|---|
| | | | Ref codon | Var codon | AA change | Ref codon | Var codon | AA change | Ref codon | Var codon | AA change | Ref allele | Freq | Var allele | Freq |
| TBXA2Ru1 | TBXA2R | 308 | TAT | TAC | Y to Y | | | | | | | T | 0.57 | C | 0.43 |
| AT3u1 | AT3 | 327 | GTG | GTA | V to V | | | | | | | G | 0.64 | A | 0.36 |
| CLanalogu1 | CLanalog | 350 | GCC | GCT | A to A | | | | | | | C | 0.68 | T | 0.32 |
| ITGB3u4 | ITGB3 | 381 | GTC | GTA | V to V | | | | | | | C | 0.50 | A | 0.50 |
| LPLu1 | LPL | 388 | ACC | ACA | T to T | | | | | | | C | 0.89 | A | 0.11 |
| LCATu3 | LCAT | 393 | CTG | TTG | L to L | | | | | | | C | 0.93 | T | 0.07 |
| F2u3 | F2 | 411 | CCG | CCA | P to P | | | | | | | G | 0.97 | A | 0.03 |
| F5u5 | F5 | 414 | AAA | AAG | K to K | | | | | | | A | 0.92 | G | 0.08 |
| CETPu7 | CETP | 433 | GTG | GTA | V to V | | | | | | | G | 0.99 | A | 0.01 |
| LDLRu9 | LDLR | 441 | ATC | ATT | I to I | | | | | | | C | 0.99 | T | 0.01 |
| AT3u4 | AT3 | 450 | AAC | AAT | N to N | | | | | | | C | 0.99 | T | 0.01 |
| F5u1 | F5 | 460 | AAC | AAT | N to N | | | | | | | C | 0.95 | T | 0.05 |
| HCF2u7 | HCF2 | 482 | CAC | CAT | H to H | | | | | | | C | 0.53 | T | 0.47 |
| ITGB3u5 | ITGB3 | 511 | GAA | GAA | E to E | | | | | | | G | 0.27 | A | 0.73 |
| ITGB3u6 | ITGB3 | 515 | CGG | CGG | R to R | | | | | | | A | 0.43 | G | 0.57 |
| F2u5 | F2 | 534 | CCG | CCA | P to P | | | | | | | C | 0.99 | T | 0.01 |
| LDLRu3 | LDLR | 539 | CCC | CCT | P to P | | | | | | | C | 0.89 | T | 0.11 |
| F5u6 | F5 | 572 | GAG | GAA | E to E | | | | | | | G | 0.94 | A | 0.06 |

| Polymorphism ID | Gene | | Codon No. | SILENT POLYMORPHISMS | | | MISSENSE POLYMORPHISMS | | | NONSENSE POLYMORPHISMS | | | ALLELE FREQUENCIES | | | |
|---|---|---|---|---|---|---|---|---|---|---|---|---|---|---|---|---|
| | | | | Ref codon | Var codon | AA change | Ref codon | Var codon | AA change | Ref codon | Var codon | AA change | Ref allele | Freq | Var allele | Freq |
| LDLRu10 | LDLR | | 575 | CTC | CTT | L to L | | | | | | | C | 0.93 | T | 0.07 |
| LDLRu6 | LDLR | | 591 | AAT | AAC | N to N | | | | | | | T | 0.77 | C | 0.23 |
| ITGA2Bu3 | ITGA2B | | 605 | CCG | CCA | P to P | | | | | | | G | 0.98 | A | 0.02 |
| LDLRu11 | LDLR | | 640 | AAC | AAT | N to N | | | | | | | C | 0.99 | T | 0.01 |
| F5u7 | F5 | | 642 | ACC | ACA | T to T | | | | | | | C | 0.96 | A | 0.04 |
| LDLRu1 | LDLR | | 653 | GTC | GTT | V to V | | | | | | | G | 0.31 | T | 0.69 |
| LDLRu12 | LDLR | | 744 | CGG | CGA | R to R | | | | | | | G | 0.85 | A | 0.15 |
| ITGA2Bu8 | ITGA2B | | 855 | CTT | CTC | L to L | | | | | | | T | 0.99 | C | 0.01 |
| ITGA2Bu4 | ITGA2B | | 972 | CCG | CCA | P to P | | | | | | | G | 0.99 | A | 0.01 |
| ITGA2Bu1 | ITGA2B | | 1021 | GTC | GTT | V to V | | | | | | | G | 0.66 | T | 0.34 |
| F5u8 | F5 | | | | | | | | | | | | G | 0.99 | T | 0.01 |
| HCF2u1 | HCF2 | | | | | | | | | | | | C | 0.96 | T | 0.04 |
| HMGCRu2 | HMGCR | | | | | | | | | | | | G | 0.97 | A | 0.03 |
| ITGB3u2 | ITGB3 | | 59 | | | | CTG | CCG | L to P | | | | T | 0.87 | C | 0.13 |
| CETPu2 | CETP | | 422 | | | | ATC | GTC | I to V | | | | A | 0.34 | G | 0.66 |
| F5u2 | F5 | | 513 | | | | AGA | AAA | R to K | | | | G | 0.85 | A | 0.15 |
| F5u3 | F5 | | 534 | | | | CGA | CAA | R to Q | | | | G | 0.99 | A | 0.01 |
| AT3u2 | AT3 | | 337 | CAG | CAA | Q to Q | | | | | | | G | 0.62 | A | 0.38 |

| Poly ID | GenBank Acc: Nuc.Position |
|---|---|
| AT3u1 | D29832:1005 |
| AT3u2 | D29832:1035 |
| AT3u3 | M21645:100 |
| AT3u4 | D29832:1374 |
| CETPu1 | M30185:1298 |
| CETPu2 | M30185:1394 |
| CETPu3 | M30185:991 |
| CETPu4 | M30185:196 |
| CETPu5 | M30185:388 |
| CETPu6 | M30185:766 |
| CETPu7 | M30185:1429 |
| CETPu8 | J02898:298 |
| CETPu9 | J02898:571 |
| CLanalogu1 | Z22555:1119 |
| CLanalogu2 | Z22555:570 |
| CLanalogu3 | Z22555:400 |
| CLanalogu4 | Z22555:472 |
| CLanalogu5 | Z22555:972 |
| F2Ru1 | M62424:496 |
| F2Ru2 | M62424:610 |
| F2Ru3 | M62424:664 |
| F2Ru4 | M62424:720 |
| F2Ru5 | M62424:740 |
| F2Ru6 | M62424:405 |
| F2Ru7 | M62424:609 |
| F2u1 | M17262:10777 |
| F2u2 | M17262:15342 |
| F2u3 | M17262:15419 |
| F2u4 | M17262:13434 |
| F2u5 | M17262:16827 |
| F3u1 | J02846:9363 |
| F5u1 | M14335:1456 |
| F5u2 | M14335:1614 |
| F5u3 | M14335:1677 |
| F5u4 | M14335:1314 |
| F5u5 | M14335:1318 |
| F5u6 | M14335:1792 |
| F5u7 | M14335:2002 |
| HCF2u1 | M58600:11907 |
| HCF2u2 | M12849:259 |
| HCF2u3 | M12849:1353 |
| HCF2u4 | M12849:47 |
| HCF2u5 | M12849:313 |
| HCF2u6 | M12849:651 |
| HCF2u7 | M12849:1474 |
| HMGCRu1 | M11058:1962 |
| HMGCRu2 | M11058:2725 |

| | |
|---|---|
| ITGA2Bu1 | M22569:194 |
| ITGA2Bu2 | J02764:2623 |
| ITGA2Bu3 | M33320:6845 |
| ITGA2Bu4 | J02764:2918 |
| ITGA2Bu5 | J02764:2904 |
| ITGA2Bu6 | J02764:120 |
| ITGA2Bu7 | J02764:2299 |
| ITGA2Bu8 | J02764:2567 |
| ITGB3u1 | J02703:526 |
| ITGB3u2 | J02703:196 |
| ITGB3u3 | J02703:902 |
| ITGB3u4 | J02703:1163 |
| ITGB3u5 | M20311:1549 |
| ITGB3u6 | M20311:1561 |
| ITGB3u7 | J02703:362 |
| ITGB3u8 | J02703:1377 |
| LCATu1 | M12625:864 |
| LCATu2 | M12625:961 |
| LCATu3 | M12625:1444 |
| LCATu4 | M12625:1167 |
| LDLRu1 | L00347:129 |
| LDLRu10 | U59436:45 |
| LDLRu11 | L00347:90 |
| LDLRu12 | L00349:107 |
| LDLRu13 | L00336:29 |
| LDLRu14 | L00351:67 |
| LDLRu2 | L00338:91 |
| LDLRu3 | L00345:46 |
| LDLRu4 | L00349:44 |
| LDLRu5 | L00344:70 |
| LDLRu6 | U59436:93 |
| LDLRu7 | L29401:691 |
| LDLRu8 | L00344:59 |
| LDLRu9 | L00343:152 |
| LPLu1 | M15856:1338 |
| LPLu2 | M15856:1453 |
| LPLu3 | M76722:3150 |
| PROCu1 | K02059:577 |
| PROCu2 | K02059:109 |
| PROCu3 | M11228:9358 |
| PROCu4 | K02059:534 |
| PTAFRu1 | D10202:794 |
| PTAFRu2 | D10202:1047 |
| PTAFRu3 | D10202:783 |
| PTAFRu4 | D10202:194 |
| PTAFRu5 | D10202:1125 |
| TBXA2Ru1 | D38081:1915 |
| TFPIu1 | J03225:1006 |

FIG. 2

```
LOCUS       HUMPAFRE     1780 bp    mRNA           PRI      10-OCT-1992
DEFINITION  Human mRNA for platelet-activating factor receptor, complete cds.
ACCESSION   D10202 D90433
NID         g219975
KEYWORDS    G-protein coupled receptor; PAF receptor; platelet-activating
            factor receptor.
SOURCE      Human leukocytes cDNA to mRNA.
  ORGANISM  Homo sapiens
            Eukaryotae; mitochondrial eukaryotes; Metazoa; Chordata;
            Vertebrata; Mammalia; Eutheria; Primates; Catarrhini; Hominidae;
            Homo.
REFERENCE   1  (bases 1 to 1780)
  AUTHORS   Nakamura,M., Honda,Z., Izumi,T., Sakanaka,C., Mutoh,H., MInami,M.,
            Bito,H., Seyama,Y., Noma,M., Mtsumoto,T. and Shimizu,T.
  TITLE     Molecular cloning and expression of platelet-activating factor
            receptor from human leukocytes
  JOURNAL   J. Biol. Chem. 266 (30), 20400-20405 (1991)
  MEDLINE   92041873
REFERENCE   2  (bases 1 to 1780)
  AUTHORS   Shimizu,T.
  TITLE     Direct Submission
  JOURNAL   Submitted (28-JUN-1991) to the DDBJ/EMBL/GenBank databases. Takao
            Shimizu, Faculty of Medicine, University of Tokyo, Department of
            Biochemistry; 7-3-1 Hongo, Bunkyo-ku, Tokyo 113, Japan
            (Tel:03-3812-2111(ex.3448), Fax:03-3813-8732)
COMMENT     Submitted (28-Jun-1991) to DDBJ by:
            Takao Shimizu
            Department of Biochemistry
            Faculty of Medicine, University of Tokyo
            7-3-1 Hongo, Bunkyo-ku
            Tokyo 113
            Japan
            Phone:  03-3812-2111 x3448
            Fax:    03-3813-8732.
FEATURES             Location/Qualifiers
     source          1..1780
                     /organism="Homo sapiens"
                     /db_xref="taxon:9606"
                     /cell_type="leukocytes"
     CDS             113..1141
                     /codon_start=1
                     /product="platelet-activating factor receptor"
                     /db_xref="PID:d1001519"
                     /db_xref="PID:g219976"

/translation="MEPHDSSHMDSEFRYTLFPIVYSIIFVLGVIANGYVLWVFARLY

PCKKFNEIKIFMVNLTMADMLFLITLPLWIVYYQNQGNWILPKFLCNVAGCLFFINTY

CSVAFLGVITYNRFQAVTRPIKTAQANTRKRGISLSLVIWVAIVGAASYFLILDSTNT

VPDSAGSGNVTRCFEHYEKGSVPVLIIHIFIVFSFFLVFLIILFCNLVIIRTLLMQPV
```

Figure 3A

QQQRNAEVKRRALWMVCTVLAVFIICFVPHHVVQLPWTLAELGFQDSKFHQAINDAHQ

VTLCLLSTNCVLDPVIYCFLTKKFRKHLTEKFYSMRSSRKCSRATTDTVTEVVVPFNQ
                IPGNSLKN"
BASE COUNT        393 a      533 c       438 g      416 t
ORIGIN
       1 ttcacgaggg ctggggccag gacccagaca gagacacacg gtcactgcag ctgaagccgc
      61 tgcccctgct acaggcacca ccaggaccag ctgatcattc cagcccacag caatggagcc
     121 acatgactcc tcccacatgg actctgagtt ccgatacact ctcttcccga ttgtttacag
     181 catcatcttt gtgctcgggg tcattgctaa tggctacgtg ctgtgggtct ttgcccgcct
     241 gtaccctttgc aagaaattca atgagataaa gatcttcatg gtgaacctca ccatggcgga
     301 catgctcttc ttgatcaccc tgccactttg gattgtctac taccaaaacc agggcaactg
     361 gatactcccc aaattcctgt gcaacgtggc tggctgcctt ttcttcatca cacctactg
     421 ctctgtggcc ttcctgggcg tcatcactta taaccgcttc caggcagtaa ctcggcccat
     481 caagactgct caggccaaca cccgcaagcg tggcatctct ttgtccttgg tcatctgggt
     541 ggccattgtg ggagctgcat cctacttcct catcctggac tccaccaaca cagtgcccga
     601 cagtgctggc tcaggcaacg tcactcgctg ctttgagcat tacgagaagg gcagcgtgcc
     661 agtcctcatc atccacatct tcatcgtgtt cagcttcttc ctggtcttcc tcatcatcct
     721 cttctgcaac ctggtcatca tccgtacctt gctcatgcag ccggtgcagc agcagcgcaa
     781 cgctgaagtc aagcgccggg cgctgtggat ggtgtgcacg gtcttggcgg tgttcatcat
     841 ctgcttcgtg ccccaccacg tggtgcagct gccctggacc cttgctgagc tgggcttcca
     901 ggacagcaaa ttccaccagg ccattaatga tgcacatcag gtcaccctct gcctccttag
     961 caccaactgt gtcttagacc ctgttatcta ctgtttcctc accaagaagt tccgcaagca
    1021 cctcaccgaa aagttctaca gcatgcgcag tagccggaaa tgctcccggg ccaccacgga
    1081 tacggtcact gaagtggttg tgccattcaa ccagatccct ggcaattccc tcaaaaatta
    1141 gtccctgctt ccaggcctga agtcttctcc tccatgaaac atcatgactg agctggggga
    1201 agaagggata tctactgtgg gtctgggcac cacctctgtg gcactggtgg gccattagat
    1261 ttggaggcta cctcacctgg gcagggatga tgcagagcca ggctgttgga aaatccagaa
    1321 ctcaaatgag ccccttcatc cgcctgtggg cgcatactac agtaactgtg actgatgact
    1381 ttatcctgag tcccttaatc ttatggggcc ggaaggaatg tcagggccag gtgcagacct
    1441 tgggggaaga cttaaaccaa cctagttctc ccactggggc atcggtctaa agctttgggg
    1501 gagtggcccc agtggctcac acctgtaatc ccagcacttt gggaggccga ggtgggcaga
    1561 tcatgggtca agatcgag acatcctggc caacattgta aaacccccatc tctactaaaa
    1621 catacaaaaa ttagccgggc atggtgcaca cgcctgtagt cccagctact caggaggctg
    1681 aggcaggaga tcgcttgaa cctgggaggc agaggttgca gtgaacctag attgcaccat
    1741 tgcactctag cctggcaaca gaggcagatt ccctcctgcc

Figure 3B

```
LOCUS       HUMATIIIV    1467 bp    mRNA           PRI       03-SEP-1996
DEFINITION  Human mRNA for antithrombin III variant, complete cds.
ACCESSION   D29832
NID         g576553
KEYWORDS    AT-III; antithrombin III.
SOURCE      Homo sapiens (individual-isolate AT-III Kyoto) cDNA to mRNA, clone
            pKF16c.
  ORGANISM  Homo sapiens
            Eukaryotae; mitochondrial eukaryotes; Metazoa; Chordata;
            Vertebrata; Mammalia; Eutheria; Primates; Catarrhini; Hominidae;
            Homo.
REFERENCE   1  (sites)
  AUTHORS   Tsuji,H., Takada,O., Nakagawa,M., Tanaka,S. and Hashimoto-Gotoh,T.
  TITLE     Hereditary antithrombin III deficiency: identification of an
            arginine-406 to methionine point mutation near protease reactive
            site
  JOURNAL   (in) Yoshida,T.O. and Wilson,J.M. (Eds.);
            MOLECULAR APPROACHES TO THE STUDY AND TREATMENT OF HUMAN DISEASES:
            51-55;
            Elsevier Science (1992)
REFERENCE   2  (bases 1 to 1467)
  AUTHORS   Hashimoto-Gotoh,T.
  JOURNAL   Unpublished (1994)
FEATURES             Location/Qualifiers
     source          1..1467
                     /organism="Homo sapiens"
                     /db_xref="taxon:9606"
     CDS             22..1419
                     /note="Wild type AT-III has 'g' instead of 't' at
position
                     1337 nt. Also amino acid residue changes from Met to Arg
                     at position 406 aa in wild type AT-III."
                     /codon_start=1
                     /product="antithrombin III (AT-III) variant"
                     /db_xref="PID:d1006776"
                     /db_xref="PID:g576554"

/translation="MYSNVIGTVTSGKRKVYLLSLLLIGFWDCVTCHGSPVDICTAKP

RDIPMNPMCIYRSPEKKATEDEGSEQKIPEATNNRRVWELSKANSRFATTFYQHLADS

KNDNDNIFLSPLSISTAFAMTKLGACNDTLQQLMEVFKFDTISEKTSDQIHFFFAKLN

CRLYRKANKSSKLVSANRLFGDKSLTFNETYQDISELVYGAKLQPLDFKENAEQSRAA

INKWVSNKTEGRITDVIPSEAINELTVLVLVNTIYFKGLWKSKFSPENTRKELFYKAD

GESCSASMMYQEGKFRYRRVAEGTQVLELPFKGDDITMVLILPKPEKSLAKVEKELTP

EVLQEWLDELEEMMLVVHMPRFRIEDGFSLKEQLQDMGLVDLFSPEKSKLPGIVAEGR

DDLYVSDAFHKAFLEVNEEGSEAAASTAVVIAGRSLNPNRVTFKANMPFLVFIREVPL
                NTIIFMGRVANPCVK"
```

Figure 4A

```
BASE COUNT      381 a     375 c     364 g     347 t
ORIGIN
        1 gaattcgagc tcgccccggc catgtattcc aatgtgatag gaactgtaac ctctggaaaa
       61 aggaaggttt atctcttgtc cttgctgctc attggcttct gggactgcgt gacctgtcac
      121 gggagccctg tggacatctg cacagccaag ccgcgggaca ttcccatgaa tcccatgtgc
      181 atttaccgct ccccggagaa gaaggcaact gaggatgagg gctcagaaca gaagatcccg
      241 gaggccacca acaaccggcg tgtctgggaa ctgtccaagg ccaattcccg ctttgctacc
      301 actttctatc agcacctggc agattccaag aatgacaatg ataacatttt cctgtcaccc
      361 ctgagtatct ctacggcttt tgctatgacc aagctgggtg cctgtaatga caccctccag
      421 caactgatgg aggtatttaa gtttgacacc atatctgaga aaacatctga tcagatccac
      481 ttcttctttg ccaaactgaa ctgccgactc tatcgaaaag ccaacaaatc ctccaagtta
      541 gtatcagcca atcgcctttt tggagacaaa tcccttacct tcaatgagac ctaccaggac
      601 atcagtgagt tggtatatgg agccaagctc cagccctgg acttcaagga aatgcagag
      661 caatccgag cggccatcaa caatgggtg tccaataaga ccgaaggccg aatcaccgat
      721 gtcattccct cggaagccat caatgagctc actgttctgg tgctggttaa caccatttac
      781 ttcaagggcc tgtggaagtc aaagttcagc cctgagaaca caaggaagga actgttctac
      841 aaggctgatg gagagtcgtg ttcagcatct atgatgtacc aggaaggcaa gttccgttat
      901 cggcgcgtgg ctgaaggcac ccaggtgctt gagttgccct caaaggtga tgacatcacc
      961 atggtcctca tcttgcccaa gcctgagaag agcctggcca aggtggagaa ggaactcacc
     1021 ccagaggtgc tgcaggagtg gctggatgaa ttggaggaga tgatgctggt ggtccacatg
     1081 ccccgcttcc gcattgagga cggcttcagt ttgaaggagc agctgcaaga catgggcctt
     1141 gtcgatctgt tcagccctga aaagtccaaa ctcccaggta ttgttgcaga aggccgagat
     1201 gacctctatg tctcagatgc attccataag gcatttcttg aggtaaatga agaaggcagt
     1261 gaagcagctg caagtaccgc tgttgtgatt gctggccgtt cgctaaaccc caacagggtg
     1321 actttcaagg ccaacatgcc tttcctggtt tttataagag aagttcctct gaacactatt
     1381 atcttcatgg gcagggtagc caaccccttgt gttaagtaaa atgttctcta gaggatcccc
     1441 catcgatggg gtaccgagct cgaattc
```

Figure 4B

```
LOCUS       HUMHTAR      2932 bp    mRNA              PRI       03-APR-1996
DEFINITION  Human mRNA for thromboxane A2 receptor, complete cds.
ACCESSION   D38081
NID         g533325
KEYWORDS    thromboxane A2 receptor.
SOURCE      Homo spaiens placenta cDNA to mRNA, clone HPL.
  ORGANISM  Homo sapiens
            Eukaryotae; mitochondrial eukaryotes; Metazoa; Chordata;
            Vertebrata; Mammalia; Eutheria; Primates; Catarrhini; Hominidae;
            Homo.
REFERENCE   1  (bases 1 to 2932)
  AUTHORS   Hirata,M., Hayashi,Y., Ushikubi,F., Yokota,Y., Kageyama,R.,
            Nakanishi,S. and Narumiya,S.
  TITLE     Cloning and expression of cDNA for a human thromboxane A2 receptor
  JOURNAL   Nature 349 (6310), 617-620 (1991)
  MEDLINE   91156030
REFERENCE   2  (sites)
  AUTHORS   Nusing,R.M., Hirata,M., Kakizuka,A., Eki,T., Ozawa,K. and
            Narumiya,S.
  TITLE     Characterization and chromosomal mapping of the human thromboxane
            A2 receptor gene
  JOURNAL   J. Biol. Chem. 268 (33), 25253-25259 (1993)
  MEDLINE   94043399
REFERENCE   3  (bases 1 to 2932)
  AUTHORS   Hirata,M.
  TITLE     Direct Submission
  JOURNAL   Submitted (26-AUG-1994) to the DDBJ/EMBL/GenBank databases.
            Masakazu Hirata, Kyoto University Faculty of Medicine, Department
            of Pharmacology; Yoshida, Sakyo-ku, Kyoto, Kyoto 606, Japan
            (Tel:81-75-753-4392, Fax:81-75-753-4693)
FEATURES             Location/Qualifiers
     source          1..2932
                     /organism="Homo sapiens"
                     /db_xref="taxon:9606"
                     /tissue_type="placenta"
     misc_feature    1..705
                     /note="This part of the cDNA clone may not belong to the
                     thromboxane A2 receptor gene. Please refer to Nuesing,
                     R.M. et al.(reference2)"
     CDS             992..2023
                     /codon_start=1
                     /evidence=experimental
                     /product="Human thromboxane A2 receptor"
                     /db_xref="PID:d1007852"
                     /db_xref="PID:g533326"
```

/translation="MWPNGSSLGPCFRPTNITLEERRLIASPWFAASFCVVGLASNLL

ALSVLAGARQGGSHTRSSFLTFLCGLVLTDFLGLLVTGTIVVSQHAALFEWHAVDPGC

RLCRFMGVVMIFFGLSPLLLGAAMASERYLGITRPFSRPAVASQRRAWATVGLVWAAA

LALGLLPLLGVGRYTVQYPGSWCFLTLGAESGDVAFGLLFSMLGGLSVGLSFLLNTVS

Figure 5A

```
        VATLCHVYHGQEAAQQRPRDSEVEMMAQLLGIMVVASVCWLPLLVFIAQTVLRNPPAM

SPAGQLSRTTEKELLIYLRVATWNQILDPWVYILFRRAVLRRLQPRLSTRPRSLSLQP
                        QLTQRSGLQ"
        repeat_unit     2221..2338
        repeat_unit     2515..2636
        polyA_signal    2908..2913
        polyA_site      2932
                        /evidence=experimental
BASE COUNT      521 a     940 c     777 g     694 t
ORIGIN
        1 gtaatgcaga gataataaaa cttcttaggt ccataggtct tataataatt taataaccta
       61 aacatggtat acaaattcct ccaaacccaa taacataatt atagtttcaa aaagttcccc
      121 aaactttcaa gttagatttt attgctttga tgagtggctt taaatatgaa aagtcttgcc
      181 tgtgaagggc aatccttttc ccgtggactg ggatctatag aaatacagaa atgtgcccag
      241 gggttcatct ccctaataac catcattcac atttctcaac ctccctaata accagccacc
      301 atgtgagaag gatccacagt tactgtttat gactataatt aactagtacc tgggactggt
      361 cagtggagtt ggttgcaacc tgatgctaag gatgtcaaag ttgtctcggc ctctgttccc
      421 agccagtaag taattccctg gcctcgggcc atacccccta atcttggtca gctgattatg
      481 acaggcagac agcacagtaa ataacactat atattaagaa acccaaagc atatgtatca
      541 atggtatata cccaacagca tcctaggaat ggagagtctg tagcaagggc tccaatgtg
      601 aaggtcaaca cagtcactgt gatgcgtgta tttccatttt gtaaagcatg atctctggtg
      661 gtcatttta tcttcctaac ttattggaaa agtctcctgt tttggggggcc cgcccctggt
      721 cacagccaga ctgactcagt ttccctggga ggtcccgctc gagcccgtcc ttcccctccc
      781 tctgcccgcc cccagccctc gccccaccct cggcgccgc acatctgcct gctcagctcc
      841 agacggcgcc cggaccccg ggcgcgggat ccagccaggt gggagccccg cagatgaggt
      901 ctctgaaggt gtgcctgaac cagtgccagc ctgccctgtc tgcagcatcg gcctgatggg
      961 gtggtgactg atccctcagg gctccggagc catgtggccc aacggcagtt ccctggggcc
     1021 ctgtttccgg cccacaaaca ttaccctgga ggagagacgg ctgatcgcct cgccctggtt
     1081 cgccgcctcc ttctgcgtgg tgggcctggc ctccaacctg ctggccctga gcgtgctggc
     1141 gggcgcgcgg cagggggggtt cgcacacgcg ctcctccttc ctcaccttcc tctgcggcct
     1201 cgtcctcacc gacttcctgg ggctgctggt gaccggtacc atcgtggtgt cccagcacgc
     1261 cgcgctcttc gagtggcacg ccgtggaccc tggctgccgt ctctgtcgct tcatgggcgt
     1321 cgtcatgatc ttcttcggcc tgtccccgct gctgctgggg gccgccatgg cctcagagcg
     1381 ctacctgggt atcacccggc ccttctcgcg cccggcggtc gcctcgcagc gccgcgcctg
     1441 ggccaccgtg gggctggtgt gggcggccgc gctggcgctg gcctgctgc cctgctggg
     1501 cgtgggtcgc tacaccgtgc aatacccggg gtcctggtgc ttcctgacgc tgggcgccga
     1561 gtccggggac gtggccttcg ggctgctctt ctccatgctg ggcggcctct cggtcgggct
     1621 gtccttcctg ctgaacacgg tcagcgtggc cacccgtgtg cacgtctacc acgggcagga
     1681 ggcggcccag cagcgtcccc gggactccga ggtggagatg atggctcagc tcctggggat
     1741 catggtggtg gccagcgtgt gttggctgcc ccttctggtc ttcattgccc agacagtgct
     1801 gcgaaacccg cctgccatga gccccgccgg gcagctgtcc cgcaccacgg agaaggagct
     1861 gctcatctac ttgcgcgtgg ccacctggaa ccagatcctg gaccctgggg tgtatatcct
     1921 gttccgccgc gccgtgctcc ggcgtctcca gcctcgcctc agcacccggc ccaggtcgct
     1981 gtccctccag ccccagctca cgcagcgctc cgggctgcag taggaagtgg acagagcgcc
     2041 cctcccgcgc ctttccgcgg agcccttggc ccctcggaca gcccatctgc ctgttctgag
     2101 gattcagggg ctggggtgc tggatggaca gtgggcatca gcagcaggt tttgggttga
     2161 ccccaatcca acccggggac ccccaactcc tccctgatcc ttttaccaag cactctcct
     2221 tcctcggccc cttttccca tccagagctc ccaccccttc tctgcgtccc tccaacccc
     2281 aggaagggca tgcagacatt ggaagagggt cttgcattgc tatttttttt tttagacgga
     2341 gtcttgctct gtccccagg ctggagtgca gtggcgcaat ctcagctcac tgcaacctcc
     2401 acctcccggg ttcaagcgat tctcctgcct cagcctcctg agtagctggg actataggcg
     2461 cgcgccacca cgcccggcta atttttgtat ttttagtaga cgggggttt caccgtgttg
```

Figure 5B

```
2521 gccaggctgg tcttgaactc ctgacctcag gtgattcacc agcctcagcc tcccaaagtg
2581 ctgggatcac aggcatgaac caccacacct ggccattttt ttttttttt tagacggagt
2641 ctcactctgt ggcccagcct ggagtacagt ggcacgatct cggctcactg caacctccgc
2701 ctcccgggtt caagcgattc tcgtgcctca gcctcccgag cagctgggat tacaggcgta
2761 agccactgcg cccggccttg catgctcttt gaccctgaat ttgacctact tgctggggta
2821 cagttgcttc cttttgaacc tccaacaggg aaggctctgt ccagaaagga ttgaatgtga
2881 aacgggggca ccccttttc ttgccaaaat atatctctgc ctttggtttt at
```

Figure 5C

```
LOCUS       HUMGP3A      3170 bp    mRNA            PRI         08-NOV-1994
DEFINITION  Human endothelial membrane glycoprotein IIIa (GPIIIa) mRNA,
            complete cds.
ACCESSION   J02703
NID         g183452
KEYWORDS    glycoprotein; glycoprotein IIIa.
SOURCE      Human umbilical vein endothelial cell, cDNA to mRNA.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 3170)
  AUTHORS   Fitzgerald,L.A., Steiner,B., Rall,S.C. Jr., Lo,S.S. and
            Phillips,D.R.
  TITLE     Protein sequence of endothelial glycoprotein IIIa derived from a
            cDNA clone. Identity with platelet glycoprotein IIIa and
similarity
            to 'integrin'
  JOURNAL   J. Biol. Chem. 262 (9), 3936-3939 (1987)
  MEDLINE   87165991
COMMENT     Draft entry and computer-readable sequence for [1] kindly provided
            by L.A.Fitzgerald, 10-FEB-1987.
            The endothelial membrane glycoprotein IIIa is probably identical
to
            the platelet glycoprotein IIIa.
FEATURES             Location/Qualifiers
     source          1..3170
                     /organism="Homo sapiens"
                     /db_xref="taxon:9606"
                     /map="17q21.32"
     sig_peptide     21..98
                     /gene="ITGB3"
                     /note="glycoprotein IIIa signal peptide (putative);
                     putative"
     CDS             21..2387
                     /gene="ITGB3"
                     /note="glycoprotein IIIa precursor"
                     /codon_start=1
                     /db_xref="GDB:G00-120-013"
                     /db_xref="PID:g306786"
```

/translation="MRARPRPRPLWVTVLALGALAGVGVGGPNICTTRGVSSCQQCLA

VSPMCAWCSDEALPLGSPRCDLKENLLKDNCAPESIEFPVSEARVLEDRPLSDKGSGD

SSQVTQVSPQRIALRLRPDDSKNFSIQVRQVEDYPVDIYYLMDLSYSMKDDLWSIQNL

GTKLATQMRKLTSNLRIGFGAFVDKPVSPYMYISPPEALENPCYDMKTTCLPMFGYKH

VLTLTDQVTRFNEEVKKQSVSRNRDAPEGGFDAIMQATVCDEKIGWRNDASHLLVFTT

DAKTHIALDGRLAGIVQPNDGQCHVGSDNHYSASTTMDYPSLGLMTEKLSQKNINLIF

AVTENVVNLYQNYSELIPGTTVGVLSMDSSNVLQLIVDAYGKIRSKVELEVRDLPEEL

Figure 6A

```
          SLSFNATCLNNEVIPGLKSCMGLKIGDTVSFSIEAKVRGCPQEKEKSFTIKPVGFKDS

LIVQVTFDCDCACQAQAEPNSHRCNNGNGTFECGVCRCGPGWLGSQCECSEEDYRPSQ

QDECSPREGQPVCSQRGECLCGQCVCHSSDFGKITGKYCECDDFSCVRYKGEMCSGHG

QCSCGDCLCDSDWTGYYCNCTTRTDTCMSSNGLLCSGRGKCECGSCVCIQPGSYGDTC

EKCPTCPDACTFKKECVECKKFDREPYMTENTCNRYCRDEIESVKELKDTGKDAVNCT

YKNEDDCVVRFQYYEDSSGKSILYVVEEPECPKGPDILVVLLSVMGAILLIGLAALLI
                            WKLLITIHDRKEFAKFEEERARAKWDTANNPLYKEATSTFTNITYRGT"
     gene            21..2387
                     /gene="ITGB3"
     mat_peptide     99..2384
                     /gene="ITGB3"
                     /note="glycoprotein IIIa"
BASE COUNT      705 a    809 c    909 g    747 t
ORIGIN      132 bp upstream of SacI site.
        1 cgccgcggga ggcggacgag atgcgagcgc ggccgcggcc ccggccgctc tgggtgactg
       61 tgctggcgct gggggcgctg gcgggcgttg gcgtaggagg gcccaacatc tgtaccacgc
      121 gaggtgtgag ctcctgccag cagtgcctgg ctgtgagccc catgtgtgcc tggtgctctg
      181 atgaggccct gcctctgggc tcacctcgct gtgacctgaa ggagaatctg ctgaaggata
      241 actgtgcccc agaatccatc gagttcccag tgagtgaggc ccgagtacta gaggacaggc
      301 ccctcagcga caagggctct ggagacagct cccaggtcac tcaagtcagt ccccagagga
      361 ttgcactccg gctccggcca gatgattcga agaatttctc catccaagtg cggcaggtgg
      421 aggattaccc tgtggacatc tactacttga tggacctgtc ttactccatg aaggatgatc
      481 tgtggagcat ccagaacctg ggtaccaagc tggccaccca gatgcgaaag ctcaccagta
      541 acctgcggat tggcttcggg gcatttgtgg acaagcctgt gtcaccatac atgtatatct
      601 ccccaccaga ggcctcgaa aaccctgct atgatatgaa gaccacctgc ttgcccatgt
      661 ttggctacaa acacgtgctg acgctaactg accaggtgac ccgcttcaat gaggaagtga
      721 agaagcagag tgtgtcacgg aaccgagatg ccccagaggg tggctttgat gccatcatgc
      781 aggctacagt ctgtgatgaa aagattggct ggaggaatga tgcatcccac ttgctggtgt
      841 ttaccactga tgccaagact catatagcat ggacggaag gctggcaggc attgtccagc
      901 ctaatgacgg gcagtgtcat gttggtagtg acaatcatta ctctgcctcc actaccatgg
      961 attatccctc tttggggctg atgactgaga agctatccca gaaaaacatc aatttgatct
     1021 ttgcagtgac tgaaaatgta gtcaatctct atcagaacta tagtgagctc atcccaggga
     1081 ccacagttgg ggttctgtcc atggattcca gcaatgtcct ccagctcatt gttgatgctt
     1141 atgggaaaat ccgttctaaa gtcgagctgg aagtgcgtga cctcctgaa gagttgtctc
     1201 tatccttcaa tgccacctgc ctcaacaatg aggtcatccc tggcctcaag tcttgtatgg
     1261 gactcaagat tggagacacg gtgagcttca gcattgaggc caaggtgcga ggctgtcccc
     1321 aggagaagga gaagtccttt accataaagc ccgtgggctt caaggacagc ctgatcgtcc
     1381 aggtcacctt tgattgtgac tgtgcctgcc aggcccaagc tgaacctaat gccatcgct
     1441 gcaacaatgg caatgggacc tttgagtgtg ggtatgccg ttgtgggcct ggctggctgg
     1501 gatcccagtg tgagtgctca gaggaggact atcgcccttc ccagcaggac gagtgcagcc
     1561 ccgagaggg tcagcccgtc tgcagccagc ggggcgagtg cctctgtggt caatgtgtct
     1621 gccacagcag tgactttggc aagatcacgg gcaagtactg cgagtgtgac gacttctcct
     1681 gtgtccgcta caagggggag atgtgctcag gccatggcca gtgcagctgt ggggactgcc
     1741 tgtgtgactc cgactggacc ggctactact gcaactgtac cacgcgtact gacacctgca
     1801 tgtccagcaa tgggctgctg tgcagcggcc gcggcaagtg taatgtggc agctgtgtct
     1861 gtatccagcc gggctcctat ggggacacct gtgagaagtg ccccacctgc ccagatgcct
     1921 gcacctttaa gaaagaatgt gtggagtgta agaagtttga ccgggagccc tacatgaccg
     1981 aaaatacctg caaccgttac tgccgtgacg agattgagtc agtgaaagag cttaaggaca
```

Figure 6B

```
2041 ctggcaagga tgcagtgaat tgtacctata agaatgagga tgactgtgtc gtcagattcc
2101 agtactatga agattctagt ggaaagtcca tcctgtatgt ggtagaagag ccagagtgtc
2161 ccaagggccc tgacatcctg gtggtcctgc tctcagtgat gggggccatt ctgctcattg
2221 gccttgccgc cctgctcatc tggaaactcc tcatcaccat ccacgaccga aaagaattcg
2281 ctaaatttga ggaagaacgc gccagagcaa aatgggacac agccaacaac ccactgtata
2341 aagaggccac gtctaccttc accaatatca cgtaccgggg cacttaatga taagcagtca
2401 tcctcagatc attatcagcc tgtgccagga ttgcaggagt ccctgccatc atgtttacag
2461 aggacagtat ttgtggggag ggatttcggg gctcagagtg gggtaggttg ggagaatgtc
2521 agtatgtgga agtgtgggtc tgtgtgtgtg tatgtggggg tctgtgtgtt tatgtgtgtg
2581 tgttgtgtgt gggagtgtgt aatttaaaat tgtgatgtgt cctgataagc tgagctcctt
2641 agcctttgtc ccagaatgcc tcctgcaggg attcttcctg cttagcttga gggtgactat
2701 ggagctgagc aggtgttctt cattacctca gtgagaagcc agctttcctc atcaggccat
2761 tgtccctgaa gagaagggca gggctgaggc ctctcattcc agaggaaggg acaccaagcc
2821 ttggctctac cctgagttca taaatttatg gttctcaggc ctgactctca gcagctatgg
2881 taggaactgc tggcttggca gcccgggtca tctgtacctc tgcctccttt cccctccctc
2941 aggccgaagg aggagtcagg gagagctgaa ctattagagc tgcctgtgcc ttttgccatc
3001 ccctcaaccc agctatggtt ctctcgcaag ggaagtcctt gcaagctaat tctttgacct
3061 gttgggagtg aggatgtctg ggccactcag gggtcattca tggcctgggg gatgtaccag
3121 catctcccag ttcataatca caacccttca gatttgcctt attggcagcg
```

Figure 6C

```
LOCUS       HUMPLG2B     3303 bp    mRNA            PRI       07-JAN-1995
DEFINITION  Human platelet membrane glycoprotein IIb (ITGA2B) mRNA, complete
            cds.
ACCESSION   J02764
NID         g190067
KEYWORDS    membrane adhesive protein; platelet membrane glycoprotein;
platelet
            receptor.
SOURCE      Human HEL cell, cDNA to mRNA.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 3303)
  AUTHORS   Poncz,M., Eisman,R., Heidenreich,R., Silver,S.M., Vilaire,G.,
            Surrey,S., Schwartz,E. and Bennett,J.S.
  TITLE     Structure of the platelet membrane glycoprotein IIb. Homology to
            the alpha subunits of the vitronectin and fibronectin membrane
            receptors
  JOURNAL   J. Biol. Chem. 262 (18), 8476-8482 (1987)
  MEDLINE   87250457
COMMENT     Draft entry and computer-readable sequence [1] kindly provided by
            M.Poncz, 15-APR-1987.
FEATURES             Location/Qualifiers
     source          1..3303
                     /organism="Homo sapiens"
                     /db_xref="taxon:9606"
                     /map="17q21.32"
     mRNA            <1..3303
                     /gene="ITGA2B"
                     /note="G00-120-012"
     gene            1..3303
                     /gene="ITGA2B"
     sig_peptide     2..94
                     /gene="ITGA2B"
                     /note="G00-120-012"
     CDS             2..3121
                     /gene="ITGA2B"
                     /codon_start=1
                     /db_xref="GDB:G00-120-012"
                     /product="platelet membrane glycoprotein IIb"
                     /db_xref="PID:g190068"
```

/translation="MARALCPLQALWLLEWVLLLLGPCAAPPAWALNLDPVQLTFYAG

PNGSQFGFSLDFHKDSHGRVAIVVGAPRTLGPSQEETGGVFLCPWRAEGGQCPSLLFD

LRDETRNVGSQTLQTFKARQGLGASVVSWSDVIVACAPWQHWNVLEKTEEAEKTPVGS

CFLAQPESGRRAEYSPCRGNTLSRIYVENDFSWDKRYCEAGFSSVVTQAGELVLGAPG

GYYFLGLLAQAPVADIFSSYRPGILLWHVSSQSLSFDSSNPEYFDGYWGYSVAVGEFD

GDLNTTEYVVGAPTWSWTLGAVEILDSYYQRLHRLRAEQMASYFGHSVAVTDVNGDGR

Figure 7A

HDLLVGAPLYMESRADRKLAEVGRVYLFLQPRGPHALGAPSLLLTGTQLYGRFGSAIA

PLGDLDRDGYNDIAVAAPYGGPSGRGQVLVFLGQSEGLRSRPSQVLDSPFPTGSAFGF

SLRGAVDIDDNGYPDLIVGAYGANQVAVYRAQPVVKASVQLLVQDSLNPAVKSCVLPQ

TKTPVSCFNIQMCVGATGHNIPQKLSLNAELQLDRQKPRQGRRVLLLGSQQAGTTLNL

DLGGKHSPICHTTMAFLRDEADFRDKLSPIVLSLNVSLPPTEAGMAPAVVLHGDTHVQ

EQTRIVLDSGEDDVCVPQLQLTASVTGSPLLVGADNVLELQMDAANEGEGAYEAELAV

HLPQGAHYMRALSNVEGFERLICNQKKENETRVVLCELGNPMKKNAQIGIAMLVSVGN

LEEAGESVSFQLQIRSKNSQNPNSKIVLLDVPVRAEAQVELRGNSFPASLVVAAEEGE

REQNSLDSWGPKVEHTYELHNNGPGTVNGLHLSIHLPGQSQPSDLLYILDIQPQGGLQ

CFPQPPVNPLKVDWGLPIPSPSPIHPAHHKRDRRQIFLPEPEQPSRLQDPVLVSCDSA

PCTVVQCDLQEMARGQRAMVTVLAFLWLPSLYQRPLDQFVLQSHAWFNVSSLPYAVPP

LSLPRGEAQVWTQLLRALEERAIPIWWVLVGVLGGLLLLTILVLAMWKVGFFKRNRPP
LEEDDEEGE"
```
        mat_peptide     95..3118
                        /gene="ITGA2B"
                        /note="G00-120-012"
                        /product="platelet membrane glycoprotein IIb"
BASE COUNT      618 a     997 c    1026 g     662 t
ORIGIN      Unreported.
        1 gatgccaga gctttgtgtc cactgcaagc cctctggctt ctggagtggg tgctgctgct
       61 cttgggacct tgtgctgccc ctccagcctg ggccttgaac ctggacccag tgcagctcac
      121 cttctatgca ggccccaatg gcagccagtt tggattttca ctggacttcc acaaggacag
      181 ccatgggaga gtggccatcg tggtgggcgc cccgcggacc ctgggcccca gccaggagga
      241 gacgggcggc gtgttcctgt gccctggag ggccgagggc ggccagtgcc cctcgctgct
      301 ctttgacctc cgtgatgaga cccgaaatgt aggctcccaa actttacaaa ccttcaaggc
      361 ccgccaagga ctgggggcgt cggtcgtcag ctggagcgac gtcattgtgg cctgcgcccc
      421 ctggcagcac tggaacgtcc tagaaaagac tgaggaggct gagaagacgc ccgtaggtag
      481 ctgcttttttg gctcagccag agagcggccg ccgcgccgag tactcccct gtcgcgggaa
      541 caccctgagc cgcatttacg tggaaaatga ttttagctgg acaagcgtt actgtgaagc
      601 gggcttcagc tccgtggtca ctcaggccgg agagctggtg cttgggctc ctggcggcta
      661 ttattcttta ggtctcctga cccaggctcc agttgcggat attttctcga gttaccgccc
      721 aggcatcctt ttgtggcacg tgtcctccca gagcctctcc tttgactcca gcaacccaga
      781 gtacttcgac ggctactggg ggtactcggt ggccgtgggc gagttcgacg gggatctcaa
      841 cactacagaa tatgtcgtcg gtgcccccac ttggagctgg accctgggag cggtggaaat
      901 tttggattcc tactaccaga ggctgcatcg gctgcgcgca gagcagatgg cgtcgtatt
      961 tgggcattca gtggctgtca ctgacgtcaa cggggatggg aagcatgatc tgctggtggg
     1021 cgctccactg tatatggaga ccgggcaga ccgaaaactg ccgaagtgg ggcgtgtgta
     1081 tttgttcctg cagccgcgag gccccacgc gctgggtgcc cccagcctcc tgctgactgg
     1141 cacacagctc tatgggcgat cggctctgc catcgcaccc ctgggcgacc tcgaccggga
     1201 tggctacaat gacattgcag tggctgcccc ctacggggt cccagtggcc ggggccaagt
     1261 gctggtgttc ctgggtcaga gtgaggggct gaggtcacgt ccctcccagg tcctggacag
     1321 ccccttcccc acaggctctg cctttggctt ctcccttcga ggtgccgtag acatcgatga
```

Figure 7B

```
1381 caacggatac ccagacctga tcgtgggagc ttacggggcc aaccaggtgg ctgtgtacag
1441 agctcagcca gtggtgaagg cctctgtcca gctactggtg caagattcac tgaatcctgc
1501 tgtgaagagc tgtgtcctac ctcagaccaa gacacccgtg agctgcttca acatccagat
1561 gtgtgttgga gccactgggc acaacattcc tcagaagcta tccctaaatg ccgagctgca
1621 gctggaccgg cagaagcccc gccagggccg gcgggtgctg ctgctgggct ctcaacaggc
1681 aggcaccacc ctgaacctgg atctgggcgg aaagcacagc cccatctgcc acaccaccat
1741 ggccttcctt cgagatgagg cagacttccg ggacaagctg agccccattg tgctcagcct
1801 caatgtgtcc ctaccgccca cggaggctgg aatggcccct gctgtcgtgc tgcatggaga
1861 cacccatgtg caggagcaga cacgaatcgt cctggactct ggggaagatg acgtatgtgt
1921 gccccagctt cagctcactg ccagcgtgac gggctccccg ctcctagttg gggcagataa
1981 tgtcctggag ctgcagatgg acgcagccaa cgagggcgag ggggcctatg aagcagagct
2041 ggccgtgcac ctgccccagg gcgcccacta catgcgggcc taagcaatg tcgagggctt
2101 tgagagactc atctgtaatc agaagaagga gaatgagacc agggtggtgc tgtgtgagct
2161 gggcaacccc atgaagaaga acgcccagat aggaatcgcg atgttggtga gcgtggggaa
2221 tctggaagag gctggggagt ctgtgtcctt ccagctgcag atacggagca agaacagcca
2281 gaatccaaac agcaagattg tgctgctgga cgtgccggtc cgggcagagg cccaagtgga
2341 gctgcgaggg aactcctttc cagcctccct ggtggtggca gcagaagaag gtgagaggga
2401 gcagaacagc ttggacagct ggggacccaa agtggagcac acctatgagc tccacaacaa
2461 tggccctggg actgtgaatg gtcttcacct cagcatccac cttccgggac agtcccagcc
2521 ctccgacctg ctctacatcc tggatataca gcccaggggg ggccttcagt gcttcccaca
2581 gcctcctgtc aaccctctca aggtggactg ggggctgccc atcccagcc cctcccccat
2641 tcacccggcc catcacaagc gggatcgcag acagatcttc ctgccagagc ccgagcagcc
2701 ctcgaggctt caggatccag ttctcgtaag ctgcgactcg gcgccctgta ctgtggtgca
2761 gtgtgacctg caggagatgg cgcgcgggca gcgggccatg gtcacggtgc tggccttcct
2821 gtggctgccc agcctctacc agaggcctct ggatcagttt gtgctgcagt cgcacgcatg
2881 gttcaacgtg tcctccctcc cctatgcggt gccccgctc agcctgcccc gaggggaagc
2941 tcaggtgtgg acacagctgc tccgggcctt ggaggagagg gccattccaa tctggtgggt
3001 gctggtgggt gtgctgggtg cctgctgct gtcaccatc ctggtcctgg ccatgtggaa
3061 ggtcggcttc ttcaagcgga accggccacc cctggaagaa gatgatgaag aggggagtg
3121 atggtgcagc ctacactatt ctagcaggag ggttgggcgt gctacctgca ccgcccttc
3181 tccaacaagt tgcctccaag ctttgggttg gagctgttcc attgggtcct cttggtgtcg
3241 tttccctccc aacagagctg ggctacccc cctcctgctg cctaataaag agactgagcc
3301 ctg
```

Figure 7C

```
LOCUS       HUMTFPB       13865 bp    DNA             PRI       14-JAN-1995
DEFINITION  Human tissue factor gene, complete cds.
ACCESSION   J02846
NID         g339505
KEYWORDS    Alu repeat; cell surface integral membrane protein; cell surface
            receptor; tissue factor.
SOURCE      Human DNA, clones lambda-TF[559,679,753,885,1377].
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 13865)
  AUTHORS   Mackman,N., Morrissey,J.H., Fowler,B. and Edgington,T.S.
  TITLE     Complete sequence of the human tissue factor gene, a highly
            regulated cellular receptor that initiates the coagulation
protease
            cascade
  JOURNAL   Biochemistry 28 (4), 1755-1762 (1989)
  MEDLINE   89247359
COMMENT     Draft entry and computer-readable sequence for [1] kindly provided
            by J.H.Morrissey, 25-OCT-1988.
FEATURES             Location/Qualifiers
     source          1..13865
                     /organism="Homo sapiens"
                     /db_xref="taxon:9606"
                     /map="1p22-p21"
     prim_transcript 799..13232
                     /note="TF mRNA and introns"
     CDS             join(922..1021,2190..2301,6392..6591,9289..9467,
                     10075..10234,11955..12091)
                     /gene="F3"
                     /note="tissue factor"
                     /codon_start=1
                     /db_xref="GDB:G00-119-895"
                     /db_xref="PID:g339506"

/translation="METPAWPRVPRPETAVARTLLLGWVFAQVAGASGTTNTVAAYNL

TWKSTNFKTILEWEPKPVNQVYTVQISTKSGDWKSKCFYTTDTECDLTDEIVKDVKQT

YLARVFSYPAGNVESTGSAGEPLYENSPEFTPYLETNLGQPTIQSFEQVGTKVNVTVE

DERTLVRRNNTFLSLRDVFGKDLIYTLYYWKSSSSGKKTAKTNTNEFLIDVDKGENYC

FSVQAVIPSRTVNRKSTDSPVECMGQEKGEFREIFYIIGAVVFVVIILVIILAISLHK
                     CRKAGVGQSWKENSPLNVS"
     exon            <922..1021
                     /gene="F3"
                     /note="tissue factor"
                     /number=1
     gene            join(922..1021,2190..2301,6392..6591,9289..9467,
                     10075..10234,11955..12091)
                     /gene="F3"
     intron          1022..2189
```

Figure 8A

```
                        /note="TF intron A"
     exon               2190..2301
                        /gene="F3"
                        /number=2
     intron             2302..6391
                        /note="TF intron B"
     repeat_region      6127..6241
                        /note="Alu repeat partial copy A"
     exon               6392..6591
                        /gene="F3"
                        /number=3
     intron             6592..9288
                        /note="TF intron C"
     repeat_region      8391..8677
                        /note="Alu repeat copy B"
     exon               9289..9467
                        /gene="F3"
                        /number=4
     intron             9468..10074
                        /note="TF intron D"
     exon               10075..10234
                        /gene="F3"
                        /number=5
     intron             10235..11954
                        /note="TF intron E"
     repeat_region      10954..11249
                        /note="Alu repeat copy C"
     exon               11955..>12091
                        /gene="F3"
                        /note="tissue factor"
                        /number=6
     repeat_region      12458..12757
                        /note="Alu repeat copy D"
BASE COUNT     3711 a   2955 c   3240 g   3959 t
ORIGIN      1 bp upstream of EcoRI site; chromosome 1.
       1 gaattctccc agaggcaaac tgccagatgt gaggctgctc ttcctcagtc actatctctg
      61 gtcgtaccgg gcgatgcctg agccaactga ccctcagacc tgtgagccga gccggtcaca
     121 ccgtggctga caccggcatt cccaccgcct ttctcctgtg cgacccgcta agggccccgc
     181 gaggtgggca ggccaagtat tcttgacctt cgtggggtag aagaagccac cgtggctggg
     241 agagggccct gctcacagcc acacgtttac ttcgctgcag gtcccgagct tctgccccag
     301 gtgggcaaag catccgggaa atgccctccg ctgcccgagg ggagcccaga gccgtgctt
     361 tctattaaat gttgtaaatg ccgcctctcc cactttatca ccaaatggaa gggaagaatt
     421 cttccaaggc gccctccctt tcctgccata gacctgcaac ccacctaagc tgcacgtcgg
     481 agtcgcgggc ctgggtgaat ccggggggcct tggggaccc gggcaactag acccgcctgc
     541 gtcctccagg gcagctccgc gctcggtggc gcggttgaat cactgggtg agtcatccct
     601 tgcagggtcc cggagtttcc taccgggagg aggcggggca ggggtgtgga ctcgccgggg
     661 gccgcccacc gcgacggcaa gtgacccggg ccggggggcgg ggagtcggga ggagcggcgg
     721 gggcgggcgc cggggggcggg cagaggcgcg ggagagcgcg ccgccggccc tttatagcgc
     781 gcggggcacc ggctcccca gactgcgagc tccccgcacc cctcgcact ccctctggcc
     841 ggcccagggc gccttcagcc caacctcccc agcccacgg gcgccacgga acccgctcga
     901 tctcgccgcc aactggtaga catggagacc cctgcctggc cccgggtccc gcgccccgag
     961 accgccgtcg ctcggacgct cctgctcggc tgggtcttcg cccaggtggc cggcgcttca
    1021 ggtgagtggc accagcccct ggaagcccgg ggcgcgccac acgcaggagg gaggcgacag
    1081 tcctggctgg cagcgggctc gccctggttc ccggggcgc ccatgttgtc ccccgcgcct
```

Figure 8B

```
1141 acgggactcg gctgcgctca cccagcccgg cttgaatgaa ccgagtccgt cgggcgccgg
1201 cgggagttgc agggagggag ttggcgcccc agacccgct gccccttccg ctggagagtt
1261 ttgctcgggg tgtccgagta attggactgt tgttgcataa gcggacttttt agctcccgct
1321 ttaactctgg ggaaagggct tcccagtgag ttgcgacctt caatatgata ggacttgtgc
1381 ctgcgtctgc acgtgttggc gtgcagaggt ttggatatta tctttcatta tatgtgcatc
1441 ttcccttaat aaagagcgtc cctggtcttt tcctggccat ctttgttcta ggtttgggta
1501 gaggcaatcc aaaagggctg gattgctgct tagattggag caggtacaac gttgtgcatg
1561 ccccgtattt ctacgaggtg ttcgggacgg cgtagagact gggacctgct gcgtactggc
1621 aaagcagacc ttcataagaa ataatcctga tccaatacag ccgacggtgt gacaggccac
1681 acgtccccgt gggtctctgt ggaagtttca gtgtagcgac atttcagata aagtggaaa
1741 aagtgaagtt tggctttttt catttgtatg cagtcctaac tcttgtcaca cgtgtgggat
1801 ttatctttt ccataactta ctgaaaaccc ttcctggcgg gctgaacctg actcttcctg
1861 agctgagtcc tggactggca cactgatggc tctgggctct tcccggtcaa gttataacaa
1921 ggctttgccc atgaataatt tcaaacgaaa atgtcaagat ccttgccggt gtcctgggat
1981 tacaaggtga atcttgtcat gaagaaattc taggtctaga aaaatttga agattctttt
2041 tctcttgata attcactaat gaagcttttg tggttgaaaa ataaaaagtg aggtttatgg
2101 tgatgtcagg tgggaaggtg ttttatacat caatacattc gagtgctctg aagtgcatgt
2161 aataatagct gtttctctgt tgtttaaagg cactacaaat actgtggcag catataattt
2221 aacttggaaa tcaactaatt tcaagacaat tttggagtgg gaacccaaac ccgtcaatca
2281 agtctacact gttcaaataa ggtaagctgg gtacagaaaa agaaaattaa ggtctttgat
2341 gtttctactg tcctatgctg aacaagaatg tctttaaagc tgattactgg atgaaattat
2401 ttaacagatg acgaagaaga agggattctt ggcaattcgc tggccggtgt catactctat
2461 taggcctgca acatttccag accttaaact gatagaacat tttaattgtt ttaattgttt
2521 ttggaaatga tgggagagtt cctaagtgga gtataaactg tggagagatg aaccatcttg
2581 agtaggcact gaagtgtgct ttgggtcatg atagattaat taatctcatc taaacattga
2641 tgtcttttc cgttgctgtc tagactgtga acaatgtcta acaccttagg gaagaggtgg
2701 ggaggaatcc caatgtatac attgcccctta agcagtgttt gattcattca tctttggact
2761 ccatgaatcg aaatctggta gaatacatga tcttagtgga ggaggccaaa tgcgtgactc
2821 actgagcctg gcagagcaga aatactctgc tgtctgcacc ctctgggtct ggtgtggctc
2881 tgcttcttgg tgcttcaact ctgactggca gctgtcccca ggaggcgata attcagcatg
2941 ttcaatctaa aggttatgac ttccttgatg gttttcacca tattcttggc aagttttgg
3001 tttttgaaat gttctaggag gcttggtaga gatcttatga aatagagaat agctgctgtg
3061 gaaattattt taatgctaat tacataaaag tacaaagta gcactagcta aaacaaaagg
3121 tattttgctg ttctgttttg ttttagcttg tgccaggcct tttacagcat taggaatgca
3181 acttctagat aacgatgcat ctttttaagtg aatgttcttg ttttttcaaaa tgaacttcat
3241 gacagtagtt gccaaaccag caaggagaac ttgcatgcat acgtgcatgc atgtgtggat
3301 atgtatgggg gtgggggag agaaagatga aggaatttca taacatgaaa taatgattac
3361 agttctggtc aaacttgtca attcagattt caccaattga gaattagtaa gtaatttctc
3421 tgatacaggc ctgaagttta ccttagtaaa cactttactt ccatatggta aaaattagat
3481 tttgggagga atgcttacct cctaaatata ttcaatctaa tatttgagga cacatgggaa
3541 tatatttatg attcatctgc ttttttaaaca taagcctttg ttaactgtaa gttcttgaac
3601 tttataaggc tgctgttatt taaatgagca cagctcctga tctgcaaaca gcagagcgca
3661 gggctacagc ttgggggatg ccagccgact cagggtggtc ctgtggactg aacaatctct
3721 tgctgctgta ctggagggcc tgggagcttt tccatcagcc tcggcctgag gtgtgcactc
3781 ttctcctgcc caccccagga ataaatgaga ttcctggtta aaaaggacca gagcagtcat
3841 tttacagttg aggaaactgt tgctctgaga agtgagggat ttattcatga ctacactgat
3901 ggtgagtgcc catgtcaggt ctggaaccaa agtctaccca gtatccacac accaccatcc
3961 ctcaggtggc tctgccacag tctgatggga ggctccaaag cgggaggaag aaggaaagtc
4021 ttgcccactg catctcctca gttggccttc ctctctgcct gttttccctc cctacagtta
4081 gcatcttaag cagctgcctc tcttccctcc cgactgctct cactactgca gcctggctcc
4141 agccgcagga cactactgct gtgcagaagc ccctacttgg aactccaact gcattttca
4201 cctttgctaa cagttttcag tggtggttgg gaaatgttat tggcttaagc cttagcacaa
4261 accgtcaccg gtgatattca ttccatggaa atgttctgaa ttctaaagct gaatttacaa
4321 agcttctgga aaacaacctg caaccaaatt agtgactgaa ttttttagtt aactcaaaat
```

Figure 8C

```
4381 tccaaatcag agggttttgc aatgcctgga ggaaccttgg aggcttttaa agtgttaatg
4441 ctattaatgg cattcagagg gatttctac agaattgtcc cttcattacc tgtttataca
4501 gttttactac ttaccagggt actgtataaa tccttgtgct aaattttgct atagagtatg
4561 tggtccctgc tgtgagctgg gaggaaccaa atactgtatc tctatgttac atagaaagcc
4621 ctaggagact ttctcctgtt atctgaacaa ctatttgctg tactgataaa aaggaaacag
4681 catagtctca ttcactttt gaaatggaaa tgataaaata aaacacattt tggtcattcg
4741 ggaacaaaat accctctcta cttttatcac ataaaattaa ataaatagaa accaaaatat
4801 ttcagtatca atcttagttt gtgcacttta ggataaagaa tgtgtttacc caaatccttt
4861 tggcctggtt acttagttca gattttgaaa gaaaatatat ttgtggcttt tatgtgtgaa
4921 tttagacaat ggaatccatg tggtgcctcg ttttccctga gattatgtat taattcaacc
4981 tgtaaatgca aaccatctaa tagtcagcga gaccctatag ccctgctgct taatgggggc
5041 acacaagggc atgcagccct cgtaccaggc agactgtgtt catattaaca gcatcgtgga
5101 gaaactcatg ctgggggaca ggggagggag atgtaaatgc tcagcaggga gatctggaga
5161 ttcctggagc aggtggagtt gggacctggc cttgaacgat gggtctggct ctggcagtca
5221 gtaatgccaa agggaagagc agcataactg tcactttcca tgggacagaa gtgtgtgaat
5281 caagttgcag tgacgcttca cctatttatt attttggtca tttagaagaa tttcattgtc
5341 agtagaagtc ctttaaatca tttcccctc agtgacgtct cacaaaaaaa agatctgtct
5401 ttagcttttt agtctcagac tttattagac agatactacc tgtactctta ttctgtaatc
5461 tttgttggga tggattcaca tcttgcaaag gaagggaggc atgtagtata atggggcaaa
5521 cagacccagc tctgccactc gttagatatg tgaccttctg caagttgctt agtgcctgtg
5581 agcttcagtg tcctcatgga taagaaagat ccaacacctt cttggaagga ttatatcaaa
5641 tgaagtaaca tgagtaaagg gtccagcaga atacctggca tatagtggag tcaatgaatg
5701 attaataata ttattaatag tggtcatgag agatatatgt ataacatgtt attatgtaga
5761 ctcactatat agactctatt ctacatagaa tatagaacat tatataacaa acaactataa
5821 taagtagact atagtaaaca acctcacttt gtctcagttg cctcatcttg atggaaaact
5881 gctctttctc tcctgttacc ctgacagaga gcgtctacat tctaaaagaa agatatttaa
5941 caaaatggtt gagtacagat ccaagagtca aatagctgtc tggttcaaag tccagctgtg
6001 tgattttgag ctagtcaccc aatctcactt tgtctcagta gccttatttg taaaaacaag
6061 gcaaattaca gagccatccc ctgggttgct atgaggactc aaacatgcat cccaagtgct
6121 cggtgttgct aggtatgatg gctcacacct gtacattcag cactttggga ggccgaagca
6181 gaaggatcag cctgggcaac atagcaggac ccatctcta caaaacaatg tttaaaaaaa
6241 agcaaagtgc tcagcacagt gactgcatca ttaggattga ttgtagggct cctgatgtta
6301 gcacagaaca ccacagccag gaagcagtct atcttgttgg gtgcaaattg taacattcca
6361 tttatgtttc ttccttcttt tctttcttta gcactaagtc aggagattgg aaaagcaaat
6421 gcttttacac aacagacaca gagtgtgacc tcaccgacga gattgtgaag gatgtgaagc
6481 agacgtactt ggcacgggtc ttctcctacc cggcagggaa tgtggagagc accggttctg
6541 ctggggagcc tctgtatgag aactccccag agttcacacc ttacctggag agtaagtggc
6601 ttgggctgta ataccgttca ttcttgttag aaacgtctga acattctcgt gatcttgtgc
6661 ctttaggggc tacaaaatta aaaatattta ttctttttt ctcagaaact ggtatgtatc
6721 acagccctct tcacacattc cagatgtggt aggaggttca cagaatgtga acttttggag
6781 ctgatgacag tgtcatcaag taactttctc ccccagtctg tccccagacc ctgttactgt
6841 cctcagtaag cggctgaatg tgtgttggga gagggcgggc cagggaagcg ggtagggata
6901 ggaaatccac caaggccggg gtttagctt ttccctatat atatatcatg tatcctgatt
6961 tttctgtccc gttatcacac taaaaatccc agttgaggat ttttcccaaa cggtcataaa
7021 tcaatgagga aagtccatgg tttccctctg agcccataat tagcctaatt atgctgacct
7081 tttctaatca gttggccatg atttgagttc cgtgatgtgc cagcacctgc ccagccatct
7141 gcctgtcacc ctcgttctgg ttttggaaag gtggaatact ttcctcctca gcctttgccc
7201 ctgtaagctg gccctaggag ccagtaaaag aatgaagaga attcctgtca gtaggagat
7261 ttattctttt gccgcaactg tgctctgag ctaggcaatt tagataaatg catgtagcac
7321 attgagtaga gtgaaattag cttctcttgt aaggccagct ggttagaatg aaggtgttgt
7381 gtgagtgtta ggcccagcga gagaacag tttctcaagg taggaatggt gaaaagaagg
7441 ggtggacgga caaccaacca accatcctcc tctggtatct actttgaggg ttgaaatagg
7501 gggcctgacc ccaggtgaat gtggctgcct tcccagagcc cccatttgca agaccctcca
7561 gacccccagg tgcttctgct tgtgtctttt gtggcaccag gcaagaatgt agcagcgtca
```

Figure 8D

```
 7621 gcagcccctc tggtgactgt ggcatggttg acattcattt ccccctaat taatggcatc
 7681 ctcatgattc tcttttatat taatagttct tgagtttttt tgtaagctac ttcaaatcct
 7741 ttgttggtgc aagatagaag atattttatg tgtttgtttt gcatgtgcac acacatattt
 7801 ggcctgtgaa ttgatgtttg ttttcctgtc atttaaccaa agcacatgag ataattgagc
 7861 cattgcagag accccgtggt taaatccggc ttctcgaggt accaaggaca tttcctgggc
 7921 tttctcacag ccctacatat ttttgaacct aaaatatcgt agtttatgct accaccctgt
 7981 tcagtatagt agccactagc cacatgtggc tgttgaccac ttgaaatatg gctaatgctc
 8041 taagtataaa gtacacactg gaatttaaga agtgtagaat atctcaaaac ttttttatat
 8101 tgattacaca ttaaaatgat tatattccag atatatgcag ttgactcaag caatgcatgg
 8161 ctgagaggca ccgactccct gtgcagttga aaatccgagt ataacttgac tccccaaaaa
 8221 cttaactact aatagcctac ctatcggttg actgttgact gcagccttac caataagata
 8281 aacagtcaat taacacacat ttttcatgtt gcgtgtatta tatactgtat tcttacaata
 8341 aagtaagcta gaggaaagaa aatgttatta agaaaattat aaggaaaaga ggctgggcat
 8401 ggtggctcgt gcctgtaatc tcagaacttt gggatgctaa ggcgggtgga tcacttgagg
 8461 tcaggagttc aagaccagcc tggccaacat ggtgaaaccc catctctact aaaaatacaa
 8521 aaattagcca ggcgtggttg tgggtgcctg taatcccagc tacttgggag gctgaggcag
 8581 gagaatcact tgacccagg tggaggaggt tgcagtgaac tgagattgcg ccactgcact
 8641 ccggcctggg tgacagagcg agactctgtc taaaaagaa agggaaagaa agaaaaaaaa
 8701 gaaaagaaaa gaaaagaaag aaggaaggaa gagaaagaat tataaggaag agaaaatata
 8761 tttactattg ataaagtgga agtggatcat cataaaggtg ttcatcctcg tcatcttcat
 8821 gttgagtagg ctgaggagga ggaggaggag gaagagcagg ggccacggca ggagaaaaga
 8881 tggaggaagt aggaggcggc acacttggtg taacttttat ttaaaaaaat ttgcatacaa
 8941 gtggatccac agagttcaaa cccatgttgt tcaggggtca actgtctttg gttaaataaa
 9001 atatattatt aaaattaatt tcacctgttc cttttactt tttctaatgt gactactaga
 9061 aaacttaaaa tgacatctga ggctccattg tcttcccctt gggccagcac taccacagaa
 9121 tgtcttagga ttcagctcca ggccgccacg cctgcttctt tcagggagct ggttctatgc
 9181 acatgtttta tatgagagat aattaagttg tcaattgtga taacaaaaca ggatttgact
 9241 ttgtacagaa ttctttggtt ccaaccaagc tcatttcctt tgtttcagca aacctcggac
 9301 agccaacaat tcagagtttt gaacaggtgg gaacaaaagt gaatgtgacc gtagaagatg
 9361 aacggacttt agtcagaagg aacaacactt tcctaagcct ccgggatgtt tttggcaagg
 9421 acttaattta tacactttat tattggaaat cttcaagttc aggaaaggtg agcatttttt
 9481 aatttgtttt tatgacctgt tttaaattgt gaatacttgg ttttacaacc catttcttcc
 9541 ccaattcaaa aatagcagaa cagagttgtt gagaaggtga tggagtagaa gggggagcgc
 9601 gcactgtggg gaggggtgga caacaggcct ggtcctacct gtgactctgc actaccctgt
 9661 gactctggca gggcccccttc ggagacccag gttcctcagc caaccggctg gatcaggtca
 9721 tctctaaagg tcccgccacg ctcacatttc tccctctatt gaggatccca ggcacaaaat
 9781 ttgttttggg ttcaatgcat aatactccct tcctttttct tttactgcag atatcttcta
 9841 aggggctca ataggggttca atatgcctaa attggatctt ctcagtcttg gaaaaggcat
 9901 ttttagcagt gatcaaggga aactgattag cgaagtcact tctaatcctt cacgtgtcag
 9961 ctgtgttctt gtaggctttg cttagaacct aggtttttac ttccacagtg acttaataaa
10021 ggggaaagaa ttgactcaga gcccagatga attaagaact ctatctttt acagaaaaca
10081 gccaaaacaa acactaatga gtttttgatt gatgtggata aaggagaaaa ctactgtttc
10141 agtgttcaag cagtgattcc ctcccgaaca gttaaccgga agagtacaga cagcccggta
10201 gagtgtatgg gccaggagaa aggggaattc agaggtgagt ggctctgcca gccatttgcc
10261 tgggggtatg ggtgctgtgg gtgacttctg gaggagtagc tccaccctca gggctgggat
10321 atacttcctt ggttaaatat tcaggaaaac aaactgcctg gaggttttt gttgttattt
10381 gttttgtttg gttttgattt tgctttggta caaaaaagat tttggacatt tagaaatgtt
10441 tctgtgttga ttgtgccctt gtattagcag gtgttttctt gagcacctgt catgtgctaa
10501 gccctctgct gagcactgga tacacaaact gtgtttagga tttagcaaca agtcacagat
10561 ttccctgggc atttttcat gcttaaattc taattctggg ggtggcttct ggaccagctg
10621 caacaggaca cagtagacat tcgtgagtac ccactgtggg ctgttgccac agaggctgta
10681 gagtctaacc catcaaggga agggattgag tatatcaaat atacccacat gcatgcatgt
10741 gtgtatatgg cggacacgtg tgtgtacatg catgtgcata tgttgggagc tcaggcccat
10801 tgtgcgagga acagtcccta accggaagtg ctgtgggcct tcagactctt gcaggaagct
```

Figure 8E

```
10861 gcaagcctgt gtgtctcgat ccatgcctta cagggaaagt attctgagta ctttcagtga
10921 agaaaagagt caggggatat aaacgatggc ttacgctggg tgtggtggct cacgcctgta
10981 gtccctgcac tttgggaggc ccagacaggc aaatcacttg aggtcaggag tttgggacca
11041 gcctggccaa catggtaaaa gcccatctct actcaaaata caaaagtag ctgggtgtgg
11101 ttgcacgtgt ctgtagtccc agctactcag gaggttgagg caggagaatt gcttgaacct
11161 gggaggcgga ggctgaagtg agctgagatt ggaccactgt actccagcct gggtgacaga
11221 gcgagattcc atctcaaaaa aaaaaaaaag aaacaacgaa aaagaaatg atggcttagc
11281 tccatgtgaa gatgatattt gaacatttta aaacacttta aataaactgt tctctcctgt
11341 ttattgccac tgacaggaga ggtttctctt tacctctggt cctgcacccc tctgagccat
11401 cctacccaca gccttcagtc attgtcctaa agcctagctc taattccact gcctctcctt
11461 ttgtgcacac acacttctct gcttccctgg ccgttctcta tcttggagag gcatttcaaa
11521 cgccacttcc accagaaggc cttgctactg caccaactag ttactatctc ttcttcaccc
11581 aaatcctggt agcactttgg atctcccact tgcacttagg gttcaccttc cgttataatc
11641 attgccatca atctcagcat cgttttaggc acttctttcc agccattgtt cttacctcca
11701 actacatatc ttttctggac tgtgcattat tcagtttatt aaatgcccat taaatgtgtt
11761 tagccattgt caattactct gaaacgttca ggttttgaca aattctttcc taatgtaagt
11821 gtggtggaaa gagtgaaaga aagtcaaatt gcacaaaaat aggatggtgt aatttggggt
11881 tatgccgtca atttgtccca ctgataaatg ggatttgagc tctccaagtt gactagatgc
11941 cctttatttt tcagaaatat tctacatcat tggagctgtg gtatttgtgg tcatcatcct
12001 tgtcatcatc ctggctatat ctctacacaa gtgtagaaag gcaggagtgg ggcagagctg
12061 gaaggagaac tccccactga atgtttcata aaggaagcac tgttggagct actgcaaatg
12121 ctatattgca ctgtgaccga gaactttaa gaggatagaa tacatggaaa cgcaaatgag
12181 tatttcggag catgaagacc ctggagttca aaaaactctt gatatgacct gttattacca
12241 ttagcattct ggttttgaca tcagcattag tcactttgaa atgtaacgaa tggtactaca
12301 accaattcca agttttaatt tttaacacca tggcaccttt tgcacataac atgctttaga
12361 ttatatattc cgcactcaag gagtaaccag gtcgtccaag caaaaacaaa tgggaaaatg
12421 tcttaaaaaa tcctgggtgg acttttgaaa agcttttttt tttttttttt ttttttgagac
12481 ggagtcttgc tctgttgccc aggctggagt gcagtagcac gatctcggct cactgcaccc
12541 tccgtctctc gggttcaagc aattgtctgc ctcagcctcc cgagtagctg ggattacagg
12601 tgcgcactac cacgccaagc taattttgt atttttagt agagatgggg tttcaccatc
12661 ttggccaggc tggtcttgaa ttcctgacct caggtgatcc acccaccttg gcctcccaaa
12721 gtgctagtat tatgggcgtg aaccaccatg cccagccgaa aagcttttga ggggctgact
12781 tcaatccatg taggaaagta aaatggaagg aaattgggtg catttctagg acttttctaa
12841 catatgtcta taatatagtg tttaggttct tttttttttc aggaatacat ttggaaattc
12901 aaaacaattg gcaaactttg tattaatgtg ttaagtgcag gagacattgg tattctgggc
12961 accttcctaa tatgctttac aatctgcact ttaactgact taagtggcat taaacatttg
13021 agagctaact atatttttat aagactacta tacaaactac agagtttatg atttaaggta
13081 cttaaagctt ctatggttga cattgtatat ataatttttt aaaaaggttt tctatatggg
13141 gattttctat ttatgtaggt aatattgttc tatttgtata tattgagata atttatttaa
13201 tatactttaa ataaaggtga ctggaattgg ttactgttgt acttattcta tcttccattt
13261 attatttatg tacaatttgg tgtttgtatt agctctacta cagtaaatga ctgtaaaatt
13321 gtcagtggct tacaacaacg tatcttttc gcttataata cattttggtg actgtaggct
13381 gactgcactt cttctcaatg ttttctcatt ctaggatgca aaccaatgga gaagccccta
13441 attagatcag ggcagaggga aaaacaaaaa actggtagaa accggcaacc acagcttcaa
13501 gctttaagcc catctcctac acttctgctc tgtacgtgcc cattgtcact tctgttcaca
13561 tgctactgtc ccaagcaagt gaccaagcct gacaatactt tgtctactgg agtcactgca
13621 aggcacatga cggggcaggg atgtcgtctt acagggaaga gaaagataa tgctctctac
13681 tgcagacttg gagagatttc ttcccattgg cagtagtttg actaattgga gatgagaaaa
13741 aaagaaacat tcttgggatg attgtattga aacaaaatta ggtaaaagga caatatagga
13801 tagggagaga tataagtgga atgagatctc tagagtccat taaaagcaag ctagattgag
13861 agctc
```

Figure 8F

```
LOCUS       HUMCETP7      894 bp    DNA             PRI       01-NOV-1994
DEFINITION  Human cholesteryl ester transfer protein (CETP) gene, exons 15 and
            16.
ACCESSION   M32998 J02898
NID         g180267
KEYWORDS    cholesteryl ester transfer protein.
SEGMENT     7 of 7
SOURCE      Human DNA.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 894)
  AUTHORS   Agellon,L.B., Quinet,E.M., Gillette,T.G., Drayna,D.T., Brown,M.L.
            and Tall,A.R.
  JOURNAL   Unpublished (1990)
REFERENCE   2  (sites)
  AUTHORS   Agellon,L.B., Quinet,E.M., Gillette,T.G., Drayna,D.T., Brown,M.L.
            and Tall,A.R.
  TITLE     Organization of the human cholesteryl ester transfer protein gene
  JOURNAL   Biochemistry 29 (6), 1372-1376 (1990)
  MEDLINE   90241928
COMMENT     [2] sites for [1]; intron/exon boundaries.
            Draft entry and computer-readable sequence for [2] kindly
submitted
            by L.B.Agellon, 16-MAR-1990.
FEATURES             Location/Qualifiers
     source          1..894
                     /organism="Homo sapiens"
                     /db_xref="taxon:9606"
     gene            join(M32992:388..1656,M32993:1..3446,M32994:1..628,
                     M32995:1..399,M32996:1..409,M32997:1..1420,1..342)
                     /gene="CETP"
     CDS             join(M32992:388..505,M32992:1408..1522,M32993:432..566,
                     M32993:654..724,M32993:954..1041,M32993:2068..2137,
                     M32993:2355..2415,M32993:3023..3114,M32994:166..345,
                     M32995:238..288,M32996:128..292,M32997:375..442,
                     M32997:770..803,M32997:1285..1357,257..342,523..597)
                     /note="cholesteryl ester transferase protein precursor"
                     /codon_start=1
                     /db_xref="PID:g180269"
```

/translation="MLAATVLTLALLGNAHACSKGTSHEAGIVCRITKPALLVLNHET

AKVIQTAFQRASYPDITGEKAMMLLGQVKYGLHNIQISHLSIASSQVELVEAKSIDVS

IQNVSVVFKGTLKYGYTTAWWLGIDQSIDFEIDSAIDLQINTQLTCDSGRVRTDAPDC

YLSFHKLLLHLQGEREPGWIKQLFTNFISFTLKLVLKGQICKEINVISNIMADFVQTR

AASILSDGDIGVDISLTGDPVITASYLESHHKGHFIYKNVSEDLPLPTFSPTLLGDSR

MLYFWFSERVFHSLAKVAFQDGRLMLSLMGDEFKAVLETWGFNTNQEIFQEVVGGFPS

Figure 9A

```
QAQVTVHCLKMPKISCQNKGVVVNSSVMVKFLFPRPDQQHSVAYTFEEDIVTTVQASY

SKKKLFLSLLDFQITPKTVSNLTESSSESVQSFLQSMITAVGIPEVMSRLEVVFTALM
                    NSKGVSLFDIINPEIITRDGFLLLQMDFGFPEHLLVDFLQSLS"
     prim_transcript <1..772
                     /note="CETP mRNA and introns"
     intron          <1..256
                     /gene="CETP"
                     /note="CETP intron N"
     mat_peptide     257..342
                     /gene="CETP"
                     /note="cholesteryl ester transferase protein"
     exon            257..342
                     /gene="CETP"
                     /note="G00-119-773"
                     /number=15
     intron          343..522
                     /note="CETP intron O"
     exon            523..>597
                     /note="cholesteryl ester transferase protein precursor"
                     /number=16
     mat_peptide     523..594
                     /note="cholesteryl ester transferase protein"
     polyA_signal    756..762
BASE COUNT        178 a    262 c    256 g    198 t
ORIGIN       About 950 bp after segment 6.
        1 ggatgggttg ggagctcaag ttttggggca gaagggaatt ttttttggca gcagagtgca
       61 agccctgccg ccaggcaaac tctgctcttc ctcatcctca gaagcacttg ctcactctgc
      121 taaatcaaag tgaaacgcat gttacagaa tattggtcca aaagggtctc agcatctccc
      181 actcccagg gtgcagagcc tcgggccggc cttgctcccc aagaagggct gactggggct
      241 ctgtcccctc gcccagggct cgaggtagtg tttacagccc tcatgaacag caaaggcgtg
      301 agcctcttcg acatcatcaa ccctgagatt atcactcgag atgtgagtac aaagcccccc
      361 tcaccagccc ctgttcctgg ggagagaggc ccagacagga ttcctggggt gactgggggc
      421 tgttggggag acagacagag gggcctctac cagcttggct ccctcctggt ggcctgggag
      481 tcagcccagc tcgcccctct ctcctactgc cctccccttc agggcttcct gctgctgcag
      541 atggactttg gcttccctga gcacctgctg tgggatttcc tccagagctt gagctagaag
      601 tctccaagga ggtcgggatg gggcttgtag cagaaggcaa gcaccaggct cacagctgga
      661 accctggtgt ctcctccagc gtggtggaag ttgggttagg agtacggaga tggagattgg
      721 ctcccaactc ctccctatcc taaaggccca ctggcattaa agtgctgtat ccaagagctg
      781 cggagtcctt cttctgtggc tggcgggtag aggggggggg aagggattgt ctcaccagtg
      841 ccgtccacct cttttcagcc cttccaagca gctgccccca aaccctccaa gctt
```

Figure 9B

```
LOCUS       HUMCILA        1431 bp    mRNA            PRI       01-NOV-1994
DEFINITION  Human lipoprotein-associated coagulation inhibitor mRNA, complete
            cds.
ACCESSION   J03225
NID         g180545
KEYWORDS    lipoprotein-associated coagulation inhibitor.
SOURCE      Human placenta, cDNA to mRNA, clone lambda-P9.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 1431)
  AUTHORS   Wun,T.C., Kretzmer,K.K., Girard,T.J., Miletich,J.P. and Broze,G.J.
            Jr.
  TITLE     Cloning and characterization of a cDNA coding for the
            lipoprotein-associated coagulation inhibitor shows that it
consists
            of three tandem Kunitz-type inhibitory domains
  JOURNAL   J. Biol. Chem. 263 (13), 6001-6004 (1988)
  MEDLINE   88198127
COMMENT     Draft entry and printed copy of sequence for [1] kindly provided
by
            T.-C.Wun, 19-MAR-1988.
FEATURES             Location/Qualifiers
     source          1..1431
                     /organism="Homo sapiens"
                     /db_xref="taxon:9606"
                     /map="2q31-q32.1"
     sig_peptide     133..216
                     /gene="TFPI"
                     /note="lipoprotein-associated coagulation inhibitor
signal
                     peptide"
     CDS             133..1047
                     /gene="TFPI"
                     /note="lipoprotein-associated coagulation inhibitor
                     precursor"
                     /codon_start=1
                     /db_xref="GDB:G00-127-364"
                     /db_xref="PID:g180546"

/translation="MIYTMKKVHALWASVCLLLNLAPAPLNADSEEDEEHTIITDTEL

PPLKLMHSFCAFKADDGPCKAIMKRFFFNIFTRQCEEFIYGGCEGNQNRFESLEECKK

MCTRDNANRIIKTTLQQEKPDFCFLEEDPGICRGYITRYFYNNQTKQCERFKYGGCLG

NMNNFETLEECKNICEDGPNGFQVDNYGTQLNAVNNSLTPQSTKVPSLFEFHGPSWCL

TPADRGLCRANENRFYYNSVIGKCRPFKYSGCGGNENNFTSKQECLRACKKGFIQRIS
                     KGGLIKTKRKRKKQRVKIAYEEIFVKNM"
     gene            133..1047
                     /gene="TFPI"
     mat_peptide     217..1044
```

Figure 10A

```
                /gene="TFPI"
                /note="lipoprotein-associated coagulation inhibitor"
BASE COUNT      479 a    244 c    267 g    441 t
ORIGIN      351 bp upstream of SspI site.
       1 ggcgggtctg cttctaaaag aagaagtaga gaagataaat cctgtcttca atacctggaa
      61 ggaaaaacaa ataacctca actccgtttt gaaaaaaaca ttccaagaac tttcatcaga
     121 gattttactt agatgattta cacaatgaag aaagtacatg cactttgggc ttctgtatgc
     181 ctgctgctta atcttgcccc tgcccctctt aatgctgatt ctgaggaaga tgaagaacac
     241 acaattatca cagatacgga gttgccacca ctgaaactta tgcattcatt ttgtgcattc
     301 aaggcggatg atggcccatg taaagcaatc atgaaaagat ttttcttcaa tatttttcact
     361 cgacagtgcg aagaatttat atatggggga tgtgaaggaa atcagaatcg atttgaaagt
     421 ctggaagagt gcaaaaaaat gtgtacaaga gataatgcaa acaggattat aaagacaaca
     481 ttgcaacaag aaaagccaga tttctgcttt ttggaagaag atcctggaat atgtcgaggt
     541 tatattacca ggtatttta taacaatcag acaaaacagt gtgaacgttt caagtatggt
     601 ggatgcctgg gcaatatgaa caattttgag acactggaag aatgcaagaa catttgtgaa
     661 gatggtccga atggtttcca ggtggataat tatggaaccc agctcaatgc tgtgaataac
     721 tccctgactc cgcaatcaac caaggttccc agccttttg aatttcacgg tccctcatgg
     781 tgtctcactc cagcagacag aggattgtgt cgtgccaatg agaacagatt ctactacaat
     841 tcagtcattg ggaaatgccg cccatttaag tacagtggat gtgggggaaa tgaaaacaat
     901 tttacttcca aacaagaatg tctgagggca tgtaaaaaag gtttcatcca aagaatatca
     961 aaaggaggcc taattaaaac caaaagaaaa agaaagaagc agagagtgaa aatagcatat
    1021 gaagaaattt ttgttaaaaa tatgtgaatt tgttatagca atgtaacatt aattctacta
    1081 aatatttat atgaaatgtt tcactatgat tttctatttt tcttctaaaa tcgttttaat
    1141 taatatgttc attaaatttt ctatgcttat tgtacttgtt atcaacacgt ttgtatcaga
    1201 gttgcttttc taatcttgtt aaattgctta ttctaggtct gtaatttatt aactggctac
    1261 tgggaaatta cttattttct ggatctatct gtattttcat ttaactacaa attatcatac
    1321 taccggctac atcaaatcag tcctttgatt ccatttggtg accatctgtt tgagaatatg
    1381 atcatgtaaa tgattatctc ctttatagcc tgtaaccaga ttaagccccc c
```

Figure 10B

```
LOCUS        HUMPRC        1366 bp      mRNA         PRI        08-JAN-1995
DEFINITION   Human protein C, mRNA.
ACCESSION    K02059
NID          g190322
KEYWORDS     glycoprotein; protease; protein C; serine protease.
SOURCE       Human liver, cDNA (library of Woo) to mRNA, clones lambda-HC1026
             and lambda-HC1375.
  ORGANISM   Homo sapiens
             Eukaryotae; mitochondrial eukaryotes; Metazoa; Chordata;
             Vertebrata; Eutheria; Primates; Catarrhini; Hominidae; Homo.
REFERENCE    1  (bases 1 to 1366)
  AUTHORS    Foster,D. and Davie,E.W.
  TITLE      Characterization of a cDNA coding for human protein C
  JOURNAL    Proc. Natl. Acad. Sci. U.S.A. 81 (15), 4766-4770 (1984)
  MEDLINE    84272714
COMMENT      Protein C is a precursor to a serine protease called 'activated
             protein C' that has a strong anticoagulant activity. The amino
acid
             sequence as determined from the cDNA indicates that protein C is
             synthesized as a single-chain polypeptide containing the light
             chain and the heavy chain connected by a dipeptide of Lys-Arg.
This
             precursor peptide is then converted to the light and heavy chains
             by cleavage of two or more internal peptide bonds. The amino acid
             sequence of human protein C shows a high homology with that of the
             bovine molecule.  Two clones were sequenced in [1] and shown to
             code for human protein C. Clone lambda-HC1026 covers bp 146-1140,
             and clone lambda-HC1375 covers bp 1-1366.  The two cDNA clones had
             a poly-A tail at different positions; both poly-A sites were
             preceded by poly-A signals [1].
FEATURES             Location/Qualifiers
     source          1..1366
                     /organism="Homo sapiens"
                     /db_xref="taxon:9606"
                     /tissue_type="liver"
                     /tissue_lib="of Woo"
                     /map="2q13-q21"
     mRNA            <1..1366
                     /gene="PROC"
                     /note="G00-120-317"
     mRNA            <1..1140
                     /gene="PROC"
                     /note="G00-120-317"
     gene            1..1366
                     /gene="PROC"
     mat_peptide     <1..277
                     /gene="PROC"
                     /note="G00-120-317"
                     /product="protein C light chain"
     CDS             <1..1073
                     /gene="PROC"
                     /note="."
                     /codon_start=2
```

Figure 11A

```
                    /db_xref="GDB:G00-120-317"
                    /product="protein C"
                    /db_xref="PID:g190323"
  /translation="QGHGTCIDGIGSFSCDCRSGWEGRFCQREVSFLNCSLDNGGCTH
  YCLEEVGWRRCSCAPGYKLGDDLLQCHPAVKFPCGRPWKRMEKKRSHLKRDTEDQEDQ
  VDPRLIDGKMTRRGDSPWQVVLLDSKKKLACGAVLIHPSWVLTAAHCMDESKKLLVRL
  GEYDLRRWEKWELDLDIKEVFVHPNYSKSTTDNDIALLHLAQPATLSQTIVPICLPDS
  GLAERELNQAGQETLVTGWGYHSSREKEAKRNRTFVLNFIKIPVVPHNECSEVMSNMV
  SENMLCAGILGDRQDACEGDSGGPMVASFHGTWFLVGLVSWGEGCGLLHNYGVYTKVS
                    RYLDWIHGHIRDKEAPQKSWAP"
       mat_peptide    284..1069
                    /gene="PROC"
                    /note="G00-120-317"
                    /product="protein C heavy chain"
       mat_peptide    320..1069
                    /gene="PROC"
                    /note="G00-120-317"
                    /product="protein C activated heavy chain"
  BASE COUNT       302 a    388 c    425 g    251 t
  ORIGIN      207 bp upstream of PstI site; chromosome 2q14-q21.
        1 ccaagggcac ggcacgtgca tcgacggcat cggcagcttc agctgcgact gccgcagcgg
       61 ctgggagggc cgcttctgcc agcgcgaggt gagcttcctc aattgctctc tggacaacgg
      121 cggctgcacg cattactgcc tagaggaggt gggctggcgg cgctgtagct gtgcgcctgg
      181 ctacaagctg ggggacgacc tcctgcagtg tcacccgca gtgaagttcc cttgtgggag
      241 gccctggaag cggatgagaa agaagcgcag tcacctgaaa cgagacacag aagaccaaga
      301 agaccaagta gatccgcggc tcattgatgg gaagatgacc aggcggggag acagcccctg
      361 gcaggtggtc ctgctggact caaagaagaa gctggcctgc ggggcagtgc tcatccaccc
      421 ctcctgggtg ctgacagcgg cccactgcat ggacgagtcc aagaagctcc ttgtcaggct
      481 tggagagtat gacctgcggc gctgggagaa gtgggagctg gacctggaca tcaaggaggt
      541 cttcgtccac cccaactaca gcaagagcac caccgacaat gacatcgcac tgctgcacct
      601 ggcccagccc gccaccctct cgcagaccat agtgcccatc tgcctcccgg acagcggcct
      661 tgcagagcgc gagctcaatc aggccggcca ggagaccctc gtgacgggct ggggctacca
      721 cagcagccga gagaaggagg ccaagagaaa ccgcaccttc gtcctcaact tcatcaagat
      781 tcccgtggtc ccgcacaatg agtgcagcga ggtcatgagc aacatggtgt ctgagaacat
      841 gctgtgtgcg ggcatcctcg ggaccggca ggatgcctgc gagggcgaca gtgggggggcc
      901 catggtcgcc tccttccacg gcacctggtt cctggtgggc ctggtgagct ggggtgaggg
      961 ctgtgggctc cttcacaact acggcgttta caccaaagtc agccgctacc tcgactggat
     1021 ccatgggcac atcagagaca aggaagcccc ccagaagagc tgggcacctt agcgaccctc
     1081 cctgcagggc tgggcttttg catggcaatg gatgggacat taagggaca tgtaacaagc
     1141 acaccggcct gctgttctgt ccttccatcc ctctttggg ctcttctgga gggaagtaac
     1201 atttactgag cacctgttgt atgtcacatg ccttatgaat agaatcttaa ctcctagagc
     1261 aactctgtcg ggtggggagg agcagatcca agttttgcgg ggtctaaagc tgtgtgtgtt
     1321 gagggggata ctctgtttat gaaaagaat aaaaaacaca accacg
```

Figure 11B

```
LOCUS       HUMLDLR02       144 bp    DNA             PRI       30-NOV-1994
DEFINITION  Human low density lipoprotein receptor gene, exon 2.
ACCESSION   L00336 K02573
NID         g187078
KEYWORDS    low density lipoprotein receptor-1; repeat region.
SEGMENT     2 of 18
SOURCE      Human DNA [2] and fetal adrenal gland, cDNA to mRNA, clone pLDLR-2
            [1].
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 16 to 138)
  AUTHORS   Yamamoto,T., Davis,C.G., Brown,M.S., Schneider,W.J., Casey,M.L.,
            Goldstein,J.L. and Russell,D.W.
  TITLE     The human LDL receptor: a cysteine-rich protein with multiple Alu
            sequences in its mRNA
  JOURNAL   Cell 39 (1), 27-38 (1984)
  MEDLINE   85024898
REFERENCE   2  (bases 1 to 23; 132 to 144)
  AUTHORS   Sudhof,T.C., Goldstein,J.L., Brown,M.S. and Russell,D.W.
  TITLE     The LDL receptor gene: a mosaic of exons shared with different
            proteins
  JOURNAL   Science 228 (4701), 815-822 (1985)
  MEDLINE   85218750
COMMENT     Draft entry and computer-readable sequence for [1] kindly provided
            by D.Russell, 01-MAR-1985.
FEATURES             Location/Qualifiers
     source          1..144
                     /organism="Homo sapiens"
                     /db_xref="taxon:9606"
                     /map="19p13.3"
     intron          <1..15
                     /gene="LDLR"
                     /note="LDL intron A"
     exon            16..138
                     /gene="LDLR"
                     /note="G00-119-362"
                     /number=2
     intron          139..>144
                     /gene="LDLR"
                     /note="LDL intron B"
BASE COUNT       33 a     33 c     46 g     32 t
ORIGIN      Chromosome 19p13.2-p13.1; about 10 kb after segment 1.
        1 tttcctctct ctcagtgggc gacagatgtg aaagaaacga gttccagtgc caagacggga
       61 aatgcatctc ctacaagtgg gtctgcgatg gcagcgctga gtgccaggat ggctctgatg
      121 agtcccagga cgtgctgt gagt
```

Figure 12

```
LOCUS       HUMLDLR04     402 bp    DNA            PRI       30-NOV-1994
DEFINITION  Human low density lipoprotein receptor gene, exon 4.
ACCESSION   L00338 K02573
NID         g187080
KEYWORDS    low density lipoprotein receptor-1; repeat region.
SEGMENT     4 of 18
SOURCE      Human DNA [2] and fetal adrenal gland, cDNA to mRNA, clone pLDLR-2
            [1].
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 16 to 396)
  AUTHORS   Yamamoto,T., Davis,C.G., Brown,M.S., Schneider,W.J., Casey,M.L.,
            Goldstein,J.L. and Russell,D.W.
  TITLE     The human LDL receptor: a cysteine-rich protein with multiple Alu
            sequences in its mRNA
  JOURNAL   Cell 39 (1), 27-38 (1984)
  MEDLINE   85024898
REFERENCE   2  (bases 1 to 23; 389 to 402)
  AUTHORS   Sudhof,T.C., Goldstein,J.L., Brown,M.S. and Russell,D.W.
  TITLE     The LDL receptor gene: a mosaic of exons shared with different
            proteins
  JOURNAL   Science 228 (4701), 815-822 (1985)
  MEDLINE   85218750
COMMENT     Draft entry and computer-readable sequence for [1] kindly provided
            by D.Russell, 01-MAR-1985.
FEATURES             Location/Qualifiers
     source          1..402
                     /organism="Homo sapiens"
                     /db_xref="taxon:9606"
                     /map="19p13.3"
     intron          <1..15
                     /gene="LDLR"
                     /note="LDL intron C"
     exon            16..396
                     /gene="LDLR"
                     /note="G00-119-362"
                     /number=4
     intron          397..>402
                     /gene="LDLR"
                     /note="LDL intron D"
BASE COUNT       73 a    131 c    120 g     78 t
ORIGIN      Chromosome 19p13.2-p13.1; about 2.4 kb after segment 3.
        1 catccatccc tgcagccccc aagacgtgct cccaggacga gtttcgctgc cacgatggga
       61 agtgcatctc tcggcagttc gtctgtgact cagaccggga ctgcttggac ggctcagacg
      121 aggcctcctg cccggtgctc acctgtggtc ccgccagctt ccagtgcaac agctccacct
      181 gcatccccca gctgtgggcc tgcgacaacg accccgactg cgaagatggc tcggatgagt
      241 ggccgcagcg ctgtaggggt ctttacgtgt tccaagggga cagtagcccc tgctcggcct
      301 tcgagttcca ctgcctaagt ggcgagtgca tccactccag ctggcgctgt gatggtggcc
      361 ccgactgcaa ggacaaatct gacgaggaaa actgcggtat gg
```

Figure 13

```
LOCUS       HUMLDLR09      193 bp    DNA             PRI       30-NOV-1994
DEFINITION  Human low density lipoprotein receptor gene, exon 9.
ACCESSION   L00343 K02573
NID         g187085
KEYWORDS    low density lipoprotein receptor-1; repeat region.
SEGMENT     9 of 18
SOURCE      Human DNA [2] and fetal adrenal gland, cDNA to mRNA, clone pLDLR-2
            [1].
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 16 to 187)
  AUTHORS   Yamamoto,T., Davis,C.G., Brown,M.S., Schneider,W.J., Casey,M.L.,
            Goldstein,J.L. and Russell,D.W.
  TITLE     The human LDL receptor: a cysteine-rich protein with multiple Alu
            sequences in its mRNA
  JOURNAL   Cell 39 (1), 27-38 (1984)
  MEDLINE   85024898
REFERENCE   2  (bases 1 to 23; 180 to 193)
  AUTHORS   Sudhof,T.C., Goldstein,J.L., Brown,M.S. and Russell,D.W.
  TITLE     The LDL receptor gene: a mosaic of exons shared with different
            proteins
  JOURNAL   Science 228 (4701), 815-822 (1985)
  MEDLINE   85218750
COMMENT     Draft entry and computer-readable sequence for [1] kindly provided
            by D.Russell, 01-MAR-1985.
FEATURES             Location/Qualifiers
     source          1..193
                     /organism="Homo sapiens"
                     /db_xref="taxon:9606"
                     /map="19p13.3"
     intron          <1..15
                     /gene="LDLR"
                     /note="LDL intron H"
     exon            16..187
                     /gene="LDLR"
                     /note="G00-119-362"
                     /number=9
     intron          188..>193
                     /gene="LDLR"
                     /note="LDL intron I"
BASE COUNT       44 a     64 c     52 g     33 t
ORIGIN      Chromosome 19p13.2-p13.1; about 1.2 kb after segment 8.
        1 tccccggacc cccaggctcc atcgcctacc tcttcttcac caaccggcac gaggtcagga
       61 agatgacgct ggaccggagc gagtacacca gcctcatccc caacctgagg aacgtggtcg
      121 ctctggacac ggaggtggcc agcaatagaa tctactggtc tgacctgtcc cagagaatga
      181 tctgcaggtg agc
```

Figure 14

```
LOCUS       HUMLDLR10      249 bp    DNA             PRI       30-NOV-1994
DEFINITION  Human low density lipoprotein receptor gene, exon 10.
ACCESSION   L00344 K02573
NID         g187086
KEYWORDS    low density lipoprotein receptor-1; repeat region.
SEGMENT     10 of 18
SOURCE      Human DNA [2] and fetal adrenal gland, cDNA to mRNA, clone pLDLR-2
            [1].
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 16 to 243)
  AUTHORS   Yamamoto,T., Davis,C.G., Brown,M.S., Schneider,W.J., Casey,M.L.,
            Goldstein,J.L. and Russell,D.W.
  TITLE     The human LDL receptor: a cysteine-rich protein with multiple Alu
            sequences in its mRNA
  JOURNAL   Cell 39 (1), 27-38 (1984)
  MEDLINE   85024898
REFERENCE   2  (bases 1 to 23; 236 to 249)
  AUTHORS   Sudhof,T.C., Goldstein,J.L., Brown,M.S. and Russell,D.W.
  TITLE     The LDL receptor gene: a mosaic of exons shared with different
            proteins
  JOURNAL   Science 228 (4701), 815-822 (1985)
  MEDLINE   85218750
COMMENT     Draft entry and computer-readable sequence for [1] kindly provided
            by D.Russell, 01-MAR-1985.
FEATURES             Location/Qualifiers
     source          1..249
                     /organism="Homo sapiens"
                     /db_xref="taxon:9606"
                     /map="19p13.3"
     intron          <1..15
                     /gene="LDLR"
                     /note="LDL intron I"
     exon            16..243
                     /gene="LDLR"
                     /note="G00-119-362"
                     /number=10
     intron          244..>249
                     /gene="LDLR"
                     /note="LDL intron J"
BASE COUNT       51 a     77 c     71 g     50 t
ORIGIN      Chromosome 19p13.2-p13.1; about 900 bp after segment 9.
        1 ctcctcctgc ctcagcaccc agcttgacag agcccacggc gtctcttcct atgacaccgt
       61 catcagcagg gacatccagg cccccgacgg gctggctgtg gactggatcc acagcaacat
      121 ctactggacc gactctgtcc tgggcactgt ctctgttgcg gataccaagg gcgtgaagag
      181 gaaaacgtta ttcagggaga acggctccaa gccaagggcc atcgtggtgg atcctgttca
      241 tgggtgcgt
```

Figure 15

```
LOCUS       HUMLDLR11     140 bp    DNA              PRI      30-NOV-1994
DEFINITION  Human low density lipoprotein receptor gene, exon 11.
ACCESSION   L00345 K02573
NID         g187087
KEYWORDS    low density lipoprotein receptor-1; repeat region.
SEGMENT     11 of 18
SOURCE      Human DNA [2] and fetal adrenal gland, cDNA to mRNA, clone pLDLR-2
            [1].
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 6 to 134)
  AUTHORS   Yamamoto,T., Davis,C.G., Brown,M.S., Schneider,W.J., Casey,M.L.,
            Goldstein,J.L. and Russell,D.W.
  TITLE     The human LDL receptor: a cysteine-rich protein with multiple Alu
            sequences in its mRNA
  JOURNAL   Cell 39 (1), 27-38 (1984)
  MEDLINE   85024898
REFERENCE   2  (bases 1 to 22; 128 to 140)
  AUTHORS   Sudhof,T.C., Goldstein,J.L., Brown,M.S. and Russell,D.W.
  TITLE     The LDL receptor gene: a mosaic of exons shared with different
            proteins
  JOURNAL   Science 228 (4701), 815-822 (1985)
  MEDLINE   85218750
COMMENT     Draft entry and computer-readable sequence for [1] kindly provided
            by D.Russell, 01-MAR-1985.
FEATURES             Location/Qualifiers
     source          1..140
                     /organism="Homo sapiens"
                     /db_xref="taxon:9606"
                     /map="19p13.3"
     intron          <1..15
                     /gene="LDLR"
                     /note="LDL intron J"
     exon            16..134
                     /gene="LDLR"
                     /note="G00-119-362"
                     /number=11
     intron          135..>140
                     /gene="LDLR"
                     /note="LDL intron K"
BASE COUNT       34 a     38 c     37 g     31 t
ORIGIN      Chromosome 19p13.2-p13.1; about 2.6 kb after segment 10.
        1 ctgtcctccc accagcttca tgtactggac tgactgggga actcccgcca agatcaagaa
       61 aggggggcctg aatggtgtgg acatctactc gctggtgact gaaaacattc agtggcccaa
      121 tggcatcacc ctaggtatgt
```

Figure 16

```
LOCUS       HUMLDLR13      163 bp    DNA             PRI       30-NOV-1994
DEFINITION  Human low density lipoprotein receptor gene, exon 13.
ACCESSION   L00347 K02573
NID         g187089
KEYWORDS    low density lipoprotein receptor-1; repeat region.
SEGMENT     13 of 18
SOURCE      Human DNA [2] and fetal adrenal gland, cDNA to mRNA, clone pLDLR-2
            [1].
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 16 to 157)
  AUTHORS   Yamamoto,T., Davis,C.G., Brown,M.S., Schneider,W.J., Casey,M.L.,
            Goldstein,J.L. and Russell,D.W.
  TITLE     The human LDL receptor: a cysteine-rich protein with multiple Alu
            sequences in its mRNA
  JOURNAL   Cell 39 (1), 27-38 (1984)
  MEDLINE   85024898
REFERENCE   2  (bases 1 to 24; 151 to 163)
  AUTHORS   Sudhof,T.C., Goldstein,J.L., Brown,M.S. and Russell,D.W.
  TITLE     The LDL receptor gene: a mosaic of exons shared with different
            proteins
  JOURNAL   Science 228 (4701), 815-822 (1985)
  MEDLINE   85218750
COMMENT     Draft entry and computer-readable sequence for [1] kindly provided
            by D.Russell, 01-MAR-1985.
FEATURES             Location/Qualifiers
     source          1..163
                     /organism="Homo sapiens"
                     /db_xref="taxon:9606"
                     /map="19p13.3"
     intron          <1..15
                     /gene="LDLR"
                     /note="LDL intron L"
     exon            16..157
                     /gene="LDLR"
                     /note="G00-119-362"
                     /number=13
     intron          158..>163
                     /gene="LDLR"
                     /note="LDL intron M"
BASE COUNT       43 a    45 c    34 g    41 t
ORIGIN      Chromosome 19p13.2-p13.1; about 3 kb after segment 12.
        1 ttgctgcctg tttaggacaa agtattttgg acagatatca tcaacgaagc cattttcagt
       61 gccaaccgcc tcacaggttc cgatgtcaac ttgttggctg aaaacctact gtccccagag
      121 gatatggtcc tcttccacaa cctcacccag ccaagaggta agg
```

Figure 17

```
LOCUS       HUMLDLR15      192 bp    DNA              PRI       30-NOV-1994
DEFINITION  Human low density lipoprotein receptor gene, exon 15.
ACCESSION   L00349 K02573
NID         g187091
KEYWORDS    low density lipoprotein receptor-1; repeat region.
SEGMENT     15 of 18
SOURCE      Human DNA [2] and fetal adrenal gland, cDNA to mRNA, clone pLDLR-2
            [1].
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 16 to 186)
  AUTHORS   Yamamoto,T., Davis,C.G., Brown,M.S., Schneider,W.J., Casey,M.L.,
            Goldstein,J.L. and Russell,D.W.
  TITLE     The human LDL receptor: a cysteine-rich protein with multiple Alu
            sequences in its mRNA
  JOURNAL   Cell 39 (1), 27-38 (1984)
  MEDLINE   85024898
REFERENCE   2  (bases 1 to 23; 179 to 192)
  AUTHORS   Sudhof,T.C., Goldstein,J.L., Brown,M.S. and Russell,D.W.
  TITLE     The LDL receptor gene: a mosaic of exons shared with different
            proteins
  JOURNAL   Science 228 (4701), 815-822 (1985)
  MEDLINE   85218750
COMMENT     Draft entry and computer-readable sequence for [1] kindly provided
            by D.Russell, 01-MAR-1985.
FEATURES             Location/Qualifiers
     source          1..192
                     /organism="Homo sapiens"
                     /db_xref="taxon:9606"
                     /map="19p13.3"
     intron          <1..15
                     /gene="LDLR"
                     /note="LDL intron N"
     exon            16..186
                     /gene="LDLR"
                     /note="G00-119-362"
                     /number=15
     intron          187..>192
                     /gene="LDLR"
                     /note="LDL intron O"
BASE COUNT       46 a     64 c     49 g     33 t
ORIGIN      Chromosome 19p13.2-p13.1; about 2.8 kb after segment 14.
        1 tatttattct ttcagaggct gaggctgcag tggccaccca ggagacatcc accgtcaggc
       61 taaaggtcag ctccacagcc gtaaggacac agcacacaac cacccggcct gttcccgaca
      121 cctcccggct gcctggggcc acccctgggc tcaccacggt ggagatagtg acaatgtctc
      181 accaaggtaa ag
```

Figure 18

```
LOCUS       HUMLDLR17     179 bp    DNA              PRI       30-NOV-1994
DEFINITION  Human low density lipoprotein receptor gene, exon 17.
ACCESSION   L00351 K02573
NID         g187093
KEYWORDS    low density lipoprotein receptor-1; repeat region.
SEGMENT     17 of 18
SOURCE      Human DNA [3] and fetal adrenal gland, cDNA to mRNA, clone pLDLR-2
            [1].
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 16 to 173)
  AUTHORS   Yamamoto,T., Davis,C.G., Brown,M.S., Schneider,W.J., Casey,M.L.,
            Goldstein,J.L. and Russell,D.W.
  TITLE     The human LDL receptor: a cysteine-rich protein with multiple Alu
            sequences in its mRNA
  JOURNAL   Cell 39 (1), 27-38 (1984)
  MEDLINE   85024898
REFERENCE   2  (bases 57 to 101)
  AUTHORS   Lehrman,M.A., Goldstein,J.L., Brown,M.S., Russell,D.W. and
            Schneider,W.J.
  TITLE     Internalization-defective LDL receptors produced by genes with
            nonsense and frameshift mutations that truncate the cytoplasmic
            domain
  JOURNAL   Cell 41 (3), 735-743 (1985)
  MEDLINE   85228224
REFERENCE   3  (bases 1 to 23; 164 to 179)
  AUTHORS   Sudhof,T.C., Goldstein,J.L., Brown,M.S. and Russell,D.W.
  TITLE     The LDL receptor gene: a mosaic of exons shared with different
            proteins
  JOURNAL   Science 228 (4701), 815-822 (1985)
  MEDLINE   85218750
COMMENT     Draft entry and computer-readable sequence for [1] kindly provided
            by D.Russell, 01-MAR-1985.
FEATURES             Location/Qualifiers
     source          1..179
                     /organism="Homo sapiens"
                     /db_xref="taxon:9606"
                     /map="19p13.3"
     intron          <1..15
                     /gene="LDLR"
                     /note="LDL intron P"
     exon            16..173
                     /gene="LDLR"
                     /note="G00-119-362"
                     /number=17
     mutation        76..77
                     /gene="LDLR"
                     /note="ac in wt; aagaac in internalization-defective
                     familial hypercholesterolemia [2]"
     intron          174..>179
                     /gene="LDLR"
                     /note="LDL intron Q"
```

Figure 19A

```
BASE COUNT        42 a     56 c     39 g     42 t
ORIGIN      Chromosome 19p13.2-p13.1; about 1.4 kb after segment 16.
       1 tgcctctccc tacagtgctc ctcgtcttcc tttgcctggg ggtcttcctt ctatggaaga
      61 actggcggct taagaacatc aacagcatca actttgacaa ccccgtctat cagaagacca
     121 cagaggatga ggtccacatt tgccacaacc aggacggcta cagctacccc tcggtgagt
```

Figure 19B

```
LOCUS       HUMLDLR01     769 bp    DNA             PRI       30-NOV-1994
DEFINITION  Human low density lipoprotein receptor gene, exon 1.
ACCESSION   L29401 K02573 M10664 N00033
NID         g460288
KEYWORDS    low density lipoprotein receptor-1; repeat region.
SEGMENT     1 of 18
SOURCE      Human DNA [2] and fetal adrenal gland, cDNA to mRNA, clone pLDLR-2
            [1].
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (sites)
  AUTHORS   Yamamoto,T., Davis,C.G., Brown,M.S., Schneider,W.J., Casey,M.L.,
            Goldstein,J.L. and Russell,D.W.
  TITLE     The human LDL receptor: a cysteine-rich protein with multiple Alu
            sequences in its mRNA
  JOURNAL   Cell 39 (1), 27-38 (1984)
  MEDLINE   85024898
REFERENCE   2  (bases 1 to 769)
  AUTHORS   Sudhof,T.C., Goldstein,J.L., Brown,M.S. and Russell,D.W.
  TITLE     The LDL receptor gene: a mosaic of exons shared with different
            proteins
  JOURNAL   Science 228 (4701), 815-822 (1985)
  MEDLINE   85218750
COMMENT     Bases 1-769 from Science 228, 815-822 (1985)
            Bases 675-754 from Cell 39, 27-38 (1984)
            Draft entry and computer-readable sequence for [1] kindly provided
            by D.Russell, 01-MAR-1985.
FEATURES             Location/Qualifiers
     source          1..769
                     /organism="Homo sapiens"
                     /db_xref="taxon:9606"
                     /map="19p13.3"
     exon            595..754
                     /gene="LDLR"
                     /note="low density lipoprotein receptor; G00-119-362"
                     /number=1
     sig_peptide     688..750
                     /gene="LDLR"
                     /note="low density lipoprotein receptor signal pept"
     intron          755..>769
                     /gene="LDLR"
                     /note="LDL intron A"
BASE COUNT      220 a    169 c    194 g    186 t
ORIGIN      Chromosome 19p13.2-p13.1; 1 bp upstream of BamHI site.
        1 ggatcccaca aaacaaaaaa tatttttttg gctgtacttt tgtgaagatt ttatttaaat
       61 tcctgattga tcagtgtcta ttaggtgatt tggaataaca atgtaaaaac aatatacaac
      121 gaaaggaagc taaaaatcta tacacaattc ctagaaagga aaaggcaaat atagaaagtg
      181 gcggaagttc ccaacatttt tagtgttttc cttttgaggc agagaggaca atggcattag
      241 gctattggag gatcttgaaa ggctgttgtt atccttctgt ggacaacaac agcaaaatgt
      301 taacagttaa acatcgagaa atttcaggag gatctttcag aagatgcgtt tccaattttg
      361 aggggcgtc  agctcttcac cggagaccca aatacaacaa atcaagtcgc ctgccctggc
      421 gacacttcg  aaggactgga gtgggaatca gagcttcacg ggttaaaagc cgatgtcaca
      481 tcggccgttc gaaactcctc ctcttgcagt gaggtgaaga catttgaaaa tcaccccact
```

Figure 20A

```
541 gcaaactcct cccctgcta gaaacctcac attgaaatgc tgtaaatgac gtgggccccg
601 agtgcaatcg cgggaagcca gggtttccag ctaggacaca gcaggtcgtg atccgggtcg
661 ggacactgcc tggcagaggc tgcgagcatg gggccctggg gctggaaatt gcgctggacc
721 gtcgccttgc tcctcgccgc ggcggggact gcaggtaagg cttgctcca
```

Figure 20B

```
LOCUS       HUMF511      279 bp    DNA              PRI       10-NOV-1994
DEFINITION  Human coagulation factor V gene, exon 11.
ACCESSION   L32765 J05368
NID         g488094
KEYWORDS    coagulation factor V; factor V.
SEGMENT     11 of 25
SOURCE      Homo sapiens DNA.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 279)
  AUTHORS   Kane,W.H. and Davie,E.W.
  TITLE     Cloning of a cDNA coding for human factor V, a blood coagulation
            factor homologous to factor VIII and ceruloplasmin
  JOURNAL   Proc. Natl. Acad. Sci. U.S.A. 83 (18), 6800-6804 (1986)
  MEDLINE   86313665
REFERENCE   2  (bases 1 to 279)
  AUTHORS   Kane,W.H., Ichinose,A., Hagen,F.S. and Davie,E.W.
  TITLE     Cloning of cDNAs coding for the heavy chain region and connecting
            region of human factor V, a blood coagulation factor with four
            types of internal repeats
  JOURNAL   Biochemistry 26 (20), 6508-6514 (1987)
  MEDLINE   88107560
REFERENCE   3  (bases 1 to 279)
  AUTHORS   Jenny,R.J., Pittman,D.D., Toole,J.J., Kriz,R.W., Aldape,R.A.,
            Hewick,R.M., Kaufman,R.J. and Mann,K.G.
  TITLE     Complete cDNA and derived amino acid sequence of human factor V
  JOURNAL   Proc. Natl. Acad. Sci. U.S.A. 84 (14), 4846-4850 (1987)
  MEDLINE   87260886
REFERENCE   4  (bases 1 to 279)
  AUTHORS   Cripe,L.D., Moore,K.D. and Kane,W.H.
  TITLE     Structure of the gene for human coagulation factor V
  JOURNAL   Biochemistry 31 (15), 3777-3785 (1992)
  MEDLINE   92232668
REFERENCE   5  (bases 1 to 279)
  AUTHORS   Shen,N.L., Fan,S.T., Pyati,J., Graff,R., LaPolla,R.J. and
            Edgington,T.S.
  TITLE     The serine protease cofactor factor V is synthesized by
lymphocytes
  JOURNAL   J. Immunol. 150 (7), 2992-3001 (1993)
  MEDLINE   93203619
FEATURES             Location/Qualifiers
     source          1..279
                     /organism="Homo sapiens"
                     /db_xref="taxon:9606"
                     /tissue_type="placenta"
                     /cell_type="fibroblast"
                     /map="1q21-q25"
     intron          order(L32764:277..>319,<1..74)
                     /gene="F5"
                     /note="3.1 kb gap; G00-119-896"
                     /number=10
     exon            75..225
```

Figure 21A

```
                /gene="F5"
                /note="G00-119-896"
                /number=11
BASE COUNT        73 a     52 c     61 g     93 t
ORIGIN
      1 tctgagttct ctattctgtt ccattggtct atgcgtctgt tcttgtacca gtactatact
     61 gttttgtcct ccagagggca gcagacatcg aacagcaggc tgtgtttgct gtgtttgatg
    121 agaacaaaag ctggtacctt gaggacaaca tcaacaagtt ttgtgaaaat cctgatgagg
    181 tgaaacgtga tgaccccaag ttttatgaat caaacatcat gagcagtaag tcagagtact
    241 atttttgttc atcagttttt cattcctgtg gttgaaata
```

Figure 21B

```
LOCUS       HUMHMGCOA     2904 bp    mRNA            PRI       08-NOV-1994
DEFINITION  Human 3-hydroxy-3-methylglutaryl coenzyme A reductase mRNA,
            complete cds.
ACCESSION   M11058
NID         g184243
KEYWORDS    3-hydroxy-3-methylglutaryl coenzyme A reductase; glycoprotein.
SOURCE      Human fetal adrenal gland, cDNA to mRNA, library of T.Maniatis,
            clone pHRed-102.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 2904)
  AUTHORS   Luskey,K.L. and Stevens,B.
  TITLE     Human 3-hydroxy-3-methylglutaryl coenzyme A reductase. Conserved
            domains responsible for catalytic activity and sterol-regulated
            degradation
  JOURNAL   J. Biol. Chem. 260 (18), 10271-10277 (1985)
  MEDLINE   85261451
COMMENT     Draft entry and sequence in computer readable form for [1] kindly
            provided by K.L.Luskey, 16-JAN-1986.
            HMG-CoA reductase is the rate-limiting enzyme for cholesterol
            synthesis and is regulated via a negative feedback mechanism
            mediated by sterols and non-sterol metabolites derived from
            mevalonate, the product of the reaction catalyzed by reductase.
            Normally in mammalian cells this enzyme is suppressed by
            cholesterol derived from the internalization and degradation of
low
            density lipoprotein (LDL) via the LDL receptor.  Competitive
            inhibitors of the reductase induce the expression of LDL receptors
            in the liver, which in turn increases the catabolism of plasma LDL
            and lowers the plasma concentration of cholesterol, an important
            determinant of atherosclerosis.
            The sequence coding for the highly conserved membrane bound region
            of the protein is located at positions 51-1067, that coding for
the
            linker part of the protein at positions 1068-1397 and for the
            strongly conserved water-soluble catalytic part at positions
            1398-2714.
FEATURES             Location/Qualifiers
     source          1..2904
                     /organism="Homo sapiens"
                     /db_xref="taxon:9606"
                     /map="5q13.3-q14"
     mRNA            <1..>2904
                     /note="HMG CoA mRNA"
     gene            51..2717
                     /gene="HMGCR"
     CDS             51..2717
                     /gene="HMGCR"
                     /note="3-hydroxy-3-methylglutaryl coenzyme A reductase"
                     /codon_start=1
                     /db_xref="GDB:G00-119-312"
                     /db_xref="PID:g306865"
```

Figure 22A

```
/translation="MLSRLFRMHGLFVASHPWEVIVGTVTLTICMMSMNMFTGNNKIC
GWNYECPKFEEDVLSSDIIILTITRCIAILYIYFQFQNLRQLGSKYILGIAGLFTIFS
SFVFSTVVIHFLDKELTGLNEALPFFLLIDLSRASTLAKFALSSNSQDEVRENIARG
MAILGPTFTLDALVECLVIGVGTMSGVRQLEIMCCFGCMSVLANYFVFMTFFPACVSL
VLELSRESREGRPIWQLSHFARVLEEEENKPNPVTQRVKMIMSLGLVLVHAHSRWIAD
PSPQNSTADTSKVSLGLDENVSKRIEPSVSLWQFYLSKMISMDIEQVITLSLALLLAV
KYIFFEQTETESTLSLKNPITSPVVTQKKVPDNCCRREPMLVRNNQKCDSVEEETGIN
RERKVEVIKPLVAETDTPNRATFVVGNSSLLDTSSVLVTQEPEIELPREPRPNEECLQ
ILGNAEKGAKFLSDAEIIQLVNAKHIPAYKLETLMETHERGVSIRRQLLSKKLSEPSS
LQYLPYRDYNYSLVMGACCENVIGYMPIPVGVAGPLCLDEKEFQVPMATTEGCLVAST
NRGCRAIGLGGGASSRVLADGMTRGPVVRLPRACDSAEVKAWLETSEGFAVIKEAFDS
TSRFARLQKLHTSIAGRNLYIRFQSRSGDAMGMNMISKGTEKALSKLHEYFPEMQILA
VSGNYCTDKKPAAINWIEGRGKSVVCEAVIPAKVVREVLKTTTEAMIEVNINKNLVGS
AMAGSIGGYNAHAANIVTAIYIACGQDAAQNVGSSNCITLMEASGPTNEDLYISCTMP
SIEIGTVGGGTNLLPQQACLQMLGVQGACKDNPGENARQLARIVCGTVMAGELSLMAA
            LAAGHLVKSHMIHNRSKINLQDLQGACTKKTA"
BASE COUNT      822 a     597 c     678 g     807 t
ORIGIN      27 bp upstream of BamHI site; chromosome 5q13.3-q14.
        1 ttcggtggcc tctagtgaga tctggaggat ccaaggattc tgtagctaca atgttgtcaa
       61 gacttttcg aatgcatggc ctctttgtgg cctcccatcc ctgggaagtc atagtgggga
      121 cagtgacact gaccatctgc atgatgtcca tgaacatgtt tactggtaac aataagatct
      181 gtggttggaa ttatgaatgt ccaaagtttg aagaggatgt tttgagcagt gacattataa
      241 ttctgacaat aacacgatgc atagccatcc tgtatattta cttccagttc cagaatttac
      301 gtcaacttgg atcaaaatat attttgggta ttgctggcct tttcacaatt ttctcaagtt
      361 ttgtattcag tacagttgtc attcacttct agacaaaga attgacaggc ttgaatgaag
      421 ctttgccctt tttcctactt ttgattgacc tttccagagc aagcacatta gcaaagtttg
      481 ccctcagttc caactcacag gatgaagtaa gggaaaatat tgctcgtgga atggcaattt
      541 taggtcctac gtttaccctc gatgctcttg ttgaatgtct tgtgattgga gttggtacca
      601 tgtcaggggt acgtcagctt gaaattatgt gctgctttgg ctgcatgtca gttcttgcca
      661 actacttcgt gttcatgact ttcttcccag cttgtgtgtc cttggtatta gagctttctc
      721 gggaaagccg cgaggtcgt ccaatttggc agctcagcca ttttgcccga gttttagaag
      781 aagaagaaaa taagccgaat cctgtaactc agagggtcaa gatgattatg tctctaggct
      841 tggttcttgt tcatgctcac agtcgctgga tagctgatcc ttctcctcaa aacagtacag
      901 cagatacttc taaggtttca ttaggactgg atgaaaatgt gtccaagaga attgaaccaa
      961 gtgtttccct ctgcagtttt tatctctcta aaatgatcag catggatatt gaacaagtta
     1021 ttaccctaag tttagctctc cttctggctg tcaagtacat cttctttgaa caaacagaga
     1081 cagaatctac actctcatta aaaaaccta tcacatctcc tgtagtgaca caaagaaag
     1141 tcccagacaa ttgttgtaga cgtgaaccta tgctggtcag aaataaccag aaatgtgatt
     1201 cagtagagga agagacaggg ataaaccgag aaagaaaagt tgaggttata aaacccttag
```

Figure 22B

```
1261 tggctgaaac agatacccca aacagagcta catttgtggt tggtaactcc tccttactcg
1321 atacttcatc agtactggtg acacaggaac ctgaaattga acttcccagg gaacctcggc
1381 ctaatgaaga atgtctacag atacttggga atgcagagaa aggtgcaaaa ttccttagtg
1441 atgctgagat catccagtta gtcaatgcta agcatatccc agcctacaag ttggaaactc
1501 tgatggaaac tcatgagcgt ggtgtatcta ttcgccgaca gttactttcc aagaagcttt
1561 cagaaccttc ttctctccag tacctacctt acagggatta taattactcc ttggtgatgg
1621 gagcttgttg tgagaatgtt attggatata tgcccatccc tgttggagtg gcaggacccc
1681 tttgcttaga tgaaaaagaa tttcaggttc caatggcaac aacagaaggt tgtcttgtgg
1741 ccagcaccaa tagaggctgc agagcaatag gtcttggtgg aggtgccagc agccgagtcc
1801 ttgcagatgg gatgactcgt ggcccagttg tgcgtcttcc acgtgcttgt gactctgcag
1861 aagtgaaagc ctggctcgaa acatctgaag ggttcgcagt gataaaggag gcatttgaca
1921 gcactagcag atttgcacgt ctacagaaac ttcatacaag tatagctgga cgcaaccttt
1981 atatccgttt ccagtccagg tcaggggatg ccatggggat gaacatgatt tcaaagggta
2041 cagagaaagc actttcaaaa cttcacgagt atttccctga aatgcagatt ctagccgtta
2101 gtggtaacta ttgtactgac aagaaacctg ctgctataaa ttggatagag ggaagaggaa
2161 aatctgttgt ttgtgaagct gtcattccag ccaaggttgt cagagaagta ttaaagacta
2221 ccacagaggc tatgattgag gtcaacatta acaagaattt agtgggctct gccatggctg
2281 ggagcatagg aggctacaac gcccatgcag caaacattgt caccgccatc tacattgcct
2341 gtggacagga tgcagcacag aatgttggta gttcaaactg tattactta atggaagcaa
2401 gtggtcccac aaatgaagat ttatatatca gctgcaccat gccatctata gagataggaa
2461 cggtgggtgg tgggaccaac ctactacctc agcaagcctg tttgcagatg ctaggtgttc
2521 aaggagcatg caaagataat cctggggaaa atgcccggca gcttgcccga attgtgtgtg
2581 ggaccgtaat ggctggggaa ttgtcactta tggcagcatt ggcagcagga catcttgtca
2641 aaagtcacat gattcacaac aggtcgaaga tcaatttaca agacctccaa ggagcttgca
2701 ccaagaagac agcctgaata gcccgacagt tctgaactgg aacatgggca ttgggttcta
2761 aaggactaac ataaaatctg tgaattaaaa aagctcaatg cattgtcttg tggaggatga
2821 ataaatgtga tcactgagac agccacttgg ttttggctc tttcagagag gtctcaggtt
2881 ctttccatgc agactcctca gatc
```

Figure 22C

```
LOCUS       HUMPRCA     11725 bp    DNA              PRI       08-JAN-1995
DEFINITION  Human protein C gene, complete cds.
ACCESSION   M11228
NID         g190333
KEYWORDS    glycoprotein; protease; protein C; serine protease.
SOURCE      Human DNA, clones PC-lambda-8 and PC-lamda-6.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 11725)
  AUTHORS   Foster,D.C., Yoshitake,S. and Davie,E.W.
  TITLE     The nucleotide sequence of the gene for human protein C
  JOURNAL   Proc. Natl. Acad. Sci. U.S.A. 82 (14), 4673-4677 (1985)
  MEDLINE   85270390
FEATURES             Location/Qualifiers
     source          1..11725
                     /organism="Homo sapiens"
                     /db_xref="taxon:9606"
                     /map="2q13-q21"
     gene            2131..2200
                     /gene="PROC"
     exon            <2131..2200
                     /gene="PROC"
                     /note="Protein C; G00-120-317"
                     /number=1
     sig_peptide     join(2131..2200,3464..3519)
                     /note="Protein C signal peptide"
     CDS             join(2131..2200,3464..3630,5093..5117,5210..5347,
                     5450..5584,8253..8395,9269..9386,10516..11105)
                     /note="Protein C"
                     /codon_start=1
                     /db_xref="PID:g190334"

/translation="MWQLTSLLLFVATWGISGTPAPLDSVFSSSERAHQVLRIRKRAN

SFLEELRHSSLERECIEEICDFEEAKEIFQNVDDTLAFWSKHVDGDQCLVLPLEHPCA

SLCCGHGTCIDGIGSFSCDCRSGWEGRFCQREVSFLNCSLDNGGCTHYCLEEVGWRRC

SCAPGYKLGDDLLQCHPAVKFPCGRPWKRMEKKRSHLKRDTEDQEDQVDPRLIDGKMT

RRGDSPWQVVLLDSKKKLACGAVLIHPSWVLTAAHCMDESKKLLVRLGEYDLRRWEKW

ELDLDIKEVFVHPNYSKSTTDNDIALLHLAQPATLSQTIVPICLPDSGLAERELNQAG

QETLVTGWGYHSSREKEAKRNRTFVLNFIKIPVVPHNECSEVMSNMVSENMLCAGILG

DRQDACEGDSGGPMVASFHGTWFLVGLVSWGEGCGLLHNYGVYTKVSRYLDWIHGHIR
                     DKEAPQKSWAP"
     intron          2201..3463
                     /note="ProC cds intron A"
     exon            3464..3630
                     /number=2
```

Figure 23A

```
mat_peptide      join(3520..3630,5093..5117,5210..5347,5450..5584,
                 8253..8395,9269..9386,10516..11102)
intron           3631..5092
                 /note="ProC cds intron B"
exon             5093..5117
                 /number=3
intron           5118..5209
                 /note="ProC cds intron C"
exon             5210..5347
                 /number=4
intron           5348..5449
                 /note="ProC cds intron D"
exon             5450..5584
                 /number=5
intron           5585..8252
                 /note="ProC cds intron E"
exon             8253..8395
                 /number=6
intron           8396..9268
                 /note="ProC cds intron F"
exon             9269..9386
                 /number=7
intron           9387..10515
                 /note="ProC cds intron G"
exon             10516..>11105
                 /note="Protein C"
                 /number=8
BASE COUNT    2444 a   3298 c   3375 g   2608 t
ORIGIN      575 bp upstream of StuI site; chromosome 2q14-q21.
     1 agtgaatctg ggcgagtaac acaaaacttg agtgtcctta cctgaaaaat agaggttaga
    61 gggatgctat gtgccattgt gtgtgtgtgt tggggtgtgg gattgggggt gatttgtgag
   121 caattggagg tgagggtgga gcccagtgcc cagcacctat gcactgggga cccaaaaagg
   181 agcatcttct catgatttta tgtatcagaa attgggatgg catgtcattg ggacagcgtc
   241 ttttttcttg tatggtggca cataaataca tgtgtcttat aattaatggt attttagatt
   301 tgacgaaata tggaatatta cctgttgtgc tgatcttggg caaactataa tatctctggg
   361 caaaaatgtc cccatctgaa aaacagggac aacgttcctc cctcagccag ccactatggg
   421 gctaaaatga gaccacatct gtcaagggtt ttgcccctca ctccctccct gctggatggc
   481 atccttggta ggcagaggtg ggcttcgggc agaaggcctca gtgctgaggg ccaagcaaat
   541 gtgctagtgc cactgtttgt ctatggagag ggaggcctca gtgctgaggg ccaagcaaat
   601 atttgtggtt atggattaac tcgaactcca ggctgtcatg gcggcaggac ggcgaacttg
   661 cagtatctcc acgacccgcc cctgtgagtc cccctccagg caggtctatg aggggtgtgg
   721 agggagggct gccccgggga gaagagagct aggtggtgat gagggctgaa tcctccagcc
   781 aggtgctcca acaagcctga gcttgggta aaaggacaca aggccctcca caggccaggc
   841 ctggcagcca cagtctcagg tccctttgcc atgcgcctcc ctctttccag gccaagggtc
   901 cccaggccca gggccattcc aacagacagt ttggagccca ggaccctcca ttctccccac
   961 cccacttcca cctttggggg tgtcggattt gaacaaatct cagaagcggc ctcagaggga
  1021 gtcggcaaga atggagagca gggtccggta gggtgtgcag aggccacgtg gcctatccac
  1081 tgggagggt tccttgatct ctgccaccca gggctatctc tgtggccttt tggagcaacc
  1141 tggtggtttg gggcaggggt tgaatttcca ggcctaaaac cacacaggcc tggccttgag
  1201 tcctggctct gcgagtaatg catggatgta aacatggaga cccaggacct tgcctcagtc
  1261 ttccgagtct ggtgcctgca gtgtactgat ggtgtgagac cctactcctg gaggatgggg
  1321 gacagaatct gatcgatccc ctgggttggt gacttccctg tgcaatcaac ggagaccagc
  1381 aagggttgga ttttaataa accacttaac tcctccgagt ctcagtttcc ccctctatga
  1441 aatggggttg acagcattaa taactacctc ttgggtggtt gtgagcctta actgaagtca
```

Figure 23B

```
1501 taatatctca tgtttactga gcatgagcta tgtgcaaagc ctgttttgag agctttatgt
1561 ggactaactc ctttaattct cacaacaccc tttaaggcac agatacacca cgttattcca
1621 tccattttac aaatgaggaa actgaggcat ggagcagtta agcatcttgc ccaacattgc
1681 cctccagtaa gtgctggagc tggaatttgc accgtgcagt ctggcttcat ggcctgccct
1741 gtgaatcctg taaaaattgt ttgaaagaca ccatgagtgt ccaatcaacg ttagctaata
1801 ttctcagccc agtcatcaga ccggcagagg cagccacccc actgtcccca gggaggacac
1861 aaacatcctg gcaccctctc cactgcattc tggagctgct ttctaggcag gcagtgtgag
1921 ctcagcccca cgtagagcgg gcagccgagg ccttctgagg ctatgtctct agcgaacaag
1981 gaccctcaat tccagcttcc gcctgacggc cagcacacag ggacagccct ttcattccgc
2041 ttccacctgg gggtgcaggc agagcagcag cgggggtagc actgcccgga gctcagaagt
2101 cctcctcaga caggtgccag tgcctccaga atgtggcagc tcacaagcct cctgctgttc
2161 gtggccacct ggggaatttc cggcacacca gctcctcttg gtaaggccac cccacccta
2221 cccccgggacc cttgtggcct ctacaaggcc ctggtggcat ctgcccaggc cttcacagct
2281 tccaccatct ctctgagccc tgggtgaggt gagggcaga tgggaatggc aggaatcaac
2341 tgacaagtcc caggtaggcc agctgccaga gtgccacaca ggggctgcca gggcaggcat
2401 gcgtgatggc agggagcccc gcgatgacct cctaaagctc cctcctccac acggggatgg
2461 tcacagagtc cctgggcct tcctctcca ccactcact ccctcaactg tgaagacccc
2521 aggcccaggc taccgtccac actatccagc acagcctccc ctactcaaat gcacactggc
2581 ctcatggctg ccctgcccca acccctttcc tggtctccac agccaacggg aggaggccat
2641 gattcttggg gaggtccgca ggcacatggg cccctaaagc cacaccaggc tgttggtttc
2701 atttgtgcct ttatagagct gtttatctgc ttgggacctg cacctccacc ctttcccaag
2761 gtgccctcag ctcaggcata ccctcctcta ggatgccttt tcccccatcc cttcttgctc
2821 acaccccaa cttgatctct ccctcctaac tgtgccctgc accaagacag acacttcaca
2881 gagcccagga cacacctggg gaccttcct gggtgatagg tctgtctatc ctccaggtgt
2941 ccctgcccaa ggggagaagc atggggaata cttggttggg ggaggaaagg aagactgggg
3001 ggatgtgtca agatgggct gcatgtggtg tactggcaga agagtgagag gatttaactt
3061 ggcagccttt acagcagcag ccagggcttg agtacttatc tctgggccag gctgtattgg
3121 atgttttaca tgacggtctc atccccatgt ttttggatga gtaaattgaa ccttagaaag
3181 gtaaagacac tggctcaagg tcacacagag atcggggtgg ggttcacagg gaggcctgtc
3241 catctcagag caaggcttcg tcctccaact gccatctgct tcctggggag gaaaagagca
3301 gaggacccct gcgccaagcc atgacctaga attagaatga gtcttgaggg ggcggagaca
3361 agaccttccc aggctctccc agctctgctt cctcagaccc cctcatggcc ccagcccctc
3421 ttaggcccct caccaaggtg agctcccctc cctccaaaac cagactcagt gttctccagc
3481 agcgagcgtg cccaccaggt gctgcggatc cgcaaacgtg ccaactcctt cctggaggag
3541 ctccgtcaca gcagcctgga gcgggagtgc atagaggaga tctgtgactt cgaggaggcc
3601 aaggaaattt tccaaaatgt ggatgacaca gtaaggccac catgggtcca gaggatgagg
3661 ctcaggggcg agctggtaac cagcaggggc ctcgaggagc aggtggggac tcaatgctga
3721 ggccctctta ggagttgtgg gggtggctga gtggagcgat taggatgctg gccctatgat
3781 gtcggccagg cacatgtgac tgcaagaaac agaattcagg aagaagctcc aggaaagagt
3841 gtggggtgac cctaggtggg gactcccaca gccacagtgt aggtggttca gtccaccctc
3901 cagccactgc tgagcaccac tgcctccccg tcccacctca caaagagggg acctaaagac
3961 caccctgctt ccacccatgc ctctgctgat cagggtgtgt gtgtgaccga aactcacttc
4021 tgtccacata aaatcgctca ctctgtgcct cacatcaaag ggagaaaatc tgattgttca
4081 ggggtcgga agacagggtc tgtgtcctat ttgtctaagg gtcagagtcc tttggagccc
4141 ccagagtcct gtggacgtgg ccctaggtag tagggtgagc ttggtaacgg ggctggcttc
4201 ctgagacaag gctcagaccc gctctgtccc tggggatcgc ttcagccacc aggacctgaa
4261 aattgtgcac gcctgggccc ccttccaagg catccaggga tgctttccag tggaggcttt
4321 cagggcagga gaccctctgg cctgcaccct ctcttgccct cagcctccac ctccttgact
4381 ggacccccat ctggacctcc atccccacca cctctttccc cagtggcctc cctggcagac
4441 accacagtga ctttctgcag gcacatatct gatcacatca gtccccacc gtgctcccac
4501 ctcacccatg gtctctcagc ccagcagcc ttggctggcc tctctgatgg agcaggcatc
4561 aggcacaggc cgtgggtctc aacgtgggct gggtggtcct ggaccagcag cagccgccgc
4621 agcagcaacc ctggtacctg gttaggaacg cagaccctct gcccccatcc tcccaactct
4681 gaaaacact ggcttaggga aaggcgcgat gctcagggt cccccaaagc ccgcaggcag
```

Figure 23C

```
4741 agggagtgat gggactggaa ggaggccgag tgacttggtg agggattcgg gtcccttgca
4801 tgcagaggct gctgtgggag cggacagtcg cgagagcagc actgcagctg catggggaga
4861 gggtgttgct ccagggacgt gggatggagg ctgggcgcgg gcgggtggcg ctggagggcg
4921 ggggaggggc aggagcacc agctcctagc agccaacgac catcgggcgt cgatccctgt
4981 ttgtctggaa gccctcccct ccctgcccg ctcaccgct gccctgcccc acccgggcgc
5041 gcccctccgc acaccggctg caggagcctg acgctgcccg ctctctccgc agctggcctt
5101 ctggtccaag cacgtcggtg agtgcgttct agatccccgg ctggactacc ggcgcccgcg
5161 cccctcggga tctctggccg ctgacccct acccgcctt gtgtcgcaga cggtgaccag
5221 tgcttggtct tgccttgga gcaccgtgc gccagcctgt gctgcgggca cggcacgtgc
5281 atcgacggca tcggcagctt cagctgcgac tgccgcagcg gctgggaggg ccgcttctgc
5341 cagcgcggtg agggggagag gtggatgctg gcgggcggcg gggcggggct ggggccgggt
5401 tggggcgcg gcaccagcac cagctgcccg cgccctcccc tgcccgcaga ggtgagcttc
5461 ctcaattgct ctctggacaa cggcggctgc acgcattact gcctagagga ggtgggctgg
5521 cggcgctgta gctgtgcgcc tggctacaag ctggggacg acctcctgca gtgtcacccc
5581 gcaggtgaga agccccaat acatcgccca ggaatcacgc tgggtgcggg gtgggcaggc
5641 ccctgacggg cgcggcgcgg ggggctcagg agggtttcta gggagggagc gaggaacaga
5701 gttgagcctt ggggcagcgg cagacgcgcc caacaccggg gccactgtta gcgcaatcag
5761 cccgggagct gggcgcgccc tccgctttcc ctgcttcctt tcttcctggc gtccccgctt
5821 cctccgggcg cccctgcgac ctggggccac ctcctggagc gcaagcccag tggtggctcc
5881 gctccccagt ctgagcgtat ctggggcgag gcgtgcagcg tcctcctcca tgtagcctgg
5941 ctgcgttttt ctctgacgtt gtccggcgtg catcgcattt ccctctttac ccccttgctt
6001 ccttgaggag agaacagaat cccgattctg ccttcttcta tattttcctt tttatgcatt
6061 ttaatcaaat ttatatatgt atgaaacttt aaaaatcaga gttttacaac tcttacactt
6121 tcagcatgct gttccttggc atgggtcctt tttcattca tttcataaa aggtggaccc
6181 ttttaatgtg gaaattccta tcttctgcct ctagggcatt tatcacttat ttcttctaca
6241 atctcccctt tacttcctct attttctctt tctggacctc ccattattca gacctctttc
6301 ctctagtttt attgtctctt ctatttccca tctctttgac tttgtgtttt ctttcaggga
6361 actttctttt ttttcttttt ttttgagatg gagtttcact cttgttgtcc caggctggag
6421 tgcaatgacg tgatctcagc tcaccacaac ctccgcctcc tggattcaag cgattctcct
6481 gccgcagcct cccgagtagc tgggattaca ggcatgcgcc accacgccca gctaattttg
6541 tgttttagt agagaagggg tttctccgtg ttggtcaagc tggtcttgaa ctcctgacct
6601 caggtgatcc acctgccttg gcctcctaaa gtgctgggat tacaggcgtg agccaccgcg
6661 cccagcctct ttcagggaac tttctacaac tttataattc aattcttctg cagaaaaaaa
6721 ttttttggcca ggctcagtag ctcagaccaa taattccagc actttgagag gctgaggtgg
6781 gaggattgct tgagcttggg agtttgagac tagcctgggc aacacagtga gaccctgtct
6841 ctatttttaa aaaagtaaa aaagatcta aaaatttaac tttttatttt gaaataatta
6901 gatatttcca ggaagctgca aagaaatgcc tggtgggcct gttggctgtg ggtttcctgc
6961 aaggccgtgg gaaggccctg tcattggcag aaccccagat cgtgagggct ttccttttag
7021 gctgctttct aagaggactc ctccaagctc ttggaggatg gaagacgctc acccatggtg
7081 ttcggcccct cagagcaggg tgggcaggg gagctggtgc ctgtgcaggc tgtggacatt
7141 tgcatgactc cctgtggtca gctaagagca ccactccttc ctgaagcggg gcctgaagtc
7201 cctagtcaga gcctctggtt caccttctgc aggcagggag aggggagtca agtcagtgag
7261 gagggctttc gcagtttctc ttacaaactc tcaacatgcc ctcccacctg cactgccttc
7321 gaggaagccc cacagcctcc tatggttccg tggtccagtc cttcagcttc tgggcgcccc
7381 catcacgggc tgagattttt gctttccagt ctgccaagtc agttactgtg tccatccatc
7441 tgctgtcagc ttctggaatt gttgctgttg tgcccttttcc attcttttgt tatgatgcag
7501 ctccccctgct gacgacgtcc cattgctctt ttaagtctag atatctggac tgggcattca
7561 aggcccattt tgagcagagt cgggctgacc tttcagccct cagttctcca tggagtatgc
7621 gctctcttct tggcagggag gcctcacaaa catgccatgc ctattgtagc agctctccaa
7681 gaatgctcac ctccttctcc ctgtaattcc tttcctctgt gaggagctca gcagcatccc
7741 attatgagac cttactaatc ccagggatca cccccaacag ccctggggta caatgagctt
7801 ttaagaagtt taaccaccta tgtaaggaga cacaggcagt gggcgatgct gcctggcctg
7861 actcttgcca ttgggtggta ctgtttgttg actgactgac tgactgactg gagggggttt
7921 gtaatttgta tctcagggat taccccccaac agccctgggg tacaatgagc cttcaagaag
```

Figure 23D

```
 7981 tttaacaacc tatgtaagga cacacagcca gtgggtgatg ctgcctggtc tgactcttgc
 8041 cattcagtgg cactgtttgt tgactgactg actgactgac tggctgactg gaggggttc
 8101 atagctaata ttaatggagt ggtctaagta tcattggttc cttgaaccct gcactgtggc
 8161 aaagtggccc acaggctgga ggaggaccaa gacaggaggg cagtctcggg aggagtgcct
 8221 ggcaggcccc tcaccacctc tgcctacctc agtgaagttc ccttgtggga ggccctggaa
 8281 gcggatggag aagaagcgca gtcacctgaa acgagacaca gaagaccaag aagaccaagt
 8341 agatccgcgc ctcattgatg gaagatgac caggcgggga gacagcccct ggcaggtggg
 8401 aggcgaggca gcaccggctc gtcacgtgct gggtccggga tcactgagtc catcctggca
 8461 gctatgctca gggtgcagaa accgagaggg aagcgctgcc attgcgtttg gggatgatg
 8521 aaggtggggg atgcttcagg gaaagatgga cgcaacctga ggggagagga gcagccaggg
 8581 tgggtgaggg gaggggcatg ggggcatgga ggggtctgca ggagggaggg ttacagtttc
 8641 taaaaagagc tggaaagaca ctgctctgct ggcgggattt taggcagaag ccctgctgat
 8701 gggagagggc taggagggag ggccgggcct gagtaccct ccagcctcca catgggaact
 8761 gacacttact gggttccct ctctgccagg catgggggag ataggaacca acaagtggga
 8821 gtatttgccc tggggactca gactctgcaa gggtcaggac cccaaagacc cggcagccca
 8881 gtgggaccac agccaggacg gcccttcaag ataggggctg agggaggcca aggggaacat
 8941 ccaggcagcc tgggggccac aaagtcttcc tggaagacac aaggcctgcc aagcctctaa
 9001 ggatgagagg agctcgctgg gcgatgttgg tgtggctgag ggtgactgaa acagtatgaa
 9061 cagtgcagga acagcatggg caaaggcagg aagacaccct gggacaggct gacactgtaa
 9121 aatgggcaaa aatagaaaac gccagaaagg cctaagccta tgcccatatg accagggaac
 9181 ccaggaaagt gcatatgaaa cccaggtgcc ctggactgga ggctgtcagg aggcagccct
 9241 gtgatgtcat catcccaccc cattccaggt ggtcctgctg gactcaaaga agaagctggc
 9301 ctgcggggca gtgctcatcc acccctcctg ggtgctgaca gcggcccact gcatggatga
 9361 gtccaagaag ctccttgtca ggcttggtat gggctggagc caggcagaag ggggctgcca
 9421 gaggcctggg taggggacc aggcaggctg ttcaggtttg ggggacccg ctccccaggt
 9481 gcttaagcaa gaggcttctt gagctccaca gaaggtgttt gggggaaga ggcctatgtg
 9541 cccccaccct gcccacccat gtacacccag tattttgcag taggggttc tctggtgccc
 9601 tcttcgaatc tgggcacagg tacctgcaca cacatgtttg tgagggcta cacagacctt
 9661 cacctctcca ctcccactca tgaggagcag gctgtgtggg cctcagcacc cttgggtgca
 9721 gagaccagca aggcctggcc tcagggctgt gcctcccaca gactgacagg gatggagctg
 9781 tacagaggga gccctagcat ctgccaaagc cacaagctgc ttccctagca ggctgggggc
 9841 tcctatgcat tggccccgat ctatggcaat ttctggaggg ggggtctggc tcaactcttt
 9901 atgccaaaaa gaaggcaaag catattgaga aaggccaaat tcacatttcc tacagcataa
 9961 tctatgccag tggccccgtg gggcttggct tagaattccc aggtgctctt cccagggaac
10021 catcagtctg gactgagagg accttctctc tcaggtggga cccggccctg tcctccctgg
10081 cagtgccgtg ttctggggt cctcctctct gggtctcact gcccctgggg tctctccagc
10141 tacctttgct ccatgttcct ttgtggctct ggtctgtgtc tggggtttcc aggggtctcg
10201 ggcttccctg ctgcccattc cttctctggt tcacggctc cgtgactcct gaaaaccaac
10261 cagcatccta cccctttgga ttgacacctg ttggccactc cttctggcag gaaaagtcac
10321 cgttgatagg gttccacggc atagacaggt ggctccgcgc cagtgcctgg gacgtgtggg
10381 tgcacagtct ccgggtgaac cttcttcagg ccctctccca ggcctgcagg gcacagcag
10441 tgggtgggcc tcaggaaagt gccactgggg agaggctccc cgcagcccac tctgactgtg
10501 ccctctgccc tgcaggagag tatgacctgc ggcgctggga gaagtgggag ctggacctgg
10561 acatcaagga ggtcttcgtc caccccaact acagcaagag caccaccgac aatgacatcg
10621 cactgctgca cctggcccag cccgccaccc tctcgcagac catagtgccc atctgcctcc
10681 cggacagcgg ccttgcagag cgcgagctca atcaggccgg ccaggagacc ctcgtgacgg
10741 gctgggcta ccacagcagc cgagagaagg aggccaagag aaaccgcacc ttcgtcctca
10801 acttcatcaa gattcccgtg gtcccgcaca atgagtgcag cgaggtcatg agcaacatgg
10861 tgtctgagaa catgctgtgt gcgggcatcc tcggggaccg gcaggatgcc tgcgagggcg
10921 acagtggggg gcccatggtc gcctccttcc acggcacctg gttcctggtg ggcctggtga
10981 gctgggtga gggctgtggg ctccttcaca actacggcgt ttacaccaaa gtcagccgct
11041 acctcgactg gatccatggg cacatcagag acaaggaagc ccccagaag agctgggcac
11101 cttagcgacc ctccctgcag ggctgggctt ttgcatggca atggatggga cattaaaggg
11161 acatgtaaca agcacaccgg cctgctgttc tgtccttcca tccctctttt gggctcttct
```

Figure 23E

```
11221 ggagggaagt aacatttact gagcacctgt tgtatgtcac atgccttatg aatagaatct
11281 taactcctag agcaactctg tggggtgggg aggagcagat ccaagttttg cggggtctaa
11341 agctgtgtgt gttgagggggg atactctgtt tatgaaaaag aataaaaaac acaaccacga
11401 agccactaga gccttttcca gggctttggg aagagcctgt gcaagccggg gatgctgaag
11461 gtgaggcttg accagctttc cagctagccc agctatgagg tagacatgtt tagctcatat
11521 cacagaggag gaaactgagg ggtctgaaag gtttacatgg tggagccagg attcaaatct
11581 aggtctgact ccaaaaccca ggtgcttttt tctgttctcc actgtcctgg aggacagctg
11641 tttcgacggt gctcagtgtg gaggccacta ttagctctgt agggaagcag ccagagaccc
11701 agaaagtgtt ggttcagccc agaat
```

Figure 23F

```
LOCUS       HUMLCAT      1744 bp    mRNA           PRI       07-JAN-1995
DEFINITION  Human lecithin-cholesterol acyltransferase mRNA, complete cds,
with
            5' and 3' flanking DNA sequences.
ACCESSION   M12625
NID         g187022
KEYWORDS    lecithin cholesterol acyltransferase.
SOURCE      Human adult liver (library of A.Ullrich and L.Coussens), cDNA to
            mRNA, clones PL[2,4,10,12,19], and DNA.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 1744)
  AUTHORS   McLean,J., Fielding,C., Drayna,D., Dieplinger,H., Baer,B.,
Kohr,W.,
            Henzel,W. and Lawn,R.
  TITLE     Cloning and expression of human lecithin-cholesterol
            acyltransferase cDNA
  JOURNAL   Proc. Natl. Acad. Sci. U.S.A. 83 (8), 2335-2339 (1986)
  MEDLINE   86205950
COMMENT     Draft entry and sequence in computer readable form for [1] kindly
            provided by J.W.McLean, 24-JUL-1986.
            Because only the 5' and 3' flanking sequences were determined from
            DNA, it is not known whether this gene contains introns.
FEATURES             Location/Qualifiers
     source          1..1744
                     /organism="Homo sapiens"
                     /db_xref="taxon:9606"
                     /map="16q22.1"
     mRNA            <257..1610
                     /note="LCAT mRNA"
     sig_peptide     268..339
                     /gene="LCAT"
                     /note="lecithin-cholesterol acyltransferase signal
                     peptide"
     gene            268..1590
                     /gene="LCAT"
     CDS             268..1590
                     /gene="LCAT"
                     /note="lecithin-cholesterol acyltransferase precursor (EC
                     2.3.1.43)"
                     /codon_start=1
                     /db_xref="GDB:G00-119-359"
                     /db_xref="PID:g307117"
```

/translation="MGPPGSPWQWVTLLLGLLLPPAAPFWLLNVLFPPHTTPKAELSN

HTRPVILVPGCLGNQLEAKLDKPDVVNWMCYRKTEDFFTIWLDLNMFLPLGVDCWIDN

TRVVYNRSSGLVSNAPGVQIRVPGFGKTYSVEYLDSSKLAGYLHTLVQNLVNNGYVRD

ETVRAAPYDWRLEPGQQEEYYRKLAGLVEEMHAAYGKPVFLIGHSLGCLHLLYFLLRQ

Figure 24A

PQAWKDRFIDGFISLGAPWGGSIKPMLVLASGDNQGIPIMSSIKLKEEQRITTTSPWM

FPSRMAWPEDHVFISTPSFNYTGRDFQRFFADLHFEEGWYMWLQSRDLLAGLPAPGVE

VYCLYGVGLPTPRTYIYDHGFPYTDPVGVLYEDGDDTVATRSTELCGLWQGRQPQPVH
              LLPLHGIQHLNMVFSNLTLEHINAILLGAYRQGPPASPTASPEPPPPE"
     mat_peptide      340..1587
                      /gene="LCAT"
                      /note="lecithin-cholesterol acyltransferase"
BASE COUNT      324 a    589 c    475 g    356 t
ORIGIN       30 bp upstream of StyI recognition sequence.
        1 tgaggcctga ctttttcaat aaaacattgt gtagttctgg gcctcctgct gccccggctc
       61 tgtttcccct ggcgccaaga gaagaaggcg gaactgaacc caggcccaga gccggctccc
      121 tgaggctgtg ccccttccg gcaatctctg gccacaaccc ccactggcca ggccgtccct
      181 cccactggcc ctagggcccc tcccactccc acaccagata aggacagccc agtgccgctt
      241 tctctggcag taggcaccag ggctggaatg gggccgcccg ctccccatg gcagtgggtg
      301 acgctgctgc tggggctgct gctccctcct gccgccccct tctggctcct caatgtgctc
      361 ttcccccgc acaccacgcc caaggctgag ctcagtaacc acacacggcc cgtcatcctc
      421 gtgcccggct gcctggggaa tcagctagaa gccaagctgg acaaaccaga tgtggtgaac
      481 tggatgtgct accgcaagac agaggacttc ttcaccatct ggctggatct caacatgttc
      541 ctacccctttg gggtagactg ctggatcgat aacaccaggg ttgtctacaa ccggagctct
      601 gggctcgtgt ccaacgcccc tggtgtccag atccgcgtcc ctggctttgg caagacctac
      661 tctgtggagt acctggacag cagcaagctg cagggtacc tgcacacact ggtgcagaac
      721 ctggtcaaca atggctacgt gcgggacgag actgtgcgcg ccgcccccta tgactggcgg
      781 ctggagcccg ccagcagga ggagtactac cgcaagctcg cagggctggt ggaggagatg
      841 cacgctgcct atgggaagcc tgtcttcctc attggccaca gcctcggctg tctacacttg
      901 ctctatttcc tgctgcgcca gccccaggcc tggaaggacc gctttattga tggcttcatc
      961 tctcttgggg ctccctgggg tggctccatc aagcccatgc tggtcttggc ctcaggtgac
     1021 aaccagggca tccccatcat gtccagcatc aagctgaaag aggagcagcg cataaccacc
     1081 acctcccct ggatgtttcc ctctcgcatg gcgtggcctg aggaccacgt gttcatttcc
     1141 acaccagct tcaactacac aggccgtgac ttccaacgct tctttgcaga cctgcactt
     1201 gaggaaggct ggtacatgtg gctgcagtca cgtgacctcc tggcaggact cccagcacct
     1261 ggtgtggaag tatactgtct ttacggcgtg ggcctgccca cgccccgcac ctacatctac
     1321 gaccacgggt tccctaccac ggaccctgtg ggtgtgctct atgaggatgg tgatgacacg
     1381 gtggcgaccc gcagcaccga gctctgtggc ctgtggcagg gccgccagcc acagcctgtg
     1441 cacctgctgc ccctgcacgg gatacagcat ctcaacatgg tcttcagcaa cctgaccctg
     1501 gagcacatca atgccatcct gctgggtgcc taccgccagg tccccctgc atcccgact
     1561 gccagcccag agccccgcc tctgaataa agaccttcct ttgctaccgt aagccctgat
     1621 ggctatgttt caggttgaag ggaggcacta gagtcccaca ctaggtttca ctcctcacca
     1681 gccacaggct cagtgctgtg tgcagtgagg caagatgggc tctgctgagg cctgggactg
     1741 agct

Figure 24B

```
LOCUS       HUMHCII      2182 bp    mRNA             PRI       08-NOV-1994
DEFINITION  Human heparin cofactor II (HC-II) mRNA, complete cds.
ACCESSION   M12849 M19241
NID         g183909
KEYWORDS    heparin cofactor II; protease inhibitor.
SOURCE      Human fetal liver, cDNA to mRNA, clone lambda-HCII.7 [1]; adult
            liver, cDNA to mRNA, clone lambda HCII.7.1 [3].
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1025 to 2182)
  AUTHORS   Inhorn,R.C. and Tollefsen,D.M.
  JOURNAL   Unpublished (1986)
REFERENCE   2  (bases 1025 to 2182)
  AUTHORS   Inhorn,R.C. and Tollefsen,D.M.
  TITLE     Isolation and characterization of a partial cDNA clone for heparin
            cofactor II1
  JOURNAL   Biochem. Biophys. Res. Commun. 137 (1), 431-436 (1986)
  MEDLINE   86242236
REFERENCE   3  (bases 1 to 2182)
  AUTHORS   Blinder,M.A., Marasa,J.C., Reynolds,C.H., Deaven,L.L. and
            Tollefsen,D.M.
  TITLE     Heparin cofactor II: cDNA sequence, chromosome localization,
            restriction fragment length polymorphism, and expression in
            Escherichia coli
  JOURNAL   Biochemistry 27 (2), 752-759 (1988)
  MEDLINE   88163663
COMMENT     [1]  revises [2].
            Draft entry and computer-readable sequence of [2] kindly provided
            by D.M.Tollefsen, 18-AUG-1986.
            Draft entry and computer-readable sequence of [3] kindly provided
            by Blinder,M.A. 24-MAR-1988.
FEATURES             Location/Qualifiers
     source          1..2182
                     /organism="Homo sapiens"
                     /db_xref="taxon:9606"
                     /map="22q11.2"
     mRNA            <1..2182
                     /note="heparin cofactor II mRNA"
     sig_peptide     29..85
                     /gene="HCF2"
                     /note="heparin cofactor II signal protein"
     gene            29..1528
                     /gene="HCF2"
     CDS             29..1528
                     /gene="HCF2"
                     /note="heparin cofactor II precursor"
                     /codon_start=1
                     /db_xref="GDB:G00-120-038"
                     /db_xref="PID:g183910"

/translation="MKHSLNALLIFLIITSAWGGSKGPLDQLEKGGETAQSADPQWEQ
```

Figure 25A

```
LNNKNLSMPLLPADFHKENTVTNDWIPEGEEDDDYLDLEKIFSEDDDYIDIVDSLSVS

PTDSDVSAGNILQLFHGKSRIQRLNILNAKFAFNLYRVLKDQVNTFDNIFIAPVGIST

AMGMISLGLKGETHEQVHSILHFKDFVNASSKYEITTIHNLFRKLTHRLFRRNFGYTL

RSVNDLYIQKQFPILLDFRTKVREYYFAEAQIADFSDPAFISKTNNHIMKLTKGLIKD

ALENIDPATQMMILNCIYFKGSWVNKFPVEMTHNHNFRLNEREVVKVSMMQTKGNFLA

ANDQELDCDILQLEYVGGISMLIVVPHKMSGMKTLEAQLTPRVVERWQKSMTNRTREV

LLPKFKLEKNYNLVESLKLMGIRMLFDKNGNMAGISDQRIAIDLFKHQGTITVNEEGT
                QATTVTTVGFMPLSTQVRFTVDRPFLFLIYEHRTSCLLFMGRVANPSRS"
     mat_peptide   86..1525
                   /gene="HCF2"
                   /note="heparin cofactor II"
BASE COUNT    603 a    581 c    500 g    498 t
ORIGIN      142 bp upstream from PstI site; chromosome 22.
        1 cgaaacacag agctttagct ccgccaaaat gaaacactca ttaaacgcac ttctcatttt
       61 cctcatcata acatctgcgt ggggtgggag caaaggcccg ctggatcagc tagagaaagg
      121 aggggaaact gctcagtctg cagatcccca gtggagcag ttaaataaca aaaacctgag
      181 catgcctctt ctccctgccg acttccacaa ggaaaacacc gtcaccaacg actggattcc
      241 agaggggag gaggacgacg actatctgga cctggagaag atattcagtg aagacgacga
      301 ctacatcgac atcgtcgaca gtctgtcagt ttccccgaca gactctgatg tgagtgctgg
      361 gaacatcctc cagctttttc atggcaagag ccggatccag cgtcttaaca tcctcaacgc
      421 caagttcgct ttcaacctct accgagtgct gaaagaccag gtcaacactt tcgataacat
      481 cttcatagca cccgttggca tttctactgc gatgggtatg atttccttag gtctgaaggg
      541 agagacccat gaacaagtgc actcgatttt gcattttaaa gactttgtta atgccagcag
      601 caagtatgaa atcacgacca ttcataatct cttccgtaag ctgactcatc gcctcttcag
      661 gaggaatttt gggtacacac tgcggtcagt caatgacctt tatatccaga agcagtttcc
      721 aatcctgctt gacttcagaa ctaaagtaag agagtattac tttgctgagg cccagatagc
      781 tgacttctca gaccctgcct tcatatcaaa aaccaacaac cacatcatga agctccaccaa
      841 gggcctcata aaagatgctc tggagaatat agaccctgct acccagatga tgattctcaa
      901 ctgcatctac ttcaaaggat cctgggtgaa taaattccca gtggaaatga cacacaacca
      961 caacttccgg ctgaatgaga gagaggtagt taaggtttcc atgatgcaga ccaaggggaa
     1021 cttcctcgca gcaaatgacc aggagctgga ctgcgacatc ctccagctgg aatacgtggg
     1081 gggcatcagc atgctaattg tggtcccaca caagatgtct gggatgaaga ccctcgaagc
     1141 gcaactgaca ccccgggtgg tggagagatg gcaaaaaagc atgacaaaca gaactcgaga
     1201 agtgcttctg ccgaaattca gctggagaa gaactacaat ctagtggagt ccctgaagtt
     1261 gatggggatc aggatgctgt ttgacaaaaa tggcaacatg gcaggcatct cagaccaaag
     1321 gatcgccatc gacctgttca gcaccaagg cacgatcaca gtgaacgagg aaggcaccca
     1381 agccaccact gtgaccacgg tggggttcat gccgctgtcc acccaagtcc gcttcactgt
     1441 cgaccgcccc tttcttttcc tcatctacga gcaccgcacc agctgcctgc tcttcatggg
     1501 aagagtggcc aacccagca ggtcctagag gtgagctct aggtgtctga agtgccttgg
     1561 gggcaccctc attttgtttc cattccaaca acgagaacag agatgttctg gcatcattta
     1621 cgtagtttac gctaccaatc tgaattcgag gcccatatga gaggagctta gaaacgacca
     1681 agaagagagg cttgttggaa tcaattctgc acaatagccc atgctgtaag ctcatagaag
     1741 tcactgtaac tgtagtgtgt ctgctgttac ctagagggtc tcacctcccc actcttcaca
     1801 gcaaacctga gcagcgcgtc ctaagcacct cccgctccgg tgaccccatc cttgcacacc
     1861 tgactctgtc actcaagcct ttctccacca ggcccctcat ctgaatacca agcacagaaa
     1921 tgagtggtgt gactaattcc ttacctctcc caaggagggt acacaactag caccattctt
     1981 gatgtccagg gaagaagcca cctcaagaca tatgagggt gccctgggct aatgttaggg
     2041 cttaattttc tcaaagcctg acctttcaaa tccatgatga atgccatcag tccctcctgc
```

```
2101 tgttgcctcc ctgtgacctg gaggacagtg tgtgccatgt ctcccatact agagataaat
2161 aaatgtagcc acatttactg tg
```

Figure 25C

```
LOCUS       HUMFVA      6893 bp    mRNA            PRI       08-AUG-1995
DEFINITION  Human coagulation factor V mRNA, complete cds.
ACCESSION   M14335 M17785
NID         g182797
KEYWORDS    coagulation factor V; factor V; glycoprotein.
SOURCE      Human liver (normal hepatocyte and HepG-2 cells), cDNA to mRNA,
            clones HV3.37, HV0.85, HV1.66 and HV2.97.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 3636 to 6893)
  AUTHORS   Kane,W.H. and Davie,E.W.
  TITLE     Cloning of a cDNA coding for human factor V, a blood coagulation
            factor homologous to factor VIII and ceruloplasmin
  JOURNAL   Proc. Natl. Acad. Sci. U.S.A. 83 (18), 6800-6804 (1986)
  MEDLINE   86313665
REFERENCE   2  (bases 1 to 4876)
  AUTHORS   Kane,W.H., Ichinose,A., Hagen,F.S. and Davie,E.W.
  TITLE     Cloning of cDNAs coding for the heavy chain region and connecting
            region of human factor V, a blood coagulation factor with four
            types of internal repeats
  JOURNAL   Biochemistry 26 (20), 6508-6514 (1987)
  MEDLINE   88107560
COMMENT     Draft entry and computer-readable sequence [1] kindly submitted by
            W.H.Kane, 13-JUN-1988.
FEATURES             Location/Qualifiers
     source          1..6893
                     /organism="Homo sapiens"
                     /db_xref="taxon:9606"
                     /map="1q21-q25"
     gene            77..6751
                     /gene="F5"
     sig_peptide     77..160
                     /gene="F5"
                     /note="factor V signal peptide"
     CDS             77..6751
                     /gene="F5"
                     /note="factor V precusor"
                     /codon_start=1
                     /db_xref="GDB:G00-119-896"
                     /db_xref="PID:g182798"
```

/translation="MFPGCPRLWVLVVLGTSWVGWGSQGTEAAQLRQFYVAAQGISWS

YRPEPTNSSLNLSVTSFKKIVYREYEPYFKKEKPQSTISGLLGPTLYAEVGDIIKVHF

KNKADKPLSIHPQGIRYSKLSEGASYLDHTFPAEKMDDAVAPGREYTYEWSISEDSGP

THDDPPCLTHIYYSHENLIEDFNSGLIGPLLICKKGTLTEGGTQKTFDKQIVLLFAVF

DESKSWSQSSSLMYTVNGYVNGTMPDITVCAHDHISWHLLGMSSGPELFSIHFNGQVL

EQNHHKVSAITLVSATSTTANMTVGPEGKWIISSLTPKHLQAGMQAYIDIKNCPKKTR

Figure 26A

NLKKITREQRRHMKRWEYFIAAEEVIWDYAPVIPANMDKKYRSQHLDNFSNQIGKHYK

KVMYTQYEDESFTKHTVNPNMKEDGILGPIIRAQVRDTLKIVFKNMASRPYSIYPHGV

TFSPYEDEVNSSFTSGRNNTMIRAVQPGETYTYKWNILEFDEPTENDAQCLTRPYYSD

VDIMRDIASGLIGLLLICKSRSLDRRGIQRAADIEQQAVFAVFDENKSWYLEDNINKF

CENPDEVKRDDPKFYESNIMSTINGYVPESITTLGFCFDDTVQWHFCSVGTQNEILTI

HFTGHSFIYGKRHEDTLTLFPMRGESVTVTMDNVGTWMLTSMNSSPRSKKLRLKFRDV

KCIPDDDEDSYEIFEPPESTVMATRKMHDRLEPEDEESDADYDYQNRLAAALGIRSFR

NSSLNQEEEEFNLTALALENGTEFVSSNTDIIVGSNYSSPSNISKFTVNNLAEPQKAP

SHQQATTAGSPLRHLIGKNSVLNSSTAEHSSPYSEDPIEDPLQPDVTGIRLLSLGAGE

FRSQEHAKRKGPKVERDQAAKHRFSWMKLLAHKVGRHLSQDTGSPSGMRPWEDLPSQD

TGSPSRMRPWEDPPSDLLLLKQSNSSKILVGRWHLASEKGSYEIIQDTDEDTAVNNWL

ISPQNASRAWGESTPLANKPGKQSGHPKFPRVRHKSLQVRQDGGKSRLKKSQFLIKTR

KKKKEKHTHHAPLSPRTFHPLRSEAYNTFSERRLKHSLVLHKSNETSLPTDLNQTLPS

MDFGWIASLPDHNQNSSNDTGQASCPPGLYQTVPPEEHYQTFPIQDPDQMHSTSDPSH

RSSSPELSEMLEYDRSHKSFPTDISQMSPSSEHEVWQTVISPDLSQVTLSPELSQTNL

SPDLSHTTLSPELIQRNLSPALGQMPISPDLSHTTLSPDLSHTTLSLDLSQTNLSPEL

SQTNLSPALGQMPLSPDLSHTTISLDFSQTNLSPELSHMTLSPELSQTNLSPALGQMP

ISPDLSHTTLSLDFSQTNLSPELSQTNLSPALGQMPLSPDPSHTTLSLDLSQTNLSPE

LSQTNLSPDLSEMPLFADLSQIPLTPDLDQMTLSPDLGETDLSPNFGQMSLSPDLSQV

TLSPDISDTTLLPDLSQISPPPDLDQIFYPSESSQSLLLQEFNESFPYPDLGQMPSPS

SPTLNDTFLSKEFNPLVIVGLSKDGTDYIEIIPKEEVQSSEDDYAEIDYVPYDDPYKT

DVRTNINSSRDPDNIAAWYLRSNNGNRRNYYIAAEEISWDYSEFVQRETDIEDSDDIP

EDTTYKKVVFRKYLDSTFTKRDPRGEYEEHLGILGPIIRAEVDDVIQVRFKNLASRPY

SLHAHGLSYEKSSEGKTYEDDSPEWFKEDNAVQPNSSYTYVWHATERSGPESPGSACR

AWAYYSAVNPEKDIHSGLIGPLLICQKGILHKDSNMPVDMREFVLLFMTFDEKKSWYY

EKKSRSSWRLTSSEMKKSHEFHAINGMIYSLPGLKMYEQEWVRLHLLNIGGSQDIHVV

HFHGQTLLENGNKQHQLGVWPLLPGSFKTLEMKASKPGWWLLNTEVGENQRAGMQTPF

Figure 26B

```
              LIMDRDCRMPMGLSTGIISDSQIKASEFLGYWEPRLARLNNGGSYNAWSVEKLAAEFA

SKPWIQVDMQKEVIITGIQTQGAKHYLKSCYTTEFYVAYSSNQINWQIFKGNSTRNVM

YFNGNSDASTIKENQFDPPIVARYIRISPTRAYNRPTLRLELQGCEVNGCSTPLGMEN

GKIENKQITASSFKKSWWGDYWEPFRARLNAQGRVNAWQAKANNNKQWLEIDLLKIKK

ITAIITQGCKSLSSEMYVKSYTIHYSEQGVEWKPYRLKSSMVDKIFEGNTNTKGHVKN
                          FFNPPIISRFIRVIPKTWNQSIALRLELFGCDIY"
     mat_peptide       161..6748
                       /gene="F5"
                       /note="factor V"
     variation         3723..4024
                       /gene="F5"
                       /note="ccctt in clone HV2.97 [1]"
                       /replace="ccctt"
BASE COUNT     2090 a   1700 c   1423 g   1680 t
ORIGIN      270 bp upstream of AccI site; chromosome 1q21-q25.
        1 ctccgggctg tcccagctcg gcaagcgctg cccaggtcct ggggtggtgg cagccagcgg
       61 gagcaggaaa ggaagcatgt tcccaggctg cccacgcctc tgggtcctgg tggtcttggg
      121 caccagctgg gtaggctggg ggagccaagg gacagaagcg gcacagctaa ggcagttcta
      181 cgtggctgct cagggcatca gttggagcta ccgacctgag cccacaaact caagtttgaa
      241 tctttctgta acttccttta agaaaattgt ctacagagag tatgaaccat attttaagaa
      301 agaaaaacca caatctacca tttcaggact tcttgggcct actttatatg ctgaagtcgg
      361 agacatcata aaagttcact ttaaaaataa ggcagataag cccttgagca tccatcctca
      421 aggaattagg tacagtaaat tatcagaagg tgcttcttac cttgaccaca cattccctgc
      481 agagaagatg gacgacgctg tggctccagg ccgagaatac acctatgaat ggagtatcag
      541 tgaggacagt ggacccaccc atgatgaccc tccatgcctc acacacatct attactccca
      601 tgaaaatctg atcgaggatt tcaactctgg gctgattggg ccctgctta tctgtaaaaa
      661 agggacccta actgagggtg ggacacagaa gacgtttgac aagcaaatcg tgctactatt
      721 tgctgtgttt gatgaaagca agagctggag ccagtcatca tccctaatgt acacagtcaa
      781 tggatatgtg aatgggacaa tgccagatat aacagtttgt gcccatgacc acatcagctg
      841 gcatctgctg gaatgagct cggggccaga attattctcc attcatttca acggcaggt
      901 cctggagcag aaccatcata aggtctcagc catcaccctt gtcagtgcta catccactac
      961 cgcaaatatg actgtgggcc cagagggaaa gtggatcata tcttctctca cccccaaaaca
     1021 tttgcaagct gggatgcagg cttacattga cattaaaaac tgcccaaaga aaaccaggaa
     1081 tcttaagaaa ataactcgtg agcagaggcg gcacatgaag aggtgggaat acttcattgc
     1141 tgcagaggaa gtcatttggg actatgcacc tgtaatacca gcgaatatgg acaaaaaata
     1201 caggtctcag catttggata atttctcaaa ccaaattgga aaacattata agaaagttat
     1261 gtacacacag tacgaagatg agtccttcac caaacataca gtgaatccca atatgaaaga
     1321 agatgggatt ttgggtccta ttatcagagc ccaggtcaga gacacactca aaatcgtgtt
     1381 caaaaatatg gccagccgcc cctatagcat ttaccctcat ggagtgacct tctcgcctta
     1441 tgaagatgaa gtcaactctt ctttcacctc aggcaggaac aacaccatga tcagagcagt
     1501 tcaaccaggg gaaacctata cttataagtg aacatctta gagtttgatg aacccacaga
     1561 aaatgatgcc cagtgcttaa caagaccata ctacagtgac gtggacatca tgagagacat
     1621 cgcctctggg ctaataggac tacttctaat ctgtaagagc agatccctgg acaggcgagg
     1681 aatacagagg gcagcagaca tcgaacagca ggctgtgttt gctgtgtttg atgagaacaa
     1741 aagctggtac cttgaggaca acatcaacaa gttttgtgaa atcctgatgg aggtgaaacg
     1801 tgatgacccc aagttttatg aatcaaacat catgagcact atcaatggct atgtgcctga
     1861 gagcataact actcttggat tctgctttga tgacactgtc cagtggcact tctgtagtgt
     1921 ggggacccag aatgaaattt tgaccatcca cttcactggg cactcattca tctatggaaa
     1981 gaggcatgag gacaccttga ccctcttccc catgcgtgga gaatctgtga cggtcacaat
```

Figure 26C

```
2041 ggataatgtt ggaacttgga tgttaacttc catgaattct agtccaagaa gcaaaaagct
2101 gaggctgaaa ttcagggatg ttaaatgtat cccagatgat gatgaagact catatgagat
2161 ttttgaacct ccagaatcta cagtcatggc tacacggaaa atgcatgatc gtttagaacc
2221 tgaagatgaa gagagtgatg ctgactatga ttaccagaac agactggctg cagcattagg
2281 aattaggtca ttccgaaact catcattgaa ccaggaagaa gaagagttca atcttactgc
2341 cctagctctg gagaatggca ctgaattcgt ttcttcgaac acagatataa ttgttggttc
2401 aaattattct tccccaagta atattagtaa gttcactgtc aataaccttg cagaacctca
2461 gaaagcccct tctcaccaac aagccaccac agctggttcc ccactgagac acctcattgg
2521 caagaactca gttctcaatt cttccacagc agagcattcc agcccatatt ctgaagaccc
2581 tatagaggat cctctacagc cagatgtcac agggatacgt ctactttcac ttggtgctgg
2641 agaattcaga agtcaagaac atgctaagcg taagggaccc aaggtagaaa gagatcaagc
2701 agcaaagcac aggttctcct ggatgaaatt actagcacat aaagttggga gacacctaag
2761 ccaagacact ggttctcctt ccggaatgag gccctgggag gaccttccta gccaagacac
2821 tggttctcct tccagaatga ggccctggga ggaccctcct agtgatctgt tactcttaaa
2881 acaaagtaac tcatctaaga ttttggttgg gagatggcat ttggcttctg agaaaggtag
2941 ctatgaaata atccaagata ctgatgaaga cacagctgtt aacaattggc tgatcagccc
3001 ccagaatgcc tcacgtgctt ggggagaaag caccccctctt gccaacaagc ctggaaagca
3061 gagtggccac ccaaagtttc ctagagttag acataaatct ctacaagtaa gacaggatgg
3121 aggaaagagt agactgaaga aaagccagtt tctcattaag acacgaaaaa agaaaaaaga
3181 gaagcacaca caccatgctc ctttatctcc gaggaccttt caccctctaa gaagtgaagc
3241 ctacaacaca ttttcagaaa gaagacttaa gcattcgttg gtgcttcata atccaatga
3301 aacatctctt cccacagacc tcaatcagac attgccctct atggattttg gctggatagc
3361 ctcacttcct gaccataatc agaattcctc aaatgacact ggtcaggcaa gctgtcctcc
3421 aggtctttat cagacagtgc ccccagagga acactatcaa acattcccca ttcaagaccc
3481 tgatcaaatg cactctactt cagaccccag tcacagatcc tcttctccag agctcagtga
3541 aatgcttgag tatgaccgaa gtcacaagtc cttccccaca gatataagtc aaatgtcccc
3601 ttcctcagaa catgaagtct ggcagacagt catctctcca gacctcagcc aggtgaccct
3661 ctctccagaa ctcagccaga caaacctctc tccagacctc agccacacga ctctctctcc
3721 agaactcatt cagagaaacc tttccccagc cctcggtcag atgcccattt ctccagacct
3781 cagccataca acccttctc cagacctcag ccatacaacc ctttctttag acctcagcca
3841 gacaaacctc tctccagaac tcagtcagac aaacctttct ccagccctcg gtcagatgcc
3901 cctttctcca gacctcagcc atacaaccat ttctctagac ttcagccaga caaacctctc
3961 tccagaactc agccatatga ctctctctcc agaactcagt cagacaaacc tttccccagc
4021 cctcggtcag atgcccattt ctccagacct cagccataca acccttctc tagacttcag
4081 ccagacaaac ctctctccag aactcagtca aacaaacctt tccccagccc tcggtcagat
4141 gccccttcct ccagaccca gccatacaac cctttctcta gacctcagcc agacaaacct
4201 ctctccagaa ctcagtcaga caaacctttc ccagacctc agtgagatgc ccctctttgc
4261 agatctcagt caaattcccc ttaccccaga cctcgaccag atgacacttt ctccagacct
4321 tggtgagaca gatctttccc caaactttgg tcagatgtcc ctttccccag acctcagcca
4381 ggtgactctc tctccagaca tcagtgacac caccttctc ccggatctca gccagatatc
4441 acctcctcca gaccttgatc agatattcta cccttctgaa tctagtcagt cattgcttct
4501 tcaagaattt aatgagtctt ttccttatcc agaccttggt cagatgccat ctccttcatc
4561 tcctactctc aatgatactt ttctatcaaa ggaatttaat ccactggtta tagtgggcct
4621 cagtaaagat ggtacagatt acattgagat cattccaaag gaagaggtcc agagcagtga
4681 agatgactat gctgaaattg attatgtgcc ctatgatgac cctacaaaa ctgatgttag
4741 gacaaacatc aactcctcca gagatcctga caacattgca gcatggtacc tccgcagcaa
4801 caatggaaac agaagaaatt attacattgc tgctgaagaa atatcctggg attattcaga
4861 atttgtacaa agggaaacag atattgaaga ctctgatgat attccagaag ataccacata
4921 taagaaagta gtttttcgaa agtacctcga cagcactttt accaaacgtg atcctcgagg
4981 ggagtatgaa gagcatctcg gaattcttgg tcctattatc agagctgaag tggatgatgt
5041 tatccaagtt cgttttaaaa atttagcatc cagaccgtat tctctacatg cccatggact
5101 ttcctatgaa aaatcatcag agggaagac ttatgaagat gactctctg aatggttaa
5161 ggaagataat gctgttcagc caaatagcag ttatacctac gtatggcatg ccactgagcg
5221 atcagggcca gaaagtcctg gctctgcctg tcgggcttgg gcctactact cagctgtgaa
```

Figure 26D

```
5281 cccagaaaaa gatattcact caggcttgat aggtcccctc ctaatctgcc aaaaaggaat
5341 actacataag gacagcaaca tgcctgtgga catgagagaa tttgtcttac tatttatgac
5401 ctttgatgaa aagaagagct ggtactatga aaagaagtcc cgaagttctt ggagactcac
5461 atcctcagaa atgaaaaaat cccatgagtt tcacgccatt aatgggatga tctacagctt
5521 gcctggcctg aaaatgtatg agcaagagtg ggtgaggtta cacctgctga acataggcgg
5581 ctcccaagac attcacgtgg ttcactttca cggccagacc ttgctggaaa atggcaataa
5641 acagcaccag ttaggggtct ggccccttct gcctggttca tttaaaactc ttgaaatgaa
5701 ggcatcaaaa cctggctggt ggctcctaaa cacagaggtt ggagaaaacc agagagcagg
5761 gatgcaaacg ccatttctta tcatggacag agactgtagg atgccaatgg gactaagcac
5821 tggtatcata tctgattcac agatcaaggc ttcagagttt ctgggttact gggagcccag
5881 attagcaaga ttaaacaatg gtggatctta taatgcttgg agtgtagaaa aacttgcagc
5941 agaatttgcc tctaaacctt ggatccaggt ggacatgcaa aaggaagtca taatcacagg
6001 gatccagacc caaggtgcca aacactacct gaagtcctgc tataccacag agttctatgt
6061 agcttacagt tccaaccaga tcaactggca gatcttcaaa gggaacagca caaggaatgt
6121 gatgtatttt aatggcaatt cagatgcctc tacaataaaa gagaatcagt ttgacccacc
6181 tattgtggct agatatatta ggatctctcc aactcgagcc tataacagac ctacccttcg
6241 attggaactg caaggttgtg aggtaaatgg atgttccaca ccctgggta tggaaaatgg
6301 aaagatagaa aacaagcaaa tcacagcttc ttcgtttaag aaatcttggt ggggagatta
6361 ctgggaaccc ttccgtgccc gtctgaatgc ccagggacgt gtgaatgcct ggcaagccaa
6421 ggcaaacaac aataagcagt ggctagaaat tgatctactc aagatcaaga agataacggc
6481 aattataaca cagggctgca agtctctgtc ctctgaaatg tatgtaaaga gctataccat
6541 ccactacagt gagcagggag tggaatggaa accatacagg ctgaaatcct ccatggtgga
6601 caagattttt gaaggaaata ctaataccaa aggacatgtg aagaactttt tcaacccccc
6661 aatcatttcc aggtttatcc gtgtcattcc taaacatgg aatcaaagta ttgcacttcg
6721 cctggaactc tttggctgtg atatttacta gaattgaaca ttcaaaaacc cctggaagag
6781 actctttaag acctcaaacc atttagaatg ggcaatgtat tttacgctgt gttaaatgtt
6841 aacagttttc cactatttct ctttcttttc tattagtgaa taaaattta tac
```

Figure 26E

```
LOCUS       HUMLPL       3549 bp    mRNA              PRI       08-AUG-1995
DEFINITION  Human lipoprotein lipase mRNA, complete cds.
ACCESSION   M15856
NID         g187209
KEYWORDS    lipoprotein lipase.
SOURCE      Human adipose tissue, cDNA to mRNA, clones LPL[35,37,46].
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 3549)
  AUTHORS   Wion,K.L., Kirchgessner,T.G., Lusis,A.J., Schotz,M.C. and
Lawn,R.M.
  TITLE     Human lipoprotein lipase complementary DNA sequence
  JOURNAL   Science 235 (4796), 1638-1641 (1987)
  MEDLINE   87149101
COMMENT     Draft entry and clean copy sequence for [1] kindly provided by
            R.Lawn, 18-MAY-1987.
            Several mRNAs ended at around position 2416.
FEATURES            Location/Qualifiers
     source          1..3549
                     /organism="Homo sapiens"
                     /db_xref="taxon:9606"
                     /map="8p22"
     mRNA            <1..3549
                     /gene="LPL"
                     /note="LPL mRNA (alt.); G00-120-700"
     mRNA            <1..3154
                     /gene="LPL"
                     /note="LPL mRNA (alt.); G00-120-700"
     gene            1..3549
                     /gene="LPL"
     sig_peptide     175..255
                     /gene="LPL"
                     /note="lipoprotein lipase signal peptide; G00-120-700"
     CDS             175..1602
                     /gene="LPL"
                     /note="lipoprotein lipase precursor"
                     /codon_start=1
                     /db_xref="GDB:G00-120-700"
                     /db_xref="PID:g307138"
```

/translation="MESKALLVLTLAVWLQSLTASRGGVAAADQRRDFIDIESKFALR

TPEDTAEDTCHLIPGVAESVATCHFNHSSKTFMVIHGWTVTGMYESWVPKLVAALYKR

EPDSNVIVVDWLSRAQEHYPVSAGYTKLVGQDVARFINWMEEEFNYPLDNVHLLGYSL

GAHAAGIAGSLTNKKVNRITGLDPAGPNFEYAEAPSRLSPDDADFVDVLHTFTRGSPG

RSIGIQKPVGHVDIYPNGGTFQPGCNIGEAIRVIAERGLGDVDQLVKCSHERSIHLFI

DSLLNEENPSKAYRCSSKEAFEKGLCLSCRKNRCNNLGYEINKVRAKRSSKMYLKTRS

Figure 27A

```
                QMPYKVFHYQVKIHFSGTESETHTNQAFEISLYGTVAESENIPFTLPEVSTNKTYSFL

IYTEVDIGELLMLKLKWKSDSYFSWSDWWSSPGFAIQKIRVKAGETQKKVIFCSREKV
                            SHLQKGKAPAVFVKCHDKSLNKKSG"
     mat_peptide    256..1599
                    /gene="LPL"
                    /note="lipoprotein lipase; G00-120-700"
     variation      1611
                    /gene="LPL"
                    /note="g can be a; G00-120-700"
                    /replace="a"
     variation      2743
                    /gene="LPL"
                    /note="t can be c; G00-120-700"
                    /replace="c"
     variation      2851
                    /gene="LPL"
                    /note="a can be g; G00-120-700"
                    /replace="g"
BASE COUNT      1020 a      739 c      806 g      984 t
ORIGIN        Unreported.
        1 cccctcttcc tcctcctcaa gggaaagctg cccacttcta gctgccctgc catccccttt
       61 aaagggcgac ttgctcagcg ccaaaccgcg gctccagccc tctccagcct ccggctcagc
      121 cggctcatca gtcggtccgc gccttgcagc tcctccagag ggacgcgccc cgagatggag
      181 agcaaagccc tgctcgtgct gactctgccc gtgtggctcc agagtctgac cgcctcccgc
      241 ggaggggtgg ccgccgccga ccaaagaaga gattttatcg acatcgaaag taaatttgcc
      301 ctaaggaccc ctgaagacac agctgaggac acttgccacc tcattccgg agtagcagag
      361 tccgtggcta cctgtcattt caatcacagc agcaaaacct tcatggtgat ccatggctgg
      421 acggtaacag gaatgtatga gagttgggtg ccaaaacttg tggccgccct gtacaagaga
      481 gaaccagact ccaatgtcat tgtggtggac tggctgtcac gggctcagga gcattaccca
      541 gtgtccgcgg gctacaccaa actggtggga caggatgtgg cccggtttat caactggatg
      601 gaggaggagt ttaactaccc tctggacaat gtccatctct gggatacag ccttggagcc
      661 catgctgctg gcattgcagg aagtctgacc aataagaaag tcaacagaat tactggcctc
      721 gatccagctg gacctaactt tgagtatgca gaagccccga gtcgtctttc tcctgatgat
      781 gcagatttg tagacgtctt acacacattc accagagggt ccctggtcg aagcattgga
      841 atccagaaac cagttgggca tgttgacatt tacccgaatg gaggtacttt tcagccagga
      901 tgtaacattg gagaagctat ccgcgtgatt gcagagagag gacttggaga gtgggaccag
      961 ctagtgaagt gctcccacga gcgctccatt catctcttca tcgactctct gttgaatgaa
     1021 gaaaatccaa gtaaggccta caggtgcagt tccaaggaag cctttgagaa agggctctgc
     1081 ttgagttgta gaaagaaccg ctgcaacaat ctgggctatg agatcaataa agtcagagcc
     1141 aaaagaagca gcaaaatgta cctgaagact cgttctcaga tgccctacaa agtcttccat
     1201 taccaagtaa agattcattt ttctgggact gagagtgaaa cccataccaa tcaggccttt
     1261 gagatttctc tgtatggcac cgtggccgag agtgagaaca tcccattcac tctgcctgaa
     1321 gtttccacaa ataagaccta ctccttccta atttacacag aggtagatat tggagaacta
     1381 ctcatgttga agctcaaatg gaagagtgat tcatacttta gctggtcaga ctggtggagc
     1441 agtcccggct cgccattcaa gaagatcaga gtaaaagcag gagagactca gaaaaaggtg
     1501 atcttctgtt ctaggagaa agtgtctcat ttgcagaaag gaaaggcacc tgcggtattt
     1561 gtgaaatgcc atgacaagtc tctgaataag aagtcaggct gaaactgggc gaatctacag
     1621 aacaaagaac ggcatgtgaa ttctgtgaag aatgaagtgg aggaagtaac ttttacaaaa
     1681 catacccagt gtttggggtg tttcaaaagt ggattttcct gaatattaat cccagcccta
     1741 cccttgttag ttattttagg agacagtctc aagcactaaa aagtggctaa ttcaatttat
     1801 ggggtatagt ggccaaatag cacatcctcc aacgttaaaa gacagtggat catgaaaagt
     1861 gctgttttgt cctttgagaa agaaataatt gtttgagcgc agagtaaaat aaggctcctt
     1921 catgtggcgt attgggccat agcctataat tggttagaac ctcctatttt aattggaatt
```

Figure 27B

```
1981 ctggatcttt cggactgagg ccttctcaaa ctttactcta agtctccaag aatacagaaa
2041 atgctttttcc gcggcacgaa tcagactcat ctacacagca gtatgaatga tgttttagaa
2101 tgattccctc ttgctattgg aatgtggtcc agacgtcaac caggaacatg taacttggag
2161 agggacgaag aaagggtctg ataaacacag aggttttaaa cagtccctac cattggcctg
2221 catcatgaca aagttacaaa ttcaaggaga tataaaatct agatcaatta attcttaata
2281 ggctttatcg tttattgctt aatccctctc tccccttct ttttgtctc aagattatat
2341 tataataatg ttctctgggt aggtgttgaa aatgagcctg taatcctcag ctgacacata
2401 atttgaatgg tgcagaaaaa aaaagatac cgtaattta ttattagatt ctccaaatga
2461 ttttcatcaa tttaaaatca ttcaatatct gacagttact cttcagtttt aggcttacct
2521 tggtcatgct tcagttgtac ttccagtgcg tctcttttgt tcctggcttt gacatgaaaa
2581 gataggtttg agttcaaatt ttgcattgtg tgagcttcta cagattttag acaaggaccg
2641 tttttactaa gtaaaagggt ggagaggttc ctggggtgga ttcctaagca gtgcttgtaa
2701 accatcgcgt gcaatgagcc agatggagta ccatgagggt tgttatttgt tgttttaac
2761 aactaatcaa gagtgagtga acaactattt ataaactaga tctcctattt ttcagaatgc
2821 tcttctacgt ataaatatga aatgataaag atgtcaaata tctcagaggc tatagctggg
2881 aacccgactg tgaaagtatg tgatatctga acacatacta gaaagctctg catgtgtgtt
2941 gtccttcagc ataattcgga agggaaaaca gtcgatcaag ggatgtattg aacatgtcg
3001 gagtagaaat tgttcctgat gtgccagaac ttcgacccct tctctgagag agatgatcgt
3061 gcctataaat agtaggacca atgttgtgat taacatcatc aggcttggaa tgaattctct
3121 ctaaaaataa aatgatgtat gatttgttgt tggcatcccc tttattaatt cattaaattt
3181 ctggatttgg gttgtgaccc agggtgcatt aacttaaaag attcactaaa gcagcacata
3241 gcactgggaa ctctggctcc gaaaaacttt gttatatata tcaaggatgt tctggcttta
3301 catttattt attagctgta aatacatgtg tggatgtgta aatggagctt gtacatattg
3361 gaaaggtcat tgtggctatc tgcatttata aatgtgtggt gctaactgta tgtgtcttta
3421 tcagtgatgg tctcacagag ccaactcact cttatgaaat gggctttaac aaaacaagaa
3481 agaaacgtac ttaactgtgt gaagaaatgg aatcagcttt taataaaatt gacaacattt
3541 tattaccac
```

Figure 27C

```
LOCUS       HUMTHB       26928 bp    DNA             PRI       14-OCT-1994
DEFINITION  Human prothrombin (F2) gene, complete cds, and Alu and KpnI
            repeats.
ACCESSION   M17262 M33691
NID         g558069
KEYWORDS    Alu repeat; KpnI repetitive sequence; liver specific; thrombin.
SOURCE      Human DNA.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 6128 to 26928)
  AUTHORS   Degen,S.J. and Davie,E.W.
  TITLE     Nucleotide sequence of the gene for human prothrombin
  JOURNAL   Biochemistry 26 (19), 6165-6177 (1987)
  MEDLINE   88077877
REFERENCE   2  (bases 1 to 6667)
  AUTHORS   Bancroft,J.D., Schaefer,L.A. and Degen,S.J.
  TITLE     Characterization of the Alu-rich 5'-flanking region of the human
            prothrombin-encoding gene: identification of a positive cis-acting
            element that regulates liver-specific expression
  JOURNAL   Gene 95 (2), 253-260 (1990)
  MEDLINE   91065538
REFERENCE   3  (bases 1 to 26928)
  AUTHORS   Degen,S.J.
  TITLE     Direct Submission
  JOURNAL   Submitted (22-SEP-1987) S.J.F. Degen, Division of Basic Science
            Research, Children's Hospital Research Foundation, Cincinnati, OH
            45229-3039, USA
FEATURES             Location/Qualifiers
     source          1..26928
                     /organism="Homo sapiens"
                     /db_xref="taxon:9606"
                     /tissue_type="placenta"
                     /clone="L[14,25,33,36,81]"
                     /clone_lib="Lambda-10"
                     /map="11p11-q12; 24 bp upstream of NcoI site"
     misc_feature    405..511
                     /note="MER sequence"
     repeat_region   563..838
                     /note="Alu repeat"
     protein_bind    725..731
                     /bound_moiety="Ap1"
     repeat_region   842..1136
                     /note="Alu repeat"
     repeat_region   1148..1344
                     /note="Alu repeat"
     repeat_region   1814..2070
                     /note="Alu repeat"
     protein_bind    2052..2059
                     /bound_moiety="Ap1"
     repeat_region   2577..2870
                     /note="Alu repeat"
     repeat_region   3122..3415
```

Figure 28A

```
                        /note="Alu repeat"
repeat_region           3804..4087
                        /note="Alu repeat"
repeat_region           4210..4511
                        /note="Alu repeat"
repeat_region           4553..4793
                        /note="Alu repeat"
repeat_region           4901..5201
                        /note="Alu repeat"
protein_bind            4957..4962
                        /bound_moiety="Sp1"
protein_bind            5084..5091
                        /bound_moiety="Ap1"
repeat_region           5231..5443
                        /note="Alu repeat"
protein_bind            5231..5238
                        /bound_moiety="EBP 20"
protein_bind            5711..5716
                        /bound_moiety="Sp1"
protein_bind            5723..5730
                        /bound_moiety="EBP 20"
protein_bind            6047..6054
                        /bound_moiety="EBP 20"
misc_feature            6198..6237
                        /note="MER sequence"
exon                    6544..6653
                        /note="prothrombin precursor"
                        /number=1
sig_peptide             join(6575..6653,7040..7089)
                        /gene="F2"
gene                    join(6575..6653,7040..7200,7860..7884,8127..8177,
                        10504..10609,10706..10842,13181..13495,13820..13948,
                        14033..14159,15317..15484,15982..16155,16698..16879,
                        26327..26397,26544..26687)
                        /gene="F2"
CDS                     join(6575..6653,7040..7200,7860..7884,8127..8177,
                        10504..10609,10706..10842,13181..13495,13820..13948,
                        14033..14159,15317..15484,15982..16155,16698..16879,
                        26327..26397,26544..26687)
                        /gene="F2"
                        /note="precursor"
                        /codon_start=1
                        /product="prothrombin"
                        /db_xref="PID:g339641"
```

/translation="MAHVRGLQLPGCLALAALCSLVHSQHVFLAPQQARSLLQRVRRA

NTFLEEVRKGNLERECVEETCSYEEAFEALESSTATDVFWAKYTACETARTPRDKLAA

CLEGNCAEGLGTNYRGHVNITRSGIECQLWRSRYPHKPEINSTTHPGADLQENFCRNP

DSSTTGPWCYTTDPTVRRQECSIPVCGQDQVTVAMTPRSEGSSVNLSPPLEQCVPDRG

QQYQGRLAVTTHGLPCLAWASAQAKALSKHQDFNSAVQLVENFCRNPDGDEEGVWCYV

Figure 28B

```
AGKPGDFGYCDLNYCEEAVEEETGDGLDEDSDRAIEGRTATSEYQTFFNPRTFGSGEA

DCGLRPLFEKKSLEDKTERELLESYIDGRIVEGSDAEIGMSPWQVMLFRKSPQELLCG

ASLISDRWVLTAAHCLLYPPWDKNFTENDLLVRIGKHSRTRYERNIEKISMLEKIYIH

PRYNWRENLDRDIALMKLKKPVAFSDYIHPVCLPDRETAASLLQAGYKGRVTGWGNLK

ETWTANVGKGQPSVLQVVNLPIVERPVCKDSTRIRITDNMFCAGYKPDEGKRGDACEG
                 DSGGPFVMKSPFNNRWYQMGIVSWGEGCDRDGKYGFYTHVFRLKKWIQKVIDQFGE"
     intron            6654..7039
                       /note="prothrombin intron A"
     exon              7040..7200
                       /gene="F2"
                       /number=2
     mat_peptide       join(7090..7200,7860..7884,8127..8177,10504..10609,
                       10706..10842,13181..13495,13820..13948,14033..14159,
                       15317..15484,15982..16155,16698..16879,26327..26397,
                       26544..26684)
                       /gene="F2"
                       /product="thrombin"
     intron            7201..7859
                       /note="prothrombin intron B"
     exon              7860..7884
                       /gene="F2"
                       /number=3
     intron            7885..8126
                       /note="prothrombin intron C"
     exon              8127..8177
                       /gene="F2"
                       /number=4
     intron            8178..10503
                       /note="prothrombin intron D"
     repeat_region     8330..8675
                       /note="Alu repeat copy A"
     repeat_region     9030..9161
                       /note="Alu repeat copy B"
     repeat_region     9176..9475
                       /note="Alu repeat copy C"
     repeat_region     9643..9937
                       /note="Alu repeat copy D"
     exon              10504..10609
                       /gene="F2"
                       /number=5
     intron            10610..10705
                       /note="prothrombin intron E"
     exon              10706..10842
                       /gene="F2"
                       /number=6
     variation         10774
                       /gene="F2"
                       /note="c in DNA; a in cDNA"
     intron            10843..13180
```

Figure 28C

```
                          /note="prothrombin intron F"
repeat_region   10933..11232
                          /note="Alu repeat copy E"
repeat_region   12089..12390
                          /note="Alu repeat copy F"
repeat_region   12391..12689
                          /note="Alu repeat copy G"
exon            13181..13495
                          /gene="F2"
                          /number=7
intron          13496..13819
                          /note="prothrombin intron G"
exon            13820..13948
                          /gene="F2"
                          /number=8
intron          13949..14032
                          /note="prothrombin intron H"
exon            14033..14159
                          /gene="F2"
                          /number=9
intron          14160..15316
                          /note="prothrombin intron I"
repeat_region   14325..14643
                          /note="Alu repeat copy H"
repeat_region   14820..15126
                          /note="Alu repeat copy I"
exon            15317..15484
                          /gene="F2"
                          /number=10
intron          15485..15981
                          /note="prothrombin intron J"
exon            15982..16155
                          /gene="F2"
                          /number=11
intron          16156..16697
                          /note="prothrombin intron K"
repeat_region   16306..16596
                          /note="Alu repeat copy J"
exon            16698..16879
                          /gene="F2"
                          /number=12
intron          16880..26326
                          /note="prothrombin intron L (no splice consensus at
                          16880); putative"
repeat_region   16952..17098
                          /note="potential new repetitive element copy A; putative"
repeat_region   17145..17206
                          /note="potential new repetitive element copy B; putative"
repeat_region   17375..17614
                          /note="Alu repeat copy K"
repeat_region   18250..18531
                          /note="Alu repeat copy L"
repeat_region   18545..18795
                          /note="Alu repeat copy M"
```

Figure 28D

```
repeat_region    19231..19527
                 /note="Alu repeat copy N"
repeat_region    19706..20012
                 /note="Alu repeat copy O"
repeat_region    20584..20815
                 /note="Alu repeat copy P"
repeat_region    21088..21375
                 /note="Alu repeat copy Q"
repeat_region    21120..21290
                 /note="KpnI repeat copy A"
repeat_region    21387..21539
                 /note="Alu repeat copy R"
repeat_region    21814..22110
                 /note="Alu repeat copy S"
repeat_region    22315..22434
                 /note="Alu repeat copy T"
repeat_region    22441..22738
                 /note="Alu repeat copy U"
repeat_region    22748..22921
                 /note="Alu repeat copy V"
repeat_region    22922..23203
                 /note="Alu repeat copy W"
repeat_region    23204..23496
                 /note="Alu repeat copy X"
repeat_region    23558..23876
                 /note="Alu repeat copy Y"
repeat_region    24037..24363
                 /note="KpnI repeat copy B"
repeat_region    24421..24720
                 /note="Alu repeat copy Z"
repeat_region    24721..25015
                 /note="Alu repeat copy AA"
repeat_region    25112..25282
                 /note="Alu repeat copy AB"
repeat_region    25283..25575
                 /note="Alu repeat copy AC"
repeat_region    25752..25998
                 /note="Alu repeat copy AD"
exon             26327..26397
                 /gene="F2"
                 /number=13
intron           26398..26543
                 /note="prothrombin intron M"
exon             26544..>26687
                 /gene="F2"
                 /note="prothrombin precursor"
                 /number=14
polyA_signal     26765..26770
repeat_region    26881..26928
                 /note="Alu repeat copy AE"
BASE COUNT     6463 a   6624 c   6755 g   7086 t
ORIGIN
      1 gcgtgagcca ctgcgccctg accacatata attttattta attataatgt tgaaagtccc
     61 tttattccac acctctcctc tcattcactc ctggtaggtc atttttaatg atttgatgta
```

Figure 28E

```
 121 tatactgaat tggatgctt cttgctacag ggcaaagacg ctaataagat tttgctggag
 181 ccttttcaca gatgcaagtc aatccaggca gtgtctatag ctgctgaacc caaaatcaga
 241 aagcgagggc tatcaaagct cttctgtcct gatttgcaac tttagtagtg caagaaaaaa
 301 aatcttagaa taaaaaatgg gtaccgttca gagaccttta gagattgcaa ggcatcacag
 361 atgataaaaa gctccatctc tagacgtgtt caggagtggg ttggggcttt gaccttgact
 421 agctgcatca acttggacaa gtcacttcgc ttccctgtgc ctcagtttcc tcatccataa
 481 aatggggata agtatagtac ctacctcata agtcctgcct acctagcaca tggtgagcaa
 541 ttactaaatt gtaggcctag tccctataat cccagccaaca ttggagaaca aggtagggga
 601 atcgcttgaa gccaggagtt ccagaccagc ctgccaaca tagtgagact gtgtttctat
 661 aaaataaaaa aaaaaaatac ccaagcttgg tggtgcaggc ctgtagtccc ggctacttgg
 721 gagtctgagt caggaggatt gcttgagccc aggagttcaa ggttgtagta agctatgatt
 781 gcaccactgc actccagcct ggcgacagag catgaccctg tctctaaaaa tataaaatta
 841 ggccaggcac agtggttcat gcctgtaatt ccaacatttt gggaggccaa ggcaggtgga
 901 tcactgtgag ctcagcagtt cgagaccagc ctgggcaaca aggcaaaatc ctgtctctac
 961 taaaattaca aaaattagcc aggagaggtg gtacacgcct gtaatcccag ttactgggga
1021 agctgaagca ggagaattgc ttgaacccgg gaggcgaagg ttgcagtgag ccaagatcgt
1081 gccattgcac tgcagcctag gagacagagc gagactcgat ctcaataaat aaataaatta
1141 attaattaat aaaaaaataa gttgggcatg gtggcacctg cctgtagtcc aagctactca
1201 ggaggctaga ggtgggagga tcacttgagc caggagttct aggctgcagt gagctattat
1261 cacgccacca tactccagcc tgctgtatgt actccagcct gggcaacaga gtgacaccct
1321 gtctcaaagt aaagtaaaat aaaaattaaa aacaaatta ctaaattgta cttaacagta
1381 ttgtcatcag tcttcctaaa taggaggaca ggcaaaatta agggacttaa catgtgccct
1441 caggtatagt agtttggggc aggccagcat cacccgcaca gtagttctgt actgtaggtg
1501 cgtgttctct gggtcaactt tatggcccag tgaggccgta ctctaccaga atgtcagggg
1561 acaaggggttg ggagaggcaa aagtgctggt ctgaagcagg agtctgggtt tccatcctag
1621 ctctaccacc aattctgtat gaccgtgccc ctccatttc ctccatgacc acatagagac
1681 atggggcagt tggatgaaat caatgattcc cagtcttggc tctatcatgg aaccatttgc
1741 taacttcttt ttttctctta tggatcccat attttttaaag attttttacta aatagaaatt
1801 gacttatact tttccaagct gggagtgtggt ggcatgattt cagctcactg caacctccgc
1861 ctcccgggtt caagtgattc tcctgcctca gcctcctgag tagctgggat tataggtgct
1921 caccaggccc ggctaatttt tttgtatttt tagtagagac agaatttcac catgttggcc
1981 aggctgattt caaactcctg acctcaagtg atctgctcac ctcagcctcc caaagtgctg
2041 ggattacagg cgtgagtcac tatgcccagc cgcttactca catttctag tcaaaataga
2101 aaactgctta agtcactgtc tgcagaagag caaaaaaaaa aaagaaata aaaaattgaa
2161 aactgctgat cagattgaga aaacataag attattcacc acctaaagag aaaaaatttc
2221 agtcgaaagg gaaaaaaatt cattttgtc ttaataaggc aaattcacaa ttttgaggt
2281 tttaacaaaa tatatgcaga aagacaaggc caccccgtag aacgtgcaca cagccctagg
2341 cttggaaatg gctggattta ataatatctg gtcttttcttt gagccctgaa attctctaac
2401 actatgtctt ggaacataat tttactgttt tcagtggtta tagagatttg ctttacaatt
2461 tagcattggt ctttacccat gattttgttt gacgccaact tgttggcagg aatgcacccc
2521 ctgccccccg ctttgttatg gccttgctcc tatagggcaa gaatatctgc tttaaggccg
2581 ggtgtggtgg ctcaggcctg taatcccagc actttgaggg ccaaggcgg gcagatcacc
2641 tgaggtcagg agtttgagac cagcctggcc agtatggtga atcctgtct ctactaaaaa
2701 taacaaaaat tagctgggtg tggtggcaca cacctgtaat cccagctatt tgggaggccg
2761 aaacaagaga accacttgaa cccaggaggc ggaggttgcg gtgagccgag attatgccac
2821 tgcactccag cctgggaaac agagcaagat tccgtctcac acacaaaaaa tatatatatg
2881 tctgctttaa gtatgcaggc cgtgtttgtg ctgaacggca ggaatgccaa acttggctgc
2941 atggtaccaa ctaggaccct cagagttcca aggagaacaa acagttggtt cctggaggct
3001 ggggcttgt atcagaccct gaagactaag catgtgctgg gtccattgtt gtcctgcacc
3061 catggtagtg cactaaacac ctaacctata tttaagtgtt tttgtttgtc caaaaaatgt
3121 ctttttttt tgggagtcaa gagtcttgct ctgttgccca ggctggagtg cagtgacacg
3181 atctcagctc actgcagcct ccgcctcccg ggttcaagct attctcctgt ctcagcctcc
3241 caaatagctg agactatagg cacgcacatc catgcccagc taattttttt attttttagta
3301 gagacgaggt gtctccatgg tggccaggtt ggtcttgaac tcctgtcctc aagtgatcca
```

Figure 28F

```
3361 cctgcctcgg cctcccaaag tggtgggatt gcaggcatga gacaccgcgc ccggcctgcc
3421 ttgtcccttc ttaaaatgag ttgtccattt gtaagctgct gatttctttg ggacattgtc
3481 tccgtaaact tttcataaag catcagtgat ttcaccattc ttccacccaa gcttcaccgt
3541 aaatttgttg tttgttcttg cttcaatttc agcagaattc atttagctct gataagggct
3601 cgcttcaaac tgatgtctta tccttcttag tgcctcaaac tacatcctgt tcactcatgt
3661 tatagcaagt tagtgtgagt ttattttggt gcacaaaaat.tttttttaaat ccatgcagtc
3721 ttttttcata atacgcattt tccatgaact tttcgaagac cccttgtaga tgtctgttgt
3781 ttaaaccacc cagtttacag taatttttt ttttttttga gatgaagtct tgctctgtcg
3841 cccaggctgg agtgcattgg cacactctcg gctcactgca acctctgcct cctgggttca
3901 agcaattttt ctgtctcagt ctcccgagta gctgggatta caggtgtgtg ccaccatgcc
3961 tagctaattt atgtgttttt agtagagacg gggtttcact atgttggcta ggctggtctc
4021 gaactcctca ccttgtgatc ggcccgcctc ggcctcccaa agtattggga ttacaggcgt
4081 gagactcttg cacttggcct acagtaattt tatagcagcc taggctaaga tagccatttc
4141 tgggtataag aatgtcatat actgaacagg cctgcaactg tgagtaaaag tctgcaaaga
4201 ggccgggcag tggctcatac ctgtaatccc agcactttgg ggggccgagg caggtggatc
4261 acctgaggtc agcagttcga gaccagcctg accaacatgg tgaaacccca tctctactaa
4321 aaatacaaaa ttagctgggc gtggtagtgc atgcttgtaa tccctagcat gcacttggga
4381 gctacttggg aggctgaggc aggagaatca cttgtactca ggaggccgag gttgcagtga
4441 gctgagatca cgccactgca ctcctttctg ggtgacagag tgagactcca tctcaaaaaa
4501 acaaaacaaa acaaaacaaa aacaaacaaa aaacccaac aggtaggtag cagtggttca
4561 cgcctgtaat ccccactttg gaggctaaag tgggcagatc acctgaggtc aggagttcac
4621 gtccagcctg gcaacatgg tgaaactctg tctctacaaa aatacaaaaa ttagccaggc
4681 atgatggcgg gtgctgtagt tccagctatt cgggaggctg aggcaggaga atcgcttgaa
4741 cctaggaggt agaggttgca gtgagccgag ttcacgctat tgcactccag cctccatctc
4801 aaaacaaaca acaaaaccca aaatatatat tataatttta ttttatttat tcaattttat
4861 tttattttat tttattttc taggaacagg tctcattcag gccaggcatg gtgctcacgc
4921 ctgtaatccc agcacttggg aggccgaggt ggaggtgggc ggatcacctg aggtcaggag
4981 ttcgagccat cctggtcaat gtggcgaaac cccatctcta ctaaaaatac aaaaattagc
5041 caggtgtggt ggcacacgcc tgtaattcca gctacttggg atactgagtc aggagaatca
5101 cttgaacagg gagatggaaa ttgcagtgag ccgagattgt tccactgcac tccagcctgg
5161 gtgacagggc gagactccgt ctcaaaaaaa aaaaaaaaaa agaaagaaag aagaaagaa
5221 agaaacagga tcttactctg ttacccaggc tggagtacag tggtgcaatc atagctcact
5281 gcaggcatgc accaccattc ccagctaatt tttaattttt tttggtagag atgagggtct
5341 tgctatgttg cccaggctgg tctcaaactc ctggcctcaa gcgatcctgc catgtcggcc
5401 tcccaaagtg ttgggattac aagtgtgagc cactatgcct ggcctaaaaa tatatatatg
5461 aaaatatata agaaatgggc ctcccaggaa ttaaggtgtt tgcgggagtc ctggtcccca
5521 gttttctgc caacactccc tgttcccaca catgacctgg tccagacccc aaacagccag
5581 gcccaaagga caggtgaggc gaggcgagaa cttgtgcctc cccgtgttcc tgctctttgt
5641 ccctctgtcc tacttagact aatatttgcc ttgggtactg caaacaggaa atggggggagg
5701 gacaggagta gggcggaggg tagggtagga ccagaagcct ctctaggcct gccatgggc
5761 aggcagccag ggagaaggag ggcccctcag tggagaccca gggatttcag tagcccctgt
5821 tccgggacag gcgcaggtcc tgggaggtga cagaagatag actaaaggcc caagagtccc
5881 tggacctgac tcctcccagc agctgccaca cacaaacaca cctccaggca ccctggacag
5941 gaaggaggag aaatgggccc ctcctccagt ggctgagaag ctggggcaaa tgttggctgt
6001 tcctatccct ggtgcatccc atggcgaggg gcaacttcca tcaggccaca cctttttatct
6061 ttgtctctat ttttgatatc tgtgtattat gattatacaa acccccacat tggcctatat
6121 gtgcagatct gattaagaac ttacgatatt ccatggacat tccattccta atctccttta
6181 gtcctcacaa caaagtatta ttcccattgt atagatgagg aaactgaggc acacagagat
6241 gacaagcaac caccgctata tgttaggatt cgaaggagct ccaggaaagt ctcatagccc
6301 cactggccag aatgggctaa atctcagagg gggagggtgg gagatggggg tgacagtgac
6361 cttttttgtg actcctccta gaccatccat ccctgctccc aggaggacct gtcctcccag
6421 atggtggaga tggacaggag gactatctac ccacccgtcc ccacggccct gaccctctga
6481 cctcaccctc tccgctgatt tcttcatgtt agttcaacat tacccagagg ggtcaggaca
6541 gacaattcct cagtgaccca ggagctgaca cactatggcg cacgtccgag gcttgcagct
```

*Figure 28G*

```
6601 gcctggctgc ctggccctgg ctgccctgtg tagccttgtg cacagccagc atggtaaggg
6661 agtgcttgca ggctggaaca ggctggagga ctggggtgtg ggcccatggg ctggggtctc
6721 ctggctggac agagcacaca gagctggccc ctaagtaggt ctcagcccca ggcggccagc
6781 ttagggaaga agtcaggagc tcagggctgg aaagagaatg gctgcttctc tcttccaata
6841 tagggagcag gctgggggca aggggcagtg taggaggggc acaggggggcc acatttagca
6901 gccttccagg ccttccacca gcccagactg cctctctcag aagccagcag gggagggtgg
6961 gcttgcttca tgcccccaga tggccaagac tgcctgttcc tgaggtcgct gttccatgac
7021 cccccaccg cctttacagt gttcctggct cctcagcaag cacggtcgct gctccagcgg
7081 gtccggcgag ccaacacctt cttgaggag gtgcgcaagg caacctaga gcgagagtgc
7141 gtggaggaga cgtgcagcta cgaggaggcc ttcgaggctc tggagtcctc cacggctacg
7201 gtgagcctgg gctgctcgga cggtgccggg cctcagacc gggcccaact ctagacactt
7261 ccacagagaa gcaagcgagg aacgccacag ccccttcgct gctcacagcc tcatttcaac
7321 tctgagcccc tcctcacagg gctggcaaga ggagcggcct cagcctttcc tgggggtctc
7381 tgtgcctgga ctgtgtccct gtgcagctcc atgacatggg gaggcctcca cagtcttcag
7441 acatccacct gccttggagc tctgtgtcca catggcctcc tcagcggcag actcccacac
7501 cacccttgag gggtgggact ctggggaggc caccacaagc ccccgggctc aagactcagt
7561 gttcctggag ctctgtgtcg cctttcctgt ctgtagggac tctgccaggg acccactgcc
7621 ccctctcctc ccatctcccc cagcctcttt cagactcggt gtgtgtgttg gaggaactcc
7681 cctatcctca aatattcttc tccttttgga aacaaagta ggaaactctg ccacaaacct
7741 ccccagagcc tgcccctgc gtgaccaggg taaggaaagt gtgaggagga gcataacatt
7801 tactaaaaca acacaaaaca ggagctgccg tagcctcact cccagccctt gttttcagg
7861 atgtgttctg ggccaagtac acaggtgagc accggaagg atttgcccca ggaagggagg
7921 cctggggacc ccagtgagag aattctaccc agagaatctt ctgctgcacc tagccatcca
7981 cccatccacc ccttccccac tccttccttg gtccctccca tctgttcatc catctttctg
8041 tttctcacca acatcccatc caccctgact ccagctcatc ctggccatac cccaatccca
8101 aaggtaaaca cctgggtctt ttccagcttg tgagacagcg aggacgcctc gagataagct
8161 tgctgcatgt ctggaaggtg agcaactgac acgggtttgg ggagcaggac atggagggga
8221 gcttgggaga agagctcagg ggtgggtttg gagtgtggct ggtggaggcc gaggcagtcc
8281 ccagcatctg acattgctcc cattcctggg gtcaagatgt ctctttgtac ctggctctgt
8341 gtctggcatg cgaacgaatg aatgaatgaa tggactaatg aattaatgtt tttttttttg
8401 agacagagtc tcgctctgtt gcccaggctg gagtgcagtg gcacgatctt ggctcactgt
8461 aaactccgcc tcccggattc aagcaattct ctgcctcaac ctcccaagta gctgggatta
8521 caggtgctcg ccaccacgcc tagctaattt ttgtatttt agtagagacg gggtttcacc
8581 atgttggcca ggctggtctt gaactcctga cctcgtgatc cacccacctc ggcctcaaag
8641 tgctggatt atagaagtga gccaccgcgc ctggccatga attcatgttt aaggcttcat
8701 tctcctttgc ctgacccgag tctctgcccc cacctagtca gagctttgat gatgtcacat
8761 tccccttcta gctttaggtg tcactgaacc aaacaggaac ccaaaccccc agctgctctg
8821 acaccaagga cttccctaag catgccaagg tgtttctagc acctggcctt gcatatgttg
8881 tcaatttcct ctggagcgac catcacatct actgaacact ttcctatcct tcaaggactg
8941 cttcaaatgt caccacttt gctgagactt cagggagcac cctccctcct gcactgtgtc
9001 tgaaggcacc tttagcacga caaaaatgga actctttgtt tatttataag agcagggtct
9061 ccctttttg ccaggctgat cttgaactct tgggctcagg caattctccc atctcagtct
9121 cccaaggag tggattataa gtgtgagcca ccatgcctgg ctgccatact ttcatttttt
9181 ttttttttt tttgaggtgg agtctcactc tgtcgcctag gctggagtgc agtggcgcga
9241 tctcggctcg ctgcaacctc cgcctggcgg ttcaagtgat tctcctgcct tagcctcctg
9301 agtagctggg attacaggca cactacca tgcccagcta attttttgta tttttagta
9361 gagacggggt ttcaccatgt tggccaggct ggtcacaaac tcctgacctc aggtgatcca
9421 ccagcctcag cctcccagag tgctgggatt acaggtgtaa tccactgcgc ccagcctcat
9481 ttgttaaatt acgtactcaa cagacatttt acaaagttcc tgctacgtgc caggcactat
9541 atcaggtgct ggggatttta agagaatcaa atacagtctc tgccttcaag gaattcaaaa
9601 tctcaaaaga gaacaaaaat acaaaatatt aaaatgattg cggccgggtg tggtggctca
9661 agcctgtaat cctagcactt gggagctga ggtggcgcc caggcaggg gtttgagacc
9721 atcttggcca acatagtgaa accccaaccc tctactaaaa atacaaaaat tagctgggt
9781 gtggtggcac gcgcctgtaa tcctagctac tagggaggct gatggggaga atttcttgaa
```

Figure 28H

```
 9841 tctgggaagc gaaggttgca gtgagctgag atcatgccac tgcaccttca gtctcggcat
 9901 cagatcaaga ctcatctcaa atacataata aataataatt caataagtga ttgcaagaaa
 9961 gttctgttca aggcaccaag agaccacagg aaaatgagtg tctggtttgc cagaaaatga
10021 gagatggctt cccaggagag gcagagttct gctggcccta gtgggatgca tggatgaaca
10081 aacaagtggg cattccagtc agaagaaaca atccgtggaa agacccagag gcatgagaag
10141 ctgagctagc agggacaggt agaccagggc cagttgaaaa ggaccttcat cactttttca
10201 tcctgctggc caagagaagc cacagaatgg aagctccatg agggcagggc tgtgactgtc
10261 ctattggttg atgtgtactg agcaccgac agtgcctgtc atatggtagg cacttagcga
10321 atatttggag gccactgttg agtgaatggg agaactgctg gttgcagagg aagagggct
10381 gggtgaatgc aggttcagga ttgtggacct gcatgagctg ggaggtgggg gatagacaac
10441 tttgcaggga gagaggaaat aagtccccag gctccaaggc tgaccgggt ggggtctccg
10501 caggtaactg tgctgagggt ctgggtacga actaccgagg gcatgtgaac atcacccggt
10561 caggcattga gtgccagcta tgaggagtc gctacccaca taagcctgag tgagtgaggg
10621 gtcggccttc ccaccatggg ctgagaacag ggagcaagcg tacctcaagt tcaacagcct
10681 cctgttgggc aatttcctct tccagaatca actccactac ccatcctggg gccgacctac
10741 aggagaattt ctgccgcaac cccgacagca gcaccacggg accctggtgc tacactacag
10801 acccaccgt gaggaggcag gaatgcagca tccctgtctg tggtaggctg ggggcagtgg
10861 ggcgacccat gaccaagccc gggggcttca tggggcctgg cagcctggga tgggaaccaa
10921 gaatactggc tacccaggca cagtggctca tgcccgtaat cccagcactt tgggaggctg
10981 aggcaggcag atcacctgag gtcaggggtt tgagaccagc tgggccaaca tggcaaaacc
11041 ccgtctctac taaaaataca aaaattgcca ggcgtggtgg tgggcgcctg taatcccaac
11101 tactctggag gctgaggcac gagaatcgct tgaacccggg aggcggagtt tgcagtgagc
11161 tgagatcctg ccactgtact tcagcctagg cgacaagagc aaaactctgt ctcaaagaaa
11221 aaaaaaagat gctggccacc ttcagagctg gcgtcagtca ttcagatcat atctgtgcct
11281 attgctcagt aaagtcaggg aatcaggga tctgagtggg gggatctgcc agcctcctcc
11341 tcccctccc cactcttgac ttccttatgg tctaggctgt ggctcattcc aaacatgcct
11401 cctttctgat caaggcactc ctccctccgg gaagccctcc ctagccattt cagtccacac
11461 accctgttct gagtatcaca gagcaagcct tgtgcagttt ggccgcggg attctgtcat
11521 tattatttcc ttggtgtgtt aagtagctat agccacccct tccctgaggc agaccacaat
11581 aagcatttct ttttcccatg agggttggca ggtgtggctg cactcgctaa tgcgtctgta
11641 gggtcaactg acggaggttg gccctggctg ggtggctctg attcaaataa tgggtccagc
11701 tgagtctggc tcctcgttga gggttgggcc tagatctgct ccacgtgcgt tcatgctggg
11761 gctgaggctg aagaaggta cctgggaaaa ctcttcttat gctgatgaca gacacagaaa
11821 acaatgaaca gaaaagcgtc ttctgtcctg aaggcctggc tcagaacagg cacagtcagc
11881 cctgccacg ttccattggc cagagcaagt atatgttcaa ggccagggtc aagaggtaaa
11941 ctacacctca gcctgtaaaa tcacagagca agggatgtgg atgcaggcag gggtaaagaa
12001 tttgtgccga ttaccagtcc acaaacatgc gttagtgttt gttctctagg caaccctgtc
12061 gggcccattg ctcattcctg gggttggtct tttttttttt tctttctaag aaggagtctc
12121 actcccttgc ccaggctgtt ggagtgcagt ggccctatct cagctcactg caacctccgc
12181 ctcctgggtt caagcgattc ccctgcttca gcctcctgag tagctaggat tacaggcgtg
12241 tgccaccact cctggctaat ttttttttat gttagtagag acggggtttc accatgttgg
12301 ccaggctgat ctcaaactcc tgaccttgtg atcctccgc ctcggcctcc caaactgctg
12361 agattacagg ggtgaggcac tgcgcccagc cattttttt ttttttttt tttgagatgg
12421 agtctcactc tcacccaggc tggagtgcag tggcataatc ttggctcact gcaacctcca
12481 cctcctgggt tcaggcgatt ctctgcctca gcctctcata tagctgggat tacaggcaca
12541 cgccaccacg ccttgctaat tttgtatttt tagtagagac ggggttcttt catgttggcc
12601 ttgcctgact tgaactcctt gttccggtga tctgcccagc tcggcctccc aaagttctgg
12661 gattacaggt gtaagccact gcgcctggcc cctggtattg gtcttatagc aagtttatcc
12721 caacaaaaac agctactatt tactccccaa cccccataca cacgcacaca cattgatgat
12781 aaataagttg caggcttgca gaaattggcc catccaggtg aacagcctag tgatccgagc
12841 aagcgtcctg ctgtgcagct ataaaaacat gactcctcca gcagctccag gcagccacta
12901 ccagttggtt acagatggcc taggaggcca aacctggtta ctatctctgg tttattatgt
12961 gccagacact tatgctgtat attttgttta atcctctcaa caaacctgca aaagtggcat
13021 tagtaacccc tttaaaggca aacggtcaga agcccagaga ggttaagtaa cctgaggtca
```

Figure 28I

```
13081 cacaggcaga aagcagcaag accggggttc acacccctgt ctgttccggt ccatgtgtgg
13141 tctcactcac tctgctgcct ccttgcccct cacccaccag gccaggatca agtcactgta
13201 gcgatgactc cacgctccga aggctccagt gtgaatctgt cacctccatt ggagcagtgt
13261 gtccctgatc gggggcagca gtaccagggg cgcctggcgg tgaccacaca tgggctcccc
13321 tgcctggcct gggccagcgc acaggccaag gccctgagca agcaccagga cttcaactca
13381 gctgtgcagc tggtggagaa cttctgccgc aacccagacg gggatgagga gggcgtgtgg
13441 tgctatgtgg ccgggaagcc tggcgacttt gggtactgcg acctcaacta ttgtggtgag
13501 ctgcctgggt aggggcctg agttgcaggg acaaatccta gtgggaataa caacagccgc
13561 ttctgcttat cgaacgctta cctcattgag tgcgctcatt acagccttac agtaaccagg
13621 tgggggtaa ggtcctgtgc ccatttcaca gataagtaca ctgaggcccc aggaggttat
13681 tgcctagtag cccaactgtg catgcacgct taacctctgc accaaatggc tccaaggcc
13741 cgtaggggaa ctgggggat ctagggatg ggtgaggaat ggcccagccc agtcccggcc
13801 ggtgcctggg tcccaacaga ggaggccgtg gaggaggaga caggagatgg gctggatgag
13861 gactcagaca gggccatcga agggcgtacc gccaccagtg agtaccagac tttcttcaat
13921 ccgaggacct ttggctcggg agaggcaggt gaggtagtgg gcatccgagg ggatgcgggg
13981 ctgcggggct ggtggccagg acttgcccct cactgcttgg cttgctctgc agactgtggg
14041 ctgcgacctc tgttcgagaa gaagtcgctg gaggacaaaa ccgaaagaga gctcctggaa
14101 tcctacatcg acgggcgcat tgtggagggc tcggatgcag agatcggcat gtcaccttgg
14161 tgtgtcctgg agccctgcgc taccattcac tcctgggggc aggtgtgctg ctggaccccc
14221 accctcaggc cctgcctgca ggcctgggct ttacagatga acagctga gcatccagga
14281 tcccaccaac tccacacagc agccacatga gatggttgt ttacttcttt ttttttgtt
14341 tcttagatgg agtcttgctc tgtcacctag gctggagtgc agtgctgcaa tctcggctca
14401 ctacctcgat ctcagctcac tgcaacttct gccttccggg ttcaaacgat tctcttgcct
14461 cagcctcctg agtagctgaa tttacagaca tgcgccacca cacccggcta attttgtat
14521 tttaagtaga gacagggttt caccatgttg gccaggctgg tcttgaactc ctgacctcaa
14581 gtgatccacc tgcctcagcc tcccaaagtg ccgggattac aggcatgagc caccacaccc
14641 ggcccatggg tcctttactt ctaagcagat ggtaaagctg agactgacgg agctggtggc
14701 tcacctccgc gcacagctaa tgggtttgaa tccagttctt ctgattccag agctgtgcta
14761 cgctatgtga actctggact ggaaggacct agttaggggg tgcaaaaagc aggaggcagg
14821 tcaggtgcag tggctcaccc ctgtaatccc agcactttgg gaggccaaga caggaagatc
14881 acttgagggc aggagttcga ggccagcttg ggcaaaatgg taaaacccccg tctctactaa
14941 aaatgcaaaa attagccagg tgtagcagca tgtccctgta gtcccagcta ctaaggaggc
15001 tgaggcggga ggatcgcctg agcccaagag gctgaggctt cagtaagctg tgactgtacc
15061 attgcactcc agcctgggtg acaagagtga gaccctgtct caaaaataaa taaataaata
15121 aataaaagt gtgaggcagc ccctcagcat cacacgagg ctccagcccc aaaggcggcc
15181 agcccaagct tggatctggg ccccggaggc agctctgccc agctgggttc ttagacctgg
15241 gattgttact tctagggctg gtgtagaggc agcccccctca tcctcagctc ctaatgcttc
15301 ctgctgcccc tcccaggcag gtgatgcttt tccggaagag tccccaggag ctgctgtgtg
15361 gggccagcct catcagtgac cgctggtcc tcaccgccgc ccactgcctc ctgtacccgc
15421 cctgggacaa gaacttcacc gagaatgacc ttctggtgcg cattggcaag cactcccgca
15481 caaggtacag aactggtggc ccgtgggtgt ctggcagggg tctgagtcct ccaaagcgat
15541 catgagggggc cttggtggct ccgggacaca taggatgttc tgtataccc ccagaatata
15601 acatcccagc agtctctgct ggaaagccat ttggtcacgt cctgactgag gcttggagcg
15661 cggggagaat ccgtctgtct ctggtccctc caacactagg atatagccca tgtgggagtc
15721 tctgaaaata gagtctgtct ggactagggc gtgcagcctg tgccctgtc ccgtcctcc
15781 aggctgtctg actccaaagc cctgcacggc tttaggccca ggaagaaaca cccagggggc
15841 tgccatggca ggaaccagcc ctatcccctc cctggtggcc tgcaggacac actgtctccc
15901 agaaccccaa gggcaggcag tttcctgctc cttgctgggt gaacctgcag cttctccatt
15961 tctttcttgg ggtctctgca ggtacgagcg aaacattgaa aagatatcca tgttggaaaa
16021 gatctacatc caccccaggt acaactggcg ggagaacctg gaccgggaca ttgccctgat
16081 gaagctgaag aagcctgttg ccttcagtga ctacattcac cctgtgtgtc tgcccgacag
16141 ggagacggca gccaggtggg ccaccagatg cttgttagct gagggggcaga agccaagttc
16201 tgggcctggc tctgatacca agtagccttg caagagcccc tttccctttt ccaggcctcg
16261 gtttcttgga gtgaacccaa aagttctttt cagtactggc gttttatttt ttatttatat
```

Figure 28J

```
16321 ttatttattt actgacggag ttccactctt gtctcccagg ctggagtgta gttgtgcgat
16381 cttggctcac tgcaacccca cctcctgggt tcaagcgact ctcctgcctc agtctcctga
16441 gtagctggga ttacaggcta attttgtat ttttagtaga gactggtggg tttcaccgtg
16501 tcggccaggt tggtctcgaa ccctgacct caagtgattc acccgcctcg gcctcccaaa
16561 gtgccgagac cacaggcgtg aacgtctgtg cccagccagc tctggcgttt tagattctgg
16621 tctctaagaa atggcgttgg ggccaggcgg ctcctgtggg ggttggctct cactaggccc
16681 ttcttccttc cccaaagctt gctccaggct ggatacaagg ggcgggtgac aggctggggc
16741 aacctgaagg agacgtggac agccaacgtt ggtaaggggc agcccagtgt cctgcaggtg
16801 gtgaacctgc ccattgtgga gcggccggtc tgcaaggact ccacccggat ccgcatcact
16861 gacaacatgt tctgtgctgg caagtctgtg cagggcggc tgagggaaca gtggggccca
16921 agctgggaga actgagttgt gcctgggttc aagccatgtg actttgagca agttgcctaa
16981 cctcttggtg gctcagtttc ttcctctgta aatggaggt aaaagtctct atcccataag
17041 gttatgggag ggttaaatga agtagtatat attaatgtac ttggcatagt atcagtcacc
17101 agtgagctca gatagcagca agaggctgcg ggtagggaaa tgccattcat tcagtcactc
17161 agcaaatatt tattgagcgc ctatcacgtt ccaggcagcg ttctagggta tacagcaggg
17221 acccagacgg acaatgtctg tgccctcaga gagcttcctt cctaggaggg cacatccata
17281 aacagatcta aacagcaat ccctgaccag tgctgtgaag aaaaatgaag cacagggaga
17341 gagaacggct gatgaagtgg gcttctaaat agggtggcca gacaaggtgg gcagatcact
17401 tgaggtcagg agttcaagac cagcctggcc aacatggtga acccccgtct ctactaaaaa
17461 tacaaaaatt agctggtcat ggtgacgcat gcctgtagtc gcagctactc aggaggctga
17521 ggcaggagaa ttgcttgagc caggaggcg gaggttgcag tgagctgaga tcgggcatca
17581 ttgcactcca gctggcaac acagcaagac tccattgatc gatcgatcaa tcaatcaatc
17641 aggtggccag agaaggttgg agaaggcctc cctgagaagg tgatgtctgg gcagggactg
17701 gaagagggga aggaaggagt gagcaggcat atctagggga ggagcaccgc aggctggggg
17761 catggcaggc actaaggccc tgaggtggga gcactcttgg cttgtctggg gagcagtagg
17821 gaggcctggg gggctgagga ggggcagcag tgggtgaggg gagagagggg ggcaggcaga
17881 ggacagccac ttcctttagg gcctggaagg acttttattga gtgagatggg aagttattga
17941 ggggcttgag gcaggttaag aaatgatgtg actgacttta aaagtaaaaa ataaaaaaat
18001 ttagtgtaat ttcagactca cagaaaagtt gtaaaataa tacaaagatt tcctgtatac
18061 tgtcatccag attgtcctcc attctgtgga tgtgtgggaa tttttatata tatatatgca
18121 tagtttgaga gcaaatcatg aatatggttt ctttttaccc ataaatactt gagtatttcc
18181 aaaaaaaaaa aaaataccca aggatgttct cttatgcaac cacaatacaa atattaaaac
18241 ccggaaattt tttttgaca tagcttcgcg tcacccaggc ttgagtgcag tggcacaatc
18301 tcggctcact gcaacctcct gctcccaggt tcaagtgatt ctcctgcctc agcctcctga
18361 gtagctggaa tcacaggcat gtactaccat gcctagctaa tttttgtatt tgtagtagag
18421 acagggtttc accatgttgg ccaggtcggt cttgaactcc gacctcaggt gattcacctg
18481 cctcggcctc ccaaagtgct gggattacag gcgtgaacca ctgtactcgg ccaaaaccag
18541 gaaatttttt ttttttttg agatggaatc ttgctctgtt gcccaggcta gagtgcagtg
18601 gcatggtctc ggcttacttg gaattacagg tgcctgccac cacgcccggc taacttttg
18661 tatttttagt attttagta gtgatggggt ttcaccatgt tggccaggct ggtcttgaac
18721 tcctgacctc gggtaatcca cccactcgg cttcccaaag tgctgggatt acaggcgtga
18781 gcaccagcac ctggcccaaa accaggaaat taatgatgat acaatattat tgtctaatct
18841 atagacctta ttcaaatttt tgttagtctt gctaatgtct tttataggga aaaaaaaaa
18901 aaaagcgtg tttctcaccc aggattcaat gaaggatctt tcttttgtctt ctatgacctt
18961 gacatgtctg atgagtgcag tctggttatt ttgtacactg gccctgaatc cgggtttgtc
19021 taaggtttcc tcacggtcag gttcgggctc agtggtcaga tgtccttctt ggtgcatcct
19081 gttaactggc acatgagaac aatttcttgc atatgtggtg agtctaactc tgacctcttg
19141 aggaaggcaa tgtctgccaa gtttctgct gtaacttctg ttttttcctt tgtaattaat
19201 aagaatctgg taaagagaca ctttgatgtt ttttttttt tttttttttg tgatggagtc
19261 tccctctatc acccgggctg gagtgtgtgg tgcgatctcg gctcactgca acctccatcc
19321 cccaggttca agtgattctc ctgcctcagc ctcccaagta gcagggatta caggcatgtg
19381 ccaccacacc cagctaattt ttgtattttt agtagagatg gggtttcacc atgttggcca
19441 ggatggtctc gaactcctga cctgtgatc cgtctgcctc agcctcccaa agtgctggga
19501 ttacaggtgt gagccaatac gcctggccta ctttgatatt ttgtattctg tttgcatcaa
```

Figure 28K

```
19561  aaccttctcc caactagggt gactaccaaa tggcacttat ctaattctgt cattccttct
19621  acatttgtta gttactttat tgcttccctt cctttcattc tatcagtgtg gacttaagga
19681  tccttacttt attctaaggg ttcacctttt ttttctttt ttttgagatg gagtttcgcc
19741  catgttgccc aggctggatg gagtgcaatg gcgtgatctc ggctcactgc aacgtcctcc
19801  tcccaggttc aagcaattct cctgcctcag cctcctgagt agctgggatt acaggcatgt
19861  gccaccacgc ctggctaatt ttttgtattt ttagtagaga cagggtttca ccatgttggc
19921  caggctggtc tcgaactcct gacctcaggt gatccgcccg cctcagcctt ccaaggttct
19981  gggattataa gcgtgagctc taccgtgcca ggccatactt tgttactact gttattttt
20041  ctgatgctca gatgatccca agtttggcct gtggaagtcc cttcaagctg cttctgtga
20101  cttggggaga tgttctgtca ttctttgagt actttctttc tttctggcac agcaaaatga
20161  ttcaggttaa tcctactttc cttactgtag tgttggaacc agccatttct ccagggaacc
20221  cttgtagtca agagtggaat ttagaactga gatctgggtg ctggcgtgtg cacattgcta
20281  gtgggatgtc attacttcta ggctctctta gtggacagaa ccagaaaaaa attatatgat
20341  gcatatacca atatctctat catctatata aaaaaccatg agttcctact gaaacctcca
20401  attccattct aacaccacag gattaatttt agcttttcct tttccatatt tgtaactctc
20461  tctgttgaca gtgagaaacc tgaccctcat tatctgtaat gcatttgcct atttgaacaa
20521  tactagaata tagtttcaaa atcctccatc cataacacta ttaaaaccaa tcctatggct
20581  gggctcagcc cactgcaacc tctgcctcct ggactcaagc cagcctccca ctttagcctc
20641  ccgagtagcc agggctacag gcacacacca ccatgcccag ctaatttttg tattttttgt
20701  agagactggg tctcactgtg ttgcccagac aggtcttgaa ctctgagctc aagtgatcca
20761  tccaactcag cctcccaaag tgctaggatt acaggtgtga gtcaccatgc ctggcctctc
20821  ctagtaaatt tttagaagtg gtgttgttag gtcaaaaggc aaacatgtat gtcatttttt
20881  agagattttt aaatttcttt ccataagggt tgtaccagtt tgcatttcca tcacagtgta
20941  tgagaatgcc tgtttcccca caaccttgcc aaaagaatgt cacagtttaa attttaccaa
21001  tctgagaggt gagaaatagt acctgaaatt gtttaacgga catcttcaaa ttgaaattga
21061  ggttgacaac gaatcatagt taggaccttt ttttttttt tttttgagtg ggtctcctcg
21121  tcaccaagct gagtgcatgg cacgatttgc tcactgcaac ttccgccttc tgggttcaag
21181  cgattctcct gcttcagcct cccaagcagc tgggactcca ggcgcgagtc accatgcccg
21241  ctaatttttg tattttagt agagacaggg ttttaccaga ttggccaggc tggtctcgaa
21301  ctccttacct tgtgatcctc ccgcctcggc ctcccaaagt gctgagatta caggcatgag
21361  ccaccacgcc tggcctaagg accatttta tataattttt tttttgagac agagtcttgc
21421  tttgtcaccc aggctggagt gcaatggtgc aatcttggct cactgcagcc tccacttccc
21481  tggttcaagt gattctcctg cctcagcctc ccgagtagct ggttccacag gtgcgtgcct
21541  ggctagtatt tgtattatat aatttttttg tgaattgtct cttcatggtt ttttgcccat
21601  ttttggtcc ctttcttatc aatttttgtg agttcttcgt atttatatta ggcctttatt
21661  tgtgatatac attgcaaatg ttttctccta gtttgtcagt ttttttaacc tcatgtataa
21721  tttttctggc catgcagttt aaaaaattac taggtagtca aatttatcaa tcattattta
21781  taaatctggt ttgaacagag ataaactttc ctggccaagt gtggtgttta cacctgtaat
21841  cccagcactc tgagaggctg aggtggggat cacctgaggt cagaagttca agaccagcct
21901  ggccaacatg gtgaaaccct gtctctacta aaaatacaaa aattagctgg gcgtggtggc
21961  tgatgcctgt agtcccagct actcaggaga ctgaggctgg agaattgctt gaacctggga
22021  ggcggaggtt gcagtgagca gagatcgtgc cgctgcactc cagcctgggt gacagagcaa
22081  gactctgtct caaaacaaa acgacaaaaa acaacaacag aaaagccttt cctgatagct
22141  aggtcattga ggaattcact catgttttct tctagtacct gatttcattt ttctgcactt
22201  agattcctga ctcatatgga gtttattttt gtatctgatg tgaggcatag atctaattta
22261  ttatttccca aatggctaac tagctgtctc taaacccttt attaaaatt attggccaag
22321  tgcggtagcc acacctgtaa tcccagcagt ttggaaggct gaggcaggat tgcttgaggc
22381  caggaattca aaaccagccc agacaacata gcaagaccct gtctctacaa gaaaatattg
22441  gtcaggtgtg gtggctcacg cctataatcc cagcactttg ggaggctgag gcaggtggat
22501  catgaggtca ggagatagag accatcctgg ccaacatggt gaaaccctcg tctctactaa
22561  aatacaaaaa attagctggg tgtggtggcg catgcctgta gtaccagcta ctcaggaggc
22621  tgaggcaggg aatcatttg aacccaggag gtggaggttg cagtgagctg agatcacgcc
22681  attgaactcc agcctggcga cagagcaaga ctccatctca aaaaaaaag gaaaagaaa
22741  atatttaaa aattagctgg gcatggtggc atgtgccttg tagtctcagc tacttgagag
```

Figure 28L

```
22801 gctgagttag gaggattgct tgagcctagg agttcaatac tgcagtgagc tatgaccgca
22861 ccattgcact ccagcctggg caacagagtg agacctgtt tctattaaaa aaaaaaaatc
22921 ggctgggcgc ggtggctcac gcctgtaatc ctagcacttt gggaggccga ggcgagcgga
22981 tcacctgagg tcaggagttc aagaccagcc tgaccaacat ggaaaaaccc tgtctctgct
23041 aaaaatacaa aattagccag acatggaggc acatgtctgt aatcccagct actcgggagg
23101 ctgaggcagg agaatcgctt gaacctggga gacggaggtt gcagtgagct gagatccctc
23161 cattgcactc cagcctgggc aacaagagta aaaactccgt ttcgccaggt gcggtgactc
23221 acacctgtaa tcccagcact ttgggaggcc gaggtgggtg aatcacaagg tcaggagttt
23281 gagacaagcc tggccgacat ggtgaaaccc catctctact aaaatacaaa aaattagcct
23341 ggcatggtgg tgtgcgcctg taatcccagc tacttgggag gctgaggcag gggaatcact
23401 tgaacctggg aggaggaggt tgcagtgagc cgagatggtg ccactgcact ccagcctggc
23461 aacagagcga gactctatct caaatcaat caatcaatca atcaatcttt gaactagtga
23521 tttgagattt cacctttatc acattctaga ttgtatctta ttttcattta tttatttgaa
23581 atatagacaa gtctccctgt gctgcccagg ctgatttcaa actcctggct gggctcgagc
23641 aagtctcccg ccttggcctc ccaaactgct gggattacag acgtgagcca ccatacctga
23701 cccaggtttt attttttagt tttatttttt cctgcatcca gctaatttga tttgatttgt
23761 agagacgggg tcttgctatg ttacctaggc tggtctcgaa ctcttgggct caagtgatcc
23821 tcctaccttg gcctcccaaa gtgttgggat taccagcatg agccacggtg cccagcccca
23881 cgttctagat ttctatggat agagtatgct taaggatgag tatgtttctg gatgttcgac
23941 tcggcttttcc tggtctgttg tctgtctgtg tacagcgtca cattgtttta atgatagagg
24001 ctttagcgta catagctggg aaggctaatg ttctctttta gttttctttt ccagtggttt
24061 cctggcaatt cttgcatgtt tgttttttcca tatgaacttt agtgtcaaca tgcctaggtc
24121 tataaaaaag cttggtggta attttattgg gattatgaca cttcaacaaa ttaactggga
24181 gaatgaacat attttttgatg ttgagtcatt ttatccaagg ataagaaacg ttttcctatt
24241 tgctcaagtc tattattgta tctttcttga ctgctgcaat gtattctctt ataatttttt
24301 ctattggtat cttatttat gtatttgtaa tatcttattt ttcttgagta aattagttaa
24361 tggcttgccg gttttctcaa acaaatatc tagggatttg atttatgaaa ttattaggcc
24421 tattattttt ctttttttttg agatggagtc tcactctgtc gcccaggctg gagtgcagtg
24481 gcgtgatctc agctcactgc aacctccacc tcctgggttc aagtgattct cctgcctcag
24541 cctccccagt agctgggatt acaggtgcac gccaccatgc ccggctaatt tttttatatt
24601 tttagtagag acggggtttc accatgttag ccaggctggt ctcgaactcc tgacctcatg
24661 atccgactgc ctcagcctcc caaagtgctg ggattacagg tgtgagccac cgtgcctggc
24721 cttttttttt ttttttttgag acagagtctt gctctgtcac ccaggctgga gtgcagtggt
24781 gcgatctcgg ctcactgaaa gctccacctc ccgggttcac gccatcctcc tgcctcagcc
24841 tcccgagtag ctgggactac aggtgtacac tgccacgccc agctaatttt ttgtatttag
24901 tagagacagg gtttcaccgc gttcgccagg atggtctcga tctcctgacc ttgtgatccg
24961 cctgcctcag cctcccaaag tgctggtatt acgggcgtga gccactgcgc cggccaggc
25021 ctattatttt tctattgtgg ttcattaatt tctgcttttt tctcttaaaa agtttgctta
25081 cgtttttgtc tggtttactt tgctgttctc ttgctagctt tttttttttt cagatagggt
25141 cttgctctgt gcccaggct ggagtgcagt ggcacagtca tagctcactg cagccttgaa
25201 ctcctgggct caagcaatcc tcttcttgct tcagcctccc acgtagctag gatcagaggt
25261 acatgccacc atgttcggct aatttttttt tttcgagaca gagtcttgtt ctgtcgctca
25321 ggcggtagtg cagtggtgca atcccggctc actgcaacct ccacctccac ctcccaggtt
25381 caagcaattc tacctcagtc tcctgagtag ctggattat aggcgcacac caacatgtct
25441 ggctaatttt tgtatttta gtagagacag gtttcacca cgttggctag gctggtctta
25501 aactcctgac ttcatgatcc gcccgccttg gcctcccaaa gtgctgagat tacaggtgtg
25561 agccacagca cctagtgaaa gtgtggtttt tttgtgtagg ttttactgtt gttagtgttg
25621 ttctgtattg tttgtagagg atacgtgggg agatttggat aaaagcaact atcattatta
25681 tcctcatcag acttgtaggt ctaactttt aattttttaa tttttaattt aaatttttt
25741 cttggtcttt tatcattaat taatttttc gagacagggt ctcactctgt tgcccaggct
25801 ggagtgtggt gacatgatca cggctcactg cagccttaac ctcccaggtg caagtgatcc
25861 tcctctctta gcctcccgag tagctgggac tccaggcatg tgccaccatg cccagctaat
25921 ttttttgtaga gagagggttt tgccatattg cccaggctgg tcttgaactg ctgagctcaa
25981 gtgatccacc cggcttgggc atgagccacc tcccctggtc tggtccaact ttttaaaagc
```

Figure 28M

```
26041 attattctgc ctgttgggtg gagaatagac tgtaggtggg caaagaatga aggaaactag
26101 tgggttcagg agctcgagct agaagtggtg agaagggttt ggatttgggg tctatgctga
26161 agtagagcc gacaagattt gctaggattg gatgtgtagg gtgaggaagt ggggacagca
26221 agaatgactg gaggggtaag tggactctca ccagctgtgt ctcgtgaagg ggcgtggctg
26281 ggctatgagc tatgctcctg agcacagacg gctgttctct ttcaaggtta caagcctgat
26341 gaagggaaac gagggatgc ctgtgaaggt gacagtgggg gacctttgt catgaaggta
26401 agcttctcta aagcccaggg cctggtgaac acatcttctg ggggtgggga gaaactctag
26461 tatctagaaa cagttgcctg gcagaggaat actgatgtga ccttgaactt gactctattg
26521 gaaacctcat ctttcttctt cagagcccct ttaacaaccg ctggtatcaa atgggcatcg
26581 tctcatgggg tgaaggctgt gaccgggatg ggaaatatgg cttctacaca catgtgttcc
26641 gcctgaagaa gtggatacag aaggtcattg atcagtttgg agagtagggg gccactcata
26701 ttctgggctc ctggaaccaa tcccgtgaaa gaattatttt tgtgtttcta aaactatggt
26761 tcccaataaa agtgactctc agcgagcctc aatgctccca gtgctattca tgggcagctc
26821 tctgggctca ggaagagcca gtaatactac tggataaaga agacttaaga atccaccacc
26881 tggtgcacgc tggtagtccg agcactcggg aggctgaggt gggaggat
```

Figure 28N

```
LOCUS       HUMPMG3BA    3997 bp    mRNA            PRI       08-JAN-1995
DEFINITION  Human platelet membrane glycoprotein IIIa beta subunit mRNA,
            complete cds.
ACCESSION   M20311
NID         g190107
KEYWORDS    cell membrane glycoprotein; platelet membrane glycoprotein IIIa.
SOURCE      Homo sapiens cDNA to mRNA.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 3997)
  AUTHORS   Zimrin,A.B., Eisman,R., Vilaire,G., Schwartz,E., Bennett,J.S. and
            Poncz,M.
  TITLE     Structure of platelet glycoprotein IIIa. A common subunit for two
            different membrane receptors
  JOURNAL   J. Clin. Invest. 81 (5), 1470-1475 (1988)
  MEDLINE   88213696
FEATURES             Location/Qualifiers
     source          1..3997
                     /organism="Homo sapiens"
                     /db_xref="taxon:9606"
                     /cell_type="erythroleukemia"
                     /map="17q21.32"
     sig_peptide     17..94
                     /gene="ITGB3"
                     /note="G00-120-013"
     CDS             17..2383
                     /gene="ITGB3"
                     /codon_start=1
                     /db_xref="GDB:G00-120-013"
                     /product="glycoprotein IIIa"
                     /db_xref="PID:g190108"

/translation="MRARPRPRPLWATVLALGALAGVGVGGPNICTTRGVSSCQQCLA

VSPMCAWCSDEALPLGSPRCDLKENLLKDNCAPESIEFPVSEARVLEDRPLSDKGSGD

SSQVTQVSPQRIALRLRPDDSKNFSIQVRQVEDYPVDIYYLMDLSYSMKDDLWSIQNL

GTKLATQMRKLTSNLRIGFGAFVDKPVSPYMYISPPEALENPCYDMKTTCLPMFGYKH

VLTLTDQVTRFNEEVKKQSVSRNRDAPEGGFDAIMQATVCDEKIGWRNDASHLLVFTT

DAKTHIALDGRLAGIVQPNDGQCHVGSDNHYSASTTMDYPSLGLMTEKLSQKNINLIF

AVTENVVNLYQNYSELIPGTTVGVLSMDSSNVLQLIVDAYGKIRSKVELEVRDLPEEL

SLSFNATCLNNEVIPGLKSCMGLKIGDTVSFSIEAKVRGCPQEKEKSFTIKPVGFKDS

LIVQVTFDCDCACQAQAEPNSHRCNNGNGTFECGVCRCGPGWLGSQCECSEEDYRPSQ

QDECSPREGQPVCSQRGECLCGQCVCHSSDFGKITGKYCECDDFSCVRYKGEMCSGHG
```

Figure 29A

```
QCSCGDCLCDSDWTGYYCNCTTRTDTCMSSNGLLCSGRGKCECGSCVCIQPGSYGDTC

EKCPTCPDACTFKKECVECKKFDREPYMTENTCNRYCRDEIESVKELKDTGKDAVNCT

YKNEDDCVVRFQYYEDSSGKSILYVVEEPECPKGPDILVVLLSVMGAILLIGLAALLI
                WKLLITIHDRKEFAKFEEERARAKWDTANNPLYKEATSTFTNITYRGT"
     gene            17..2383
                     /gene="ITGB3"
     mat_peptide     95..2380
                     /gene="ITGB3"
                     /note="G00-120-013"
                     /product="glycoprotein IIIa beta subunit"
BASE COUNT      917 a    993 c   1099 g    988 t
ORIGIN        Chromosome 17.
        1 gcgggaggcg gacgagatgc gagcgcggcc gcggccccgg ccgctctggg cgactgtgct
       61 ggcgctgggg gcgctggcgg gcgttggcgt aggagggccc aacatctgta ccacgcgagg
      121 tgtgagctcc tgccagcagt gcctggctgt gagccccatg tgtgcctggt gctctgatga
      181 ggccctgcct ctgggctcac ctcgctgtga cctgaaggag aatctgctga aggataactg
      241 tgccccagaa tccatcgagt tcccagtgag tgaggcccga gtactagagg acaggcccct
      301 cagcgacaag ggctctggag acagctccca ggtcactcaa gtcagtcccc agaggattgc
      361 actccggctc cggccagatg attcgaagaa tttctccatc caagtgcggc aggtggagga
      421 ttaccctgtg gacatctact acttgatgga cctgtcttac tccatgaagg atgatctgtg
      481 gagcatccag aacctgggta ccaagctggc cacccagatg cgaaagctca ccagtaacct
      541 gcggattggc ttcggggcat tgtggacaa gcctgtgtca ccatacatgt atatctcccc
      601 accagaggcc ctcgaaaacc cctgctatga tatgaagacc acctgcttgc ccatgtttgg
      661 ctacaaacac gtgctgacgc taactgacca ggtgacccgc ttcaatgagg aagtgaagaa
      721 gcagagtgtg tcacggaacc gagatgcccc agagggtggc tttgatgcca tcatgcaggc
      781 tacagtctgt gatgaaaaga ttggctggag gaatgatgca tcccacttgc tggtgtttac
      841 cactgatgcc aagactcata tagcattgga cggaaggctg gcaggcattg tccagcctaa
      901 tgacggcagt gtcatgttg gtagtgacaa tcattactct gcctccacta ccatggatta
      961 tccctctttg gggctgatga ctgagaagct atcccagaaa acatcaatt tgatctttgc
     1021 agtgactgaa atgtagtca atctctatca gaactatagt gagctcatcc cagggaccac
     1081 agttgggggtt ctgtccatgg attccagcaa tgtcctccag ctcattgttg atgcttatgg
     1141 gaaaatccgt tctaaagtag agctggaagt gcgtgacctc cctgaagagt tgtctctatc
     1201 cttcaatgcc acctgcctca acaatgaggt catccctggc ctcaagtctt gtatgggact
     1261 caagattgga gacacggtga gcttcagcat tgaggccaag gtgcgaggct gtcccagga
     1321 gaaggagaag tcctttacca taaagcccgt gggcttcaag gacagcctga tcgtccaggt
     1381 caccttttgat tgtgactgtg cctgccaggc ccaagctgaa cctaatagcc atcgctgcaa
     1441 caatgcaat gggaccttg agtgtggggt atgccgttgt gggcctggct ggctgggatc
     1501 ccagtgtgag tgctcagagg aggactatcg cccttcccag caggacgaat gcagccccg
     1561 ggagggtcag cccgtctgca gccagcgggg cgagtgcctc tgtggtcaat gtgtctgcca
     1621 cagcagtgac tttggcaaga tcacgggcaa gtactgcgag tgtgacgact tctcctgtgt
     1681 ccgctacaag gggagatgt gctcaggcca tggccagtgc agctgtgggg actgcctgtg
     1741 tgactccgac tggaccggct actactgcaa ctgtaccacg cgtactgaca cctgcatgtc
     1801 cagcaatggg ctgctgtgca gcgggcgcgg caagtgtgaa tgtggcagct gtgtctgtat
     1861 ccagccgggc tcctatgggc acacctgtga gaagtgcccc acctgcccag atgcctgcac
     1921 ctttaagaaa gaatgtgtgg agtgtaagaa gtttgaccgg gagccctaca tgaccgaaaa
     1981 tacctgcaac cgttactgcc gtgacgagat tgagtcagtg aaagagctta aggacactgg
     2041 caaggatgca gtgaattgta cctataagaa tgaggatgac tgtgtcgtca gattccagta
     2101 ctatgaagat tctagtggaa agtccatcct gtatgtggta gaagagccag agtgtcccaa
     2161 gggccctgac atcctggtgg tcctgctctc agtgatgggg gccattctgc tcattggcct
     2221 tgccgccctg ctcatctgga aactcctcat caccatccac gaccgaaaag aattcgctaa
     2281 atttgaggaa gaacgcgcca gagcaaaatg ggacacagcc aacaacccac tgtataaaga
     2341 ggccacgtct accttcacca atatcacgta ccggggcact taatgataag cagtcatcct
```

```
2401 cagatcatta tcagcctgtg ccacgattgc aggagtccct gccatcatgt ttacagagga
2461 cagtatttgt ggggagggat ttggggctca gagtggggta ggttgggaga atgtcagtat
2521 gtggaagtgt gggtctgtgt gtgtgtatgt ggggtctgt gtgtttatgt gtgtgtgttg
2581 tgtgtgggag tgtgtaattt aaaattgtga tgtgtcctga taagctgagc tccttagcct
2641 ttgtcccaga atgcctcctg cagggattct tcctgcttag cttgagggtg actatggagc
2701 tgagcaggtg ttcttcatta cctcagtgag aagccagctt tcctcatcag gccattgtcc
2761 ctgaagagaa gggcagggct gaggcctctc attccagagg aagggacacc aagccttggc
2821 tctaccctga gttcataaat ttatggttct caggcctgac tctcagcagc tatggtagga
2881 actgctgggc ttggcagccc gggtcatctg tacctctgcc tcctttcccc tccctcaggc
2941 cgaaggagga gtcagggaga gctgaactat tagagctgcc tgtgcctttt gccatcccct
3001 caacccagct atggttctct cgcaagggaa gtccttgcaa gctaattctt tgacctgttg
3061 ggagtgagga tgtctgggcc actcaggggt cattcatggc ctgggggatg taccagcatc
3121 tcccagttca taatcacaac ccttcagatt tgccttattg gcagctctac tctggaggtt
3181 tgtttagaag aagtgtgtca cccttaggcc agcaccatct ctttacctcc taattccaca
3241 ccctcactgc tgtagacatt tgctatgagc tggggatgtc tctcatgacc aaatgctttt
3301 cctcaaaggg agagagtgct attgtagagc cagaggtctg gccctatgct tccggcctcc
3361 tgtccctcat ccatagcacc tccacatacc tggccctgag ccttggtgtg ctgtatccat
3421 ccatggggct gattgtattt accttctacc tcttggctgc cttgtgaagg aattattccc
3481 atgagttggc tgggaataag tgccaggatg gaatgatggg tcagttgtat cagcacgtgt
3541 ggcctgttct tctatgggtt ggacaacctc attttaactc agtctttaat ctgagaggcc
3601 acagtgcaat tttatttat ttttctcatg atgaggtttt cttaacttaa aagaacatgt
3661 atataaacat gcttgcatta tatttgtaaa tttatgtgta tggcaaagaa ggagagcata
3721 ggaaaccaca cagacttggg cagggtacag acactcccac ttggcatcat tcacagcaag
3781 tcactggcca gtggctggat ctgtgagggg ctctctcatg atagaaggct atggggatag
3841 atgtgtggac acattggacc tttcctgagg aagagggact gttcttttgt cccagaaaag
3901 cagtggctcc attggtgttg acatacatcc aacattaaaa gccaccccca aatgcccaag
3961 aaaaaaagaa agacttatca acatttgttc catgagg
```

Figure 29C

```
LOCUS       HUMATH3A3      238 bp    DNA              PRI       31-OCT-1994
DEFINITION  Human antithrombin III (ATIII) gene, exon 6.
ACCESSION   M21645
NID         g179149
KEYWORDS    antithrombin; antithrombin III.
SEGMENT     3 of 3
SOURCE      Homo sapiens (individual_isolate Patient II-9) DNA.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 238)
  AUTHORS   Bock,S.C., Marrinan,J.A. and Radziejewska,E.
  TITLE     Antithrombin III Utah: proline-407 to leucine mutation in a highly
            conserved region near the inhibitor reactive site [published
            erratum appears in Biochemistry 1989 Apr 18;28(8):3628]
  JOURNAL   Biochemistry 27 (16), 6171-6178 (1988)
  MEDLINE   89050967
COMMENT     Draft entry and computer-readable sequence [1] kindly submitted by
            S.C.Bock, 20-JAN-1989.
FEATURES             Location/Qualifiers
     source          1..238
                     /organism="Homo sapiens"
                     /isolate="Patient II-9"
                     /db_xref="taxon:9606"
                     /cell_type="peripheral blood cell"
                     /map="1q23-q25.1"
     gene            join(M21643:1..398,M21644:1..469,1..183)
                     /gene="AT3"
     intron          <1..6
                     /gene="AT3"
                     /note="antithrombin III, intron F"
     CDS             <7..183
                     /gene="AT3"
                     /note="exon 6"
                     /codon_start=1
                     /db_xref="GDB:G00-119-024"
                     /product="antithrombin III"
                     /db_xref="PID:g179152"

/translation="VNEEGSEAAASTAVVIAGRSLNPNRVTFKANRPFLVFIREVPLN
                 TIIFMGRVANPCVK"
BASE COUNT      63 a     50 c      53 g      72 t
ORIGIN      About 7.8 kb from segment 3B; chromosome 1q23.
        1 ctgcaggtaa atgaagaagg cagtgaagca gctgcaagta ccgctgttgt gattgctggc
       61 cgttcgctaa accccaacag ggtgacttc aaggccaaca ggcctttcct ggttttata
      121 agagaagttc ctctgaacac tattatcttc atgggcagag tagccaaccc ttgtgttaag
      181 taaaatgttc ttattctttg cacctcttcc tattttggt ttgtgaacag aagtaaaa
```

Figure 30

```
LOCUS       HUMGP2B2     623 bp    DNA              PRI      08-NOV-1994
DEFINITION  Human platelet glycoprotein IIb mRNA, C-terminal exon.
ACCESSION   M22569
NID         g183449
KEYWORDS    platelet glycoprotein IIb.
SEGMENT     2 of 2
SOURCE      Homo sapiens (tissue library: lambda-EMBL 4) DNA.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 623)
  AUTHORS   Prandini,M.H., Denarier,E., Frachet,P., Uzan,G. and Marguerie,G.
  TITLE     Isolation of the human platelet glycoprotein IIb gene and
            characterization of the 5' flanking region
  JOURNAL   Biochem. Biophys. Res. Commun. 156 (1), 595-601 (1988)
  MEDLINE   89025907
COMMENT     Draft entry and computer-readable sequence [1] kindly submitted by
            M.H.Prandini, 16-FEB-1989.
FEATURES             Location/Qualifiers
     source          1..623
                     /organism="Homo sapiens"
                     /db_xref="taxon:9606"
                     /cell_type="leucocyte"
                     /tissue_lib="lambda-EMBL 4"
                     /map="17q21.32"
     gene            join(M22568:1254..1869,1..434)
                     /gene="ITGA2B"
     intron          <1..191
                     /gene="ITGA2B"
                     /note="G00-120-012"
     exon            192..434
                     /partial
                     /gene="ITGA2B"
                     /note="last exon; G00-120-012"
     CDS             <192..251
                     /gene="ITGA2B"
                     /codon_start=1
                     /db_xref="GDB:G00-120-012"
                     /product="platelet glycoprotein IIb"
                     /db_xref="PID:g463108"
                     /translation="VGFFKRNRHTLEEDDEEGE"
BASE COUNT      144 a    158 c    181 g    140 t
ORIGIN      About 15 kb after segment 1.
        1 aaaactcagg aagaaacaaa cccaccaatc gttccaggca tatctcaaat gcaaaaggca
       61 tccattgtga gtacagtggg ctttcatgtt ctgcgctggt ccagggaggt gctcatagct
      121 acttcctcac atgtgctctg gggccagcaa atcatctgta taccctgacc ttggcccccg
      181 tgtaccccca ggtcggcttc ttcaagcgga accggcacac cctggaagaa gatgatgaag
      241 aggggagtg atggtgcagc ctacactatt ctagcaggag ggttgggcgt gctacctgca
      301 ccgccccttc tccaacaagt tgcctccaag ctttgggttg gagctgttcc attgggtcct
      361 cttggtgtcg tttccctccc aacagagctg ggctaccccc cctcctgctg cctaataaag
      421 agactgagcc ctgatgctga gcatgctgcc tccttttggg gccagagaag agagtaccga
      481 agaatgtttt ggacggggac ctagggctgg tggaagtatg aacgagagag tcactgccag
      541 ggcgaagttt gcaaatcact gtctttgggg agtgtcaggg agtacagagt tggggtggta
```

Figure 31A 601 ggtgtaacag aagacggaga gcc

Figure 31B

```
LOCUS       HUMCETP       1787 bp    mRNA            PRI       01-NOV-1994
DEFINITION  Human cholesteryl ester transfer protein mRNA, complete cds.
ACCESSION   M30185
NID         g180259
KEYWORDS    cholesteryl ester transfer protein; transfer protein.
SOURCE      Human adult liver, cDNA to mRNA.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 1787)
  AUTHORS   Drayna,D., Jarnagin,A.S., McLean,J., Henzel,W., Kohr,W.,
            Fielding,C. and Lawn,R.
  TITLE     Cloning and sequencing of human cholesteryl ester transfer protein
            cDNA
  JOURNAL   Nature 327 (6123), 632-634 (1987)
  MEDLINE   87258172
FEATURES             Location/Qualifiers
     source          1..1787
                     /organism="Homo sapiens"
                     /db_xref="taxon:9606"
                     /dev_stage="adult"
                     /tissue_type="liver"
     mRNA            <1..1787
                     /note="CETP mRNA"
     sig_peptide     131..181
                     /gene="CETP"
                     /note="cholesteryl ester transfer protein signal peptide"
     gene            131..1612
                     /gene="CETP"
     CDS             131..1612
                     /gene="CETP"
                     /note="cholesteryl ester transfer protein precursor"
                     /codon_start=1
                     /db_xref="GDB:G00-119-773"
                     /db_xref="PID:g180260"
```

/translation="MLAATVLTLALLGNAHACSKGTSHEAGIVCRITKPALLVLNHET

AKVIQTAFQRASYPDITGEKAMMLLGQVKYGLHNIQISHLSIASSQVELVEAKSIDVS

IQNVSVVFKGTLKYGYTTAWWLGIDQSIDFEIDSAIDLQINTQLTCDSGRVRTDAPDC

YLSFHKLLLHLQGEREPGWIKQLFTNFISFTLKLVLKGQICKEINVISNIMADFVQTR

AASILSDGDIGVDISLTGDPVITASYLESHHKGHFIYKNVSEDLPLPTFSPTLLGDSR

MLYFWFSERVFHSLAKVAFQDGRLMLSLMGDEFKAVLETWGFNTNQEIFQEVVGGFPS

QAQVTVHCLKMPKISCQNKGVVVNSSVMVKFLFPRPDQQHSVAYTFEEDIVTTVQASY

SKKKLFLSLLDFQITPKTVSNLTESSSESIQSFLQSMITAVGIPEVMSRLEVVFTALM
                NSKGVSLFDIINPEIITRDGFLLLQMDFGFPEHLLVDFLQSLS"
```
     mat_peptide     182..1609
```

Figure 32A

/gene="CETP"  /note="cholesteryl ester transfer protein"
BASE COUNT     397 a    531 c    456 g    403 t
ORIGIN
```
   1 gtgaatctct ggggccagga agaccctgct gcccggaaga gcctcatgtt ccgtgggggc
  61 tgggcggaca tacatatacg ggctccaggc tgaacggctc gggccactta cacaccactg
 121 cctgataacc atgctggctg ccacagtcct gaccctggcc ctgctgggca atgcccatgc
 181 ctgctccaaa ggcacctcgc acgaggcagg catcgtgtgc cgcatcacca agcctgccct
 241 cctggtgttg aaccacgaga ctgccaaggt gatccagacc gccttccagc gagccagcta
 301 cccagatatc acgggcgaga aggccatgat gctccttggc caagtcaagt atgggttgca
 361 caacatccag atcagccact tgtccatcgc cagcagccag gtggagctgg tggaagccaa
 421 gtccattgat gtctccattc agaacgtgtc tgtggtcttc aaggggaccc tgaagtatgg
 481 ctacaccact gcctggtggc tgggtattga tcagtccatt gacttcgaga tcgactctgc
 541 cattgacctc cagatcaaca cacagctgac ctgtgactct ggtagagtgc ggaccgatgc
 601 ccctgactgc tacctgtctt tccataagct gctcctgcat ctccaagggg agcgagagcc
 661 tgggtggatc aagcagctgt tcacaaattt catctccttc acctgaagc tggtcctgaa
 721 gggacagatc tgcaaagaga tcaacgtcat ctctaacatc atggccgatt ttgtccagac
 781 aagggctgcc agcatcettt cagatggaga cattggggtg gacatttccc tgacaggtga
 841 tcccgtcatc acagcctcct acctggagtc ccatcacaag ggtcatttca tctacaagaa
 901 tgtctcagag gacctccccc tccccacctt ctcgcccaca ctgctggggg actcccgcat
 961 gctgtacttc tggttctctg agcgagtctt ccactcgctg gccaaggtag ctttccagga
1021 tggccgcctc atgctcagcc tgatgggaga cgagttcaag gcagtgctgg agacctgggg
1081 cttcaacacc aaccaggaaa tcttccaaga ggttgtcggc ggcttcccca gccaggccca
1141 agtcaccgtc cactgcctca agatgcccaa gatctcctgc caaaacaagg gagtcgtggt
1201 caattcttca gtgatggtga aattcctctt tccacgccca gaccagcaac attctgtagc
1261 ttacacattt gaagaggata tcgtgactac cgtccaggcc tcctattcta agaaaaagct
1321 cttcttaagc ctcttggatt tccagattac accaaagact gtttccaact tgactgagag
1381 cagctccgag tccatccaga gcttcctgca gtcaatgatc accgctgtgg gcatccctga
1441 ggtcatgtct cggctcgagg tagtgtttac agccctcatg aacagcaaag gcgtgagcct
1501 cttcgacatc atcaaccctg agattatcac tcgagatggc ttcctgctgc tgcagatgga
1561 ctttggcttc cctgagcacc tgctggtgga tttcctccag agcttgagct agaagtctcc
1621 aaggaggtcg ggatgggct tgtagcagaa ggcaagcacc aggctcacag ctggaaccct
1681 ggtgtctcct ccagcgtggt ggaagttggg ttaggagtac ggagatggag attggctccc
1741 aactcctccc tatcctaaag gcccactggc attaaagtgc tgtatcc
```

Figure 32B

```
LOCUS       HUMGPIIB2    13204 bp    DNA             PRI       10-NOV-1994
DEFINITION  Human platelet Glycoprotein IIb (GPIIb) gene, exons 2-29.
ACCESSION   M33320
NID         g183506
KEYWORDS    platelet Glycoprotein IIb.
SEGMENT     2 of 3
SOURCE      Human leukocyte DNA.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 13204)
  AUTHORS   Heidenreich,R., Eisman,R., Surrey,S., Delgrosso,K., Bennett,J.S.,
            Schwartz,E. and Poncz,M.
  TITLE     Organization of the gene for platelet glycoprotein IIb
  JOURNAL   Biochemistry 29 (5), 1232-1244 (1990)
  MEDLINE   90212612
FEATURES             Location/Qualifiers
     source          1..13204
                     /organism="Homo sapiens"
                     /db_xref="taxon:9606"
                     /map="17q21.32"
     prim_transcript <1..>13204
                     /note="GPIIb mRNA and introns"
     intron          <1..497
                     /note="GPIIb intron A"
     exon            498..619
                     /gene="ITGA2B"
                     /number=2
     intron          620..708
                     /note="GPIIb intron B"
     exon            709..806
                     /gene="ITGA2B"
                     /note="platelet Glycoprotein IIb"
                     /number=3
     intron          807..911
                     /note="GPIIb intron C"
     exon            912..1077
                     /gene="ITGA2B"
                     /note="platelet Glycoprotein IIb"
                     /number=4
     intron          1078..1292
                     /note="GPIIb intron D"
     exon            1293..1342
                     /gene="ITGA2B"
                     /note="platelet Glycoprotein IIb"
                     /number=5
     intron          1343..1418
                     /note="GPIIb intron E (no splice consensus); putative;
                     does not fit consensus"
     exon            1419..1464
                     /gene="ITGA2B"
                     /note="platelet Glycoprotein IIb"
                     /number=6
```

Figure 33A

```
intron          1465..1551
                /note="GPIIb intron F"
exon            1552..1680
                /gene="ITGA2B"
                /note="platelet Glycoprotein IIb"
                /number=7
intron          1681..2041
                /note="GPIIb intron G"
exon            2042..2089
                /gene="ITGA2B"
                /note="platelet Glycoprotein IIb"
                /number=8
intron          2090..2244
                /note="GPIIb intron H (no splice consensus); putative;
                does not fit consensus"
exon            2245..2288
                /gene="ITGA2B"
                /note="platelet Glycoprotein IIb"
                /number=9
intron          2289..2460
                /note="GPIIb intron I"
exon            2461..2514
                /gene="ITGA2B"
                /note="platelet Glycoprotein IIb"
                /number=10
intron          2515..2652
                /note="GPIIb intron J"
exon            2653..2705
                /gene="ITGA2B"
                /note="platelet Glycoprotein IIb"
                /number=11
intron          2706..2896
                /note="GPIIb intron K"
exon            2897..3108
                /gene="ITGA2B"
                /note="platelet Glycoprotein IIb"
                /number=12
intron          3109..5535
                /note="GPIIb intron L"
exon            5536..5718
                /gene="ITGA2B"
                /note="platelet Glycoprotein IIb"
                /number=13
intron          5719..5951
                /note="GPIIb intron M"
exon            5952..5997
                /gene="ITGA2B"
                /note="platelet Glycoprotein IIb"
                /number=14
intron          5998..6105
                /note="GPIIb intron N"
exon            6106..6210
                /gene="ITGA2B"
                /note="platelet Glycoprotein IIb"
```

Figure 33B

```
                        /number=15
    intron              6211..6294
                        /note="GPIIb intron O"
    exon                6295..6350
                        /gene="ITGA2B"
                        /note="platelet Glycoprotein IIb"
                        /number=16
    intron              6351..6442
                        /note="GPIIb intron P"
    exon                6443..6594
                        /gene="ITGA2B"
                        /note="platelet Glycoprotein IIb"
                        /number=17
    intron              6595..6782
                        /note="GPIIb intron Q"
    exon                6783..6908
                        /gene="ITGA2B"
                        /note="platelet Glycoprotein IIb"
                        /number=18
    intron              6909..7885
                        /note="GPIIb intron R"
    exon                7886..7953
                        /gene="ITGA2B"
                        /note="platelet Glycoprotein IIb"
                        /number=19
    intron              7954..8086
                        /note="GPIIb intron S"
    exon                8087..8234
                        /gene="ITGA2B"
                        /note="platelet Glycoprotein IIb"
                        /number=20
    intron              8235..8802
                        /note="GPIIb intron T"
    exon                8803..8895
                        /gene="ITGA2B"                      /note="platelet
Glycoprotein IIb"
                        /number=21
    intron              8896..9505
                        /note="GPIIb intron U"
    exon                9506..9585
                        /gene="ITGA2B"
                        /note="platelet Glycoprotein IIb"
                        /number=22
    intron              9586..10201
                        /note="GPIIb intron V"
    exon                10202..10282
                        /gene="ITGA2B"
                        /note="platelet Glycoprotein IIb"
                        /number=23
    intron              10283..10405
                        /note="GPIIb intron W"
    exon                10406..10505
                        /gene="ITGA2B"
                        /note="platelet Glycoprotein IIb"
```

Figure 33C

```
                        /number=24
        intron          10506..10604
                        /note="GPIIb intron X"
        exon            10605..10757
                        /gene="ITGA2B"
                        /note="platelet Glycoprotein IIb"
                        /number=25
        intron          10758..10873
                        /note="GPIIb intron Y"
        exon            10874..10999
                        /gene="ITGA2B"
                        /note="platelet Glycoprotein IIb"
                        /number=26
        intron          11000..11477
                        /note="GPIIb intron Z"
        exon            11478..11591
                        /gene="ITGA2B"
                        /note="platelet Glycoprotein IIb"
                        /number=27
        intron          11592..11827
                        /note="GPIIb intron AA"
        exon            11828..11929
                        /gene="ITGA2B"
                        /note="platelet Glycoprotein IIb"
                        /number=28
        intron          11930..12116
                        /note="GPIIb intron BB"
        exon            12117..12233
                        /gene="ITGA2B"
                        /note="platelet Glycoprotein IIb"
                        /number=29
        intron          12234..>13204
                        /note="GPIIb intron CC"
BASE COUNT      3046 a    3579 c    3857 g    2722 t
ORIGIN      About 2000 bp after segment 1.
        1 ctgcaggtca acggatctgc tagggtcctc ctatcagcac acacactcca gccccacttt
       61 agaggtaccc gctaccttcc ctcattaaaa ccagctctca gaggggatc tggtaacagt
      121 ctaggcaggc attccaggga gcatgtgaac cgctggttct tgttgcgggt ggaggatgga
      181 ggtgttgtac agagtttagg tcttttcag caaagatctc caaacccgg gtgttcaaaa
      241 tcaaaccaaa ggggattata gtcccagctc tactcacaac tcactggtta ctttagccac
      301 gagattgccc tcgctgagag tcggtttcac tgtccataag atgaagaagt acatcacggt
      361 ggtctgtgag gtgtcattga ggaaagatgg tccagtgccc ccatgccaca tggccttcgg
      421 gcagtgctcc cagcgccggc gccagggcct gggatacgct ggaatctgcg cggcgctcac
      481 ccagcttttcc tatgcagagt ggccatcgtg gtgggcgccc cgcggaccct gggccccagc
      541 caggaggaga cgggcggcgt gttcctgtgc ccctggaggg ccgagggcgg ccagtgcccc
      601 tcgctgctct ttgacctccg tgagtccag gcaaggagag caaggttggg gtcagaggga
      661 cgtggactgc ccgggcttca gcgcccace ccttcttgtg ccttccaggt gatgagaccc
      721 gaaatgtagg ctcccaaact ttacaaacct tcaaggcccg ccaaggactg ggggcgtcgg
      781 tcgtcagctg gagcgacgtc attgtggtgg gcccgcggt acagggcaca gggaacaatc
      841 ggggcaggg acactggggc caggaggagc ccaagtctcg cgccccgtcc ccatctgtgg
      901 cccttttctca ggcctgcgcc ccctggcagc actggaacgt cctagaaaag actgaggagg
      961 ctgagaagac gcccgtaggt agctgctttt tggctcagcc agagagcggc cgccgcgccg
     1021 agtactcccc ctgtcgcggg aacaccctga gccgcattta cgtggaaaat gattttagta
     1081 agcgccagct acgacctggc cccgcccact cgcgacgggct tggccccgcc cccatcgga
```

Figure 33D

```
1141 tcccgccccc agcgccgcag cccttgcttt ggatctggcc tcgccccagg gccccgccga
1201 ctcaaggccc cgccctgtc ccccagccct cctccgggct cgcgcgcgcc tccttcacc
1261 cctgggctga cccctcctcc ttgtctcctc aggctgggac aagcgttact gtgaagcggg
1321 cttcagctcc gtggtcactc aggcgagtag ggagcaaaag cgcagtgggg gcggctccca
1381 aacagggccc cctctcaccc tcaggacttc ccttccaggc cggagagctg gtgcttgggg
1441 ctcctggcgg ctattatttc ttaggtacgt gccatccgt acacctccct cccttctcgc
1501 ggccgaagga gaccgctttg ggcttcacac ccgctgtccc tcccgccta gtctcctgg
1561 cccaggctcc agttgcggat attttctcga gttaccgccc aggcatcctt ttgtggcacg
1621 tgtcctccca gagcctctcc tttgactcca gcaacccaga gtacttcgac ggctactggg
1681 gtaacaccgc cattccagac ttccagcacc ccgagggtca.ccgcccaccg cagacggtca
1741 ggtcctgccc ctgtgggagc ctccatggcc acccctgccg gccaacccac cgcctaagcc
1801 gctccgccc tccgctcctg cgcttccccg cagaccgccc acctcccatg cgcccaccgc
1861 tccttccac tgcggactcg tagcgcagcc tggggcaggg cttggcccct cgaaggcctc
1921 cgttttccca tctgcacaat gcagggctgg ggctgagtgg ccttaatctc ctccttcttt
1981 gccctccgtc ccctctgtgc ttcctcccct ggaaaagact aatttgcgcc cttgtcctca
2041 gggtactcgg tggccgtggg cgagttcgac ggggatctca acactacagg caagaaatcc
2101 acttagggcg ggagttgggt agcccagccc ggggaggagc gccttcctga aatctcccct
2161 atgtagctgg gtgcagaacg gggagcggga agtgggtagg ttctaaggct ctcattccct
2221 gagcctggct ctccctatcg ccagaatatg tcgtcgtgcc ccccacttgg agctggaccc
2281 tgggagcggt aagtgccccc accactgggc ctcccgaagc cccttatccc agttctcagg
2341 ctgacaactc ctgagcgccc cccacccccg ccccgcctcc accaaaccac cctttctcac
2401 ctggagtggg aggttgcttt gggtacaaga atgatgctct cgcctgcgct gtccgtgcag
2461 gtggaaattt tggattccta ctaccagagg ctgcatcggc tgcgcggaga gcaggtgggg
2521 gccaggtccc agtgggcgtg gctgggtgga ggggaactg agacttcaga atatttcatg
2581 ggaggtgagg gcccatttct taaagaggat gcttgtccag cggcgtgaat gatggtgctc
2641 ctcatcttgc agatggcgtc gtattttggg cattcagtgg ctgtcactga cgtcaacggg
2701 gatgggtgag gagggacatg cccccacccc tacccagttg ggtcccaaat taccagagct
2761 gcccctctgt ctcccttttcc tagccctagt ctcacgtatc cactggagga acaggagagc
2821 aagggtcgag gagatttggc cctagcccca atataccct ggtccagtcc catgtaacca
2881 ctcatctggc ccacaggagg catgatctgc tggtgggcgc tccactgtat atggagagcc
2941 gggcagaccg aaaactggcc gaagtggggc gtgtgtattt gttcctgcag ccgcgaggcc
3001 cccacgcgct gggtgccccc agcctcctgc tgactggcac acagctctat gggcgattcg
3061 gctctgccat cgcacccctg ggcgacctcg accgggatgg ctacaatggt gagggaagag
3121 aggagcccta cttgctgcag aggggttaac agccactcaa aaagcatgga gttggcctga
3181 gggcagccag aaccaggatg ggttttaagc atataagtat gtggcttaga cacatgggt
3241 gctgagtgga gagcagatgg gagagttgaa gactaattag gaagtgtttg ccttaatcca
3301 agcaagagac aatgaccacc tggatgtgga ttttggcagt ggagttagag atgggagtga
3361 cttcacagat atttaggact cggattatta ggacttggtg ggagactgga tgtggggcca
3421 ggggagaggt tggagttggg tgcctgtgat ggcctccact gctggaact caggccgtgc
3481 agcaggtgct ggggagaggc gggagatcag cagttcagct ctggacctgt tgagcttgaa
3541 gggcttgggt gtttaggcg gaaatatcca aagaacagtt gggagtggct ctccccgctt
3601 ccacaagaga gatctgaatg ggagacaggg gtttggggaa agtggatgag gtcccgggac
3661 ctgtgaaata agaggcccag gatagagccc tagggagcaa aagcatttag gtgactccta
3721 caggaggtaa gtctgagaag gagacagagg agtgtccaga gagggaggag ggaacccagg
3781 gggtctgatg gcccgggact caaggaagag catgcgttaa agagcatgca caggaggaag
3841 tgggcgctgc agctcctgct gctgctgcaa gatacaatta ggtggggctg gagaaatatt
3901 catgggcttt agcaagaaga gggtgccagg catggtggct catacctgta atcccagcta
3961 cttgggaaat tgaagcagga gaatctcttg aacccgggaa gtggaggttg cactgagctg
4021 agcttgcgcc actactgcac tccagcctgg gtgacagagc aagactccat ctcaacaaaa
4081 taaaaaaaaa aatagagaaa gaaaggaaga aagaaaaaag aaggggaggt tattggtgac
4141 agtgacataa attgattcag gccaagatag ggtcagaagc cagaatgcaa tggggtaagg
4201 tatgaatgga gatgaaaaat tggatgcagc taatgtagac agctcttttca acaggtttgt
4261 ggtaaaaagg aatttgagga atagaaagga aaaaaaaaa catgtttgac tataagagga
4321 aaagagaaa aggtgatcac agaaaagaga tgagggtcaa gggaagatta tttcaatgtg
```

Figure 33E

```
4381 gaagaacatg tagtaggttg aaaatgatgt tgtgggaaa tgggggatg agccagcaga
4441 gagtccctgt gatgcctcag ggggtgggag ggtgactggc ccagtgtcag ggtgaaggaa
4501 ggaaacctct tccagggtca aatggggaaa gggaaaaaga aagttggtgt gggattatag
4561 cataacagtg ggctgcctct cttcctgaag taagagatta cgtcacctgc tgaaggaagt
4621 gtgggggtc tgggagtttg atggaatgga gaaggctaga aatagatgct agatggccag
4681 gcacggtggc tcacacctgg aatcccagca ctttgggagg ccgaggcagg aggatcactg
4741 gagcctagga gtttgacacc agcctggcca acataggag atctcgtctc cataaaaatt
4801 tttaaaaatt agctgggcat ggtggctata gtctcaactg cttgggaagc tgaggtggga
4861 ggattgcttt agtccagaag gttgaggctg cagtaagcca tggttgcacc actgcacttc
4921 agcctgaatg acaagtgcaa gactgtctta aaataaaaaa tttaaagggc ttgggcacgg
4981 tggctcacac ctgtaatcca gcactttggg agcccaaggt gggcagatca cttgaggtca
5041 ggagttcgag atcagcctgg ccaatgtggt gaaacccgt ctctactgaa aatacaaaaa
5101 ttagccgggc atggtggtag cgcctgtaa tcccagctac tgaagaggct gaggcacaag
5161 aatcacttta acggggagg cagaggttgc agtgagccga gatcgcacca ctgcactcca
5221 gccaggacaa cagagcgaga ctccatctca aaaaaaaaa aatttagaaa agggaataat
5281 gatgcttaat tttcaggata tattttcctc aatagacagt gagagttgtc actgtttta
5341 taacaatcct acttggcagg tccctctccc acctgattgt taactcctgg agggtagggc
5401 agtgcctcct tcacccacac tttgcacccc tttcctagtc tcctgggatg ttcccagaga
5461 agctcaggaa agttttacag tcatctaggg aggctgaata acaatcagcc acttccttc
5521 tgttactcct tccagacatt gcagtggctg ccccctacgg gggtcccagt ggccgggcc
5581 aagtgctggt gttcctgggt cagagtgagg ggctgaggtc acgtccctcc caggtcctgg
5641 acagcccctt ccccacaggc tctgcctttg gcttctccct tcgaggtgcc gtagacatcg
5701 atgacaacgg atacccaggt gccctggact gcctccagct agaaatgccc aagaaaggcc
5761 cttggacatt cgctggaagt gccaagagac acggccaggg ctcatgcctg gcctggtgtc
5821 ccactatgga ctgccagagg ggctgggtga aacctccagt ggggaggtg gtgtggggaa
5881 ccctgggaa gatgagatga ggatcccat accctaatcg ccaattctga cccattcctc
5941 gatgtctata gacctgatcg tgggagctta cggggccaac caggtggctg tgtacaggtg
6001 agcactggct ccaggggcgg gatggggaag gtcctgtgcc atcaagagga ggccaggcca
6061 ggaggagcca caatggcaag cctccccatc accctatccc atcagagctc agccagtggt
6121 gaaggcctct gtccagctac tggtgcaaga ttcactgaat cctgctgtga agagctgtgt
6181 cctacctcag accaagacac ccgtgagctg gtgaggaggc agagggcatg ggccttaaag
6241 gatctgggac ctcagaaagg ctccaacccc tgagccccac ttacgtcttt gcagcttcaa
6301 catccagatg tgtgttggag ccactgggca caacattcct cagaagctat gtgagtggca
6361 tgaaggggc aggagggagg tgggcttgga ctcccccgga ggctggccag ggaggtcctg
6421 actcttctgc ttgccctgcc agcctaaat gccgagctgc agctggaccg gcagaagccc
6481 cgccagggcc ggcgggtgct gctgctgggc tctcaacagg caggcaccac cctgaacctg
6541 gatctgggcg gaaagcacag cccatctgc cacaccacca tggccttcct tcgagtacgc
6601 ccaggcaggg gattggcagg gctgggagag tagaacttac ccactggact tgttcatcta
6661 gccctggggc actgagctgg gtgctgtgag tccgggggtg gtcaggacac aggtgcctac
6721 tggccaggag aaggtgggat gtgtatggta gcaagatggc ctgactcttg ccctgtcct
6781 aggatgaggc agacttccgg gacaagctga gcccattgt gctcatggagac acccatgtgc
6841 taccgcccac ggaggctgga atggccctg ctgtcgtgct gcatggagac acccatgtgc
6901 aggagcaggt agggacaggc agggacaggc cagggaggtg caggacccct gatagcaaat
6961 caggattagg gttagtgcca agtcacaatg taaccccaaa accttgatgt cattccaaac
7021 cctaatgaaa acctcaaaat ccagccagtc atggtggctg acacctgtaa tcccagcact
7081 ttgggagacc gaggcaggca gattgcctga ggtcaggagt tagagaccaa cctggccaac
7141 atggtgaaaa cccatctcta ctaaaaatac aaaaaaaatt agccgggtgt ggtgacgcat
7201 gcctgtaatt ccagctactc gggaggctga agcaggagaa tcacttgaac ccaggaggca
7261 gaggttgcag tgagccaaga gtgtgccaca gcactccagc ctgggtgaca gagcaagact
7321 ctgtctcaaa aaaaaaaaa aaagccaggc gcagtggcct cacgcctgta atcccagcac
7381 tttgggaggc caaggcgggt ggatcacgag gtcaggagat caagaccatc ctggctaaca
7441 cagtgaaacc ccgtctacta aaaatacaaa aaaaaaaaa aaattagctg gcgtggtgg
7501 cgggtacctg tagtcccagc tactgggag gctgaggcag gagaatggcg tgaacccgg
7561 gggcggacgt tgcagtgagc cgagatagtg ccactgcact ccagcctgga cgacagagcg
```

Figure 33F

```
7621 agactccgtc tccaaaaata aaaaaacacc tgaaaatccc agtatcccct aagctctgat
7681 gtaaattgac aaaccctgac attgtcccaa acctccaaat ataacccgag ccccgatacc
7741 atctacaaac tccttttcgt cctcagatct tcttactccc taagcccta tgtgaacccc
7801 aagcccactg ttttcctaac cctgatgtaa tccctaaacc tcacacatcc ccaacttacc
7861 cgcacacccc aatgtgcccc tctagacacg aatcgtcctg gactgtgggg aagatgacgt
7921 atgtgtgccc cagcttcagc tcactgccag cgtgtgagga ggcctcccat tctgcccgac
7981 cctggccctt tctgcctatc atacctgctc cacacttag tcccctcttt tcccacatcc
8041 tgggcccaga cccaggctcc ctggcttcac tcctctttcc ccacaggacg ggctcccgc
8101 tcctagttgg ggcagataat gtcctggagc tgcagatgga cgcagccaac gagggcgagg
8161 gggcctatga agcagagctg gccgtgcacc tgccccaggg cgcccactac atgcgggccc
8221 taagcaatgt cgaggtatgg ccccaccct gggaacagta cccgggacct gggaggcact
8281 ggagccttgg ctctctcatc tccctccctg agagtccctc ttctcttctg ctttgctgtc
8341 aaagatgtaa ttttttttt aatttggagg aggatacttg ctaatggtca gtcagaattc
8401 caaaactcta ttacaaaaac cagaaaaaca aaaaggttt aggaaccaaa tgttaacagg
8461 aacctctgtt aacatttggt ggatttcctt ccagtctttt tttcaatatt gactcacact
8521 cacataagta tatatttatt ttttatgttg ttaatatagt ttataataat ggggtcata
8581 ctctaatgtt ttgtgttttt tatttccaaa atgaaaatgc ctaaaaagta gtagtgctac
8641 agcaatacac acactagcat gtgacagtcc cttgagcgac cccacccaa gaaacccccc
8701 cctccctacc ttggcacaca aatctttcca gaccttccaa gggagcttaa atatatatat
8761 atgatgctct gtaatttctt tcttggaact gccttcctga agggctttga gagactcatc
8821 tgtaatcaga agaaggagaa tgagaccagg tggtgctgt gtgagctggg caacccatg
8881 aagaagaacg cccaggtgag gctgctgggt cgtggtaccg ggtctccacc aggggctcat
8941 gaataaccag atttaggg tgaggtttta gagccacata gttctgggcc agaatcttgg
9001 tcctcacact ccctttgcca acattgtcct tgggtgagtg actttccctc tctgagcccc
9061 tttaccagtg ggcttccagg taaaatagaa ataataatgg tggcctggtg cggtcgtcac
9121 gcctgtaatc ccagcactct gggaggccag agcgggtgga tcacgaggtc aggagttcaa
9181 gaccagcctg gccaacatag caaaacccg tctctactaa aaatacaaaa attcccggg
9241 catggtggcg cacgcctata gtcagagcta ctcgggaggt tgaggcagaa aaatcacttg
9301 aacctgggag gtggaggttg cagtgagccg agatcatgcc actgcactcc agcctgggtg
9361 acagagtgag actccgtctc ggaaaaaaaa aaaagaaaa agaatagtgg tgatcttgga
9421 gggtgaagac tggaggccac attcagggca gggctgtcct aagtggggca cttgggcagt
9481 gaccttggcc ctcctcatct cccagatagg aatcgcgatg ttggtgagcg tggggaatct
9541 ggaagaggct ggggagtctg tgtccttcca gctgcagata cggaggtact gacctggcga
9601 gcgtgcctac ccaccaccct tccccgtct gaccccgtg cagagcccct caggtccctt
9661 ccatacagaa gggtctttcg aggccaggcg cagtggctca cacctgtaat cccagcacgt
9721 tgcgaggcca aggcagaagg atcactggag gtcaggagtt ggagaccagc ctggccaaca
9781 tggtgaaacc ccatctctac taaaatataa aattagctgg catggtggt gcgcacctac
9841 aatcccagct actcgggagg ctgaggcagg agaatagctt gaaccgaacc tgggaggtgg
9901 aggttgcagt gagctgagat tgggccactg cactccagcc ttccagcctg ggcgacagtg
9961 cgagattcta tctcaaaaga aaaaaaaaa aaggtcttga agaagcctgg ttcccttct
10021 tcctcagaga tttagcgagt cttggagccc tagaggaagt tctttcccag gtctaacttc
10081 agtgtggcat gctctttgta taattagctc tctctgaact ctctaaaatt ctggcctcac
10141 ccccagaaag tcactgggct ggtgtccctg ccctgtttc tcctcatccc ctccctcta
10201 gcaagaacag ccagaatcca aacagcaaga ttgtgctgct ggacgtgccg gtccgggcag
10261 aggcccaagt ggagctgcga gggtgagagg ccaggggtgg agaagggaga tggcattcag
10321 ggctctaaac tccagggggc gctgggaaa cctcacaggc caatcagggc atcacactct
10381 ctctgggggt cttgggcacc tgcaggaact cctttccagc ctccctggtg gtggcagcag
10441 aagaaggtga gagggagcag aacagcttgg acagctgggg acccaaagtg gagcacacct
10501 atgaggtatt ggggagcctc gcgtcccctgg ctgggtgag cgggtcctca gaactccggg
10561 tgaggcgcta agctccccac accctgccac caccacccct tcagctccac aacaatggcc
10621 ctggactgt gaatggtctt cacctcagca tccaccttcc gggacagtcc cagccctccg
10681 acctgctcta catcctggat atacagcccc aggggggcct tcagtgcttc ccacagcctc
10741 ctgtcaaccc tctcaaggta agagctgggt ggaagaaaga cctgggaagg cggccccaga
10801 ccaaccaccg gggcacctct gtgggctggg gttcggggga gacctgggcc tgaccactcc
```

Figure 33G

```
10861 tttgcccccc caggtggact gggggctgcc catccccagc ccctccccca ttcacccggc
10921 ccatcacaag cgggatcgca gacagatctt cctgccagag cccgagcagc cctcgaggct
10981 tcaggatcca gttctcgtag tgagcaggct ctctggtctc gggcccggcc tccccgggac
11041 ccacgggcca gaggggatgg gaggagggag aggggtccgg gtgtgctgtg ggcctctgtg
11101 ggccacgctt ggtccctggg agcacttcaa gtgaacatgg aggagcatgc tggcttgtgt
11161 ctggggtgag ctgaaagaca cttgcactt ttaaaagctt cccagtacgt taaggagcat
11221 aaaacaatgc caaagcaagg ttatcataga tctgagcatt gtgcgctggg ggatgaccct
11281 ccctgcatct ctggactat gtgagcaagc ccgtggaaag acagcatccg aagcttggat
11341 ccaaggccct tcctgatggg aaggccaccg cttcctgaac ccccggcccc ttctgcgttg
11401 ggtcctgggg gtaaggggt ggggatgat ggggtgatgg gccgggacgg ctggggactg
11461 acgatgcttc ccctcagagc tgcgactcgg cgccctgtac tgtggtgcag tgtgacctgc
11521 aggagatggc gcgcgggcag cgggccatgg tcacggtgct ggccttcctg tggctgccca
11581 gcctctacca ggtggggtgg gccgtggtgg ggcggggccg ggccttctgg gccgggacca
11641 ctttgctctg ggaggggcgg ggtttggtgt gggagggcag gaagagaggg aaggcaaggt
11701 ttactttggg ggattgcagt gggattaggt cagaggcagg gcttccccgc cgggtgtggg
11761 acctggactc cgtgcaacca ataggcctct tgtgggtgta aacggctttc aaccccaacc
11821 tgtccagagg cctctggatc agtttgtgct gcagtcgcac gcatggttca acgtgtcctc
11881 cctcccctat gcggtggccc cgctcagcct gccccgaggg gaagctcagg tgagtgtggg
11941 gggatggagc agagaccagt cctgcaggac ccattgtccc ccagtcagtg cccagccaga
12001 aaagtctgag gggtggtacg ggtgggtggc atggctggag gtcaccagcc tgaggtttga
12061 gtctttgtga aaggcaggtg tcaaggtgac tgaggagaca cgtgggtttg ccccaggtgt
12121 ggacacagct gctccgggcc ttggaggaga gggccattcc aatctggtgg gtgctggtgg
12181 gtgtgctggg tggcctgctg ctgctcacca tcctggtcct ggccatgtgg aaggtgaggt
12241 gtgaaggacg gtggagtccc cagcgggca caggcttggc tctgccctgc ctcacaggga
12301 gtcaaggaga gatggtggcc cacccaagtg ggtaatccag ggaccagggg tctatgtctc
12361 cactattaga atgtcattct cgtccagggg ggtggctcac acctgtaatc ccagcacttt
12421 ggcaggcaaa gcgtttagat cacctgaggt caagagttcg agaccagcct ggccaacatg
12481 gtgaaacccc atctctacta aaaataccaa attagccggg cgtgttgaca catgcctgta
12541 atctcagcta ctcgggaggc tgaggcagta gaattgcatg aacccaggag gcggaggttg
12601 cagtgagccg agatcacacc actgcactcc agcttgggca acagagcgag cctccatctc
12661 aaaaaaaaaa caaaaaaata gaatgtcttt ctctagtaga gcaaaaggca aaacaaacac
12721 aaaaatgtca ttctcctggg aaccttcca gacacatacc actggaaagg atagcacctg
12781 aaattctgag gcctttagac accctgcca ccaaaaagat tcagaggata tagagggtat
12841 agagggtgta agtcctgcct tcaggaattc ctggctggtc tcaaggacaa gatgcacttc
12901 ttcctagccc tgccctccc cttgagtgag gaagaggcca aggattggtc tagaccctat
12961 tccatacctt cctatgtggc cctggagggt cactcgctcc tctgcacctg gaggagtctc
13021 aagcacactg aagggaagac atggtgcttt tagggaaaac cacgcactag acccacaata
13081 atcaaataca tatcatcata tgctcgagtc atgcagacac aaacttcagt ataagaaaaa
13141 ttccaggctg ggcgttggtg gctcacaccg gtaaaatccc agcactttgg gaggccgagg
13201 tggg
```

Figure 33H

```
LOCUS       HUMHCF2      15849 bp    DNA              PRI       08-NOV-1994
DEFINITION  Human heparin cofactor II (HCF2) gene, exons 1 through 5.
ACCESSION   M58600 J05309
NID         g183907
KEYWORDS    heparin cofactor II; serpin.
SOURCE      Human DNA.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 15849)
  AUTHORS   Herzog,R., Lutz,S., Blin,N., Marasa,J.C., Blinder,M.A. and
            Tollefsen,D.M.
  TITLE     Complete nucleotide sequence of the gene for human heparin
cofactor
            II and mapping to chromosomal band 22q11
  JOURNAL   Biochemistry 30 (5), 1350-1357 (1991)
  MEDLINE   91120782
FEATURES             Location/Qualifiers
     source          1..15849
                     /organism="Homo sapiens"
                     /db_xref="taxon:9606"
                     /map="22q11.2"
     exon            1750..1796
                     /gene="HCF2"
                     /note="G00-120-038"
                     /number=1
                     /product="heparin cofactor II"
     gene            join(1750..1796,6948..7852,11623..11896,13654..13798,
                     14527..15372)
                     /gene="HCF2"
     mRNA            join(1750..1796,6948..7852,11623..11896,13654..13798,
                     14527..15372)
                     /gene="HCF2"
                     /note="G00-120-038"
                     /product="heparin cofactor II"
     exon            6948..7852
                     /gene="HCF2"
                     /note="G00-120-038"
                     /number=2
                     /product="heparin cofactor II"
     CDS             join(6964..7852,11623..11896,13654..13798,14527..14718)
                     /gene="HCF2"
                     /codon_start=1
                     /db_xref="GDB:G00-120-038"
                     /product="heparin cofactor II"
                     /db_xref="PID:g183908"
```

/translation="MKHSLNALLIFLIITSAWGGSKGPLDQLEKGGETAQSADPQWEQ

LNNKNLSMPLLPADFHKENTVTNDWIPEGEEDDDYLDLEKIFSEDDDYIDIVDSLSVS

PTDSDVSAGNILQLFHGKSRIQRLNILNAKFAFNLYRVLKDQVNTFDNIFIAPVGIST

Figure 34A

```
          AMGMISLGLKGETHEQVHSILHFKDFVNASSKYEITTIHNLFRKLTHRLFRRNFGYTL
          RSVNDLYIQKQFPILLDFKTKVREYYFAEAQIADFSDPAFISKTNNHIMKLTKGLIKD
          ALENIDPATQMMILNCIYFKGSWVNKFPVEMTHNHNFRLNEREVVKVSMMQTKGNFLA
          ANDQELDCDILQLEYVGGISMLIVVPHKMSGMKTLEAQLTPRVVERWQKSMTNRTREV
          LLPKFKLEKNYNLVESLKLMGIRMLFDKNGNMAGISDQRIAIDLFKHQGTITVNEEGT
                          QATTVTTVGFMPLSTQVRFTVDRPFLFLIYEHRTSCLLFMGRVANPSRS"
     exon            11623..11896
                     /gene="HCF2"
                     /note="G00-120-038"
                     /number=3
                     /product="heparin cofactor II"
     exon            13654..13798
                     /gene="HCF2"
                     /note="G00-120-038"
                     /number=4
                     /product="heparin cofactor II"
     exon            14527..15372
                     /gene="HCF2"
                     /note="G00-120-038"
                     /number=5
                     /product="heparin cofactor II"
BASE COUNT     4477 a   3814 c   3642 g   3916 t
ORIGIN
        1 gggctttgca tgtgtgagaa caagacagag aatgagggag gtgggcccca cgaggagtgt
       61 gggcacagac agcagcctct gcctgtggtg ccacgctgaa gactcagtat tgtatgtgac
      121 agatgaaggc tctaagaaga cagctctgac aaaagctaga gtgcaaaatc agactcagac
      181 acaaccaccg gtctgtgtcc tgaacacaat ggacctttac actctggaat ttctcaaacg
      241 gagcaatgca cagacacccc catgggcccc ttgcacaccc gcagattctc ctaggagtca
      301 cattctctct tcagatagac tctgggtgcc gacactccca aacatgctct tgaggagcag
      361 tctctgtgat aagctgatct tccagacaat ccagaatatt cttaaaactt tttagatcat
      421 aaaatttaaa acacaaatta aaaacaaat tatcataagg ccgggcacag tgactcatgc
      481 ctgtaatccc agcactttgc aaggctgaag caggaggatc acttgagccc aagagttcaa
      541 gaccagccta ggcaacatag tgagaccctg tctctacaaa aaagtcaaaa gttagctaga
      601 catggtggtg tgcacctgta ttcccagcta cttgcagggc tgaggtgagg aggattgctt
      661 cagctcggga ggttgaggct gcagtgagcc aagatcacgc cactgcactc cagcctgggt
      721 aacagagtga gaccctgtct caaaaaacac ataggccag gcgtggtggc tcacgcatgt
      781 aatcccagca ctttgggagg ccgagacggg aggatcactt cactccagga gttcaacacc
      841 agcctggcca acatagtgaa acccgtctc tactaaaaat acaaaaaatt agttggacat
      901 ggtggtgtgc gcctgtaatc tcagccactc aggaggctga ggcaggagaa cgcttgaact
      961 tgggagacag aggttgcagt gagctgagat cgcaccactg cactccagca tgggcagcag
     1021 cgcgaaactc tgtctcaaaa caaacaaaca aacaaacaaa cacccataaa cacaaaatgt
     1081 atcacagcct cagagatccc cacgaatgcc taagtggccc tgaatttggg aggcactgct
     1141 cagtaatagt cctatctgtc ccacaacaga caggagtgct gggctgcacc tactggcaac
     1201 aaacacagca accttgact gaagaaaggt ccatgccaca atccccttat tctgtaagcc
     1261 actaattttg tcctctctcc tccacctttc actgaggaac gagctcttgg aaggacaggg
     1321 acacccgcct agtagctgag ccagccacat cagtcctgga gagcaggtgg agggcagatg
     1381 ctgtgatcat cccagaagag aggacacagt tggaggcaga tgcatggtct ctactttcag
     1441 ctaccctcaa tgcagcctgg tccccagagg cctgaagagc gccttgttta tgtggtgacc
     1501 tcaagagggg ctgctcctgc accaaggcta tgtgtgcatg ctaacacagt aaccgtcata
     1561 tactcaaagt gtcagctcta agaactggag atgaggagct gcaagccact ctacagttat
```

Figure 34B

```
1621 caaaggcaca gctgaggggg tttgtgctga ccaagctggt tgcctggtgt ttggattggg
1681 acttatttac tttggaaaat atgcagcaac agcccagcac caaagttcac atcaaaatcc
1741 cactgatgac cttggctgct ttcatctctg aagcgccact tctcagaaac acagaggtaa
1801 gttgggtttc taatgtttct gctgattata aattattttt ggtgtttacg gataggcaac
1861 tggttcattt ttctagcaaa ctaagaattc agaagctttc tacactgttt tagaagtggg
1921 aaatggtttc attttcagt gtgcctatta taaaattgtg tcagttccat tgttgggaga
1981 gttgacaaac ttagaatagg agctgtggaa tagatgaaaa tattgtactt atattaaatt
2041 aatcgaattg gataactgtc ctgtgattat gtatgagaat atccttgctc ttgggtattt
2101 tccctgaagt attagtatta aaggttagag gggccgggtg cagtggctca cgcctgtaat
2161 cccaacactt tgggaggccg aggcgggtgg atcacgaggt caggagttca agaccagcct
2221 gaccaacatg gtgaagccaa gtctctacta aaaatacaaa aattagctgg gcgtggtggc
2281 acgcgcctgt aatcccagct actcaggagg ctgaggcagg agaatcgctt aaacccggga
2341 ggcagaggtt gcagtgagcg gagatcgtgc cactgcactc cagcctggac aacagagtta
2401 gactccgtca aaaaaaaaaa aaaaagaag aaaaagaaa aatgttaga ggaacaagat
2461 ataggagacc tactctcaaa tggtctagaa gaaaaaatgt gtatgtgcat gcctgtgaga
2521 acacacacgt acgtacacac acacacagat aatgacaggg caaaggttcc aaaatttaa
2581 acctggtaaa tctcggtacg ggtatacagg agttgttcta ctacactatt ctttcaacat
2641 ttttggaagt ttgaacttac ttcaaaataa aaagttttcc aaactttagg cagttacttc
2701 tctcccattc tgcctgctct gttgggcctg gagaccatac accaggaggg atgacggttt
2761 atcaagtgtt atgctctgat gcgtgactga aaaggccaac ccagctctgg caattagcaa
2821 gaaagcacaa tatgaagttc ccaggaaaaa aaaaagcaa aacaaacttt tgaatgattt
2881 atctttaaaa tatattgttt ctcttcaaac agtaatctgg atttaatcac aacctagtga
2941 tagtttttaa acgtcttcta caatgtttgt tatactaaat agcaaaacat caggaagatt
3001 taccttcaga tctttaattt caatccataa aagatatcag agatatttc tccttcctct
3061 ggtaagggaa tgacgaaaac tatttttggc ttttatcag ataatgtggg aacagggtat
3121 aagaagtttc caaatataac ttctgaatac cgggataaaa catgcatgtc tttactctgc
3181 cactctatct ggcctcagat acgttttcct gaatgcttat ttattcaagt tggttttttgt
3241 tttgttcttt aaccttattt ttatctgaga agaaaacatt tccccccttt gttccttctt
3301 cttttggctt tctttttta aatagagatg aggtcttgct atgttgctcc agctggtctt
3361 gaactcctgg gctcaagcga tcctcctgcc ttggcctccc aagatgctaa gattacaggt
3421 gtgagcccct atgcctggtc ttcttcttct tgatcttagc caaaaggcca agaagtgata
3481 agaggaggac acttgaagtg tagttgggca aggagccttc taccagctgc ttactttctt
3541 tgttcctgac ttttaaaagt gtgttgctat tgatacacag tctcctgata tgtaaaatgc
3601 tgggaggatg aagctaagtt actcaaagtg ccattcagaa actgggccca gttctatttg
3661 cagctacata cattagaaat catttctaga ggctgagcat ggtaactcat acctgtaatt
3721 ccagcacttt gggaggccaa ggcaggagaa ttgcctgagc tcaggagttt gagacctgtc
3781 tgggcaacat ggtaaaaccc catctttacc aaaaacacaa aaattaact gggtttggtg
3841 gcacacacct gtggtcccag ctacttcaaa aggctgaggt gggagggtct cttgagcctg
3901 agaggaacag gtggcagtga accaatattg tgccactgca ctccagcctg ggtgacagag
3961 tgagaccccg ccgtctcaaa ataaaaataa aaagaaatcg tttctagaaa ctgttttccc
4021 gtgtgtaaac tagtggcact gcagcctgag gcaggtgctg agatggggac ctggaaaagg
4081 caacaggcat tttgagtcag aaacaatgtg actttcctgc tccaaaatgt gcaattcaaa
4141 agtctttctt agttgtgact aaaacaaact ttgaacttac tatttcaaca gtattataag
4201 gggaagaccc aaggaatggg actggcactg ggaaaacagc taggaagctg ctctgcacgg
4261 ccagggagtc tggaagcatc ctggtactcc agagcgaaca aggctgagcg cttgatgtgg
4321 ggcttagagg cttaaccaac ttggttcgaa tctagccact gccacttatt agtgacagtg
4381 acgaaaggct cagtctcctg atatataaaa tgttgggagg atgaaactaa gttacacgaa
4441 gtgccttata cagcgtgtca ggcatccaac agaggccatt atcaacatta accacactga
4501 cagcatttca agcagagtat ccgaacagtt accccatctt caggcctact gagttcaaat
4561 atttgcttaa caagagcagc cagtaactct tacctggcct caactggcag cagatattct
4621 gggcctcaaa tatctatcta ataggaaatg gtcacagaca caaataagc ttaacaaaag
4681 gcagtttttt tttgttttt ttttgttttc tgttttttga gataaggact cactctatcc
4741 cccaggttgg agtgcagtag tggcgtgatc acggctcact gcagactcaa gtgatcctcc
4801 tacttcagcc tctcaagtag atgggaccac aggcgtgtgc catcacacca ggctaattat
```

Figure 34C

```
4861 ttttcttttc tttttttttt ttttgagacg gagtttcgct cttttttgccc aggctggagt
4921 gcaatggtgc gatcttggct caccacaacc tctgcctcct gaattcaaac gaatctcctg
4981 cctcagcctc ctaagtatct gggattacag gcatgcgcca ccacgccggc taatttttttt
5041 gtatttttttg tagagacagg gtttctccat gttggccagg ctggtctcga actcccgacc
5101 tcagatgatc cgcccacctc ggcctcccaa agtgctggga ttactgacct gagccaccgc
5161 acccagccta tttatttaat ttttcacaga gatgaggtct tgctatgttg cccacactgg
5221 tcttgagctc ctgggctcaa gtgatcttcc tgccttggtc tcccagtgtt gggattatag
5281 gcgtaagcca cagcgcctgg ccggcagttc tttctggggt gattagaagt tgggaccatg
5341 tattacctgt ctgagtcagc attataaaca cctatggtca ctgtcctggc aaaacatgga
5401 atcatcaaag ctcatctaac cagagtgcag ttaataacca ggaagtaagc aagagaaaga
5461 caaggatttt ggcagtcaaa acagatttga caggccaagt cagatcctcc tctgaacgag
5521 tcagaggaac aaataaagac aggattgcca taatgcctct gtgctaaaag cttatcttgt
5581 ttacttaaat aaagggagtg cccctcaggt cttgagtaag agcttgctga catcaccctc
5641 acacagactt tatctcttgt ttctaaccct gtgttagaag cagtaacaca gaagatttag
5701 ttgctcctga cagcagtggg agctattgtc taagagatac aaaggagaaa aaagtatacc
5761 tgcagcaagt gatatcacct ctggggctgc caccacatca cctcactacg ccctgagggg
5821 gtctcagcac tagacaagtt ccaaatcttt tgcaaattaa acaaccccag gtcaggcgtg
5881 gtggcttatg cctgtaatcc cagcactttg ggggctgag gtgggtggat cacctgaggt
5941 caggagtttg agaccagcct ggccaacaga gcaaaacccc atctctacta aacaaaatac
6001 aaaaattaac caggcgtagt ggtgtgcacc tgtagtccca gctacttggg aggctgaggc
6061 aagagaattg cttgagtcca ggaggccgaa gttgcagtaa gccgagatcg cgccactgca
6121 ctccagcctg ggtgacagag tgagactcca tttcaaaaaa taaaaacaac aaaagccaat
6181 tacaacaaca acaacaaaaa aacaacgaat taaacaaccc caaagattgc acaaatttca
6241 agtatcttta gaatatgttt tcagaaagcc tggcccatgg acattttttca acagcatctc
6301 cattgcaaag gtggaatggt gtgagtcaca caggcatggc tgagtcccac taatgcacat
6361 cccttctagg tactctccaa tcaccagccc caggtgccca ctcaagccca gctcttagtg
6421 aggtttccct gactctctgg gcacttccac tcctaccaca cagggtagag ccacacccct
6481 ttccgtaccc ccatgtgctc tggcagcatt attttgagag ccttcgcttt actgcacgtc
6541 tgtcccatct gtccctgac tggtccatga gcccctggtt ggaactttgt ctctggtaac
6601 taaacactgt ctggaggtgg tggacaaggt gtctggagaa aaacaaactc ctccctggga
6661 tgcctgagct cccaggattc tagaaggtta gttttgcaaa ccttttaaga agggatttttc
6721 atcaaggggc ccacagatcc ttcattgagg tttatgagtc ccacatcaaa ggttgggtgt
6781 ctatctacat cagattctct taaagtccat gatcctaaaa cagttaagaa ctaatgctgt
6841 gagggcctct tcctgggtca aagccacagg gaacctgcca tgtggatgct gcagcggggt
6901 gtggatcagc caggccgcct ttcactgtgt tctgttttcc ctcccagctt tagctccgcc
6961 aaaatgaaaac actcattaaa cgcacttctc attttcctca tcataacatc tgcgtggggt
7021 gggagcaaag gcccgctgga tcagctagag aaaggagggg aaactgctca gtctgcagat
7081 ccccagtggg agcagttaaa taacaaaaac ctgagcatgc ctcttctccc tgccgacttc
7141 cacaaggaaa acaccgtcac caacgactgg attccagagg gggaggagga cgacgactat
7201 ctggacctgg agaagatatt cagtgaagac gacgactaca tcgacatcgt cgacagtctg
7261 tcagtttccc cgacagactc tgatgtgagt gctgggaaca tcctccagct tttttcatggc
7321 aagagccgga tccagcgtct taacatcctc aacgccaagt tcgctttcaa cctctaccga
7381 gtgctgaaag accaggtcaa cacttttcgat aacatcttca tagcacccgt tggcatttct
7441 actgcgatgg gtatgatttc cttaggtctg aagggagaga cccatgaaca agtgcactcg
7501 attttgcatt ttaaagactt tgttaatgcc agcagcaagt atgaaatcac gaccattcat
7561 aatctcttcc gtaagctgac tcatcgcctc ttcaggagga attttgggta cacactgcgg
7621 tcagtcaatg acctttatat ccagaagcag tttccaatcc tgcttgactt caaaactaaa
7681 gtaagagagt attactttgc tgaggcccag atagctgact tctcagaccc tgccttcata
7741 tcaaaaacca acaaccacat catgaagctc accaagggcc tcataaaaga tgctctggag
7801 aatatagacc ctgctaccca gatgatgatt ctcaactgca tctacttcaa aggtaagagg
7861 cacctttaca gttctcacag caaacccaca acatactatt tttgtatgtg ggtagattga
7921 atgccaagaa ctgtactgta gctataattt atccaggaaa actagacaca agattgactc
7981 tggaacgggg acagggaagg ccaagctgaa gtgacagtag catctgacac ttactgagcc
8041 ctaactctgt gctttaacac agccttgtga ggtcatcact gttattagca tccccatttt
```

Figure 34D

```
8101  acagaggaag ccaccaacac atgaagtaaa aggatgggct gggcgcggtg gctcacgcct
8161  gtaatcccag cactttggga ggccgaggca ggcagatcac ttgaggtcag gagttcgaga
8221  tcagcctgac caacagacca acatggtgaa aacctggctc tactaaaaat acaaaaatta
8281  gctgggcctg gcggtgggtg cctgtactcc cagctacttg ggaggctgag gcaggagaat
8341  cacttgaacc tggaaggcag agattgcagt gagccgagac tgtgccactg cactctagcc
8401  tggacgacag agtgagactc catctcaaaa aaaaaaaaaa aagaagtaaa acgatgctcc
8461  aagggcaccc agttattaag gggcagagcc aaagctgaac ccagggaggc caaccctagc
8521  aatctgttaa attggaagaa ataatacaaa aactgtttta gcatttggcc agcctggatt
8581  tgagttttct cttttccttt cccaattatc aataagcagg aatatagaca aaaggctaaa
8641  gaaatgcacc tgtgaactat tcagcttgag cagctgacat tgacacctac aagtgctttt
8701  caggatactt ttgaactact gggcaggtgg gatggagaaa taaattacta tttccccagc
8761  aactgttctg ggctgagcac aagggcactt tttaaggagg tcacccccaca cccatcacac
8821  acacatagga cccctggaat cctaggaata aataagcatg gatttgtaaa atccaaacct
8881  ctcttttcaa atatcctcac ctggaccaga ccagaagaaa cctctacttt actctctaag
8941  ctgagagtgt ggaaggggaa acacgaggaa tggttcggct tcaggactaa ttgcggtgac
9001  acacaaccac ttctctttgc caccaaggac taccaggtac ctgcaaaggg cagtacttgg
9061  aggccagtgc tttctgctag ttagctcccg tggttttata gcagcccagg cgaaggaagg
9121  agaccccccc cagctcctgg cttctgttca gggaaagggg gccagagccc ctcctgatct
9181  gtccacacac ctgctctgtg ccttggctga ggcccctgca gctctacaag gcaggcattc
9241  tgctggatag gccaagcagg gtcactctga cacccaggtt tccacccccaa ggcatggcac
9301  aatgctggcc tcctgtgggt ggaatcaaag gctgagttct aacaggcttg cggcagacac
9361  acacacagag accacatgta catgatgaac acacatatcc tttcattac aggttattag
9421  tacaagtttt ggaattgagc aaacaagagt ctaagcgctg gtttcaccac ttctcgtttg
9481  tgtgacctca gacaagtcat tcaacatctc tatgactcag tttccttatc tttatcacag
9541  agatgacacc cactctgaca gggccgaggg aagaaccata agcgatggca atgcaacaga
9601  gtggcacatg acaagagctc agcgaatttg agggaatgaa actgtagatt acaatactag
9661  tacaatatga taaacatatg atattgttag tgacatttat tttacttcta ctagcaaata
9721  acctatgttt aggactgact ttagaacagg ctggcagaag catttttggc agcatcaaag
9781  tcctccaacc tactggtctg ttggagcccc ccaagtacac caaagagcct ctgcattagc
9841  cctggctgag ggttcaggga caggcagaga agtacagcag tgagccatcc ctgcctgcat
9901  ggaggtggag aaatgatcag gcatggtcag ttgacaatct cctaaacaca gtaacccgtg
9961  tcataccaca gtgtaaacac acgtgcaaat gcttctgctt cctttcccca tcatgagaat
10021 agtcactcaa tgccggcat cacaagggat caaatgctag gagtacccaa tcattcatgg
10081 atgcttctca aaggggacga gtgtctagaa gtgtaatttt aatttcactt aatttcatat
10141 ggaatcatct ccattactaa ttttgttcta attttaatgt gataatcact ttgtaaagca
10201 caataaacag aggcaggctc tcatgaggaa gtcagaagga aagaatccca agagacatgg
10261 gacagctcca tccaaactga aagggccgtg attcccaaaa gagcaatttt gtccccaagg
10321 tctgaagaca cttttggttg tcacaacctg gggggttgga gtaagcatta ctggtatcta
10381 gaaggggag gctgggatg ttgctaaaca ccctaccatg cacagggcag cccacattgc
10441 cacaaactat tatgtggccc aaatgtcaaa aatgctgagg ttgagaaacc ctgggtgagg
10501 cagactcagg gagaagggaa tcgagcttca ctcacaggca ggcaggagct gtctggtact
10561 tcaacctcca agacacctcc tgctcatctc atcctggctg ctctacccac cagctagaaa
10621 ccttgaacaa gttacttcac ttctttgtgc ctctgtttcc tcatatgtaa aagagggata
10681 acaaaacgca cacaacttgc atgttgctag gagcagaaat gagataatac aggaaaggtg
10741 ctgagaagaa tgcccggcac atggccagtt tcaactact agtcacccat tactattagt
10801 tactcacatc ttagagctaa catagacatg ggcttattcc tggatacaca gcactgtccc
10861 catatctaca gtggtgatcc taagggcaac atggcatcac ccaaatgtct tgttagtcac
10921 tacagaatca cagtgtgagg gatgaaggcc atcaagacag agctgaggct ggcagggtgg
10981 ctcatgccta taatcccagt gctttggaag gctgaggcag gaggattgct tgaggccaag
11041 ggtttgagac cagcctaggt aacatagcaa gaccccatct acaattaaaa aaaaaaaaaa
11101 aaagacagaa agaaaaaata gccaggcgtg gcatgtgctt gtagtccaag ctactgggga
11161 gggaggctga ggcaggagga ttccttgagc ctgggagtgt gaggctgcag tgagctatga
11221 tggcatcgcc gcactccagc ctgcatgaca cagtgagacc tggtctcaaa aaccaaataa
11281 taataacagt aataaaagct ggaaagagct caaagttact catttgacag atgtgacaga
```

Figure 34E

```
11341 tgaagaaata gaagcgagtt aggtgcctta ccatggtcaa acaactagtt cgtatcagac
11401 cctactccag aaactattcc agtccgggta acctctcgtt aacctctctt gttagaaatg
11461 caaatttctg cccaaatcag gcctcaggaa tcaagagact gtggggtcgg ctctgcaggc
11521 tatctgaatg aggcctccag ggaaatcaga ttcactctca agggtgagac gatttcccta
11581 aaggaacctt ctcataacag cctcttcctg tggcctttac aggatcctgg gtgaataaat
11641 tcccagtgga aatgacacac aaccacaact tccggctgaa tgagagagag gtagttaagg
11701 tttccatgat gcagaccaag gggaacttcc tcgcagcaaa tgaccaggag ctggactgcg
11761 acatcctcca gctggaatac gtgggggggca tcagcatgct aattgtggtc ccacacaaga
11821 tgtctgggat gaagaccctc gaagcgcaac tgacaccccg gtggtggag agatggcaaa
11881 aaagcatgac aaacaggtat tcacactgt gtgtttgttc ttttgagctc ccagatgctg
11941 ggggtgtctg ggaatactgg aaaatggatc attttttaa aagggagaa ttatgtacaa
12001 gtacccaaga acttccatac agggccactc tgttaattca gccccaattt gttgcttgag
12061 ataagagatg attagagagc attcataagg gacacatctg ccctctaggg gccagtttca
12121 gaagttagag gcagatgact tagagacagc ttggtgcttg ctttgtggct tcgagtccca
12181 gcttcatcat ccctaaaatg ggtataattc cattacttcc ccgggtcact tgagaaaata
12241 acagaatcag cgatgctgag cgcccctccc agtacttgga acctaggagg cactcaaaaa
12301 aagattggct caactcttcc ctgcccagga aattccaagg tcctcttagc ctaccgagga
12361 cacatcattc atgatttcct ctattattat tcgttacttt gtagttaaaa ctgcaggtgt
12421 taagtactta ttgagattat tattgggtca tggcagaaag aatggagagg tcttatttct
12481 gtcttactgg atactggcta ggcccatatg aagaagtgat tctggtttga acctccttat
12541 aggacaagaa tacaaacata tgcaaccaaa ctgagaaaag taggctctca gaggaaggta
12601 tttgcccggg tagccagtca tcatgctctg tgaattttc cttaacaacg tcccttctgt
12661 acctgcctcc ttccattcct ccctgcagcc cggcagctct tgagaaaggg actgcatctt
12721 tttttttttt ttttttttga gacagggtct tgttctgtca cccaggctgg agtgcagtgg
12781 catcatcatg gctcactgca gcctcaacct cctgaactta agtgatcctc tcacctcagc
12841 ctcctgaata gttgagacta caggcgtgca ccttcatgcc cagctaatta aactttttttt
12901 ggtagagatg aggtctcgct gtgttgccca ggctggtctt gaactcctgg cctcaagcag
12961 tcctcctgcc ttggccttcc aaagtgctgg gattaacagg cgtgagccgc tgtgcctggc
13021 ccatttgact tttaattgag atcttacttg gtgcaaggta tgagctaggt aaaagagtga
13081 agaagatcaa gccttcctgc ccatccagct gggattgcac cttaaatctc tttatcccct
13141 gcaaagtgcc agactaactc cacaggcact actgttgcta tccgccccct tagggattga
13201 gtaagttgag gcaaagattg agatattcag cattgtctag tatatacagg aaaggttctt
13261 tttaaaagta cactaccaga tattcgactc cttaattaca aaaaaaaaac caaatgccta
13321 aaattgggaa accaaaccag agaattattt tagatgcctt tttaaaccat aaaccaggaa
13381 aagttctgct gctaaccttg aagataggaa acgaaccata cagtctcaag gaaataatca
13441 tgcaacagaa aacacacctc agttttcagt agcggaatta caaaggagtg tgcttcctaa
13501 aatcctcaac tgacagtccc ggaatataaa ttttaataag tgctatatca attctgtgat
13561 aaatataacc cgtggccctt taaaggaaa atcatgattc ttttgtaact tgtggttcaa
13621 taaaactggg cccccctttc cttttctgtc tagaactcga gaagtgcttc tgccgaaatt
13681 caagctggag aagaactaca atctagtgga gtccctgaag ttgatgggga tcaggatgct
13741 gtttgacaaa aatggcaaca tggcaggcat ctcagaccaa aggatcgcca tcgacctggt
13801 aaccactccc ttgtccaccc ccgaccgtc cccagggtct gcctcagcac agcccccacct
13861 ccacttgccc ttcctaccca cccccaatc tcatgtccca gcttggggtg ctgagtctgc
13921 tcttcggcct gggtgggata cacagaatgc ctagtttcat ggatgccagc tggagagcac
13981 ggcacctggc agacacttac tgggcagggg ggatcccaag agcagccatg gggtgagccc
14041 cactcccgct gacaccagag acaggggaga catgtgctgc ggtctgggaa atagctaccc
14101 ccagccaaat catgaaagag ccattaaaca ccgcactata caacatactt aacttaaacc
14161 aatcgggtcg ctcagcaaaa gagagagaac accagtccaa acagtgcagc agacccagtt
14221 ccccatcccg gagaagtgcg cagcagtgtg gggagctgga gctggggtgg ctgtcctgca
14281 ccagccccca cgaccctcag accacaggca ctgccaagag gaacatgaa cctagccggc
14341 ctctaagtgc aacggctgcc cctgacaggt ggtgacagat attttcaaga gtgactctga
14401 ccagctgtga tttccacctt acatgttgtc tttggatcct ttccctgaat gatatgagat
14461 tgtgctggga actctagccc tctgtgtgct gacctccaga atctgacaac tttccttttcc
14521 aaacagttca agcaccaagg cacgatcaca gtgaacgagg aaggcaccca agccaccact
```

Figure 34F

```
14581 gtgaccacgg tggggttcat gccgctgtcc acccaagtcc gcttcactgt cgaccgcccc
14641 tttctttcc tcatctacga gcatcgcacc agctgcctgc tcttcatggg aagagtggcc
14701 aaccccagca ggtcctagag gtggaggtct aggtgtctga agtgccttgg gggcaccctc
14761 attttgtttc cattccaaca acgagaacag agatgttctg gcatcattta cgtagtttac
14821 gctaccaatc tgaattcgag gcccatatga gaggagctta gaaacgacca agaagagagg
14881 cttgttggaa tcaattctgc acaatagccc atgctgtaag ctcatagaag tcactgtaac
14941 tgtagtgtgt ctgctgttac ctagagggtc tcacctcccc actcttcaca gcaaacctga
15001 gcagcgcgtc ctaagcacct cccgctccgg tgacccatc cttgcacacc tgactctgtc
15061 actcaagcct ttctccacca ggcccctcat ctgaatacca agcacagaaa tgagtggtgt
15121 gactaattcc ttacctctcc caaggagggt acacaactag caccattctt gatgtccagg
15181 gaagaagcca cctcaagaca tatgaggggt gccctgggct aatgttaggg cttaattttc
15241 tcaaagcctg acctttcaaa tccatgatga atgccatcag tccctcctgc tgttgcctcc
15301 ctgtgacctg gaggacagtg tgtgccatgt ctcccatact agagataaat aaatgtagcc
15361 acatttactg tgtatctgtt ataattctct attttttgaa gctcaaatat caaaagccaa
15421 atccaaattc ctggataact ccaggtatga taaaggctga gaggaagtca cttgagcacc
15481 acaatgtgcc acagcagggc atgttctcag gacaggacag gtgtgtgctg aatcctgggg
15541 agggtctgtg cagtacccca gaactgtggg gtgctaagtg gcacacaagc cccagggctc
15601 ccacagtcta tgccaggctg ctgcagcttt catccctcat acctggtcct gcagtgggtc
15661 tggtttgaca gagcagatga cacctgagga atatgtttct ggatccttca atccctgggt
15721 aagacaagtg aaatccacag aggctgttca gcacgcaaga gtgccagtgc tctttcagtg
15781 aggggatgac tgacggtcac aggtgctgtg tgtgcaggtg tctaactgta accccacagc
15841 ctggcagat
```

Figure 34G

```
LOCUS       HUMTHRR      3472 bp    mRNA             PRI       10-OCT-1991
DEFINITION  Human thrombin receptor mRNA, complete cds.
ACCESSION   M62424
NID         g339676
KEYWORDS    thrombin receptor.
SOURCE      Human DNA.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 3472)
  AUTHORS   Vu,T.H., Hung,D.T., Wheaton,V.I. and Coughlin,S.R.
  TITLE     Molecular cloning of a functional thrombin receptor reveals a novel
            proteolytic mechanism of receptor activation
  JOURNAL   Cell 64, 1057-1068 (1991)
  MEDLINE   91168254
FEATURES             Location/Qualifiers
     source          1..3472
                     /organism="Homo sapiens"
                     /db_xref="taxon:9606"
     CDS             225..1502
                     /codon_start=1
                     /product="thrombin receptor"
                     /db_xref="PID:g339677"
```

/translation="MGPRRLLLVAACFSLCGPLLSARTRARRPESKATNATLDPRSFL

LRNPNDKYEPFWEDEEKNESGLTEYRLVSINKSSPLQKQLPAFISEDASGYLTSSWLT

LFVPSVYTGVFVVSLPLNIMAIVVFILKMKVKKPAVVYMLHLATADVLFVSVLPFKIS

YYFSGSDWQFGSELCRFVTAAFYCNMYASILLMTVISIDRFLAVVYPMQSLSWRTLGR

ASFTCLAIWALAIAGVVPLVLKEQTIQVPGLNITTCHDVLNETLLEGYYAYYFSAFSA

VFFFVPLIISTVCYVSIIRCLSSSAVANRSKKSRALFLSAAVFCIFIICFGPTNVLLI

AHYSFLSHTSTTEAAYFAYLLCVCVSSISCIDPLIYYYASSECQRYVYSILCCKESS
           DPSSYNSSGQLMASKMDTCSSNLNNSIYKKLLT"

```
BASE COUNT      933 a    817 c    785 g    937 t
ORIGIN
        1 gcgcccgcgc gaccgcgcgc cccagtcccg ccccgccccg ctaaccgccc cagacacagc
       61 gctcgccgag ggtcgcttgg accctgatct tacccgtggg caccctgcgc tctgcctgcc
      121 gcgaagaccg gctccccgac ccgcagaagt caggagagag ggtgaagcgg agcagcccga
      181 ggcggggcag cctcccggag cagcgcgcg cagagcccgg gacaatgggg cgcggcggc
      241 tgctgctggt ggccgcctgc ttcagtctgt gcgggcccgct gttgtctgcc cgcacccggg
      301 cccgcaggcc agaatcaaaa gcaacaaatg ccaccttaga tccccggtca tttcttctca
      361 ggaaccccaa tgataaatat gaaccatttt gggaggatga ggagaaaaat gaaagtgggt
      421 taactgaata cagattagtc tccatcaata aaagcagtcc tcttcaaaaa caacttcctg
      481 cattcatctc agaagatgcc tccggatatt tgaccagctc ctggctgaca ctctttgtcc
      541 catctgtgta caccggagtg tttgtagtca gcctcccact aaacatcatg gccatcgttg
      601 tgttcatcct gaaaatgaag gtcaagaagc cggcggtggt gtacatgctg cacctggcca
      661 cggcagatgt gctgtttgtg tctgtgctcc cctttaagat cagctattac ttttccggca
```

```
 721 gtgattggca gtttgggtct gaattgtgtc gcttcgtcac tgcagcattt tactgtaaca
 781 tgtacgcctc tatcttgctc atgacagtca taagcattga ccggtttctg gctgtggtgt
 841 atcccatgca gtccctctcc tggcgtactc tgggaagggc ttccttcact tgtctggcca
 901 tctgggcttt ggccatcgca ggggtagtgc ctctcgtcct caaggagcaa accatccagg
 961 tgcccgggct caacatcact acctgtcatg atgtgctcaa tgaaaccctg ctcgaaggct
1021 actatgccta ctacttctca gccttctctg ctgtcttctt ttttgtgccg ctgatcattt
1081 ccacggtctg ttatgtgtct atcattcgat gtcttagctc ttccgcagtt gccaaccgca
1141 gcaagaagtc ccgggctttg ttcctgtcag ctgctgtttt ctgcatcttc atcatttgct
1201 tcggacccac aaacgtcctc ctgattgcgc attactcatt cctttctcac acttccacca
1261 cagaggctgc ctactttgcc tacctcctct gtgtctgtgt cagcagcata agctcgtgca
1321 tcgaccccct aatttactat tacgcttcct ctgagtgcca gaggtacgtc tacagtatct
1381 tatgctgcaa agaaagttcc gatcccagca gttataacag cagtgggcag ttgatggcaa
1441 gtaaaatgga tacctgctct agtaacctga ataacagcat atacaaaaag ctgttaactt
1501 aggaaaaggg actgctggga ggttaaaaag aaaagtttat aaaagtgaat aacctgagga
1561 ttctattagt ccccacccaa actttattga ttcacctcct aaaacaacag atgtacgact
1621 tgcatacctg cttttatgg gagctgtcaa gcatgtattt ttgtcaatta ccagaaagat
1681 aacaggacga gatgacggtg ttattccaag ggaatattgc caatgctaca gtaataaatg
1741 aatgtcactt ctggatatag ctaggtgaca tacacatact tacatgtgtg tatatgtaga
1801 tgtatgcaca cacatatatt atttgcagtg cagtatagaa taggcacttt aaaacactct
1861 ttccccgcac cccagcaatt atgaaaataa tctctgattc cctgatttaa tatgcaaagt
1921 ctaggttggt agagtttagc cctgaacatt tcatggtgtt catcaacagt gagagactcc
1981 atagtttggg cttgtaccac ttttgcaaat aagtgtattt tgaaattgtt tgacggcaag
2041 gtttaagtta ttaagaggta agacttagta ctatctgtgc gtagaagttc tagtgttttc
2101 aattttaaac atatccaagt ttgaattcct aaaattatgg aaacagatga aaagcctctg
2161 ttttgatatg ggtagtattt tttacatttt acacactgta cacataagcc aaaactgagc
2221 ataagtcctc tagtgaatgt aggctggctt tcagagtagg ctattcctga gagctgcatg
2281 tgtccgcccc cgatgaggga ctccaggcag cagacacatg ccagggccat gtcagacaca
2341 gattggccag aaaccttcct gctgagcctc acagcagtga gactggggcc actacatttg
2401 ctccatcctc ctgggattgg ctgtgaactg atcatgttta tgagaaactg gcaaagcaga
2461 atgtgatatc ctaggaggta atgaccatga aagacttctc tacccatctt aaaaacaacg
2521 aaagaaggca tggacttctg gatgcccatc cactgggtgt aaacacatct agtagttgtt
2581 ctgaaatgtc agttctgata tggaagcacc cattatgcgc tgtggccact ccaataggtg
2641 ctgagtgtac agagtggaat aagacagaga cctgccctca agagcaaagt agatcatgca
2701 tagagtgtga tgtatgtgta ataaatatgt ttcacacaaa caaggcctgt cagctaaaga
2761 agtttgaaca tttgggttac tatttcttgt ggttataact taatgaaaac aatgcagtac
2821 aggacatata ttttttaaaa taagtctgat ttaattgggc actatttatt tacaaatgtt
2881 ttgctcaata gattgctcaa atcaggtttt cttttaagaa tcaatcatgt cagtctgctt
2941 agaaataaca gaagaaaata gaattgacat tgaaatctag gaaaattatt ctataatttc
3001 catttactta agacttaatg agactttaaa agcattttt aacctcctaa gtatcaagta
3061 tagaaaatct tcatggaatt cacaaagtaa tttggaaatt aggttgaaac atatctctta
3121 tcttacgaaa aaatggtagc attttaaaca aaatagaaag ttgcaaggca aatgtttatt
3181 taaaagagca ggccaggcgc ggtggctcac gcctgtaatc ccagcacttt gggaggctga
3241 ggcgggtgga tcacgaggtc aggagatcga gccatcctg ctaacacgg tgaaacccgt
3301 ctctactaaa aatgcaaaaa aaattagccg ggcgtggtgg caggcacctg tagtcccagc
3361 tactcgggag gctgaggcag gagactggcg tgaacccagg aggcggacct tgtagtgagc
3421 cgagatcgcg ccactgtgct ccagcctggg caacagagca agactccatc tc
```

Figure 35B

```
LOCUS       HUMLPLFI     3877 bp    DNA            PRI       07-JAN-1995
DEFINITION  H.sapiens lipoprotein lipase (LPL) gene, exons 7,8,and 9, and an
            Alu repetative element.
ACCESSION   M76722 M76723
NID         g187215
KEYWORDS    Alu repeat; lipoprotein lipase; plasma protein.
SOURCE      Homo sapiens blood DNA.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 3877)
  AUTHORS   Chuat,J.C., Raisonnier,A., Etienne,J. and Galibert,F.
  TITLE     The lipoprotein lipase-encoding human gene: sequence from intron-6
            to intron-9 and presence in intron-7 of a 40-million-year-old Alu
            sequence
  JOURNAL   Gene 110 (2), 257-261 (1992)
  MEDLINE   92165069
FEATURES             Location/Qualifiers
     source          1..3877
                     /organism="Homo sapiens"
                     /db_xref="taxon:9606"
                     /cell_type="lymphocyte"
                     /tissue_type="blood"
                     /map="8p22"
     intron          1..198
                     /partial
                     /gene="LPL"
                     /note="G00-120-700"
                     /number=6
     CDS             join(199..319,1840..2022,3052..3156)
                     /partial
                     /gene="LPL"
                     /codon_start=3
                     /db_xref="GDB:G00-120-700"
                     /product="lipoprotein lipase"
                     /db_xref="PID:g553523"

/translation="FHYQVKIHFSGTESETHTNQAFEISLYGTVAESENIPFTLPEVS

TNKTYSFLIYTEVDIGELLMLKLKWKSDSYFSWSDWWSSPGFAIQKIRVKAGETQKKV
                     IFCSREKVSHLQKGKAPAVFVKCHDKSLNKKSG"
     exon            199..319
                     /gene="LPL"
                     /note="G00-120-700"
                     /number=7
     gene            join(199..319,1840..2022,3052..3156)
                     /gene="LPL"
     intron          320..1839
                     /gene="LPL"
                     /note="G00-120-700"
                     /number=7
     repeat_region   complement(746..1027)
                     /gene="LPL"
```

Figure 36A

```
                    /note="G00-120-700"
                    /rpt_family="Alu repeat"
     exon           1840..2022
                    /gene="LPL"
                    /note="G00-120-700"
                    /number=8
     intron         2023..3051
                    /gene="LPL"
                    /note="G00-120-700"
                    /number=8
     exon           3052..3156
                    /gene="LPL"
                    /note="stop codon (tga) is interrupted by intron 9,
                    between tg and a; G00-120-700"
                    /number=9
     intron         3157..3877
                    /partial
                    /gene="LPL"
                    /note="G00-120-700"
                    /number=9
BASE COUNT     1145 a     787 c     746 g    1199 t
ORIGIN
        1 gaattcaagg tctgcatttt ctaggtatga acactgtgca tgatgaagtc tttccaagcc
       61 acaccagtgg ttccatgtgt gtgcacttcc ggtttgagtg ctagtgagat acttctgtgg
      121 ttctgaattg cctgactatt tggggttgtg atatttcat aaagattgat caacatgttc
      181 gaatttcctc cccaacagtc ttccattacc aagtaaagat tcattttct gggactgaga
      241 gtgaaaccca taccaatcag gcctttgaga tttctctgta tggcaccgtg gccgagagtg
      301 agaacatccc attcactctg tgagtagcac agggggggcgg tcatcatggc accagtccct
      361 ctcctgccat aacccttggt ctgagcagca gaagcagaga gcgatgccta gaaaacaagt
      421 ctttagttaa aaaaatcaga atttcaaaat tgaggtcttt cctctatttg atattgagaa
      481 aaaaatgctt caaattggcc atttatttt cacttactag ttatattttt ttatttatca
      541 tcttatatct gtttatttct tttataaagc tgctgttaaa caatataatt aaactatctc
      601 aaaaggtttg acattaaaga aaatgagcaa tggtaacagg aaaccactct atagatgtac
      661 atataatatg tacagaaaat ataagtagta agaagtccat gacaaagtgt tagctctttt
      721 tttttttttt tttttttttt ttttgagat ggagtctctc tctattgccc aggctgggt
      781 gcagtgattc gatctcagct cactgcaacc tctacctccc gagttcaaac aattcttctg
      841 tctcagcctc ccgagtagct ggggctgcag gtgcccacca ccatgcccag ctaattttg
      901 tattttagt agcgacaggg tctcaccatg ttggccaagc tggtcttgaa ttcctgatct
      961 caggtgatcc acccgcctcg gcctcccaaa gtgctgggat tacaggtgtg agccaccatg
     1021 cccagcctac cctttactac taatcaaaga aataaaagta aggcaacttg atacttttac
     1081 aattactaga tgaacaaatc tttaaaaata gccagtgcag acaaggtggt gaagcagaac
     1141 atgcgaacct accatgcatc attcacggct agaaccctcc aggtgcggaa ggtagtattt
     1201 taataacttt ccatagctac aaaatattat tacatagaag gggatggatt tttttctaata
     1261 tttatcctaa agaaaatgtc aacaaacatt tttaaaaaca tcaattacag tcgtacctat
     1321 actagcataa attagaaacc cagtatccaa cattgaggca gtgggtaaat gaatcgtggt
     1381 ttatcaagtc attaaaatca atctagcctt taaaaactat aattgtagga acccaggaa
     1441 aacatagtaa aaaatggaat ataaaatctg aagagaataa agaatagaga atcgtatgtg
     1501 tgctatgatt gtagctaaat aatgttcaag tatcaacaca aattgaaaag gaatacatga
     1561 aaatgaaaat tatatttctg aatgattgac ttcaggatt tcttttagaa ttgtattaaa
     1621 tagttcatgt cattaggata aatgctggaa tgtggatata atttaaaata tactaaatgc
     1681 catcgacctt catttttgagt tctttgttgg acattttgt gcatttttaa aatatcccct
     1741 aaataataaa gctatttata tttggagagg agaaaaaaaa gtgggggggca gggagagctg
     1801 atctctataa ctaaccaaat ttattgcttt tttgtttagg cctgaagttt ccacaaataa
     1861 gacctactcc ttcctaattt acacagaggt agatattgga gaactactca tgttgaagct
```

Figure 36B

```
1921 caaatggaag agtgattcat actttagctg gtcagactgg tggagcagtc ccggcttcgc
1981 cattcagaag atcagagtaa aagcaggaga gactcagaaa aagtaattaa atgtattttt
2041 cttccttcac tttagacccc cacctgatgt caggacctag gggctgtatt tcagggcct
2101 tcacaattca gggagagctt taggaaacct tgtatttatt actgtatgat gtagattttc
2161 tttaggagtc ttcttttatt ttcttatttt tggggggcgg gggggaagt gacagtattt
2221 ttgtatttca tgtaaggaaa acataagccc tgaatcgctc acagttattc agtgagagct
2281 gggattagaa gtcaggaatc tcagcttctc atttggcact gtttcttgta agtacaaaat
2341 agttagggaa caaacctccg agatgctacc tggataatca aagattcaaa ccaacctctt
2401 ccagaagggt gagattccaa gataatctca acctgtctcc gcagccccac ccatgtgtac
2461 ccataaaatg aattacacag agatcgctat aggatttaaa gcttttatac taaatgtgct
2521 gggatttttgc aaactatagt gtgctgttat tgttaattta aaaaaactct aagttaggat
2581 tgacaaatta tttctcttta gtcatttgct tgtatcacca aagaagcaaa caaacaaaca
2641 aaaaaaaaaa gaaaaagatc ttggggatgg aaatgttata aagaatcttt tttacactag
2701 caatgtctag ctgaaggcag atgccctaat tccttaatgc agatgctaag agatggcaga
2761 gttgatcttt tatcatctct tggtgaaagc ccagtaacat aagactgctc taggctgtct
2821 gcatgcctgt ctatctaaat taactagctt ggttgctgaa caccaggtta ggctctcaaa
2881 ttaccctctg attctgatgt ggcctgagtg tgacagttaa ttattgggaa tatcaaaaca
2941 attacccagc atgatcatgt attatttaaa cagtcctgac agaactgtac ctttgtgaac
3001 agtgcttttg attgttctac atggcatatt cacatccatt ttcttccaca gggtgatctt
3061 ctgttctagg gagaaagtgt ctcatttgca gaaaggaaag gcacctgcgg tatttgtgaa
3121 atgccatgac aagtctctga ataagaagtc aggctggtga gcattctggg ctaaagctga
3181 ctgggcatcc tgagcttgca ccctaaggga ggcagcttca tgcattcctc ttcaccccat
3241 caccagcagc ttgccctgac tcatgtgatc aaagcattca atcagtcttt cttagtcctt
3301 ctgcatatgt atcaaatggg tctgttgctt tatgcaatac ttcctcttt tttctttctc
3361 ctcttgtttc tcccagcccg gaccttcaac ccaggcacac attttaggtt ttattttact
3421 ccttgaacta ccctgaatc ttcacttctc cttttttctc tactgcgtct ctgctgactt
3481 tgcagatgcc atctgcagag catgtaacac aagtttagta gttgccgttc tggctgtggg
3541 tgcagctctt cccaggatgt attcagggaa gtaaaaagat ctcactgcat cacctgcagc
3601 cacatagttc ttgattctcc aagtgccagc atactccggg acacacagcc aacagggctg
3661 ccccaagcac ccattctcaa aaccctcaaa gctgccaagc aaacagaatg agagttatag
3721 gaaactgttc tctcttctat ctccaaacaa ctctgtgcct ctttcctacc tgacctttag
3781 ggctaatcca tgtggcagct gttagctgca tctttccaga gcgtcagtac tgagaggaca
3841 ctaagcatgt gaccttcact actcctgttc tgaattc
```

Figure 36C

```
LOCUS       HSU59436      182 bp    DNA           PRI       19-JUN-1996
DEFINITION  Human low-density lipoprotein receptor (ldlr) gene, exon 12,
            partial cds.
ACCESSION   U59436
NID         g1381233
KEYWORDS    .
SOURCE      human.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 182)
  AUTHORS   Sibul,H. and Metspalu,A.
  TITLE     A new polymorphism in exon 12 of the human low-density lipoprotein
            receptor (LDLR) gene
  JOURNAL   Unpublished
REFERENCE   2  (bases 1 to 182)
  AUTHORS   Sibul,H.
  TITLE     Direct Submission
  JOURNAL   Submitted (29-MAY-1996) Hiljar Sibul, Estonian Biocentre,
            Biotechnology, Riia 23, Tartu, Estonia, 2400
FEATURES             Location/Qualifiers
     source          1..182
                     /organism="Homo sapiens"
                     /db_xref="taxon:9606"
     intron          <1..25
                     /gene="ldlr"
                     /number=11
     primer_bind     1..21
                     /gene="ldlr"
     gene            1..182
                     /gene="ldlr"
     exon            26..165
                     /gene="ldlr"
                     /number=12
                     /product="low-density lipoprotein receptor"
     CDS             <26..>165
                     /gene="ldlr"
                     /note="LDLR"
                     /codon_start=3
                     /product="low-density lipoprotein receptor"
                     /db_xref="PID:g1381234"

/translation="LLSGRLYWVDSKLHSISSIDVNGGNRKTILEDEKRLAHPFSLAV
                     FE"
     variation       replace(45,"t")
                     /gene="ldlr"
                     /frequency="0.17"
     primer_bind     complement(163..182)
                     /gene="ldlr"
     intron          166..>182
                     /gene="ldlr"
                     /number=12
BASE COUNT         36 a     53 c     44 g     49 t
```

Figure 37A

```
ORIGIN
        1 tctccttatc cacttgtgtg tctagatctc ctcagtggcc gcctctactg ggttgactcc
       61 aaacttcact ccatctcaag catcgatgtc aatggggca accggaagac catcttggag
      121 gatgaaaaga ggctggccca ccccttctcc ttggccgtct ttgaggtgtg gcttacgtac
      181 ga
```

Figure 37B

```
LOCUS       HSCLA1GNA     2566 bp    RNA              PRI      06-OCT-1993
DEFINITION  H.sapiens encoding CLA-1 mRNA.
ACCESSION   Z22555
NID         g397606
KEYWORDS    CLA-1.
SOURCE      human.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 2566)
  AUTHORS   Calvo,D. and Vega,M.A.
  TITLE     Identification, primary structure, and distribution of CLA-1, a
            novel member of the CD36/LIMPII gene family
  JOURNAL   J. Biol. Chem. 268 (25), 18929-18935 (1993)
  MEDLINE   93366811
REFERENCE   2  (bases 1 to 2566)
  AUTHORS   VEGA,M.
  TITLE     Direct Submission
  JOURNAL   Submitted (15-APR-1993) VEGA M., HOSPITAL DE LA PRINCESA, UNIDAD
DE
            BIOLOGIA MOLECULAR, C/ DIEGO DE LEON 62, MADRID, MADRID, SPAIN,
            28006
FEATURES            Location/Qualifiers
     source         1..2566
                    /organism="Homo sapiens"
                    /db_xref="taxon:9606"
                    /cell_type="promyelocytes"
                    /cell_line="HL60"
                    /clone_lib="HL60 cDNA library, Angel L. Corbi"
     5'UTR          1..69
     CDS            70..1599
                    /codon_start=1
                    /product="CLA-1"
                    /db_xref="PID:g397607"
```

/translation="MGCSAKARWAAGALGVAGLLCAVLGAVMIVMVPSLIKQQVLKNV

RIDPSSLSFNMWKEIPIPFYLSVYFFDVMNPSEILKGEKPQVRERGPYVYRESRHKSN

ITFNNNDTVSFLEYRTFQFQPSKSHGSESDYIVMPNILVLGAAVMMENKPMTLKLIMT

LAFTTLGERAFMNRTVGEIMWGYKDPLVNLINKYFPGMFPFKDKFGLFAELNNSDSGL

FTVFTGVQNISRIHLVDKWNGLSKVDFWHSDQCNMINGTSGQMWPPFMTPESSLEFYS

PEACRSMKLMYKESGVFEGIPTYRFVAPKTLFANGSIYPPNEGFCPCLESGIQNVSTC

RFSAPLFLSHPHFLNADPVLAEAVTGLHPNQEAHSLFLDIHPVTGIPMNCSVKLQLSL

YMKSVAGIGQTGKIEPVVLPLLWFAESGAMEGETLHTFYTQLVLMPKVMHYAQYVLLA

LGCVLLLVPVICQIRSQEKCYLFWSSSKKGSKDKEAIQAYSESLMTSAPKGSVLQEAK
L"

```
     3'UTR          1600..2566
```

Figure 38A

```
     polyA_site     2532..2537
BASE COUNT      528 a     811 c     695 g     532 t
ORIGIN
        1 cgtcgccgtc cccgtctcct gccaggcgcg gagccctgcg agccgcgggt gggccccagg
       61 cgcgcagaca tgggctgctc cgccaaagcg cgctgggctg ccggggcgct gggcgtcgcg
      121 gggctactgt gcgctgtgct gggcgctgtc atgatcgtga tggtgccgtc gctcatcaag
      181 cagcaggtcc ttaagaacgt gcgcatcgac cccagtagcc tgtccttcaa catgtggaag
      241 gagatcccta tccccttcta tctctccgtc tacttctttg acgtcatgaa ccccagcgag
      301 atcctgaagg gcgagaagcc gcaggtgcgg gagcgcgggc cctacgtgta cagggagtcc
      361 aggcacaaaa gcaacatcac cttcaacaac aacgacaccg tgtccttcct cgagtaccgc
      421 accttccagt tccagccctc caagtcccac ggctcggaga gcgactacat cgtcatgccc
      481 aacatcctgg tcttgggtgc ggcggtgatg atggagaata agcccatgac cctgaagctc
      541 atcatgacct tggcattcac caccctcggc gaacgtgcct tcatgaaccg cactgtgggt
      601 gagatcatgt ggggctacaa ggaccccctt gtgaatctca tcaacaagta ctttccaggc
      661 atgttcccct tcaaggacaa gttcggatta tttgctgagc tcaacaactc cgactctggg
      721 ctcttcacgg tgttcacggg ggtccagaac atcagcagga tccacctcgt ggacaagtgg
      781 aacgggctga gcaaggttga cttctggcat tccgatcagt gcaacatgat caatggaact
      841 tctgggcaaa tgtggccgcc cttcatgact cctgagtcct cgctggagtt ctacagcccg
      901 gaggcctgcc gatccatgaa gctaatgtac aaggagtcag gggtgtttga aggcatcccc
      961 acctatcgct tcgtggctcc caaaaccctg tttgccaacg ggtccatcta cccacccaac
     1021 gaaggcttct gcccgtgcct ggagtctgga attcagaacg tcagcacctg caggttcagt
     1081 gcccccttgt ttctctccca tcctcacttc ctcaacgccg acccggttct ggcagaagcg
     1141 gtgactggcc tgcaccctaa ccaggaggca cactccttgt tcctggacat ccacccggtc
     1201 acgggaatcc ccatgaactg ctctgtgaaa ctgcagctga gcctctacat gaaatctgtc
     1261 gcaggcattg gacaaactgg gaagattgag cctgtggtcc tgccgctgct ctggtttgca
     1321 gagagcgggg ccatggaggg ggagactctt cacacattct acactcagct ggtgttgatg
     1381 cccaaggtga tgcactatgc ccagtacgtc ctcctggcgc tgggctgcgt cctgctgctg
     1441 gtccctgtca tctgccaaat ccgagccaaa gagaaatgct atttattttg gagtagtagt
     1501 aaaaagggct caaaggataa ggaggccatt caggcctatt ctgaatccct gatgacatca
     1561 gctcccaagg gctctgtgct gcaggaagca aaactgtagg gtcctgagga caccgtgagc
     1621 cagccaggcc tggccgctgg gctgaccggg ccccccagcc cctacacccc gcttctcccg
     1681 gactctccca gcagacagcc cccagcccca cagcctgagc ctcccagct gccatgtgcc
     1741 tgttgcacac ctgcacacac gccctggcac acatacacac atgcgtgcag gcttgtgcag
     1801 acactcaggg atggagctgc tgctgaaggc acttgtaggg agaggctcgt caacaagcac
     1861 tgttctggaa ccttctctcc acgtggccca caggctgacc acaggggctg tgggtcctgc
     1921 gtcccccttcc tcgggtgagc ctggcctgtc ccgttcagcc gttgggccag gcttcctccc
     1981 ctccaaggtg aaaacactgca gtccccggtgt ggtggctccc catgcaggac gggccaggct
     2041 gggagtgccg ccttcctgtg ccaaattcag tggggactca gtgcccaggc cctggcacga
     2101 gctttggcct tggtctacct gccaggccag gcaaagcgcc tttacacagg cctcggaaaa
     2161 caatggagtg agcacaagat gccctgtgca gctgcccgag ggtctccgcc caccccggcc
     2221 ggactttgat cccccgaag tcttcacagg cactgcatcg ggttgtctgg cgccctttc
     2281 ctccagccta aactgacatc atcctatgga ctgagccggc cactctctgg ccgaagtggc
     2341 gcaggctgtg ccccgagct gccccaccc cctcacaggg tccctcagat tataggtgcc
     2401 caggctgagg tgaagaggcc tgggggccct gccttccggg cgctcctgga ccctgggca
     2461 aacctgtgac ccttttctac tggaatagaa atgagtttta tcatctttga aaaataattc
     2521 actcttgaag taataaacgt ttaaaaaaat ggaaaaaaaa aaaaa
```

Figure 38B

CODING SEQUENCE POLYMORPHISMS IN VASCULAR PATHOLOGY GENES

BACKGROUND OF THE INVENTION

The genomes of all organisms undergo spontaneous mutation in the course of their continuing evolution, generating variant forms of progenitor sequences (Gusella, *Ann. Rev. Biochem.* 55, 831–854 (1986)). The variant form may confer an evolutionary advantage or disadvantage relative to a progenitor form or may be neutral. In some instances, a variant form confers a lethal disadvantage and is not transmitted to subsequent generations of the organism. In other instances, a variant form confers an evolutionary advantage to the species and is eventually incorporated into the DNA of many or most members of the species and effectively becomes the progenitor form. In many instances, both progenitor and variant form(s) survive and co-exist in a species population. The coexistence of multiple forms of a sequence gives rise to polymorphisms.

Several different types of polymorphism have been reported. A restriction fragment length polymorphism (RFLP) Is a variation in DNA sequence that alters the length of a restriction fragment (Botstein et al., *Am. J. Hum. Genet.* 32, 314–331 (1980)). The restriction fragment length polymorphism may create or delete a restriction site, thus changing the length of the restriction fragment. RFLPs have been widely used in human and animal genetic analyses (see WO 90/13668; WO90/11369; Donis-Keller, *Cell* 51, 319–337 (1987); Lander et al., *Genetics* 121, 85–99 (1989)). When a heritable trait can be linked to a particular RFLP, the presence of the RFLP in an individual can be used to predict the likelihood that the animal will also exhibit the trait.

Other polymorphisms take the form of short tandem repeats (STRs) that include tandem di-, tri- and tetra-nucleotide repeated motifs. These tandem repeats are also referred to as variable number tandem repeat (VNTR) polymorphisms. VNTRs have been used in identity and paternity analysis (U.S. Pat. No. 5,075,217; Armour et al., *FEBS Lett.* 307, 113–115 (1992); Horn et al., WO 91/14003; Jeffreys, EP 370,719), and in a large number of genetic mapping studies.

Other polymorphisms take the form of single nucleotide variations between individuals of the same species. Such polymorphisms are far more frequent than RFLPs, STRs and VNTRs. Some single nucleotide polymorphisms (SNP) occur in protein-coding sequences (coding sequence SNP (cSNP)), in which case, one of the polymorphic forms may give rise to the expression of a defective or otherwise variant protein and, potentially, a genetic disease. Examples of genes in which polymorphisms within coding sequences give rise to genetic disease include β-globin (sickle cell anemia), apoE4 (Alzheimer's Disease), Factor V Leiden (thrombosis), and CFTR (cystic fibrosis). cSNPs can alter the codon sequence of the gene and therefore specify an alternative amino acid. Such changes are called "missense" when another amino acid is substituted, and "nonsense" when the alternative codon specifies a stop signal in protein translation. When the cSNP does not alter the amino acid specified the cSNP is called "silent".

Other single nucleotide polymorphisms occur in noncoding regions. Some of these polymorphisms may also result in defective protein expression (e.g., as a result of defective splicing). Other single nucleotide polymorphisms have no phenotypic effects.

Single nucleotide polymorphisms can be used in the same manner as RFLPs and VNTRs, but offer several advantages. Single nucleotide polymorphisms occur with greater frequency and are spaced more uniformly throughout the genome than other forms of polymorphism. The greater frequency and uniformity of single nucleotide polymorphisms means that there is a greater probability that such a polymorphism will be found in close proximity to a genetic locus of interest than would be the case for other polymorphisms. The different forms of characterized single nucleotide polymorphisms are often easier to distinguish than other types of polymorphism (e.g., by use of assays employing allele-specific hybridization probes or primers).

Only a small percentage of the total repository of polymorphisms in humans and other organisms has been identified. The limited number of polymorphisms identified to date is due to the large amount of work required for their detection by conventional methods. For example, a conventional approach to identifying polymorphisms might be to sequence the same stretch of DNA in a population of individuals by dideoxy sequencing. In this type of approach, the amount of work increases in proportion to both the length of sequence and the number of individuals in a population and becomes impractical for large stretches of DNA or large numbers of persons.

SUMMARY OF THE INVENTION

Work described herein pertains to the identification of polymorphisms which can predispose individuals to disease, particularly vascular pathologies, by resequencing large numbers of genes in a large number of individuals. Eighteen genes in a minimum of 30 individuals have been resequenced as described herein, and 92 SNPs have been discovered (see the Table). Forty of these SNPs are cSNPs which specify a different amino acid sequence, while 49 of the SNPs are silent cSNPs. Three of the SNPs were located in non-coding regions.

The invention relates to a gene which comprises a single nucleotide polymorphism at a specific location. In a particular embodiment the invention relates to the variant allele of a gene having a single nucleotide polymorphism, which variant allele differs from a reference allele by one nucleotide at the site(s) identified in the Table. Complements of these nucleic acid segments are also included. The segments can be DNA or RNA, and can be double- or single-stranded. Segments can be, for example, 5–10, 5–15, 10–20, 5–25, 10–30, 10–50 or 10–100 bases long.

The invention further provides allele-specific oligonucleotides that hybridize to a gene comprising a single nucleotide polymorphism or to the complement of the gene. These oligonucleotides can be probes or primers.

The invention further provides a method of analyzing a nucleic acid from an individual. The method determines which base is present at any one of the polymorphic sites shown in the Table. Optionally, a set of bases occupying a set of the polymorphic sites shown in the Table is determined. This type of analysis can be performed on a number of individuals, who are tested for the presence of a disease phenotype. The presence or absence of disease phenotype is then correlated with a base or set of bases present at the polymorphic site or sites in the individuals tested.

BRIEF DESCRIPTION OF THE DRAWINGS

FIGS. 1A–1C are a table illustrating the locations of single nucleotide polymorphisms of various genes.

FIG. 2 is a listing of the genes from FIGS. 1A–C with their corresponding GenBank Accession numbers and the nucleotide position within that sequence at which the single nucleotide polymorphism is located.

FIGS. 3A–B are a listing of the nucleotide sequence and amino acid sequence corresponding to GenBank Accession number D10202 for the gene PTAFR SEQ ID NOS 1–2, respectively.

FIGS. 4A–B are a listing of the nucleotide sequence and amino acid sequence corresponding to the GenBank Accession number D29832 for the gene AT3 SEQ ID NOS 3–4, respectively.

FIGS. 5A–C are a listing of the nucleotide sequence and amino acid sequence corresponding to the GenBank Accession number D38081 for the gene TBXA2R SEQ ID NOS 5–6, respectively.

FIGS. 6A–C are a listing of the nucleotide sequence and amino acid sequence corresponding to the GenBank Accession number J02703 for the gene ITGB3 SEQ ID NOS 7–8, respectively.

FIGS. 7A–C are a listing of the nucleotide sequence and amino acid sequence corresponding to the GenBank Accession number J02764 for the gene ITGA2B SEQ ID NOS 9–10, respectively.

FIGS. 8A–F are a listing of the nucleotide sequence and amino acid sequence corresponding to the GenBank Accession number J02846 for the gene F3 SEQ ID NOS 11–12, respectively.

FIGS. 9A–B are a listing of the nucleotide sequence and amino acid sequence corresponding to the GenBank Accession number J02898 for the gene CETPA SEQ ID NOS 13–14, respectively.

FIGS. 10A–B are a listing of the nucleotide sequence and amin acid sequence corresponding to the GenBank Accession number J03225 for the gene TFPI SEQ ID NOS 15–16, respectively.

FIGS. 11A–B are a listing of the nucleotide sequence and amino acid sequence corresponding to the GenBank Accession number K02059 for the gene PROC SEQ ID NOS 17–18, respectively.

FIG. 12 is a listing of the nucleotide sequence corresponding to the GenBank Accession number L00336 for the gene LDLR SEQ ID NO 19.

FIG. 13 is a listing of the nucleotide sequence corresponding to the GenBank Accession number L00338 SEQ ID NO 20.

FIG. 14 is a listing of the nucleotide sequence corresponding to the GenBank Accession number L00343 for the gene LDLR SEQ ID NO 21.

FIG. 15 is a listing of the nucleotide sequence corresponding to the GenBank Accession number L00344 for the gene LDLR SEQ ID NO 22.

FIG. 16 is a listing of the nucleotide sequence corresponding to the GenBank Accession number L00345 for the gene LDLR SEQ ID NO 23.

FIG. 17 is a listing of the nucleotide sequence corresponding to the GenBank Accession number L00347 for the gene LDLR SEQ ID NO 24.

FIG. 18 is a listing of the nucleotide sequence corresponding to the GenBank Accession number L00349 for the gene LDLR SEQ ID NO 25.

FIGS. 19A–B are a listing of the nucleotide sequence corresponding to the GenBank Accession number L00351 for the gene LDLR SEQ ID NO 26.

FIGS. 20A–B are a listing of the nucleotide sequence corresponding to the GenBank Accession number L29401 for the gene LDLR SEQ ID NO 27.

FIGS. 21A–B are a listing of the nucleotide sequence corresponding to the GenBank Accession number L32765 for the gene F5 SEQ ID NO 28.

FIGS. 22A–C are a listing of the nucleotide sequence and amino acid sequence corresponding to the GenBank Accession number M11058 for the gene HMGCR SEQ ID NOS 29–30, respectively.

FIGS. 23A–F are a listing of the nucleotide sequence and amino acid sequence corresponding to the GenBank Accession number M11228 for the gene PROC SEQ ID NOS 31–32, respectively.

FIGS. 24A–B are a listing of the nucleotide sequence and amino acid sequence corresponding to the GenBank Accession number M12625 for the gene LCAT SEQ ID NOS 33–34, respectively.

FIGS. 25A–C are a listing of the nucleotide sequence and amino acid sequence corresponding to the GenBank Accession number M12849 for the gene HCF2 SEQ ID NOS 35–36, respectively.

FIGS. 26A–E are a listing of the nucleotide sequence and amino acid sequence corresponding to the GenBank Accession number M14335 for the gene F5 SEQ ID NOS 37–38, respectively.

FIGS. 27A–C are a listing of the nucleotide sequence and amino acid sequence corresponding to the GenBank Accession number M15856 for the gene LPL SEQ ID NOS 39–40, respectively.

FIGS. 28A–N are a listing of the nucleotide sequence and amino acid sequence corresponding to the GenBank Accession number M17262 for the gene F2 SEQ ID NOS 41–42, respectively.

FIGS. 29A–C are a listing of the nucleotide sequence and amino acid sequence corresponding to the GenBank Accession number M20311 for the gene ITGB3 SEQ ID NOS 43–44, respectively.

FIG. 30 is a listing of the nucleotide sequence corresponding to the GenBank Accession number M21645 for the gene AT3 SEQ ID NO 45.

FIGS. 31A–B are a listing of the nucleotide sequence corresponding to the GenBank Accession number M22569 for the gene ITGA2B SEQ ID NO 46.

FIGS. 32A–B are a listing of the nucleotide sequence and amino acid sequence corresponding to the GenBank Accession number M30185 for the gene CETP SEQ ID NOS 47–48, respectively.

FIGS. 33A–H are a listing of the nucleotide sequence corresponding to the GenBank Accession number M33320 for the gene ITGA2B SEQ ID NO 49.

FIGS. 34A–G are a listing of the nucleotide sequence and amino acid sequence corresponding to the GenBank Accession number M58600 for the gene HCF2 SEQ ID NOS 50–51, respectively.

FIGS. 35A–B are a listing of the nucleotide sequence and amino acid sequence corresponding to the GenBank Accession number M62424 for the gene F2R SEQ ID NOS 52–53, respectively.

FIGS. 36A–C are a listing of the nucleotide sequence and amino acid sequence corresponding to the GenBank Accession number M76722 for the gene LPL SEQ ID NOS 54–55, respectively.

FIGS. 37A–B are a listing of the nucleotide sequence and amino acid sequence corresponding to the GenBank Accession number U59436 for the gene LDLR SEQ ID NOS 56–57, respectively.

FIGS. 38A–B are a listing of the nucleotide sequence and amino acid sequence corresponding to the GenBank Accession number Z22555 for the gene CLanalog SEQ ID NOS 58–59, respectively.

DETAILED DESCRIPTION OF THE INVENTION

The present invention relates to a gene which comprises a single nucleotide polymorphism (SNP) at a specific location. The gene which includes the SNP has at least two alleles, referred to herein as the reference allele and the variant allele. The reference allele (prototypical or wild type allele) has been designated arbitrarily and typically corresponds to the nucleotide sequence of the gene which has been deposited with GenBank under a given Accession number. The variant allele differs from the reference allele by one nucleotide at the site(s) identified in the Table. The present invention also relates to variant alleles of the described genes and to complements of the variant alleles. The invention further relates to portions of the variant alleles and portions of complements of the variant alleles which comprise (encompass) the site of the SNP and are at least 5 nucleotides in length. Portions can be, for example, 5–10, 5–15, 10–20, 5–25, 10–30, 10–50 or 10–100 bases long. For example, a portion of a variant allele which is 5 nucleotides in length includes the single nucleotide polymorphism (the nucleotide which differs from the reference allele at that site) and four additional nucleotides which flank the site in the variant allele. These nucleotides can be on one or both sides of the polymorphism. Polymorphisms which are the subject of this invention are defined in the Table with respect to the reference sequence deposited in GenBank under the Accession number indicated. For example, the invention relates to a portion of a gene (e.g., AT3) having a nucleotide sequence as deposited in GenBank (e.g., M21645) comprising a single nucleotide polymorphism at a specific position (e.g., nucleotide 100). The reference allele for AT3 is shown in column 15 and the variant allele is shown in column 17 of the Table. The nucleotide sequences of the invention can be double- or single-stranded.

The invention further provides allele-specific oligonucleotides that hybridize to a gene comprising a single nucleotide polymorphism or to the complement of the gene. These oligonucleotides can be probes or primers.

The invention further provides a method of analyzing a nucleic acid from an individual. The method determines which base is present at any one of the polymorphic sites shown in the Table. Optionally, a set of bases occupying a set of the polymorphic sites shown in the Table is determined. This type of analysis can be performed on a number of individuals, who are tested for the presence of a disease phenotype. The presence or absence of disease phenotype is then correlated with a base or set of bases present at the polymorphic site or sites in the individuals tested.

DEFINITIONS

An oligonucleotide can be DNA or RNA, and single- or double-stranded. Oligonucleotides can be naturally occurring or synthetic, but are typically prepared by synthetic means. Preferred oligonucleotides of the invention include segments of DNA, or their complements, which include any one of the polymorphic sites shown in the Table. The segments can be between 5 and 250 bases, and, in specific embodiments, are between 5–10, 5–20, 10–20, 10–50, 20–50 or 10–100 bases. The polymorphic site can occur within any position of the segment. The segments can be from any of the allelic forms of DNA shown in the Table.

As used herein, the terms "nucleotide" and "nucleic acid" are intended to be equivalent. The terms "nucleotide sequence", "nucleic acid sequence" and "segment" are intended to be equivalent.

Hybridization probes are oligonucleotides which bind in a base-specific manner to a complementary strand of nucleic acid. Such probes include peptide nucleic acids, as described in Nielsen et al., *Science* 254, 1497–1500 (1991). Probes can be any length suitable for specific hybridization to the target nucleic acid sequence. The most appropriate length of the probe may vary depending upon the hybridization method in which it is being used; for example, particular lengths may be more appropriate for use in microfabricated arrays, while other lengths may be more suitable for use in classical hybridization methods. Suitable probes and primers can range from about 5 nucleotides to about 30 nucleotides in length. For example, probes and primers can be 5, 6, 8, 10, 12, 14, 16, 18, 20, 22, 24, 25, 26, 28 or 30 nucleotides in length. The probe or primer preferably contains at least one polymorphic site occupied by any of the possible variant nucleotides. The nucleotide sequence can correspond to the coding sequence of the allele or to the complement of the coding sequence of the allele.

As used herein, the term "primer" refers to a single-stranded oligonucleotide which acts as a point of initiation of template-directed DNA synthesis under appropriate conditions (e.g., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term primer site refers to the area of the target DNA to which a primer hybridizes. The term primer pair refers to a set of primers including a 5' (upstream) primer that hybridizes with the 5' end of the DNA sequence to be amplified and a 3' (downstream) primer that hybridizes with the complement of the 3' end of the sequence to be amplified.

As used herein, linkage describes the tendency of genes, alleles, loci or genetic markers to be inherited together as a result of their location on the same chromosome. It can be measured by percent recombination between the two genes, alleles, loci or genetic markers.

As used herein, polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic or biallelic polymorphism has two forms. A triallelic polymorphism has three forms.

Work described herein pertains to the resequencing of large numbers of genes in a large number of individuals to identify polymorphisms which can predispose individuals to disease, particularly vascular pathologies. Eighteen genes in a minimum of 30 individuals have been resequenced as described herein, and 92 SNPs have been discovered (see the Table). Forty of these SNPs are cSNPs which specify a different amino acid sequence, while 49 of the SNPs are silent cSNPs. Three of the SNPs were located in non-coding regions.

The 18 genes which were subjected to analysis encode proteins that are involved in biochemical pathways that regulate blood coagulation, lipid metabolism, and platelet and endothelial cell function. Polymorphisms in all 18 genes are candidates for genetic factors that influence the pathophysiology of the blood and blood vessels and thus can be relevant to the genetic risk of cardiovascular diseases. The identified polymorphisms can also be relevant to other disease categories.

By altering amino acid sequence, SNPs may alter the function of the encoded proteins. The discovery of the SNP facilitates biochemical analysis of the variants and the development of assays to characterize the variants and to screen for pharmaceutical that would interact directly with on or another form of the protein. SNPs (including silent SNPs) may also alter the regulation of the gene at the transcriptional or post-transcriptional level. SNPs (including silent SNPs) also enable the development of specific DNA, RNA, or protein-based diagnostics that detect the presence or absence of the polymorphism in particular conditions.

A single nucleotide polymorphism occurs at a polymorphic site occupied by a single nucleotide, which is the site of variation between allelic sequences. The site is usually preceded by and followed by highly conserved sequences of the allele (e.g., sequences that vary in less than $1/100$ or $1/1000$ members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele. Typically the polymorphic site is occupied by a base other than the reference base. For example, where the reference allele contains the base "T" at the polymorphic site, the altered allele can contain a "C", "G" or "A" at the polymorphic site.

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25–30° C., or equivalent conditions, are suitable for allele-specific probe hybridizations. Equivalent conditions can be determined by varying one or more of the parameters given as an example, as known in the art, while maintaining a similar degree of identity or similarity between the target nucleotide sequence and the primer or probe used.

The term "isolated" is used herein to indicate that the material in question exists in a physical milieu distinct from that in which it occurs in nature. For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. Preferably, an isolated nucleic acid comprises at least about 50, 80 or 90 percent (on a molar basis) of all macromolecular species present.

I. Novel Polymorphisms of the Invention

The novel polymorphisms of the invention are shown in the Table.

II. Analysis of Polymorphisms

A. Preparation of Samples

Polymorphisms are detected in a target nucleic acid from an individual being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed. For example, if the target nucleic acid is a cytochrome P450, the liver is a suitable source.

Many of the methods described below require amplification of DNA from target samples. This can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

B. Detection of Polymorphisms in Target DNA

There are two distinct types of analysis of target DNA for detecting polymorphisms. The first type of analysis, sometimes referred to as de novo characterization, is carried out to identify polymorphic sites not previously characterized (i.e., to identify new polymorphisms). This analysis compares target sequences in different individuals to identify points of variation, i.e., polymorphic sites. By analyzing groups of individuals representing the greatest ethnic diversity among humans and greatest breed and species variety in plants and animals, patterns characteristic of the most common alleles/haplotypes of the locus can be identified, and the frequencies of such alleles/haplotypes in the population can be determined. Additional allelic frequencies can be determined for subpopulations characterized by criteria such as geography, race, or gender. The de novo identification of polymorphisms of the invention is described in the Examples section. The second type of analysis determines which form(s) of a characterized (known) polymorphism are present in individuals under test. There are a variety of suitable procedures, which are discussed in turn.

1. Allele-Specific Probes

The design and use of allele-specific probes for analyzing polymorphisms is described by e.g., Saiki et al., *Nature* 324, 163–166 (1986); Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

2. Tiling Arrays

The polymorphisms can also be identified by hybridization to nucleic acid arrays, some examples of which are described in WO 95/11995. One form of such arrays is described in the Examples section in connection with de novo identification of polymorphisms. The same array or a different array can be used for analysis of characterized polymorphisms. WO 95/11995 also describes subarrays that are optimized for detection of a variant form of a precharacterized polymorphism. Such a subarray contains probes designed to be complementary to a second reference sequence, which is an allelic variant of the first reference sequence. The second group of probes is designed by the same principles as described in the Examples, except that the probes exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to 21 bases).

3. Allele-Specific Primers

An allele-specific primer hybridizes to a site on target DNA overlapping a polymorphism and only primes amplification of an allelic form to which the primer exhibits perfect complementarity. See Gibbs, *Nucleic Acid Res.* 17, 2427–2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

4. Direct-Sequencing

The direct analysis of the sequence of polymorphisms of the present invention can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)).

5. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., *PCR Technology, Principles and Applications for DNA Amplification,* (W. H. Freeman and Co, New York, 1992), Chapter 7.

6. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., *Proc. Nat. Acad. Sci.* 86, 2766–2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence differences between alleles of target sequences.

III. Methods of Use

After determining polymorphic form(s) present in an individual at one or more polymorphic sites, this information can be used in a number of methods.

A. Forensics

Determination of which polymorphic forms occupy a set of polymorphic sites in an individual identifies a set of polymorphic forms that distinguishes the individual. See generally National Research Council, *The Evaluation of Forensic DNA Evidence* (Eds. Pollard et al., National Academy Press, DC, 1996). The more sites that are analyzed, the lower the probability that the set of polymorphic forms in one individual is the same as that in an unrelated individual. Preferably, if multiple sites are analyzed, the sites are unlinked. Thus, polymorphisms of the invention are often used in conjunction with polymorphisms in distal genes. Preferred polymorphisms for use in forensics are biallelic because the population frequencies of two polymorphic forms can usually be determined with greater accuracy than those of multiple polymorphic forms at multi-allelic loci.

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance.

p(ID) is the probability that two random individuals have the same polymorphic or allelic form at a given polymorphic site. In biallelic loci, four genotypes are possible: AA, AB, BA, and BB. If alleles A and B occur in a haploid genome of the organism with frequencies x and y, the probability of each genotype in a diploid organism is (see WO 95/12607):

Homozygote: $p(AA)=x^2$

Homozygote: $p(BB)=y^2=(1-x)^2$

Single Heterozygote: $p(AB)=p(BA)=xy=x(1-x)$

Both Heterozygotes: $p(AB+BA)=2xy=2x(1-x)$

The probability of identity at one locus (i.e, the probability that two individuals, picked at random from a population will have identical polymorphic forms at a given locus) is given by the equation:

$$p(ID)=(x^2)^2+(2xy)^2+(y^2)^2.$$

These calculations can be extended for any number of polymorphic forms at a given locus. For example, the probability of identity p(ID) for a 3-allele system where the alleles have the frequencies in the population of x, y and z, respectively, is equal to the sum of the squares of the genotype frequencies:

$$p(ID)=x^4+(2xy)^2+(2yz)^2+(2xz)^2+z^4+y^4$$

In a locus of n alleles, the appropriate binomial expansion is used to calculate p(ID) and p(exc).

The cumulative probability of identity (cum p(ID)) for each of multiple unlinked loci is determined by multiplying the probabilities provided by each locus.

$$\text{cum } p(ID)=p(ID1)p(ID2)p(ID3)\ldots p(IDn)$$

The cumulative probability of non-identity for n loci (i.e. the probability that two random individuals will be different at 1 or more loci) is given by the equation:

$$\text{cum } p(nonID)=1-\text{cum } p(ID).$$

If several polymorphic loci are tested, the cumulative probability of non-identity for random individuals becomes very high (e.g., one billion to one). Such probabilities can be taken into account together with other evidence in determining the guilt or innocence of the suspect.

B. Paternity Testing

The object of paternity testing is usually to determine whether a male is the father of a child. In most cases, the mother of the child is known and thus, the mother's contribution to the child's genotype can be traced. Paternity testing investigates whether the part of the child's genotype not attributable to the mother is consistent with that of the putative father. Paternity testing can be performed by analyzing sets of polymorphisms in the putative father and the child.

If the set of polymorphisms in the child attributable to the father does not match the set of polymorphisms of the putative father, it can be concluded, barring experimental error, that the putative father is not the real father. If the set of polymorphisms in the child attributable to the father does match the set of polymorphisms of the putative father, a statistical calculation can be performed to determine the probability of coincidental match.

The probability of parentage exclusion (representing the probability that a random male will have a polymorphic form at a given polymorphic site that makes him incompatible as the father) is given by the equation (see WO 95/12607):

$$p(exc)=xy(1-xy)$$

where x and y are the population frequencies of alleles A and B of a biallelic polymorphic site.

(At a triallelic site $p(exc)=xy(1-xy)+yz(1-yz)+xz(1-xz)+3xyz(1-xyz)$), where x, y and z and the respective population frequencies of alleles A, B and C).

The probability of non-exclusion is $$p(\text{non-exc})=1-p(\text{exc})$$

The cumulative probability of non-exclusion (representing the value obtained when n loci are used) is thus:

$$\text{cum } p(\text{non-exc})=p(\text{non-exc1})p(\text{non-exc2})p(\text{non-exc3})\ldots p(\text{non-excn})$$

The cumulative probability of exclusion for n loci (representing the probability that a random male will be excluded)

$$\text{cum } p(\text{exc})=1-\text{cum } p(\text{non-exc}).$$

If several polymorphic loci are included in the analysis, the cumulative probability of exclusion of a random male is very high. This probability can be taken into account in assessing the liability of a putative father whose polymorphic marker set matches the child's polymorphic marker set attributable to his/her father.

C. Correlation of Polymorphisms with Phenotypic Traits

The polymorphisms of the invention may contribute to the phenotype of an organism in different ways. Some polymorphisms occur within a protein coding sequence and contribute to phenotype by affecting protein structure. The effect may be neutral, beneficial or detrimental, or both beneficial and detrimental, depending on the circumstances. For example, a heterozygous sickle cell mutation confers resistance to malaria, but a homozygous sickle cell mutation is usually lethal. Other polymorphisms occur in noncoding regions but may exert phenotypic effects indirectly via influence on replication, transcription, and translation. A single polymorphism may affect more than one phenotypic trait. Likewise, a single phenotypic trait may be affected by polymorphisms in different genes. Further, some polymorphisms predispose an individual to a distinct mutation that is causally related to a certain phenotype.

Phenotypic traits include diseases that have known but hitherto unmapped genetic components (e.g., agammaglobulimenia, diabetes insipidus, Lesch-Nyhan syndrome, muscular dystrophy, Wiskott-Aldrich syndrome, Fabry's disease, familial hypercholesterolemia, polycystic kidney disease, hereditary spherocytosis, von Willebrand's disease, tuberous sclerosis, hereditary hemorrhagic telangiectasia, familial colonic polyposis, Ehlers-Danlos syndrome, osteogenesis imperfecta, and acute intermittent porphyria). Phenotypic traits also include symptoms of, or susceptibility to, multifactorial diseases of which a component is or may be genetic, such as autoimmune diseases, inflammation, cancer, diseases of the nervous system, and infection by pathogenic microorganisms. Some examples of autoimmune diseases include rheumatoid arthritis, multiple sclerosis, diabetes (insulin-dependent and non-independent), systemic lupus erythematosus and Graves disease. Some examples of cancers include cancers of the bladder, brain, breast, colon, esophagus, kidney, leukemia, liver, lung, oral cavity, ovary, pancreas, prostate, skin, stomach and uterus. Phenotypic traits also include characteristics such as longevity, appearance (e.g., baldness, obesity), strength, speed, endurance, fertility, and susceptibility or receptivity to particular drugs or therapeutic treatments.

The correlation of one or more polymorphisms with phenotypic traits can be facilitated by knowledge of the gene product of the wild type (reference) gene. The genes in which cSNPs of the present invention have been identified are genes which have been previously sequenced and characterized in one of their allelic forms. For example, genes of the present invention in which cSNPs have been identified include genes encoding antithrombin III (Humphries, *Semin Hematol* 32:8–16 (1995); Mammen, *Semin Hematol* 32:2–6 (1995)), cholesterol ester transfer protein (Bruce and Tall, *Curr Opin Lipidol* 6:306–311 (1995)), CLanalog (HDL/scavenger receptor) (Freeman, *Curr Opin Hematol* 4:41–47 (1997); Knecht and Glass, *Adv Genet* 32:141–198 (1995); Rigotti et al., *Curr Opin Lipidol* 8:181–188 (1997)), thrombin receptor (Brass and Molino, *Thromb Haemost* 78:234–241 (1997); Jamieson, *Thromb Haemost* 78:242–246 (1997)), thrombin (Eisenberg, *Coron Artery Dis* 7:400–408 (1996); Jamieson, *Thromb Haemost* 78:242–246 (1997)), and heparin cofactor II (Bick and Pegram, *Semin Thromb Hemost* 20:109–132 (1994)). Also included are the genes encoding HMG coA-reductase (Bjelajac et al., *Ann Pharmacother* 30:1304–1315 (1996)), platelet glycoprotein IIB and IIIA (Jamieson, *Thromb Haemost* 78:242–246 (1997); Lefkovits et al., *N Engl J Med* 332:1553–1559 (1995); Nurden, *Thromb Haemost* 74:345–351 (1995)), lecithin:cholesterol acyltransferase (Kuivenhoven et al., *J Lipid Res* 38:191–205 (1997)), LDL receptor (Holvoet and Collen, *Curr Opin Lipidol* 8:320–328 (1997); Rigotti et al., *Curr Opin Lipidol* 8:181–188 (1997)), protein C (Bertina, *Clin Chem* 43:1678–1683 (1997); Bick and Pegram, *Semin Thromb Hemost* 20:109–132 (1994); Humphries, *Semin Hematol* 32:8–16 (1995); Koeleman et al., *Semin Hematol* 34:256–264 (1997)), platelet activating factor receptor (Feuerstein et al., *J Lipid Mediat Cell Signal* 15:255–284 (1997); Shimizu and Mutoh, *Adv Exp Med Biol* 407:197–204 (1997)), tissue factor (Abildgaard, *Blood Coagul Fibrinolysis* 6:S45–49(1995); Bick and Pegram, *Semin Thromb Hemost* 20:109–132 (1994); Harker et al., *Haemostasis* 1:76–82 (1996); Ruf and Edgington, *Faseb J* 8:385–390 (1994)), tissue factor pathway inhibitor (Shimizu and Mutoh, *Adv Exp Med Biol* 407:197–204 (1997); Feuerstein et al., *J Lipid Mediat Cell Signal* 15:255–284 (1997)), thromboxane A2 receptor (Feuerstein et al., *J Lipid Mediat Cell Signal* 15:255–284 (1997); Kinsella et al., *Ann NY Acad Sci* 714:270–278 (1994); Patrono and Renda, *Am J Cardiol* 80:17E–20E (1997)), lipoprotein lipase (Applebaum-Bowden, *Curr Opin Lipidol* 6:130–135 (1995)), and factor V (Bertina, *Clin Chem* 43:1678–1683 (1997); Harker et al., *Haemostasis* 1:76–82 (1996); Koeleman et al., *Semin Hematol* 34:256–264 (1997)).

Correlation is performed for a population of individuals who have been tested for the presence or absence of a phenotypic trait of interest and for polymorphic markers sets. To perform such analysis, the presence or absence of a set of polymorphisms (i.e. a polymorphic set) is determined for a set of the individuals, some of whom exhibit a particular trait, and some of which exhibit lack of the trait. The alleles of each polymorphism of the set are then reviewed to determine whether the presence or absence of a particular allele is associated with the trait of interest. Correlation can be performed by standard statistical methods such as a κ-squared test and statistically significant correlations between polymorphic form(s) and phenotypic characteristics are noted. For example, it might be found that the presence of allele A1 at polymorphism A correlates with heart disease. As a further example, it might be found that the combined presence of allele A1 at polymorphism A and allele B1 at polymorphism B correlates with increased milk production of a farm animal.

Such correlations can be exploited in several ways. In the case of a strong correlation between a set of one or more polymorphic forms and a disease for which treatment is available, detection of the polymorphic form set in a human or animal patient may justify immediate administration of treatment, or at least the institution of regular monitoring of the patient. Detection of a polymorphic form correlated with serious disease in a couple contemplating a family may also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic set and human disease, immediate therapeutic intervention or monitoring may not be justified. Nevertheless, the patient can be motivated to begin simple life-style changes (e.g., diet, exercise) that can be accomplished at little cost to the patient but confer potential benefits in reducing the risk of conditions to which the patient may have increased susceptibility by virtue of variant alleles. Identification of a polymorphic set in a patient correlated with enhanced receptiveness to one of several treatment regimes for a disease indicates that this treatment regime should be followed.

For animals and plants, correlations between characteristics and phenotype are useful for breeding for desired characteristics. For example, Beitz et al., U.S. Pat. No. 5,292,639 discuss use of bovine mitochondrial polymorphisms in a breeding program to improve milk production in cows. To evaluate the effect of mtDNA D-loop sequence polymorphism on milk production, each cow was assigned a value of 1 if variant or 0 if wildtype with respect to a prototypical mitochondrial DNA sequence at each of 17 locations considered. Each production trait was analyzed individually with the following animal model:

$$Y_{ijkpn} = \mu + YS_i + P_j + X_k + \beta_1 + \ldots \beta_{17} + PE_n + a_n + e_p$$

where $Y_{ijknp}$ is the milk, fat, fat percentage, SNF, SNF percentage, energy concentration, or lactation energy record; $\mu$ is an overall mean; $YS_i$ is the effect common to all cows calving in year-season; $X_k$ is the effect common to cows in either the high or average selection line; $\beta_1$ to $\beta_{17}$ are the binomial regressions of production record on mtDNA D-loop sequence polymorphisms; $PE_n$ is permanent environmental effect common to all records of cow n; $a_n$ is effect of animal n and is composed of the additive genetic contribution of sire and dam breeding values and a Mendelian sampling effect; and $e_p$ is a random residual. It was found that eleven of seventeen polymorphisms tested influenced at least one production trait. Bovines having the best polymorphic forms for milk production at these eleven loci are used as parents for breeding the next generation of the herd.

D. Genetic Mapping of Phenotypic Traits

The previous section concerns identifying correlations between phenotypic traits and polymorphisms that directly or indirectly contribute to those traits. The present section describes identification of a physical linkage between a genetic locus associated with a trait of interest and polymorphic markers that are not associated with the trait, but are in physical proximity with the genetic locus responsible for the trait and co-segregate with it. Such analysis is useful for mapping a genetic locus associated with a phenotypic trait to a chromosomal position, and thereby cloning gene(s) responsible for the trait. See Lander et al., *Proc. Natl. Acad. Sci.* (*USA*) 83, 7353–7357 (1986); Lander et al., *Proc. Natl. Acad. Sci.* (*USA*) 84, 2363–2367 (1987); Donis-Keller et al., *Cell* 51, 319–337 (1987); Lander et al., *Genetics* 121, 185–199 (1989)). Genes localized by linkage can be cloned by a process known as directional cloning. See Wainwright, *Med. J. Australia* 159, 170–174 (1993); Collins, *Nature Genetics* 1, 3–6 (1992).

Linkage studies are typically performed on members of a family. Available members of the family are characterized for the presence or absence of a phenotypic trait and for a set of polymorphic markers. The distribution of polymorphic markers in an informative meiosis is then analyzed to determine which polymorphic markers co-segregate with a phenotypic trait. See, e.g., Kerem et al., *Science* 245, 1073–1080 (1989); Monaco et al., *Nature* 316, 842 (1985); Yamoka et al., *Neurology* 40, 222–226 (1990); Rossiter et al., *FASEB Journal* 5, 21–27 (1991).

Linkage is analyzed by calculation of LOD (log of the odds) values. A lod value is the relative likelihood of obtaining observed segregation data for a marker and a genetic locus when the two are located at a recombination fraction $\theta$, versus the situation in which the two are not linked, and thus segregating independently (Thompson & Thompson, *Genetics in Medicine* (5th ed, W. B. Saunders Company, Philadelphia, 1991); Strachan,"Mapping the human genome" in *The Human Genome* (BIOS Scientific Publishers Ltd, Oxford), Chapter 4). A series of likelihood ratios are calculated at various recombination fractions ($\theta$), ranging from $\theta=0.0$ (coincident loci) to $\theta=0.50$ (unlinked). Thus, the likelihood at a given value of $\theta$ is: probability of data if loci linked at $\theta$ to probability of data if loci unlinked. The computed likelihoods are usually expressed as the $\log_{10}$ of this ratio (i.e., a lod score). For example, a lod score of 3 indicates 1000:1 odds against an apparent observed linkage being a coincidence. The use of logarithms allows data collected from different families to be combined by simple addition. Computer programs are available for the calculation of lod scores for differing values of $\theta$ (e.g., LIPED, MLINK (Lathrop, *Proc. Nat. Acad. Sci.* (*USA*) 81, 3443–3446 (1984)). For any particular lod score, a recombination fraction may be determined from mathematical tables. See Smith et al., *Mathematical tables for research workers in human genetics* (Churchill, London, 1961); Smith, *Ann. Hum. Genet.* 32, 127–150 (1968). The value of $\theta$ at which the lod score is the highest is considered to be the best estimate of the recombination fraction.

Positive lod score values suggest that the two loci are linked, whereas negative values suggest that linkage is less likely (at that value of $\theta$) than the possibility that the two loci are unlinked. By convention, a combined lod score of +3 or greater (equivalent to greater than 1000:1 odds in favor of linkage) is considered definitive evidence that two loci are linked. Similarly, by convention, a negative lod score of –2 or less is taken as definitive evidence against linkage of the two loci being compared. Negative linkage data are useful in excluding a chromosome or a segment thereof from consideration. The search focuses on the remaining non-excluded chromosomal locations.

IV. Modified Polypeptides and Gene Sequences

The invention further provides variant forms of nucleic acids and corresponding proteins. The nucleic acids comprise one of the sequences described in the Table, column 8, in which the polymorphic position is occupied by one of the alternative bases for that position. Some nucleic acids encode full-length variant forms of proteins. Similarly, variant proteins have the prototypical amino acid sequences encoded by nucleic acid sequences shown in the Table, column 8, (read so as to be in-frame with the full-length coding sequence of which it is a component) except at an amino acid encoded by a codon including one of the polymorphic positions shown in the Table. That position is occupied by the amino acid coded by the corresponding codon in any of the alternative forms shown in the Table.

Variant genes can be expressed in an expression vector in which a variant gene is operably linked to a native or other promoter. Usually, the promoter is a eukaryotic promoter for expression in a mammalian cell. The transcription regulation sequences typically include a heterologous promoter and optionally an enhancer which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as *E. coli,* yeast, filamentous fungi, insect cells, mammalian cells, typically immortalized, e.g., mouse, CHO, human and monkey cell lines and derivatives thereof. Preferred host cells are able to process the variant gene product to produce an appropriate mature polypeptide. Processing includes glycosylation, ubiquitination, disulfide bond formation, general post-translational modification, and the like.

The protein may be isolated by conventional means of protein biochemistry and purification to obtain a substantially pure product, i.e., 80, 95 or 99% free of cell component contaminants, as described in Jacoby, *Methods in Enzymology* Volume 104, Academic Press, New York (1984); Scopes, *Protein Purification, Principles and Practice,* 2nd Edition, Springer-Verlag, New York (1987); and Deutscher (ed), *Guide to Protein Purification, Methods in Enzymology,* Vol. 182 (1990). If the protein is secreted, it can be isolated from the supernatant in which the host cell is grown. If not secreted, the protein can be isolated from a lysate of the host cells.

The invention further provides transgenic nonhuman animals capable of expressing an exogenous variant gene and/or having one or both alleles of an endogenous variant gene inactivated. Expression of an exogenous variant gene is usually achieved by operably linking the gene to a promoter and optionally an enhancer, and microinjecting the construct into a zygote. See Hogan et al., "Manipulating the Mouse Embryo, A Laboratory Manual," Cold Spring Harbor Laboratory. Inactivation of endogenous variant genes can be achieved by forming a transgene in which a cloned variant gene is inactivated by insertion of a positive selection marker. See Capecchi, *Science* 244, 1288–1292 (1989). The transgene is then introduced into an embryonic stem cell, where it undergoes homologous recombination with an endogenous variant gene. Mice and other rodents are preferred animals. Such animals provide useful drug screening systems.

In addition to substantially full-length polypeptides expressed by variant genes, the present invention includes biologically active fragments of the polypeptides, or analogs thereof, including organic molecules which simulate the interactions of the peptides. Biologically active fragments include any portion of the full-length polypeptide which confers a biological function on the variant gene product, including ligand binding, and antibody binding. Ligand binding includes binding by nucleic acids, proteins or polypeptides, small biologically active molecules, or large cellular structures.

Polyclonal and/or monoclonal antibodies that specifically bind to variant gene products but not to corresponding prototypical gene products are also provided. Antibodies can be made by injecting mice or other animals with the variant gene product or synthetic peptide fragments thereof. Monoclonal antibodies are screened as are described, for example, in Harlow & Lane, *Antibodies, A Laboratory Manual,* Cold Spring Harbor Press, New York (1988); Goding, *Monoclonal antibodies, Principles and Practice* (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

V. Kits

The invention further provides kits comprising at least one allele-specific oligonucleotide as described above. Often, the kits contain one or more pairs of allele-specific oligonucleotides hybridizing to different forms of a polymorphism. In some kits, the allele-specific oligonucleotides are provided immobilized to a substrate. For example, the same substrate can comprise allele-specific oligonucleotide probes for detecting at least 10, 100 or all of the polymorphisms shown in the Table. Optional additional components of the kit include, for example, restriction enzymes, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. Usually, the kit also contains instructions for carrying out the methods.

The following Examples are offered for the purpose of illustrating the present invention and are not to be construed to limit the scope of this invention. The teachings of all references cited herein are hereby incorporated herein by reference.

EXAMPLES

The polymorphisms shown in the Table were identified by resequencing of target sequences from a minimum of 50 unrelated individuals of diverse ethnic and geographic backgrounds by hybridization to probes immobilized to microfabricated arrays. The strategy and principles for design and use of such arrays are generally described in WO 95/11995.

A typical probe array used in this analysis has two groups of four sets of probes that respectively tile both strands of a reference sequence. A first probe set comprises a plurality of probes exhibiting perfect complementarily with one of the reference sequences. Each probe in the first probe set has an interrogation position that corresponds to a nucleotide in the reference sequence. That is, the interrogation position is aligned with the corresponding nucleotide in the reference sequence, when the probe and reference sequence are aligned to maximize complementarily between the two. For each probe in the first set, there are three corresponding probes from three additional probe sets. Thus, there are four probes corresponding to each nucleotide in the reference sequence. The probes from the three additional probe sets are identical to the corresponding probe from the first probe set except at the interrogation position, which occurs in the same position in each of the four corresponding probes from the four probe sets, and is occupied by a different nucleotide in the four probe sets. In the present analysis, probes were 25 nucleotides long. Arrays tiled for multiple different references sequences were included on the same substrate.

Publicly available sequences for a given gene were assembled into Gap4 (http://www.biozentrum.unibas.ch/~biocomp/staden/Overview.html). PCR primers covering each exon were designed using Primer 3 (http://www-genome.wi.mit.edu/cgibin/primer/primer3.cgi). Primers were not designed in regions where there were sequence discrepancies between reads. For CLA1, whose genomic sequence is not published, nested primers were designed from the cDNA. For all genes except CLA1, genomic DNA was amplified in at least 50 individuals using 2.5 pmol each primer, 1.5 mM $MgCl_2$, 100 μM dNTPs, 0.75 μM AmpliTaq GOLD polymerase, and 19 ng DNA in a 15 μl reaction. Reactions were assembled using a PACKARD MultiPROBE robotic pipetting station and then put in MJ 96-well tetrad thermocyclers (96° C. for 10 minutes, followed by 35 cycles of 96° C. for 30 seconds, 59° C. for 2 minutes, and 72° C. for 2 minutes). A subset of the PCR assays for each individual were run on 3% NuSieve gels in 0.5×TBE to confirm that the reaction worked.

For CLA1, first strand cDNA was made using the Gibco BRL SuperScript Preamplification Kit (#18089-011) and following the manufacturers instructions except that 150 ng of random hexamers were used to primer 1 μg of total RNA. The cDNA was amplified using the outermost primer pairs and the above conditions; 1/20 of the reaction was used as a template for the secondary PCR using the innermost primers. All RT-PCR products were run on 2% NuSieve gels in 1×TAE to confirm the presence of a product.

For a given DNA, 5 μl (about 50 ng) of each PCR or RT-PCR product were pooled (Final volume=150–200 μl). The products were purified using QiaQuick PCR purification from Qiagen. The samples were eluted once in 35 μl sterile water and 4 μl 10×One-Phor-All buffer (Pharmacia). The pooled samples were digested with 0.2μ DNaseI (Promega) for 10 minutes at 37° C. and then labeled with 0.5 nmols biotin-N6-ddATP and 15μ Terminal Transferase (GibcoBPL Life Technology) for 60 minutes at 37° C. Both fragmentation and labeling reactions were terminated by incubating the pooled sample for 15 minutes at 100° C.

Low-density DNA chips (Affymetrix, Calif.) were hybridized following the manufacturer's instructions. Briefly, the hybridization cocktail consisted of 3M TMACl, 10 mM Tris pH 7.8, 0.01% Triton X-100, 100 mg/ml herring sperm DNA (Gibco BPL), 200 pM control biotin-labeled oligo. The processed PCR products were denatured for 7 minutes at 100° C. and then added to prewarmed (37° C.) hybridization solution. The chips were hybridized overnight at 44° C. Chips were washed in 1×SSPET and 6×SSPET followed by staining with 2 μg/ml SARPE and 0.5 mg/ml acetylated BSA in 200 μl of 6×SSPET for 8 minutes at room temperature. Chips were scanned using a Molecular Dynamics scanner.

Chip image files were analyzed using Ulysses (Affymetrix, Calif.) which uses four algorithms to identify potential polymorphisms. Candidate polymorphisms were visually inspected and assigned a confidence value: high confidence candidates displayed all three genotypes, while likely candidates showed only two genotypes (homozygous for reference sequence and heterozygous for reference and variant). Some of the candidate polymorphisms were confirmed by ABI sequencing. Identified polymorphisms were compared to SwissProt and the Mutation Database to determine if they were novel. Results are shown in the Table.

In the Table, the genes listed in column 2 are as follows: antithrombin III (AT3); cholesterol ester transfer protein (CETP); CLanalog (HDL/scavenger receptor) (CLanalog); thrombin receptor (F2R); thrombin (F2); heparin Cofactor II (HCF2); HMG coA-reductase (HMGCR); platelet glycoprotein IIB (ITGA2B); platelet glycoprotein IIIA (ITGB3); lecithin:cholesterol acyltransferase (LCAT); LDL receptor (LDLR); protein C (PROC); platelet activating factor receptor (PTAFR); tissue factor pathway inhibitor (TFPI); thromboxane A2 receptor (TBXA2R); lipoprotein lipase (LPL); tissue factor (F3); and factor V (F5).

Column 1 of the Table shows the laboratory name for the particular gene. Column 3 shows the GenBank Accession number for the wild type (reference) allele. Column 4 shows the nucleotide number location of the polymorphism relative to the numbering of the sequence deposited with GenBank having the listed Accession number; the GenBank sequence is understood to be the nucleotide sequence present in the GenBank database on Apr. 1, 1998, which sequences are incorporated herein by reference in their entirety. These GenBank sequences are illustrated in FIGS. 3–38.

Column 5 shows the codon which is altered by the polymorphism. Columns 6, 7 and 8 show the reference codon, variant codon and amino acid change, resepctivley, for the silent polymorphisms. Columns 9, 10 and 11 show the reference codon, variant codon and amino acid change, resepctively, for the missense polymorphisms. Columns 12, 13 and 14 show the reference codon, variant codon and amino acid change, resepctively, for the nonsense polymorphisms. Columns 15 and 16 show the nucleotide of the reference allele and the frequency of that allele, resepctively. This base is arbitrarily designated the reference or prototypical form, but it is not necessarily the most frequently occurring form. Columns 17 and 18 show the nucleotide of the variant allele and the frequency of that allele, resepctively. It is noted that the genes with polymorphism IDs of F5u8, HCF2u1 and HMGCRu2 contained the indicated polymorphism at the indicated nucleotide position, but that these nucleotide positions are in the non-coding region of the gene.

TABLE

| Polymorphism ID | Gene | GenBank Accession No. | Wt. Position | Codon No. | Silent PM Ref codon | Var codon | AA change |
|---|---|---|---|---|---|---|---|
| AT3u3 | AT3 | M21645 | 100 | 438 | | | |
| CETPu1 | CETP | M30185 | 1298 | 390 | | | |
| CETPu6 | CETP | J02898 | 298 | 455 | | | |
| CETPu9 | CETP | J02898 | 571 | 486 | | | |
| CLanalogu3 | CLanalog | Z225555 | 400 | 111 | | | |
| CLanalogu4 | CLanalog | Z225555 | 472 | 135 | | | |
| F2Ru1 | F2R | M62424 | 496 | 91 | | | |
| F2Ru2 | F2R | M62424 | 610 | 129 | | | |
| F2Ru3 | F2R | M62424 | 664 | 147 | | | |
| F2Ru4 | F2R | M62424 | 720 | 166 | | | |
| F2Ru6 | F2R | M62424 | 405 | 61 | | | |
| F2u1 | F2 | M17262 | 10777 | 165 | | | |
| F2u2 | F2 | M17262 | 15342 | 386 | | | |
| F3u1 | F3 | J02846 | 9363 | 163 | | | |
| F5u4 | F5 | M14335 | 1314 | 413 | | | |
| HCF2u3 | HCF2 | M12849 | 1353 | 442 | | | |
| HCF2u4 | HCF2 | M12849 | 47 | 7 | | | |
| HCF2u6 | HCF2 | M12849 | 651 | 208 | | | |
| HMGCRu1 | HMGCR | M11058 | 1962 | 638 | | | |
| ITGA2Bu2 | ITGA2B | J02764 | 2623 | 874 | | | |
| ITGA2Bu5 | ITGA2B | J02764 | 2904 | 968 | | | |
| ITGA2Bu6 | ITGA2B | J02764 | 120 | 40 | | | |
| ITCA2Bu7 | ITGA2B | J02764 | 2299 | 766 | | | |
| ITGB3u1 | ITGB3 | J02703 | 526 | 169 | | | |
| ITGB3u8 | ITGB3 | J02703 | 1377 | 453 | | | |
| LCATu2 | LCAT | M12625 | 961 | 232 | | | |
| LDLRu14 | LDLR | L00351 | 67 | 814 | | | |
| LDLRu7 | LDLR | L29401 | 691 | 2 | | | |
| LDLRu8 | LDLR | L00344 | 59 | 468 | | | |
| LPLu2 | LPL | M15856 | 1453 | 427 | | | |
| PROCu4 | PROC | K02059 | 534 | 283 | | | |
| PTAFRu3 | PTAFR | D10202 | 783 | 224 | | | |
| PTAFRu4 | PTAFR | D10202 | 194 | 28 | | | |
| PTAFRu5 | PTAFR | D10202 | 1125 | 338 | | | |
| TFPIu1 | TFPI | J03225 | 1006 | 292 | | | |
| CETPu4 | CETP | M30185 | 196 | 22 | ACC | ACA | T to T |
| LDLRu13 | LDLR | L00336 | 29 | 27 | TGT | TGC | C to C |
| HCF2u2 | HCF2 | M12849 | 259 | 77 | GAC | GAT | D to D |
| CETPu5 | CETP | M30185 | 388 | 86 | ATC | ATT | I to I |
| HCF2u5 | HCF2 | M12849 | 313 | 95 | ATC | ATT | I to I |
| ITGB3u7 | ITGB3 | J02703 | 362 | 114 | ATT | ATC | I to I |
| F2Ru7 | F2R | M62424 | 609 | 329 | CTG | TTG | L to L |
| PROCu2 | PROC | K02059 | 109 | 141 | TCT | TCG | S to S |
| CLanalogu2 | CLanalog | Z22555 | 570 | 167 | GGC | GGT | G to G |
| F2Ru5 | F2R | M62424 | 740 | 172 | TCT | TCG | S to S |
| LCATu1 | LCAT | M12625 | 864 | 199 | GTC | GTT | V to V |
| CETPu6 | CETP | M30185 | 766 | 212 | GCC | GCT | A to A |
| PROCu3 | PROC | M11228 | 9358 | 256 | GAT | GAC | D to D |
| F2u4 | F2 | M17262 | 13434 | 271 | GGC | GGT | G to G |
| ITGB3u3 | ITGB3 | J02703 | 902 | 294 | CCT | CCC | P to P |
| PROCu1 | PROC | K02059 | 577 | 297 | GAC | GAT | D to D |

TABLE-continued

| | | | | | | | | |
|---|---|---|---|---|---|---|---|---|
| LCATu4 | LCAT | M12625 | 1167 | 300 | CGT | CGC | R to R | |
| CLanalogu5 | CLanalog | Z22555 | 972 | 301 | TTC | TTT | F to F | |
| TBXA2Ru1 | TBXA2R | D38081 | 1915 | 308 | TAT | TAC | Y to Y | |
| AT3u1 | AT3 | D29832 | 1005 | 327 | GTG | GTA | V to V | |
| CLanalogu1 | CLanalog | Z22555 | 1119 | 350 | GCC | GCT | A to A | |
| ITGB3u4 | ITGB3 | J02703 | 1163 | 381 | GTC | GTA | V to V | |
| LPLu1 | LPL | M15856 | 1338 | 388 | ACC | ACA | T to T | |
| LCATu3 | LCAT | M12625 | 1444 | 393 | CTG | TTG | L to L | |
| F2u3 | F2 | M17262 | 15419 | 411 | CCG | CCA | P to P | |
| F5u5 | F5 | M14335 | 1318 | 414 | AAA | AAG | K to K | |
| CETPu7 | CETP | M30185 | 1429 | 433 | GTG | GTA | V to V | |
| LDLRu9 | LDLR | L00343 | 152 | 441 | ATC | ATT | I to I | |
| AT3u4 | AT3 | D29832 | 1374 | 450 | AAC | AAT | N to N | |
| F5u1 | F5 | M14335 | 1456 | 460 | AAC | AAT | N to N | |
| HCF2u7 | HCF2 | M12849 | 1474 | 482 | CAC | CAT | H to H | |
| ITGB3u5 | ITGB3 | M20311 | 1549 | 511 | GAG | GAA | E to E | |
| ITGB3u6 | ITGB3 | M20311 | 1561 | 515 | CGA | CGG | R to R | |
| F2u5 | F2 | M17262 | 16827 | 534 | CCG | CCA | P to P | |
| LDLRu3 | LDLR | L00345 | 46 | 539 | CCC | CCT | P to P | |
| F5u6 | F5 | M14335 | 1792 | 572 | GAG | GAA | E to E | |
| LDLRu10 | LDLR | U59436 | 45 | 575 | CTC | CTT | L to L | |
| LDLRu6 | LDLR | U59436 | 93 | 591 | AAT | AAC | N to N | |
| ITGA2Bu3 | ITGA2B | M33320 | 6845 | 605 | CCG | CCA | P to P | |
| LDLRu11 | LDLR | L00347 | 90 | 640 | AAC | AAT | N to N | |
| F5u7 | F5 | M14335 | 2002 | 642 | ACC | ACA | T to T | |
| LDLRu1 | LDLR | L00347 | 129 | 653 | GTC | GTT | V to V | |
| LDLRu12 | LDLR | L00349 | 107 | 744 | CGG | CGA | R to R | |
| ITGA2Bu8 | ITGA2B | J02764 | 2567 | 855 | CTT | CTC | L to L | |
| ITGA2Bu4 | ITGA2B | J02764 | 2918 | 972 | CCG | CCA | P to P | |
| ITGA2Bu1 | ITGA2B | M22569 | 194 | 1021 | GTC | GTT | V to V | |
| F5u8 | F5 | L32765 | 66 | | | | | |
| HCF2u1 | HCF2 | M58600 | 11907 | | | | | |
| HMGCRu2 | HMGCR | M11058 | 2725 | | | | | |
| ITGB3u2 | ITGB3 | J02703 | 196 | 59 | | | | |
| CETPu2 | CETP | M30185 | 1394 | 422 | | | | |
| F5u2 | F5 | M14335 | 1614 | 513 | | | | |
| F5u3 | F5 | M14335 | 1677 | 534 | | | | |
| AT3u2 | AT3 | D29832 | 1035 | 337 | CAG | CAA | Q to Q | |
| LDLRu5 | LDLR | L00344 | 70 | 471 | AGG | AGA | R to R | |
| LPLu3 | LPL | M76722 | 3150 | 474 | | | | |

| | Missense PM | | | Nonsense PM | | | Allele Freq | | | |
|---|---|---|---|---|---|---|---|---|---|---|
| Polymorphism ID | Ref codon | Var codon | AA change | Ref codon | Var codon | AA change | Ref allele | Freq | Var allele | Freq |
| AT3u3 | AGG | GGG | R to G | | | | A | 0.99 | G | 0.01 |
| CETPu1 | GCC | CCC | A to P | | | | G | 0.95 | C | 0.05 |
| CETPu6 | GTG | ATG | V to M | | | | G | 0.99 | A | 0.01 |
| CETPu9 | GTG | ATG | V to M | | | | G | 0.99 | A | 0.01 |
| CLanalogu3 | GTG | ATG | V to M | | | | G | 0.99 | A | 0.01 |
| CLanalogu4 | GTC | ATC | V to I | | | | G | 0.99 | A | 0.01 |
| F2Ru1 | GAT | GGT | D to G | | | | A | 0.99 | G | 0.01 |
| F2Ru2 | CTG | CGG | L to R | | | | T | 0.98 | G | 0.02 |
| F2Ru3 | GCA | GAA | A to E | | | | C | 0.91 | A | 0.09 |
| F2Ru4 | AGT | GGT | S to G | | | | A | 0.99 | G | 0.01 |
| F2Ru6 | AAA | CAA | K to Q | | | | A | 0.93 | C | 0.07 |
| F2u1 | ACG | ATG | T to H | | | | C | 0.97 | T | 0.03 |
| F2u2 | CCC | ACC | P to T | | | | C | 0.99 | A | 0.01 |
| F3u1 | CGG | TGG | R to W | | | | C | 0.99 | T | 0.01 |
| F5u4 | ATG | ACG | M to T | | | | T | 0.94 | C | 0.06 |
| HCF2u3 | ACG | ATG | T to M | | | | C | 0.99 | T | 0.01 |
| HCF2u4 | GCA | ACA | A to T | | | | G | 0.98 | A | 0.02 |
| HCF2u6 | CGC | CAC | R to H | | | | G | 0.99 | A | 0.01 |
| HMGCRu1 | ATA | GTA | I to V | | | | A | 0.99 | G | 0.01 |
| ITGA2Bu2 | ATC | AGC | I to S | | | | T | 0.79 | G | 0.21 |
| ITGA2Bu5 | TAT | AAT | Y to N | | | | T | 0.99 | A | 0.01 |
| ITGA2Bu6 | ACC | ATC | T to I | | | | C | 0.97 | T | 0.03 |
| ITCA2Bu7 | ATT | AGT | I to S | | | | T | 0.99 | G | 0.01 |
| ITGB3u1 | CGA | CAA | R to Q | | | | G | 0.99 | A | 0.01 |
| ITGB3u8 | GTC | ATC | V to I | | | | G | 0.99 | A | 0.01 |
| LCATu2 | TCT | ACT | S to T | | | | T | 0.98 | A | 0.02 |
| LDLRu14 | CGG | CAG | R to Q | | | | G | 0.99 | A | 0.01 |
| LDLRu7 | CGG | CGG | G to R | | | | G | 0.99 | C | 0.01 |
| LDLRu8 | GTC | ATC | V to I | | | | G | 0.99 | A | 0.01 |
| LPLu2 | GCC | ACC | A to T | | | | G | 0.99 | A | 0.01 |
| PROCu4 | AAG | AGG | K to R | | | | A | 0.99 | G | 0.01 |
| PTAFRu3 | GCT | GAT | A to D | | | | C | 0.99 | A | 0.01 |
| PTAFRu4 | CTC | TTC | L to F | | | | C | 0.99 | T | 0.01 |

TABLE-continued

| | | | | | | | |
|---|---|---|---|---|---|---|---|
| PTAFRu5 | AAT | AGT | N to S | A | 0.98 | G | 0.02 |
| TFPIu1 | GTG | ATG | V to M | G | 0.99 | A | 0.01 |
| CETPu4 | | | | C | 0.99 | A | 0.01 |
| LDLRu13 | | | | T | 0.62 | C | 0.38 |
| HCF2u2 | | | | C | 0.97 | T | 0.03 |
| CETPu5 | | | | C | 0.99 | C | 0.01 |
| HCF2u5 | | | | C | 0.99 | T | 0.01 |
| ITGB3u7 | | | | T | 0.97 | C | 0.03 |
| F2Ru7 | | | | C | 0.98 | T | 0.02 |
| PROCu2 | | | | T | 0.46 | G | 0.54 |
| CLanalogu2 | | | | C | 0.88 | T | 0.12 |
| F2Ru5 | | | | T | 0.99 | G | 0.01 |
| LCATu1 | | | | C | 0.99 | T | 0.01 |
| CETPu6 | | | | C | 0.98 | T | 0.02 |
| PROCu3 | | | | T | 0.98 | C | 0.02 |
| F2u4 | | | | C | 0.98 | T | 0.02 |
| ITGB3u3 | | | | T | 0.87 | C | 0.13 |
| PROCu1 | | | | C | 0.99 | T | 0.01 |
| LCATu4 | | | | T | 0.99 | C | 0.01 |
| CLanalogu5 | | | | C | 0.95 | T | 0.05 |
| TBXA2Ru1 | | | | T | 0.57 | C | 0.43 |
| AT3u1 | | | | G | 0.64 | A | 0.36 |
| CLanalogu1 | | | | C | 0.68 | T | 0.32 |
| ITGB3u4 | | | | C | 0.50 | A | 0.50 |
| LPLu1 | | | | C | 0.89 | A | 0.11 |
| LCATu3 | | | | C | 0.93 | T | 0.07 |
| F2u3 | | | | G | 0.57 | A | 0.03 |
| F5u5 | | | | A | 0.92 | G | 0.08 |
| CETPu7 | | | | G | 0.99 | A | 0.01 |
| LDLRu9 | | | | C | 0.99 | T | 0.01 |
| AT3u4 | | | | C | 0.99 | T | 0.01 |
| F5u1 | | | | C | 0.95 | T | 0.05 |
| HCF2u7 | | | | C | 0.53 | T | 0.47 |
| ITGB3u5 | | | | G | 0.27 | A | 0.73 |
| ITGB3u6 | | | | A | 0.43 | G | 0.57 |
| F2u5 | | | | C | 0.99 | A | 0.01 |
| LDLRu3 | | | | C | 0.89 | T | 0.11 |
| F5u6 | | | | G | 0.94 | A | 0.06 |
| LDLRu10 | | | | C | 0.93 | T | 0.07 |
| LDLRu6 | | | | T | 0.77 | C | 0.23 |
| ITGA2Bu3 | | | | G | 0.98 | A | 0.02 |
| LDLRu11 | | | | C | 0.99 | T | 0.01 |
| F5u7 | | | | C | 0.96 | A | 0.04 |
| LDLRu1 | | | | C | 0.31 | T | 0.69 |
| LDLRu12 | | | | G | 0.85 | A | 0.15 |
| ITGA2Bu8 | | | | T | 0.99 | C | 0.01 |
| ITGA2Bu4 | | | | G | 0.99 | A | 0.01 |
| ITGA2Bu1 | | | | C | 0.66 | V | 0.34 |
| F5u8 | | | | G | 0.99 | T | 0.01 |
| HCF2u1 | | | | C | 0.96 | T | 0.04 |
| HMGCRu2 | | | | G | 0.97 | A | 0.03 |
| ITGB3u2 | CTG | CCG | L to P | T | 0.87 | C | 0.13 |
| CETPu2 | ATC | GTC | I to V | A | 0.34 | G | 0.66 |
| F5u2 | AGA | AAA | R to K | G | 0.85 | A | 0.15 |
| F5u3 | CGA | CAA | R to Q | G | 0.99 | A | 0.01 |
| AT3u2 | | | | G | 0.62 | A | 0.38 |
| LDLRu5 | | | | G | 0.08 | A | 0.32 |
| LPLu3 | | | TCA | TGA | S to * | C | 0.85 | G | 0.15 |

From the foregoing, it is apparent that the invention includes a number of general uses that can be expressed concisely as follows. The invention provides for the use of any of the nucleic acid segments described above in the diagnosis or monitoring of diseases, such as cancer, inflammation, heart disease, diseases of the cardiovascular system, and infection by microorganisms. The invention further provides for the use of any of the nucleic acid segments in the manufacture of a medicament for the treatment or prophylaxis of such diseases. The invention further provides for the use of any of the DNA segments as a pharmaceutical.

All references cited above are incorporated by reference in their entirety for all purposes to the same extent as if each individual publication or patent application were specifically and individually indicated to be so incorporated by reference.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. An isolated nucleic acid molecule having polymorphic sites, wherein the nucleic acid molecule is SEQ ID NO:37 and the polymorphic sites are nucleotide position 1314, nucleotide position 1318, nucleotide position 1456, nucleotide position 1782 and nucleotide position 2002, wherein the reference nucleotide for said polymorphic sites is a thymine at nucleotide position 1314, an adenine at nucleotide position 1318, a cytosine at nucleotide position 1456, a guanine at nucleotide position 1792, and a cytosine at nucleotide position 2002 and wherein the nucleotide at at least one polymorphic site in the isolated nucleic acid molecule is a nucleotide other than the reference nucleotide.

2. An isolated nucleic acid molecule according to claim 1, wherein said nucleic acid molecule comprises one or more of a cytosine at nucleotide position 1314, a guanine at nucleotide position 1318, a thymine at nucleotide position 1456, an adenine at nucleotide position 1792, and an adenine at nucleotide position 2002.

3. An oligonucleotide that hybridizes to an isolated nucleic acid molecule having polymorphic sites, wherein the nucleic acid molecule is SEQ ID NO:37 and the polymorphic sites are nucleotide position 1314, nucleotide position 1318, nucleotide position 1456, nucleotide position 1782 and nucleotide position 2002, wherein the reference nucleotide for said polymorphic sites is a thymine at nucleotide position 1314, an adenine at nucleotide position 1318, a cytosine at nucleotide position 1456, a guanine at nucleotide position 1792, and a cytosine at nucleotide position 2002 and wherein the nucleotide at at least one polymorphic site in the isolated nucleic acid molecule is a nucleotide other than the reference nucleotide, and wherein said oligonucleotide hybridizes to a portion of said isolated nucleic acid molecule comprising a polymorphic site which is occupied by a nucleotide other than the reference nucleotide for that polymorphic site.

4. An oligonucleotide according to claim 3 that is a probe.

5. An oligonucleotide according to claim 4, wherein a central nucleotide of the probe hybridizes with the polymorphic site of the portion of the nucleic acid molecule.

6. An oligonucleotide according to claim 3 that is a primer.

7. An oligonucleotide according to claim 6, wherein the nucleotide at the 3' end of the primer hybridizes with the polymorphic site of the portion of the nucleic acid molecule.

8. A method of analyzing a nucleic acid sample comprising a nucleic acid molecule having polymorphic sites, wherein the nucleic acid molecule is SEQ ID NO:37 and the polymorphic sites are nucleotide position 1314, nucleotide position 1318, nucleotide position 1456, nucleotide position 1782 and nucleotide position 2002, wherein the reference nucleotide for said polymorphic sites is a thymine at nucleotide position 1314, an adenine at nucleotide position 1318, a cytosine at nucleotide position 1456, a guanine at nucleotide position 1792, and a cytosine at nucleotide position 2002 and wherein the nucleotide at at least one polymorphic site in the isolated nucleic acid molecule is a nucleotide other than the reference nucleotide, the method comprising obtaining nucleic acid molecules from a nucleic acid sample and determining a nucleotide occupying one or more of the polymorphic sites of the nucleic acid molecule.

9. A method according to claim 8, wherein the nucleic acid sample is obtained from a plurality of individuals, and the nucleotide occupying one or more polymorphic sites is determined in each of the individuals, and wherein the method further comprises testing each individual for the presence of a disease phenotype and correlating the presence of the disease phenotype with the nucleotide occupying one or more polymorphic sites.

10. A portion of an isolated nucleic acid molecule having polymorphic sites, wherein the nucleic acid molecule is SEQ ID NO:37 and the polymorphic sites are nucleotide position 1314, nucleotide position 1318, nucleotide position 1456, nucleotide position 1782 and nucleotide position 2002, wherein the reference nucleotide for said polymorphic sites is a thymine at nucleotide position 1314, an adenine at nucleotide position 1318, a cytosine at nucleotide position 1456, a guanine at nucleotide position 1792, and a cytosine at nucleotide position 2002 and wherein the nucleotide at at least one polymorphic site in the isolated nucleic acid molecule is a nucleotide other than the reference nucleotide, and further wherein said portion has a length of at least 5 nucleotides and comprises a polymorphic site of the isolated nucleic acid molecule which is occupied by a nucleotide other than the reference nucleotide.

11. A portion of an isolated nucleic acid molecule according to claim 10, wherein the portion has a length of at least 10 nucleotides.

12. A portion of an isolated nucleic acid molecule according to claim 10, wherein the portion has a length of at least 20 nucleotides.

\* \* \* \* \*

UNITED STATES PATENT AND TRADEMARK OFFICE
CERTIFICATE OF CORRECTION

PATENT NO. : 6,692,909 B1  
DATED : February 17, 2004  
INVENTOR(S) : Lander et al.

Page 1 of 1

It is certified that error appears in the above-identified patent and that said Letters Patent is hereby corrected as shown below:

Column 261,  
Line 60, "1782" should read -- 1792 --.  
Line 65, after "nucleotide at" delete "at".

Column 262,  
Line 65, "1782" should read -- 1792 --.

Column 263,  
Lines 4 and 30, after "nucleotide at" delete "at".  
Line 25, "1782" should read -- 1792 --.

Column 264,  
Line 15, "1782" should read -- 1792 --.  
Line 20, after "nucleotide at" delete "at".

Signed and Sealed this

Thirteenth Day of July, 2004

JON W. DUDAS  
*Acting Director of the United States Patent and Trademark Office*

SEQUENCE LISTING (1) GENERAL INFORMATION:

(iii) NUMBER OF SEQUENCES: 59

(2) INFORMATION FOR SEQ ID NO:1:

(i) SEQUENCE CHARACTERISTICS:
      (A) LENGTH: 1780 base pairs
      (B) TYPE: nucleic acid
      (C) STRANDEDNESS: single
      (D) TOPOLOGY: linear (ii) MOLECULE TYPE: Genomic DNA (ix) FEATURE:
      (A) NAME/KEY: Coding Sequence
      (B) LOCATION: 113...1138
      (D) OTHER INFORMATION:

(xi) SEQUENCE DESCRIPTION: SEQ ID NO:1:

```
TTCACGAGGG CTGGGGCCAG GACCCAGACA GAGACACACG GTCACTGCAG CTGAAGCCGC           60

TGCCCCTGCT ACAGGCACCA CCAGGACCAG CTGATCATTC CAGCCCACAG CA ATG GAG         118
                                                         Met Glu
                                                           1

CCA CAT GAC TCC TCC CAC ATG GAC TCT GAG TTC CGA TAC ACT CTC TTC           166
Pro His Asp Ser Ser His Met Asp Ser Glu Phe Arg Tyr Thr Leu Phe
          5                  10                  15

CCG ATT GTT TAC AGC ATC ATC TTT GTG CTC GGG GTC ATT GCT AAT GGC           214
Pro Ile Val Tyr Ser Ile Ile Phe Val Leu Gly Val Ile Ala Asn Gly
     20                  25                  30

TAC GTG CTG TGG GTC TTT GCC CGC CTG TAC CCT TGC AAG AAA TTC AAT           262
Tyr Val Leu Trp Val Phe Ala Arg Leu Tyr Pro Cys Lys Lys Phe Asn
 35                  40                  45                  50

GAG ATA AAG ATC TTC ATG GTG AAC CTC ACC ATG GCG GAC ATG CTC TTC           310
Glu Ile Lys Ile Phe Met Val Asn Leu Thr Met Ala Asp Met Leu Phe
                 55                  60                  65

TTG ATC ACC CTG CCA CTT TGG ATT GTC TAC TAC CAA AAC CAG GGC AAC           358
Leu Ile Thr Leu Pro Leu Trp Ile Val Tyr Tyr Gln Asn Gln Gly Asn
             70                  75                  80

TGG ATA CTC CCC AAA TTC CTG TGC AAC GTG GCT GGC TGC CTT TTC TTC           406
Trp Ile Leu Pro Lys Phe Leu Cys Asn Val Ala Gly Cys Leu Phe Phe
         85                  90                  95

ATC AAC ACC TAC TGC TCT GTG GCC TTC CTG GGC GTC ATC ACT TAT AAC           454
Ile Asn Thr Tyr Cys Ser Val Ala Phe Leu Gly Val Ile Thr Tyr Asn
     100                 105                 110

CGC TTC CAG GCA GTA ACT CGG CCC ATC AAG ACT GCT CAG GCC AAC ACC           502
Arg Phe Gln Ala Val Thr Arg Pro Ile Lys Thr Ala Gln Ala Asn Thr
115                 120                 125                 130

CGC AAG CGT GGC ATC TCT TTG TCC TTG GTC ATC TGG GTG GCC ATT GTG           550
Arg Lys Arg Gly Ile Ser Leu Ser Leu Val Ile Trp Val Ala Ile Val
                135                 140                 145

GGA GCT GCA TCC TAC TTC CTC ATC CTG GAC TCC ACC AAC ACA GTG CCC           598
Gly Ala Ala Ser Tyr Phe Leu Ile Leu Asp Ser Thr Asn Thr Val Pro
            150                 155                 160

GAC AGT GCT GGC TCA GGC AAC GTC ACT CGC TGC TTT GAG CAT TAC GAG           646
Asp Ser Ala Gly Ser Gly Asn Val Thr Arg Cys Phe Glu His Tyr Glu
        165                 170                 175

AAG GGC AGC GTG CCA GTC CTC ATC ATC CAC ATC TTC ATC GTG TTC AGC           694
Lys Gly Ser Val Pro Val Leu Ile Ile His Ile Phe Ile Val Phe Ser
    180                 185                 190
```

```
TTC TTC CTG GTC TTC CTC ATC ATC CTC TTC TGC AAC CTG GTC ATC ATC         742
Phe Phe Leu Val Phe Leu Ile Ile Leu Phe Cys Asn Leu Val Ile Ile
195                 200                 205                 210

CGT ACC TTG CTC ATG CAG CCG GTG CAG CAG CAG CGC AAC GCT GAA GTC         790
Arg Thr Leu Leu Met Gln Pro Val Gln Gln Gln Arg Asn Ala Glu Val
                215                 220                 225

AAG CGC CGG GCG CTG TGG ATG GTG TGC ACG GTC TTG GCG GTG TTC ATC         838
Lys Arg Arg Ala Leu Trp Met Val Cys Thr Val Leu Ala Val Phe Ile
        230                 235                 240

ATC TGC TTC GTG CCC CAC CAC GTG GTG CAG CTG CCC TGG ACC CTT GCT         886
Ile Cys Phe Val Pro His His Val Val Gln Leu Pro Trp Thr Leu Ala
            245                 250                 255

GAG CTG GGC TTC CAG GAC AGC AAA TTC CAC CAG GCC ATT AAT GAT GCA         934
Glu Leu Gly Phe Gln Asp Ser Lys Phe His Gln Ala Ile Asn Asp Ala
260                 265                 270

CAT CAG GTC ACC CTC TGC CTC CTT AGC ACC AAC TGT GTC TTA GAC CCT         982
His Gln Val Thr Leu Cys Leu Leu Ser Thr Asn Cys Val Leu Asp Pro
275                 280                 285                 290

GTT ATC TAC TGT TTC CTC ACC AAG AAG TTC CGC AAG CAC CTC ACC GAA        1030
Val Ile Tyr Cys Phe Leu Thr Lys Lys Phe Arg Lys His Leu Thr Glu
                295                 300                 305

AAG TTC TAC AGC ATG CGC AGT AGC CGG AAA TGC TCC CGG GCC ACC ACG        1078
Lys Phe Tyr Ser Met Arg Ser Ser Arg Lys Cys Ser Arg Ala Thr Thr
            310                 315                 320

GAT ACG GTC ACT GAA GTG GTT GTG CCA TTC AAC CAG ATC CCT GGC AAT        1126
Asp Thr Val Thr Glu Val Val Val Pro Phe Asn Gln Ile Pro Gly Asn
        325                 330                 335

TCC CTC AAA AAT TAGTCCCTGC TTCCAGGCCT GAAGTCTTCT CCTCCATGAA            1178
Ser Leu Lys Asn
    340

ACATCATGAC TGAGCTGGGG AAGAAGGGA TATCTACTGT GGGTCTGGGC ACCACCTCTG       1238

TGGCACTGGT GGGCCATTAG ATTTGGAGGC TACCTCACCT GGGCAGGGAT GATGCAGAGC      1298

CAGGCTGTTG GAAAATCCAG AACTCAAATG AGCCCCTTCA TCCGCCTGTG GGCGCATACT      1358

ACAGTAACTG TGACTGATGA CTTTATCCTG AGTCCCTTAA TCTTATGGGG CCGGAAGGAA      1418

TGTCAGGGCC AGGTGCAGAC CTTGGGGGAA GACTTTAAAC CACCTAGTTC TCCCACTGGG      1478

GCATCGGTCT AAAGCTTTGG GGGAGTGGCC CCAGTGGCTC ACACCTGTAA TCCCAGCACT      1538

TTGGGAGGCC GAGGTGGGCA GATCATGGGT CAAGAGATCG AGACATCCTG GCCAACATTG      1598

TAAAACCCCA TCTCTACTAA AACATACAAA AATTAGCCGG GCATGGTGCA CACGCCTGTA      1658

GTCCCAGCTA CTCAGGAGGC TGAGGCAGGA GAATCGCTTG AACCTGGGAG GCAGAGGTTG      1718

CAGTGAACCT AGATTGCACC ATTGCACTCT AGCCTGGCAA CAGAGGCAGA TTCCCTCCTG      1778

CC                                                                    1780

(2) INFORMATION FOR SEQ ID NO:2:

(i) SEQUENCE CHARACTERISTICS:
        (A) LENGTH: 342 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Glu Pro His Asp Ser Ser His Met Asp Ser Glu Phe Arg Tyr Thr
1               5                   10                  15
```

```
Leu Phe Pro Ile Val Tyr Ser Ile Ile Phe Val Leu Gly Val Ile Ala
            20                  25                  30

Asn Gly Tyr Val Leu Trp Val Phe Ala Arg Leu Tyr Pro Cys Lys Lys
        35                  40                  45

Phe Asn Glu Ile Lys Ile Phe Met Val Asn Leu Thr Met Ala Asp Met
 50                  55                  60

Leu Phe Leu Ile Thr Leu Pro Leu Trp Ile Val Tyr Tyr Gln Asn Gln
 65                  70                  75                  80

Gly Asn Trp Ile Leu Pro Lys Phe Leu Cys Asn Val Ala Gly Cys Leu
                85                  90                  95

Phe Phe Ile Asn Thr Tyr Cys Ser Val Ala Phe Leu Gly Val Ile Thr
               100                 105                 110

Tyr Asn Arg Phe Gln Ala Val Thr Arg Pro Ile Lys Thr Ala Gln Ala
           115                 120                 125

Asn Thr Arg Lys Arg Gly Ile Ser Leu Ser Leu Val Ile Trp Val Ala
       130                 135                 140

Ile Val Gly Ala Ala Ser Tyr Phe Leu Ile Leu Asp Ser Thr Asn Thr
145                 150                 155                 160

Val Pro Asp Ser Ala Gly Ser Gly Asn Val Thr Arg Cys Phe Glu His
                165                 170                 175

Tyr Glu Lys Gly Ser Val Pro Val Leu Ile Ile His Ile Phe Ile Val
            180                 185                 190

Phe Ser Phe Phe Leu Val Phe Leu Ile Ile Leu Phe Cys Asn Leu Val
        195                 200                 205

Ile Ile Arg Thr Leu Leu Met Gln Pro Val Gln Gln Gln Arg Asn Ala
210                 215                 220

Glu Val Lys Arg Arg Ala Leu Trp Met Val Cys Thr Val Leu Ala Val
225                 230                 235                 240

Phe Ile Ile Cys Phe Val Pro His His Val Val Gln Leu Pro Trp Thr
                245                 250                 255

Leu Ala Glu Leu Gly Phe Gln Asp Ser Lys Phe His Gln Ala Ile Asn
            260                 265                 270

Asp Ala His Gln Val Thr Leu Cys Leu Leu Ser Thr Asn Cys Val Leu
        275                 280                 285

Asp Pro Val Ile Tyr Cys Phe Leu Thr Lys Lys Phe Arg Lys His Leu
290                 295                 300

Thr Glu Lys Phe Tyr Ser Met Arg Ser Ser Arg Lys Cys Ser Arg Ala
305                 310                 315                 320

Thr Thr Asp Thr Val Thr Glu Val Val Val Pro Phe Asn Gln Ile Pro
                325                 330                 335

Gly Asn Ser Leu Lys Asn
            340

(2) INFORMATION FOR SEQ ID NO:3:

(i) SEQUENCE CHARACTERISTICS:
        (A) LENGTH: 1467 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 22...1416
        (D) OTHER INFORMATION:
```

(xi) SEQUENCE DESCRIPTION: SEQ ID NO:3:

```
GAATTCGAGC TCGCCCCGGC C ATG TAT TCC AAT GTG ATA GGA ACT GTA ACC          51
                         Met Tyr Ser Asn Val Ile Gly Thr Val Thr
                          1               5                  10

TCT GGA AAA AGG AAG GTT TAT CTC TTG TCC TTG CTG CTC ATT GGC TTC          99
Ser Gly Lys Arg Lys Val Tyr Leu Leu Ser Leu Leu Leu Ile Gly Phe
            15                  20                  25

TGG GAC TGC GTG ACC TGT CAC GGG AGC CCT GTG GAC ATC TGC ACA GCC         147
Trp Asp Cys Val Thr Cys His Gly Ser Pro Val Asp Ile Cys Thr Ala
        30                  35                  40

AAG CCG CGG GAC ATT CCC ATG AAT CCC ATG TGC ATT TAC CGC TCC CCG         195
Lys Pro Arg Asp Ile Pro Met Asn Pro Met Cys Ile Tyr Arg Ser Pro
    45                  50                  55

GAG AAG AAG GCA ACT GAG GAT GAG GGC TCA GAA CAG AAG ATC CCG GAG         243
Glu Lys Lys Ala Thr Glu Asp Glu Gly Ser Glu Gln Lys Ile Pro Glu
60                  65                  70

GCC ACC AAC AAC CGG CGT GTC TGG GAA CTG TCC AAG GCC AAT TCC CGC         291
Ala Thr Asn Asn Arg Arg Val Trp Glu Leu Ser Lys Ala Asn Ser Arg
75                  80                  85                  90

TTT GCT ACC ACT TTC TAT CAG CAC CTG GCA GAT TCC AAG AAT GAC AAT         339
Phe Ala Thr Thr Phe Tyr Gln His Leu Ala Asp Ser Lys Asn Asp Asn
                95                 100                 105

GAT AAC ATT TTC CTG TCA CCC CTG AGT ATC TCT ACG GCT TTT GCT ATG         387
Asp Asn Ile Phe Leu Ser Pro Leu Ser Ile Ser Thr Ala Phe Ala Met
            110                 115                 120

ACC AAG CTG GGT GCC TGT AAT GAC ACC CTC CAG CAA CTG ATG GAG GTA         435
Thr Lys Leu Gly Ala Cys Asn Asp Thr Leu Gln Gln Leu Met Glu Val
        125                 130                 135

TTT AAG TTT GAC ACC ATA TCT GAG AAA ACA TCT GAT CAG ATC CAC TTC         483
Phe Lys Phe Asp Thr Ile Ser Glu Lys Thr Ser Asp Gln Ile His Phe
    140                 145                 150

TTC TTT GCC AAA CTG AAC TGC CGA CTC TAT CGA AAA GCC AAC AAA TCC         531
Phe Phe Ala Lys Leu Asn Cys Arg Leu Tyr Arg Lys Ala Asn Lys Ser
155                 160                 165                 170

TCC AAG TTA GTA TCA GCC AAT CGC CTT TTT GGA GAC AAA TCC CTT ACC         579
Ser Lys Leu Val Ser Ala Asn Arg Leu Phe Gly Asp Lys Ser Leu Thr
                175                 180                 185

TTC AAT GAG ACC TAC CAG GAC ATC AGT GAG TTG GTA TAT GGA GCC AAG         627
Phe Asn Glu Thr Tyr Gln Asp Ile Ser Glu Leu Val Tyr Gly Ala Lys
            190                 195                 200

CTC CAG CCC CTG GAC TTC AAG GAA AAT GCA GAG CAA TCC AGA GCG GCC         675
Leu Gln Pro Leu Asp Phe Lys Glu Asn Ala Glu Gln Ser Arg Ala Ala
        205                 210                 215

ATC AAC AAA TGG GTG TCC AAT AAG ACC GAA GGC CGA ATC ACC GAT GTC         723
Ile Asn Lys Trp Val Ser Asn Lys Thr Glu Gly Arg Ile Thr Asp Val
    220                 225                 230

ATT CCC TCG GAA GCC ATC AAT GAG CTC ACT GTT CTG GTG CTG GTT AAC         771
Ile Pro Ser Glu Ala Ile Asn Glu Leu Thr Val Leu Val Leu Val Asn
235                 240                 245                 250

ACC ATT TAC TTC AAG GGC CTG TGG AAG TCA AAG TTC AGC CCT GAG AAC         819
Thr Ile Tyr Phe Lys Gly Leu Trp Lys Ser Lys Phe Ser Pro Glu Asn
                255                 260                 265

ACA AGG AAG GAA CTG TTC TAC AAG GCT GAT GGA GAG TCG TGT TCA GCA         867
Thr Arg Lys Glu Leu Phe Tyr Lys Ala Asp Gly Glu Ser Cys Ser Ala
            270                 275                 280

TCT ATG ATG TAC CAG GAA GGC AAG TTC CGT TAT CGG CGC GTG GCT GAA         915
Ser Met Met Tyr Gln Glu Gly Lys Phe Arg Tyr Arg Arg Val Ala Glu
        285                 290                 295
```

```
GGC ACC CAG GTG CTT GAG TTG CCC TTC AAA GGT GAT GAC ATC ACC ATG         963
Gly Thr Gln Val Leu Glu Leu Pro Phe Lys Gly Asp Asp Ile Thr Met
        300                 305                 310

GTC CTC ATC TTG CCC AAG CCT GAG AAG AGC CTG GCC AAG GTG GAG AAG         1011
Val Leu Ile Leu Pro Lys Pro Glu Lys Ser Leu Ala Lys Val Glu Lys
315                 320                 325                 330

GAA CTC ACC CCA GAG GTG CTG CAG GAG TGG CTG GAT GAA TTG GAG GAG         1059
Glu Leu Thr Pro Glu Val Leu Gln Glu Trp Leu Asp Glu Leu Glu Glu
                335                 340                 345

ATG ATG CTG GTG GTC CAC ATG CCC CGC TTC CGC ATT GAG GAC GGC TTC         1107
Met Met Leu Val Val His Met Pro Arg Phe Arg Ile Glu Asp Gly Phe
        350                 355                 360

AGT TTG AAG GAG CAG CTG CAA GAC ATG GGC CTT GTC GAT CTG TTC AGC         1155
Ser Leu Lys Glu Gln Leu Gln Asp Met Gly Leu Val Asp Leu Phe Ser
        365                 370                 375

CCT GAA AAG TCC AAA CTC CCA GGT ATT GTT GCA GAA GGC CGA GAT GAC         1203
Pro Glu Lys Ser Lys Leu Pro Gly Ile Val Ala Glu Gly Arg Asp Asp
        380                 385                 390

CTC TAT GTC TCA GAT GCA TTC CAT AAG GCA TTT CTT GAG GTA AAT GAA         1251
Leu Tyr Val Ser Asp Ala Phe His Lys Ala Phe Leu Glu Val Asn Glu
395                 400                 405                 410

GAA GGC AGT GAA GCA GCT GCA AGT ACC GCT GTT GTG ATT GCT GGC CGT         1299
Glu Gly Ser Glu Ala Ala Ala Ser Thr Ala Val Val Ile Ala Gly Arg
                415                 420                 425

TCG CTA AAC CCC AAC AGG GTG ACT TTC AAG GCC AAC ATG CCT TTC CTG         1347
Ser Leu Asn Pro Asn Arg Val Thr Phe Lys Ala Asn Met Pro Phe Leu
        430                 435                 440

GTT TTT ATA AGA GAA GTT CCT CTG AAC ACT ATT ATC TTC ATG GGC AGG         1395
Val Phe Ile Arg Glu Val Pro Leu Asn Thr Ile Ile Phe Met Gly Arg
        445                 450                 455

GTA GCC AAC CCT TGT GTT AAG TAAAATGTTC TCTAGAGGAT CCCCCATCGA            1446
Val Ala Asn Pro Cys Val Lys
        460                 465

TGGGGTACCG AGCTCGAATT C                                                 1467

(2) INFORMATION FOR SEQ ID NO:4:

(i) SEQUENCE CHARACTERISTICS:
        (A) LENGTH: 465 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

Met Tyr Ser Asn Val Ile Gly Thr Val Thr Ser Gly Lys Arg Lys Val
1               5                   10                  15

Tyr Leu Leu Ser Leu Leu Ile Gly Phe Trp Asp Cys Val Thr Cys
                20                  25                  30

His Gly Ser Pro Val Asp Ile Cys Thr Ala Lys Pro Arg Asp Ile Pro
            35                  40                  45

Met Asn Pro Met Cys Ile Tyr Arg Ser Pro Glu Lys Lys Ala Thr Glu
50                  55                  60

Asp Glu Gly Ser Glu Gln Lys Ile Pro Glu Ala Thr Asn Asn Arg Arg
65                  70                  75                  80

Val Trp Glu Leu Ser Lys Ala Asn Ser Arg Phe Ala Thr Thr Phe Tyr
                85                  90                  95
```

```
Gln His Leu Ala Asp Ser Lys Asn Asp Asn Asp Asn Ile Phe Leu Ser
            100                 105                 110

Pro Leu Ser Ile Ser Thr Ala Phe Ala Met Thr Lys Leu Gly Ala Cys
            115                 120                 125

Asn Asp Thr Leu Gln Gln Leu Met Glu Val Phe Lys Phe Asp Thr Ile
        130                 135                 140

Ser Glu Lys Thr Ser Asp Gln Ile His Phe Phe Phe Ala Lys Leu Asn
145                 150                 155                 160

Cys Arg Leu Tyr Arg Lys Ala Asn Lys Ser Ser Lys Leu Val Ser Ala
                165                 170                 175

Asn Arg Leu Phe Gly Asp Lys Ser Leu Thr Phe Asn Glu Thr Tyr Gln
            180                 185                 190

Asp Ile Ser Glu Leu Val Tyr Gly Ala Lys Leu Gln Pro Leu Asp Phe
            195                 200                 205

Lys Glu Asn Ala Glu Gln Ser Arg Ala Ala Ile Asn Lys Trp Val Ser
        210                 215                 220

Asn Lys Thr Glu Gly Arg Ile Thr Asp Val Ile Pro Ser Glu Ala Ile
225                 230                 235                 240

Asn Glu Leu Thr Val Leu Val Leu Val Asn Thr Ile Tyr Phe Lys Gly
                245                 250                 255

Leu Trp Lys Ser Lys Phe Ser Pro Glu Asn Thr Arg Lys Glu Leu Phe
            260                 265                 270

Tyr Lys Ala Asp Gly Glu Ser Cys Ser Ala Ser Met Met Tyr Gln Glu
            275                 280                 285

Gly Lys Phe Arg Tyr Arg Arg Val Ala Glu Gly Thr Gln Val Leu Glu
        290                 295                 300

Leu Pro Phe Lys Gly Asp Asp Ile Thr Met Val Leu Ile Leu Pro Lys
305                 310                 315                 320

Pro Glu Lys Ser Leu Ala Lys Val Glu Lys Glu Leu Thr Pro Glu Val
                325                 330                 335

Leu Gln Glu Trp Leu Asp Glu Leu Glu Glu Met Met Leu Val Val His
            340                 345                 350

Met Pro Arg Phe Arg Ile Glu Asp Gly Phe Ser Leu Lys Glu Gln Leu
            355                 360                 365

Gln Asp Met Gly Leu Val Asp Leu Phe Ser Pro Glu Lys Ser Lys Leu
        370                 375                 380

Pro Gly Ile Val Ala Glu Gly Arg Asp Asp Leu Tyr Val Ser Asp Ala
385                 390                 395                 400

Phe His Lys Ala Phe Leu Glu Val Asn Glu Glu Gly Ser Glu Ala Ala
                405                 410                 415

Ala Ser Thr Ala Val Val Ile Ala Gly Arg Ser Leu Asn Pro Asn Arg
            420                 425                 430

Val Thr Phe Lys Ala Asn Met Pro Phe Leu Val Phe Ile Arg Glu Val
            435                 440                 445

Pro Leu Asn Thr Ile Ile Phe Met Gly Arg Val Ala Asn Pro Cys Val
        450                 455                 460

Lys
465

(2) INFORMATION FOR SEQ ID NO:5:

(i) SEQUENCE CHARACTERISTICS:
        (A) LENGTH: 2932 base pairs
        (B) TYPE: nucleic acid
```

```
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 992...2020
        (D) OTHER INFORMATION:

(xi) SEQUENCE DESCRIPTION: SEQ ID NO:5:

GTAATGCAGA GATAATAAAA CTTCTTAGGT CCATAGGTCT TATAATAATT TAATAACCTA      60

AACATGGTAT ACAAATTCCT CCAAACCCAA TAACATAATT ATAGTTTCAA AAAGTTCCCC     120

AAACTTTCAA GTTAGATTTT ATTGCTTTGA TGAGTGGCTT TAAATATGAA AAGTCTTGCC     180

TGTGAAGGGC AATCCTTTTC CCGTGGACTG GGATCTATAG AAATACAGAA ATGTGCCCAG     240

GGGTTCATCT CCCTAATAAC CATCATTCAC ATTTCTCAAC CTCCCTAATA ACCAGCCACC     300

ATGTGAGAAG GATCCACAGT TACTGTTTAT GACTATAATT AACTAGTACC TGGGACTGGT     360

CAGTGGAGTT GGTTGCAACC TGATGCTAAG GATGTCAAAG TTGTCTCGGC CTCTGTTCCC     420

AGCCAGTAAG TAATTCCCTG GCCTCGGGCC ATACCCCCTA ATCTTGGTCA GCTGATTATG     480

ACAGGCAGAC AGCACAGTAA ATAACACTAT ATATTAAGAA AACCCAAAGC ATATGTATCA     540

ATGGTATATA CCCAACAGCA TCCTAGGAAT GGAGAGTCTG TAGCAAGGGC CTCCAATGTG     600

AAGGTCAACA CAGTCACTGT GATGCGTGTA TTTCCATTTT GTAAAGCATG ATCTCTGGTG     660

GTCATTTTTA TCTTCCTAAC TTATTGGAAA AGTCTCCTGT TTTGGGGGCC CGCCCCTGGT     720

CACAGCCAGA CTGACTCAGT TTCCCTGGGA GGTCCCGCTC GAGCCCGTCC TTCCCCTCCC     780

TCTGCCCGCC CCCAGCCCTC GCCCCACCCT CGGCGCCCGC ACATCTGCCT GCTCAGCTCC     840

AGACGGCGCC CGGACCCCCG GGCGCGGGAT CCAGCCAGGT GGGAGCCCCG CAGATGAGGT     900

CTCTGAAGGT GTGCCTGAAC CAGTGCCAGC CTGCCCTGTC TGCAGCATCG GCCTGATGGG     960

GTGGTGACTG ATCCCTCAGG GCTCCGGAGC C ATG TGG CCC AAC GGC AGT TCC        1012
                                  Met Trp Pro Asn Gly Ser Ser
                                    1               5

CTG GGG CCC TGT TTC CGG CCC ACA AAC ATT ACC CTG GAG GAG AGA CGG      1060
Leu Gly Pro Cys Phe Arg Pro Thr Asn Ile Thr Leu Glu Glu Arg Arg
         10              15                  20

CTG ATC GCC TCG CCC TGG TTC GCC GCC TCC TTC TGC GTG GTG GGC CTG      1108
Leu Ile Ala Ser Pro Trp Phe Ala Ala Ser Phe Cys Val Val Gly Leu
 25              30                  35

GCC TCC AAC CTG CTG GCC CTG AGC GTG CTG GCG GGC GCG CGG CAG GGG      1156
Ala Ser Asn Leu Leu Ala Leu Ser Val Leu Ala Gly Ala Arg Gln Gly
40                  45                  50                  55

GGT TCG CAC ACG CGC TCC TCC TTC CTC ACC TTC CTC TGC GGC CTC GTC      1204
Gly Ser His Thr Arg Ser Ser Phe Leu Thr Phe Leu Cys Gly Leu Val
             60                  65                  70

CTC ACC GAC TTC CTG GGG CTG CTG GTG ACC GGT ACC ATC GTG GTG TCC      1252
Leu Thr Asp Phe Leu Gly Leu Leu Val Thr Gly Thr Ile Val Val Ser
         75                  80                  85

CAG CAC GCC GCG CTC TTC GAG TGG CAC GCC GTG GAC CCT GGC TGC CGT      1300
Gln His Ala Ala Leu Phe Glu Trp His Ala Val Asp Pro Gly Cys Arg
 90                  95                 100

CTC TGT CGC TTC ATG GGC GTC GTC ATG ATC TTC TTC GGC CTG TCC CCG      1348
Leu Cys Arg Phe Met Gly Val Val Met Ile Phe Phe Gly Leu Ser Pro
    105                 110                 115

CTG CTG CTG GGG GCC GCC ATG GCC TCA GAG CGC TAC CTG GGT ATC ACC      1396
Leu Leu Leu Gly Ala Ala Met Ala Ser Glu Arg Tyr Leu Gly Ile Thr
120                 125                 130                 135
```

```
CGG CCC TTC TCG CGC CCG GCG GTC GCC TCG CAG CGC CGC GCC TGG GCC      1444
Arg Pro Phe Ser Arg Pro Ala Val Ala Ser Gln Arg Arg Ala Trp Ala
                140                 145                 150

ACC GTG GGG CTG GTG TGG GCG GCC GCG CTG GCG CTG GGC CTG CTG CCC      1492
Thr Val Gly Leu Val Trp Ala Ala Ala Leu Ala Leu Gly Leu Leu Pro
            155                 160                 165

CTG CTG GGC GTG GGT CGC TAC ACC GTG CAA TAC CCG GGG TCC TGG TGC      1540
Leu Leu Gly Val Gly Arg Tyr Thr Val Gln Tyr Pro Gly Ser Trp Cys
        170                 175                 180

TTC CTG ACG CTG GGC GCC GAG TCC GGG GAC GTG GCC TTC GGG CTG CTC      1588
Phe Leu Thr Leu Gly Ala Glu Ser Gly Asp Val Ala Phe Gly Leu Leu
    185                 190                 195

TTC TCC ATG CTG GGC GGC CTC TCG GTC GGG CTG TCC TTC CTG CTG AAC      1636
Phe Ser Met Leu Gly Gly Leu Ser Val Gly Leu Ser Phe Leu Leu Asn
200                 205                 210                 215

ACG GTC AGC GTG GCC ACC CTG TGC CAC GTC TAC CAC GGG CAG GAG GCG      1684
Thr Val Ser Val Ala Thr Leu Cys His Val Tyr His Gly Gln Glu Ala
                220                 225                 230

GCC CAG CAG CGT CCC CGG GAC TCC GAG GTG GAG ATG ATG GCT CAG CTC      1732
Ala Gln Gln Arg Pro Arg Asp Ser Glu Val Glu Met Met Ala Gln Leu
            235                 240                 245

CTG GGG ATC ATG GTG GTG GCC AGC GTG TGT TGG CTG CCC CTT CTG GTC      1780
Leu Gly Ile Met Val Val Ala Ser Val Cys Trp Leu Pro Leu Leu Val
        250                 255                 260

TTC ATT GCC CAG ACA GTG CTG CGA AAC CCG CCT GCC ATG AGC CCC GCC      1828
Phe Ile Ala Gln Thr Val Leu Arg Asn Pro Pro Ala Met Ser Pro Ala
    265                 270                 275

GGG CAG CTG TCC CGC ACC ACG GAG AAG GAG CTG CTC ATC TAC TTG CGC      1876
Gly Gln Leu Ser Arg Thr Thr Glu Lys Glu Leu Leu Ile Tyr Leu Arg
280                 285                 290                 295

GTG GCC ACC TGG AAC CAG ATC CTG GAC CCC TGG GTG TAT ATC CTG TTC      1924
Val Ala Thr Trp Asn Gln Ile Leu Asp Pro Trp Val Tyr Ile Leu Phe
                300                 305                 310

CGC CGC GCC GTG CTC CGG CGT CTC CAG CCT CGC CTC AGC ACC CGG CCC      1972
Arg Arg Ala Val Leu Arg Arg Leu Gln Pro Arg Leu Ser Thr Arg Pro
            315                 320                 325

AGG TCG CTG TCC CTC CAG CCC CAG CTC ACG CAG CGC TCC GGG CTG CAG      2020
Arg Ser Leu Ser Leu Gln Pro Gln Leu Thr Gln Arg Ser Gly Leu Gln
        330                 335                 340

TAGGAAGTGG ACAGAGCGCC CCTCCCGCGC CTTTCCGCGG AGCCCTTGGC CCCTCGGACA    2080
GCCCATCTGC CTGTTCTGAG GATTCAGGGG CTGGGGGTGC TGGATGGACA GTGGGCATCA    2140
GCAGCAGGGT TTTGGGTTGA CCCCAATCCA ACCCGGGGAC CCCCAACTCC TCCCTGATCC    2200
TTTTACCAAG CACTCTCCCT TCCTCGGCCC CTTTTTCCCA TCCAGAGCTC CCACCCCTTC    2260
TCTGCGTCCC TCCCAACCCC AGGAAGGGCA TGCAGACATT GGAAGAGGGT CTTGCATTGC    2320
TATTTTTTTT TTTAGACGGA GTCTTGCTCT GTCCCCCAGG CTGGAGTGCA GTGGCGCAAT    2380
CTCAGCTCAC TGCAACCTCC ACCTCCCGGG TTCAAGCGAT TCTCCTGCCT CAGCCTCCTG    2440
AGTAGCTGGG ACTATAGGCG CGCGCCACCA CGCCCGGCTA ATTTTTGTAT TTTTAGTAGA    2500
GACGGGGTTT CACCGTGTTG GCCAGGCTGG TCTTGAACTC CTGACCTCAG GTGATTCACC    2560
AGCCTCAGCC TCCCAAAGTG CTGGGATCAC AGGCATGAAC CACCACACCT GGCCATTTTT    2620
TTTTTTTTTT TAGACGGAGT CTCACTCTGT GGCCCAGCCT GGAGTACAGT GGCACGATCT    2680
CGGCTCACTG CAACCTCCGC CTCCCGGGTT CAAGCGATTC TCGTGCCTCA GCCTCCCGAG    2740
CAGCTGGGAT TACAGGCGTA AGCCACTGCG CCCGGCCTTG CATGCTCTTT GACCCTGAAT    2800
```

```
TTGACCTACT TGCTGGGGTA CAGTTGCTTC CTTTTGAACC TCCAACAGGG AAGGCTCTGT      2860

CCAGAAAGGA TTGAATGTGA ACGGGGGCA CCCCCTTTTC TTGCCAAAAT ATATCTCTGC       2920

CTTTGGTTTT AT                                                          2932
```

(2) INFORMATION FOR SEQ ID NO:6:

(i) SEQUENCE CHARACTERISTICS:
        (A) LENGTH: 343 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:6:

```
Met Trp Pro Asn Gly Ser Ser Leu Gly Pro Cys Phe Arg Pro Thr Asn
 1               5                  10                  15

Ile Thr Leu Glu Glu Arg Arg Leu Ile Ala Ser Pro Trp Phe Ala Ala
            20                  25                  30

Ser Phe Cys Val Val Gly Leu Ala Ser Asn Leu Leu Ala Leu Ser Val
        35                  40                  45

Leu Ala Gly Ala Arg Gln Gly Gly Ser His Thr Arg Ser Ser Phe Leu
    50                  55                  60

Thr Phe Leu Cys Gly Leu Val Leu Thr Asp Phe Leu Gly Leu Leu Val
65                  70                  75                  80

Thr Gly Thr Ile Val Ser Gln His Ala Ala Leu Phe Glu Trp His
                85                  90                  95

Ala Val Asp Pro Gly Cys Arg Leu Cys Arg Phe Met Gly Val Val Met
            100                 105                 110

Ile Phe Phe Gly Leu Ser Pro Leu Leu Leu Gly Ala Ala Met Ala Ser
        115                 120                 125

Glu Arg Tyr Leu Gly Ile Thr Arg Pro Phe Ser Arg Pro Ala Val Ala
    130                 135                 140

Ser Gln Arg Arg Ala Trp Ala Thr Val Gly Leu Val Trp Ala Ala Ala
145                 150                 155                 160

Leu Ala Leu Gly Leu Leu Pro Leu Leu Gly Val Gly Arg Tyr Thr Val
                165                 170                 175

Gln Tyr Pro Gly Ser Trp Cys Phe Leu Thr Leu Gly Ala Glu Ser Gly
            180                 185                 190

Asp Val Ala Phe Gly Leu Leu Phe Ser Met Leu Gly Gly Leu Ser Val
        195                 200                 205

Gly Leu Ser Phe Leu Leu Asn Thr Val Ser Val Ala Thr Leu Cys His
    210                 215                 220

Val Tyr His Gly Gln Glu Ala Ala Gln Gln Arg Pro Arg Asp Ser Glu
225                 230                 235                 240

Val Glu Met Met Ala Gln Leu Leu Gly Ile Met Val Val Ala Ser Val
                245                 250                 255

Cys Trp Leu Pro Leu Leu Val Phe Ile Ala Gln Thr Val Leu Arg Asn
            260                 265                 270

Pro Pro Ala Met Ser Pro Ala Gly Gln Leu Ser Arg Thr Thr Glu Lys
        275                 280                 285

Glu Leu Leu Ile Tyr Leu Arg Val Ala Thr Trp Asn Gln Ile Leu Asp
    290                 295                 300

Pro Trp Val Tyr Ile Leu Phe Arg Arg Ala Val Leu Arg Arg Leu Gln
```

|     |     |     |     |
| --- | --- | --- | --- |
| 305 | 310 | 315 | 320 |

Pro Arg Leu Ser Thr Arg Pro Arg Ser Leu Ser Leu Gln Pro Gln Leu
              325                 330                 335

Thr Gln Arg Ser Gly Leu Gln
        340

(2) INFORMATION FOR SEQ ID NO:7:

(i) SEQUENCE CHARACTERISTICS:
      (A) LENGTH: 3170 base pairs
      (B) TYPE: nucleic acid
      (C) STRANDEDNESS: single
      (D) TOPOLOGY: linear (ii) MOLECULE TYPE: Genomic DNA (ix) FEATURE:
      (A) NAME/KEY: Coding Sequence
      (B) LOCATION: 21...2384
      (D) OTHER INFORMATION:

(xi) SEQUENCE DESCRIPTION: SEQ ID NO:7:

```
CGCCGCGGGA GGCGGACGAG  ATG CGA GCG CGG CCG CGG CCC CGG CCG CTC           50
                      Met Arg Ala Arg Pro Arg Pro Arg Pro Leu
                       1               5                  10

TGG GTG ACT GTG CTG GCG CTG GGG GCG CTG GCG GGC GTT GGC GTA GGA          98
Trp Val Thr Val Leu Ala Leu Gly Ala Leu Ala Gly Val Gly Val Gly
             15                  20                  25

GGG CCC AAC ATC TGT ACC ACG CGA GGT GTG AGC TCC TGC CAG CAG TGC         146
Gly Pro Asn Ile Cys Thr Thr Arg Gly Val Ser Ser Cys Gln Gln Cys
             30                  35                  40

CTG GCT GTG AGC CCC ATG TGT GCC TGG TGC TCT GAT GAG GCC CTG CCT         194
Leu Ala Val Ser Pro Met Cys Ala Trp Cys Ser Asp Glu Ala Leu Pro
         45                  50                  55

CTG GGC TCA CCT CGC TGT GAC CTG AAG GAG AAT CTG CTG AAG GAT AAC         242
Leu Gly Ser Pro Arg Cys Asp Leu Lys Glu Asn Leu Leu Lys Asp Asn
         60                  65                  70

TGT GCC CCA GAA TCC ATC GAG TTC CCA GTG AGT GAG GCC CGA GTA CTA         290
Cys Ala Pro Glu Ser Ile Glu Phe Pro Val Ser Glu Ala Arg Val Leu
 75              80                  85                  90

GAG GAC AGG CCC CTC AGC GAC AAG GGC TCT GGA GAC AGC TCC CAG GTC         338
Glu Asp Arg Pro Leu Ser Asp Lys Gly Ser Gly Asp Ser Ser Gln Val
                 95                 100                 105

ACT CAA GTC AGT CCC CAG AGG ATT GCA CTC CGG CTC CGG CCA GAT GAT         386
Thr Gln Val Ser Pro Gln Arg Ile Ala Leu Arg Leu Arg Pro Asp Asp
             110                 115                 120

TCG AAG AAT TTC TCC ATC CAA GTG CGG CAG GTG GAG GAT TAC CCT GTG         434
Ser Lys Asn Phe Ser Ile Gln Val Arg Gln Val Glu Asp Tyr Pro Val
             125                 130                 135

GAC ATC TAC TAC TTG ATG GAC CTG TCT TAC TCC ATG AAG GAT GAT CTG         482
Asp Ile Tyr Tyr Leu Met Asp Leu Ser Tyr Ser Met Lys Asp Asp Leu
         140                 145                 150

TGG AGC ATC CAG AAC CTG GGT ACC AAG CTG GCC ACC CAG ATG CGA AAG         530
Trp Ser Ile Gln Asn Leu Gly Thr Lys Leu Ala Thr Gln Met Arg Lys
155                 160                 165                 170

CTC ACC AGT AAC CTG CGG ATT GGC TTC GGG GCA TTT GTG GAC AAG CCT         578
Leu Thr Ser Asn Leu Arg Ile Gly Phe Gly Ala Phe Val Asp Lys Pro
                 175                 180                 185

GTG TCA CCA TAC ATG TAT ATC TCC CCA CCA GAG GCC CTC GAA AAC CCC         626
Val Ser Pro Tyr Met Tyr Ile Ser Pro Pro Glu Ala Leu Glu Asn Pro
             190                 195                 200

TGC TAT GAT ATG AAG ACC ACC TGC TTG CCC ATG TTT GGC TAC AAA CAC         674
```

```
                                    -continued

Cys Tyr Asp Met Lys Thr Thr Cys Leu Pro Met Phe Gly Tyr Lys His
        205                 210                 215

GTG CTG ACG CTA ACT GAC CAG GTG ACC CGC TTC AAT GAG GAA GTG AAG        722
Val Leu Thr Leu Thr Asp Gln Val Thr Arg Phe Asn Glu Glu Val Lys
        220                 225                 230

AAG CAG AGT GTG TCA CGG AAC CGA GAT GCC CCA GAG GGT GGC TTT GAT        770
Lys Gln Ser Val Ser Arg Asn Arg Asp Ala Pro Glu Gly Gly Phe Asp
235                 240                 245                 250

GCC ATC ATG CAG GCT ACA GTC TGT GAT GAA AAG ATT GGC TGG AGG AAT        818
Ala Ile Met Gln Ala Thr Val Cys Asp Glu Lys Ile Gly Trp Arg Asn
                    255                 260                 265

GAT GCA TCC CAC TTG CTG GTG TTT ACC ACT GAT GCC AAG ACT CAT ATA        866
Asp Ala Ser His Leu Leu Val Phe Thr Thr Asp Ala Lys Thr His Ile
                270                 275                 280

GCA TTG GAC GGA AGG CTG GCA GGC ATT GTC CAG CCT AAT GAC GGG CAG        914
Ala Leu Asp Gly Arg Leu Ala Gly Ile Val Gln Pro Asn Asp Gly Gln
            285                 290                 295

TGT CAT GTT GGT AGT GAC AAT CAT TAC TCT GCC TCC ACT ACC ATG GAT        962
Cys His Val Gly Ser Asp Asn His Tyr Ser Ala Ser Thr Thr Met Asp
        300                 305                 310

TAT CCC TCT TTG GGG CTG ATG ACT GAG AAG CTA TCC CAG AAA AAC ATC       1010
Tyr Pro Ser Leu Gly Leu Met Thr Glu Lys Leu Ser Gln Lys Asn Ile
315                 320                 325                 330

AAT TTG ATC TTT GCA GTG ACT GAA AAT GTA GTC AAT CTC TAT CAG AAC       1058
Asn Leu Ile Phe Ala Val Thr Glu Asn Val Val Asn Leu Tyr Gln Asn
                    335                 340                 345

TAT AGT GAG CTC ATC CCA GGG ACC ACA GTT GGG GTT CTG TCC ATG GAT       1106
Tyr Ser Glu Leu Ile Pro Gly Thr Thr Val Gly Val Leu Ser Met Asp
                350                 355                 360

TCC AGC AAT GTC CTC CAG CTC ATT GTT GAT GCT TAT GGG AAA ATC CGT       1154
Ser Ser Asn Val Leu Gln Leu Ile Val Asp Ala Tyr Gly Lys Ile Arg
            365                 370                 375

TCT AAA GTC GAG CTG GAA GTG CGT GAC CTC CCT GAA GAG TTG TCT CTA       1202
Ser Lys Val Glu Leu Glu Val Arg Asp Leu Pro Glu Glu Leu Ser Leu
        380                 385                 390

TCC TTC AAT GCC ACC TGC CTC AAC AAT GAG GTC ATC CCT GGC CTC AAG       1250
Ser Phe Asn Ala Thr Cys Leu Asn Asn Glu Val Ile Pro Gly Leu Lys
395                 400                 405                 410

TCT TGT ATG GGA CTC AAG ATT GGA GAC ACG GTG AGC TTC AGC ATT GAG       1298
Ser Cys Met Gly Leu Lys Ile Gly Asp Thr Val Ser Phe Ser Ile Glu
                    415                 420                 425

GCC AAG GTG CGA GGC TGT CCC CAG GAG AAG GAG AAG TCC TTT ACC ATA       1346
Ala Lys Val Arg Gly Cys Pro Gln Glu Lys Glu Lys Ser Phe Thr Ile
                430                 435                 440

AAG CCC GTG GGC TTC AAG GAC AGC CTG ATC GTC CAG GTC ACC TTT GAT       1394
Lys Pro Val Gly Phe Lys Asp Ser Leu Ile Val Gln Val Thr Phe Asp
            445                 450                 455

TGT GAC TGT GCC TGC CAG GCC CAA GCT GAA CCT AAT AGC CAT CGC TGC       1442
Cys Asp Cys Ala Cys Gln Ala Gln Ala Glu Pro Asn Ser His Arg Cys
460                 465                 470

AAC AAT GGC AAT GGG ACC TTT GAG TGT GGG GTA TGC CGT TGT GGG CCT       1490
Asn Asn Gly Asn Gly Thr Phe Glu Cys Gly Val Cys Arg Cys Gly Pro
475                 480                 485                 490

GGC TGG CTG GGA TCC CAG TGT GAG TGC TCA GAG GAG GAC TAT CGC CCT       1538
Gly Trp Leu Gly Ser Gln Cys Glu Cys Ser Glu Glu Asp Tyr Arg Pro
                    495                 500                 505

TCC CAG CAG GAC GAG TGC AGC CCC CGA GAG GGT CAG CCC GTC TGC AGC       1586
Ser Gln Gln Asp Glu Cys Ser Pro Arg Glu Gly Gln Pro Val Cys Ser
                510                 515                 520
```

```
CAG CGG GGC GAG TGC CTC TGT GGT CAA TGT GTC TGC CAC AGC AGT GAC      1634
Gln Arg Gly Glu Cys Leu Cys Gly Gln Cys Val Cys His Ser Ser Asp
        525                 530                 535

TTT GGC AAG ATC ACG GGC AAG TAC TGC GAG TGT GAC GAC TTC TCC TGT      1682
Phe Gly Lys Ile Thr Gly Lys Tyr Cys Glu Cys Asp Asp Phe Ser Cys
    540                 545                 550

GTC CGC TAC AAG GGG GAG ATG TGC TCA GGC CAT GGC CAG TGC AGC TGT      1730
Val Arg Tyr Lys Gly Glu Met Cys Ser Gly His Gly Gln Cys Ser Cys
555                 560                 565                 570

GGG GAC TGC CTG TGT GAC TCC GAC TGG ACC GGC TAC TAC TGC AAC TGT      1778
Gly Asp Cys Leu Cys Asp Ser Asp Trp Thr Gly Tyr Tyr Cys Asn Cys
            575                 580                 585

ACC ACG CGT ACT GAC ACC TGC ATG TCC AGC AAT GGG CTG CTG TGC AGC      1826
Thr Thr Arg Thr Asp Thr Cys Met Ser Ser Asn Gly Leu Leu Cys Ser
        590                 595                 600

GGC CGC GGC AAG TGT GAA TGT GGC AGC TGT GTC TGT ATC CAG CCG GGC      1874
Gly Arg Gly Lys Cys Glu Cys Gly Ser Cys Val Cys Ile Gln Pro Gly
    605                 610                 615

TCC TAT GGG GAC ACC TGT GAG AAG TGC CCC ACC TGC CCA GAT GCC TGC      1922
Ser Tyr Gly Asp Thr Cys Glu Lys Cys Pro Thr Cys Pro Asp Ala Cys
620                 625                 630

ACC TTT AAG AAA GAA TGT GTG GAG TGT AAG AAG TTT GAC CGG GAG CCC      1970
Thr Phe Lys Lys Glu Cys Val Glu Cys Lys Lys Phe Asp Arg Glu Pro
635                 640                 645                 650

TAC ATG ACC GAA AAT ACC TGC AAC CGT TAC TGC CGT GAC GAG ATT GAG      2018
Tyr Met Thr Glu Asn Thr Cys Asn Arg Tyr Cys Arg Asp Glu Ile Glu
            655                 660                 665

TCA GTG AAA GAG CTT AAG GAC ACT GGC AAG GAT GCA GTG AAT TGT ACC      2066
Ser Val Lys Glu Leu Lys Asp Thr Gly Lys Asp Ala Val Asn Cys Thr
        670                 675                 680

TAT AAG AAT GAG GAT GAC TGT GTC GTC AGA TTC CAG TAC TAT GAA GAT      2114
Tyr Lys Asn Glu Asp Asp Cys Val Val Arg Phe Gln Tyr Tyr Glu Asp
    685                 690                 695

TCT AGT GGA AAG TCC ATC CTG TAT GTG GTA GAA GAG CCA GAG TGT CCC      2162
Ser Ser Gly Lys Ser Ile Leu Tyr Val Val Glu Glu Pro Glu Cys Pro
700                 705                 710

AAG GGC CCT GAC ATC CTG GTG GTC CTG CTC TCA GTG ATG GGG GCC ATT      2210
Lys Gly Pro Asp Ile Leu Val Val Leu Leu Ser Val Met Gly Ala Ile
715                 720                 725                 730

CTG CTC ATT GGC CTT GCC GCC CTG CTC ATC TGG AAA CTC CTC ATC ACC      2258
Leu Leu Ile Gly Leu Ala Ala Leu Leu Ile Trp Lys Leu Leu Ile Thr
            735                 740                 745

ATC CAC GAC CGA AAA GAA TTC GCT AAA TTT GAG GAA GAA CGC GCC AGA      2306
Ile His Asp Arg Lys Glu Phe Ala Lys Phe Glu Glu Glu Arg Ala Arg
        750                 755                 760

GCA AAA TGG GAC ACA GCC AAC AAC CCA CTG TAT AAA GAG GCC ACG TCT      2354
Ala Lys Trp Asp Thr Ala Asn Asn Pro Leu Tyr Lys Glu Ala Thr Ser
    765                 770                 775

ACC TTC ACC AAT ATC ACG TAC CGG GGC ACT TAATGATAAG CAGTCATCCT        2404
Thr Phe Thr Asn Ile Thr Tyr Arg Gly Thr
    780                 785

CAGATCATTA TCAGCCTGTG CCAGGATTGC AGGAGTCCCT GCCATCATGT TTACAGAGGA   2464

CAGTATTTGT GGGGAGGGAT TTCGGGGCTC AGAGTGGGGT AGGTTGGGAG AATGTCAGTA   2524

TGTGGAAGTG TGGGTCTGTG TGTGTGTATG TGGGGGTCTG TGTGTTTATG TGTGTGTGTT   2584

GTGTGTGGGA GTGTGTAATT TAAAATTGTG ATGTGTCCTG ATAAGCTGAG CTCCTTAGCC   2644

TTTGTCCCAG AATGCCTCCT GCAGGGATTC TTCCTGCTTA GCTTGAGGGT GACTATGGAG   2704

CTGAGCAGGT GTTCTTCATT ACCTCAGTGA GAAGCCAGCT TTCCTCATCA GGCCATTGTC   2764
```

```
CCTGAAGAGA AGGGCAGGGC TGAGGCCTCT CATTCCAGAG GAAGGGACAC CAAGCCTTGG    2824

CTCTACCCTG AGTTCATAAA TTTATGGTTC TCAGGCCTGA CTCTCAGCAG CTATGGTAGG    2884

AACTGCTGGC TTGGCAGCCC GGGTCATCTG TACCTCTGCC TCCTTTCCCC TCCCTCAGGC    2944

CGAAGGAGGA GTCAGGGAGA GCTGAACTAT TAGAGCTGCC TGTGCCTTTT GCCATCCCCT    3004

CAACCCAGCT ATGGTTCTCT CGCAAGGGAA GTCCTTGCAA GCTAATTCTT TGACCTGTTG    3064

GGAGTGAGGA TGTCTGGGCC ACTCAGGGGT CATTCATGGC CTGGGGGATG TACCAGCATC    3124

TCCCAGTTCA TAATCACAAC CCTTCAGATT TGCCTTATTG GCAGCG                  3170
```

(2) INFORMATION FOR SEQ ID NO:8:

(i) SEQUENCE CHARACTERISTICS:
        (A) LENGTH: 788 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:8:

```
Met Arg Ala Arg Pro Arg Pro Arg Pro Leu Trp Val Thr Val Leu Ala
 1               5                  10                  15

Leu Gly Ala Leu Ala Gly Val Gly Val Gly Pro Asn Ile Cys Thr
                20                  25                  30

Thr Arg Gly Val Ser Ser Cys Gln Gln Cys Leu Ala Val Ser Pro Met
            35                  40                  45

Cys Ala Trp Cys Ser Asp Glu Ala Leu Pro Leu Gly Ser Pro Arg Cys
    50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
    130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
                165                 170                 175

Ile Gly Phe Gly Ala Phe Val Asp Lys Pro Val Ser Pro Tyr Met Tyr
            180                 185                 190

Ile Ser Pro Pro Glu Ala Leu Glu Asn Pro Cys Tyr Asp Met Lys Thr
        195                 200                 205

Thr Cys Leu Pro Met Phe Gly Tyr Lys His Val Leu Thr Leu Thr Asp
    210                 215                 220

Gln Val Thr Arg Phe Asn Glu Glu Val Lys Gln Ser Val Ser Arg
225                 230                 235                 240

Asn Arg Asp Ala Pro Glu Gly Gly Phe Asp Ala Ile Met Gln Ala Thr
                245                 250                 255

Val Cys Asp Glu Lys Ile Gly Trp Arg Asn Asp Ala Ser His Leu Leu
```

```
                260               265               270
Val Phe Thr Thr Asp Ala Lys Thr His Ile Ala Leu Asp Gly Arg Leu
                275               280               285
Ala Gly Ile Val Gln Pro Asn Asp Gly Gln Cys His Val Gly Ser Asp
        290               295               300
Asn His Tyr Ser Ala Ser Thr Thr Met Asp Tyr Pro Ser Leu Gly Leu
305               310               315               320
Met Thr Glu Lys Leu Ser Gln Lys Asn Ile Asn Leu Ile Phe Ala Val
                325               330               335
Thr Glu Asn Val Val Asn Leu Tyr Gln Asn Tyr Ser Glu Leu Ile Pro
            340               345               350
Gly Thr Thr Val Gly Val Leu Ser Met Asp Ser Ser Asn Val Leu Gln
            355               360               365
Leu Ile Val Asp Ala Tyr Gly Lys Ile Arg Ser Lys Val Glu Leu Glu
        370               375               380
Val Arg Asp Leu Pro Glu Glu Leu Ser Leu Ser Phe Asn Ala Thr Cys
385               390               395               400
Leu Asn Asn Glu Val Ile Pro Gly Leu Lys Ser Cys Met Gly Leu Lys
                405               410               415
Ile Gly Asp Thr Val Ser Phe Ser Ile Glu Ala Lys Val Arg Gly Cys
            420               425               430
Pro Gln Glu Lys Glu Lys Ser Phe Thr Ile Lys Pro Val Gly Phe Lys
                435               440               445
Asp Ser Leu Ile Val Gln Val Thr Phe Asp Cys Asp Cys Ala Cys Gln
        450               455               460
Ala Gln Ala Glu Pro Asn Ser His Arg Cys Asn Asn Gly Asn Gly Thr
465               470               475               480
Phe Glu Cys Gly Val Cys Arg Cys Gly Pro Gly Trp Leu Gly Ser Gln
            485               490               495
Cys Glu Cys Ser Glu Glu Asp Tyr Arg Pro Ser Gln Gln Asp Glu Cys
            500               505               510
Ser Pro Arg Glu Gly Gln Pro Val Cys Ser Gln Arg Gly Glu Cys Leu
        515               520               525
Cys Gly Gln Cys Val Cys His Ser Ser Asp Phe Gly Lys Ile Thr Gly
        530               535               540
Lys Tyr Cys Glu Cys Asp Asp Phe Ser Cys Val Arg Tyr Lys Gly Glu
545               550               555               560
Met Cys Ser Gly His Gly Gln Cys Ser Cys Gly Asp Cys Leu Cys Asp
                565               570               575
Ser Asp Trp Thr Gly Tyr Tyr Cys Asn Cys Thr Thr Arg Thr Asp Thr
            580               585               590
Cys Met Ser Ser Asn Gly Leu Leu Cys Ser Gly Arg Gly Lys Cys Glu
            595               600               605
Cys Gly Ser Cys Val Cys Ile Gln Pro Gly Ser Tyr Gly Asp Thr Cys
        610               615               620
Glu Lys Cys Pro Thr Cys Pro Asp Ala Cys Thr Phe Lys Lys Glu Cys
625               630               635               640
Val Glu Cys Lys Lys Phe Asp Arg Glu Pro Tyr Met Thr Glu Asn Thr
                645               650               655
Cys Asn Arg Tyr Cys Arg Asp Glu Ile Glu Ser Val Lys Glu Leu Lys
            660               665               670
Asp Thr Gly Lys Asp Ala Val Asn Cys Thr Tyr Lys Asn Glu Asp Asp
        675               680               685
```

```
Cys Val Val Arg Phe Gln Tyr Tyr Glu Asp Ser Ser Gly Lys Ser Ile
    690                 695                 700
Leu Tyr Val Val Glu Glu Pro Glu Cys Pro Lys Gly Pro Asp Ile Leu
705                 710                 715                 720
Val Val Leu Leu Ser Val Met Gly Ala Ile Leu Ile Gly Leu Ala
                725                 730                 735
Ala Leu Leu Ile Trp Lys Leu Leu Ile Thr Ile His Asp Arg Lys Glu
            740                 745                 750
Phe Ala Lys Phe Glu Glu Glu Arg Ala Arg Ala Lys Trp Asp Thr Ala
        755                 760                 765
Asn Asn Pro Leu Tyr Lys Glu Ala Thr Ser Thr Phe Thr Asn Ile Thr
    770                 775                 780
Tyr Arg Gly Thr
785
```

(2) INFORMATION FOR SEQ ID NO:9:

(i) SEQUENCE CHARACTERISTICS:
        (A) LENGTH: 3303 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 2...3118
        (D) OTHER INFORMATION:

(xi) SEQUENCE DESCRIPTION: SEQ ID NO:9:

```
G ATG GCC AGA GCT TTG TGT CCA CTG CAA GCC CTC TGG CTT CTG GAG TGG        49
  Met Ala Arg Ala Leu Cys Pro Leu Gln Ala Leu Trp Leu Leu Glu Trp
  1               5                   10                  15

GTG CTG CTG CTC TTG GGA CCT TGT GCT GCC CCT CCA GCC TGG GCC TTG          97
Val Leu Leu Leu Leu Gly Pro Cys Ala Ala Pro Pro Ala Trp Ala Leu
                20                  25                  30

AAC CTG GAC CCA GTG CAG CTC ACC TTC TAT GCA GGC CCC AAT GGC AGC         145
Asn Leu Asp Pro Val Gln Leu Thr Phe Tyr Ala Gly Pro Asn Gly Ser
            35                  40                  45

CAG TTT GGA TTT TCA CTG GAC TTC CAC AAG GAC AGC CAT GGG AGA GTG         193
Gln Phe Gly Phe Ser Leu Asp Phe His Lys Asp Ser His Gly Arg Val
50                  55                  60

GCC ATC GTG GTG GGC GCC CCG CGG ACC CTG GGC CCC AGC CAG GAG GAG         241
Ala Ile Val Val Gly Ala Pro Arg Thr Leu Gly Pro Ser Gln Glu Glu
65                  70                  75                  80

ACG GGC GGC GTG TTC CTG TGC CCC TGG AGG GCC GAG GGC GGC CAG TGC         289
Thr Gly Gly Val Phe Leu Cys Pro Trp Arg Ala Glu Gly Gly Gln Cys
                85                  90                  95

CCC TCG CTG CTC TTT GAC CTC CGT GAT GAG ACC CGA AAT GTA GGC TCC         337
Pro Ser Leu Leu Phe Asp Leu Arg Asp Glu Thr Arg Asn Val Gly Ser
            100                 105                 110

CAA ACT TTA CAA ACC TTC AAG GCC CGC CAA GGA CTG GGG GCG TCG GTC         385
Gln Thr Leu Gln Thr Phe Lys Ala Arg Gln Gly Leu Gly Ala Ser Val
        115                 120                 125

GTC AGC TGG AGC GAC GTC ATT GTG GCC TGC GCC CCC TGG CAG CAC TGG         433
Val Ser Trp Ser Asp Val Ile Val Ala Cys Ala Pro Trp Gln His Trp
    130                 135                 140

AAC GTC CTA GAA AAG ACT GAG GAG GCT GAG AAG ACG CCC GTA GGT AGC         481
Asn Val Leu Glu Lys Thr Glu Glu Ala Glu Lys Thr Pro Val Gly Ser
145                 150                 155                 160
```

```
TGC TTT TTG GCT CAG CCA GAG AGC GGC CGC CGC GCC GAG TAC TCC CCC      529
Cys Phe Leu Ala Gln Pro Glu Ser Gly Arg Arg Ala Glu Tyr Ser Pro
                165                 170                 175

TGT CGC GGG AAC ACC CTG AGC CGC ATT TAC GTG GAA AAT GAT TTT AGC      577
Cys Arg Gly Asn Thr Leu Ser Arg Ile Tyr Val Glu Asn Asp Phe Ser
            180                 185                 190

TGG GAC AAG CGT TAC TGT GAA GCG GGC TTC AGC TCC GTG GTC ACT CAG      625
Trp Asp Lys Arg Tyr Cys Glu Ala Gly Phe Ser Ser Val Val Thr Gln
        195                 200                 205

GCC GGA GAG CTG GTG CTT GGG GCT CCT GGC GGC TAT TAT TTC TTA GGT      673
Ala Gly Glu Leu Val Leu Gly Ala Pro Gly Gly Tyr Tyr Phe Leu Gly
    210                 215                 220

CTC CTG GCC CAG GCT CCA GTT GCG GAT ATT TTC TCG AGT TAC CGC CCA      721
Leu Leu Ala Gln Ala Pro Val Ala Asp Ile Phe Ser Ser Tyr Arg Pro
225                 230                 235                 240

GGC ATC CTT TTG TGG CAC GTG TCC TCC CAG AGC CTC TCC TTT GAC TCC      769
Gly Ile Leu Leu Trp His Val Ser Ser Gln Ser Leu Ser Phe Asp Ser
                245                 250                 255

AGC AAC CCA GAG TAC TTC GAC GGC TAC TGG GGG TAC TCG GTG GCC GTG      817
Ser Asn Pro Glu Tyr Phe Asp Gly Tyr Trp Gly Tyr Ser Val Ala Val
            260                 265                 270

GGC GAG TTC GAC GGG GAT CTC AAC ACT ACA GAA TAT GTC GTC GGT GCC      865
Gly Glu Phe Asp Gly Asp Leu Asn Thr Thr Glu Tyr Val Val Gly Ala
        275                 280                 285

CCC ACT TGG AGC TGG ACC CTG GGA GCG GTG GAA ATT TTG GAT TCC TAC      913
Pro Thr Trp Ser Trp Thr Leu Gly Ala Val Glu Ile Leu Asp Ser Tyr
    290                 295                 300

TAC CAG AGG CTG CAT CGG CTG CGC GCA GAG CAG ATG GCG TCG TAT TTT      961
Tyr Gln Arg Leu His Arg Leu Arg Ala Glu Gln Met Ala Ser Tyr Phe
305                 310                 315                 320

GGG CAT TCA GTG GCT GTC ACT GAC GTC AAC GGG GAT GGG AGG CAT GAT     1009
Gly His Ser Val Ala Val Thr Asp Val Asn Gly Asp Gly Arg His Asp
                325                 330                 335

CTG CTG GTG GGC GCT CCA CTG TAT ATG GAG AGC CGG GCA GAC CGA AAA     1057
Leu Leu Val Gly Ala Pro Leu Tyr Met Glu Ser Arg Ala Asp Arg Lys
            340                 345                 350

CTG GCC GAA GTG GGG CGT GTG TAT TTG TTC CTG CAG CCG CGA GGC CCC     1105
Leu Ala Glu Val Gly Arg Val Tyr Leu Phe Leu Gln Pro Arg Gly Pro
        355                 360                 365

CAC GCG CTG GGT GCC CCC AGC CTC CTG CTG ACT GGC ACA CAG CTC TAT     1153
His Ala Leu Gly Ala Pro Ser Leu Leu Leu Thr Gly Thr Gln Leu Tyr
    370                 375                 380

GGG CGA TTC GGC TCT GCC ATC GCA CCC CTG GGC GAC CTC GAC CGG GAT     1201
Gly Arg Phe Gly Ser Ala Ile Ala Pro Leu Gly Asp Leu Asp Arg Asp
385                 390                 395                 400

GGC TAC AAT GAC ATT GCA GTG GCT GCC CCC TAC GGG GGT CCC AGT GGC     1249
Gly Tyr Asn Asp Ile Ala Val Ala Ala Pro Tyr Gly Gly Pro Ser Gly
                405                 410                 415

CGG GGC CAA GTG CTG GTG TTC CTG GGT CAG AGT GAG GGG CTG AGG TCA     1297
Arg Gly Gln Val Leu Val Phe Leu Gly Gln Ser Glu Gly Leu Arg Ser
            420                 425                 430

CGT CCC TCC CAG GTC CTG GAC AGC CCC TTC CCC ACA GGC TCT GCC TTT     1345
Arg Pro Ser Gln Val Leu Asp Ser Pro Phe Pro Thr Gly Ser Ala Phe
        435                 440                 445

GGC TTC TCC CTT CGA GGT GCC GTA GAC ATC GAT GAC AAC GGA TAC CCA     1393
Gly Phe Ser Leu Arg Gly Ala Val Asp Ile Asp Asp Asn Gly Tyr Pro
    450                 455                 460

GAC CTG ATC GTG GGA GCT TAC GGG GCC AAC CAG GTG GCT GTG TAC AGA     1441
Asp Leu Ile Val Gly Ala Tyr Gly Ala Asn Gln Val Ala Val Tyr Arg
```

```
                                                        -continued
465                   470                   475                   480
GCT CAG CCA GTG GTG AAG GCC TCT GTC CAG CTA CTG GTG CAA GAT TCA                1489
Ala Gln Pro Val Val Lys Ala Ser Val Gln Leu Leu Val Gln Asp Ser
                        485                   490                   495

CTG AAT CCT GCT GTG AAG AGC TGT GTC CTA CCT CAG ACC AAG ACA CCC                1537
Leu Asn Pro Ala Val Lys Ser Cys Val Leu Pro Gln Thr Lys Thr Pro
                500                   505                   510

GTG AGC TGC TTC AAC ATC CAG ATG TGT GTT GGA GCC ACT GGG CAC AAC                1585
Val Ser Cys Phe Asn Ile Gln Met Cys Val Gly Ala Thr Gly His Asn
            515                   520                   525

ATT CCT CAG AAG CTA TCC CTA AAT GCC GAG CTG CAG CTG GAC CGG CAG                1633
Ile Pro Gln Lys Leu Ser Leu Asn Ala Glu Leu Gln Leu Asp Arg Gln
        530                   535                   540

AAG CCC CGC CAG GGC CGG CGG GTG CTG CTG CTG GGC TCT CAA CAG GCA                1681
Lys Pro Arg Gln Gly Arg Arg Val Leu Leu Leu Gly Ser Gln Gln Ala
545                   550                   555                   560

GGC ACC ACC CTG AAC CTG GAT CTG GGC GGA AAG CAC AGC CCC ATC TGC                1729
Gly Thr Thr Leu Asn Leu Asp Leu Gly Gly Lys His Ser Pro Ile Cys
                        565                   570                   575

CAC ACC ACC ATG GCC TTC CTT CGA GAT GAG GCA GAC TTC CGG GAC AAG                1777
His Thr Thr Met Ala Phe Leu Arg Asp Glu Ala Asp Phe Arg Asp Lys
                580                   585                   590

CTG AGC CCC ATT GTG CTC AGC CTC AAT GTG TCC CTA CCG CCC ACG GAG                1825
Leu Ser Pro Ile Val Leu Ser Leu Asn Val Ser Leu Pro Pro Thr Glu
            595                   600                   605

GCT GGA ATG GCC CCT GCT GTC GTG CTG CAT GGA GAC ACC CAT GTG CAG                1873
Ala Gly Met Ala Pro Ala Val Val Leu His Gly Asp Thr His Val Gln
        610                   615                   620

GAG CAG ACA CGA ATC GTC CTG GAC TCT GGG GAA GAT GAC GTA TGT GTG                1921
Glu Gln Thr Arg Ile Val Leu Asp Ser Gly Glu Asp Asp Val Cys Val
625                   630                   635                   640

CCC CAG CTT CAG CTC ACT GCC AGC GTG ACG GGC TCC CCG CTC CTA GTT                1969
Pro Gln Leu Gln Leu Thr Ala Ser Val Thr Gly Ser Pro Leu Leu Val
                        645                   650                   655

GGG GCA GAT AAT GTC CTG GAG CTG CAG ATG GAC GCA GCC AAC GAG GGC                2017
Gly Ala Asp Asn Val Leu Glu Leu Gln Met Asp Ala Ala Asn Glu Gly
                660                   665                   670

GAG GGG GCC TAT GAA GCA GAG CTG GCC GTG CAC CTG CCC CAG GGC GCC                2065
Glu Gly Ala Tyr Glu Ala Glu Leu Ala Val His Leu Pro Gln Gly Ala
            675                   680                   685

CAC TAC ATG CGG GCC CTA AGC AAT GTC GAG GGC TTT GAG AGA CTC ATC                2113
His Tyr Met Arg Ala Leu Ser Asn Val Glu Gly Phe Glu Arg Leu Ile
        690                   695                   700

TGT AAT CAG AAG AAG GAG AAT GAG ACC AGG GTG GTG CTG TGT GAG CTG                2161
Cys Asn Gln Lys Lys Glu Asn Glu Thr Arg Val Val Leu Cys Glu Leu
705                   710                   715                   720

GGC AAC CCC ATG AAG AAG AAC GCC CAG ATA GGA ATC GCG ATG TTG GTG                2209
Gly Asn Pro Met Lys Lys Asn Ala Gln Ile Gly Ile Ala Met Leu Val
                        725                   730                   735

AGC GTG GGG AAT CTG GAA GAG GCT GGG GAG TCT GTG TCC TTC CAG CTG                2257
Ser Val Gly Asn Leu Glu Glu Ala Gly Glu Ser Val Ser Phe Gln Leu
                740                   745                   750

CAG ATA CGG AGC AAG AAC AGC CAG AAT CCA AAC AGC AAG ATT GTG CTG                2305
Gln Ile Arg Ser Lys Asn Ser Gln Asn Pro Asn Ser Lys Ile Val Leu
            755                   760                   765

CTG GAC GTG CCG GTC CGG GCA GAG GCC CAA GTG GAG CTG CGA GGG AAC                2353
Leu Asp Val Pro Val Arg Ala Glu Ala Gln Val Glu Leu Arg Gly Asn
        770                   775                   780

TCC TTT CCA GCC TCC CTG GTG GTG GCA GCA GAA GAA GGT GAG AGG GAG                2401
```

```
Ser Phe Pro Ala Ser Leu Val Val Ala Ala Glu Glu Gly Glu Arg Glu
785                 790                 795                 800

CAG AAC AGC TTG GAC AGC TGG GGA CCC AAA GTG GAG CAC ACC TAT GAG      2449
Gln Asn Ser Leu Asp Ser Trp Gly Pro Lys Val Glu His Thr Tyr Glu
                805                 810                 815

CTC CAC AAC AAT GGC CCT GGG ACT GTG AAT GGT CTT CAC CTC AGC ATC      2497
Leu His Asn Asn Gly Pro Gly Thr Val Asn Gly Leu His Leu Ser Ile
            820                 825                 830

CAC CTT CCG GGA CAG TCC CAG CCC TCC GAC CTG CTC TAC ATC CTG GAT      2545
His Leu Pro Gly Gln Ser Gln Pro Ser Asp Leu Leu Tyr Ile Leu Asp
        835                 840                 845

ATA CAG CCC CAG GGG GGC CTT CAG TGC TTC CCA CAG CCT CCT GTC AAC      2593
Ile Gln Pro Gln Gly Gly Leu Gln Cys Phe Pro Gln Pro Pro Val Asn
    850                 855                 860

CCT CTC AAG GTG GAC TGG GGG CTG CCC ATC CCC AGC CCC TCC CCC ATT      2641
Pro Leu Lys Val Asp Trp Gly Leu Pro Ile Pro Ser Pro Ser Pro Ile
865                 870                 875                 880

CAC CCG GCC CAT CAC AAG CGG GAT CGC AGA CAG ATC TTC CTG CCA GAG      2689
His Pro Ala His His Lys Arg Asp Arg Arg Gln Ile Phe Leu Pro Glu
                885                 890                 895

CCC GAG CAG CCC TCG AGG CTT CAG GAT CCA GTT CTC GTA AGC TGC GAC      2737
Pro Glu Gln Pro Ser Arg Leu Gln Asp Pro Val Leu Val Ser Cys Asp
            900                 905                 910

TCG GCG CCC TGT ACT GTG GTG CAG TGT GAC CTG CAG GAG ATG GCG CGC      2785
Ser Ala Pro Cys Thr Val Val Gln Cys Asp Leu Gln Glu Met Ala Arg
        915                 920                 925

GGG CAG CGG GCC ATG GTC ACG GTG CTG GCC TTC CTG TGG CTG CCC AGC      2833
Gly Gln Arg Ala Met Val Thr Val Leu Ala Phe Leu Trp Leu Pro Ser
    930                 935                 940

CTC TAC CAG AGG CCT CTG GAT CAG TTT GTG CTG CAG TCG CAC GCA TGG      2881
Leu Tyr Gln Arg Pro Leu Asp Gln Phe Val Leu Gln Ser His Ala Trp
945                 950                 955                 960

TTC AAC GTG TCC TCC CTC CCC TAT GCG GTG CCC CCG CTC AGC CTG CCC      2929
Phe Asn Val Ser Ser Leu Pro Tyr Ala Val Pro Pro Leu Ser Leu Pro
                965                 970                 975

CGA GGG GAA GCT CAG GTG TGG ACA CAG CTG CTC CGG GCC TTG GAG GAG      2977
Arg Gly Glu Ala Gln Val Trp Thr Gln Leu Leu Arg Ala Leu Glu Glu
            980                 985                 990

AGG GCC ATT CCA ATC TGG TGG GTG CTG GTG GGT GTG CTG GGT GGC CTG      3025
Arg Ala Ile Pro Ile Trp Trp Val Leu Val Gly Val Leu Gly Gly Leu
        995                 1000                1005

CTG CTG CTC ACC ATC CTG GTC CTG GCC ATG TGG AAG GTC GGC TTC TTC      3073
Leu Leu Leu Thr Ile Leu Val Leu Ala Met Trp Lys Val Gly Phe Phe
    1010                1015                1020

AAG CGG AAC CGG CCA CCC CTG GAA GAA GAT GAT GAA GAG GGG GAG          3118
Lys Arg Asn Arg Pro Pro Leu Glu Glu Asp Asp Glu Glu Gly Glu
1025                1030                1035

TGATGGTGCA GCCTACACTA TTCTAGCAGG AGGGTTGGGC GTGCTACCTG CACCGCCCCT    3178

TCTCCAACAA GTTGCCTCCA AGCTTTGGGT TGGAGCTGTT CCATTGGGTC CTCTTGGTGT    3238

CGTTTCCCTC CCAACAGAGC TGGGCTACCC CCCCTCCTGC TGCCTAATAA AGAGACTGAG    3298

CCCTG                                                                3303

(2) INFORMATION FOR SEQ ID NO:10:

(i) SEQUENCE CHARACTERISTICS:
        (A) LENGTH: 1039 amino acids
        (B) TYPE: amino acid
        (C) STRANDEDNESS: single
        (D) TOPOLOGY: linear
```

-continued (ii) MOLECULE TYPE: protein (v) FRAGMENT TYPE: internal (xi) SEQUENCE DESCRIPTION: SEQ ID NO:10:

```
Met Ala Arg Ala Leu Cys Pro Leu Gln Ala Leu Trp Leu Leu Glu Trp
 1               5                  10                  15

Val Leu Leu Leu Gly Pro Cys Ala Ala Pro Ala Trp Ala Leu
             20                  25                  30

Asn Leu Asp Pro Val Gln Leu Thr Phe Tyr Ala Gly Pro Asn Gly Ser
             35                  40                  45

Gln Phe Gly Phe Ser Leu Asp Phe His Lys Asp Ser His Gly Arg Val
 50                  55                  60

Ala Ile Val Val Gly Ala Pro Arg Thr Leu Gly Pro Ser Gln Glu Glu
 65                  70                  75                  80

Thr Gly Gly Val Phe Leu Cys Pro Trp Arg Ala Glu Gly Gly Gln Cys
             85                  90                  95

Pro Ser Leu Leu Phe Asp Leu Arg Asp Glu Thr Arg Asn Val Gly Ser
             100                 105                 110

Gln Thr Leu Gln Thr Phe Lys Ala Arg Gln Gly Leu Gly Ala Ser Val
             115                 120                 125

Val Ser Trp Ser Asp Val Ile Val Ala Cys Ala Pro Trp Gln His Trp
 130                 135                 140

Asn Val Leu Glu Lys Thr Glu Glu Ala Lys Thr Pro Val Gly Ser
 145                 150                 155                 160

Cys Phe Leu Ala Gln Pro Glu Ser Gly Arg Arg Ala Glu Tyr Ser Pro
             165                 170                 175

Cys Arg Gly Asn Thr Leu Ser Arg Ile Tyr Val Glu Asn Asp Phe Ser
             180                 185                 190

Trp Asp Lys Arg Tyr Cys Glu Ala Gly Phe Ser Ser Val Val Thr Gln
             195                 200                 205

Ala Gly Glu Leu Val Leu Gly Ala Pro Gly Gly Tyr Tyr Phe Leu Gly
             210                 215                 220

Leu Leu Ala Gln Ala Pro Val Ala Asp Ile Phe Ser Ser Tyr Arg Pro
 225                 230                 235                 240

Gly Ile Leu Leu Trp His Val Ser Ser Gln Ser Leu Ser Phe Asp Ser
             245                 250                 255

Ser Asn Pro Glu Tyr Phe Asp Gly Tyr Trp Gly Tyr Ser Val Ala Val
             260                 265                 270

Gly Glu Phe Asp Gly Asp Leu Asn Thr Thr Glu Tyr Val Val Gly Ala
             275                 280                 285

Pro Thr Trp Ser Trp Thr Leu Gly Ala Val Glu Ile Leu Asp Ser Tyr
             290                 295                 300

Tyr Gln Arg Leu His Arg Leu Arg Ala Glu Gln Met Ala Ser Tyr Phe
 305                 310                 315                 320

Gly His Ser Val Ala Val Thr Asp Val Asn Gly Asp Gly Arg His Asp
             325                 330                 335

Leu Leu Val Gly Ala Pro Leu Tyr Met Glu Ser Arg Ala Asp Arg Lys
             340                 345                 350

Leu Ala Glu Val Gly Arg Val Tyr Leu Phe Leu Gln Pro Arg Gly Pro
             355                 360                 365

His Ala Leu Gly Ala Pro Ser Leu Leu Leu Thr Gly Thr Gln Leu Tyr
             370                 375                 380
```

-continued

```
Gly Arg Phe Gly Ser Ala Ile Ala Pro Leu Gly Asp Leu Arg Asp
385                 390                 395                 400

Gly Tyr Asn Asp Ile Ala Val Ala Ala Pro Tyr Gly Pro Ser Gly
                405                 410                 415

Arg Gly Gln Val Leu Val Phe Leu Gly Gln Ser Glu Gly Leu Arg Ser
            420                 425                 430

Arg Pro Ser Gln Val Leu Asp Ser Pro Phe Pro Thr Gly Ser Ala Phe
        435                 440                 445

Gly Phe Ser Leu Arg Gly Ala Val Asp Ile Asp Asp Asn Gly Tyr Pro
450                 455                 460

Asp Leu Ile Val Gly Ala Tyr Gly Ala Asn Gln Val Ala Val Tyr Arg
465                 470                 475                 480

Ala Gln Pro Val Val Lys Ala Ser Val Gln Leu Leu Val Gln Asp Ser
                485                 490                 495

Leu Asn Pro Ala Val Lys Ser Cys Val Leu Pro Gln Thr Lys Thr Pro
            500                 505                 510

Val Ser Cys Phe Asn Ile Gln Met Cys Val Gly Ala Thr Gly His Asn
        515                 520                 525

Ile Pro Gln Lys Leu Ser Leu Asn Ala Glu Leu Gln Leu Asp Arg Gln
530                 535                 540

Lys Pro Arg Gln Gly Arg Arg Val Leu Leu Leu Gly Ser Gln Gln Ala
545                 550                 555                 560

Gly Thr Thr Leu Asn Leu Asp Leu Gly Gly Lys His Ser Pro Ile Cys
                565                 570                 575

His Thr Thr Met Ala Phe Leu Arg Asp Glu Ala Asp Phe Arg Asp Lys
            580                 585                 590

Leu Ser Pro Ile Val Leu Ser Leu Asn Val Ser Leu Pro Pro Thr Glu
        595                 600                 605

Ala Gly Met Ala Pro Ala Val Val Leu His Gly Asp Thr His Val Gln
610                 615                 620

Glu Gln Thr Arg Ile Val Leu Asp Ser Gly Glu Asp Asp Val Cys Val
625                 630                 635                 640

Pro Gln Leu Gln Leu Thr Ala Ser Val Thr Gly Ser Pro Leu Leu Val
                645                 650                 655

Gly Ala Asp Asn Val Leu Glu Leu Gln Met Asp Ala Ala Asn Glu Gly
            660                 665                 670

Glu Gly Ala Tyr Glu Ala Glu Leu Ala Val His Leu Pro Gln Gly Ala
        675                 680                 685

His Tyr Met Arg Ala Leu Ser Asn Val Glu Gly Phe Glu Arg Leu Ile
690                 695                 700

Cys Asn Gln Lys Lys Glu Asn Glu Thr Arg Val Val Leu Cys Glu Leu
705                 710                 715                 720

Gly Asn Pro Met Lys Lys Asn Ala Gln Ile Gly Ile Ala Met Leu Val
                725                 730                 735

Ser Val Gly Asn Leu Glu Glu Ala Gly Glu Ser Val Ser Phe Gln Leu
            740                 745                 750

Gln Ile Arg Ser Lys Asn Ser Gln Asn Pro Asn Ser Lys Ile Val Leu
        755                 760                 765

Leu Asp Val Pro Val Arg Ala Glu Ala Gln Val Glu Leu Arg Gly Asn
770                 775                 780

Ser Phe Pro Ala Ser Leu Val Val Ala Ala Glu Glu Gly Glu Arg Glu
785                 790                 795                 800

Gln Asn Ser Leu Asp Ser Trp Gly Pro Lys Val Glu His Thr Tyr Glu
```

```
                        805                 810                 815
Leu His Asn Asn Gly Pro Gly Thr Val Asn Gly Leu His Leu Ser Ile
                820                 825                 830
His Leu Pro Gly Gln Ser Gln Pro Ser Asp Leu Leu Tyr Ile Leu Asp
                835                 840                 845
Ile Gln Pro Gln Gly Gly Leu Gln Cys Phe Pro Gln Pro Pro Val Asn
850                 855                 860
Pro Leu Lys Val Asp Trp Gly Leu Pro Ile Pro Ser Pro Ser Pro Ile
865                 870                 875                 880
His Pro Ala His His Lys Arg Asp Arg Arg Gln Ile Phe Leu Pro Glu
                885                 890                 895
Pro Glu Gln Pro Ser Arg Leu Gln Asp Pro Val Leu Val Ser Cys Asp
                900                 905                 910
Ser Ala Pro Cys Thr Val Val Gln Cys Asp Leu Gln Glu Met Ala Arg
                915                 920                 925
Gly Gln Arg Ala Met Val Thr Val Leu Ala Phe Leu Trp Leu Pro Ser
                930                 935                 940
Leu Tyr Gln Arg Pro Leu Asp Gln Phe Val Leu Gln Ser His Ala Trp
945                 950                 955                 960
Phe Asn Val Ser Ser Leu Pro Tyr Ala Val Pro Pro Leu Ser Leu Pro
                965                 970                 975
Arg Gly Glu Ala Gln Val Trp Thr Gln Leu Leu Arg Ala Leu Glu Glu
                980                 985                 990
Arg Ala Ile Pro Ile Trp Trp Val Leu Val Gly Val Leu Gly Gly Leu
                995                 1000                1005
Leu Leu Leu Thr Ile Leu Val Leu Ala Met Trp Lys Val Gly Phe Phe
                1010                1015                1020
Lys Arg Asn Arg Pro Pro Leu Glu Glu Asp Asp Glu Glu Gly Glu
1025                1030                1035
```

(2) INFORMATION FOR SEQ ID NO:11:

(i) SEQUENCE CHARACTERISTICS:
        (A) LENGTH: 13865 base pairs
        (B) TYPE: nucleic acid
        (C) STRANDEDNESS: single
        (D) TOPOLOGY: linear (ii) MOLECULE TYPE: Genomic DNA (ix) FEATURE:

(xi) SEQUENCE DESCRIPTION: SEQ ID NO:11:

```
GAATTCTCCC AGAGGCAAAC TGCCAGATGT GAGGCTGCTC TTCCTCAGTC ACTATCTCTG      60
GTCGTACCGG GCGATGCCTG AGCCAACTGA CCCTCAGACC TGTGAGCCGA GCCGGTCACA     120
CCGTGGCTGA CACCGGCATT CCCACCGCCT TTCTCCTGTG CGACCCGCTA AGGGCCCCGC     180
GAGGTGGGCA GGCCAAGTAT TCTTGACCTT CGTGGGGTAG AAGAAGCCAC CGTGGCTGGG     240
AGAGGGCCCT GCTCACAGCC ACACGTTTAC TTCGCTGCAG GTCCCGAGCT TCTGCCCCAG     300
GTGGGCAAAG CATCCGGGAA ATGCCCTCCG CTGCCCGAGG GGAGCCCAGA GCCCGTGCTT     360
TCTATTAAAT GTTGTAAATG CCGCCTCTCC CACTTTATCA CCAAATGGAA GGGAAGAATT     420
CTTCCAAGGC GCCCTCCCTT TCCTGCCATA GACCTGCAAC CCACCTAAGC TGCACGTCGG     480
AGTCGCGGGC CTGGGTGAAT CCGGGGGCCT TGGGGGACCC GGGCAACTAG ACCCGCCTGC     540
GTCCTCCAGG GCAGCTCCGC GCTCGGTGGC GCGGTTGAAT CACTGGGGTG AGTCATCCCT     600
```

-continued

```
TGCAGGGTCC CGGAGTTTCC TACCGGGAGG AGGCGGGGCA GGGGTGTGGA CTCGCCGGGG    660

GCCGCCCACC GCGACGGCAA GTGACCCGGG CCGGGGCGG GGAGTCGGGA GGAGCGGCGG     720

GGGCGGGCGC CGGGGGCGGG CAGAGGCGCG GGAGAGCGCG CCGCCGGCCC TTTATAGCGC    780

GCGGGGCACC GGCTCCCCAA GACTGCGAGC TCCCCGCACC CCCTCGCACT CCCTCTGGCC    840

GGCCCAGGGC GCCTTCAGCC CAACCTCCCC AGCCCCACGG GCGCCACGGA ACCCGCTCGA    900

TCTCGCCGCC AACTGGTAGA CATGGAGACC CCTGCCTGGC CCCGGGTCCC GCGCCCCGAG    960

ACCGCCGTCG CTCGGACGCT CCTGCTCGGC TGGGTCTTCG CCCAGGTGGC CGGCGCTTCA   1020

GGTGAGTGGC ACCAGCCCCT GGAAGCCCGG GGCGCGCCAC ACGCAGGAGG GAGGCGACAG   1080

TCCTGGCTGG CAGCGGGCTC GCCCTGGTTC CCCGGGGCGC CCATGTTGTC CCCCGCGCCT   1140

ACGGGACTCG GCTGCGCTCA CCCAGCCCGG CTTGAATGAA CCGAGTCCGT CGGGCGCCGG   1200

CGGGAGTTGC AGGGAGGGAG TTGGCGCCCC AGACCCGCT GCCCCTTCCG CTGGAGAGTT    1260

TTGCTCGGGG TGTCCGAGTA ATTGGACTGT TGTTGCATAA GCGGACTTTT AGCTCCCGCT   1320

TTAACTCTGG GGAAAGGGCT TCCCAGTGAG TTGCGACCTT CAATATGATA GGACTTGTGC   1380

CTGCGTCTGC ACGTGTTGGC GTGCAGAGGT TTGGATATTA TCTTTCATTA TATGTGCATC   1440

TTCCCTTAAT AAAGAGCGTC CCTGGTCTTT TCCTGGCCAT CTTTGTTCTA GGTTTGGGTA   1500

GAGGCAATCC AAAAGGGCTG GATTGCTGCT TAGATTGGAG CAGGTACAAC GTTGTGCATG   1560

CCCCGTATTT CTACGAGGTG TTCGGGACGG CGTAGAGACT GGGACCTGCT GCGTACTGGC   1620

AAAGCAGACC TTCATAAGAA ATAATCCTGA TCCAATACAG CCGACGGTGT GACAGGCCAC   1680

ACGTCCCCGT GGGTCTCTGT GGAAGTTTCA GTGTAGCGAC ATTTCAGATA AAAGTGGAAA   1740

AAGTGAAGTT TGGCTTTTTT CATTTGTATG CAGTCCTAAC TCTTGTCACA CGTGTGGGAT   1800

TTATCTTTTT CCATAACTTA CTGAAAACCC TTCCTGGCGG GCTGAACCTG ACTCTTCCTG   1860

AGCTGAGTCC TGGACTGGCA CACTGATGGC TCTGGGCTCT TCCCGGTCAA GTTATAACAA   1920

GGCTTTGCCC ATGAATAATT TCAAACGAAA ATGTCAAGAT CCTTGCCGGT GTCCTGGGAT   1980

TACAAGGTGA ATCTTGTCAT GAAGAAATTC TAGGTCTAGA AAAAATTTGA AGATTCTTTT   2040

TCTCTTGATA ATTCACTAAT GAAGCTTTTG TGGTTGAAAA ATAAAAAGTG AGGTTTATGG   2100

TGATGTCAGG TGGGAAGGTG TTTTATACAT CAATACATTC GAGTGCTCTG AAGTGCATGT   2160

AATAATAGCT GTTTCTCTGT TGTTTAAAGG CACTACAAAT ACTGTGGCAG CATATAATTT   2220

AACTTGGAAA TCAACTAATT TCAAGACAAT TTTGGAGTGG GAACCCAAAC CCGTCAATCA   2280

AGTCTACACT GTTCAAATAA GGTAAGCTGG GTACAGAAAA AGAAAATTAA GGTCTTTGAT   2340

GTTTCTACTG TCCTATGCTG AACAAGAATG TCTTTAAAGC TGATTACTGG ATGAAAATTAT  2400

TTAACAGATG ACGAAGAAGA AGGGATTCTT GGCAATTCGC TGGCCGGTGT CATACTCTAT   2460

TAGGCCTGCA ACATTTCCAG ACCTTAAACT GATAGAACAT TTTAATTGTT TTAATTGTTT   2520

TTGGAAATGA TGGGAGAGTT CCTAAGTGGA GTATAAACTG TGGAGAGATG AACCATCTTG   2580

AGTAGGCACT GAAGTGTGCT TTGGGTCATG ATAGATTAAT TAATCTCATC TAAACATTGA   2640

TGTCTTTTTC CGTTGCTGTC TAGACTGTGA ACAATGTCTA ACACCTTAGG GAAGAGGTGG   2700

GGAGGAATCC CAATGTATAC ATTGCCCTTA AGCAGTGTTT GATTCATTCA TCTTTGGACT   2760

CCATGAATCG AAATCTGGTA GAATACATGA TCTTAGTGGA GGAGGCCAAA TGCGTGACTC   2820

ACTGAGCCTG GCAGAGCAGA AATACTCTGC TGTCTGCACC CTCTGGGTCT GGTGTGGCTC   2880

TGCTTCTTGG TGCTTCAACT CTGACTGGCA GCTGTCCCCA GGAGGCGATA ATTCAGCATG   2940

TTCAATCTAA AGGTTATGAC TTCCTTGATG GTTTTCACCA TATTCTTGGC AAGTTTTTGG   3000
```

-continued

```
TTTTTGAAAT GTTCTAGGAG GCTTGGTAGA GATCTTATGA AATAGAGAAT AGCTGCTGTG    3060

GAAATTATTT TAATGCTAAT TACATAAAAG TACAAAAGTA GCACTAGCTA AAACAAAAGG    3120

TATTTTGCTG TTCTGTTTTG TTTTAGCTTG TGCCAGGCCT TTACAGCAT TAGGAATGCA    3180

ACTTCTAGAT AACGATGCAT CTTTTAAGTG AATGTTCTTG TTTTTCAAAA TGAACTTCAT    3240

GACAGTAGTT GCCAAACCAG CAAGGAGAAC TTGCATGCAT ACGTGCATGC ATGTGTGGAT    3300

ATGTATGGGG GTGGGGGGAG AGAAAGATGA AGGAATTTCA TAACATGAAA TAATGATTAC    3360

AGTTCTGGTC AAACTTGTCA ATTCAGATTT CACCAATTGA GAATTAGTAA GTAATTTCTC    3420

TGATACAGGC CTGAAGTTTA CCTTAGTAAA CACTTTACTT CCATATGGTA AAAATTAGAT    3480

TTTGGGAGGA ATGCTTACCT CCTAAATATA TTCAATCTAA TATTTGAGGA CACATGGGAA    3540

TATATTTATG ATTCATCTGC TTTTTAAACA TAAGCCTTTG TTAACTGTAA GTTCTTGAAC    3600

TTTATAAGGC TGCTGTTATT TAAATGAGCA CAGCTCCTGA TCTGCAAACA GCAGAGCGCA    3660

GGGCTACAGC TTGGGGATG CCAGCCGACT CAGGGTGGTC CTGTGGACTG AACAATCTCT    3720

TGCTGCTGTA CTGGAGGGCC TGGGAGCTTT TCCATCAGCC TCGGCCTGAG GTGTGCACTC    3780

TTCTCCTGCC CACCCCAGGA ATAAATGAGA TTCCTGGTTA AAAGGACCA GAGCAGTCAT    3840

TTTACAGTTG AGGAAACTGT TGCTCTGAGA AGTGAGGGAT TTATTCATGA CTACACTGAT    3900

GGTGAGTGCC CATGTCAGGT CTGGAACCAA AGTCTACCCA GTATCCACAC ACCACCATCC    3960

CTCAGGTGGC TCTGCCACAG TCTGATGGGA GGCTCCAAAG CGGGAGGAAG AAGGAAAGTC    4020

TTGCCCACTG CATCTCCTCA GTTGGCCTTC CTCTCTGCCT GTTTTCCCTC CCTACAGTTA    4080

GCATCTTAAG CAGCTGCCTC TCTTCCCTCC CGACTGCTCT CACTACTGCA GCCTGGCTCC    4140

AGCCGCAGGA CACTACTGCT GTGCAGAAGC CCCTACTTGG AACTCCAACT GCATTTTTCA    4200

CCTTTGCTAA CAGTTTTCAG TGGTGGTTGG GAAATGTTAT TGGCTTAAGC CTTAGCACAA    4260

ACCGTCACCG GTGATATTCA TTCCATGGAA ATGTTCTGAA TTCTAAAGCT GAATTTACAA    4320

AGCTTCTGGA AAACAACCTG CAACCAAATT AGTGACTGAA TTTTTTAGTT AACTCAAAAT    4380

TCCAAATCAG AGGGTTTTGC AATGCCTGGA GGAACCTTGG AGGCTTTTAA AGTGTTAATG    4440

CTATTAATGG CATTCAGAGG GATTTTCTAC AGAATTGTCC CTTCATTACC TGTTTATACA    4500

GTTTTACTAC TTACCAGGGT ACTGTATAAA TCCTTGTGCT AAAATTTTGCT ATAGAGTATG    4560

TGGTCCCTGC TGTGAGCTGG GAGGAACCAA ATACTGTATC TCTATGTTAC ATAGAAAGCC    4620

CTAGGAGACT TTCTCCTGTT ATCTGAACAA CTATTTGCTG TACTGATAAA AAGGAAACAG    4680

CATAGTCTCA TTCACTTTTT GAAATGGAAA TGATAAAATA AAACACATTT TGGTCATTCG    4740

GGAACAAAAT ACCCTCTCTA CTTTTATCAC ATAAAATTAA ATAAATAGAA ACCAAAATAT    4800

TTCAGTATCA ATCTTAGTTT GTGCACTTTA GGATAAAGAA TGTGTTTACC CAAATCCTTT    4860

TGGCCTGGTT ACTTAGTTCA GATTTTGAAA GAAAATATAT TTGTGGCTTT TATGTGTGAA    4920

TTTAGACAAT GGAATCCATG TGGTGCCTCG TTTTCCCTGA GATTATGTAT TAATTCAACC    4980

TGTAAATGCA AACCATCTAA TAGTCAGCGA GACCCTATAG CCCTGCTGCT TAATGGGGGC    5040

ACACAAGGGC ATGCAGCCCT CGTACCAGGC AGACTGTGTT CATATTAACA GCATCGTGGA    5100

GAAACTCATG CTGGGGACA GGGGAGGGAG ATGTAAATGC TCAGCAGGGA GATCTGGAGA    5160

TTCCTGGAGC AGGTGGAGTT GGGACCTGGC CTTGAACGAT GGGTCTGGCT CTGGCAGTCA    5220

GTAATGCCAA AGGGAAGAGC AGCATAACTG TCACTTTCCA TGGGACAGAA GTGTGTGAAT    5280

CAAGTTGCAG TGACGCTTCA CCTATTTATT ATTTTGGTCA TTTAGAAGAA TTTCATTGTC    5340
```

-continued

```
AGTAGAAGTC CTTTAAATCA TTTCCCCTTC AGTGACGTCT CACAAAAAAA AGATCTGTCT    5400

TTAGCTTTTT AGTCTCAGAC TTTATTAGAC AGATACTACC TGTACTCTTA TTCTGTAATC    5460

TTTGTTGGGA TGGATTCACA TCTTGCAAAG GAAGGGAGGC ATGTAGTATA ATGGGGCAAA    5520

CAGACCCAGC TCTGCCACTC GTTAGATATG TGACCTTCTG CAAGTTGCTT AGTGCCTGTG    5580

AGCTTCAGTG TCCTCATGGA TAAGAAAGAT CCAACACCTT CTTGGAAGGA TTATATCAAA    5640

TGAAGTAACA TGAGTAAAGG GTCCAGCAGA ATACCTGGCA TATAGTGGAG TCAATGAATG    5700

ATTAATAATA TTATTAATAG TGGTCATGAG AGATATATGT ATAACATGTT ATTATGTAGA    5760

CTCACTATAT AGACTCTATT CTACATAGAA TATAGAACAT TATATAACAA ACAACTATAA    5820

TAAGTAGACT ATAGTAAACA ACCTCACTTT GTCTCAGTTG CCTCATCTTG ATGGAAAACT    5880

GCTCTTTCTC TCCTGTTACC CTGACAGAGA GCGTCTACAT TCTAAAAGAA AGATATTTAA    5940

CAAAATGGTT GAGTACAGAT CCAAGAGTCA AATAGCTGTC TGGTTCAAAG TCCAGCTGTG    6000

TGATTTTGAG CTAGTCACCC AATCTCACTT TGTCTCAGTA GCCTTATTTG TAAAAACAAG    6060

GCAAATTACA GAGCCATCCC CTGGGTTGCT ATGAGGACTC AAACATGCAT CCCAAGTGCT    6120

CGGTGTTGCT AGGTATGATG GCTCACACCT GTACATTCAG CACTTTGGGA GGCCGAAGCA    6180

GAAGGATCAG CCTGGGCAAC ATAGCAGGAC CCCATCTCTA CAAACAATG TTTAAAAAAA    6240

AGCAAAGTGC TCAGCACAGT GACTGCATCA TTAGGATTGA TTGTAGGGCT CCTGATGTTA    6300

GCACAGAACA CCACAGCCAG GAAGCAGTCT ATCTTGTTGG GTGCAAATTG TAACATTCCA    6360

TTTATGTTTC TTCCTTCTTT TCTTTCTTTA GCACTAAGTC AGGAGATTGG AAAAGCAAAT    6420

GCTTTTACAC AACAGACACA GAGTGTGACC TCACCGACGA GATTGTGAAG GATGTGAAGC    6480

AGACGTACTT GGCACGGGTC TTCTCCTACC CGGCAGGGAA TGTGGAGAGC ACCGGTTCTG    6540

CTGGGGAGCC TCTGTATGAG AACTCCCCAG AGTTCACACC TTACCTGGAG AGTAAGTGGC    6600

TTGGGCTGTA ATACCGTTCA TTCTTGTTAG AAACGTCTGA ACATTCTCGT GATCTTGTGC    6660

CTTTAGGGGC TACAAAATTA AAAATATTTA TTCTTTTTTT CTCAGAAACT GGTATGTATC    6720

ACAGCCCTCT TCACACATTC CAGATGTGGT AGGAGGTTCA CAGAATGTGA ACTTTTGGAG    6780

CTGATGACAG TGTCATCAAG TAACTTTCTC CCCCAGTCTG TCCCCAGACC CTGTTACTGT    6840

CCTCAGTAAG CGGCTGAATG TGTGTTGGGA GAGGGCGGGC CAGGGAAGCG GGTAGGGATA    6900

GGAAATCCAC CAAGGCCGGG GTTTTAGCTT TTCCCTATAT ATATATCATG TATCCTGATT    6960

TTTCTGTCCC GTTATCACAC TAAAAATCCC AGTTGAGGAT TTTTCCCAAA CGGTCATAAA    7020

TCAATGAGGA AAGTCCATGG TTTCCCTCTG AGCCCATAAT TAGCCTAATT ATGCTGACCT    7080

TTTCTAATCA GTTGGCCATG ATTTGAGTTC CGTGATGTGC CAGCACCTGC CCAGCCATCT    7140

GCCTGTCACC CTCGTTCTGG TTTTGGAAAG GTGGAATACT TTCCTCCTCA GCCTTTGCCC    7200

CTGTAAGCTG GCCCTAGGAG CCAGTAAAAG AATGAAGAGA ATTCCTGTCA AGTAGGAGAT    7260

TTATTCTTTT GCCGCAACTG TGGCTCTGAG CTAGGCAATT TAGATAAATG CATGTAGCAC    7320

ATTGAGTAGA GTGAAATTAG CTTCTCTTGT AAGGCCAGCT GGTTAGAATG AAGGTGTTGT    7380

GTGAGTGTTA GGCCCAGCGA GAGAGAACAG TTTCTCAAGG TAGGAATGGT GAAAAGAAGG    7440

GGTGGACGGA CAACCAACCA ACCATCCTCC TCTGGTATCT ACTTTGAGGG TTGAAATAGG    7500

GGGCCTGACC CCAGGTGAAT GTGGCTGCCT TCCCAGAGCC CCCATTTGCA AGACCCTCCA    7560

GACCCCCAGG TGCTTCTGCT TGTGTCTTTT GTGGCACCAG GCAAGAATGT AGCAGCGTCA    7620

GCAGCCCCTC TGGTGACTGT GGCATGGTTG ACATTCATTT CCCCCCTAAT TAATGGCATC    7680

CTCATGATTC TCTTTTATAT TAATAGTTCT TGAGTTTTTT TGTAAGCTAC TTCAAATCCT    7740
```

-continued

```
TTGTTGGTGC AAGATAGAAG ATATTTTATG TGTTTGTTTT GCATGTGCAC ACACATATTT   7800

GGCCTGTGAA TTGATGTTTG TTTTCCTGTC ATTTAACCAA AGCACATGAG ATAATTGAGC   7860

CATTGCAGAG ACCCCGTGGT TAAATCCGGC TTCTCGAGGT ACCAAGGACA TTTCCTGGGC   7920

TTTCTCACAG CCCTACATAT TTTTGAACCT AAAATATCGT AGTTTATGCT ACCACCCTGT   7980

TCAGTATAGT AGCCACTAGC CACATGTGGC TGTTGACCAC TTGAAATATG GCTAATGCTC   8040

TAAGTATAAA GTACACACTG GAATTTAAGA AGTGTAGAAT ATCTCAAAAC TTTTTTATAT   8100

TGATTACACA TTAAAATGAT TATATTCCAG ATATATGCAG TTGACTCAAG CAATGCATGG   8160

CTGAGAGGCA CCGACTCCCT GTGCAGTTGA AAATCCGAGT ATAACTTGAC TCCCCAAAAA   8220

CTTAACTACT AATAGCCTAC CTATCGGTTG ACTGTTGACT GCAGCCTTAC CAATAAGATA   8280

AACAGTCAAT TAACACACAT TTTTCATGTT GCGTGTATTA TATACTGTAT TCTTACAATA   8340

AAGTAAGCTA GAGGAAAGAA AATGTTATTA AGAAAATTAT AAGGAAAAGA GGCTGGGCAT   8400

GGTGGCTCGT GCCTGTAATC TCAGAACTTT GGGATGCTAA GGCGGGTGGA TCACTTGAGG   8460

TCAGGAGTTC AAGACCAGCC TGGCCAACAT GGTGAAACCC CATCTCTACT AAAAATACAA   8520

AAATTAGCCA GGCGTGGTTG TGGGTGCCTG TAATCCCAGC TACTTGGGAG GCTGAGGCAG   8580

GAGAATCACT TCGACCCAGG TGGAGGAGGT TGCAGTGAAC TGAGATTGCG CCACTGCACT   8640

CCGGCCTGGG TGACAGAGCG AGACTCTGTC TAAAAAAGAA AGGGAAAGAA AGAAAAAAAA   8700

GAAAAGAAAA GAAAAGAAAG AAGGAAGGAA GAGAAAGAAT TATAAGGAAG AGAAAATATA   8760

TTTACTATTG ATAAAGTGGA AGTGGATCAT CATAAAGGTG TTCATCCTCG TCATCTTCAT   8820

GTTGAGTAGG CTGAGGAGGA GGAGGAGGAG GAAGAGCAGG GGCCACGGCA GGAGAAAAGA   8880

TGGAGGAAGT AGGAGGCGGC ACACTTGGTG TAACTTTTAT TTAAAAAAAT TTGCATACAA   8940

GTGGATCCAC AGAGTTCAAA CCCATGTTGT TCAGGGGTCA ACTGTCTTTG GTTAAATAAA   9000

ATATATTATT AAAATTAATT TCACCTGTTC CTTTTTACTT TTTCTAATGT GACTACTAGA   9060

AAACTTAAAA TGCATCTGA GGCTCCATTG TCTTCCCCTT GGGCCAGCAC TACCACAGAA   9120

TGTCTTAGGA TTCAGCTCCA GGCCGCCACG CCTGCTTCTT TCAGGGAGCT GGTTCTATGC   9180

ACATGTTTTA TATGAGAGAT AATTAAGTTG TCAATTGTGA TAACAAAACA GGATTTGACT   9240

TTGTACAGAA TTCTTTGGTT CCAACCAAGC TCATTTCCTT TGTTTCAGCA AACCTCGGAC   9300

AGCCAACAAT TCAGAGTTTT GAACAGGTGG GAACAAAAGT GAATGTGACC GTAGAAGATG   9360

AACGGACTTT AGTCAGAAGG AACAACACTT TCCTAAGCCT CCGGGATGTT TTTGGCAAGG   9420

ACTTAATTTA TACACTTTAT TATTGGAAAT CTTCAAGTTC AGGAAAGGTG AGCATTTTTT   9480

AATTTGTTTT TATGACCTGT TTTAAATTGT GAATACTTGG TTTTACAACC CATTTCTTCC   9540

CCAATTCAAA AATAGCAGAA CAGAGTTGTT GAGAAGGTGA TGGAGTAGAA GGGGGAGCGC   9600

GCACTGTGGG GAGGGGTGGA CAACAGGCCT GGTCCTACCT GTGACTCTGC ACTACCCTGT   9660

GACTCTGGCA GGGCCCCCTC GGAGACCCAG GTTCCTCAGC CAACCGGCTG GATCAGGTCA   9720

TCTCTAAAGG TCCCGCCACG CTCACATTTC TCCCTCTATT GAGGATCCCA GGCACAAAAT   9780

TTGTTTTTGG TTCAATGCAT AATACTCCCT TCCTTTTTCT TTTACTGCAG ATATCTTCTA   9840

AAGGGGCTCA ATAGGGTTCA ATATGCCTAA ATTGGATCTT CTCAGTCTTG GAAAAGGCAT   9900

TTTTAGCAGT GATCAAGGGA AACTGATTAG CGAAGTCACT TCTAATCCTT CACGTGTCAG   9960

CTGTGTTCTT GTAGGCTTTG CTTAGAACCT AGGTTTTTAC TTCCACAGTG ACTTAATAAA  10020

GGGGAAAGAA TTGACTCAGA GCCCAGATGA ATTAAGAACT CTATCTTTTT ACAGAAAACA  10080
```

```
GCCAAAACAA ACACTAATGA GTTTTTGATT GATGTGGATA AAGGAGAAAA CTACTGTTTC   10140
AGTGTTCAAG CAGTGATTCC CTCCCGAACA GTTAACCGGA AGAGTACAGA CAGCCCGGTA   10200
GAGTGTATGG GCCAGGAGAA AGGGGAATTC AGAGGTGAGT GGCTCTGCCA GCCATTTGCC   10260
TGGGGGTATG GGTGCTGTGG GTGACTTCTG GAGGAGTAGC TCCACCCTCA GGGCTGGGAT   10320
ATACTTCCTT GGTTAAATAT TCAGGAAAAC AAACTGCCTG GAGGTTTTTT GTTGTTATTT   10380
GTTTGTTTTG GTTTTGATTT TGCTTTGGTA CAAAAAAGAT TTTGGACATT TAGAAATGTT   10440
TCTGTGTTGA TTGTGCCCTT GTATTAGCAG GTGTTTTCTT GAGCACCTGT CATGTGCTAA   10500
GCCCTCTGCT GAGCACTGGA TACACAAACT GTGTTTAGGA TTTAGCAACA AGTCACAGAT   10560
TTCCCTGGGC ATTTTTTCAT GCTTAAATTC TAATTCTGGG GGTGGCTTCT GGACCAGCTG   10620
CAACAGGACA CAGTAGACAT TCGTGAGTAC CCACTGTGGG CTGTTGCCAC AGAGGCTGTA   10680
GAGTCTAACC CATCAAGGGA AGGGATTGAG TATATCAAAT ATACCCACAT GCATGCATGT   10740
GTGTATATGG CGGACACGTG TGTGTACATG CATGTGCATA TGTTGGGAGC TCAGGCCCAT   10800
TGTGCGAGGA ACAGTCCCTA ACCGGAAGTG CTGTGGGCCT TCAGACTCTT GCAGGAAGCT   10860
GCAAGCCTGT GTGTCTCGAT CCATGCCTTA CAGGGAAAGT ATTCTGAGTA CTTTCAGTGA   10920
AGAAAAGAGT CAGGGGATAT AAACGATGGC TTACGCTGGG TGTGGTGGCT CACGCCTGTA   10980
GTCCCTGCAC TTTGGGAGGC CCAGACAGGC AAATCACTTG AGGTCAGGAG TTTGGGACCA   11040
GCCTGGCCAA CATGGTAAAA GCCCATCTCT ACTCAAAATA CAAAAAGTAG CTGGGTGTGG   11100
TTGCACGTGT CTGTAGTCCC AGCTACTCAG GAGGTTGAGG CAGGAGAATT GCTTGAACCT   11160
GGGAGGCGGA GGCTGAAGTG AGCTGAGATT GGACCACTGT ACTCCAGCCT GGGTGACAGA   11220
GCGAGATTCC ATCTCAAAAA AAAAAAAAAG AAACAACGAA AAAGAAATG ATGGCTTAGC    11280
TCCATGTGAA GATGATATTT GAACATTTTA AAACACTTTA AATAAACTGT TCTCTCCTGT   11340
TTATTGCCAC TGACAGGAGA GGTTTCTCTT TACCTCTGGT CCTGCACCCC TCTGAGCCAT   11400
CCTACCCACA GCCTTCAGTC ATTGTCCTAA AGCCTAGCTC TAATTCCACT GCCTCTCCTT   11460
TTGTGCACAC ACACTTCTCT GCTTCCCTGG CCGTTCTCTA TCTTGGAGAG GCATTTCAAA   11520
CGCCACTTCC ACCAGAAGGC CTTGCTACTG CACCAACTAG TTACTATCTC TTCTTCACCC   11580
AAATCCTGGT AGCACTTTGG ATCTCCCACT TGCACTTAGG GTTCACCTTC CGTTATAATC   11640
ATTGCCATCA ATCTCAGCAT CGTTTTAGGC ACTTCTTTCC AGCCATTGTT CTTACCTCCA   11700
ACTACATATC TTTTCTGGAC TGTGCATTAT TCAGTTTATT AAATGCCCAT TAAATGTGTT   11760
TAGCCATTGT CAATTACTCT GAAACGTTCA GGTTTTGACA AATTCTTTCC TAATGTAAGT   11820
GTGGTGGAAA GAGTGAAAGA AAGTCAAATT GCACAAAAAT AGGATGGTGT AATTTGGGGT   11880
TATGCCGTCA ATTTTGTCCA CTGATAAATG GGATTTGAGC TCTCCAAGTT GACTAGATGC   11940
CCTTTATTTT TCAGAAATAT TCTACATCAT TGGAGCTGTG GTATTTGTGG TCATCATCCT   12000
TGTCATCATC CTGGCTATAT CTCTACACAA GTGTAGAAAG GCAGGAGTGG GGCAGAGCTG   12060
GAAGGAGAAC TCCCCACTGA ATGTTTCATA AAGGAAGCAC TGTTGGAGCT ACTGCAAATG   12120
CTATATTGCA CTGTGACCGA GAACTTTTAA GAGGATAGAA TACATGGAAA CGCAAATGAG   12180
TATTTCGGAG CATGAAGACC CTGGAGTTCA AAAAACTCTT GATATGACCT GTTATTACCA   12240
TTAGCATTCT GGTTTTGACA TCAGCATTAG TCACTTTGAA ATGTAACGAA TGGTACTACA   12300
ACCAATTCCA AGTTTTAATT TTTAACACCA TGGCACCTTT TGCACATAAC ATGCTTTAGA   12360
TCTTAAAAAA TCCTGGGTGG ACTTTTGAAA AGCTTTTTTT TTTTTTTTT TTTTTGAGAC    12480
GGAGTCTTGC TCTGTTGCCC AGGCTGGAGT GCAGTAGCAC GATCTCGGCT CACTGCACCC   12540
```

-continued

```
TCCGTCTCTC GGGTTCAAGC AATTGTCTGC CTCAGCCTCC CGAGTAGCTG GGATTACAGG   12600

TGCGCACTAC CACGCCAAGC TAATTTTTGT ATTTTTTAGT AGAGATGGGG TTTCACCATC   12660

TTGGCCAGGC TGGTCTTGAA TTCCTGACCT CAGGTGATCC ACCCACCTTG GCCTCCCAAA   12720

GTGCTAGTAT TATGGGCGTG AACCACCATG CCCAGCCGAA AAGCTTTTGA GGGGCTGACT   12780

TCAATCCATG TAGGAAAGTA AAATGGAAGG AAATTGGGTG CATTTCTAGG ACTTTTCTAA   12840

CATATGTCTA TAATATAGTG TTTAGGTTCT TTTTTTTTTC AGGAATACAT TTGGAAATTC   12900

AAAACAATTG GCAAACTTTG TATTAATGTG TTAAGTGCAG GAGACATTGG TATTCTGGGC   12960

ACCTTCCTAA TATGCTTTAC AATCTGCACT TTAACTGACT TAAGTGGCAT TAAACATTTG   13020

AGAGCTAACT ATATTTTTAT AAGACTACTA TACAAACTAC AGAGTTTATG ATTTAAGGTA   13080

CTTAAAGCTT CTATGGTTGA CATTGTATAT ATAATTTTTT AAAAAGGTTT TCTATATGGG   13140

GATTTTCTAT TTATGTAGGT AATATTGTTC TATTTGTATA TATTGAGATA ATTTATTTAA   13200

TATACTTTAA ATAAAGGTGA CTGGGAATTG TTACTGTTGT ACTTATTCTA TCTTCCATTT   13260

ATTATTTATG TACAATTTGG TGTTTGTATT AGCTCTACTA CAGTAAATGA CTGTAAAATT   13320

GTCAGTGGCT TACAACAACG TATCTTTTTC GCTTATAATA CATTTGGTG ACTGTAGGCT   13380

GACTGCACTT CTTCTCAATG TTTTCTCATT CTAGGATGCA AACCAATGGA GAAGCCCCTA   13440

ATTAGATCAG GGCAGAGGGA AAAACAAAAA ACTGGTAGAA ACCGGCAACC ACAGCTTCAA   13500

GCTTTAAGCC CATCTCCTAC ACTTCTGCTC TGTACGTGCC CATTGTCACT TCTGTTCACA   13560

TGCTACTGTC CCAAGCAAGT GACCAAGCCT GACAATACTT TGTCTACTGG AGTCACTGCA   13620

AGGCACATGA CGGGGCAGGG ATGTCGTCTT ACAGGGAAGA GAAAAGATAA TGCTCTCTAC   13680

TGCAGACTTG GAGAGATTTC TTCCCATTGG CAGTAGTTTG ACTAATTGGA GATGAGAAAA   13740

AAAGAAACAT TCTTGGGATG ATTGTATTGA AACAAAATTA GGTAAAAGGA CAATATAGGA   13800

TAGGGAGAGA TATAAGTGGA ATGAGATCTC TAGAGTCCAT TAAAAGCAAG CTAGATTGAG   13860

AGCTC                                                              13865
```

(2) INFORMATION FOR SEQ ID NO:12:

(i) SEQUENCE CHARACTERISTICS:
        (A) LENGTH: 295 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Met Glu Thr Pro Ala Trp Pro Arg Val Pro Arg Pro Glu Thr Ala Val
 1               5                  10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
```

```
            100                 105                 110
Gly Asn Val Glu Ser Thr Gly Ser Ala Gly Glu Pro Leu Tyr Glu Asn
                115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
                180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
                260                 265                 270

Ser Leu His Lys Cys Arg Lys Ala Gly Val Gly Gln Ser Trp Lys Glu
        275                 280                 285

Asn Ser Pro Leu Asn Val Ser
    290                 295

(2) INFORMATION FOR SEQ ID NO:13:

(i) SEQUENCE CHARACTERISTICS:
        (A) LENGTH: 894 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:13:

GGATGGGTTG GGAGCTCAAG TTTTGGGGCA GAAGGGAATT TTTTTTGGCA GCAGAGTGCA    60

AGCCCTGCCG CCAGGCAAAC TCTGCTCTTC CTCATCCTCA GAAGCACTTG CTCACTCTGC   120

TAAATCAAAG TGAAACGCAT GTTTACAGAA TATTGGTCCA AAAGGGTCTC AGCATCTCCC   180

ACTACCCAGG GTGCAGAGCC TCGGGCCGGC CTTGCTCCCC AAGAAGGGCT GACTGGGGCT   240

CTGTCCCCTC GCCCAGGGCT CGAGGTAGTG TTTACAGCCC TCATGAACAG CAAAGGCGTG   300

AGCCTCTTCG ACATCATCAA CCCTGAGATT ATCACTCGAG ATGTGAGTAC AAAGCCCCCC   360

TCACCAGCCC CTGTTCCTGG GGAGAGAGGC CCAGACAGGA TTCCTGGGGT GACTGGGGGC   420

TGTTGGGGAG ACAGACAGAG GGGCCTCTAC CAGCTTGGCT CCCTCCTGGT GGCCTGGGAG   480

TCAGCCCAGC TCGCCCCTCT CTCCTACTGC CCCTCCCTTC AGGGCTTCCT GCTGCTGCAG   540

ATGGACTTTG GCTTCCCTGA GCACCTGCTG GTGGATTTCC TCCAGAGCTT GAGCTAGAAG   600

TCTCCAAGGA GGTCGGGATG GGGCTTGTAG CAGAAGGCAA GCACCAGGCT CACAGCTGGA   660

ACCCTGGTGT CTCCTCCAGC GTGGTGGAAG TTGGGTTAGG AGTACGGAGA TGGAGATTGG   720

CTCCCAACTC CTCCCTATCC TAAAGGCCCA CTGGCATTAA AGTGCTGTAT CCAAGAGCTG   780

CGGAGTCCTT CTTCTGTGGC TGGCGGGTAG AGGGGGGGGG AAGGGATTGT CTCACCAGTG   840
```

CCGTCCACCT CTTTTCAGCC CTTCCAAGCA GCTGCCCCCA AACCCTCCAA GCTT          894

(2) INFORMATION FOR SEQ ID NO:14:

(i) SEQUENCE CHARACTERISTICS:
        (A) LENGTH: 493 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Met Leu Ala Ala Thr Val Leu Thr Leu Ala Leu Leu Gly Asn Ala His
 1               5                  10                  15

Ala Cys Ser Lys Gly Thr Ser His Glu Ala Gly Ile Val Cys Arg Ile
                20                  25                  30

Thr Lys Pro Ala Leu Leu Val Leu Asn His Glu Thr Ala Lys Val Ile
            35                  40                  45

Gln Thr Ala Phe Gln Arg Ala Ser Tyr Pro Asp Ile Thr Gly Glu Lys
        50                  55                  60

Ala Met Met Leu Leu Gly Gln Val Lys Tyr Gly Leu His Asn Ile Gln
65                  70                  75                  80

Ile Ser His Leu Ser Ile Ala Ser Ser Gln Val Glu Leu Val Glu Ala
                85                  90                  95

Lys Ser Ile Asp Val Ser Ile Gln Asn Val Ser Val Val Phe Lys Gly
                100                 105                 110

Thr Leu Lys Tyr Gly Tyr Thr Thr Ala Trp Trp Leu Gly Ile Asp Gln
            115                 120                 125

Ser Ile Asp Phe Glu Ile Asp Ser Ala Ile Asp Leu Gln Ile Asn Thr
        130                 135                 140

Gln Leu Thr Cys Asp Ser Gly Arg Val Arg Thr Asp Ala Pro Asp Cys
145                 150                 155                 160

Tyr Leu Ser Phe His Lys Leu Leu His Leu Gln Gly Glu Arg Glu
                165                 170                 175

Pro Gly Trp Ile Lys Gln Leu Phe Thr Asn Phe Ile Ser Phe Thr Leu
            180                 185                 190

Lys Leu Val Leu Lys Gly Gln Ile Cys Lys Glu Ile Asn Val Ile Ser
        195                 200                 205

Asn Ile Met Ala Asp Phe Val Gln Thr Arg Ala Ala Ser Ile Leu Ser
    210                 215                 220

Asp Gly Asp Ile Gly Val Asp Ile Ser Leu Thr Gly Asp Pro Val Ile
225                 230                 235                 240

Thr Ala Ser Tyr Leu Glu Ser His His Lys Gly His Phe Ile Tyr Lys
                245                 250                 255

Asn Val Ser Glu Asp Leu Pro Leu Pro Thr Phe Ser Pro Thr Leu Leu
                260                 265                 270

Gly Asp Ser Arg Met Leu Tyr Phe Trp Phe Ser Glu Arg Val Phe His
            275                 280                 285

Ser Leu Ala Lys Val Ala Phe Gln Asp Gly Arg Leu Met Leu Ser Leu
        290                 295                 300

Met Gly Asp Glu Phe Lys Ala Val Leu Glu Thr Trp Gly Phe Asn Thr
305                 310                 315                 320

Asn Gln Glu Ile Phe Gln Glu Val Gly Gly Phe Pro Ser Gln Ala
                325                 330                 335

Gln Val Thr Val His Cys Leu Lys Met Pro Lys Ile Ser Cys Gln Asn
```

```
                        340                 345                 350
Lys Gly Val Val Asn Ser Ser Val Met Val Lys Phe Leu Phe Pro
        355                 360                 365

Arg Pro Asp Gln Gln His Ser Val Ala Tyr Thr Phe Glu Glu Asp Ile
    370                 375                 380

Val Thr Thr Val Gln Ala Ser Tyr Ser Lys Lys Leu Phe Leu Ser
385                 390                 395                 400

Leu Leu Asp Phe Gln Ile Thr Pro Lys Thr Val Ser Asn Leu Thr Glu
                405                 410                 415

Ser Ser Ser Glu Ser Val Gln Ser Phe Leu Gln Ser Met Ile Thr Ala
                420                 425                 430

Val Gly Ile Pro Glu Val Met Ser Arg Leu Glu Val Val Phe Thr Ala
        435                 440                 445

Leu Met Asn Ser Lys Gly Val Ser Leu Phe Asp Ile Ile Asn Pro Glu
    450                 455                 460

Ile Ile Thr Arg Asp Gly Phe Leu Leu Leu Gln Met Asp Gly Phe
465                 470                 475                 480

Pro Glu His Leu Leu Val Asp Phe Leu Gln Ser Leu Ser
                485                 490
```

(2) INFORMATION FOR SEQ ID NO:15:

(i) SEQUENCE CHARACTERISTICS:
        (A) LENGTH: 1431 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 133...1044
        (D) OTHER INFORMATION:

(xi) SEQUENCE DESCRIPTION: SEQ ID NO:15:

```
GGCGGGTCTG CTTCTAAAAG AAGAAGTAGA GAAGATAAAT CCTGTCTTCA ATACCTGGAA      60

GGAAAAACAA AATAACCTCA ACTCCGTTTT GAAAAAAACA TTCCAAGAAC TTTCATCAGA    120

GATTTTACTT AG ATG ATT TAC ACA ATG AAG AAA GTA CAT GCA CTT TGG GCT    171
              Met Ile Tyr Thr Met Lys Lys Val His Ala Leu Trp Ala
                1               5                  10

TCT GTA TGC CTG CTG CTT AAT CTT GCC CCT GCC CCT CTT AAT GCT GAT      219
Ser Val Cys Leu Leu Leu Asn Leu Ala Pro Ala Pro Leu Asn Ala Asp
    15                  20                  25

TCT GAG GAA GAT GAA GAA CAC ACA ATT ATC ACA GAT ACG GAG TTG CCA      267
Ser Glu Glu Asp Glu Glu His Thr Ile Ile Thr Asp Thr Glu Leu Pro
30                  35                  40                  45

CCA CTG AAA CTT ATG CAT TCA TTT TGT GCA TTC AAG GCG GAT GAT GGC      315
Pro Leu Lys Leu Met His Ser Phe Cys Ala Phe Lys Ala Asp Asp Gly
                50                  55                  60

CCA TGT AAA GCA ATC ATG AAA AGA TTT TTC TTC AAT ATT TTC ACT CGA      363
Pro Cys Lys Ala Ile Met Lys Arg Phe Phe Phe Asn Ile Phe Thr Arg
            65                  70                  75

CAG TGC GAA GAA TTT ATA TAT GGG GGA TGT GAA GGA AAT CAG AAT CGA      411
Gln Cys Glu Glu Phe Ile Tyr Gly Gly Cys Glu Gly Asn Gln Asn Arg
        80                  85                  90

TTT GAA AGT CTG GAA GAG TGC AAA AAA ATG TGT ACA AGA GAT AAT GCA      459
Phe Glu Ser Leu Glu Glu Cys Lys Lys Met Cys Thr Arg Asp Asn Ala
    95                 100                 105
```

```
AAC AGG ATT ATA AAG ACA ACA TTG CAA CAA GAA AAG CCA GAT TTC TGC    507
Asn Arg Ile Ile Lys Thr Thr Leu Gln Gln Glu Lys Pro Asp Phe Cys
110             115                 120                 125

TTT TTG GAA GAA GAT CCT GGA ATA TGT CGA GGT TAT ATT ACC AGG TAT    555
Phe Leu Glu Glu Asp Pro Gly Ile Cys Arg Gly Tyr Ile Thr Arg Tyr
                130                 135                 140

TTT TAT AAC AAT CAG ACA AAA CAG TGT GAA CGT TTC AAG TAT GGT GGA    603
Phe Tyr Asn Asn Gln Thr Lys Gln Cys Glu Arg Phe Lys Tyr Gly Gly
            145                 150                 155

TGC CTG GGC AAT ATG AAC AAT TTT GAG ACA CTG GAA GAA TGC AAG AAC    651
Cys Leu Gly Asn Met Asn Asn Phe Glu Thr Leu Glu Glu Cys Lys Asn
        160                 165                 170

ATT TGT GAA GAT GGT CCG AAT GGT TTC CAG GTG GAT AAT TAT GGA ACC    699
Ile Cys Glu Asp Gly Pro Asn Gly Phe Gln Val Asp Asn Tyr Gly Thr
    175                 180                 185

CAG CTC AAT GCT GTG AAT AAC TCC CTG ACT CCG CAA TCA ACC AAG GTT    747
Gln Leu Asn Ala Val Asn Asn Ser Leu Thr Pro Gln Ser Thr Lys Val
190                 195                 200                 205

CCC AGC CTT TTT GAA TTT CAC GGT CCC TCA TGG TGT CTC ACT CCA GCA    795
Pro Ser Leu Phe Glu Phe His Gly Pro Ser Trp Cys Leu Thr Pro Ala
                210                 215                 220

GAC AGA GGA TTG TGT CGT GCC AAT GAG AAC AGA TTC TAC TAC AAT TCA    843
Asp Arg Gly Leu Cys Arg Ala Asn Glu Asn Arg Phe Tyr Tyr Asn Ser
            225                 230                 235

GTC ATT GGG AAA TGC CGC CCA TTT AAG TAC AGT GGA TGT GGG GGA AAT    891
Val Ile Gly Lys Cys Arg Pro Phe Lys Tyr Ser Gly Cys Gly Gly Asn
        240                 245                 250

GAA AAC AAT TTT ACT TCC AAA CAA GAA TGT CTG AGG GCA TGT AAA AAA    939
Glu Asn Asn Phe Thr Ser Lys Gln Glu Cys Leu Arg Ala Cys Lys Lys
    255                 260                 265

GGT TTC ATC CAA AGA ATA TCA AAA GGA GGC CTA ATT AAA ACC AAA AGA    987
Gly Phe Ile Gln Arg Ile Ser Lys Gly Gly Leu Ile Lys Thr Lys Arg
270                 275                 280                 285

AAA AGA AAG AAG CAG AGA GTG AAA ATA GCA TAT GAA GAA ATT TTT GTT    1035
Lys Arg Lys Lys Gln Arg Val Lys Ile Ala Tyr Glu Glu Ile Phe Val
                290                 295                 300

AAA AAT ATG TGAATTTGTT ATAGCAATGT AACATTAATT CTACTAAATA            1084
Lys Asn Met

TTTTATATGA AATGTTTCAC TATGATTTTC TATTTTTCTT CTAAAATCGT TTAATTAAT   1144

ATGTTCATTA AATTTTCTAT GCTTATTGTA CTTGTTATCA ACACGTTTGT ATCAGAGTTG  1204

CTTTTCTAAT CTTGTTAAAT TGCTTATTCT AGGTCTGTAA TTTATTAACT GGCTACTGGG  1264

AAATTACTTA TTTTCTGGAT CTATCTGTAT TTTCATTTAA CTACAAATTA TCATACTACC  1324

GGCTACATCA AATCAGTCCT TGATTCCAT TTGGTGACCA TCTGTTTGAG AATATGATCA   1384

TGTAAATGAT TATCTCCTTT ATAGCCTGTA ACCAGATTAA GCCCCCC               1431
```

(2) INFORMATION FOR SEQ ID NO:16:

(i) SEQUENCE CHARACTERISTICS:
        (A) LENGTH: 304 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:16:

Met Ile Tyr Thr Met Lys Lys Val His Ala Leu Trp Ala Ser Val Cys

|   |   |   |   |   |   |   |   |   |   |   |   |   |   |   |   |
|---|---|---|---|---|---|---|---|---|---|---|---|---|---|---|---|
| 1 |   |   |   | 5 |   |   |   |   | 10 |   |   |   |   | 15 |   |
| Leu | Leu | Leu | Asn | Leu | Ala | Pro | Ala | Pro | Leu | Asn | Ala | Asp | Ser | Glu | Glu |
|   |   |   |   |   | 20 |   |   |   |   | 25 |   |   |   |   | 30 |
| Asp | Glu | Glu | His | Thr | Ile | Ile | Thr | Asp | Thr | Glu | Leu | Pro | Pro | Leu | Lys |
|   |   |   | 35 |   |   |   |   | 40 |   |   |   |   | 45 |   |   |
| Leu | Met | His | Ser | Phe | Cys | Ala | Phe | Lys | Ala | Asp | Asp | Gly | Pro | Cys | Lys |
|   | 50 |   |   |   |   | 55 |   |   |   |   | 60 |   |   |   |   |
| Ala | Ile | Met | Lys | Arg | Phe | Phe | Phe | Asn | Ile | Phe | Thr | Arg | Gln | Cys | Glu |
| 65 |   |   |   |   | 70 |   |   |   |   | 75 |   |   |   |   | 80 |
| Glu | Phe | Ile | Tyr | Gly | Gly | Cys | Glu | Gly | Asn | Gln | Asn | Arg | Phe | Glu | Ser |
|   |   |   |   | 85 |   |   |   |   | 90 |   |   |   |   | 95 |   |
| Leu | Glu | Glu | Cys | Lys | Lys | Met | Cys | Thr | Arg | Asp | Asn | Ala | Asn | Arg | Ile |
|   |   |   | 100 |   |   |   |   | 105 |   |   |   |   | 110 |   |   |
| Ile | Lys | Thr | Thr | Leu | Gln | Gln | Glu | Lys | Pro | Asp | Phe | Cys | Phe | Leu | Glu |
|   |   |   | 115 |   |   |   |   | 120 |   |   |   |   | 125 |   |   |
| Glu | Asp | Pro | Gly | Ile | Cys | Arg | Gly | Tyr | Ile | Thr | Arg | Tyr | Phe | Tyr | Asn |
|   |   | 130 |   |   |   |   | 135 |   |   |   |   | 140 |   |   |   |
| Asn | Gln | Thr | Lys | Gln | Cys | Glu | Arg | Phe | Lys | Tyr | Gly | Gly | Cys | Leu | Gly |
| 145 |   |   |   |   | 150 |   |   |   |   | 155 |   |   |   |   | 160 |
| Asn | Met | Asn | Asn | Phe | Glu | Thr | Leu | Glu | Glu | Cys | Lys | Asn | Ile | Cys | Glu |
|   |   |   |   | 165 |   |   |   |   | 170 |   |   |   |   | 175 |   |
| Asp | Gly | Pro | Asn | Gly | Phe | Gln | Val | Asp | Asn | Tyr | Gly | Thr | Gln | Leu | Asn |
|   |   |   | 180 |   |   |   |   | 185 |   |   |   |   | 190 |   |   |
| Ala | Val | Asn | Asn | Ser | Leu | Thr | Pro | Gln | Ser | Thr | Lys | Val | Pro | Ser | Leu |
|   |   | 195 |   |   |   |   | 200 |   |   |   |   | 205 |   |   |   |
| Phe | Glu | Phe | His | Gly | Pro | Ser | Trp | Cys | Leu | Thr | Pro | Ala | Asp | Arg | Gly |
|   | 210 |   |   |   |   | 215 |   |   |   |   | 220 |   |   |   |   |
| Leu | Cys | Arg | Ala | Asn | Glu | Asn | Arg | Phe | Tyr | Tyr | Asn | Ser | Val | Ile | Gly |
| 225 |   |   |   | 230 |   |   |   |   | 235 |   |   |   |   | 240 |   |
| Lys | Cys | Arg | Pro | Phe | Lys | Tyr | Ser | Gly | Cys | Gly | Gly | Asn | Glu | Asn | Asn |
|   |   |   | 245 |   |   |   |   | 250 |   |   |   |   | 255 |   |   |
| Phe | Thr | Ser | Lys | Gln | Glu | Cys | Leu | Arg | Ala | Cys | Lys | Lys | Gly | Phe | Ile |
|   |   | 260 |   |   |   |   | 265 |   |   |   |   | 270 |   |   |   |
| Gln | Arg | Ile | Ser | Lys | Gly | Gly | Leu | Ile | Lys | Thr | Lys | Arg | Lys | Arg | Lys |
|   |   | 275 |   |   |   |   | 280 |   |   |   |   | 285 |   |   |   |
| Lys | Gln | Arg | Val | Lys | Ile | Ala | Tyr | Glu | Glu | Ile | Phe | Val | Lys | Asn | Met |
|   | 290 |   |   |   |   | 295 |   |   |   |   | 300 |   |   |   |   |

(2) INFORMATION FOR SEQ ID NO:17:

(i) SEQUENCE CHARACTERISTICS:
        (A) LENGTH: 1366 base pairs
        (B) TYPE: nucleic acid
        (C) STRANDEDNESS: single
        (D) TOPOLOGY: linear (ii) MOLECULE TYPE: Genomic DNA (ix) FEATURE:

(xi) SEQUENCE DESCRIPTION: SEQ ID NO:17:

```
CCAAGGGCAC GGCACGTGCA TCGACGGCAT CGGCAGCTTC AGCTGCGACT GCCGCAGCGG    60

CTGGGAGGGC CGCTTCTGCC AGCGCGAGGT GAGCTTCCTC AATTGCTCTC TGGACAACGG   120

CGGCTGCACG CATTACTGCC TAGAGGAGGT GGGCTGGCGG CGCTGTAGCT GTGCGCCTGG   180

CTACAAGCTG GGGGACGACC TCCTGCAGTG TCACCCCGCA GTGAAGTTCC CTTGTGGGAG   240
```

```
GCCCTGGAAG CGGATGGAGA AGAAGCGCAG TCACCTGAAA CGAGACACAG AAGACCAAGA    300

AGACCAAGTA GATCCGCGGC TCATTGATGG GAAGATGACC AGGCGGGGAG ACAGCCCCTG    360

GCAGGTGGTC CTGCTGGACT CAAAGAAGAA GCTGGCCTGC GGGGCAGTGC TCATCCACCC    420

CTCCTGGGTG CTGACAGCGG CCCACTGCAT GGACGAGTCC AAGAAGCTCC TTGTCAGGCT    480

TGGAGAGTAT GACCTGCGGC GCTGGGAGAA GTGGGAGCTG GACCTGGACA TCAAGGAGGT    540

CTTCGTCCAC CCCAACTACA GCAAGAGCAC CACCGACAAT GACATCGCAC TGCTGCACCT    600

GGCCCAGCCC GCCACCCTCT CGCAGACCAT AGTGCCCATC TGCCTCCCGG ACAGCGGCCT    660

TGCAGAGCGC GAGCTCAATC AGGCCGGCCA GGAGACCCTC GTGACGGGCT GGGGCTACCA    720

CAGCAGCCGA GAGAAGGAGG CCAAGAGAAA CCGCACCTTC GTCCTCAACT TCATCAAGAT    780

TCCCGTGGTC CCGCACAATG AGTGCAGCGA GGTCATGAGC AACATGGTGT CTGAGAACAT    840

GCTGTGTGCG GCATCCTCG GGACCGGCA GGATGCCTGC GAGGGCGACA GTGGGGGGCC    900

CATGGTCGCC TCCTTCCACG GCACCTGGTT CCTGGTGGGC CTGGTGAGCT GGGGTGAGGG    960

CTGTGGGCTC CTTCACAACT ACGGCGTTTA CACCAAAGTC AGCCGCTACC TCGACTGGAT    1020

CCATGGGCAC ATCAGAGACA AGGAAGCCCC CCAGAAGAGC TGGGCACCTT AGCGACCCTC    1080

CCTGCAGGGC TGGGCTTTTG CATGGCAATG GATGGGACAT TAAAGGGACA TGTAACAAGC    1140

ACACCGGCCT GCTGTTCTGT CCTTCCATCC CTCTTTTGGG CTCTTCTGGA GGGAAGTAAC    1200

ATTTACTGAG CACCTGTTGT ATGTCACATG CCTTATGAAT AGAATCTTAA CTCCAGAGC    1260

AACTCTGTCG GGTGGGAGG AGCAGATCCA AGTTTTGCGG GGTCTAAAGC TGTGTGTGTT    1320

GAGGGGGATA CTCTGTTTAT GAAAAAGAAT AAAAAACACA ACCACG                  1366
```

(2) INFORMATION FOR SEQ ID NO:18:

(i) SEQUENCE CHARACTERISTICS:
        (A) LENGTH: 356 amino acids
        (B) TYPE: amino acid
        (C) STRANDEDNESS: single
        (D) TOPOLOGY: linear (xi) SEQUENCE DESCRIPTION: SEQ ID NO:18:

```
Gln Gly His Gly Thr Cys Ile Asp Gly Ile Gly Ser Phe Ser Cys Asp
 1               5                  10                  15

Cys Arg Ser Gly Trp Glu Gly Arg Phe Cys Gln Arg Glu Val Ser Phe
            20                  25                  30

Leu Asn Cys Ser Leu Asp Asn Gly Gly Cys Thr His Tyr Cys Leu Glu
        35                  40                  45

Glu Val Gly Trp Arg Arg Cys Ser Cys Ala Pro Gly Tyr Lys Leu Gly
    50                  55                  60

Asp Asp Leu Leu Gln Cys His Pro Ala Val Lys Phe Pro Cys Gly Arg
65                  70                  75                  80

Pro Trp Lys Arg Met Glu Lys Lys Arg Ser His Leu Lys Arg Asp Thr
                85                  90                  95

Glu Asp Gln Glu Asp Gln Val Asp Pro Arg Leu Ile Asp Gly Lys Met
            100                 105                 110

Thr Arg Arg Gly Asp Ser Pro Trp Gln Val Val Leu Leu Asp Ser Lys
        115                 120                 125

Lys Lys Leu Ala Cys Gly Ala Val Leu Ile His Pro Ser Trp Val Leu
    130                 135                 140

Thr Ala Ala His Cys Met Asp Glu Ser Lys Leu Leu Val Arg Leu
145                 150                 155                 160
```

```
Gly Glu Tyr Asp Leu Arg Arg Trp Glu Lys Trp Glu Leu Asp Leu Asp
                165                 170                 175

Ile Lys Glu Val Phe Val His Pro Asn Tyr Ser Lys Ser Thr Thr Asp
            180                 185                 190

Asn Asp Ile Ala Leu Leu His Leu Ala Gln Pro Ala Thr Leu Ser Gln
        195                 200                 205

Thr Ile Val Pro Ile Cys Leu Pro Asp Ser Gly Leu Ala Glu Arg Glu
    210                 215                 220

Leu Asn Gln Ala Gly Gln Glu Thr Leu Val Thr Gly Trp Gly Tyr His
225                 230                 235                 240

Ser Ser Arg Glu Lys Glu Ala Lys Arg Asn Arg Thr Phe Val Leu Asn
                245                 250                 255

Phe Ile Lys Ile Pro Val Val Pro His Asn Glu Cys Ser Glu Val Met
            260                 265                 270

Ser Asn Met Val Ser Glu Asn Met Leu Cys Ala Gly Ile Leu Gly Asp
        275                 280                 285

Arg Gln Asp Ala Cys Glu Gly Asp Ser Gly Gly Pro Met Val Ala Ser
    290                 295                 300

Phe His Gly Thr Trp Phe Leu Val Gly Leu Val Ser Trp Gly Glu Gly
305                 310                 315                 320

Cys Gly Leu Leu His Asn Tyr Gly Val Tyr Thr Lys Val Ser Arg Tyr
                325                 330                 335

Leu Asp Trp Ile His Gly His Ile Arg Asp Lys Glu Ala Pro Gln Lys
            340                 345                 350

Ser Trp Ala Pro
        355

(2) INFORMATION FOR SEQ ID NO:19:

(i) SEQUENCE CHARACTERISTICS:
        (A) LENGTH: 144 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:19:

TTTCCTCTCT CTCAGTGGGC GACAGATGTG AAAGAAACGA GTTCCAGTGC CAAGACGGGA      60

AATGCATCTC CTACAAGTGG GTCTGCGATG GCAGCGCTGA GTGCCAGGAT GGCTCTGATG     120

AGTCCCAGGA GACGTGCTGT GAGT                                           144

(2) INFORMATION FOR SEQ ID NO:20:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:20:

CATCCATCCC TGCAGCCCCC AAGACGTGCT CCCAGGACGA GTTTCGCTGC CACGATGGGA      60

AGTGCATCTC TCGGCAGTTC GTCTGTGACT CAGACCGGGA CTGCTTGGAC GGCTCAGACG     120

AGGCCTCCTG CCCCGGTGCTC ACCTGTGGTC CCGCCAGCTT CCAGTGCAAC AGCTCCACCT     180

GCATCCCCCA GCTGTGGGCC TGCGACAACG ACCCCGACTG CGAAGATGGC TCGGATGAGT     240
```

```
GGCCGCAGCG CTGTAGGGGT CTTTACGTGT TCCAAGGGGA CAGTAGCCCC TGCTCGGCCT      300

TCGAGTTCCA CTGCCTAAGT GGCGAGTGCA TCCACTCCAG CTGGCGCTGT GATGGTGGCC      360

CCGACTGCAA GGACAAATCT GACGAGGAAA ACTGCGGTAT GG                         402
```

(2) INFORMATION FOR SEQ ID NO:21:

(i) SEQUENCE CHARACTERISTICS:
        (A) LENGTH: 193 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:21:

```
TCCCCGGACC CCCAGGCTCC ATCGCCTACC TCTTCTTCAC CAACCGGCAC GAGGTCAGGA       60

AGATGACGCT GGACCGGAGC GAGTACACCA GCCTCATCCC CAACCTGAGG AACGTGGTCG      120

CTCTGGACAC GGAGGTGGCC AGCAATAGAA TCTACTGGTC TGACCTGTCC CAGAGAATGA      180

TCTGCAGGTG AGC                                                         193
```

(2) INFORMATION FOR SEQ ID NO:22:

(i) SEQUENCE CHARACTERISTICS:
        (A) LENGTH: 249 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:22:

```
CTCCTCCTGC CTCAGCACCC AGCTTGACAG AGCCCACGGC GTCTCTTCCT ATGACACCGT       60

CATCAGCAGG GACATCCAGG CCCCCGACGG GCTGGCTGTG GACTGGATCC ACAGCAACAT      120

CTACTGGACC GACTCTGTCC TGGGCACTGT CTCTGTTGCG GATACCAAGG GCGTGAAGAG      180

GAAAACGTTA TTCAGGGAGA ACGGCTCCAA GCCAAGGGCC ATCGTGGTGG ATCCTGTTCA      240

TGGGTGCGT                                                              249
```

(2) INFORMATION FOR SEQ ID NO:23:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:23:

```
CTGTCCTCCC ACCAGCTTCA TGTACTGGAC TGACTGGGGA ACTCCCGCCA AGATCAAGAA       60

AGGGGGCCTG AATGGTGTGG ACATCTACTC GCTGGTGACT GAAAACATTC AGTGGCCCAA      120

TGGCATCACC CTAGGTATGT                                                  140
```

(2) INFORMATION FOR SEQ ID NO:24:

(i) SEQUENCE CHARACTERISTICS:
        (A) LENGTH: 163 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:24:

```
TTGCTGCCTG TTTAGGACAA AGTATTTTGG ACAGATATCA TCAACGAAGC CATTTTCAGT     60

GCCAACCGCC TCACAGGTTC CGATGTCAAC TTGTTGGCTG AAAACCTACT GTCCCCAGAG    120

GATATGGTCC TCTTCCACAA CCTCACCCAG CCAAGAGGTA AGG                      163
```

(2) INFORMATION FOR SEQ ID NO:25:

(i) SEQUENCE CHARACTERISTICS:
        (A) LENGTH: 192 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:25:

```
TATTTATTCT TTCAGAGGCT GAGGCTGCAG TGGCCACCCA GGAGACATCC ACCGTCAGGC     60

TAAAGGTCAG CTCCACAGCC GTAAGGACAC AGCACACAAC CACCCGGCCT GTTCCCGACA    120

CCTCCCGGCT GCCTGGGGCC ACCCCTGGGC TCACCACGGT GGAGATAGTG ACAATGTCTC    180

ACCAAGGTAA AG                                                        192
```

(2) INFORMATION FOR SEQ ID NO:26:

(i) SEQUENCE CHARACTERISTICS:
        (A) LENGTH: 179 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:26:

```
TGCCTCTCCC TACAGTGCTC CTCGTCTTCC TTTGCCTGGG GGTCTTCCTT CTATGGAAGA     60

ACTGGCGGCT TAAGAACATC AACAGCATCA ACTTTGACAA CCCCGTCTAT CAGAAGACCA    120

CAGAGGATGA GGTCCACATT TGCCACAACC AGGACGGCTA CAGCTACCCC TCGGTGAGT    179
```

(2) INFORMATION FOR SEQ ID NO:27:

(i) SEQUENCE CHARACTERISTICS:
        (A) LENGTH: 769 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:27:

```
GGATCCCACA AAACAAAAAA TATTTTTTTG GCTGTACTTT TGTGAAGATT TTATTTAAAT     60

TCCTGATTGA TCAGTGTCTA TTAGGTGATT TGGAATAACA ATGTAAAAAC AATATACAAC    120

GAAAGGAAGC TAAAAATCTA TACACAATTC CTAGAAAGGA AAAGGCAAAT ATAGAAAGTG    180

GCGGAAGTTC CCAACATTTT TAGTGTTTTC CTTTTGAGGC AGAGAGGACA ATGGCATTAG    240

GCTATTGGAG GATCTTGAAA GGCTGTTGTT ATCCTTCTGT GGACAACAAC AGCAAAATGT    300

TAACAGTTAA ACATCGAGAA ATTTCAGGAG GATCTTTCAG AAGATGCGTT TCCAATTTTG    360

AGGGGGCGTC AGCTCTTCAC CGGAGACCCA AATACAACAA ATCAAGTCGC CTGCCCTGGC    420

GACACTTTCG AAGGACTGGA GTGGGAATCA GAGCTTCACG GGTTAAAAGC CGATGTCACA    480

TCGGCCGTTC GAAACTCCTC CTCTTGCAGT GAGGTGAAGA CATTTGAAAA TCACCCCACT    540
```

```
GCAAACTCCT CCCCCTGCTA GAAACCTCAC ATTGAAATGC TGTAAATGAC GTGGGCCCCG    600

AGTGCAATCG CGGGAAGCCA GGGTTTCCAG CTAGGACACA GCAGGTCGTG ATCCGGGTCG    660

GGACACTGCC TGGCAGAGGC TGCGAGCATG GGGCCCTGGG GCTGGAAATT GCGCTGGACC    720

GTCGCCTTGC TCCTCGCCGC GGCGGGGACT GCAGGTAAGG CTTGCTCCA                769
```

(2) INFORMATION FOR SEQ ID NO:28:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:28:

```
TCTGAGTTCT CTATTCTGTT CCATTGGTCT ATGCGTCTGT TCTTGTACCA GTACTATACT     60

GTTTTGTCCT CCAGAGGGCA GCAGACATCG AACAGCAGGC TGTGTTTGCT GTGTTTGATG    120

AGAACAAAAG CTGGTACCTT GAGGACAACA TCAACAAGTT TTGTGAAAAT CCTGATGAGG    180

TGAAACGTGA TGACCCCAAG TTTTATGAAT CAAACATCAT GAGCAGTAAG TCAGAGTACT    240

ATTTTTGTTC ATCAGTTTTT CATTCCTGTG GTTGAAATA                           279
```

(2) INFORMATION FOR SEQ ID NO:29:

(i) SEQUENCE CHARACTERISTICS:
        (A) LENGTH: 2904 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 51...2714
        (D) OTHER INFORMATION:

(xi) SEQUENCE DESCRIPTION: SEQ ID NO:29:

```
TTCGGTGGCC TCTAGTGAGA TCTGGAGGAT CCAAGGATTC TGTAGCTACA   ATG TTG       56
                                                        Met Leu
                                                          1

TCA AGA CTT TTT CGA ATG CAT GGC CTC TTT GTG GCC TCC CAT CCC TGG       104
Ser Arg Leu Phe Arg Met His Gly Leu Phe Val Ala Ser His Pro Trp
         5                  10                  15

GAA GTC ATA GTG GGG ACA GTG ACA CTG ACC ATC TGC ATG ATG TCC ATG       152
Glu Val Ile Val Gly Thr Val Thr Leu Thr Ile Cys Met Met Ser Met
 20                  25                  30

AAC ATG TTT ACT GGT AAC AAT AAG ATC TGT GGT TGG AAT TAT GAA TGT       200
Asn Met Phe Thr Gly Asn Asn Lys Ile Cys Gly Trp Asn Tyr Glu Cys
 35                  40                  45                  50

CCA AAG TTT GAA GAG GAT GTT TTG AGC AGT GAC ATT ATA ATT CTG ACA       248
Pro Lys Phe Glu Glu Asp Val Leu Ser Ser Asp Ile Ile Ile Leu Thr
                 55                  60                  65

ATA ACA CGA TGC ATA GCC ATC CTG TAT ATT TAC TTC CAG TTC CAG AAT       296
Ile Thr Arg Cys Ile Ala Ile Leu Tyr Ile Tyr Phe Gln Phe Gln Asn
             70                  75                  80

TTA CGT CAA CTT GGA TCA AAA TAT ATT TTG GGT ATT GCT GGC CTT TTC       344
Leu Arg Gln Leu Gly Ser Lys Tyr Ile Leu Gly Ile Ala Gly Leu Phe
         85                  90                  95

ACA ATT TTC TCA AGT TTT GTA TTC AGT ACA GTT GTC ATT CAC TTC TTA       392
```

```
Thr Ile Phe Ser Ser Phe Val Phe Ser Thr Val Val Ile His Phe Leu
    100                 105                 110

GAC AAA GAA TTG ACA GGC TTG AAT GAA GCT TTG CCC TTT TTC CTA CTT      440
Asp Lys Glu Leu Thr Gly Leu Asn Glu Ala Leu Pro Phe Phe Leu Leu
115                 120                 125                 130

TTG ATT GAC CTT TCC AGA GCA AGC ACA TTA GCA AAG TTT GCC CTC AGT      488
Leu Ile Asp Leu Ser Arg Ala Ser Thr Leu Ala Lys Phe Ala Leu Ser
                    135                 140                 145

TCC AAC TCA CAG GAT GAA GTA AGG GAA AAT ATT GCT CGT GGA ATG GCA      536
Ser Asn Ser Gln Asp Glu Val Arg Glu Asn Ile Ala Arg Gly Met Ala
                150                 155                 160

ATT TTA GGT CCT ACG TTT ACC CTC GAT GCT CTT GTT GAA TGT CTT GTG      584
Ile Leu Gly Pro Thr Phe Thr Leu Asp Ala Leu Val Glu Cys Leu Val
            165                 170                 175

ATT GGA GTT GGT ACC ATG TCA GGG GTA CGT CAG CTT GAA ATT ATG TGC      632
Ile Gly Val Gly Thr Met Ser Gly Val Arg Gln Leu Glu Ile Met Cys
        180                 185                 190

TGC TTT GGC TGC ATG TCA GTT CTT GCC AAC TAC TTC GTG TTC ATG ACT      680
Cys Phe Gly Cys Met Ser Val Leu Ala Asn Tyr Phe Val Phe Met Thr
195                 200                 205                 210

TTC TTC CCA GCT TGT GTG TCC TTG GTA TTA GAG CTT TCT CGG GAA AGC      728
Phe Phe Pro Ala Cys Val Ser Leu Val Leu Glu Leu Ser Arg Glu Ser
                    215                 220                 225

CGC GAG GGT CGT CCA ATT TGG CAG CTC AGC CAT TTT GCC CGA GTT TTA      776
Arg Glu Gly Arg Pro Ile Trp Gln Leu Ser His Phe Ala Arg Val Leu
                230                 235                 240

GAA GAA GAA GAA AAT AAG CCG AAT CCT GTA ACT CAG AGG GTC AAG ATG      824
Glu Glu Glu Glu Asn Lys Pro Asn Pro Val Thr Gln Arg Val Lys Met
            245                 250                 255

ATT ATG TCT CTA GGC TTG GTT CTT GTT CAT GCT CAC AGT CGC TGG ATA      872
Ile Met Ser Leu Gly Leu Val Leu Val His Ala His Ser Arg Trp Ile
260                 265                 270

GCT GAT CCT TCT CCT CAA AAC AGT ACA GCA GAT ACT TCT AAG GTT TCA      920
Ala Asp Pro Ser Pro Gln Asn Ser Thr Ala Asp Thr Ser Lys Val Ser
275                 280                 285                 290

TTA GGA CTG GAT GAA AAT GTG TCC AAG AGA ATT GAA CCA AGT GTT TCC      968
Leu Gly Leu Asp Glu Asn Val Ser Lys Arg Ile Glu Pro Ser Val Ser
                    295                 300                 305

CTC TGG CAG TTT TAT CTC TCT AAA ATG ATC AGC ATG GAT ATT GAA CAA     1016
Leu Trp Gln Phe Tyr Leu Ser Lys Met Ile Ser Met Asp Ile Glu Gln
                310                 315                 320

GTT ATT ACC CTA AGT TTA GCT CTC CTT CTG GCT GTC AAG TAC ATC TTC     1064
Val Ile Thr Leu Ser Leu Ala Leu Leu Leu Ala Val Lys Tyr Ile Phe
            325                 330                 335

TTT GAA CAA ACA GAG ACA GAA TCT ACA CTC TCA TTA AAA AAC CCT ATC     1112
Phe Glu Gln Thr Glu Thr Glu Ser Thr Leu Ser Leu Lys Asn Pro Ile
        340                 345                 350

ACA TCT CCT GTA GTG ACA CAA AAG AAA GTC CCA GAC AAT TGT TGT AGA     1160
Thr Ser Pro Val Val Thr Gln Lys Lys Val Pro Asp Asn Cys Cys Arg
355                 360                 365                 370

CGT GAA CCT ATG CTG GTC AGA AAT AAC CAG AAA TGT GAT TCA GTA GAG     1208
Arg Glu Pro Met Leu Val Arg Asn Asn Gln Lys Cys Asp Ser Val Glu
                    375                 380                 385

GAA GAG ACA GGG ATA AAC CGA GAA AGA AAA GTT GAG GTT ATA AAA CCC     1256
Glu Glu Thr Gly Ile Asn Arg Glu Arg Lys Val Glu Val Ile Lys Pro
                390                 395                 400

TTA GTG GCT GAA ACA GAT ACC CCA AAC AGA GCT ACA TTT GTG GTT GGT     1304
Leu Val Ala Glu Thr Asp Thr Pro Asn Arg Ala Thr Phe Val Val Gly
            405                 410                 415
```

| | | |
|---|---|---|
| AAC TCC TCC TTA CTC GAT ACT TCA TCA GTA CTG GTG ACA CAG GAA CCT<br>Asn Ser Ser Leu Leu Asp Thr Ser Ser Val Leu Val Thr Gln Glu Pro<br>420 425 430 | | 1352 |
| GAA ATT GAA CTT CCC AGG GAA CCT CGG CCT AAT GAA GAA TGT CTA CAG<br>Glu Ile Glu Leu Pro Arg Glu Pro Arg Pro Asn Glu Glu Cys Leu Gln<br>435 440 445 450 | | 1400 |
| ATA CTT GGG AAT GCA GAG AAA GGT GCA AAA TTC CTT AGT GAT GCT GAG<br>Ile Leu Gly Asn Ala Glu Lys Gly Ala Lys Phe Leu Ser Asp Ala Glu<br>455 460 465 | | 1448 |
| ATC ATC CAG TTA GTC AAT GCT AAG CAT ATC CCA GCC TAC AAG TTG GAA<br>Ile Ile Gln Leu Val Asn Ala Lys His Ile Pro Ala Tyr Lys Leu Glu<br>470 475 480 | | 1496 |
| ACT CTG ATG GAA ACT CAT GAG CGT GGT GTA TCT ATT CGC CGA CAG TTA<br>Thr Leu Met Glu Thr His Glu Arg Gly Val Ser Ile Arg Arg Gln Leu<br>485 490 495 | | 1544 |
| CTT TCC AAG AAG CTT TCA GAA CCT TCT TCT CTC CAG TAC CTA CCT TAC<br>Leu Ser Lys Lys Leu Ser Glu Pro Ser Ser Leu Gln Tyr Leu Pro Tyr<br>500 505 510 | | 1592 |
| AGG GAT TAT AAT TAC TCC TTG GTG ATG GGA GCT TGT TGT GAG AAT GTT<br>Arg Asp Tyr Asn Tyr Ser Leu Val Met Gly Ala Cys Cys Glu Asn Val<br>515 520 525 530 | | 1640 |
| ATT GGA TAT ATG CCC ATC CCT GTT GGA GTG GCA GGA CCC CTT TGC TTA<br>Ile Gly Tyr Met Pro Ile Pro Val Gly Val Ala Gly Pro Leu Cys Leu<br>535 540 545 | | 1688 |
| GAT GAA AAA GAA TTT CAG GTT CCA ATG GCA ACA ACA GAA GGT TGT CTT<br>Asp Glu Lys Glu Phe Gln Val Pro Met Ala Thr Thr Glu Gly Cys Leu<br>550 555 560 | | 1736 |
| GTG GCC AGC ACC AAT AGA GGC TGC AGA GCA ATA GGT CTT GGT GGA GGT<br>Val Ala Ser Thr Asn Arg Gly Cys Arg Ala Ile Gly Leu Gly Gly Gly<br>565 570 575 | | 1784 |
| GCC AGC AGC CGA GTC CTT GCA GAT GGG ATG ACT CGT GGC CCA GTT GTG<br>Ala Ser Ser Arg Val Leu Ala Asp Gly Met Thr Arg Gly Pro Val Val<br>580 585 590 | | 1832 |
| CGT CTT CCA CGT GCT TGT GAC TCT GCA GAA GTG AAA GCC TGG CTC GAA<br>Arg Leu Pro Arg Ala Cys Asp Ser Ala Glu Val Lys Ala Trp Leu Glu<br>595 600 605 610 | | 1880 |
| ACA TCT GAA GGG TTC GCA GTG ATA AAG GAG GCA TTT GAC AGC ACT AGC<br>Thr Ser Glu Gly Phe Ala Val Ile Lys Glu Ala Phe Asp Ser Thr Ser<br>615 620 625 | | 1928 |
| AGA TTT GCA CGT CTA CAG AAA CTT CAT ACA AGT ATA GCT GGA CGC AAC<br>Arg Phe Ala Arg Leu Gln Lys Leu His Thr Ser Ile Ala Gly Arg Asn<br>630 635 640 | | 1976 |
| CTT TAT ATC CGT TTC CAG TCC AGG TCA GGG GAT GCC ATG GGG ATG AAC<br>Leu Tyr Ile Arg Phe Gln Ser Arg Ser Gly Asp Ala Met Gly Met Asn<br>645 650 655 | | 2024 |
| ATG ATT TCA AAG GGT ACA GAG AAA GCA CTT TCA AAA CTT CAC GAG TAT<br>Met Ile Ser Lys Gly Thr Glu Lys Ala Leu Ser Lys Leu His Glu Tyr<br>660 665 670 | | 2072 |
| TTC CCT GAA ATG CAG ATT CTA GCC GTT AGT GGT AAC TAT TGT ACT GAC<br>Phe Pro Glu Met Gln Ile Leu Ala Val Ser Gly Asn Tyr Cys Thr Asp<br>675 680 685 690 | | 2120 |
| AAG AAA CCT GCT GCT ATA AAT TGG ATA GAG GGA AGA GGA AAA TCT GTT<br>Lys Lys Pro Ala Ala Ile Asn Trp Ile Glu Gly Arg Gly Lys Ser Val<br>695 700 705 | | 2168 |
| GTT TGT GAA GCT GTC ATT CCA GCC AAG GTT GTC AGA GAA GTA TTA AAG<br>Val Cys Glu Ala Val Ile Pro Ala Lys Val Val Arg Glu Val Leu Lys<br>710 715 720 | | 2216 |
| ACT ACC ACA GAG GCT ATG ATT GAG GTC AAC ATT AAC AAG AAT TTA GTG<br>Thr Thr Thr Glu Ala Met Ile Glu Val Asn Ile Asn Lys Asn Leu Val<br>725 730 735 | | 2264 |

```
GGC TCT GCC ATG GCT GGG AGC ATA GGA GGC TAC AAC GCC CAT GCA GCA        2312
Gly Ser Ala Met Ala Gly Ser Ile Gly Gly Tyr Asn Ala His Ala Ala
        740                 745                 750

AAC ATT GTC ACC GCC ATC TAC ATT GCC TGT GGA CAG GAT GCA GCA CAG        2360
Asn Ile Val Thr Ala Ile Tyr Ile Ala Cys Gly Gln Asp Ala Ala Gln
755                 760                 765                 770

AAT GTT GGT AGT TCA AAC TGT ATT ACT TTA ATG GAA GCA AGT GGT CCC        2408
Asn Val Gly Ser Ser Asn Cys Ile Thr Leu Met Glu Ala Ser Gly Pro
                775                 780                 785

ACA AAT GAA GAT TTA TAT ATC AGC TGC ACC ATG CCA TCT ATA GAG ATA        2456
Thr Asn Glu Asp Leu Tyr Ile Ser Cys Thr Met Pro Ser Ile Glu Ile
        790                 795                 800

GGA ACG GTG GGT GGT GGG ACC AAC CTA CTA CCT CAG CAA GCC TGT TTG        2504
Gly Thr Val Gly Gly Gly Thr Asn Leu Leu Pro Gln Gln Ala Cys Leu
                805                 810                 815

CAG ATG CTA GGT GTT CAA GGA GCA TGC AAA GAT AAT CCT GGG GAA AAT        2552
Gln Met Leu Gly Val Gln Gly Ala Cys Lys Asp Asn Pro Gly Glu Asn
820                 825                 830

GCC CGG CAG CTT GCC CGA ATT GTG TGT GGG ACC GTA ATG GCT GGG GAA        2600
Ala Arg Gln Leu Ala Arg Ile Val Cys Gly Thr Val Met Ala Gly Glu
835                 840                 845                 850

TTG TCA CTT ATG GCA GCA TTG GCA GCA GGA CAT CTT GTC AAA AGT CAC        2648
Leu Ser Leu Met Ala Ala Leu Ala Ala Gly His Leu Val Lys Ser His
                855                 860                 865

ATG ATT CAC AAC AGG TCG AAG ATC AAT TTA CAA GAC CTC CAA GGA GCT        2696
Met Ile His Asn Arg Ser Lys Ile Asn Leu Gln Asp Leu Gln Gly Ala
        870                 875                 880

TGC ACC AAG AAG ACA GCC TGAATAGCCC GACAGTTCTG AACTGGAACA               2744
Cys Thr Lys Lys Thr Ala
                885

TGGGCATTGG GTTCTAAAGG ACTAACATAA AATCTGTGAA TTAAAAAAGC TCAATGCATT     2804

GTCTTGTGGA GGATGAATAA ATGTGATCAC TGAGACAGCC ACTTGGTTTT TGGCTCTTTC     2864

AGAGAGGTCT CAGGTTCTTT CCATGCAGAC TCCTCAGATC                           2904

(2) INFORMATION FOR SEQ ID NO:30:

(i) SEQUENCE CHARACTERISTICS:
        (A) LENGTH: 888 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:30:

Met Leu Ser Arg Leu Phe Arg Met His Gly Leu Phe Val Ala Ser His
1               5                   10                  15

Pro Trp Glu Val Ile Val Gly Thr Val Thr Leu Thr Ile Cys Met Met
                20                  25                  30

Ser Met Asn Met Phe Thr Gly Asn Asn Lys Ile Cys Gly Trp Asn Tyr
            35                  40                  45

Glu Cys Pro Lys Phe Glu Glu Asp Val Leu Ser Ser Asp Ile Ile Ile
    50                  55                  60

Leu Thr Ile Thr Arg Cys Ile Ala Ile Leu Tyr Ile Tyr Phe Gln Phe
65                  70                  75                  80

Gln Asn Leu Arg Gln Leu Gly Ser Lys Tyr Ile Leu Gly Ile Ala Gly
                85                  90                  95
```

```
Leu Phe Thr Ile Phe Ser Ser Phe Val Phe Ser Thr Val Val Ile His
                100                 105                 110
Phe Leu Asp Lys Glu Leu Thr Gly Leu Asn Glu Ala Leu Pro Phe Phe
            115                 120                 125
Leu Leu Leu Ile Asp Leu Ser Arg Ala Ser Thr Leu Ala Lys Phe Ala
        130                 135                 140
Leu Ser Ser Asn Ser Gln Asp Glu Val Arg Glu Asn Ile Ala Arg Gly
145                 150                 155                 160
Met Ala Ile Leu Gly Pro Thr Phe Thr Leu Asp Ala Leu Val Glu Cys
                165                 170                 175
Leu Val Ile Gly Val Gly Thr Met Ser Gly Val Arg Gln Leu Glu Ile
            180                 185                 190
Met Cys Cys Phe Gly Cys Met Ser Val Leu Ala Asn Tyr Phe Val Phe
        195                 200                 205
Met Thr Phe Phe Pro Ala Cys Val Ser Leu Val Leu Glu Leu Ser Arg
    210                 215                 220
Glu Ser Arg Glu Gly Arg Pro Ile Trp Gln Leu Ser His Phe Ala Arg
225                 230                 235                 240
Val Leu Glu Glu Glu Glu Asn Lys Pro Asn Pro Val Thr Gln Arg Val
                245                 250                 255
Lys Met Ile Met Ser Leu Gly Leu Val Leu Val His Ala His Ser Arg
            260                 265                 270
Trp Ile Ala Asp Pro Ser Pro Gln Asn Ser Thr Ala Asp Thr Ser Lys
        275                 280                 285
Val Ser Leu Gly Leu Asp Glu Asn Val Ser Lys Arg Ile Glu Pro Ser
    290                 295                 300
Val Ser Leu Trp Gln Phe Tyr Leu Ser Lys Met Ile Ser Met Asp Ile
305                 310                 315                 320
Glu Gln Val Ile Thr Leu Ser Leu Ala Leu Leu Ala Val Lys Tyr
                325                 330                 335
Ile Phe Phe Glu Gln Thr Glu Thr Glu Ser Thr Leu Ser Leu Lys Asn
            340                 345                 350
Pro Ile Thr Ser Pro Val Val Thr Gln Lys Lys Val Pro Asp Asn Cys
        355                 360                 365
Cys Arg Arg Glu Pro Met Leu Val Arg Asn Asn Gln Lys Cys Asp Ser
    370                 375                 380
Val Glu Glu Glu Thr Gly Ile Asn Arg Glu Arg Lys Val Glu Val Ile
385                 390                 395                 400
Lys Pro Leu Val Ala Glu Thr Asp Thr Pro Asn Arg Ala Thr Phe Val
                405                 410                 415
Val Gly Asn Ser Ser Leu Leu Asp Thr Ser Ser Val Leu Val Thr Gln
            420                 425                 430
Glu Pro Glu Ile Glu Leu Pro Arg Glu Pro Arg Pro Asn Glu Glu Cys
        435                 440                 445
Leu Gln Ile Leu Gly Asn Ala Glu Lys Gly Ala Lys Phe Leu Ser Asp
    450                 455                 460
Ala Glu Ile Ile Gln Leu Val Asn Ala Lys His Ile Pro Ala Tyr Lys
465                 470                 475                 480
Leu Glu Thr Leu Met Glu Thr His Glu Arg Gly Val Ser Ile Arg Arg
                485                 490                 495
Gln Leu Leu Ser Lys Lys Leu Ser Glu Pro Ser Ser Leu Gln Tyr Leu
            500                 505                 510
```

```
Pro Tyr Arg Asp Tyr Asn Tyr Ser Leu Val Met Gly Ala Cys Cys Glu
            515                 520                 525
Asn Val Ile Gly Tyr Met Pro Ile Pro Val Gly Val Ala Gly Pro Leu
        530                 535                 540
Cys Leu Asp Glu Lys Glu Phe Gln Val Pro Met Ala Thr Thr Glu Gly
545                 550                 555                 560
Cys Leu Val Ala Ser Thr Asn Arg Gly Cys Arg Ala Ile Gly Leu Gly
            565                 570                 575
Gly Gly Ala Ser Ser Arg Val Leu Ala Asp Gly Met Thr Arg Gly Pro
        580                 585                 590
Val Val Arg Leu Pro Arg Ala Cys Asp Ser Ala Glu Val Lys Ala Trp
            595                 600                 605
Leu Glu Thr Ser Glu Gly Phe Ala Val Ile Lys Glu Ala Phe Asp Ser
        610                 615                 620
Thr Ser Arg Phe Ala Arg Leu Gln Lys Leu His Thr Ser Ile Ala Gly
625                 630                 635                 640
Arg Asn Leu Tyr Ile Arg Phe Gln Ser Arg Ser Gly Asp Ala Met Gly
            645                 650                 655
Met Asn Met Ile Ser Lys Gly Thr Glu Lys Ala Leu Ser Lys Leu His
        660                 665                 670
Glu Tyr Phe Pro Glu Met Gln Ile Leu Ala Val Ser Gly Asn Tyr Cys
            675                 680                 685
Thr Asp Lys Lys Pro Ala Ala Ile Asn Trp Ile Glu Gly Arg Gly Lys
        690                 695                 700
Ser Val Val Cys Glu Ala Val Ile Pro Ala Lys Val Val Arg Glu Val
705                 710                 715                 720
Leu Lys Thr Thr Thr Glu Ala Met Ile Glu Val Asn Ile Asn Lys Asn
            725                 730                 735
Leu Val Gly Ser Ala Met Ala Gly Ser Ile Gly Gly Tyr Asn Ala His
        740                 745                 750
Ala Ala Asn Ile Val Thr Ala Ile Tyr Ile Ala Cys Gly Gln Asp Ala
            755                 760                 765
Ala Gln Asn Val Gly Ser Ser Asn Cys Ile Thr Leu Met Glu Ala Ser
        770                 775                 780
Gly Pro Thr Asn Glu Asp Leu Tyr Ile Ser Cys Thr Met Pro Ser Ile
785                 790                 795                 800
Glu Ile Gly Thr Val Gly Gly Gly Thr Asn Leu Leu Pro Gln Gln Ala
            805                 810                 815
Cys Leu Gln Met Leu Gly Val Gln Gly Ala Cys Lys Asp Asn Pro Gly
        820                 825                 830
Glu Asn Ala Arg Gln Leu Ala Arg Ile Val Cys Gly Thr Val Met Ala
            835                 840                 845
Gly Glu Leu Ser Leu Met Ala Ala Leu Ala Ala Gly His Leu Val Lys
        850                 855                 860
Ser His Met Ile His Asn Arg Ser Lys Ile Asn Leu Gln Asp Leu Gln
865                 870                 875                 880
Gly Ala Cys Thr Lys Lys Thr Ala
            885

(2) INFORMATION FOR SEQ ID NO:31:

(i) SEQUENCE CHARACTERISTICS:
        (A) LENGTH: 11725 base pairs
        (B) TYPE: nucleic acid
        (C) STRANDEDNESS: single
```

(D) TOPOLOGY: linear (ii) MOLECULE TYPE: Genomic DNA (xi) SEQUENCE DESCRIPTION: SEQ ID NO:31:

```
AGTGAATCTG GGCGAGTAAC ACAAAACTTG AGTGTCCTTA CCTGAAAAAT AGAGGTTAGA      60

GGGATGCTAT GTGCCATTGT GTGTGTGTGT TGGGGGTGGG GATTGGGGGT GATTTGTGAG     120

CAATTGGAGG TGAGGGTGGA GCCCAGTGCC CAGCACCTAT GCACTGGGGA CCCAAAAAGG     180

AGCATCTTCT CATGATTTTA TGTATCAGAA ATTGGGATGG CATGTCATTG GACAGCGTC     240

TTTTTTCTTG TATGGTGGCA CATAAATACA TGTGTCTTAT AATTAATGGT ATTTTAGATT    300

TGACGAAATA TGGAATATTA CCTGTTGTGC TGATCTTGGG CAAACTATAA TATCTCTGGG    360

CAAAAATGTC CCCATCTGAA AAACAGGGAC AACGTTCCTC CCTCAGCCAG CCACTATGGG    420

GCTAAAATGA GACCACATCT GTCAAGGGTT TTGCCCTCAC CTCCCTCCCT GCTGGATGGC    480

ATCCTTGGTA GGCAGAGGTG GGCTTCGGGC AGAACAAGCC GTGCTGAGCT AGGACCAGGA    540

GTGCTAGTGC CACTGTTTGT CTATGGAGAG GGAGGCCTCA GTGCTGAGGG CCAAGCAAAT    600

ATTTGTGGTT ATGGATTAAC TCGAACTCCA GGCTGTCATG GCGGCAGGAC GGCGAACTTG    660

CAGTATCTCC ACGACCCGCC CCTGTGAGTC CCCCTCCAGG CAGGTCTATG AGGGGTGTGG    720

AGGGAGGGCT GCCCCCGGGA GAAGAGAGCT AGGTGGTGAT GAGGGCTGAA TCCTCCAGCC    780

AGGGTGCTCA ACAAGCCTGA GCTTGGGGTA AAAGGACACA AGGCCCTCCA CAGGCCAGGC    840

CTGGCAGCCA CAGTCTCAGG TCCCTTTGCC ATGCGCCTCC CTCTTTCCAG GCCAAGGGTC    900

CCCAGGCCCA GGGCCATTCC AACAGACAGT TTGGAGCCCA GGACCCTCCA TTCTCCCCAC    960

CCCACTTCCA CCTTTGGGGG TGTCGGATTT GAACAAATCT CAGAAGCGGC CTCAGAGGGA   1020

GTCGGCAAGA ATGGAGAGCA GGGTCCGGTA GGGTGTGCAG AGGCCACGTG GCCTATCCAC   1080

TGGGGAGGGT TCCTTGATCT CTGGCCACCA GGGCTATCTC TGTGGCCTTT TGGAGCAACC   1140

TGGTGGTTTG GGGCAGGGGT TGAATTTCCA GGCCTAAAAC CACACAGGCC TGGCCTTGAG   1200

TCCTGGCTCT GCGAGTAATG CATGGATGTA AACATGGAGA CCCAGGACCT TGCCTCAGTC   1260

TTCCGAGTCT GGTGCCTGCA GTGTACTGAT GGTGTGAGAC CCTACTCCTG GAGGATGGGG   1320

GACAGAATCT GATCGATCCC CTGGGTTGGT GACTTCCCTG TGCAATCAAC GGAGACCAGC   1380

AAGGGTTGGA TTTTTAATAA ACCACTTAAC TCCTCCGAGT CTCAGTTTCC CCCTCTATGA   1440

AATGGGGTTG ACAGCATTAA TAACTACCTC TTGGGTGGTT GTGAGCCTTA ACTGAAGTCA   1500

TAATATCTCA TGTTTACTGA GCATGAGCTA TGTGCAAAGC CTGTTTTGAG AGCTTTATGT   1560

GGACTAACTC CTTTAATTCT CACAACACCC TTTAAGGCAC AGATACACCA CGTTATTCCA   1620

TCCATTTTAC AAATGAGGAA ACTGAGGCAT GGAGCAGTTA AGCATCTTGC CAACATTGC    1680

CCTCCAGTAA GTGCTGGAGC TGGAATTTGC ACCGTGCAGT CTGGCTTCAT GGCCTGCCCT   1740

GTGAATCCTG TAAAAATTGT TTGAAAGACA CCATGAGTGT CCAATCAACG TTAGCTAATA   1800

TTCTCAGCCC AGTCATCAGA CCGGCAGAGG CAGCCACCCC ACTGTCCCCA GGAGGACAC    1860

AAACATCCTG GCACCCTCTC CACTGCATTC TGGAGCTGCT TTCTAGGCAG GCAGTGTGAG   1920

CTCAGCCCCA CGTAGAGCGG GCAGCCGAGG CCTTCTGAGG CTATGTCTCT AGCGAACAAG   1980

GACCCTCAAT TCCAGCTTCC GCCTGACGGC CAGCACACAG GGACAGCCCT TTCATTCCGC   2040

TTCCACCTGG GGGTGCAGGC AGAGCAGCAG CGGGGGTAGC ACTGCCCGGA GCTCAGAAGT   2100

CCTCCTCAGA CAGGTGCCAG TGCCTCCAGA ATGTGGCAGC TCACAAGCCT CCTGCTGTTC   2160

GTGGCCACCT GGGGAATTTC CGGCACACCA GCTCCTCTTG GTAAGGCCAC CCCACCCCTA   2220
```

```
CCCCGGGACC CTTGTGGCCT CTACAAGGCC CTGGTGGCAT CTGCCCAGGC CTTCACAGCT    2280

TCCACCATCT CTCTGAGCCC TGGGTGAGGT GAGGGGCAGA TGGGAATGGC AGGAATCAAC    2340

TGACAAGTCC CAGGTAGGCC AGCTGCCAGA GTGCCACACA GGGGCTGCCA GGGCAGGCAT    2400

GCGTGATGGC AGGGAGCCCC GCGATGACCT CCTAAAGCTC CCTCCTCCAC ACGGGGATGG    2460

TCACAGAGTC CCCTGGGCCT TCCCTCTCCA CCCACTCACT CCCTCAACTG TGAAGACCCC    2520

AGGCCCAGGC TACCGTCCAC ACTATCCAGC ACAGCCTCCC CTACTCAAAT GCACACTGGC    2580

CTCATGGCTG CCCTGCCCCA ACCCCTTTCC TGGTCTCCAC AGCCAACGGG AGGAGGCCAT    2640

GATTCTTGGG GAGGTCCGCA GGCACATGGG CCCCTAAAGC CACACCAGGC TGTTGGTTTC    2700

ATTTGTGCCT TTATAGAGCT GTTTATCTGC TTGGGACCTG CACCTCCACC CTTTCCCAAG    2760

GTGCCCTCAG CTCAGGCATA CCCTCCTCTA GGATGCCTTT TCCCCCATCC CTTCTTGCTC    2820

ACACCCCAA CTTGATCTCT CCCTCCTAAC TGTGCCCTGC ACCAAGACAG ACACTTCACA    2880

GAGCCCAGGA CACACCTGGG GACCCTTCCT GGGTGATAGG TCTGTCTATC CTCCAGGTGT    2940

CCCTGCCCAA GGGGAGAAGC ATGGGGAATA CTTGGTTGGG GGAGGAAAGG AAGACTGGGG    3000

GGATGTGTCA AGATGGGGCT GCATGTGGTG TACTGGCAGA AGAGTGAGAG GATTTAACTT    3060

GGCAGCCTTT ACAGCAGCAG CCAGGGCTTG AGTACTTATC TCTGGGCCAG GCTGTATTGG    3120

ATGTTTTACA TGACGGTCTC ATCCCCATGT TTTTGGATGA GTAAATTGAA CCTTAGAAAG    3180

GTAAAGACAC TGGCTCAAGG TCACACAGAG ATCGGGTGG GGTTCACAGG GAGGCCTGTC    3240

CATCTCAGAG CAAGGCTTCG TCCTCCAACT GCCATCTGCT TCCTGGGGAG GAAAAGAGCA    3300

GAGGACCCCT GCGCCAAGCC ATGACCTAGA ATTAGAATGA GTCTTGAGGG GGCGGAGACA    3360

AGACCTTCCC AGGCTCTCCC AGCTCTGCTT CCTCAGACCC CCTCATGGCC CCAGCCCCTC    3420

TTAGGCCCCT CACCAAGGTG AGCTCCCCTC CCTCCAAAAC CAGACTCAGT GTTCTCCAGC    3480

AGCGAGCGTG CCCACCAGGT GCTGCGGATC CGCAAACGTG CCAACTCCTT CCTGGAGGAG    3540

CTCCGTCACA GCAGCCTGGA GCGGGAGTGC ATAGAGGAGA TCTGTGACTT CGAGGAGGCC    3600

AAGGAAATTT TCCAAAATGT GGATGACACA GTAAGGCCAC CATGGGTCCA GAGGATGAGG    3660

CTCAGGGGCG AGCTGGTAAC CAGCAGGGGC CTCGAGGAGC AGGTGGGGAC TCAATGCTGA    3720

GGCCCTCTTA GGAGTTGTGG GGGTGGCTGA GTGGAGCGAT TAGGATGCTG GCCCTATGAT    3780

GTCGGCCAGG CACATGTGAC TGCAAGAAAC AGAATTCAGG AAGAAGCTCC AGGAAAGAGT    3840

GTGGGGTGAC CCTAGGTGGG GACTCCCACA GCCACAGTGT AGGTGGTTCA GTCCACCCTC    3900

CAGCCACTGC TGAGCACCAC TGCCTCCCCG TCCCACCTCA CAAAGAGGGG ACCTAAAGAC    3960

CACCCTGCTT CCACCCATGC CTCTGCTGAT CAGGGTGTGT GTGTGACCGA AACTCACTTC    4020

TGTCCACATA AAATCGCTCA CTCTGTGCCT CACATCAAAG GGAGAAAATC TGATTGTTCA    4080

GGGGGTCGGA AGACAGGGTC TGTGTCCTAT TTGTCTAAGG GTCAGAGTCC TTTGGAGCCC    4140

CCAGAGTCCT GTGGACGTGG CCCTAGGTAG TAGGGTGAGC TTGGTAACGG GGCTGGCTTC    4200

CTGAGACAAG GCTCAGACCC GCTCTGTCCC TGGGGATCGC TTCAGCCACC AGGACCTGAA    4260

AATTGTGCAC GCCTGGGCCC CCTTCCAAGG CATCCAGGGA TGCTTTCCAG TGGAGGCTTT    4320

CAGGGCAGGA GACCCTCTGG CCTGCACCCT CTCTTGCCCT CAGCCTCCAC CTCCTTGACT    4380

GGACCCCCAT CTGGACCTCC ATCCCCACCA CCTCTTTCCC CAGTGGCCTC CCTGGCAGAC    4440

ACCACAGTGA CTTTCTGCAG GCACATATCT GATCACATCA AGTCCCCACC GTGCTCCCAC    4500

CTCACCCATG GTCTCTCAGC CCCAGCAGCC TTGGCTGGCC TCTCTGATGG AGCAGGCATC    4560
```

```
AGGCACAGGC CGTGGGTCTC AACGTGGGCT GGGTGGTCCT GGACCAGCAG CAGCCGCCGC    4620

AGCAGCAACC CTGGTACCTG GTTAGGAACG CAGACCCTCT GCCCCCATCC TCCCAACTCT    4680

GAAAAACACT GGCTTAGGGA AAGGCGCGAT GCTCAGGGGT CCCCCAAAGC CCGCAGGCAG    4740

AGGGAGTGAT GGGACTGGAA GGAGGCCGAG TGACTTGGTG AGGGATTCGG GTCCCTTGCA    4800

TGCAGAGGCT GCTGTGGGAG CGGACAGTCG CGAGAGCAGC ACTGCAGCTG CATGGGGAGA    4860

GGGTGTTGCT CCAGGGACGT GGGATGGAGG CTGGGCGCGG GCGGGTGGCG CTGGAGGGCG    4920

GGGGAGGGGC AGGGAGCACC AGCTCCTAGC AGCCAACGAC CATCGGGCGT CGATCCCTGT    4980

TTGTCTGGAA GCCCTCCCCT CCCCTGCCCG CTCACCCGCT GCCCTGCCCC ACCCGGGCGC    5040

GCCCCTCCGC ACACCGGCTG CAGGAGCCTG ACGCTGCCCG CTCTCTCCGC AGCTGGCCTT    5100

CTGGTCCAAG CACGTCGGTG AGTGCGTTCT AGATCCCCGG CTGGACTACC GGCGCCCGCG    5160

CCCCTCGGGA TCTCTGGCCG CTGACCCCCT ACCCGCCTT GTGTCGCAGA CGGTGACCAG    5220

TGCTTGGTCT TGCCCTTGGA GCACCCGTGC GCCAGCCTGT GCTGCGGGCA CGGCACGTGC    5280

ATCGACGGCA TCGGCAGCTT CAGCTGCGAC TGCCGCAGCG GCTGGGAGGG CCGCTTCTGC    5340

CAGCGCGGTG AGGGGGAGAG GTGGATGCTG GCGGGCGGCG GGGCGGGGCT GGGGCCGGGT    5400

TGGGGGCGCG GCACCAGCAC CAGCTGCCCG CGCCCTCCCC TGCCCGCAGA GGTGAGCTTC    5460

CTCAATTGCT CTCTGGACAA CGGCGGCTGC ACGCATTACT GCCTAGAGGA GGTGGGCTGG    5520

CGGCGCTGTA GCTGTGCGCC TGGCTACAAG CTGGGGACG ACCTCCTGCA GTGTCACCCC    5580

GCAGGTGAGA AGCCCCCAAT ACATCGCCCA GGAATCACGC TGGGTGCGGG GTGGGCAGGC    5640

CCCTGACGGG CGCGGCGCGG GGGGCTCAGG AGGGTTTCTA GGGAGGGAGC GAGGAACAGA    5700

GTTGAGCCTT GGGGCAGCGG CAGACGCGCC CAACACCGGG GCCACTGTTA GCGCAATCAG    5760

CCCGGGAGCT GGGCGCGCCC TCCGCTTTCC CTGCTTCCTT TCTTCCTGGC GTCCCCGCTT    5820

CCTCCGGGCG CCCCTGCGAC CTGGGGCCAC CTCCTGGAGC GCAAGCCCAG TGGTGGCTCC    5880

GCTCCCCAGT CTGAGCGTAT CTGGGGCGAG GCGTGCAGCG TCCTCCTCCA TGTAGCCTGG    5940

CTGCGTTTTT CTCTGACGTT GTCCGGCGTG CATCGCATTT CCCTCTTTAC CCCCTTGCTT    6000

CCTTGAGGAG AGAACAGAAT CCCGATTCTG CCTTCTTCTA TATTTTCCTT TTTATGCATT    6060

TTAATCAAAT TTATATATGT ATGAAACTTT AAAAATCAGA GTTTTACAAC TCTTACACTT    6120

TCAGCATGCT GTTCCTTGGC ATGGGTCCTT TTTTCATTCA TTTTCATAAA AGGTGGACCC    6180

TTTTAATGTG GAAATTCCTA TCTTCTGCCT CTAGGGCATT TATCACTTAT TCTTCTACA    6240

ATCTCCCCTT TACTTCCTCT ATTTTCTCTT TCTGGACCTC CCATTATTCA GACCTCTTTC    6300

CTCTAGTTTT ATTGTCTCTT CTATTTCCCA TCTCTTTGAC TTTGTGTTTT CTTTCAGGGA    6360

ACTTTCTTTT TTTTCTTTTT TTTTGAGATG GAGTTTCACT CTTGTTGTCC CAGGCTGGAG    6420

TGCAATGACG TGATCTCAGC TCACCACAAC CTCCGCCTCC TGGATTCAAG CGATTCTCCT    6480

GCCGCAGCCT CCCGAGTAGC TGGGATTACA GGCATGCGCC ACCACGCCCA GCTAATTTTG    6540

TGTTTTAGT AGAGAAGGGG TTTCTCCGTG TTGGTCAAGC TGGTCTTGAA CTCCTGACCT    6600

CAGGTGATCC ACCTGCCTTG GCCTCCTAAA GTGCTGGGAT TACAGGCGTG AGCCACCGCG    6660

CCCAGCCTCT TTCAGGGAAC TTTCTACAAC TTTATAATTC AATTCTTCTG CAGAAAAAAA    6720

TTTTTGGCCA GGCTCAGTAG CTCAGACCAA TAATTCCAGC ACTTTGAGAG GCTGAGGTGG    6780

GAGGATTGCT TGAGCTTGGG AGTTTGAGAC TAGCCTGGGC AACACAGTGA GACCCTGTCT    6840

CTATTTTTAA AAAAGTAAA AAAAGATCTA AAAATTTAAC TTTTTATTTT GAAATAATTA    6900

GATATTTCCA GGAAGCTGCA AAGAAATGCC TGGTGGGCCT GTTGGCTGTG GGTTTCCTGC    6960
```

```
AAGGCCGTGG GAAGGCCCTG TCATTGGCAG AACCCCAGAT CGTGAGGGCT TTCCTTTTAG   7020

GCTGCTTTCT AAGAGGACTC CTCCAAGCTC TTGGAGGATG GAAGACGCTC ACCCATGGTG   7080

TTCGGCCCCT CAGAGCAGGG TGGGGCAGGG GAGCTGGTGC CTGTGCAGGC TGTGGACATT   7140

TGCATGACTC CCTGTGGTCA GCTAAGAGCA CCACTCCTTC CTGAAGCGGG GCCTGAAGTC   7200

CCTAGTCAGA GCCTCTGGTT CACCTTCTGC AGGCAGGGAG AGGGGAGTCA AGTCAGTGAG   7260

GAGGGCTTTC GCAGTTTCTC TTACAAACTC TCAACATGCC CTCCCACCTG CACTGCCTTC   7320

CTGGAAGCCC CACAGCCTCC TATGGTTCCG TGGTCCAGTC CTTCAGCTTC TGGGCGCCCC   7380

CATCACGGGC TGAGATTTTT GCTTTCCAGT CTGCCAAGTC AGTTACTGTG TCCATCCATC   7440

TGCTGTCAGC TTCTGGAATT GTTGCTGTTG TGCCCTTTCC ATTCTTTTGT TATGATGCAG   7500

CTCCCCTGCT GACGACGTCC CATTGCTCTT TTAAGTCTAG ATATCTGGAC TGGGCATTCA   7560

AGGCCCATTT TGAGCAGAGT CGGGCTGACC TTTCAGCCCT CAGTTCTCCA TGGAGTATGC   7620

GCTCTCTTCT TGGCAGGGAG GCCTCACAAA CATGCCATGC CTATTGTAGC AGCTCTCCAA   7680

GAATGCTCAC CTCCTTCTCC CTGTAATTCC TTTCCTCTGT GAGGAGCTCA GCAGCATCCC   7740

ATTATGAGAC CTTACTAATC CCAGGGATCA CCCCCAACAG CCCTGGGGTA CAATGAGCTT   7800

TTAAGAAGTT TAACCACCTA TGTAAGGAGA CACAGGCAGT GGGCGATGCT GCCTGGCCTG   7860

ACTCTTGCCA TTGGGTGGTA CTGTTTGTTG ACTGACTGAC TGACTGACTG GAGGGGGTTT   7920

GTAATTTGTA TCTCAGGGAT TACCCCCAAC AGCCCTGGGG TACAATGAGC CTTCAAGAAG   7980

TTTAACAACC TATGTAAGGA CACACAGCCA GTGGGTGATG CTGCCTGGTC TGACTCTTGC   8040

CATTCAGTGG CACTGTTTGT TGACTGACTG ACTGACTGAC TGGCTGACTG GAGGGGGTTC   8100

ATAGCTAATA TTAATGGAGT GGTCTAAGTA TCATTGGTTC CTTGAACCCT GCACTGTGGC   8160

AAAGTGGCCC ACAGGCTGGA GGAGGACCAA GACAGGAGGG CAGTCTCGGG AGGAGTGCCT   8220

GGCAGGCCCC TCACCACCTC TGCCTACCTC AGTGAAGTTC CCTTGTGGGA GGCCCTGGAA   8280

GCGGATGGAG AAGAAGCGCA GTCACCTGAA ACGAGACACA GAAGACCAAG AAGACCAAGT   8340

AGATCCGCGG CTCATTGATG GGAAGATGAC CAGGCGGGGA GACAGCCCCT GGCAGGTGGG   8400

AGGCGAGGCA GCACCGGCTC GTCACGTGCT GGGTCCGGGA TCACTGAGTC CATCCTGGCA   8460

GCTATGCTCA GGGTGCAGAA ACCGAGAGGG AAGCGCTGCC ATTGCGTTTG GGGGATGATG   8520

AAGGTGGGGG ATGCTTCAGG GAAAGATGGA CGCAACCTGA GGGGAGAGGA GCAGCCAGGG   8580

TGGGTGAGGG GAGGGGCATG GGGGCATGGA GGGGTCTGCA GGAGGGAGGG TTACAGTTTC   8640

TAAAAAGAGC TGGAAAGACA CTGCTCTGCT GGCGGGATTT TAGGCAGAAG CCCTGCTGAT   8700

GGGAGAGGGC TAGGAGGGAG GGCCGGGCCT GAGTACCCCT CCAGCCTCCA CATGGGAACT   8760

GACACTTACT GGGTTCCCCT CTCTGCCAGG CATGGGGGAG ATAGGAACCA ACAAGTGGGA   8820

GTATTTGCCC TGGGGACTCA GACTCTGCAA GGGTCAGGAC CCCAAAGACC CGGCAGCCCA   8880

GTGGGACCAC AGCCAGGACG GCCCTTCAAG ATAGGGGCTG AGGGAGGCCA AGGGAACAT    8940

CCAGGCAGCC TGGGGCCAC AAAGTCTTCC TGGAAGACAC AAGGCCTGCC AAGCCTCTAA    9000

GGATGAGAGG AGCTCGCTGG GCGATGTTGG TGTGGCTGAG GGTGACTGAA ACAGTATGAA   9060

CAGTGCAGGA ACAGCATGGG CAAAGGCAGG AAGCACCCT GGGACAGGCT GACACTGTAA    9120

AATGGGCAAA AATAGAAAAC GCCAGAAAGG CCTAAGCCTA TGCCCATATG ACCAGGGAAC   9180

CCAGGAAAGT GCATATGAAA CCCAGGTGCC CTGGACTGGA GGCTGTCAGG AGGCAGCCCT   9240

GTGATGTCAT CATCCCACCC CATTCCAGGT GGTCCTGCTG GACTCAAAGA AGAAGCTGGC   9300
```

-continued

```
CTGCGGGGCA GTGCTCATCC ACCCCTCCTG GGTGCTGACA GCGGCCCACT GCATGGATGA   9360

GTCCAAGAAG CTCCTTGTCA GGCTTGGTAT GGGCTGGAGC CAGGCAGAAG GGGGCTGCCA   9420

GAGGCCTGGG TAGGGGGACC AGGCAGGCTG TTCAGGTTTG GGGGACCCCG CTCCCCAGGT   9480

GCTTAAGCAA GAGGCTTCTT GAGCTCCACA GAAGGTGTTT GGGGGGAAGA GGCCTATGTG   9540

CCCCCACCCT GCCCACCCAT GTACACCCAG TATTTTGCAG TAGGGGGTTC TCTGGTGCCC   9600

TCTTCGAATC TGGGCACAGG TACCTGCACA CACATGTTTG TGAGGGGCTA CACAGACCTT   9660

CACCTCTCCA CTCCCACTCA TGAGGAGCAG GCTGTGTGGG CCTCAGCACC CTTGGGTGCA   9720

GAGACCAGCA AGGCCTGGCC TCAGGGCTGT GCCTCCCACA GACTGACAGG GATGGAGCTG   9780

TACAGAGGGA GCCCTAGCAT CTGCCAAAGC ACAAGCTGC TTCCCTAGCA GGCTGGGGGC   9840

TCCTATGCAT TGGCCCCGAT CTATGGCAAT TTCTGGAGGG GGGTCTGGC TCAACTCTTT    9900

ATGCCAAAAA GAAGGCAAAG CATATTGAGA AAGGCCAAAT TCACATTTCC TACAGCATAA   9960

TCTATGCCAG TGGCCCCGTG GGGCTTGGCT TAGAATTCCC AGGTGCTCTT CCCAGGGAAC   10020

CATCAGTCTG GACTGAGAGG ACCTTCTCTC TCAGGTGGGA CCCGGCCCTG TCCTCCCTGG   10080

CAGTGCCGTG TTCTGGGGGT CCTCCTCTCT GGGTCTCACT GCCCCTGGGG TCTCTCCAGC   10140

TACCTTTGCT CCATGTTCCT TTGTGGCTCT GGTCTGTGTC TGGGGTTTCC AGGGGTCTCG   10200

GGCTTCCCTG CTGCCCATTC CTTCTCTGGT CTCACGGCTC CGTGACTCCT GAAAACCAAC   10260

CAGCATCCTA CCCCTTTGGA TTGACACCTG TTGGCCACTC CTTCTGGCAG GAAAAGTCAC   10320

CGTTGATAGG GTTCCACGGC ATAGACAGGT GGCTCCGCGC CAGTGCCTGG GACGTGTGGG   10380

TGCACAGTCT CCGGGTGAAC CTTCTTCAGG CCCTCTCCCA GGCCTGCAGG GGCACAGCAG   10440

TGGGTGGGCC TCAGGAAAGT GCCACTGGGG AGAGGCTCCC CGCAGCCCAC TCTGACTGTG   10500

CCCTCTGCCC TGCAGGAGAG TATGACCTGC GGCGCTGGGA GAAGTGGGAG CTGGACCTGG   10560

ACATCAAGGA GGTCTTCGTC CACCCCAACT ACAGCAAGAG CACCACCGAC AATGACATCG   10620

CACTGCTGCA CCTGGCCCAG CCCGCCACCC TCTCGCAGAC CATAGTGCCC ATCTGCCTCC   10680

CGGACAGCGG CCTTGCAGAG CGCGAGCTCA ATCAGGCCGG CCAGGAGACC CTCGTGACGG   10740

GCTGGGGCTA CCACAGCAGC CGAGAGAAGG AGGCCAAGAG AAACCGCACC TTCGTCCTCA   10800

ACTTCATCAA GATTCCCGTG GTCCCGCACA ATGAGTGCAG CGAGGTCATG AGCAACATGG   10860

TGTCTGAGAA CATGCTGTGT GCGGGCATCC TCGGGGACCG GCAGGATGCC TGCGAGGGCG   10920

ACAGTGGGGG GCCCATGGTC GCCTCCTTCC ACGGCACCTG GTTCCTGGTG GCCTGGTGA    10980

GCTGGGGTGA GGGCTGTGGG CTCCTTCACA ACTACGGCGT TTACACCAAA GTCAGCCGCT   11040

ACCTCGACTG GATCCATGGG CACATCAGAG ACAAGGAAGC CCCCCAGAAG AGCTGGGCAC   11100

CTTAGCGACC CTCCCTGCAG GGCTGGGCTT TTGCATGGCA ATGGATGGGA CATTAAAGGG   11160

ACATGTAACA AGCACACCGG CCTGCTGTTC TGTCCTTCCA TCCCTCTTTT GGGCTCTTCT   11220

GGAGGGAAGT AACATTTACT GAGCACCTGT TGTATGTCAC ATGCCTTATG AATAGAATCT   11280

TAACTCCTAG AGCAACTCTG TGGGTGGGG AGGAGCAGAT CCAAGTTTTG CGGGGTCTAA     11340

AGCTGTGTGT GTTGAGGGGG ATACTCTGTT TATGAAAAAG AATAAAAAAC ACAACCACGA   11400

AGCCACTAGA GCCTTTTCCA GGGCTTTGGG AAGAGCCTGT GCAAGCCGGG GATGCTGAAG   11460

GTGAGGCTTG ACCAGCTTTC CAGCTAGCCC AGCTATGAGG TAGACATGTT TAGCTCATAT   11520

CACAGAGGAG GAAACTGAGG GGTCTGAAAG GTTTACATGG TGGAGCCAGG ATTCAAATCT   11580

AGGTCTGACT CCAAAACCCA GGTGCTTTTT TCTGTTCTCC ACTGTCCTGG AGGACAGCTG   11640

TTTCGACGGT GCTCAGTGTG GAGGCCACTA TTAGCTCTGT AGGGAAGCAG CCAGAGACCC   11700
```

```
AGAAAGTGTT GGTTCAGCCC AGAAT                                            11725
```

(2) INFORMATION FOR SEQ ID NO:32:

(i) SEQUENCE CHARACTERISTICS:
        (A) LENGTH: 461 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

```
Met Trp Gln Leu Thr Ser Leu Leu Phe Val Ala Thr Trp Gly Ile
1               5                   10                  15

Ser Gly Thr Pro Ala Pro Leu Asp Ser Val Phe Ser Ser Glu Arg
            20                  25                  30

Ala His Gln Val Leu Arg Ile Arg Lys Arg Ala Asn Ser Phe Leu Glu
        35                  40                  45

Glu Leu Arg His Ser Ser Leu Glu Arg Glu Cys Ile Glu Glu Ile Cys
50                  55                  60

Asp Phe Glu Glu Ala Lys Glu Ile Phe Gln Asn Val Asp Asp Thr Leu
65                  70                  75                  80

Ala Phe Trp Ser Lys His Val Asp Gly Asp Gln Cys Leu Val Leu Pro
                85                  90                  95

Leu Glu His Pro Cys Ala Ser Leu Cys Cys Gly His Gly Thr Cys Ile
            100                 105                 110

Asp Gly Ile Gly Ser Phe Ser Cys Asp Cys Arg Ser Gly Trp Glu Gly
        115                 120                 125

Arg Phe Cys Gln Arg Glu Val Ser Phe Leu Asn Cys Ser Leu Asp Asn
130                 135                 140

Gly Gly Cys Thr His Tyr Cys Leu Glu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Trp Lys Arg Met Glu Lys
            180                 185                 190

Lys Arg Ser His Leu Lys Arg Asp Thr Glu Asp Gln Glu Asp Gln Val
        195                 200                 205

Asp Pro Arg Leu Ile Asp Gly Lys Met Thr Arg Arg Gly Asp Ser Pro
210                 215                 220

Trp Gln Val Val Leu Leu Asp Ser Lys Lys Lys Leu Ala Cys Gly Ala
225                 230                 235                 240

Val Leu Ile His Pro Ser Trp Val Leu Thr Ala Ala His Cys Met Asp
                245                 250                 255

Glu Ser Lys Lys Leu Leu Val Arg Leu Gly Glu Tyr Asp Leu Arg Arg
            260                 265                 270

Trp Glu Lys Trp Glu Leu Asp Leu Asp Ile Lys Glu Val Phe Val His
        275                 280                 285

Pro Asn Tyr Ser Lys Ser Thr Thr Asp Asn Asp Ile Ala Leu Leu His
290                 295                 300

Leu Ala Gln Pro Ala Thr Leu Ser Gln Thr Ile Val Pro Ile Cys Leu
305                 310                 315                 320

Pro Asp Ser Gly Leu Ala Glu Arg Glu Leu Asn Gln Ala Gly Gln Glu
                325                 330                 335
```

-continued

```
Thr Leu Val Thr Gly Trp Gly Tyr His Ser Ser Arg Glu Lys Glu Ala
            340                 345                 350

Lys Arg Asn Arg Thr Phe Val Leu Asn Phe Ile Lys Ile Pro Val Val
            355                 360                 365

Pro His Asn Glu Cys Ser Glu Val Met Ser Asn Met Val Ser Glu Asn
    370                 375                 380

Met Leu Cys Ala Gly Ile Leu Gly Asp Arg Gln Asp Ala Cys Glu Gly
385                 390                 395                 400

Asp Ser Gly Gly Pro Met Val Ala Ser Phe His Gly Thr Trp Phe Leu
                405                 410                 415

Val Gly Leu Val Ser Trp Gly Glu Gly Cys Gly Leu Leu His Asn Tyr
            420                 425                 430

Gly Val Tyr Thr Lys Val Ser Arg Tyr Leu Asp Trp Ile His Gly His
            435                 440                 445

Ile Arg Asp Lys Glu Ala Pro Gln Lys Ser Trp Ala Pro
    450                 455                 460
```

(2) INFORMATION FOR SEQ ID NO:33:

(i) SEQUENCE CHARACTERISTICS:
        (A) LENGTH: 1744 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 268...1587
        (D) OTHER INFORMATION:

(xi) SEQUENCE DESCRIPTION: SEQ ID NO:33:

```
TGAGGCCTGA CTTTTTCAAT AAAACATTGT GTAGTTCTGG GCCTCCTGCT GCCCCGGCTC      60

TGTTTCCCCT GGCGCCAAGA GAAGAAGGCG GAACTGAACC CAGGCCCAGA GCCGGCTCCC     120

TGAGGCTGTG CCCCTTTCCG GCAATCTCTG GCCACAACCC CCACTGGCCA GGCCGTCCCT     180

CCCACTGGCC CTAGGGCCCC TCCCACTCCC ACACCAGATA AGGACAGCCC AGTGCCGCTT     240

TCTCTGGCAG TAGGCACCAG GGCTGGA ATG GGG CCG CCC GGC TCC CCA TGG CAG     294
                        Met Gly Pro Pro Gly Ser Pro Trp Gln
                          1               5

TGG GTG ACG CTG CTG CTG GGG CTG CTG CTC CCT CCT GCC GCC CCC TTC       342
Trp Val Thr Leu Leu Leu Gly Leu Leu Leu Pro Pro Ala Ala Pro Phe
 10              15                  20                  25

TGG CTC CTC AAT GTG CTC TTC CCC CCG CAC ACC ACG CCC AAG GCT GAG       390
Trp Leu Leu Asn Val Leu Phe Pro Pro His Thr Thr Pro Lys Ala Glu
                30                  35                  40

CTC AGT AAC CAC ACA CGG CCC GTC ATC CTC GTG CCC GGC TGC CTG GGG       438
Leu Ser Asn His Thr Arg Pro Val Ile Leu Val Pro Gly Cys Leu Gly
            45                  50                  55

AAT CAG CTA GAA GCC AAG CTG GAC AAA CCA GAT GTG GTG AAC TGG ATG       486
Asn Gln Leu Glu Ala Lys Leu Asp Lys Pro Asp Val Val Asn Trp Met
        60                  65                  70

TGC TAC CGC AAG ACA GAG GAC TTC TTC ACC ATC TGG CTG GAT CTC AAC       534
Cys Tyr Arg Lys Thr Glu Asp Phe Phe Thr Ile Trp Leu Asp Leu Asn
    75                  80                  85

ATG TTC CTA CCC CTT GGG GTA GAC TGC TGG ATC GAT AAC ACC AGG GTT       582
Met Phe Leu Pro Leu Gly Val Asp Cys Trp Ile Asp Asn Thr Arg Val
 90                  95                 100                 105

GTC TAC AAC CGG AGC TCT GGG CTC GTG TCC AAC GCC CCT GGT GTC CAG       630
```

```
                                                               -continued

Val Tyr Asn Arg Ser Ser Gly Leu Val Ser Asn Ala Pro Gly Val Gln
                110                 115                 120

ATC CGC GTC CCT GGC TTT GGC AAG ACC TAC TCT GTG GAG TAC CTG GAC         678
Ile Arg Val Pro Gly Phe Gly Lys Thr Tyr Ser Val Glu Tyr Leu Asp
            125                 130                 135

AGC AGC AAG CTG GCA GGG TAC CTG CAC ACA CTG GTG CAG AAC CTG GTC         726
Ser Ser Lys Leu Ala Gly Tyr Leu His Thr Leu Val Gln Asn Leu Val
        140                 145                 150

AAC AAT GGC TAC GTG CGG GAC GAG ACT GTG CGC GCC GCC CCC TAT GAC         774
Asn Asn Gly Tyr Val Arg Asp Glu Thr Val Arg Ala Ala Pro Tyr Asp
    155                 160                 165

TGG CGG CTG GAG CCC GGC CAG CAG GAG GAG TAC TAC CGC AAG CTC GCA         822
Trp Arg Leu Glu Pro Gly Gln Gln Glu Glu Tyr Tyr Arg Lys Leu Ala
170                 175                 180                 185

GGG CTG GTG GAG GAG ATG CAC GCT GCC TAT GGG AAG CCT GTC TTC CTC         870
Gly Leu Val Glu Glu Met His Ala Ala Tyr Gly Lys Pro Val Phe Leu
                190                 195                 200

ATT GGC CAC AGC CTC GGC TGT CTA CAC TTG CTC TAT TTC CTG CTG CGC         918
Ile Gly His Ser Leu Gly Cys Leu His Leu Leu Tyr Phe Leu Leu Arg
            205                 210                 215

CAG CCC CAG GCC TGG AAG GAC CGC TTT ATT GAT GGC TTC ATC TCT CTT         966
Gln Pro Gln Ala Trp Lys Asp Arg Phe Ile Asp Gly Phe Ile Ser Leu
        220                 225                 230

GGG GCT CCC TGG GGT GGC TCC ATC AAG CCC ATG CTG GTC TTG GCC TCA        1014
Gly Ala Pro Trp Gly Gly Ser Ile Lys Pro Met Leu Val Leu Ala Ser
    235                 240                 245

GGT GAC AAC CAG GGC ATC CCC ATC ATG TCC AGC ATC AAG CTG AAA GAG        1062
Gly Asp Asn Gln Gly Ile Pro Ile Met Ser Ser Ile Lys Leu Lys Glu
250                 255                 260                 265

GAG CAG CGC ATA ACC ACC ACC TCC CCC TGG ATG TTT CCC TCT CGC ATG        1110
Glu Gln Arg Ile Thr Thr Thr Ser Pro Trp Met Phe Pro Ser Arg Met
                270                 275                 280

GCG TGG CCT GAG GAC CAC GTG TTC ATT TCC ACA CCC AGC TTC AAC TAC        1158
Ala Trp Pro Glu Asp His Val Phe Ile Ser Thr Pro Ser Phe Asn Tyr
            285                 290                 295

ACA GGC CGT GAC TTC CAA CGC TTC TTT GCA GAC CTG CAC TTT GAG AAA        1206
Thr Gly Arg Asp Phe Gln Arg Phe Phe Ala Asp Leu His Phe Glu Glu
        300                 305                 310

GGC TGG TAC ATG TGG CTG CAG TCA CGT GAC CTC CTG GCA GGA CTC CCA        1254
Gly Trp Tyr Met Trp Leu Gln Ser Arg Asp Leu Leu Ala Gly Leu Pro
    315                 320                 325

GCA CCT GGT GTG GAA GTA TAC TGT CTT TAC GGC GTG GGC CTG CCC ACG        1302
Ala Pro Gly Val Glu Val Tyr Cys Leu Tyr Gly Val Gly Leu Pro Thr
330                 335                 340                 345

CCC CGC ACC TAC ATC TAC GAC CAC GGC TTC CCC TAC ACG GAC CCT GTG        1350
Pro Arg Thr Tyr Ile Tyr Asp His Gly Phe Pro Tyr Thr Asp Pro Val
                350                 355                 360

GGT GTG CTC TAT GAG GAT GGT GAT GAC ACG GTG GCG ACC CGC AGC ACC        1398
Gly Val Leu Tyr Glu Asp Gly Asp Asp Thr Val Ala Thr Arg Ser Thr
            365                 370                 375

GAG CTC TGT GGC CTG TGG CAG GGC CGC CAG CCA CAG CCT GTG CAC CTG        1446
Glu Leu Cys Gly Leu Trp Gln Gly Arg Gln Pro Gln Pro Val His Leu
        380                 385                 390

CTG CCC CTG CAC GGG ATA CAG CAT CTC AAC ATG GTC TTC AGC AAC CTG        1494
Leu Pro Leu His Gly Ile Gln His Leu Asn Met Val Phe Ser Asn Leu
    395                 400                 405

ACC CTG GAG CAC ATC AAT GCC ATC CTG CTG GGT GCC TAC CGC CAG GGT        1542
Thr Leu Glu His Ile Asn Ala Ile Leu Leu Gly Ala Tyr Arg Gln Gly
410                 415                 420                 425
```

-continued

```
CCC CCT GCA TCC CCG ACT GCC AGC CCA GAG CCC CCG CCT CCT GAA          1587
Pro Pro Ala Ser Pro Thr Ala Ser Pro Glu Pro Pro Pro Pro Glu
                430                 435                 440

TAAAGACCTT CCTTTGCTAC CGTAAGCCCT GATGGCTATG TTTCAGGTTG AAGGGAGGCA    1647

CTAGAGTCCC ACACTAGGTT TCACTCCTCA CCAGCCACAG GCTCAGTGCT GTGTGCAGTG    1707

AGGCAAGATG GGCTCTGCTG AGGCCTGGGA CTGAGCT                             1744
```

(2) INFORMATION FOR SEQ ID NO:34:

(i) SEQUENCE CHARACTERISTICS:
        (A) LENGTH: 440 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:34:

```
Met Gly Pro Pro Gly Ser Pro Trp Gln Trp Val Thr Leu Leu Gly
 1               5                  10                  15

Leu Leu Leu Pro Pro Ala Ala Pro Phe Trp Leu Leu Asn Val Leu Phe
                20                  25                  30

Pro Pro His Thr Thr Pro Lys Ala Glu Leu Ser Asn His Thr Arg Pro
                35                  40                  45

Val Ile Leu Val Pro Gly Cys Leu Gly Asn Gln Leu Glu Ala Lys Leu
 50                  55                  60

Asp Lys Pro Asp Val Val Asn Trp Met Cys Tyr Arg Lys Thr Glu Asp
 65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
                100                 105                 110

Leu Val Ser Asn Ala Pro Gly Val Gln Ile Arg Val Pro Gly Phe Gly
                115                 120                 125

Lys Thr Tyr Ser Val Glu Tyr Leu Asp Ser Ser Lys Leu Ala Gly Tyr
 130                 135                 140

Leu His Thr Leu Val Gln Asn Leu Val Asn Asn Gly Tyr Val Arg Asp
 145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
                180                 185                 190

Ala Ala Tyr Gly Lys Pro Val Phe Leu Ile Gly His Ser Leu Gly Cys
                195                 200                 205

Leu His Leu Leu Tyr Phe Leu Leu Arg Gln Pro Gln Ala Trp Lys Asp
 210                 215                 220

Arg Phe Ile Asp Gly Phe Ile Ser Leu Gly Ala Pro Trp Gly Gly Ser
 225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
                260                 265                 270

Ser Pro Trp Met Phe Pro Ser Arg Met Ala Trp Pro Glu Asp His Val
                275                 280                 285
```

```
Phe Ile Ser Thr Pro Ser Phe Asn Tyr Thr Gly Arg Asp Phe Gln Arg
    290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
                340                 345                 350

His Gly Phe Pro Tyr Thr Asp Pro Val Gly Val Leu Tyr Glu Asp Gly
                355                 360                 365

Asp Asp Thr Val Ala Thr Arg Ser Thr Glu Leu Cys Gly Leu Trp Gln
    370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
                420                 425                 430

Ser Pro Glu Pro Pro Pro Glu
    435                 440

(2) INFORMATION FOR SEQ ID NO:35:

(i) SEQUENCE CHARACTERISTICS:
        (A) LENGTH: 2182 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 29...1525
        (D) OTHER INFORMATION:

(xi) SEQUENCE DESCRIPTION: SEQ ID NO:35:

CGAAACACAG AGCTTTAGCT CCGCCAAA ATG AAA CAC TCA TTA AAC GCA CTT         52
                              Met Lys His Ser Leu Asn Ala Leu
                                1               5

CTC ATT TTC CTC ATC ATA ACA TCT GCG TGG GGT GGG AGC AAA GGC CCG       100
Leu Ile Phe Leu Ile Ile Thr Ser Ala Trp Gly Gly Ser Lys Gly Pro
    10                  15                  20

CTG GAT CAG CTA GAG AAA GGA GGG GAA ACT GCT CAG TCT GCA GAT CCC       148
Leu Asp Gln Leu Glu Lys Gly Gly Glu Thr Ala Gln Ser Ala Asp Pro
25                  30                  35                  40

CAG TGG GAG CAG TTA AAT AAC AAA AAC CTG AGC ATG CCT CTT CTC CCT       196
Gln Trp Glu Gln Leu Asn Asn Lys Asn Leu Ser Met Pro Leu Leu Pro
                45                  50                  55

GCC GAC TTC CAC AAG GAA AAC ACC GTC ACC AAC GAC TGG ATT CCA GAG       244
Ala Asp Phe His Lys Glu Asn Thr Val Thr Asn Asp Trp Ile Pro Glu
                60                  65                  70

GGG GAG GAG GAC GAC GAC TAT CTG GAC CTG GAG AAG ATA TTC AGT GAA       292
Gly Glu Glu Asp Asp Asp Tyr Leu Asp Leu Glu Lys Ile Phe Ser Glu
            75                  80                  85

GAC GAC GAC TAC ATC GAC ATC GTC GAC AGT CTG TCA GTT TCC CCG ACA       340
Asp Asp Asp Tyr Ile Asp Ile Val Asp Ser Leu Ser Val Ser Pro Thr
        90                  95                  100

GAC TCT GAT GTG AGT GCT GGG AAC ATC CTC CAG CTT TTT CAT GGC AAG       388
Asp Ser Asp Val Ser Ala Gly Asn Ile Leu Gln Leu Phe His Gly Lys
105                 110                 115                 120
```

```
AGC CGG ATC CAG CGT CTT AAC ATC CTC AAC GCC AAG TTC GCT TTC AAC    436
Ser Arg Ile Gln Arg Leu Asn Ile Leu Asn Ala Lys Phe Ala Phe Asn
            125                 130                 135

CTC TAC CGA GTG CTG AAA GAC CAG GTC AAC ACT TTC GAT AAC ATC TTC    484
Leu Tyr Arg Val Leu Lys Asp Gln Val Asn Thr Phe Asp Asn Ile Phe
                140                 145                 150

ATA GCA CCC GTT GGC ATT TCT ACT GCG ATG GGT ATG ATT TCC TTA GGT    532
Ile Ala Pro Val Gly Ile Ser Thr Ala Met Gly Met Ile Ser Leu Gly
            155                 160                 165

CTG AAG GGA GAG ACC CAT GAA CAA GTG CAC TCG ATT TTG CAT TTT AAA    580
Leu Lys Gly Glu Thr His Glu Gln Val His Ser Ile Leu His Phe Lys
170                 175                 180

GAC TTT GTT AAT GCC AGC AGC AAG TAT GAA ATC ACG ACC ATT CAT AAT    628
Asp Phe Val Asn Ala Ser Ser Lys Tyr Glu Ile Thr Thr Ile His Asn
185                 190                 195                 200

CTC TTC CGT AAG CTG ACT CAT CGC CTC TTC AGG AGG AAT TTT GGG TAC    676
Leu Phe Arg Lys Leu Thr His Arg Leu Phe Arg Arg Asn Phe Gly Tyr
                205                 210                 215

ACA CTG CGG TCA GTC AAT GAC CTT TAT ATC CAG AAG CAG TTT CCA ATC    724
Thr Leu Arg Ser Val Asn Asp Leu Tyr Ile Gln Lys Gln Phe Pro Ile
            220                 225                 230

CTG CTT GAC TTC AGA ACT AAA GTA AGA GAG TAT TAC TTT GCT GAG GCC    772
Leu Leu Asp Phe Arg Thr Lys Val Arg Glu Tyr Tyr Phe Ala Glu Ala
        235                 240                 245

CAG ATA GCT GAC TTC TCA GAC CCT GCC TTC ATA TCA AAA ACC AAC AAC    820
Gln Ile Ala Asp Phe Ser Asp Pro Ala Phe Ile Ser Lys Thr Asn Asn
        250                 255                 260

CAC ATC ATG AAG CTC ACC AAG GGC CTC ATA AAA GAT GCT CTG GAG AAT    868
His Ile Met Lys Leu Thr Lys Gly Leu Ile Lys Asp Ala Leu Glu Asn
265                 270                 275                 280

ATA GAC CCT GCT ACC CAG ATG ATG ATT CTC AAC TGC ATC TAC TTC AAA    916
Ile Asp Pro Ala Thr Gln Met Met Ile Leu Asn Cys Ile Tyr Phe Lys
            285                 290                 295

GGA TCC TGG GTG AAT AAA TTC CCA GTG GAA ATG ACA CAC AAC CAC AAC    964
Gly Ser Trp Val Asn Lys Phe Pro Val Glu Met Thr His Asn His Asn
        300                 305                 310

TTC CGG CTG AAT GAG AGA GAG GTA GTT AAG GTT TCC ATG ATG CAG ACC   1012
Phe Arg Leu Asn Glu Arg Glu Val Val Lys Val Ser Met Met Gln Thr
        315                 320                 325

AAG GGG AAC TTC CTC GCA GCA AAT GAC CAG GAG CTG GAC TGC GAC ATC   1060
Lys Gly Asn Phe Leu Ala Ala Asn Asp Gln Glu Leu Asp Cys Asp Ile
        330                 335                 340

CTC CAG CTG GAA TAC GTG GGG GGC ATC AGC ATG CTA ATT GTG GTC CCA   1108
Leu Gln Leu Glu Tyr Val Gly Gly Ile Ser Met Leu Ile Val Val Pro
345                 350                 355                 360

CAC AAG ATG TCT GGG ATG AAG ACC CTC GAA GCG CAA CTG ACA CCC CGG   1156
His Lys Met Ser Gly Met Lys Thr Leu Glu Ala Gln Leu Thr Pro Arg
            365                 370                 375

GTG GTG GAG AGA TGG CAA AAA AGC ATG ACA AAC AGA ACT CGA GAA GTG   1204
Val Val Glu Arg Trp Gln Lys Ser Met Thr Asn Arg Thr Arg Glu Val
                380                 385                 390

CTT CTG CCG AAA TTC AAG CTG GAG AAG AAC TAC AAT CTA GTG GAG TCC   1252
Leu Leu Pro Lys Phe Lys Leu Glu Lys Asn Tyr Asn Leu Val Glu Ser
            395                 400                 405

CTG AAG TTG ATG GGG ATC AGG ATG CTG TTT GAC AAA AAT GGC AAC ATG   1300
Leu Lys Leu Met Gly Ile Arg Met Leu Phe Asp Lys Asn Gly Asn Met
        410                 415                 420

GCA GGC ATC TCA GAC CAA AGG ATC GCC ATC GAC CTG TTC AAG CAC CAA   1348
Ala Gly Ile Ser Asp Gln Arg Ile Ala Ile Asp Leu Phe Lys His Gln
```

```
                425            430            435            440
GGC ACG ATC ACA GTG AAC GAG GAA GGC ACC CAA GCC ACC ACT GTG ACC    1396
Gly Thr Ile Thr Val Asn Glu Glu Gly Thr Gln Ala Thr Thr Val Thr
                445                450                455

ACG GTG GGG TTC ATG CCG CTG TCC ACC CAA GTC CGC TTC ACT GTC GAC    1444
Thr Val Gly Phe Met Pro Leu Ser Thr Gln Val Arg Phe Thr Val Asp
            460                465                470

CGC CCC TTT CTT TTC CTC ATC TAC GAG CAC CGC ACC AGC TGC CTG CTC    1492
Arg Pro Phe Leu Phe Leu Ile Tyr Glu His Arg Thr Ser Cys Leu Leu
        475                480                485

TTC ATG GGA AGA GTG GCC AAC CCC AGC AGG TCC TAGAGGTGGA GGTCTAGGTG  1545
Phe Met Gly Arg Val Ala Asn Pro Ser Arg Ser
    490                495

TCTGAAGTGC CTTGGGGGCA CCCTCATTTT GTTTCCATTC CAACAACGAG AACAGAGATG  1605

TTCTGGCATC ATTACGTAG TTTACGCTAC CAATCTGAAT TCGAGGCCCA TATGAGAGGA   1665

GCTTAGAAAC GACCAAGAAG AGAGGCTTGT TGGAATCAAT TCTGCACAAT AGCCCATGCT  1725

GTAAGCTCAT AGAAGTCACT GTAACTGTAG TGTGTCTGCT GTTACCTAGA GGGTCTCACC  1785

TCCCCACTCT TCACAGCAAA CCTGAGCAGC GCGTCCTAAG CACCTCCCGC TCCGGTGACC  1845

CCATCCTTGC ACACCTGACT CTGTCACTCA AGCCTTTCTC CACCAGGCCC CTCATCTGAA  1905

TACCAAGCAC AGAAATGAGT GGTGTGACTA ATTCCTTACC TCTCCCAAGG AGGGTACACA  1965

ACTAGCACCA TTCTTGATGT CCAGGGAAGA AGCCACCTCA AGACATATGA GGGGTGCCCT  2025

GGGCTAATGT TAGGGCTTAA TTTTCTCAAA GCCTGACCTT TCAAATCCAT GATGAATGCC  2085

ATCAGTCCCT CCTGCTGTTG CCTCCCTGTG ACCTGGAGGA CAGTGTGTGC CATGTCTCCC  2145

ATACTAGAGA TAAATAAATG TAGCCACATT TACTGTG                          2182
```

(2) INFORMATION FOR SEQ ID NO:36:

(i) SEQUENCE CHARACTERISTICS:
        (A) LENGTH: 499 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:36:

```
Met Lys His Ser Leu Asn Ala Leu Leu Ile Phe Leu Ile Ile Thr Ser
1               5                   10                  15

Ala Trp Gly Gly Ser Lys Gly Pro Leu Asp Gln Leu Glu Lys Gly Gly
            20                  25                  30

Glu Thr Ala Gln Ser Ala Asp Pro Gln Trp Glu Gln Leu Asn Asn Lys
        35                  40                  45

Asn Leu Ser Met Pro Leu Leu Pro Ala Asp Phe His Lys Glu Asn Thr
    50                  55                  60

Val Thr Asn Asp Trp Ile Pro Glu Gly Glu Asp Asp Asp Tyr Leu
65                  70                  75                  80

Asp Leu Glu Lys Ile Phe Ser Glu Asp Asp Tyr Ile Asp Ile Val
                85                  90                  95

Asp Ser Leu Ser Val Ser Pro Thr Asp Ser Asp Val Ser Ala Gly Asn
            100                 105                 110

Ile Leu Gln Leu Phe His Gly Lys Ser Arg Ile Gln Arg Leu Asn Ile
        115                 120                 125
```

```
Leu Asn Ala Lys Phe Ala Phe Asn Leu Tyr Arg Val Leu Lys Asp Gln
    130                 135                 140

Val Asn Thr Phe Asp Asn Ile Phe Ile Ala Pro Val Gly Ile Ser Thr
145                 150                 155                 160

Ala Met Gly Met Ile Ser Leu Gly Leu Lys Gly Glu Thr His Glu Gln
                165                 170                 175

Val His Ser Ile Leu His Phe Lys Asp Phe Val Asn Ala Ser Ser Lys
            180                 185                 190

Tyr Glu Ile Thr Thr Ile His Asn Leu Phe Arg Lys Leu Thr His Arg
            195                 200                 205

Leu Phe Arg Arg Asn Phe Gly Tyr Thr Leu Arg Ser Val Asn Asp Leu
    210                 215                 220

Tyr Ile Gln Lys Gln Phe Pro Ile Leu Leu Asp Phe Arg Thr Lys Val
225                 230                 235                 240

Arg Glu Tyr Tyr Phe Ala Glu Ala Gln Ile Ala Asp Phe Ser Asp Pro
                245                 250                 255

Ala Phe Ile Ser Lys Thr Asn Asn His Ile Met Lys Leu Thr Lys Gly
            260                 265                 270

Leu Ile Lys Asp Ala Leu Glu Asn Ile Asp Pro Ala Thr Gln Met Met
    275                 280                 285

Ile Leu Asn Cys Ile Tyr Phe Lys Gly Ser Trp Val Asn Lys Phe Pro
    290                 295                 300

Val Glu Met Thr His Asn His Asn Phe Arg Leu Asn Glu Arg Glu Val
305                 310                 315                 320

Val Lys Val Ser Met Met Gln Thr Lys Gly Asn Phe Leu Ala Ala Asn
                325                 330                 335

Asp Gln Glu Leu Asp Cys Asp Ile Leu Gln Leu Glu Tyr Val Gly Gly
            340                 345                 350

Ile Ser Met Leu Ile Val Val Pro His Lys Met Ser Gly Met Lys Thr
            355                 360                 365

Leu Glu Ala Gln Leu Thr Pro Arg Val Val Glu Arg Trp Gln Lys Ser
    370                 375                 380

Met Thr Asn Arg Thr Arg Glu Val Leu Leu Pro Lys Phe Lys Leu Glu
385                 390                 395                 400

Lys Asn Tyr Asn Leu Val Glu Ser Leu Lys Leu Met Gly Ile Arg Met
                405                 410                 415

Leu Phe Asp Lys Asn Gly Asn Met Ala Gly Ile Ser Asp Gln Arg Ile
            420                 425                 430

Ala Ile Asp Leu Phe Lys His Gln Gly Thr Ile Thr Val Asn Glu Glu
            435                 440                 445

Gly Thr Gln Ala Thr Thr Val Thr Thr Val Gly Phe Met Pro Leu Ser
    450                 455                 460

Thr Gln Val Arg Phe Thr Val Asp Arg Pro Phe Leu Phe Leu Ile Tyr
465                 470                 475                 480

Glu His Arg Thr Ser Cys Leu Leu Phe Met Gly Arg Val Ala Asn Pro
                485                 490                 495

Ser Arg Ser (2) INFORMATION FOR SEQ ID NO:37:

(i) SEQUENCE CHARACTERISTICS:
        (A) LENGTH: 6893 base pairs
        (B) TYPE: nucleic acid
        (C) STRANDEDNESS: single
        (D) TOPOLOGY: linear
```

(ii) MOLECULE TYPE: Genomic DNA (ix) FEATURE:
        (A) NAME/KEY: Coding Sequence
        (B) LOCATION: 77...6748
        (D) OTHER INFORMATION:

(xi) SEQUENCE DESCRIPTION: SEQ ID NO:37:

```
CTCCGGGCTG TCCCAGCTCG GCAAGCGCTG CCCAGGTCCT GGGGTGGTGG CAGCCAGCGG          60

GAGCAGGAAA GGAAGC ATG TTC CCA GGC TGC CCA CGC CTC TGG GTC CTG GTG         112
               Met Phe Pro Gly Cys Pro Arg Leu Trp Val Leu Val
                 1               5                  10

GTC TTG GGC ACC AGC TGG GTA GGC TGG GGG AGC CAA GGG ACA GAA GCG           160
Val Leu Gly Thr Ser Trp Val Gly Trp Gly Ser Gln Gly Thr Glu Ala
         15                  20                  25

GCA CAG CTA AGG CAG TTC TAC GTG GCT GCT CAG GGC ATC AGT TGG AGC           208
Ala Gln Leu Arg Gln Phe Tyr Val Ala Ala Gln Gly Ile Ser Trp Ser
     30                  35                  40

TAC CGA CCT GAG CCC ACA AAC TCA AGT TTG AAT CTT TCT GTA ACT TCC           256
Tyr Arg Pro Glu Pro Thr Asn Ser Ser Leu Asn Leu Ser Val Thr Ser
 45                  50                  55                  60

TTT AAG AAA ATT GTC TAC AGA GAG TAT GAA CCA TAT TTT AAG AAA GAA           304
Phe Lys Lys Ile Val Tyr Arg Glu Tyr Glu Pro Tyr Phe Lys Lys Glu
                 65                  70                  75

AAA CCA CAA TCT ACC ATT TCA GGA CTT CTT GGG CCT ACT TTA TAT GCT           352
Lys Pro Gln Ser Thr Ile Ser Gly Leu Leu Gly Pro Thr Leu Tyr Ala
             80                  85                  90

GAA GTC GGA GAC ATC ATA AAA GTT CAC TTT AAA AAT AAG GCA GAT AAG           400
Glu Val Gly Asp Ile Ile Lys Val His Phe Lys Asn Lys Ala Asp Lys
         95                  100                 105

CCC TTG AGC ATC CAT CCT CAA GGA ATT AGG TAC AGT AAA TTA TCA GAA           448
Pro Leu Ser Ile His Pro Gln Gly Ile Arg Tyr Ser Lys Leu Ser Glu
     110                 115                 120

GGT GCT TCT TAC CTT GAC CAC ACA TTC CCT GCA GAG AAG ATG GAC GAC           496
Gly Ala Ser Tyr Leu Asp His Thr Phe Pro Ala Glu Lys Met Asp Asp
125                 130                 135                 140

GCT GTG GCT CCA GGC CGA GAA TAC ACC TAT GAA TGG AGT ATC AGT GAG           544
Ala Val Ala Pro Gly Arg Glu Tyr Thr Tyr Glu Trp Ser Ile Ser Glu
                 145                 150                 155

GAC AGT GGA CCC ACC CAT GAT GAC CCT CCA TGC CTC ACA CAC ATC TAT           592
Asp Ser Gly Pro Thr His Asp Asp Pro Pro Cys Leu Thr His Ile Tyr
             160                 165                 170

TAC TCC CAT GAA AAT CTG ATC GAG GAT TTC AAC TCT GGG CTG ATT GGG           640
Tyr Ser His Glu Asn Leu Ile Glu Asp Phe Asn Ser Gly Leu Ile Gly
         175                 180                 185

CCC CTG CTT ATC TGT AAA AAA GGG ACC CTA ACT GAG GGT GGG ACA CAG           688
Pro Leu Leu Ile Cys Lys Lys Gly Thr Leu Thr Glu Gly Gly Thr Gln
     190                 195                 200

AAG ACG TTT GAC AAG CAA ATC GTG CTA CTA TTT GCT GTG TTT GAT GAA           736
Lys Thr Phe Asp Lys Gln Ile Val Leu Leu Phe Ala Val Phe Asp Glu
205                 210                 215                 220

AGC AAG AGC TGG AGC CAG TCA TCA TCC CTA ATG TAC ACA GTC AAT GGA           784
Ser Lys Ser Trp Ser Gln Ser Ser Ser Leu Met Tyr Thr Val Asn Gly
                 225                 230                 235

TAT GTG AAT GGG ACA ATG CCA GAT ATA ACA GTT TGT GCC CAT GAC CAC           832
Tyr Val Asn Gly Thr Met Pro Asp Ile Thr Val Cys Ala His Asp His
             240                 245                 250

ATC AGC TGG CAT CTG CTG GGA ATG AGC TCG GGG CCA GAA TTA TTC TCC           880
Ile Ser Trp His Leu Leu Gly Met Ser Ser Gly Pro Glu Leu Phe Ser
         255                 260                 265
```

```
ATT CAT TTC AAC GGC CAG GTC CTG GAG CAG AAC CAT CAT AAG GTC TCA        928
Ile His Phe Asn Gly Gln Val Leu Glu Gln Asn His His Lys Val Ser
    270                 275                 280

GCC ATC ACC CTT GTC AGT GCT ACA TCC ACT ACC GCA AAT ATG ACT GTG        976
Ala Ile Thr Leu Val Ser Ala Thr Ser Thr Thr Ala Asn Met Thr Val
285                 290                 295                 300

GGC CCA GAG GGA AAG TGG ATC ATA TCT TCT CTC ACC CCA AAA CAT TTG       1024
Gly Pro Glu Gly Lys Trp Ile Ile Ser Ser Leu Thr Pro Lys His Leu
                305                 310                 315

CAA GCT GGG ATG CAG GCT TAC ATT GAC ATT AAA AAC TGC CCA AAG AAA       1072
Gln Ala Gly Met Gln Ala Tyr Ile Asp Ile Lys Asn Cys Pro Lys Lys
            320                 325                 330

ACC AGG AAT CTT AAG AAA ATA ACT CGT GAG CAG AGG CGG CAC ATG AAG       1120
Thr Arg Asn Leu Lys Lys Ile Thr Arg Glu Gln Arg Arg His Met Lys
        335                 340                 345

AGG TGG GAA TAC TTC ATT GCT GCA GAG GAA GTC ATT TGG GAC TAT GCA       1168
Arg Trp Glu Tyr Phe Ile Ala Ala Glu Glu Val Ile Trp Asp Tyr Ala
    350                 355                 360

CCT GTA ATA CCA GCG AAT ATG GAC AAA AAA TAC AGG TCT CAG CAT TTG       1216
Pro Val Ile Pro Ala Asn Met Asp Lys Lys Tyr Arg Ser Gln His Leu
365                 370                 375                 380

GAT AAT TTC TCA AAC CAA ATT GGA AAA CAT TAT AAG AAA GTT ATG TAC       1264
Asp Asn Phe Ser Asn Gln Ile Gly Lys His Tyr Lys Lys Val Met Tyr
                385                 390                 395

ACA CAG TAC GAA GAT GAG TCC TTC ACC AAA CAT ACA GTG AAT CCC AAT       1312
Thr Gln Tyr Glu Asp Glu Ser Phe Thr Lys His Thr Val Asn Pro Asn
            400                 405                 410

ATG AAA GAA GAT GGG ATT TTG GGT CCT ATT ATC AGA GCC CAG GTC AGA       1360
Met Lys Glu Asp Gly Ile Leu Gly Pro Ile Ile Arg Ala Gln Val Arg
        415                 420                 425

GAC ACA CTC AAA ATC GTG TTC AAA AAT ATG GCC AGC CGC CCC TAT AGC       1408
Asp Thr Leu Lys Ile Val Phe Lys Asn Met Ala Ser Arg Pro Tyr Ser
    430                 435                 440

ATT TAC CCT CAT GGA GTG ACC TTC TCG CCT TAT GAA GAT GAA GTC AAC       1456
Ile Tyr Pro His Gly Val Thr Phe Ser Pro Tyr Glu Asp Glu Val Asn
445                 450                 455                 460

TCT TCT TTC ACC TCA GGC AGG AAC AAC ACC ATG ATC AGA GCA GTT CAA       1504
Ser Ser Phe Thr Ser Gly Arg Asn Asn Thr Met Ile Arg Ala Val Gln
                465                 470                 475

CCA GGG GAA ACC TAT ACT TAT AAG TGG AAC ATC TTA GAG TTT GAT GAA       1552
Pro Gly Glu Thr Tyr Thr Tyr Lys Trp Asn Ile Leu Glu Phe Asp Glu
            480                 485                 490

CCC ACA GAA AAT GAT GCC CAG TGC TTA ACA AGA CCA TAC TAC AGT GAC       1600
Pro Thr Glu Asn Asp Ala Gln Cys Leu Thr Arg Pro Tyr Tyr Ser Asp
        495                 500                 505

GTG GAC ATC ATG AGA GAC ATC GCC TCT GGG CTA ATA GGA CTA CTT CTA       1648
Val Asp Ile Met Arg Asp Ile Ala Ser Gly Leu Ile Gly Leu Leu Leu
    510                 515                 520

ATC TGT AAG AGC AGA TCC CTG GAC AGG CGA GGA ATA CAG AGG GCA GCA       1696
Ile Cys Lys Ser Arg Ser Leu Asp Arg Arg Gly Ile Gln Arg Ala Ala
525                 530                 535                 540

GAC ATC GAA CAG CAG GCT GTG TTT GCT GTG TTT GAT GAG AAC AAA AGC       1744
Asp Ile Glu Gln Gln Ala Val Phe Ala Val Phe Asp Glu Asn Lys Ser
                545                 550                 555

TGG TAC CTT GAG GAC AAC ATC AAC AAG TTT TGT GAA AAT CCT GAT GAG       1792
Trp Tyr Leu Glu Asp Asn Ile Asn Lys Phe Cys Glu Asn Pro Asp Glu
            560                 565                 570

GTG AAA CGT GAT GAC CCC AAG TTT TAT GAA TCA AAC ATC ATG AGC ACT       1840
Val Lys Arg Asp Asp Pro Lys Phe Tyr Glu Ser Asn Ile Met Ser Thr
```

```
              575                 580                 585
ATC AAT GGC TAT GTG CCT GAG AGC ATA ACT ACT CTT GGA TTC TGC TTT     1888
Ile Asn Gly Tyr Val Pro Glu Ser Ile Thr Thr Leu Gly Phe Cys Phe
    590                 595                 600

GAT GAC ACT GTC CAG TGG CAC TTC TGT AGT GTG GGG ACC CAG AAT GAA     1936
Asp Asp Thr Val Gln Trp His Phe Cys Ser Val Gly Thr Gln Asn Glu
605                 610                 615                 620

ATT TTG ACC ATC CAC TTC ACT GGG CAC TCA TTC ATC TAT GGA AAG AGG     1984
Ile Leu Thr Ile His Phe Thr Gly His Ser Phe Ile Tyr Gly Lys Arg
                625                 630                 635

CAT GAG GAC ACC TTG ACC CTC TTC CCC ATG CGT GGA GAA TCT GTG ACG     2032
His Glu Asp Thr Leu Thr Leu Phe Pro Met Arg Gly Glu Ser Val Thr
            640                 645                 650

GTC ACA ATG GAT AAT GTT GGA ACT TGG ATG TTA ACT TCC ATG AAT TCT     2080
Val Thr Met Asp Asn Val Gly Thr Trp Met Leu Thr Ser Met Asn Ser
        655                 660                 665

AGT CCA AGA AGC AAA AAG CTG AGG CTG AAA TTC AGG GAT GTT AAA TGT     2128
Ser Pro Arg Ser Lys Lys Leu Arg Leu Lys Phe Arg Asp Val Lys Cys
    670                 675                 680

ATC CCA GAT GAT GAT GAA GAC TCA TAT GAG ATT TTT GAA CCT CCA GAA     2176
Ile Pro Asp Asp Asp Glu Asp Ser Tyr Glu Ile Phe Glu Pro Pro Glu
685                 690                 695                 700

TCT ACA GTC ATG GCT ACA CGG AAA ATG CAT GAT CGT TTA GAA CCT GAA     2224
Ser Thr Val Met Ala Thr Arg Lys Met His Asp Arg Leu Glu Pro Glu
                705                 710                 715

GAT GAA GAG AGT GAT GCT GAC TAT GAT TAC CAG AAC AGA CTG GCT GCA     2272
Asp Glu Glu Ser Asp Ala Asp Tyr Asp Tyr Gln Asn Arg Leu Ala Ala
            720                 725                 730

GCA TTA GGA ATT AGG TCA TTC CGA AAC TCA TCA TTG AAC CAG GAA GAA     2320
Ala Leu Gly Ile Arg Ser Phe Arg Asn Ser Ser Leu Asn Gln Glu Glu
        735                 740                 745

GAA GAG TTC AAT CTT ACT GCC CTA GCT CTG GAG AAT GGC ACT GAA TTC     2368
Glu Glu Phe Asn Leu Thr Ala Leu Ala Leu Glu Asn Gly Thr Glu Phe
    750                 755                 760

GTT TCT TCG AAC ACA GAT ATA ATT GTT GGT TCA AAT TAT TCT TCC CCA     2416
Val Ser Ser Asn Thr Asp Ile Ile Val Gly Ser Asn Tyr Ser Ser Pro
765                 770                 775                 780

AGT AAT ATT AGT AAG TTC ACT GTC AAT AAC CTT GCA GAA CCT CAG AAA     2464
Ser Asn Ile Ser Lys Phe Thr Val Asn Asn Leu Ala Glu Pro Gln Lys
                785                 790                 795

GCC CCT TCT CAC CAA CAA GCC ACC ACA GCT GGT TCC CCA CTG AGA CAC     2512
Ala Pro Ser His Gln Gln Ala Thr Thr Ala Gly Ser Pro Leu Arg His
            800                 805                 810

CTC ATT GGC AAG AAC TCA GTT CTC AAT TCT TCC ACA GCA GAG CAT TCC     2560
Leu Ile Gly Lys Asn Ser Val Leu Asn Ser Ser Thr Ala Glu His Ser
        815                 820                 825

AGC CCA TAT TCT GAA GAC CCT ATA GAG GAT CCT CTA CAG CCA GAT GTC     2608
Ser Pro Tyr Ser Glu Asp Pro Ile Glu Asp Pro Leu Gln Pro Asp Val
    830                 835                 840

ACA GGG ATA CGT CTA CTT TCA CTT GGT GCT GGA GAA TTC AGA AGT CAA     2656
Thr Gly Ile Arg Leu Leu Ser Leu Gly Ala Gly Glu Phe Arg Ser Gln
845                 850                 855                 860

GAA CAT GCT AAG CGT AAG GGA CCC AAG GTA GAA AGA GAT CAA GCA GCA     2704
Glu His Ala Lys Arg Lys Gly Pro Lys Val Glu Arg Asp Gln Ala Ala
                865                 870                 875

AAG CAC AGG TTC TCC TGG ATG AAA TTA CTA GCA CAT AAA GTT GGG AGA     2752
Lys His Arg Phe Ser Trp Met Lys Leu Leu Ala His Lys Val Gly Arg
            880                 885                 890

CAC CTA AGC CAA GAC ACT GGT TCT CCT TCC GGA ATG AGG CCC TGG GAG     2800
```

```
                                                        -continued
His Leu Ser Gln Asp Thr Gly Ser Pro Ser Gly Met Arg Pro Trp Glu
        895                 900                 905

GAC CTT CCT AGC CAA GAC ACT GGT TCT CCT TCC AGA ATG AGG CCC TGG         2848
Asp Leu Pro Ser Gln Asp Thr Gly Ser Pro Ser Arg Met Arg Pro Trp
910                 915                 920

GAG GAC CCT CCT AGT GAT CTG TTA CTC TTA AAA CAA AGT AAC TCA TCT         2896
Glu Asp Pro Pro Ser Asp Leu Leu Leu Leu Lys Gln Ser Asn Ser Ser
925                 930                 935                 940

AAG ATT TTG GTT GGG AGA TGG CAT TTG GCT TCT GAG AAA GGT AGC TAT         2944
Lys Ile Leu Val Gly Arg Trp His Leu Ala Ser Glu Lys Gly Ser Tyr
                945                 950                 955

GAA ATA ATC CAA GAT ACT GAT GAA GAC ACA GCT GTT AAC AAT TGG CTG         2992
Glu Ile Ile Gln Asp Thr Asp Glu Asp Thr Ala Val Asn Asn Trp Leu
                960                 965                 970

ATC AGC CCC CAG AAT GCC TCA CGT GCT TGG GGA GAA AGC ACC CCT CTT         3040
Ile Ser Pro Gln Asn Ala Ser Arg Ala Trp Gly Glu Ser Thr Pro Leu
            975                 980                 985

GCC AAC AAG CCT GGA AAG CAG AGT GGC CAC CCA AAG TTT CCT AGA GTT         3088
Ala Asn Lys Pro Gly Lys Gln Ser Gly His Pro Lys Phe Pro Arg Val
990                 995                 1000

AGA CAT AAA TCT CTA CAA GTA AGA CAG GAT GGA GGA AAG AGT AGA CTG         3136
Arg His Lys Ser Leu Gln Val Arg Gln Asp Gly Gly Lys Ser Arg Leu
1005                1010                1015                1020

AAG AAA AGC CAG TTT CTC ATT AAG ACA CGA AAA AAG AAA AAA GAG AAG         3184
Lys Lys Ser Gln Phe Leu Ile Lys Thr Arg Lys Lys Lys Lys Glu Lys
                1025                1030                1035

CAC ACA CAC CAT GCT CCT TTA TCT CCG AGG ACC TTT CAC CCT CTA AGA         3232
His Thr His His Ala Pro Leu Ser Pro Arg Thr Phe His Pro Leu Arg
                1040                1045                1050

AGT GAA GCC TAC AAC ACA TTT TCA GAA AGA AGA CTT AAG CAT TCG TTG         3280
Ser Glu Ala Tyr Asn Thr Phe Ser Glu Arg Arg Leu Lys His Ser Leu
            1055                1060                1065

GTG CTT CAT AAA TCC AAT GAA ACA TCT CTT CCC ACA GAC CTC AAT CAG         3328
Val Leu His Lys Ser Asn Glu Thr Ser Leu Pro Thr Asp Leu Asn Gln
    1070                1075                1080

ACA TTG CCC TCT ATG GAT TTT GGC TGG ATA GCC TCA CTT CCT GAC CAT         3376
Thr Leu Pro Ser Met Asp Phe Gly Trp Ile Ala Ser Leu Pro Asp His
1085                1090                1095                1100

AAT CAG AAT TCC TCA AAT GAC ACT GGT CAG GCA AGC TGT CCT CCA GGT         3424
Asn Gln Asn Ser Ser Asn Asp Thr Gly Gln Ala Ser Cys Pro Pro Gly
                1105                1110                1115

CTT TAT CAG ACA GTG CCC CCA GAG GAA CAC TAT CAA ACA TTC CCC ATT         3472
Leu Tyr Gln Thr Val Pro Pro Glu Glu His Tyr Gln Thr Phe Pro Ile
                1120                1125                1130

CAA GAC CCT GAT CAA ATG CAC TCT ACT TCA GAC CCC AGT CAC AGA TCC         3520
Gln Asp Pro Asp Gln Met His Ser Thr Ser Asp Pro Ser His Arg Ser
            1135                1140                1145

TCT TCT CCA GAG CTC AGT GAA ATG CTT GAG TAT GAC CGA AGT CAC AAG         3568
Ser Ser Pro Glu Leu Ser Glu Met Leu Glu Tyr Asp Arg Ser His Lys
        1150                1155                1160

TCC TTC CCC ACA GAT ATA AGT CAA ATG TCC CCT TCC TCA GAA CAT GAA         3616
Ser Phe Pro Thr Asp Ile Ser Gln Met Ser Pro Ser Ser Glu His Glu
1165                1170                1175                1180

GTC TGG CAG ACA GTC ATC TCT CCA GAC CTC AGC CAG GTG ACC CTC TCT         3664
Val Trp Gln Thr Val Ile Ser Pro Asp Leu Ser Gln Val Thr Leu Ser
                1185                1190                1195

CCA GAA CTC AGC CAG ACA AAC CTC TCT CCA GAC CTC AGC CAC ACG ACT         3712
Pro Glu Leu Ser Gln Thr Asn Leu Ser Pro Asp Leu Ser His Thr Thr
            1200                1205                1210
```

```
CTC TCT CCA GAA CTC ATT CAG AGA AAC CTT TCC CCA GCC CTC GGT CAG         3760
Leu Ser Pro Glu Leu Ile Gln Arg Asn Leu Ser Pro Ala Leu Gly Gln
        1215                1220                1225

ATG CCC ATT TCT CCA GAC CTC AGC CAT ACA ACC CTT TCT CCA GAC CTC         3808
Met Pro Ile Ser Pro Asp Leu Ser His Thr Thr Leu Ser Pro Asp Leu
1230                1235                1240

AGC CAT ACA ACC CTT TCT TTA GAC CTC AGC CAG ACA AAC CTC TCT CCA         3856
Ser His Thr Thr Leu Ser Leu Asp Leu Ser Gln Thr Asn Leu Ser Pro
1245                1250                1255                1260

GAA CTC AGT CAG ACA AAC CTT TCT CCA GCC CTC GGT CAG ATG CCC CTT         3904
Glu Leu Ser Gln Thr Asn Leu Ser Pro Ala Leu Gly Gln Met Pro Leu
                1265                1270                1275

TCT CCA GAC CTC AGC CAT ACA ACC ATT TCT CTA GAC TTC AGC CAG ACA         3952
Ser Pro Asp Leu Ser His Thr Thr Ile Ser Leu Asp Phe Ser Gln Thr
        1280                1285                1290

AAC CTC TCT CCA GAA CTC AGC CAT ATG ACT CTC TCT CCA GAA CTC AGT         4000
Asn Leu Ser Pro Glu Leu Ser His Met Thr Leu Ser Pro Glu Leu Ser
            1295                1300                1305

CAG ACA AAC CTT TCC CCA GCC CTC GGT CAG ATG CCC ATT TCT CCA GAC         4048
Gln Thr Asn Leu Ser Pro Ala Leu Gly Gln Met Pro Ile Ser Pro Asp
        1310                1315                1320

CTC AGC CAT ACA ACC CTT TCT CTA GAC TTC AGC CAG ACA AAC CTC TCT         4096
Leu Ser His Thr Thr Leu Ser Leu Asp Phe Ser Gln Thr Asn Leu Ser
1325                1330                1335                1340

CCA GAA CTC AGT CAA ACA AAC CTT TCC CCA GCC CTC GGT CAG ATG CCC         4144
Pro Glu Leu Ser Gln Thr Asn Leu Ser Pro Ala Leu Gly Gln Met Pro
                1345                1350                1355

CTT TCT CCA GAC CCC AGC CAT ACA ACC CTT TCT CTA GAC CTC AGC CAG         4192
Leu Ser Pro Asp Pro Ser His Thr Thr Leu Ser Leu Asp Leu Ser Gln
        1360                1365                1370

ACA AAC CTC TCT CCA GAA CTC AGT CAG ACA AAC CTT TCC CCA GAC CTC         4240
Thr Asn Leu Ser Pro Glu Leu Ser Gln Thr Asn Leu Ser Pro Asp Leu
            1375                1380                1385

AGT GAG ATG CCC CTC TTT GCA GAT CTC AGT CAA ATT CCC CTT ACC CCA         4288
Ser Glu Met Pro Leu Phe Ala Asp Leu Ser Gln Ile Pro Leu Thr Pro
        1390                1395                1400

GAC CTC GAC CAG ATG ACA CTT TCT CCA GAC CTT GGT GAG ACA GAT CTT         4336
Asp Leu Asp Gln Met Thr Leu Ser Pro Asp Leu Gly Glu Thr Asp Leu
1405                1410                1415                1420

TCC CCA AAC TTT GGT CAG ATG TCC CTT TCC CCA GAC CTC AGC CAG GTG         4384
Ser Pro Asn Phe Gly Gln Met Ser Leu Ser Pro Asp Leu Ser Gln Val
                1425                1430                1435

ACT CTC TCT CCA GAC ATC AGT GAC ACC ACC CTT CTC CCG GAT CTC AGC         4432
Thr Leu Ser Pro Asp Ile Ser Asp Thr Thr Leu Leu Pro Asp Leu Ser
        1440                1445                1450

CAG ATA TCA CCT CCT CCA GAC CTT GAT CAG ATA TTC TAC CCT TCT GAA         4480
Gln Ile Ser Pro Pro Pro Asp Leu Asp Gln Ile Phe Tyr Pro Ser Glu
            1455                1460                1465

TCT AGT CAG TCA TTG CTT CTT CAA GAA TTT AAT GAG TCT TTT CCT TAT         4528
Ser Ser Gln Ser Leu Leu Leu Gln Glu Phe Asn Glu Ser Phe Pro Tyr
        1470                1475                1480

CCA GAC CTT GGT CAG ATG CCA TCT CCT TCA TCT CCT ACT CTC AAT GAT         4576
Pro Asp Leu Gly Gln Met Pro Ser Pro Ser Ser Pro Thr Leu Asn Asp
1485                1490                1495                1500

ACT TTT CTA TCA AAG GAA TTT AAT CCA CTG GTT ATA GTG GGC CTC AGT         4624
Thr Phe Leu Ser Lys Glu Phe Asn Pro Leu Val Ile Val Gly Leu Ser
            1505                1510                1515

AAA GAT GGT ACA GAT TAC ATT GAG ATC ATT CCA AAG GAA GAG GTC CAG         4672
Lys Asp Gly Thr Asp Tyr Ile Glu Ile Ile Pro Lys Glu Glu Val Gln
                1520                1525                1530
```

| | | |
|---|---|---|
| AGC AGT GAA GAT GAC TAT GCT GAA ATT GAT TAT GTG CCC TAT GAT GAC<br>Ser Ser Glu Asp Asp Tyr Ala Glu Ile Asp Tyr Val Pro Tyr Asp Asp<br>      1535                    1540                    1545 | 4720 |
| CCC TAC AAA ACT GAT GTT AGG ACA AAC ATC AAC TCC TCC AGA GAT CCT<br>Pro Tyr Lys Thr Asp Val Arg Thr Asn Ile Asn Ser Ser Arg Asp Pro<br>1550                    1555                    1560 | 4768 |
| GAC AAC ATT GCA GCA TGG TAC CTC CGC AGC AAC AAT GGA AAC AGA AGA<br>Asp Asn Ile Ala Ala Trp Tyr Leu Arg Ser Asn Asn Gly Asn Arg Arg<br>1565                    1570                    1575                    1580 | 4816 |
| AAT TAT TAC ATT GCT GCT GAA GAA ATA TCC TGG GAT TAT TCA GAA TTT<br>Asn Tyr Tyr Ile Ala Ala Glu Glu Ile Ser Trp Asp Tyr Ser Glu Phe<br>                  1585                    1590                    1595 | 4864 |
| GTA CAA AGG GAA ACA GAT ATT GAA GAC TCT GAT GAT ATT CCA GAA GAT<br>Val Gln Arg Glu Thr Asp Ile Glu Asp Ser Asp Asp Ile Pro Glu Asp<br>      1600                    1605                    1610 | 4912 |
| ACC ACA TAT AAG AAA GTA GTT TTT CGA AAG TAC CTC GAC AGC ACT TTT<br>Thr Thr Tyr Lys Lys Val Val Phe Arg Lys Tyr Leu Asp Ser Thr Phe<br>1615                    1620                    1625 | 4960 |
| ACC AAA CGT GAT CCT CGA GGG GAG TAT GAA GAG CAT CTC GGA ATT CTT<br>Thr Lys Arg Asp Pro Arg Gly Glu Tyr Glu Glu His Leu Gly Ile Leu<br>      1630                    1635                    1640 | 5008 |
| GGT CCT ATT ATC AGA GCT GAA GTG GAT GAT GTT ATC CAA GTT CGT TTT<br>Gly Pro Ile Ile Arg Ala Glu Val Asp Asp Val Ile Gln Val Arg Phe<br>1645                    1650                    1655                    1660 | 5056 |
| AAA AAT TTA GCA TCC AGA CCG TAT TCT CTA CAT GCC CAT GGA CTT TCC<br>Lys Asn Leu Ala Ser Arg Pro Tyr Ser Leu His Ala His Gly Leu Ser<br>                  1665                    1670                    1675 | 5104 |
| TAT GAA AAA TCA TCA GAG GGA AAG ACT TAT GAA GAT GAC TCT CCT GAA<br>Tyr Glu Lys Ser Ser Glu Gly Lys Thr Tyr Glu Asp Asp Ser Pro Glu<br>1680                    1685                    1690 | 5152 |
| TGG TTT AAG GAA GAT AAT GCT GTT CAG CCA AAT AGC AGT TAT ACC TAC<br>Trp Phe Lys Glu Asp Asn Ala Val Gln Pro Asn Ser Ser Tyr Thr Tyr<br>                  1695                    1700                    1705 | 5200 |
| GTA TGG CAT GCC ACT GAG CGA TCA GGG CCA GAA AGT CCT GGC TCT GCC<br>Val Trp His Ala Thr Glu Arg Ser Gly Pro Glu Ser Pro Gly Ser Ala<br>      1710                    1715                    1720 | 5248 |
| TGT CGG GCT TGG GCC TAC TAC TCA GCT GTG AAC CCA GAA AAA GAT ATT<br>Cys Arg Ala Trp Ala Tyr Tyr Ser Ala Val Asn Pro Glu Lys Asp Ile<br>1725                    1730                    1735                    1740 | 5296 |
| CAC TCA GGC TTG ATA GGT CCC CTC CTA ATC TGC CAA AAA GGA ATA CTA<br>His Ser Gly Leu Ile Gly Pro Leu Leu Ile Cys Gln Lys Gly Ile Leu<br>                  1745                    1750                    1755 | 5344 |
| CAT AAG GAC AGC AAC ATG CCT GTG GAC ATG AGA GAA TTT GTC TTA CTA<br>His Lys Asp Ser Asn Met Pro Val Asp Met Arg Glu Phe Val Leu Leu<br>1760                    1765                    1770 | 5392 |
| TTT ATG ACC TTT GAT GAA AAG AAG AGC TGG TAC TAT GAA AAG AAG TCC<br>Phe Met Thr Phe Asp Glu Lys Lys Ser Trp Tyr Tyr Glu Lys Lys Ser<br>                  1775                    1780                    1785 | 5440 |
| CGA AGT TCT TGG AGA CTC ACA TCC TCA GAA ATG AAA AAA TCC CAT GAG<br>Arg Ser Ser Trp Arg Leu Thr Ser Ser Glu Met Lys Lys Ser His Glu<br>      1790                    1795                    1800 | 5488 |
| TTT CAC GCC ATT AAT GGG ATG ATC TAC AGC TTG CCT GGC CTG AAA ATG<br>Phe His Ala Ile Asn Gly Met Ile Tyr Ser Leu Pro Gly Leu Lys Met<br>1805                    1810                    1815                    1820 | 5536 |
| TAT GAG CAA GAG TGG GTG AGG TTA CAC CTG CTG AAC ATA GGC GGC TCC<br>Tyr Glu Gln Glu Trp Val Arg Leu His Leu Leu Asn Ile Gly Gly Ser<br>                  1825                    1830                    1835 | 5584 |
| CAA GAC ATT CAC GTG GTT CAC TTT CAC GGC CAG ACC TTG CTG GAA AAT<br>Gln Asp Ile His Val Val His Phe His Gly Gln Thr Leu Leu Glu Asn | 5632 |

-continued

```
              1840                1845                1850

GGC AAT AAA CAG CAC CAG TTA GGG GTC TGG CCC CTT CTG CCT GGT TCA      5680
Gly Asn Lys Gln His Gln Leu Gly Val Trp Pro Leu Leu Pro Gly Ser
        1855                1860                1865

TTT AAA ACT CTT GAA ATG AAG GCA TCA AAA CCT GGC TGG TGG CTC CTA      5728
Phe Lys Thr Leu Glu Met Lys Ala Ser Lys Pro Gly Trp Trp Leu Leu
    1870                1875                1880

AAC ACA GAG GTT GGA GAA AAC CAG AGA GCA GGG ATG CAA ACG CCA TTT      5776
Asn Thr Glu Val Gly Glu Asn Gln Arg Ala Gly Met Gln Thr Pro Phe
1885                1890                1895                1900

CTT ATC ATG GAC AGA GAC TGT AGG ATG CCA ATG GGA CTA AGC ACT GGT      5824
Leu Ile Met Asp Arg Asp Cys Arg Met Pro Met Gly Leu Ser Thr Gly
            1905                1910                1915

ATC ATA TCT GAT TCA CAG ATC AAG GCT TCA GAG TTT CTG GGT TAC TGG      5872
Ile Ile Ser Asp Ser Gln Ile Lys Ala Ser Glu Phe Leu Gly Tyr Trp
        1920                1925                1930

GAG CCC AGA TTA GCA AGA TTA AAC AAT GGT GGA TCT TAT AAT GCT TGG      5920
Glu Pro Arg Leu Ala Arg Leu Asn Asn Gly Gly Ser Tyr Asn Ala Trp
    1935                1940                1945

AGT GTA GAA AAA CTT GCA GCA GAA TTT GCC TCT AAA CCT TGG ATC CAG      5968
Ser Val Glu Lys Leu Ala Ala Glu Phe Ala Ser Lys Pro Trp Ile Gln
1950                1955                1960

GTG GAC ATG CAA AAG GAA GTC ATA ATC ACA GGG ATC CAG ACC CAA GGT      6016
Val Asp Met Gln Lys Glu Val Ile Ile Thr Gly Ile Gln Thr Gln Gly
1965                1970                1975                1980

GCC AAA CAC TAC CTG AAG TCC TGC TAT ACC ACA GAG TTC TAT GTA GCT      6064
Ala Lys His Tyr Leu Lys Ser Cys Tyr Thr Thr Glu Phe Tyr Val Ala
            1985                1990                1995

TAC AGT TCC AAC CAG ATC AAC TGG CAG ATC TTC AAA GGG AAC AGC ACA      6112
Tyr Ser Ser Asn Gln Ile Asn Trp Gln Ile Phe Lys Gly Asn Ser Thr
        2000                2005                2010

AGG AAT GTG ATG TAT TTT AAT GGC AAT TCA GAT GCC TCT ACA ATA AAA      6160
Arg Asn Val Met Tyr Phe Asn Gly Asn Ser Asp Ala Ser Thr Ile Lys
    2015                2020                2025

GAG AAT CAG TTT GAC CCA CCT ATT GTG GCT AGA TAT ATT AGG ATC TCT      6208
Glu Asn Gln Phe Asp Pro Pro Ile Val Ala Arg Tyr Ile Arg Ile Ser
2030                2035                2040

CCA ACT CGA GCC TAT AAC AGA CCT ACC CTT CGA TTG GAA CTG CAA GGT      6256
Pro Thr Arg Ala Tyr Asn Arg Pro Thr Leu Arg Leu Glu Leu Gln Gly
2045                2050                2055                2060

TGT GAG GTA AAT GGA TGT TCC ACA CCC CTG GGT ATG GAA AAT GGA AAG      6304
Cys Glu Val Asn Gly Cys Ser Thr Pro Leu Gly Met Glu Asn Gly Lys
            2065                2070                2075

ATA GAA AAC AAG CAA ATC ACA GCT TCT TCG TTT AAG AAA TCT TGG TGG      6352
Ile Glu Asn Lys Gln Ile Thr Ala Ser Ser Phe Lys Lys Ser Trp Trp
        2080                2085                2090

GGA GAT TAC TGG GAA CCC TTC CGT GCC CGT CTG AAT GCC CAG GGA CGT      6400
Gly Asp Tyr Trp Glu Pro Phe Arg Ala Arg Leu Asn Ala Gln Gly Arg
    2095                2100                2105

GTG AAT GCC TGG CAA GCC AAG GCA AAC AAC AAT AAG CAG TGG CTA GAA      6448
Val Asn Ala Trp Gln Ala Lys Ala Asn Asn Asn Lys Gln Trp Leu Glu
2110                2115                2120

ATT GAT CTA CTC AAG ATC AAG AAG ATA ACG GCA ATT ATA ACA CAG GGC      6496
Ile Asp Leu Leu Lys Ile Lys Lys Ile Thr Ala Ile Ile Thr Gln Gly
2125                2130                2135                2140

TGC AAG TCT CTG TCC TCT GAA ATG TAT GTA AAG AGC TAT ACC ATC CAC      6544
Cys Lys Ser Leu Ser Ser Glu Met Tyr Val Lys Ser Tyr Thr Ile His
            2145                2150                2155

TAC AGT GAG CAG GGA GTG GAA TGG AAA CCA TAC AGG CTG AAA TCC TCC      6592
```

```
Tyr Ser Glu Gln Gly Val Glu Trp Lys Pro Tyr Arg Leu Lys Ser Ser
        2160                2165                2170

ATG GTG GAC AAG ATT TTT GAA GGA AAT ACT AAT ACC AAA GGA CAT GTG      6640
Met Val Asp Lys Ile Phe Glu Gly Asn Thr Asn Thr Lys Gly His Val
    2175                2180                2185

AAG AAC TTT TTC AAC CCC CCA ATC ATT TCC AGG TTT ATC CGT GTC ATT      6688
Lys Asn Phe Phe Asn Pro Pro Ile Ile Ser Arg Phe Ile Arg Val Ile
    2190                2195                2200

CCT AAA ACA TGG AAT CAA AGT ATT GCA CTT CGC CTG GAA CTC TTT GGC      6736
Pro Lys Thr Trp Asn Gln Ser Ile Ala Leu Arg Leu Glu Leu Phe Gly
2205                2210                2215                2220

TGT GAT ATT TAC TAGAATTGAA CATTCAAAAA CCCCTGGAAG AGACTCTTTA          6788
Cys Asp Ile Tyr
            2

AGACCTCAAA CCATTTAGAA TGGGCAATGT ATTTTACGCT GTGTTAAATG TTAACAGTTT    6848

TCCACTATTT CTCTTTCTTT TCTATTAGTG AATAAAATTT TATAC                    6893

(2) INFORMATION FOR SEQ ID NO:38:

(i) SEQUENCE CHARACTERISTICS:
        (A) LENGTH: 2224 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:38:

Met Phe Pro Gly Cys Pro Arg Leu Trp Val Leu Val Leu Gly Thr
1               5                   10                  15

Ser Trp Val Gly Trp Gly Ser Gln Gly Thr Glu Ala Ala Gln Leu Arg
            20                  25                  30

Gln Phe Tyr Val Ala Ala Gln Gly Ile Ser Trp Ser Tyr Arg Pro Glu
            35                  40                  45

Pro Thr Asn Ser Ser Leu Asn Leu Ser Val Thr Ser Phe Lys Lys Ile
        50                  55                  60

Val Tyr Arg Glu Tyr Glu Pro Tyr Phe Lys Lys Glu Lys Pro Gln Ser
65              70                  75                  80

Thr Ile Ser Gly Leu Leu Gly Pro Thr Leu Tyr Ala Glu Val Gly Asp
            85                  90                  95

Ile Ile Lys Val His Phe Lys Asn Lys Ala Asp Lys Pro Leu Ser Ile
            100                 105                 110

His Pro Gln Gly Ile Arg Tyr Ser Lys Leu Ser Glu Gly Ala Ser Tyr
            115                 120                 125

Leu Asp His Thr Phe Pro Ala Glu Lys Met Asp Asp Ala Val Ala Pro
    130                 135                 140

Gly Arg Glu Tyr Thr Tyr Glu Trp Ser Ile Ser Glu Asp Ser Gly Pro
145                 150                 155                 160

Thr His Asp Asp Pro Pro Cys Leu Thr His Ile Tyr Tyr Ser His Glu
                165                 170                 175

Asn Leu Ile Glu Asp Phe Asn Ser Gly Leu Ile Gly Pro Leu Leu Ile
            180                 185                 190

Cys Lys Lys Gly Thr Leu Thr Glu Gly Gly Thr Gln Lys Thr Phe Asp
            195                 200                 205

Lys Gln Ile Val Leu Leu Phe Ala Val Phe Asp Glu Ser Lys Ser Trp
    210                 215                 220
```

```
Ser Gln Ser Ser Ser Leu Met Tyr Thr Val Asn Gly Tyr Val Asn Gly
225                 230                 235                 240

Thr Met Pro Asp Ile Thr Val Cys Ala His Asp His Ile Ser Trp His
            245                 250                 255

Leu Leu Gly Met Ser Ser Gly Pro Glu Leu Phe Ser Ile His Phe Asn
                260                 265                 270

Gly Gln Val Leu Glu Gln Asn His His Lys Val Ser Ala Ile Thr Leu
            275                 280                 285

Val Ser Ala Thr Ser Thr Thr Ala Asn Met Thr Val Gly Pro Glu Gly
    290                 295                 300

Lys Trp Ile Ile Ser Ser Leu Thr Pro Lys His Leu Gln Ala Gly Met
305                 310                 315                 320

Gln Ala Tyr Ile Asp Ile Lys Asn Cys Pro Lys Lys Thr Arg Asn Leu
                325                 330                 335

Lys Lys Ile Thr Arg Glu Gln Arg Arg His Met Lys Arg Trp Glu Tyr
            340                 345                 350

Phe Ile Ala Ala Glu Glu Val Ile Trp Asp Tyr Ala Pro Val Ile Pro
            355                 360                 365

Ala Asn Met Asp Lys Lys Tyr Arg Ser Gln His Leu Asp Asn Phe Ser
370                 375                 380

Asn Gln Ile Gly Lys His Tyr Lys Lys Val Met Tyr Thr Gln Tyr Glu
385                 390                 395                 400

Asp Glu Ser Phe Thr Lys His Thr Val Asn Pro Asn Met Lys Glu Asp
                405                 410                 415

Gly Ile Leu Gly Pro Ile Ile Arg Ala Gln Val Arg Asp Thr Leu Lys
            420                 425                 430

Ile Val Phe Lys Asn Met Ala Ser Arg Pro Tyr Ser Ile Tyr Pro His
            435                 440                 445

Gly Val Thr Phe Ser Pro Tyr Glu Asp Glu Val Asn Ser Ser Phe Thr
            450                 455                 460

Ser Gly Arg Asn Asn Thr Met Ile Arg Ala Val Gln Pro Gly Glu Thr
465                 470                 475                 480

Tyr Thr Tyr Lys Trp Asn Ile Leu Glu Phe Asp Glu Pro Thr Glu Asn
            485                 490                 495

Asp Ala Gln Cys Leu Thr Arg Pro Tyr Tyr Ser Asp Val Asp Ile Met
            500                 505                 510

Arg Asp Ile Ala Ser Gly Leu Ile Gly Leu Leu Leu Ile Cys Lys Ser
            515                 520                 525

Arg Ser Leu Asp Arg Arg Gly Ile Gln Arg Ala Ala Asp Ile Glu Gln
530                 535                 540

Gln Ala Val Phe Ala Val Phe Asp Glu Asn Lys Ser Trp Tyr Leu Glu
545                 550                 555                 560

Asp Asn Ile Asn Lys Phe Cys Glu Asn Pro Asp Glu Val Lys Arg Asp
                565                 570                 575

Asp Pro Lys Phe Tyr Glu Ser Asn Ile Met Ser Thr Ile Asn Gly Tyr
            580                 585                 590

Val Pro Glu Ser Ile Thr Thr Leu Gly Phe Cys Phe Asp Asp Thr Val
            595                 600                 605

Gln Trp His Phe Cys Ser Val Gly Thr Gln Asn Glu Ile Leu Thr Ile
            610                 615                 620

His Phe Thr Gly His Ser Phe Ile Tyr Gly Lys Arg His Glu Asp Thr
625                 630                 635                 640
```

-continued

Leu Thr Leu Phe Pro Met Arg Gly Glu Ser Val Thr Val Thr Met Asp
                645                 650                 655

Asn Val Gly Thr Trp Met Leu Thr Ser Met Asn Ser Ser Pro Arg Ser
            660                 665                 670

Lys Lys Leu Arg Leu Lys Phe Arg Asp Val Lys Cys Ile Pro Asp Asp
        675                 680                 685

Asp Glu Asp Ser Tyr Glu Ile Phe Glu Pro Pro Glu Ser Thr Val Met
    690                 695                 700

Ala Thr Arg Lys Met His Asp Arg Leu Glu Pro Glu Asp Glu Glu Ser
705                 710                 715                 720

Asp Ala Asp Tyr Asp Tyr Gln Asn Arg Leu Ala Ala Ala Leu Gly Ile
                725                 730                 735

Arg Ser Phe Arg Asn Ser Ser Leu Asn Gln Glu Glu Glu Glu Phe Asn
            740                 745                 750

Leu Thr Ala Leu Ala Leu Glu Asn Gly Thr Glu Phe Val Ser Ser Asn
        755                 760                 765

Thr Asp Ile Ile Val Gly Ser Asn Tyr Ser Ser Pro Ser Asn Ile Ser
770                 775                 780

Lys Phe Thr Val Asn Asn Leu Ala Glu Pro Gln Lys Ala Pro Ser His
785                 790                 795                 800

Gln Gln Ala Thr Thr Ala Gly Ser Pro Leu Arg His Leu Ile Gly Lys
                805                 810                 815

Asn Ser Val Leu Asn Ser Ser Thr Ala Glu His Ser Ser Pro Tyr Ser
            820                 825                 830

Glu Asp Pro Ile Glu Asp Pro Leu Gln Pro Asp Val Thr Gly Ile Arg
        835                 840                 845

Leu Leu Ser Leu Gly Ala Gly Glu Phe Arg Ser Gln Glu His Ala Lys
    850                 855                 860

Arg Lys Gly Pro Lys Val Glu Arg Asp Gln Ala Ala Lys His Arg Phe
865                 870                 875                 880

Ser Trp Met Lys Leu Leu Ala His Lys Val Gly Arg His Leu Ser Gln
                885                 890                 895

Asp Thr Gly Ser Pro Ser Gly Met Arg Pro Trp Glu Asp Leu Pro Ser
            900                 905                 910

Gln Asp Thr Gly Ser Pro Ser Arg Met Arg Pro Trp Glu Asp Pro Pro
        915                 920                 925

Ser Asp Leu Leu Leu Leu Lys Gln Ser Asn Ser Ser Lys Ile Leu Val
    930                 935                 940

Gly Arg Trp His Leu Ala Ser Glu Lys Gly Ser Tyr Glu Ile Ile Gln
945                 950                 955                 960

Asp Thr Asp Glu Asp Thr Ala Val Asn Asn Trp Leu Ile Ser Pro Gln
                965                 970                 975

Asn Ala Ser Arg Ala Trp Gly Ser Thr Pro Leu Ala Asn Lys Pro
            980                 985                 990

Gly Lys Gln Ser Gly His Pro Lys Phe Pro Arg Val Arg His Lys Ser
        995                 1000                1005

Leu Gln Val Arg Gln Asp Gly Gly Lys Ser Arg Leu Lys Lys Ser Gln
    1010                1015                1020

Phe Leu Ile Lys Thr Arg Lys Lys Lys Glu Lys His Thr His
1025                1030                1035                104

Ala Pro Leu Ser Pro Arg Thr Phe His Pro Leu Arg Ser Glu Ala Tyr
                1045                1050                1055

Asn Thr Phe Ser Glu Arg Arg Leu Lys His Ser Leu Val Leu His Lys

-continued

```
                    1060                1065                1070
Ser Asn Glu Thr Ser Leu Pro Thr Asp Leu Asn Gln Thr Leu Pro Ser
        1075                1080                1085

Met Asp Phe Gly Trp Ile Ala Ser Leu Pro Asp His Asn Gln Asn Ser
    1090                1095                1100

Ser Asn Asp Thr Gly Gln Ala Ser Cys Pro Pro Gly Leu Tyr Gln Thr
1105                1110                1115                    112

Val Pro Pro Glu Glu His Tyr Gln Thr Phe Pro Ile Gln Asp Pro Asp
                1125                1130                1135

Gln Met His Ser Thr Ser Asp Pro Ser His Arg Ser Ser Pro Glu
            1140                1145                1150

Leu Ser Glu Met Leu Glu Tyr Asp Arg Ser His Lys Ser Phe Pro Thr
        1155                1160                1165

Asp Ile Ser Gln Met Ser Pro Ser Ser Glu His Glu Val Trp Gln Thr
    1170                1175                1180

Val Ile Ser Pro Asp Leu Ser Gln Val Thr Leu Ser Pro Glu Leu Ser
1185                1190                1195                    120

Gln Thr Asn Leu Ser Pro Asp Leu Ser His Thr Thr Leu Ser Pro Glu
            1205                1210                1215

Leu Ile Gln Arg Asn Leu Ser Pro Ala Leu Gly Gln Met Pro Ile Ser
            1220                1225                1230

Pro Asp Leu Ser His Thr Thr Leu Ser Pro Asp Leu Ser His Thr Thr
            1235                1240                1245

Leu Ser Leu Asp Leu Ser Gln Thr Asn Leu Ser Pro Glu Leu Ser Gln
        1250                1255                1260

Thr Asn Leu Ser Pro Ala Leu Gly Gln Met Pro Leu Ser Pro Asp Leu
1265                1270                1275                    128

Ser His Thr Thr Ile Ser Leu Asp Phe Ser Gln Thr Asn Leu Ser Pro
            1285                1290                1295

Glu Leu Ser His Met Thr Leu Ser Pro Glu Leu Ser Gln Thr Asn Leu
            1300                1305                1310

Ser Pro Ala Leu Gly Gln Met Pro Ile Ser Pro Asp Leu Ser His Thr
            1315                1320                1325

Thr Leu Ser Leu Asp Phe Ser Gln Thr Asn Leu Ser Pro Glu Leu Ser
        1330                1335                1340

Gln Thr Asn Leu Ser Pro Ala Leu Gly Gln Met Pro Leu Ser Pro Asp
1345                1350                1355                    136

Pro Ser His Thr Thr Leu Ser Leu Asp Leu Ser Gln Thr Asn Leu Ser
            1365                1370                1375

Pro Glu Leu Ser Gln Thr Asn Leu Ser Pro Asp Leu Ser Glu Met Pro
            1380                1385                1390

Leu Phe Ala Asp Leu Ser Gln Ile Pro Leu Thr Pro Asp Leu Asp Gln
        1395                1400                1405

Met Thr Leu Ser Pro Asp Leu Gly Glu Thr Asp Leu Ser Pro Asn Phe
    1410                1415                1420

Gly Gln Met Ser Leu Ser Pro Asp Leu Ser Gln Val Thr Leu Ser Pro
1425                1430                1435                    144

Asp Ile Ser Asp Thr Thr Leu Leu Pro Asp Leu Ser Gln Ile Ser Pro
            1445                1450                1455

Pro Pro Asp Leu Asp Gln Ile Phe Tyr Pro Ser Glu Ser Ser Gln Ser
            1460                1465                1470

Leu Leu Leu Gln Glu Phe Asn Glu Ser Phe Pro Tyr Pro Asp Leu Gly
        1475                1480                1485
```

-continued

```
Gln Met Pro Ser Pro Ser Ser Pro Thr Leu Asn Asp Thr Phe Leu Ser
    1490                1495                1500
Lys Glu Phe Asn Pro Leu Val Ile Val Gly Leu Ser Lys Asp Gly Thr
1505                1510                1515                152
Asp Tyr Ile Glu Ile Ile Pro Lys Glu Glu Val Gln Ser Ser Glu Asp
                1525                1530                1535
Asp Tyr Ala Glu Ile Asp Tyr Val Pro Tyr Asp Asp Pro Tyr Lys Thr
            1540                1545                1550
Asp Val Arg Thr Asn Ile Asn Ser Ser Arg Asp Pro Asp Asn Ile Ala
            1555                1560                1565
Ala Trp Tyr Leu Arg Ser Asn Asn Gly Asn Arg Arg Asn Tyr Tyr Ile
        1570                1575                1580
Ala Ala Glu Glu Ile Ser Trp Asp Tyr Ser Glu Phe Val Gln Arg Glu
1585                1590                1595                160
Thr Asp Ile Glu Asp Ser Asp Asp Ile Pro Glu Asp Thr Thr Tyr Lys
                1605                1610                1615
Lys Val Val Phe Arg Lys Tyr Leu Asp Ser Thr Phe Thr Lys Arg Asp
                1620                1625                1630
Pro Arg Gly Glu Tyr Glu Glu His Leu Gly Ile Leu Gly Pro Ile Ile
            1635                1640                1645
Arg Ala Glu Val Asp Asp Val Ile Gln Val Arg Phe Lys Asn Leu Ala
        1650                1655                1660
Ser Arg Pro Tyr Ser Leu His Ala His Gly Leu Ser Tyr Glu Lys Ser
1665                1670                1675                168
Ser Glu Gly Lys Thr Tyr Glu Asp Asp Ser Pro Glu Trp Phe Lys Glu
                1685                1690                1695
Asp Asn Ala Val Gln Pro Asn Ser Ser Tyr Thr Tyr Val Trp His Ala
            1700                1705                1710
Thr Glu Arg Ser Gly Pro Glu Ser Pro Gly Ser Ala Cys Arg Ala Trp
            1715                1720                1725
Ala Tyr Tyr Ser Ala Val Asn Pro Glu Lys Asp Ile His Ser Gly Leu
        1730                1735                1740
Ile Gly Pro Leu Leu Ile Cys Gln Lys Gly Ile Leu His Lys Asp Ser
1745                1750                1755                176
Asn Met Pro Val Asp Met Arg Glu Phe Val Leu Leu Phe Met Thr Phe
                1765                1770                1775
Asp Glu Lys Lys Ser Trp Tyr Tyr Glu Lys Lys Ser Arg Ser Ser Trp
            1780                1785                1790
Arg Leu Thr Ser Ser Glu Met Lys Lys Ser His Glu Phe His Ala Ile
        1795                1800                1805
Asn Gly Met Ile Tyr Ser Leu Pro Gly Leu Lys Met Tyr Glu Gln Glu
    1810                1815                1820
Trp Val Arg Leu His Leu Leu Asn Ile Gly Ser Gln Asp Ile His
1825                1830                1835                184
Val Val His Phe His Gly Gln Thr Leu Leu Glu Asn Gly Asn Lys Gln
                1845                1850                1855
His Gln Leu Gly Val Trp Pro Leu Leu Pro Gly Ser Phe Lys Thr Leu
            1860                1865                1870
Glu Met Lys Ala Ser Lys Pro Gly Trp Trp Leu Leu Asn Thr Glu Val
        1875                1880                1885
Gly Glu Asn Gln Arg Ala Gly Met Gln Thr Pro Phe Leu Ile Met Asp
    1890                1895                1900
```

```
Arg Asp Cys Arg Met Pro Met Gly Leu Ser Thr Gly Ile Ile Ser Asp
1905                1910                1915                192

Ser Gln Ile Lys Ala Ser Glu Phe Leu Gly Tyr Trp Glu Pro Arg Leu
        1925                1930                1935

Ala Arg Leu Asn Asn Gly Gly Ser Tyr Asn Ala Trp Ser Val Glu Lys
        1940                1945                1950

Leu Ala Ala Glu Phe Ala Ser Lys Pro Trp Ile Gln Val Asp Met Gln
        1955                1960                1965

Lys Glu Val Ile Ile Thr Gly Ile Gln Thr Gln Gly Ala Lys His Tyr
    1970                1975                1980

Leu Lys Ser Cys Tyr Thr Thr Glu Phe Tyr Val Ala Tyr Ser Ser Asn
1985                1990                1995                200

Gln Ile Asn Trp Gln Ile Phe Lys Gly Asn Ser Thr Arg Asn Val Met
                2005                2010                2015

Tyr Phe Asn Gly Asn Ser Asp Ala Ser Thr Ile Lys Glu Asn Gln Phe
                2020                2025                2030

Asp Pro Pro Ile Val Ala Arg Tyr Ile Arg Ile Ser Pro Thr Arg Ala
                2035                2040                2045

Tyr Asn Arg Pro Thr Leu Arg Leu Glu Leu Gln Gly Cys Glu Val Asn
    2050                2055                2060

Gly Cys Ser Thr Pro Leu Gly Met Glu Asn Gly Lys Ile Glu Asn Lys
2065                2070                2075                208

Gln Ile Thr Ala Ser Ser Phe Lys Lys Ser Trp Trp Gly Asp Tyr Trp
        2085                2090                2095

Glu Pro Phe Arg Ala Arg Leu Asn Ala Gln Gly Arg Val Asn Ala Trp
        2100                2105                2110

Gln Ala Lys Ala Asn Asn Asn Lys Gln Trp Leu Glu Ile Asp Leu Leu
        2115                2120                2125

Lys Ile Lys Lys Ile Thr Ala Ile Ile Thr Gln Gly Cys Lys Ser Leu
    2130                2135                2140

Ser Ser Glu Met Tyr Val Lys Ser Tyr Thr Ile His Tyr Ser Glu Gln
2145                2150                2155                216

Gly Val Glu Trp Lys Pro Tyr Arg Leu Lys Ser Ser Met Val Asp Lys
        2165                2170                2175

Ile Phe Glu Gly Asn Thr Asn Thr Lys Gly His Val Lys Asn Phe Phe
        2180                2185                2190

Asn Pro Pro Ile Ile Ser Arg Phe Ile Arg Val Ile Pro Lys Thr Trp
        2195                2200                2205

Asn Gln Ser Ile Ala Leu Arg Leu Glu Leu Phe Gly Cys Asp Ile Tyr
    2210                2215                2220

(2) INFORMATION FOR SEQ ID NO:39:

(i) SEQUENCE CHARACTERISTICS:
        (A) LENGTH: 3549 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 175...1599
        (D) OTHER INFORMATION:

(xi) SEQUENCE DESCRIPTION: SEQ ID NO:39:

CCCCTCTTCC TCCTCCTCAA GGGAAAGCTG CCCACTTCTA GCTGCCCTGC CATCCCCTTT      60
```

-continued

```
AAAGGGCGAC TTGCTCAGCG CCAAACCGCG GCTCCAGCCC TCTCCAGCCT CCGGCTCAGC        120

CGGCTCATCA GTCGGTCCGC GCCTTGCAGC TCCTCCAGAG GGACGCGCCC CGAG ATG          177
                                                            Met
                                                            1

GAG AGC AAA GCC CTG CTC GTG CTG ACT CTG GCC GTG TGG CTC CAG AGT          225
Glu Ser Lys Ala Leu Leu Val Leu Thr Leu Ala Val Trp Leu Gln Ser
         5               10                  15

CTG ACC GCC TCC CGC GGA GGG GTG GCC GCC GCC GAC CAA AGA AGA GAT          273
Leu Thr Ala Ser Arg Gly Gly Val Ala Ala Ala Asp Gln Arg Arg Asp
             20                  25                  30

TTT ATC GAC ATC GAA AGT AAA TTT GCC CTA AGG ACC CCT GAA GAC ACA          321
Phe Ile Asp Ile Glu Ser Lys Phe Ala Leu Arg Thr Pro Glu Asp Thr
         35                  40                  45

GCT GAG GAC ACT TGC CAC CTC ATT CCC GGA GTA GCA GAG TCC GTG GCT          369
Ala Glu Asp Thr Cys His Leu Ile Pro Gly Val Ala Glu Ser Val Ala
50                  55                  60                  65

ACC TGT CAT TTC AAT CAC AGC AGC AAA ACC TTC ATG GTG ATC CAT GGC          417
Thr Cys His Phe Asn His Ser Ser Lys Thr Phe Met Val Ile His Gly
                 70                  75                  80

TGG ACG GTA ACA GGA ATG TAT GAG AGT TGG GTG CCA AAA CTT GTG GCC          465
Trp Thr Val Thr Gly Met Tyr Glu Ser Trp Val Pro Lys Leu Val Ala
             85                  90                  95

GCC CTG TAC AAG AGA GAA CCA GAC TCC AAT GTC ATT GTG GTG GAC TGG          513
Ala Leu Tyr Lys Arg Glu Pro Asp Ser Asn Val Ile Val Val Asp Trp
             100                 105                 110

CTG TCA CGG GCT CAG GAG CAT TAC CCA GTG TCC GCG GGC TAC ACC AAA          561
Leu Ser Arg Ala Gln Glu His Tyr Pro Val Ser Ala Gly Tyr Thr Lys
    115                 120                 125

CTG GTG GGA CAG GAT GTG GCC CGG TTT ATC AAC TGG ATG GAG GAG GAG          609
Leu Val Gly Gln Asp Val Ala Arg Phe Ile Asn Trp Met Glu Glu Glu
130                 135                 140                 145

TTT AAC TAC CCT CTG GAC AAT GTC CAT CTC TTG GGA TAC AGC CTT GGA          657
Phe Asn Tyr Pro Leu Asp Asn Val His Leu Leu Gly Tyr Ser Leu Gly
             150                 155                 160

GCC CAT GCT GCT GGC ATT GCA GGA AGT CTG ACC AAT AAG AAA GTC AAC          705
Ala His Ala Ala Gly Ile Ala Gly Ser Leu Thr Asn Lys Lys Val Asn
             165                 170                 175

AGA ATT ACT GGC CTC GAT CCA GCT GGA CCT AAC TTT GAG TAT GCA GAA          753
Arg Ile Thr Gly Leu Asp Pro Ala Gly Pro Asn Phe Glu Tyr Ala Glu
             180                 185                 190

GCC CCG AGT CGT CTT TCT CCT GAT GAT GCA GAT TTT GTA GAC GTC TTA          801
Ala Pro Ser Arg Leu Ser Pro Asp Asp Ala Asp Phe Val Asp Val Leu
    195                 200                 205

CAC ACA TTC ACC AGA GGG TCC CCT GGT CGA AGC ATT GGA ATC CAG AAA          849
His Thr Phe Thr Arg Gly Ser Pro Gly Arg Ser Ile Gly Ile Gln Lys
210                 215                 220                 225

CCA GTT GGG CAT GTT GAC ATT TAC CCG AAT GGA GGT ACT TTT CAG CCA          897
Pro Val Gly His Val Asp Ile Tyr Pro Asn Gly Gly Thr Phe Gln Pro
             230                 235                 240

GGA TGT AAC ATT GGA GAA GCT ATC CGC GTG ATT GCA GAG AGA GGA CTT          945
Gly Cys Asn Ile Gly Glu Ala Ile Arg Val Ile Ala Glu Arg Gly Leu
             245                 250                 255

GGA GAT GTG GAC CAG CTA GTG AAG TGC TCC CAC GAG CGC TCC ATT CAT          993
Gly Asp Val Asp Gln Leu Val Lys Cys Ser His Glu Arg Ser Ile His
             260                 265                 270

CTC TTC ATC GAC TCT CTG TTG AAT GAA GAA AAT CCA AGT AAG GCC TAC         1041
Leu Phe Ile Asp Ser Leu Leu Asn Glu Glu Asn Pro Ser Lys Ala Tyr
    275                 280                 285
```

```
AGG TGC AGT TCC AAG GAA GCC TTT GAG AAA GGG CTC TGC TTG AGT TGT    1089
Arg Cys Ser Ser Lys Glu Ala Phe Glu Lys Gly Leu Cys Leu Ser Cys
290             295             300             305

AGA AAG AAC CGC TGC AAC AAT CTG GGC TAT GAG ATC AAT AAA GTC AGA    1137
Arg Lys Asn Arg Cys Asn Asn Leu Gly Tyr Glu Ile Asn Lys Val Arg
                310             315             320

GCC AAA AGA AGC AGC AAA ATG TAC CTG AAG ACT CGT TCT CAG ATG CCC    1185
Ala Lys Arg Ser Ser Lys Met Tyr Leu Lys Thr Arg Ser Gln Met Pro
            325             330             335

TAC AAA GTC TTC CAT TAC CAA GTA AAG ATT CAT TTT TCT GGG ACT GAG    1233
Tyr Lys Val Phe His Tyr Gln Val Lys Ile His Phe Ser Gly Thr Glu
        340             345             350

AGT GAA ACC CAT ACC AAT CAG GCC TTT GAG ATT TCT CTG TAT GGC ACC    1281
Ser Glu Thr His Thr Asn Gln Ala Phe Glu Ile Ser Leu Tyr Gly Thr
    355             360             365

GTG GCC GAG AGT GAG AAC ATC CCA TTC ACT CTG CCT GAA GTT TCC ACA    1329
Val Ala Glu Ser Glu Asn Ile Pro Phe Thr Leu Pro Glu Val Ser Thr
370             375             380             385

AAT AAG ACC TAC TCC TTC CTA ATT TAC ACA GAG GTA GAT ATT GGA GAA    1377
Asn Lys Thr Tyr Ser Phe Leu Ile Tyr Thr Glu Val Asp Ile Gly Glu
                390             395             400

CTA CTC ATG TTG AAG CTC AAA TGG AAG AGT GAT TCA TAC TTT AGC TGG    1425
Leu Leu Met Leu Lys Leu Lys Trp Lys Ser Asp Ser Tyr Phe Ser Trp
            405             410             415

TCA GAC TGG TGG AGC AGT CCC GGC TTC GCC ATT CAG AAG ATC AGA GTA    1473
Ser Asp Trp Trp Ser Ser Pro Gly Phe Ala Ile Gln Lys Ile Arg Val
        420             425             430

AAA GCA GGA GAG ACT CAG AAA AAG GTG ATC TTC TGT TCT AGG GAG AAA    1521
Lys Ala Gly Glu Thr Gln Lys Lys Val Ile Phe Cys Ser Arg Glu Lys
    435             440             445

GTG TCT CAT TTG CAG AAA GGA AAG GCA CCT GCG GTA TTT GTG AAA TGC    1569
Val Ser His Leu Gln Lys Gly Lys Ala Pro Ala Val Phe Val Lys Cys
450             455             460             465

CAT GAC AAG TCT CTG AAT AAG AAG TCA GGC TGAAACTGGG CGAATCTACA      1619
His Asp Lys Ser Leu Asn Lys Lys Ser Gly
                470             475

GAACAAAGAA CGGCATGTGA ATTCTGTGAA GAATGAAGTG GAGGAAGTAA CTTTTACAAA  1679

ACATACCCAG TGTTTGGGGT GTTTCAAAAG TGGATTTTCC TGAATATTAA TCCCAGCCCT  1739

ACCCTTGTTA GTTATTTTAG GAGACAGTCT CAAGCACTAA AAAGTGGCTA ATTCAATTTA  1799

TGGGGTATAG TGGCCAAATA GCACATCCTC CAACGTTAAA AGACAGTGGA TCATGAAAAG  1859

TGCTGTTTTG TCCTTTGAGA AAGAAATAAT TGTTTGAGCG CAGAGTAAAA TAAGGCTCCT  1919

TCATGTGGCG TATTGGGCCA TAGCCTATAA TTGGTTAGAA CCTCCTATTT TAATTGGAAT  1979

TCTGGATCTT TCGGACTGAG GCCTTCTCAA ACTTTACTCT AAGTCTCCAA GAATACAGAA  2039

AATGCTTTTC CGCGGCACGA ATCAGACTCA TCTACACAGC AGTATGAATG ATGTTTTAGA  2099

ATGATTCCCT CTTGCTATTG GAATGTGGTC CAGACGTCAA CCAGGAACAT GTAACTTGGA  2159

GAGGGACGAA GAAAGGGTCT GATAAACACA GAGGTTTTAA ACAGTCCCTA CCATTGGCCT  2219

GCATCATGAC AAAGTTACAA ATTCAAGGAG ATATAAAATC TAGATCAATT AATTCTTAAT  2279

AGGCTTTATC GTTATTGCT TAATCCCTCT CTCCCCCTTC TTTTTTGTCT CAAGATTATA   2339

TTATAATAAT GTTCTCTGGG TAGGTGTTGA AAATGAGCCT GTAATCCTCA GCTGACACAT  2399

AATTTGAATG GTGCAGAAAA AAAAAAGATA CCGTAATTTT ATTATTAGAT CTCCAAATG   2459

ATTTTCATCA ATTTAAAATC ATTCAATATC TGACAGTTAC TCTTCAGTTT TAGGCTTACC  2519

TTGGTCATGC TTCAGTTGTA CTTCCAGTGC GTCTCTTTTG TTCCTGGCTT TGACATGAAA  2579
```

```
AGATAGGTTT GAGTTCAAAT TTTGCATTGT GTGAGCTTCT ACAGATTTTA GACAAGGACC    2639

GTTTTTACTA AGTAAAAGGG TGGAGAGGTT CCTGGGGTGG ATTCCTAAGC AGTGCTTGTA    2699

AACCATCGCG TGCAATGAGC CAGATGGAGT ACCATGAGGG TTGTTATTTG TTGTTTTTAA    2759

CAACTAATCA AGAGTGAGTG AACAACTATT TATAAACTAG ATCTCCTATT TTTCAGAATG    2819

CTCTTCTACG TATAAATATG AAATGATAAA GATGTCAAAT ATCTCAGAGG CTATAGCTGG    2879

GAACCCGACT GTGAAAGTAT GTGATATCTG AACACATACT AGAAAGCTCT GCATGTGTGT    2939

TGTCCTTCAG CATAATTCGG AAGGGAAAAC AGTCGATCAA GGGATGTATT GGAACATGTC    2999

GGAGTAGAAA TTGTTCCTGA TGTGCCAGAA CTTCGACCCT TTCTCTGAGA GAGATGATCG    3059

TGCCTATAAA TAGTAGGACC AATGTTGTGA TTAACATCAT CAGGCTTGGA ATGAATTCTC    3119

TCTAAAAATA AAATGATGTA TGATTTGTTG TTGGCATCCC CTTTATTAAT TCATTAAATT    3179

TCTGGATTTG GGTTGTGACC CAGGGTGCAT TAACTTAAAA GATTCACTAA AGCAGCACAT    3239

AGCACTGGGA ACTCTGGCTC CGAAAAACTT TGTTATATAT ATCAAGGATG TTCTGGCTTT    3299

ACATTTTATT TATTAGCTGT AAATACATGT GTGGATGTGT AAATGGAGCT TGTACATATT    3359

GGAAAGGTCA TTGTGGCTAT CTGCATTTAT AAATGTGTGG TGCTAACTGT ATGTGTCTTT    3419

ATCAGTGATG GTCTCACAGA GCCAACTCAC TCTTATGAAA TGGGCTTTAA CAAAACAAGA    3479

AAGAAACGTA CTTAACTGTG TGAAGAAATG GAATCAGCTT TTAATAAAAT TGACAACATT    3539

TTATTACCAC                                                            3549

(2) INFORMATION FOR SEQ ID NO:40:

(i) SEQUENCE CHARACTERISTICS:
        (A) LENGTH: 475 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:40:

Met Glu Ser Lys Ala Leu Leu Val Leu Thr Leu Ala Val Trp Leu Gln
 1               5                  10                  15

Ser Leu Thr Ala Ser Arg Gly Gly Val Ala Ala Ala Asp Gln Arg Arg
                20                  25                  30

Asp Phe Ile Asp Ile Glu Ser Lys Phe Ala Leu Arg Thr Pro Glu Asp
            35                  40                  45

Thr Ala Glu Asp Thr Cys His Leu Ile Pro Gly Val Ala Glu Ser Val
        50                  55                  60

Ala Thr Cys His Phe Asn His Ser Ser Lys Thr Phe Met Val Ile His
65                  70                  75                  80

Gly Trp Thr Val Thr Gly Met Tyr Glu Ser Trp Val Pro Lys Leu Val
                85                  90                  95

Ala Ala Leu Tyr Lys Arg Glu Pro Asp Ser Asn Val Ile Val Val Asp
               100                 105                 110

Trp Leu Ser Arg Ala Gln Glu His Tyr Pro Val Ser Ala Gly Tyr Thr
           115                 120                 125

Lys Leu Val Gly Gln Asp Val Ala Arg Phe Ile Asn Trp Met Glu Glu
       130                 135                 140

Glu Phe Asn Tyr Pro Leu Asp Asn Val His Leu Leu Gly Tyr Ser Leu
145                 150                 155                 160
```

```
Gly Ala His Ala Ala Gly Ile Ala Gly Ser Leu Thr Asn Lys Lys Val
                165                 170                 175
Asn Arg Ile Thr Gly Leu Asp Pro Ala Gly Pro Asn Phe Glu Tyr Ala
            180                 185                 190
Glu Ala Pro Ser Arg Leu Ser Pro Asp Asp Ala Asp Phe Val Asp Val
                195                 200                 205
Leu His Thr Phe Thr Arg Gly Ser Pro Gly Arg Ser Ile Gly Ile Gln
            210                 215                 220
Lys Pro Val Gly His Val Asp Ile Tyr Pro Asn Gly Gly Thr Phe Gln
225                 230                 235                 240
Pro Gly Cys Asn Ile Gly Glu Ala Ile Arg Val Ile Ala Glu Arg Gly
                245                 250                 255
Leu Gly Asp Val Asp Gln Leu Val Lys Cys Ser His Glu Arg Ser Ile
            260                 265                 270
His Leu Phe Ile Asp Ser Leu Leu Asn Glu Asn Pro Ser Lys Ala
            275                 280                 285
Tyr Arg Cys Ser Ser Lys Glu Ala Phe Glu Lys Gly Leu Cys Leu Ser
            290                 295                 300
Cys Arg Lys Asn Arg Cys Asn Asn Leu Gly Tyr Glu Ile Asn Lys Val
305                 310                 315                 320
Arg Ala Lys Arg Ser Ser Lys Met Tyr Leu Lys Thr Arg Ser Gln Met
                325                 330                 335
Pro Tyr Lys Val Phe His Tyr Gln Val Lys Ile His Phe Ser Gly Thr
                340                 345                 350
Glu Ser Glu Thr His Thr Asn Gln Ala Phe Glu Ile Ser Leu Tyr Gly
            355                 360                 365
Thr Val Ala Glu Ser Glu Asn Ile Pro Phe Thr Leu Pro Glu Val Ser
370                 375                 380
Thr Asn Lys Thr Tyr Ser Phe Leu Ile Tyr Thr Glu Val Asp Ile Gly
385                 390                 395                 400
Glu Leu Leu Met Leu Lys Leu Trp Lys Ser Asp Ser Tyr Phe Ser
                405                 410                 415
Trp Ser Asp Trp Trp Ser Ser Pro Gly Phe Ala Ile Gln Lys Ile Arg
                420                 425                 430
Val Lys Ala Gly Glu Thr Gln Lys Lys Val Ile Phe Cys Ser Arg Glu
            435                 440                 445
Lys Val Ser His Leu Gln Lys Gly Lys Ala Pro Ala Val Phe Val Lys
            450                 455                 460
Cys His Asp Lys Ser Leu Asn Lys Lys Ser Gly
465                 470                 475
```

(2) INFORMATION FOR SEQ ID NO:41:

(i) SEQUENCE CHARACTERISTICS:
        (A) LENGTH: 26928 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:41:

```
GCGTGAGCCA CTGCGCCCTG ACCACATATA ATTTTTATTA ATTATAATGT TGAAAGTCCC      60
TTTATTCCAC ACCTCTCCTC TCATTCACTC CTGGTAGGTC ATTTTTAATG ATTTGATGTA     120
TATACTGAAT TTGGATGCTT CTTGCTACAG GGCAAAGACG CTAATAAGAT TTTGCTGGAG     180
```

-continued

| | | | | |
|---|---|---|---|---|
|CCTTTTCACA|GATGCAAGTC|AATCCAGGCA|GTGTCTATAG|CTGCTGAACC CAAAATCAGA 240|
|AAGCGAGGGC|TATCAAAGCT|CTTCTGTCCT|GATTTGCAAC|TTTAGTAGTG CAAGAAAAAA 300|
|AATCTTAGAA|TAAAAAATGG|GTACCGTTCA|GAGACCTTTA|GAGATTGCAA GGCATCACAG 360|
|ATGATAAAAA|GCTCCATCTC|TAGACGTGTT|CAGGAGTGGG|TTGGGCTTT GACCTTGACT 420|
|AGCTGCATCA|ACTTGGACAA|GTCACTTCGC|TTCCCTGTGC|CTCAGTTTCC TCATCCATAA 480|
|AATGGGGATA|AGTATAGTAC|CTACCTCATA|AGTCCTGCCT|ACCTAGCACA TGGTGAGCAA 540|
|TTACTAAATT|GTAGGCCTAG|TCCCTATAAT|CCCAGCACTT|TGGAGAACA AGGTAGGGGA 600|
|ATCGCTTGAA|GCCAGGAGTT|CCAGACCAGC|CTGGCCAACA|TAGTGAGACT GTGTTTCTAT 660|
|AAAATAAAAA|AAAAAAATAC|CCAAGCTTGG|TGGTGCAGGC|CTGTAGTCCC GGCTACTTGG 720|
|GAGTCTGAGT|CAGGAGGATT|GCTTGAGCCC|AGGAGTTCAA|GGTTGTAGTA AGCTATGATT 780|
|GCACCACTGC|ACTCCAGCCT|GGCGACAGAG|CATGACCCTG|TCTCTAAAAA TATAAAATTA 840|
|GGCCAGGCAC|AGTGGTTCAT|GCCTGTAATT|CCAACATTTT|GGGAGGCCAA GGCAGGTGGA 900|
|TCACTGTGAG|CTCAGCAGTT|CGAGACCAGC|CTGGGCAACA|AGGCAAAATC CTGTCTCTAC 960|
|TAAAATTACA|AAAATTAGCC|AGGAGAGGTG|GTACACGCCT|GTAATCCCAG TTACTGGGGA 1020|
|AGCTGAAGCA|GGAGAATTGC|TTGAACCCGG|GAGGCGAAGG|TTGCAGTGAG CCAAGATCGT 1080|
|GCCATTGCAC|TGCAGCCTAG|GAGACAGAGC|GAGACTCGAT|CTCAATAAAT AAATAAATTA 1140|
|ATTAATTAAT|AAAAAAATAA|GTTGGGCATG|GTGGCACCTG|CCTGTAGTCC AAGCTACTCA 1200|
|GGAGGCTAGA|GGTGGGAGGA|TCACTTGAGC|CAGGAGTTCT|AGGCTGCAGT GAGCTATTAT 1260|
|CACGCCACCA|TACTCCAGCC|TGCTGTATGT|ACTCCAGCCT|GGGCAACAGA GTGACACCCT 1320|
|GTCTCAAAGT|AAAGTAAAAT|AAAAATTAAA|AAACAAATTA|CTAAATTGTA CTTAACAGTA 1380|
|TTGTCATCAG|TCTTCCTAAA|TAGGAGGACA|GGCAAAATTA|AGGGACTTAA CATGTGCCCT 1440|
|CAGGTATAGT|AGTTTGGGGC|AGGCCAGCAT|CACCCGCACA|GTAGTTCTGT ACTGTAGGTG 1500|
|CGTGTTCTCT|GGGTCAACTT|TATGGCCCAG|TGAGGCCGTA|CTCTACCAGA ATGTCAGGGG 1560|
|ACAAGGGTTG|GGAGAGGCAA|AAGTGCTGGT|CTGAAGCAGG|AGTCTGGGTT TCCATCCTAG 1620|
|CTCTACCACC|AATTCTGTAT|GACCGTGCCC|CCTCCATTTC|CTCCATGACC ACATAGAGAC 1680|
|ATGGGGCAGT|TGGATGAAAT|CAATGATTCC|CAGTCTTGGC|TCTATCATGG AACCATTTGC 1740|
|TAACTTCTTT|TTTTCTCTTA|TGGATCCCAT|ATTTTTAAAG|ATTTTTACTA AATAGAAATT 1800|
|GACTTATACT|TTTCCAAGCT|GGAGTGTGGT|GGCATGATTT|CAGCTCACTG CAACCTCCGC 1860|
|CTCCCGGGTT|CAAGTGATTC|TCCTGCCTCA|GCCTCCTGAG|TAGCTGGGAT TATAGGTGCT 1920|
|CACCAGGCCC|GGCTAATTTT|TTTGTATTTT|TAGTAGAGAC|AGAATTTCAC CATGTTGGCC 1980|
|AGGCTGATTT|CAAACTCCTG|ACCTCAAGTG|ATCTGCTCAC|CTCAGCCTCC CAAAGTGCTG 2040|
|GGATTACAGG|CGTGAGTCAC|TATGCCCAGC|CGCTTACTCA|CATTTCTAG TCAAAATAGA 2100|
|AAACTGCTTA|AGTCACTGTC|TGCAGAAGAG|CAAAAAAAAA|AAAGAAATA AAAATTGAA 2160|
|AACTGCTGAT|CAGATTGAGA|AAAACATAAG|ATTATTCACC|ACCTAAAGAG AAAAAATTTC 2220|
|AGTCGAAAGG|GAAAAAAATT|CATTTTGTC|TTAATAAGGC|AAATTCACAA TTTTTGAGGT 2280|
|TTTAACAAAA|TATATGCAGA|AAGACAAGGC|CACCCCGTAG|AACGTGCACA CAGCCCTAGG 2340|
|CTTGGAAATG|GCTGGATTTA|ATAATATCTG|GTCTTTCTTT|GAGCCCTGAA ATTCTCTAAC 2400|
|ACTATGTCTT|GGAACATAAT|TTTACTGTTT|TCAGTGGTTA|TAGAGATTTG CTTTACAATT 2460|
|TAGCATTGGT|CTTTACCCAT|GATTTTGTTT|GACGCCAACT|TGTTGGCAGG AATGCACCCC 2520|

```
CTGCCCCCG   CTTTGTTATG  GCCTTGCTCC  TATAGGGCAA  GAATATCTGC  TTTAAGGCCG  2580
GGTGTGGTGG  CTCAGGCCTG  TAATCCCAGC  ACTTTGAGGG  GCCAAGGCGG  GCAGATCACC  2640
TGAGGTCAGG  AGTTTGAGAC  CAGCCTGGCC  AGTATGGTGA  AATCCTGTCT  CTACTAAAAA  2700
TAACAAAAAT  TAGCTGGGTG  TGGTGGCACA  CACCTGTAAT  CCCAGCTATT  TGGGAGGCCG  2760
AAACAAGAGA  ACCACTTGAA  CCCAGGAGGC  GGAGGTTGCG  GTGAGCCGAG  ATTATGCCAC  2820
TGCACTCCAG  CCTGGGAAAC  AGAGCAAGAT  TCCGTCTCAC  ACACAAAAAA  TATATATATG  2880
TCTGCTTTAA  GTATGCAGGC  CGTGTTTGTG  CTGAACGGCA  GGAATGCCAA  ACTTGGCTGC  2940
ATGGTACCAA  CTAGGGACCT  CAGAGTTCCA  AGGAGAACAA  ACAGTTGGTT  CCTGGAGGCT  3000
GGGGGCTTGT  ATCAGACCCT  GAAGACTAAG  CATGTGCTGG  GTCCATTGTT  GTCCTGCACC  3060
CATGGTAGTG  CACTAAACAC  CTAACCTATA  TTTAAGTGTT  TTTGTTTGTC  CAAAAAATGT  3120
CTTTTTTTTT  TGGGAGTCAA  GAGTCTTGCT  CTGTTGCCCA  GGCTGGAGTG  CAGTGACACG  3180
ATCTCAGCTC  ACTGCAGCCT  CCGCCTCCCG  GGTTCAAGCT  ATTCTCCTGT  CTCAGCCTCC  3240
CAAATAGCTG  AGACTATAGG  CACGCACATC  CATGCCCAGC  TAATTTTTTT  ATTTTTAGTA  3300
GAGACGAGGT  GTCTCCATGG  TGGCCAGGTT  GGTCTTGAAC  TCCTGTCCTC  AAGTGATCCA  3360
CCTGCCTCGG  CCTCCCAAAG  TGGTGGGATT  GCAGGCATGA  GACACCGCGC  CCGGCCTGCC  3420
TTGTCCCTTC  TTAAAATGAG  TTGTCCATTT  GTAAGCTGCT  GATTTCTTTG  GGACATTGTC  3480
TCCGTAAACT  TTTCATAAAG  CATCAGTGAT  TTCACCATTC  TTCCACCCAA  GCTTCACCGT  3540
AAATTTGTTG  TTTGTTCTTG  CTTCAATTTC  AGCAGAATTC  ATTTAGCTCT  GATAAGGGCT  3600
CGCTTCAAAC  TGATGTCTTA  TCCTTCTTAG  TGCCTCAAAC  TACATCCTGT  TCACTCATGT  3660
TATAGCAAGT  TAGTGTGAGT  TTATTTTGGT  GCACAAAAAT  TTTTTTAAAT  CCATGCAGTC  3720
TTTTTTCATA  ATACGCATTT  TCCATGAACT  TTTCGAAGAC  CCCTTGTAGA  TGTCTGTTGT  3780
TTAAACCACC  CAGTTTACAG  TAATTTTTTT  TTTTTTTTGA  GATGAAGTCT  TGCTCTGTCG  3840
CCCAGGCTGG  AGTGCATTGG  CACACTCTCG  GCTCACTGCA  ACCTCTGCCT  CCTGGGTTCA  3900
AGCAATTTTT  CTGTCTCAGT  CTCCCGAGTA  GCTGGGATTA  CAGGTGTGTG  CCACCATGCC  3960
TAGCTAATTT  ATGTGTTTTT  AGTAGAGACG  GGGTTTCACT  ATGTTGGCTA  GGCTGGTCTC  4020
GAACTCCTCA  CCTTGTGATC  GGCCCGCCTC  GGCCTCCCAA  AGTATTGGGA  TTACAGGCGT  4080
GAGACTCTTG  CACTTGGCCT  ACAGTAATTT  TATAGCAGCC  TAGGCTAAGA  TAGCCATTTC  4140
TGGGTATAAG  AATGTCATAT  ACTGAACAGG  CCTGCAACTG  TGAGTAAAAG  TCTGCAAAGA  4200
GGCCGGGCAG  TGGCTCATAC  CTGTAATCCC  AGCACTTTGG  GGGGCCGAGG  CAGGTGGATC  4260
ACCTGAGGTC  AGCAGTTCGA  GACCAGCCTG  ACCAACATGG  TGAAACCCCA  TCTCTACTAA  4320
AAATACAAAA  TTAGCTGGGC  GTGGTAGTGC  ATGCTTGTAA  TCCCTAGCAT  GCACTTGGGA  4380
GCTACTTGGG  AGGCTGAGGC  AGGAGAATCA  CTTGTACTCA  GGAGGCCGAG  GTTGCAGTGA  4440
GCTGAGATCA  CGCCACTGCA  CTCCTTTCTG  GGTGACAGAG  TGAGACTCCA  TCTCAAAAAA  4500
ACAAAACAAA  ACAAAACAAA  AACAAACAAA  AAACCCAAC   AGGTAGGTAG  CAGTGGTTCA  4560
CGCCTGTAAT  CCCACTTTG   GAGGCTAAAG  TGGGCAGATC  ACCTGAGGTC  AGGAGTTCAC  4620
GTCCAGCCTG  GCAACATGG   TGAAACTCTG  TCTCTACAAA  AATACAAAAA  TTAGCCAGGC  4680
ATGATGGCGG  GTGCTGTAGT  TCCAGCTATT  CGGGAGGCTG  AGGCAGGAGA  ATCGCTTGAA  4740
CCTAGGAGGT  AGAGGTTGCA  GTGAGCCGAG  TTCACGCTAT  TGCACTCCAG  CCTCCATCTC  4800
AAAACAAACA  ACAAAACCCA  AATATATAT   TATAATTTTA  TTTTATTTAT  TCAATTTTAT  4860
TTTATTTTAT  TTTATTTTTC  TAGGAACAGG  TCTCATTCAG  GCCAGGCATG  GTGCTCACGC  4920
```

-continued

```
CTGTAATCCC AGCACTTGGG AGGCCGAGGT GGAGGTGGGC GGATCACCTG AGGTCAGGAG    4980

TTCGAGCCAT CCTGGTCAAT GTGGCGAAAC CCCATCTCTA CTAAAAATAC AAAAATTAGC    5040

CAGGTGTGGT GGCACACGCC TGTAATTCCA GCTACTTGGG ATACTGAGTC AGGAGAATCA    5100

CTTGAACAGG GAGATGGAAA TTGCAGTGAG CCGAGATTGT TCCACTGCAC TCCAGCCTGG    5160

GTGACAGGGC GAGACTCCGT CTCAAAAAAA AAAAAAAAA AGAAAGAAAG AAAGAAAGAA     5220

AGAAACAGGA TCTTACTCTG TTACCCAGGC TGGAGTACAG TGGTGCAATC ATAGCTCACT    5280

GCAGGCATGC ACCACCATTC CCAGCTAATT TTTAATTTTT TTTGGTAGAG ATGAGGGTCT    5340

TGCTATGTTG CCCAGGCTGG TCTCAAACTC CTGGCCTCAA GCGATCCTGC CATGTCGGCC    5400

TCCCAAAGTG TTGGGATTAC AAGTGTGAGC CACTATGCCT GGCCTAAAAA TATATATATG    5460

AAAATATATA AGAAATGGGC CTCCCAGGAA TTAAGGTGTT TGCGGGAGTC CTGGTCCCCA    5520

GTTTTTCTGC CAACACTCCC TGTTCCCACA CATGACCTGG TCCAGACCCC AAACAGCCAG    5580

GCCCAAAGGA CAGGTGAGGC GAGGCGAGAA CTTGTGCCTC CCCGTGTTCC TGCTCTTTGT    5640

CCCTCTGTCC TACTTAGACT AATATTTGCC TTGGGTACTG CAAACAGGAA ATGGGGGAGG    5700

GACAGGAGTA GGGCGGAGGG TAGGGTAGGA CCAGAAGCCT CTCTAGGCCT GCCATGGGGC    5760

AGGCAGCCAG GGAGAAGGAG GGCCCCTCAG TGGAGACCCA GGGATTTCAG TAGCCCCTGT    5820

TCCGGGACAG GCGCAGGTCC TGGGAGGTGA CAGAAGATAG ACTAAAGGCC CAAGAGTCCC    5880

TGGACCTGAC TCCTCCCAGC AGCTGCCACA CACAAACACA CCTCCAGGCA CCCTGGACAG    5940

GAAGGAGGAG AAATGGGCCC CTCCTCCAGT GGCTGAGAAG CTGGGGCAAA TGTTGGCTGT    6000

TCCTATCCCT GGTGCATCCC ATGGCGAGGG GCAACTTCCA TCAGGCCACA CCTTTTATCT    6060

TTGTCTCTAT TTTTGATATC TGTGTATTAT GATTATACAA ACCCCACAT TGGCCTATAT     6120

GTGCAGATCT GATTAAGAAC TTACGATATT CCATGGACAT TCCATTCCTA ATCTCCTTTA    6180

GTCCTCACAA CAAAGTATTA TTCCCATTGT ATAGATGAGG AAACTGAGGC ACACAGAGAT    6240

GACAAGCAAC CACCGCTATA TGTTAGGATT CGAAGGAGCT CCAGGAAAGT CTCATAGCCC    6300

CACTGGCCAG AATGGGCTAA ATCTCAGAGG GGGAGGGTGG GAGATGGGGG TGACAGTGAC    6360

CTTTTTTGTG ACTCCTCCTA GACCATCCAT CCCTGCTCCC AGGAGGACCT GTCCTCCCAG    6420

ATGGTGGAGA TGGACAGGAG GACTATCTAC CCACCCGTCC CCACGGCCCT GACCCTCTGA    6480

CCTCACCCTC TCCGCTGATT TCTTCATGTT AGTTCAACAT TACCCAGAGG GGTCAGGACA    6540

GACAATTCCT CAGTGACCCA GGAGCTGACA CACTATGGCG CACGTCCGAG GCTTGCAGCT    6600

GCCTGGCTGC CTGGCCCTGG CTGCCCTGTG TAGCCTTGTG CACAGCCAGC ATGGTAAGGG    6660

AGTGCTTGCA GGCTGGAACA GGCTGGAGGA CTGGGTGTG GGCCCATGGG CTGGGTCTC     6720

CTGGCTGGAC AGAGCACACA GAGCTGGCCC CTAAGTAGGT CTCAGCCCCA GGCGGCCAGC    6780

TTAGGGAAGA AGTCAGGAGC TCAGGGCTGG AAAGAGAATG GCTGCTTCTC TCTTCCAATA    6840

TAGGGAGCAG GCTGGGGGCA AGGGGCAGTG TAGGAGGGGC ACAGGGGCC ACATTTAGCA     6900

GCCTTCCAGG CCTTCCACCA GCCCAGACTG CCTCTCTCAG AAGCCAGCAG GGAGGGTGG     6960

GCTTGCTTCA TGCCCCAGA TGGCCAAGAC TGCCTGTTCC TGAGGTCGCT GTTCCATGAC     7020

CCCCCCACCG CCTTTACAGT GTTCCTGGCT CCTCAGCAAG CACGGTCGCT GCTCCAGCGG    7080

GTCCGGCGAG CCAACACCTT CTTGGAGGAG GTGCGCAAGG GCAACCTAGA GCGAGAGTGC    7140

GTGGAGGAGA CGTGCAGCTA CGAGGAGGCC TTCGAGGCTC TGGAGTCCTC CACGGCTACG    7200

GTGAGCCTGG GCTGCTCGGA CGGTGCCGGG GCCTCAGACC GGGCCCAACT CTAGACACTT    7260
```

```
CCACAGAGAA GCAAGCGAGG AACGCCACAG CCCCTTCGCT GCTCACAGCC TCATTTCAAC   7320

TCTGAGCCCC TCCTCACAGG GCTGGCAAGA GGAGCGGCCT CAGCCTTTCC TGGGGGTCTC   7380

TGTGCCTGGA CTGTGTCCCT GTGCAGCTCC ATGACATGGG GAGGCCTCCA CAGTCTTCAG   7440

ACATCCACCT GCCTTGGAGC TCTGTGTCCA CATGGCCTCC TCAGCGGCAG ACTCCCACAC   7500

CACCCTTGAG GGGTGGGACT CTGGGGAGGC CACCACAAGC CCCGGGCTC AAGACTCAGT    7560

GTTCCTGGAG CTCTGTGTCG CCTTTCCTGT CTGTAGGGAC TCTGCCAGGG ACCCACTGCC   7620

CCCTCTCCTC CCATCTCCCC CAGCCTCTTT CAGACTCGGT GTGTGTGTTG GAGGAACTCC   7680

CCTATCCTCA AATATTCTTC TCCTTTTGGA AACAAAAGTA GGAAACTCTG CCACAAACCT   7740

CCCCAGAGCC TGCCCCCTGC GTGACCAGGG TAAGGAAAGT GTGAGGAGGA GCATAACATT   7800

TACTAAAACA ACACAAAACA GGAGCTGCCG TAGCCTCACT CCCAGCCCTT GTTTTTCAGG   7860

ATGTGTTCTG GGCCAAGTAC ACAGGTGAGC ACCGGGAAGG ATTTGCCCCA GGAAGGGAGG   7920

CCTGGGGACC CCAGTGAGAG AATTCTACCC AGAGAATCTT CTGCTGCACC TAGCCATCCA   7980

CCCATCCACC CCTTCCCCAC TCCTTCCTTG GTCCCTCCCA TCTGTTCATC CATCTTTCTG   8040

TTTCTCACCA ACATCCCATC CACCCTGACT CCAGCTCATC CTGGCCATAC CCCAATCCCA   8100

AAGGTAAACA CCTGGGTCTT TTCCAGCTTG TGAGACAGCG AGGACGCCTC GAGATAAGCT   8160

TGCTGCATGT CTGGAAGGTG AGCAACTGAC ACGGGTTTGG GGAGCAGGAC ATGGAGGGGA   8220

GCTTGGGAGA AGAGCTCAGG GGTGGGTTTG GAGTGTGGCT GGTGGAGGCC GAGGCAGTCC   8280

CCAGCATCTG ACATTGCTCC CATTCCTGGG GTCAAGATGT CTCTTTGTAC CTGGCTCTGT   8340

GTCTGGCATG CGAACGAATG AATGAATGAA TGGACTAATG AATTAATGTT TTTTTTTTG   8400

AGACAGAGTC TCGCTCTGTT GCCCAGGCTG GAGTGCAGTG GCACGATCTT GGCTCACTGT   8460

AAACTCCGCC TCCCGGATTC AAGCAATTCT CTGCCTCAAC CTCCCAAGTA GCTGGGATTA   8520

CAGGTGCTCG CCACCACGCC TAGCTAATTT TTGTATTTTT AGTAGAGACG GGGTTTCACC   8580

ATGTTGGCCA GGCTGGTCTT GAACTCCTGA CCTCGTGATC CACCCACCTC GGCCTCAAAG   8640

TGCTGGGATT ATAGAAGTGA GCCACCGCGC CTGGCCATGA ATTCATGTTT AAGGCTTCAT   8700

TCTCCTTTGC CTGACCCGAG TCTCTGCCCC CACCTAGTCA GAGCTTTGAT GATGTCACAT   8760

TCCCCTTCTA GCTTTAGGTG TCACTGAACC AAACAGGAAC CCAAACCCCC AGCTGCTCTG   8820

ACACCAAGGA CTTCCCTAAG CATGCCAAGG TGTTTCTAGC ACCTGGCCTT GCATATGTTG   8880

TCAATTTCCT CTGGAGCGAC CATCACATCT ACTGAACACT TTCCTATCCT TCAAGGACTG   8940

CTTCAAATGT CACCACTTTT GCTGAGACTT CAGGGAGCAC CCTCCCTCCT GCACTGTGTC   9000

TGAAGGCACC TTTAGCACGA CAAAAATGGA ACTCTTTGTT TATTTATAAG AGCAGGGTCT   9060

CCCTTTTTTG CCAGGCTGAT CTTGAACTCT TGGGCTCAGG CAATTCTCCC ATCTCAGTCT   9120

CCCAAAGGAG TGGATTATAA GTGTGAGCCA CCATGCCTGG CTGCCATACT TTCATTTTTT   9180

TTTTTTTTTT TTTGAGGTGG AGTCTCACTC TGTCGCCTAG GCTGGAGTGC AGTGGCGCGA   9240

TCTCGGCTCG CTGCAACCTC CGCCTGGCGG TTCAAGTGAT TCTCCTGCCT TAGCCTCCTG   9300

AGTAGCTGGG ATTACAGGCA CACACTACCA TGCCCAGCTA ATTTTTTGTA TTTTTAGTA    9360

GAGACGGGGT TTCACCATGT TGGCCAGGCT GGTCACAAAC TCCTGACCTC AGGTGATCCA   9420

CCAGCCTCAG CCTCCCAGAG TGCTGGGATT ACAGGTGTAA TCCACTGCGC CCAGCCTCAT   9480

TTGTTAAATT ACGTACTCAA CAGACATTTT ACAAAGTTCC TGCTACGTGC CAGGCACTAT   9540

ATCAGGTGCT GGGGATTTTA AGAGAATCAA ATACAGTCTC TGCCTTCAAG GAATTCAAAA   9600

TCTCAAAAGA GAACAAAAAT ACAAAATATT AAAATGATTG CGGCCGGGTG TGGTGGCTCA   9660
```

```
AGCCTGTAAT CCTAGCACTT TGGGAGCTGA GGTGGGCGCC CAGGCCAGGG GTTTGAGACC   9720

ATCTTGGCCA ACATAGTGAA ACCCCCAACC TCTACTAAAA ATACAAAAAT TAGCTGGGGT   9780

GTGGTGGCAC GCGCCTGTAA TCCTAGCTAC TAGGGAGGCT GATGGGGAGA ATTTCTTGAA   9840

TCTGGGAAGC GAAGGTTGCA GTGAGCTGAG ATCATGCCAC TGCACCTTCA GTCTCGGCAT   9900

CAGATCAAGA CTCATCTCAA ATACATAATA AATAATAATT CAATAAGTGA TTGCAAGAAA   9960

GTTCTGTTCA AGGCACCAAG AGACCACAGG AAAATGAGTG TCTGGTTTGC CAGAAAATGA  10020

GAGATGGCTT CCCAGGAGAG GCAGAGTTCT GCCTGGCCTA GTGGGATGCA TGGATGAACA  10080

AACAAGTGGG CATTCCAGTC AGAAGAAACA ATCCGTGGAA AGACCCAGAG GCATGAGAAG  10140

CTGAGCTAGC AGGGACAGGT AGACCAGGGC CAGTTGAAAA GGACCTTCAT CACTTTTTCA  10200

TCCTGCTGGC CAAGAGAAGC CACAGAATGG AAGCTCCATG AGGGCAGGGC TGTGACTGTC  10260

CTATTGGTTG ATGTGTACTG AGCACCCGAC AGTGCCTGTC ATATGGTAGG CACTTAGCGA  10320

ATATTTGGAG GCCACTGTTG AGTGAATGGG AGAACTGCTG GTTGCAGAGG AAGAGGGGCT  10380

GGGTGAATGC AGGTTCAGGA TTGTGGACCT GCATGAGCTG GGAGGTGGGG GATAGACAAC  10440

TTTGCAGGGA GAGAGGAAAT AAGTCCCCAG GCTCCAAGGC TGACCGGGGT GGGGTCTCCG  10500

CAGGTAACTG TGCTGAGGGT CTGGGTACGA ACTACCGAGG GCATGTGAAC ATCACCCGGT  10560

CAGGCATTGA GTGCCAGCTA TGGAGGAGTC GCTACCCACA TAAGCCTGAG TGAGTGAGGG  10620

GTCGGCCTTC CCACCATGGG CTGAGAACAG GGAGCAAGCG TACCTCAAGT TCAACAGCCT  10680

CCTGTTGGGC AATTTCCTCT TCCAGAATCA ACTCCACTAC CCATCCTGGG GCCGACCTAC  10740

AGGAGAATTT CTGCCGCAAC CCCGACAGCA GCACCACGGG ACCCTGGTGC TACACTACAG  10800

ACCCCACCGT GAGGAGGCAG GAATGCAGCA TCCCTGTCTG TGGTAGGCTG GGGGCAGTGG  10860

GGCGACCCAT GACCAAGCCC GGGGGCTTCA TGGGGCCTGG CAGCCTGGGA TGGGAACCAA  10920

GAATACTGGC TACCCAGGCA CAGTGGCTCA TGCCCGTAAT CCCAGCACTT TGGGAGGCTG  10980

AGGCAGGCAG ATCACCTGAG GTCAGGGGTT TGAGACCAGC TGGGCCAACA TGGCAAAACC  11040

CCGTCTCTAC TAAAAATACA AAAATTGCCA GGCGTGGTGG TGGGCGCCTG TAATCCCAAC  11100

TACTCTGGAG GCTGAGGCAC GAGAATCGCT TGAACCCGGG AGGCGGAGTT TGCAGTGAGC  11160

TGAGATCCTG CCACTGTACT TCAGCCTAGG CGACAAGAGC AAAACTCTGT CTCAAAGAAA  11220

AAAAAAGAT GCTGGCCACC TTCAGAGCTG GCGTCAGTCA TTCAGATCAT ATCTGTGCCT  11280

ATTGCTCAGT AAAGTCAGGG AATCAGGGGA TCTGAGTGGG GGGATCTGCC AGCCTCCTCC  11340

TCCCCCTCCC CACTCTTGAC TTCCTTATGG TCTAGGCTGT GGCTCATTCC AAACATGCCT  11400

CCTTTCTGAT CAAGGCACTC CTCCCTCCGG GAAGCCCTCC CTAGCCATTT CAGTCCACAC  11460

ACCCTGTTCT GAGTATCACA GAGCAAGCCT TGTGCAGTTT GGCCCGCGGG ATTCTGTCAT  11520

TATTATTTCC TTGGTGTGTT AAGTAGCTAT AGCCACCCCT TCCCTGAGGC AGACCACAAT  11580

AAGCATTTCT TTTTCCCATG AGGGTTGGCA GGTGTGGCTG CACTCGCTAA TGCGTCTGTA  11640

GGGTCAACTG ACGGAGGTTG GCCCTGGCTG GGTGGCTCTG ATTCAAATAA TGGGTCCAGC  11700

TGAGTCTGGC TCCTCGTTGA GGGTTGGGCC TAGATCTGCT CCACGTGCGT TCATGCTGGG  11760

GCTGAGGCTG AAAGAAGGTA CCTGGGAAAA CTCTTCTTAT GCTGATGACA GACACAGAAA  11820

ACAATGAACA GAAAAGCGTC TTCTGTCCTG AAGGCCTGGC TCAGAACAGG CACAGTCAGC  11880

CCTGCCCACG TTCCATTGGC CAGAGCAAGT ATATGTTCAA GGCCAGGGTC AAGAGGTAAA  11940

CTACACCTCA GCCTGTAAAA TCACAGAGCA AGGGATGTGG ATGCAGGCAG GGGTAAAGAA  12000
```

-continued

```
TTTGTGCCGA TTACCAGTCC ACAAACATGC GTTAGTGTTG GTTCTCTAGG CAACCCTGTC  12060

GGGCCCATTG CTCATTCCTG GGGTTGGTCT TTTTTTTTTT TCTTTCTAAG AAGGAGTCTC  12120

ACTCCCTTGC CCAGGCTGTT GGAGTGCAGT GGCCCTATCT CAGCTCACTG CAACCTCCGC  12180

CTCCTGGGTT CAAGCGATTC CCCTGCTTCA GCCTCCTGAG TAGCTAGGAT TACAGGCGTG  12240

TGCCACCACT CCTGGCTAAT TTTTTTTTAT GTTAGTAGAG ACGGGGTTTC ACCATGTTGG  12300

CCAGGCTGAT CTCAAACTCC TGACCTTGTG ATCCTCCCGC CTCGGCCTCC CAAACTGCTG  12360

AGATTACAGG GGTGAGGCAC TGCGCCCAGC CATTTTTTTT TTTTTTTTTT TTTGAGATGG  12420

AGTCTCACTC TCACCCAGGC TGGAGTGCAG TGGCATAATC TTGGCTCACT GCAACCTCCA  12480

CCTCCTGGGT TCAGGCGATT CTCTGCCTCA GCCTCTCATA TAGCTGGGAT TACAGGCACA  12540

CGCCACCACG CCTTGCTAAT TTTGTATTTT TAGTAGAGAC GGGGTTTCTT CATGTTGGCC  12600

TTGCCTGACT TGAACTCCTT GTTCCGGTGA TCTGCCCAGC TCGGCCTCCC AAAGTTCTGG  12660

GATTACAGGT GTAAGCCACT GCGCCTGGCC CCTGGTATTG GTCTTATAGC AAGTTTATCC  12720

CAACAAAAAC AGCTACTATT TACTCCCCAA CCCCCATACA CACGCACACA CATTGATGAT  12780

AAATAAGTTG CAGGCTTGCA GAAATTGGCC CATCCAGGTG AACAGCCTAG TGATCCGAGC  12840

AAGCGTCCTG CTGTGCAGCT ATAAAAACAT GACTCCTCCA GCAGCTCCAG GCAGCCACTA  12900

CCAGTTGGTT ACAGATGGCC TAGGAGGCCA AACCTGGTTA CTATCTCTGG TTTATTATGT  12960

GCCAGACACT TATGCTGTAT ATTTTGTTTA ATCCTCTCAA CAAACCTGCA AAAGTGGCAT  13020

TAGTAACCCC TTTAAAGGCA AACGGTCAGA AGCCCAGAGA GGTTAAGTAA CCTGAGGTCA  13080

CACAGGCAGA AAGCAGCAAG ACCGGGGTTC ACACCCCTGT CTGTTCCGGT CCATGTGTGG  13140

TCTCACTCAC TCTGCTGCCT CCTTGCCCCT CACCCACCAG GCCAGGATCA AGTCACTGTA  13200

GCGATGACTC CACGCTCCGA AGGCTCCAGT GTGAATCTGT CACCTCCATT GGAGCAGTGT  13260

GTCCCTGATC GGGGGCAGCA GTACCAGGGG CGCCTGGCGG TGACCACACA TGGGCTCCCC  13320

TGCCTGGCCT GGGCCAGCGC ACAGGCCAAG GCCCTGAGCA AGCACCAGGA CTTCAACTCA  13380

GCTGTGCAGC TGGTGGAGAA CTTCTGCCGC AACCCAGACG GGGATGAGGA GGGCGTGTGG  13440

TGCTATGTGG CCGGGAAGCC TGGCGACTTT GGGTACTGCG ACCTCAACTA TTGTGGTGAG  13500

CTGCCTGGGT AGGGGGCCTG AGTTGCAGGG ACAAATCCTA GTGGGAATAA CAACAGCCGC  13560

TTCTGCTTAT CGAACGCTTA CCTCATTGAG TGCGCTCATT ACAGCCTTAC AGTAACCAGG  13620

TGGGGGGTAA GGTCCTGTGC CCATTTCACA GATAAGTACA CTGAGGCCCC AGGAGGTTAT  13680

TGCCTAGTAG CCCAACTGTG CATGCACGCT TAACCTCTGC ACCAAATGGC CTCCAAGGCC  13740

CGTAGGGGAA CTGGGGGGAT CTAGGGGATG GGTGAGGAAT GGCCCAGCCC AGTCCCGGCC  13800

GGTGCCTGGG TCCCAACAGA GGAGGCCGTG GAGGAGGAGA CAGGAGATGG GCTGGATGAG  13860

GACTCAGACA GGGCCATCGA AGGGCGTACC GCCACCAGTG AGTACCAGAC TTTCTTCAAT  13920

CCGAGGACCT TTGGCTCGGG AGAGGCAGGT GAGGTAGTGG GCATCCGAGG GGATGCGGGG  13980

CTGCGGGGCT GGTGGCCAGG ACTTGCCCCT CACTGCTTGG CTTGCTCTGC AGACTGTGGG  14040

CTGCGACCTC TGTTCGAGAA GAAGTCGCTG GAGGACAAAA CCGAAAGAGA GCTCCTGGAA  14100

TCCTACATCG ACGGGCGCAT TGTGGAGGGC TCGGATGCAG AGATCGGCAT GTCACCTTGG  14160

TGTGTCCTGG AGCCCTGCGC TACCATTCAC TCCTGGGGGC AGGTGTGCTG CTGGACCCCC  14220

ACCCTCAGGC CCTGCCTGCA GGCCTGGGCT TTACAGATGA CAACAGCTGA GCATCCAGGA  14280

TCCCACCAAC TCCACACAGC AGCCACATGA GATGGGTTGT TTACTTCTTT TTTTTTTGTT  14340

TCTTAGATGG AGTCTTGCTC TGTCACCTAG GCTGGAGTGC AGTGCTGCAA TCTCGGCTCA  14400
```

```
CTACCTCGAT CTCAGCTCAC TGCAACTTCT GCCTTCCGGG TTCAAACGAT TCTCTTGCCT    14460

CAGCCTCCTG AGTAGCTGAA TTTACAGACA TGCGCCACCA CACCCGGCTA ATTTTTGTAT    14520

TTTAAGTAGA GACAGGGTTT CACCATGTTG GCCAGGCTGG TCTTGAACTC CTGACCTCAA    14580

GTGATCCACC TGCCTCAGCC TCCCAAAGTG CCGGGATTAC AGGCATGAGC CACCACACCC    14640

GGCCCATGGG TCCTTTACTT CTAAGCAGAT GGTAAAGCTG AGACTGACGG AGCTGGTGGC    14700

TCACCTCCGC GCACAGCTAA TGGGTTTGAA TCCAGTTCTT CTGATTCCAG AGCTGTGCTA    14760

CGCTATGTGA ACTCTGGACT GGAAGGACCT AGTTAGGGGG TGCAAAAAGC AGGAGGCAGG    14820

TCAGGTGCAG TGGCTCACCC CTGTAATCCC AGCACTTTGG GAGGCCAAGA CAGGAAGATC    14880

ACTTGAGGGC AGGAGTTCGA GGCCAGCTTG GGCAAAATGG TAAAACCCCG TCTCTACTAA    14940

AAATGCAAAA ATTAGCCAGG TGTAGCAGCA TGTCCCTGTA GTCCCAGCTA CTAAGGAGGC    15000

TGAGGCGGGA GGATCGCCTG AGCCCAAGAG GCTGAGGCTT CAGTAAGCTG TGACTGTACC    15060

ATTGCACTCC AGCCTGGGTG ACAAGAGTGA GACCCTGTCT CAAAAATAAA TAAATAAATA    15120

AATAAAAAGT GTGAGGCAGC CCCTCAGCAT CACACGGAGG CTCCAGCCCC AAAGGCGGCC    15180

AGCCCAAGCT TGGATCTGGG CCCCGGAGGC AGCTCTGCCC AGCTGGGTTC TTAGACCTGG    15240

GATTGTTACT TCTAGGGCTG GTGTAGAGGC AGCCCCCTCA TCCTCAGCTC CTAATGCTTC    15300

CTGCTGCCCC TCCCAGGCAG GTGATGCTTT TCCGGAAGAG TCCCCAGGAG CTGCTGTGTG    15360

GGGCCAGCCT CATCAGTGAC CGCTGGGTCC TCACCGCCGC CCACTGCCTC CTGTACCCGC    15420

CCTGGGACAA GAACTTCACC GAGAATGACC TTCTGGTGCG CATTGGCAAG CACTCCCGCA    15480

CAAGGTACAG AACTGGTGGC CCGTGGGTGT CTGGCAGGGG TCTGAGTCCT CCAAAGCGAT    15540

CATGAGGGGC CTTGGTGGCT CCGGGACACA TAGGATGTTC TGTATACCCC CCAGAATATA    15600

ACATCCCAGC AGTCTCTGCT GGAAAGCCAT TTGGTCACGT CCTGACTGAG GCTTGGAGCG    15660

CGGGGAGAAT CCGTCTGTCT CTGGTCCCTC CAACACTAGG ATATAGCCCA TGTGGGAGTC    15720

TCTGAAAATA GAGTCTGTCT GGACTAGGGC GTGCAGCCTG TGCCCCTGTC CCGTCCTCC    15780

AGGCTGTCTG ACTCCAAAGC CCTGCACGGC TTTAGGCCCA GGAAGAAACA CCCAGGGGGC    15840

TGCCATGGCA GGAACCAGCC CTATCCCCTC CCTGGTGGCC TGCAGGACAC ACTGTCTCCC    15900

AGAACCCCAA GGGCAGGCAG TTTCCTGCTC CTTGCTGGGT GAACCTGCAG CTTCTCCATT    15960

TCTTTCTTGG GGTCTCTGCA GGTACGAGCG AAACATTGAA AAGATATCCA TGTTGGAAAA    16020

GATCTACATC CACCCCAGGT ACAACTGGCG GGAGAACCTG GACCGGGACA TTGCCCTGAT    16080

GAAGCTGAAG AAGCCTGTTG CCTTCAGTGA CTACATTCAC CCTGTGTGTC TGCCCGACAG    16140

GGAGACGGCA GCCAGGTGGG CCACCAGATG CTTGTTAGCT GAGGGGCAGA AGCCAAGTTC    16200

TGGGCCTGGC TCTGATACCA AGTAGCCTTG CAAGAGCCCC TTTCCCTTTT CCAGGCCTCG    16260

GTTTCTTGGA GTGAACCCAA AAGTTCTTTT CAGTACTGGC GTTTTATTTT TTATTTTAT    16320

TTATTTATTT ACTGACGGAG TTCCACTCTT GTCTCCCAGG CTGGAGTGTA GTTGTGCGAT    16380

CTTGGCTCAC TGCAACCCCA CCTCCTGGGT TCAAGCGACT CTCCTGCCTC AGTCTCCTGA    16440

GTAGCTGGGA TTACAGGCTA ATTTTTGTAT TTTTAGTAGA GACTGGTGGG TTTCACCGTG    16500

TCGGCCAGGT TGGTCTCGAA CCCCTGACCT CAAGTGATTC ACCCGCCTCG GCCTCCCAAA    16560

GTGCCGAGAC CACAGGCGTG AACGTCTGTG CCCAGCCAGC TCTGGCGTTT TAGATTCTGG    16620

TCTCTAAGAA ATGGCGTTGG GGCCAGGCGG CTCCTGTGGG GGTTGGCTCT CACTAGGCCC    16680

TTCTTCCTTC CCCAAAGCTT GCTCCAGGCT GGATACAAGG GGCGGGTGAC AGGCTGGGGC    16740
```

```
AACCTGAAGG AGACGTGGAC AGCCAACGTT GGTAAGGGGC AGCCCAGTGT CCTGCAGGTG 16800

GTGAACCTGC CCATTGTGGA GCGGCCGGTC TGCAAGGACT CCACCCGGAT CCGCATCACT 16860

GACAACATGT TCTGTGCTGG CAAGTCTGTG CAGGGCGGGC TGAGGGAACA GTGGGGCCCA 16920

AGCTGGGAGA ACTGAGTTGT GCCTGGGTTC AAGCCATGTG ACTTTGAGCA AGTTGCCTAA 16980

CCTCTTGGTG GCTCAGTTTC TTCCTCTGTA AAATGGAGGT AAAAGTCTCT ATCCCATAAG 17040

GTTATGGGAG GGTTAAATGA AGTAGTATAT ATTAATGTAC TTGGCATAGT ATCAGTCACC 17100

AGTGAGCTCA GATAGCAGCA AGAGGCTGCG GGTAGGGAAA TGCCATTCAT TCAGTCACTC 17160

AGCAAATATT TATTGAGCGC CTATCACGTT CCAGGCAGCG TTCTAGGGTA TACAGCAGGG 17220

ACCCAGACGG ACAATGTCTG TGCCCTCAGA GAGCTTCCTT CCTAGGAGGG CACATCCATA 17280

AACAGATCTA AACAGCAAT CCCTGACCAG TGCTGTGAAG AAAAATGAAG CACAGGGAGA 17340

GAGAACGGCT GATGAAGTGG GCTTCTAAAT AGGGTGGCCA GACAAGGTGG GCAGATCACT 17400

TGAGGTCAGG AGTTCAAGAC CAGCCTGGCC AACATGGTGA AACCCCGTCT CTACTAAAAA 17460

TACAAAAATT AGCTGGTCAT GGTGACGCAT GCCTGTAGTC GCAGCTACTC AGGAGGCTGA 17520

GGCAGGAGAA TTGCTTGAGC CAGGGAGGCG GAGGTTGCAG TGAGCTGAGA TCGGGCATCA 17580

TTGCACTCCA GCTGGGCAAC ACAGCAAGAC TCCATTGATC GATCGATCAA TCAATCAATC 17640

AGGTGGCCAG AGAAGGTTGG AGAAGGCCTC CCTGAGAAGG TGATGTCTGG GCAGGGACTG 17700

GAAGAGGGGA AGGAAGGAGT GAGCAGGCAT ATCTAGGGGA GGAGCACCGC AGGCTGGGGG 17760

CATGGCAGGC ACTAAGGCCC TGAGGTGGGA GCACTCTTGG CTTGTCTGGG GAGCAGTAGG 17820

GAGGCCTGGG GGGCTGAGGA GGGGCAGCAG TGGGTGAGGG GAGAGAGGGG GGCAGGCAGA 17880

GGACAGCCAC TTCCTTTAGG GCCTGGAAGG ACTTTATTGA GTGAGATGGG AAGTTATTGA 17940

GGGGCTTGAG GCAGGTTAAG AAATGATGTG ACTGACTTTA AAAGTAAAAA ATAAAAAAAT 18000

TTAGTGTAAT TTCAGACTCA CAGAAAAGTT GTAAAAATAA TACAAAGATT TCCTGTATAC 18060

TGTCATCCAG ATTGTCCTCC ATTCTGTGGA TGTGTGGGAA TTTTTATATA TATATATGCA 18120

TAGTTTGAGA GCAAATCATG AATATGGTTT CTTTTTACCC ATAAATACTT GAGTATTTCC 18180

AAAAAAAAAA AAAATACCCA AGGATGTTCT CTTATGCAAC CACAATACAA ATATTAAAAC 18240

CCGGAAATTT TTTTTTGACA TAGCTTCGCG TCACCCAGGC TTGAGTGCAG TGGCACAATC 18300

TCGGCTCACT GCAACCTCCT GCTCCCAGGT TCAAGTGATT CTCCTGCCTC AGCCTCCTGA 18360

GTAGCTGGAA TCACAGGCAT GTACTACCAT GCCTAGCTAA TTTTTGTATT TGTAGTAGAG 18420

ACAGGGTTTC ACCATGTTGG CCAGGTCGGT CTTGAACTCC GACCTCAGGT GATTCACCTG 18480

CCTCGGCCTC CCAAAGTGCT GGGATTACAG GCGTGAACCA CTGTACTCGG CCAAAACCAG 18540

GAAATTTTTT TTTTTTTTTG AGATGGAATC TTGCTCTGTT GCCCAGGCTA GAGTGCAGTG 18600

GCATGGTCTC GGCTTACTTG GAATTACAGG TGCCTGCCAC CACGCCCGGC TAACTTTTTG 18660

TATTTTTAGT ATTTTTAGTA GTGATGGGGT TTCACCATGT TGGCCAGGCT GGTCTTGAAC 18720

TCCTGACCTC GGGTAATCCA CCCACCTCGG CTTCCCAAAG TGCTGGGATT ACAGGCGTGA 18780

GCACCAGCAC CTGGCCCAAA ACCAGGAAAT TAATGATGAT ACAATATTAT TGTCTAATCT 18840

ATAGACCTTA TTCAAATTTT TGTTAGTCTT GCTAATGTCT TTTATAGGGA AAAAAAAAA 18900

AAAAAGCGTG TTTCTCACCC AGGATTCAAT GAAGGATCTT TCTTTGTCTT CTATGACCTT 18960

GACATGTCTG ATGAGTGCAG TCTGGTTATT TTGTACACTG GCCCTGAATC CGGGTTTGTC 19020

TAAGGTTTCC TCACGGTCAG GTTCGGGCTC AGTGGTGCCA TGTCCTTCTT GGTGCATCCT 19080

GTTAACTGGC ACATGAGAAC AATTTGTCTC ATATGTGGTG AGTCTAACTC TGACCTCTTG 19140
```

```
AGGAAGGCAA TGTCTGCCAA GTTTCTTGCT GTAACTTCTG TTTTTCCCTT TGTAATTAAT 19200

AAGAATCTGG TAAAGAGACA CTTTGATGTT TTTTTTTTTT TTTTTTTTTG TGATGGAGTC 19260

TCCCTCTATC ACCCGGGCTG GAGTGTGTGG TGCGATCTCG GCTCACTGCA ACCTCCATCC 19320

CCCAGGTTCA AGTGATTCTC CTGCCTCAGC CTCCCAAGTA GCAGGGATTA CAGGCATGTG 19380

CCACCACACC CAGCTAATTT TTGTATTTTT AGTAGAGATG GGGTTTCACC ATGTTGGCCA 19440

GGATGGTCTC GAACTCCTGA CCTTGTGATC CGTCTGCCTC AGCCTCCCAA AGTGCTGGGA 19500

TTACAGGTGT GAGCCAATAC GCCTGGCCTA CTTTGATATT TTGTATTCTG TTTGCATCAA 19560

AACCTTCTCC CAACTAGGGT GACTACCAAA TGGCACTTAT CTAATTCTGT CATTCCTTCT 19620

ACATTTGTTA GTTACTTTAT TGCTTTCCTT CCTTTCATTC TATCAGTGTG GACTTAAGGA 19680

TCCTTACTTT ATTCTAAGGG TTCACCTTTT TTTTCTTTTT TTTTGAGATG GAGTTTCGCC 19740

CATGTTGCCC AGGCTGGATG GAGTGCAATG GCGTGATCTC GGCTCACTGC AACGTCCTCC 19800

TCCCAGGTTC AAGCAATTCT CCTGCCTCAG CCTCCTGAGT AGCTGGGATT ACAGGCATGT 19860

GCCACCACGC CTGGCTAATT TTTTGTATTT TTAGTAGAGA CAGGGTTTCA CCATGTTGGC 19920

CAGGCTGGTC TCGAACTCCT GACCTCAGGT GATCCGCCCG CCTCAGCCTT CCAAGGTTCT 19980

GGGATTATAA GCGTGAGCTC TACCGTGCCA GGCCATACTT TGTTACTACT GTTATTTTTT 20040

CTGATGCTCA GATGATCCCA AGTTTGGCCT GTGGAAGTCC CTTCAAGCTG GCTTCTGTGA 20100

CTTGGGAGA TGTTCTGTCA TTCTTTGAGT ACTTTCTTTC TTTCTGGCAC AGCAAAATGA 20160

TTCAGGTTAA TCCTACTTTC CTTACTGTAG TGTTGGAACC AGCCATTTCT CCAGGGAACC 20220

CTTGTAGTCA AGAGTGGAAT TTAGAACTGA GATCTGGGTG CTGGCGTGTG CACATTGCTA 20280

GTGGGATGTC ATTACTTCTA GGCTCTCTTA GTGGACAGAA CCAGAAAAAA ATTATATGAT 20340

GCATATACCA ATATCTCTAT CATCTATATA AAAAACCATG AGTTCCTACT GAAACCTCCA 20400

ATTCCATTCT AACACCACAG GATTAATTTT AGCTTTTCCT TTTCCATATT TGTAACTCTC 20460

TCTGTTGACA GTGAGAAACC TGACCCTCAT TATCTGTAAT GCATTTGCCT ATTTGAACAA 20520

TACTAGAATA TAGTTTCAAA ATCCTCCATC CATAACACTA TTAAAACCAA TCCTATGGCT 20580

GGGCTCAGCC CACTGCAACC TCTGCCTCCT GGACTCAAGC CAGCCTCCCA CTTTAGCCTC 20640

CCGAGTAGCC AGGGCTACAG GCACACACCA CCATGCCCAG CTAATTTTTG TATTTTTTGT 20700

AGAGACTGGG TCTCACTGTG TTGCCCAGAC AGGTCTTGAA CTCTGAGCTC AAGTGATCCA 20760

TCCAACTCAG CCTCCCAAAG TGCTAGGATT ACAGGTGTGA GTCACCATGC CTGGCCTCTC 20820

CTAGTAAATT TTTAGAAGTG GTGTTGTTAG GTCAAAAGGC AAACATGTAT GTCATTTTTT 20880

AGAGATTTTT AAATTTCTTT CCATAAGGGT TGTACCAGTT TGCATTTCCA TCACAGTGTA 20940

TGAGAATGCC TGTTTCCCCA CAACCTTGCC AAAAGAATGT CACAGTTTAA ATTTTACCAA 21000

TCTGAGAGGT GAGAAATAGT ACCTGAAATT GTTTAACGGA CATCTTCAAA TTGAAATTGA 21060

GGTTGACAAC GAATCATAGT TAGGACCTTT TTTTTTTTTT TTTTTGAGTG GGTCTCCTCG 21120

TCACCAAGCT GAGTGCATGG CACGATTTGC TCACTGCAAC TTCCGCCTTC TGGGTTCAAG 21180

CGATTCTCCT GCTTCAGCCT CCCAAGCAGC TGGGACTCCA GGCGCGAGTC ACCATGCCCG 21240

CTAATTTTTG TATTTTTAGT AGAGACAGGG TTTTACCAGA TTGGCCAGGC TGGTCTCGAA 21300

CTCCTTACCT TGTGATCCTC CCGCCTCGGC CTCCCAAAGT GCTGAGATTA CAGGCATGAG 21360

CCACCACGCC TGGCCTAAGG ACCATTTTTA TATAATTTTT TTTTTGAGAC AGAGTCTTGC 21420

TTTGTCACCC AGGCTGGAGT GCAATGGTGC AATCTTGGCT CACTGCAGCC TCCACTTCCC 21480
```

```
TGGTTCAAGT GATTCTCCTG CCTCAGCCTC CCGAGTAGCT GGTTCCACAG GTGCGTGCCT 21540

GGCTAGTATT TGTATTATAT AATTTTTTTG TGAATTGTCT CTTCATGGTT TTTTGCCCAT 21600

TTTTTGGTCC CTTTCTTATC AATTTTTGTG AGTTCTTCGT ATTTATATTA GGCCTTTATT 21660

TGTGATATAC ATTGCAAATG TTTTCTCCTA GTTTGTCAGT TTTTTTAACC TCATGTATAA 21720

TTTTTCTGGC CATGCAGTTT AAAAAATTAC TAGGTAGTCA AATTTATCAA TCATTATTTA 21780

TAAATCTGGT TTGAACAGAG ATAAACTTTC CTGGCCAAGT GTGGTGTTTA CACCTGTAAT 21840

CCCAGCACTC TGAGAGGCTG AGGTGGGGAT CACCTGAGGT CAGAAGTTCA AGACCAGCCT 21900

GGCCAACATG GTGAAACCCT GTCTCTACTA AAAATACAAA AATTAGCTGG GCGTGGTGGC 21960

TGATGCCTGT AGTCCCAGCT ACTCAGGAGA CTGAGGCTGG AGAATTGCTT GAACCTGGGA 22020

GGCGGAGGTT GCAGTGAGCA GAGATCGTGC CGCTGCACTC CAGCCTGGGT GACAGAGCAA 22080

GACTCTGTCT CAAAAACAAA ACGACAAAAA ACAACAACAG AAAAGCCTTT CCTGATAGCT 22140

AGGTCATTGA GGAATTCACT CATGTTTTCT TCTAGTACCT GATTTCATTT TTCTGCACTT 22200

AGATTCCTGA CTCATATGGA GTTTATTTTT GTATCTGATG TGAGGCATAG ATCTAATTTA 22260

TTATTTTCCA AATGGCTAAC TAGCTGTCTC TAAACCCTTT ATTAAAAATT ATTGGCCAAG 22320

TGCGGTAGCC ACACCTGTAA TCCCAGCAGT TTGGAAGGCT GAGGCAGGAT TGCTTGAGGC 22380

CAGGAATTCA AAACCAGCCC AGACAACATA GCAAGACCCT GTCTCTACAA GAAAATATTG 22440

GTCAGGTGTG GTGGCTCACG CCTATAATCC CAGCACTTTG GGAGGCTGAG GCAGGTGGAT 22500

CATGAGGTCA GGAGATAGAG ACCATCCTGG CCAACATGGT GAAACCCTCG TCTCTACTAA 22560

AATACAAAAA ATTAGCTGGG TGTGGTGGCG CATGCCTGTA GTACCAGCTA CTCAGGAGGC 22620

TGAGGCAGGG GAATCATTTG AACCCAGGAG GTGGAGGTTG CAGTGAGCTG AGATCACGCC 22680

ATTGAACTCC AGCCTGGCGA CAGAGCAAGA CTCCATCTCA AAAAAAAAG GAAAAGAAA 22740

ATATTTTAAA AATTAGCTGG GCATGGTGGC ATGTGCCTTG TAGTCTCAGC TACTTGAGAG 22800

GCTGAGTTAG GAGGATTGCT TGAGCCTAGG AGTTCAATAC TGCAGTGAGC TATGACCGCA 22860

CCATTGCACT CCAGCCTGGG CAACAGAGTG AGACCCTGTT TCTATTAAAA AAAAAAAATC 22920

GGCTGGGCGC GGTGGCTCAC GCCTGTAATC CTAGCACTTT GGGAGGCCGA GGCGAGCGGA 22980

TCACCTGAGG TCAGGAGTTC AAGACCAGCC TGACCAACAT GGAAAAACCC TGTCTCTGCT 23040

AAAAATACAA AATTAGCCAG ACATGGAGGC ACATGTCTGT AATCCCAGCT ACTCGGGAGG 23100

CTGAGGCAGG AGAATCGCTT GAACCTGGGA GACGGAGGTT GCAGTGAGCT GAGATCCCTC 23160

CATTGCACTC CAGCCTGGGC AACAAGAGTA AAAACTCCGT TTCGCCAGGT GCGGTGACTC 23220

ACACCTGTAA TCCCAGCACT TTGGGAGGCC GAGGTGGGTG AATCACAAGG TCAGGAGTTT 23280

GAGACAAGCC TGGCCGACAT GGTGAAACCC CATCTCTACT AAAATACAAA AAATTAGCCT 23340

GGCATGGTGG TGTGCGCCTG TAATCCCAGC TACTTGGGAG GCTGAGGCAG GGGAATCACT 23400

TGAACCTGGG AGGAGGAGGT TGCAGTGAGC CGAGATGGTG CCACTGCACT CCAGCCTGGC 23460

AACAGAGCGA GACTCTATCT CAAAATCAAT CAATCAATCA ATCAATCTTT GAACTAGTGA 23520

TTTGAGATTT CACCTTTATC ACATTCTAGA TTGTATCTTA TTTTCATTTA TTTATTTGAA 23580

ATATAGACAA GTCTCCCTGT GCTGCCCAGG CTGATTTCAA ACTCCTGGCT GGGCTCGAGC 23640

AAGTCTCCCG CCTTGGCCTC CCAAACTGCT GGGATTACAG ACGTGAGCCA CCATACCTGA 23700

CCCAGGTTTT ATTTTTTAGT TTTATTTTTT CCTGCATCCA GCTAATTTGA TTTGATTTGT 23760

AGAGACGGGG TCTTGCTATG TTACCTAGGC TGGTCTCGAA CTCTTGGGCT CAAGTGATCC 23820

TCCTACCTTG GCCTCCCAAA GTGTTGGGAT TACCAGCATG AGCCACGGTG CCCAGCCCCA 23880
```

-continued

```
CGTTCTAGAT TTCTATGGAT AGAGTATGCT TAAGGATGAG TATGTTTCTG GATGTTCGAC  23940

TCGGCTTTCC TGGTCTGTTG TCTGTCTGTG TACAGCGTCA CATTGTTTTA ATGATAGAGG  24000

CTTTAGCGTA CATAGCTGGG AAGGCTAATG TTCTCTTTTA GTTTTTCTTT CCAGTGGTTT  24060

CCTGGCAATT CTTGCATGTT TGTTTTTCCA TATGAACTTT AGTGTCAACA TGCCTAGGTC  24120

TATAAAAAAG CTTGGTGGTA ATTTTATTGG GATTATGACA CTTCAACAAA TTAACTGGGA  24180

GAATGAACAT ATTTTTGATG TTGAGTCATT TTATCCAAGG ATAAGAAACG TTTTCCTATT  24240

TGCTCAAGTC TATTATTGTA TCTTTCTTGA CTGCTGCAAT GTATTCTCTT ATAATTTTTT  24300

CTATTGGTAT CTTATTTTAT GTATTTGTAA TATCTTATTT TTCTTGAGTA AATTAGTTAA  24360

TGGCTTGCCG GTTTTCTCAA AACAAATATC TAGGGATTTG ATTTATGAAA TTATTAGGCC  24420

TATTATTTTT CTTTTTTTTG AGATGGAGTC TCACTCTGTC GCCCAGGCTG GAGTGCAGTG  24480

GCGTGATCTC AGCTCACTGC AACCTCCACC TCCTGGGTTC AAGTGATTCT CCTGCCTCAG  24540

CCTCCCCAGT AGCTGGGGTT ACAGGTGCAC GCCACCATGC CCGGCTAATT TTTTTATATT  24600

TTTAGTAGAG ACGGGGTTTC ACCATGTTAG CCAGGCTGGT CTCGAACTCC TGACCTCATG  24660

ATCCGACTGC CTCAGCCTCC CAAAGTGCTG GGATTACAGG TGTGAGCCAC CGTGCCTGGC  24720

CTTTTTTTTT TTTTTTTGAG ACAGAGTCTT GCTCTGTCAC CCAGGCTGGA GTGCAGTGGT  24780

GCGATCTCGG CTCACTGAAA GCTCCACCTC CCGGGTTCAC GCCATCCTCC TGCCTCAGCC  24840

TCCCGAGTAG CTGGGACTAC AGGTGTACAC TGCCACGCCC AGCTAATTTT TTGTATTTAG  24900

TAGAGACAGG GTTTCACCGC GTTCGCCAGG ATGGTCTCGA TCTCCTGACC TTGTGATCCG  24960

CCTGCCTCAG CCTCCCAAAG TGCTGGTATT ACGGGCGTGA GCCACTGCGC CCGGCCAGGC  25020

CTATTATTTT TCTATTGTGG TTCATTAATT TCTGCTTTTT TCTCTTAAAA AGTTTGCTTA  25080

CGTTTTTGTC TGGTTTACTT TGCTGTTCTC TTGCTAGCTT TTTTTTTTTT CAGATAGGGT  25140

CTTGCTCTGT TGCCCAGGCT GGAGTGCAGT GGCACAGTCA TAGCTCACTG CAGCCTTGAA  25200

CTCCTGGGCT CAAGCAATCC TCTTCTTGCT TCAGCCTCCC ACGTAGCTAG GATCAGAGGT  25260

ACATGCCACC ATGTTCGGCT AATTTTTTTT TTTCGAGACA GAGTCTTGTT CTGTCGCTCA  25320

GGCGGTAGTG CAGTGGTGCA ATCCCGGCTC ACTGCAACCT CCACCTCCAC CTCCCAGGTT  25380

CAAGCAATTC TACCTCAGTC TCCTGAGTAG CTGGGATTAT AGGCGCACAC CAACATGTCT  25440

GGCTAATTTT TGTATTTTTA GTAGAGACAG GGTTTCACCA CGTTGGCTAG GCTGGTCTTA  25500

AACTCCTGAC TTCATGATCC GCCCGCCTTG GCCTCCCAAA GTGCTGAGAT TACAGGTGTG  25560

AGCCACAGCA CCTAGTGAAA GTGTGGTTTT TTTGTGTAGG TTTTACTGTT GTTAGTGTTG  25620

TTCTGTATTG TTTGTAGAGG ATACGTGGGG AGATTTGGAT AAAAGCAACT ATCATTATTA  25680

TCCTCATCAG ACTTGTAGGT CTAACTTTTT AATTTTTTAA TTTTTAATTT AAATTTTTTT  25740

CTTGGTCTTT TATCATTAAT TAATTTTTTC GAGACAGGGT CTCACTCTGT TGCCCAGGCT  25800

GGAGTGTGGT GACATGATCA CGGCTCACTG CAGCCTTAAC CTCCCAGGTG CAAGTGATCC  25860

TCCTCTCTTA GCCTCCCGAG TAGCTGGGAC TCCAGGCATG TGCCACCATG CCCAGCTAAT  25920

TTTTGTAGA GAGAGGGTTT TGCCATATTG CCCAGGCTGG TCTTGAACTG CTGAGCTCAA  25980

GTGATCCACC CGGCTTGGGC ATGAGCCACC TCCCCTGGTC TGGTCCAACT TTTTAAAAGC  26040

ATTATTCTGC CTGTTGGGTG GAGAATAGAC TGTAGGTGGG CAAAGAATGA AGGAAACTAG  26100

TGGGTTCAGG AGCTCGAGCT AGAAGTGGTG AGAAGGGTTT GGATTGGGG TCTATGCTGA  26160

AGGTAGAGCC GACAAGATTT GCTAGGATTG GATGTGTAGG GTGAGGAAGT GGGGACAGCA  26220
```

-continued

```
AGAATGACTG GAGGGGTAAG TGGACTCTCA CCAGCTGTGT CTCGTGAAGG GGCGTGGCTG    26280

GGCTATGAGC TATGCTCCTG AGCACAGACG GCTGTTCTCT TTCAAGGTTA CAAGCCTGAT    26340

GAAGGGAAAC GAGGGGATGC CTGTGAAGGT GACAGTGGGG GACCCTTTGT CATGAAGGTA    26400

AGCTTCTCTA AAGCCCAGGG CCTGGTGAAC ACATCTTCTG GGGGTGGGGA GAAACTCTAG    26460

TATCTAGAAA CAGTTGCCTG GCAGAGGAAT ACTGATGTGA CCTTGAACTT GACTCTATTG    26520

GAAACCTCAT CTTTCTTCTT CAGAGCCCCT TTAACAACCG CTGGTATCAA ATGGGCATCG    26580

TCTCATGGGG TGAAGGCTGT GACCGGGATG GGAAATATGG CTTCTACACA CATGTGTTCC    26640

GCCTGAAGAA GTGGATACAG AAGGTCATTG ATCAGTTTGG AGAGTAGGGG GCCACTCATA    26700

TTCTGGGCTC CTGGAACCAA TCCCGTGAAA GAATTATTTT TGTGTTTCTA AAACTATGGT    26760

TCCCAATAAA AGTGACTCTC AGCGAGCCTC AATGCTCCCA GTGCTATTCA TGGGCAGCTC    26820

TCTGGGCTCA GGAAGAGCCA GTAATACTAC TGGATAAAGA AGACTTAAGA ATCCACCACC    26880

TGGTGCACGC TGGTAGTCCG AGCACTCGGG AGGCTGAGGT GGGAGGAT               26928
```

(2) INFORMATION FOR SEQ ID NO:42:

(i) SEQUENCE CHARACTERISTICS:
        (A) LENGTH: 622 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:42:

```
Met Ala His Val Arg Gly Leu Gln Leu Pro Gly Cys Leu Ala Leu Ala
 1               5                  10                  15

Ala Leu Cys Ser Leu Val His Ser Gln His Val Phe Leu Ala Pro Gln
             20                  25                  30

Gln Ala Arg Ser Leu Leu Gln Arg Val Arg Arg Ala Asn Thr Phe Leu
         35                  40                  45

Glu Glu Val Arg Lys Gly Asn Leu Glu Arg Glu Cys Val Glu Glu Thr
 50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                 85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220
```

```
Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
            245                 250                 255

Leu Val Glu Asn Phe Cys Arg Asn Pro Asp Gly Asp Glu Glu Gly Val
        260                 265                 270

Trp Cys Tyr Val Ala Gly Lys Pro Gly Asp Phe Gly Tyr Cys Asp Leu
    275                 280                 285

Asn Tyr Cys Glu Glu Ala Val Glu Glu Glu Thr Gly Asp Gly Leu Asp
290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
        355                 360                 365

Asp Ala Glu Ile Gly Met Ser Pro Trp Gln Val Met Leu Phe Arg Lys
370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
    450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
        515                 520                 525

Pro Ile Val Glu Arg Pro Val Cys Lys Asp Ser Thr Arg Ile Arg Ile
    530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
        595                 600                 605

Leu Lys Lys Trp Ile Gln Lys Val Ile Asp Gln Phe Gly Glu
    610                 615                 620
```

(2) INFORMATION FOR SEQ ID NO:43:

(i) SEQUENCE CHARACTERISTICS:

(A) LENGTH: 3997 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 17...2380
        (D) OTHER INFORMATION:

(xi) SEQUENCE DESCRIPTION: SEQ ID NO:43:

```
GCGGGAGGCG GACGAG ATG CGA GCG CGG CCG CGG CCC CGG CCG CTC TGG GCG      52
               Met Arg Ala Arg Pro Arg Pro Arg Pro Leu Trp Ala
                 1               5                  10

ACT GTG CTG GCG CTG GGG GCG CTG GCG GGC GTT GGC GTA GGA GGG CCC       100
Thr Val Leu Ala Leu Gly Ala Leu Ala Gly Val Gly Val Gly Gly Pro
             15                  20                  25

AAC ATC TGT ACC ACG CGA GGT GTG AGC TCC TGC CAG CAG TGC CTG GCT       148
Asn Ile Cys Thr Thr Arg Gly Val Ser Ser Cys Gln Gln Cys Leu Ala
     30                  35                  40

GTG AGC CCC ATG TGT GCC TGG TGC TCT GAT GAG GCC CTG CCT CTG GGC       196
Val Ser Pro Met Cys Ala Trp Cys Ser Asp Glu Ala Leu Pro Leu Gly
 45                  50                  55                  60

TCA CCT CGC TGT GAC CTG AAG GAG AAT CTG CTG AAG GAT AAC TGT GCC       244
Ser Pro Arg Cys Asp Leu Lys Glu Asn Leu Leu Lys Asp Asn Cys Ala
                 65                  70                  75

CCA GAA TCC ATC GAG TTC CCA GTG AGT GAG GCC CGA GTA CTA GAG GAC       292
Pro Glu Ser Ile Glu Phe Pro Val Ser Glu Ala Arg Val Leu Glu Asp
             80                  85                  90

AGG CCC CTC AGC GAC AAG GGC TCT GGA GAC AGC TCC CAG GTC ACT CAA       340
Arg Pro Leu Ser Asp Lys Gly Ser Gly Asp Ser Ser Gln Val Thr Gln
         95                  100                 105

GTC AGT CCC CAG AGG ATT GCA CTC CGG CTC CGG CCA GAT GAT TCG AAG       388
Val Ser Pro Gln Arg Ile Ala Leu Arg Leu Arg Pro Asp Asp Ser Lys
    110                 115                 120

AAT TTC TCC ATC CAA GTG CGG CAG GTG GAG GAT TAC CCT GTG GAC ATC       436
Asn Phe Ser Ile Gln Val Arg Gln Val Glu Asp Tyr Pro Val Asp Ile
125                 130                 135                 140

TAC TAC TTG ATG GAC CTG TCT TAC TCC ATG AAG GAT GAT CTG TGG AGC       484
Tyr Tyr Leu Met Asp Leu Ser Tyr Ser Met Lys Asp Asp Leu Trp Ser
                145                 150                 155

ATC CAG AAC CTG GGT ACC AAG CTG GCC ACC CAG ATG CGA AAG CTC ACC       532
Ile Gln Asn Leu Gly Thr Lys Leu Ala Thr Gln Met Arg Lys Leu Thr
            160                 165                 170

AGT AAC CTG CGG ATT GGC TTC GGG GCA TTT GTG GAC AAG CCT GTG TCA       580
Ser Asn Leu Arg Ile Gly Phe Gly Ala Phe Val Asp Lys Pro Val Ser
        175                 180                 185

CCA TAC ATG TAT ATC TCC CCA CCA GAG GCC CTC GAA AAC CCC TGC TAT       628
Pro Tyr Met Tyr Ile Ser Pro Pro Glu Ala Leu Glu Asn Pro Cys Tyr
    190                 195                 200

GAT ATG AAG ACC ACC TGC TTG CCC ATG TTT GGC TAC AAA CAC GTG CTG       676
Asp Met Lys Thr Thr Cys Leu Pro Met Phe Gly Tyr Lys His Val Leu
205                 210                 215                 220

ACG CTA ACT GAC CAG GTG ACC CGC TTC AAT GAG GAA GTG AAG AAG CAG       724
Thr Leu Thr Asp Gln Val Thr Arg Phe Asn Glu Glu Val Lys Lys Gln
                225                 230                 235

AGT GTG TCA CGG AAC CGA GAT GCC CCA GAG GGT GGC TTT GAT GCC ATC       772
Ser Val Ser Arg Asn Arg Asp Ala Pro Glu Gly Gly Phe Asp Ala Ile
            240                 245                 250

ATG CAG GCT ACA GTC TGT GAT GAA AAG ATT GGC TGG AGG AAT GAT GCA       820
```

```
                Met Gln Ala Thr Val Cys Asp Glu Lys Ile Gly Trp Arg Asn Asp Ala
                            255                 260                 265

TCC CAC TTG CTG GTG TTT ACC ACT GAT GCC AAG ACT CAT ATA GCA TTG            868
Ser His Leu Leu Val Phe Thr Thr Asp Ala Lys Thr His Ile Ala Leu
        270                 275                 280

GAC GGA AGG CTG GCA GGC ATT GTC CAG CCT AAT GAC GGG CAG TGT CAT            916
Asp Gly Arg Leu Ala Gly Ile Val Gln Pro Asn Asp Gly Gln Cys His
285                 290                 295                 300

GTT GGT AGT GAC AAT CAT TAC TCT GCC TCC ACT ACC ATG GAT TAT CCC            964
Val Gly Ser Asp Asn His Tyr Ser Ala Ser Thr Thr Met Asp Tyr Pro
                305                 310                 315

TCT TTG GGG CTG ATG ACT GAG AAG CTA TCC CAG AAA AAC ATC AAT TTG           1012
Ser Leu Gly Leu Met Thr Glu Lys Leu Ser Gln Lys Asn Ile Asn Leu
        320                 325                 330

ATC TTT GCA GTG ACT GAA AAT GTA GTC AAT CTC TAT CAG AAC TAT AGT           1060
Ile Phe Ala Val Thr Glu Asn Val Val Asn Leu Tyr Gln Asn Tyr Ser
335                 340                 345

GAG CTC ATC CCA GGG ACC ACA GTT GGG GTT CTG TCC ATG GAT TCC AGC           1108
Glu Leu Ile Pro Gly Thr Thr Val Gly Val Leu Ser Met Asp Ser Ser
                350                 355                 360

AAT GTC CTC CAG CTC ATT GTT GAT GCT TAT GGG AAA ATC CGT TCT AAA           1156
Asn Val Leu Gln Leu Ile Val Asp Ala Tyr Gly Lys Ile Arg Ser Lys
365                 370                 375                 380

GTA GAG CTG GAA GTG CGT GAC CTC CCT GAA GAG TTG TCT CTA TCC TTC           1204
Val Glu Leu Glu Val Arg Asp Leu Pro Glu Glu Leu Ser Leu Ser Phe
                385                 390                 395

AAT GCC ACC TGC CTC AAC AAT GAG GTC ATC CCT GGC CTC AAG TCT TGT           1252
Asn Ala Thr Cys Leu Asn Asn Glu Val Ile Pro Gly Leu Lys Ser Cys
            400                 405                 410

ATG GGA CTC AAG ATT GGA GAC ACG GTG AGC TTC AGC ATT GAG GCC AAG           1300
Met Gly Leu Lys Ile Gly Asp Thr Val Ser Phe Ser Ile Glu Ala Lys
            415                 420                 425

GTG CGA GGC TGT CCC CAG GAG AAG GAG AAG TCC TTT ACC ATA AAG CCC           1348
Val Arg Gly Cys Pro Gln Glu Lys Glu Lys Ser Phe Thr Ile Lys Pro
        430                 435                 440

GTG GGC TTC AAG GAC AGC CTG ATC GTC CAG GTC ACC TTT GAT TGT GAC           1396
Val Gly Phe Lys Asp Ser Leu Ile Val Gln Val Thr Phe Asp Cys Asp
445                 450                 455                 460

TGT GCC TGC CAG GCC CAA GCT GAA CCT AAT AGC CAT CGC TGC AAC AAT           1444
Cys Ala Cys Gln Ala Gln Ala Glu Pro Asn Ser His Arg Cys Asn Asn
                465                 470                 475

GGC AAT GGG ACC TTT GAG TGT GGG GTA TGC CGT TGT GGG CCT GGC TGG           1492
Gly Asn Gly Thr Phe Glu Cys Gly Val Cys Arg Cys Gly Pro Gly Trp
            480                 485                 490

CTG GGA TCC CAG TGT GAG TGC TCA GAG GAG GAC TAT CGC CCT TCC CAG           1540
Leu Gly Ser Gln Cys Glu Cys Ser Glu Glu Asp Tyr Arg Pro Ser Gln
            495                 500                 505

CAG GAC GAA TGC AGC CCC CGG GAG GGT CAG CCC GTC TGC AGC CAG CGG           1588
Gln Asp Glu Cys Ser Pro Arg Glu Gly Gln Pro Val Cys Ser Gln Arg
        510                 515                 520

GGC GAG TGC CTC TGT GGT CAA TGT GTC TGC CAC AGC AGT GAC TTT GGC           1636
Gly Glu Cys Leu Cys Gly Gln Cys Val Cys His Ser Ser Asp Phe Gly
525                 530                 535                 540

AAG ATC ACG GGC AAG TAC TGC GAG TGT GAC GAC TTC TCC TGT GTC CGC           1684
Lys Ile Thr Gly Lys Tyr Cys Glu Cys Asp Asp Phe Ser Cys Val Arg
                545                 550                 555

TAC AAG GGG GAG ATG TGC TCA GGC CAT GGC CAG TGC AGC TGT GGG GAC           1732
Tyr Lys Gly Glu Met Cys Ser Gly His Gly Gln Cys Ser Cys Gly Asp
            560                 565                 570
```

-continued

```
TGC CTG TGT GAC TCC GAC TGG ACC GGC TAC TAC TGC AAC TGT ACC ACG         1780
Cys Leu Cys Asp Ser Asp Trp Thr Gly Tyr Tyr Cys Asn Cys Thr Thr
        575                 580                 585

CGT ACT GAC ACC TGC ATG TCC AGC AAT GGG CTG CTG TGC AGC GGC CGC         1828
Arg Thr Asp Thr Cys Met Ser Ser Asn Gly Leu Leu Cys Ser Gly Arg
        590                 595                 600

GGC AAG TGT GAA TGT GGC AGC TGT GTC TGT ATC CAG CCG GGC TCC TAT         1876
Gly Lys Cys Glu Cys Gly Ser Cys Val Cys Ile Gln Pro Gly Ser Tyr
605                 610                 615                 620

GGG GAC ACC TGT GAG AAG TGC CCC ACC TGC CCA GAT GCC TGC ACC TTT         1924
Gly Asp Thr Cys Glu Lys Cys Pro Thr Cys Pro Asp Ala Cys Thr Phe
            625                 630                 635

AAG AAA GAA TGT GTG GAG TGT AAG AAG TTT GAC CGG GAG CCC TAC ATG         1972
Lys Lys Glu Cys Val Glu Cys Lys Lys Phe Asp Arg Glu Pro Tyr Met
                640                 645                 650

ACC GAA AAT ACC TGC AAC CGT TAC TGC CGT GAC GAG ATT GAG TCA GTG         2020
Thr Glu Asn Thr Cys Asn Arg Tyr Cys Arg Asp Glu Ile Glu Ser Val
                    655                 660                 665

AAA GAG CTT AAG GAC ACT GGC AAG GAT GCA GTG AAT TGT ACC TAT AAG         2068
Lys Glu Leu Lys Asp Thr Gly Lys Asp Ala Val Asn Cys Thr Tyr Lys
670                 675                 680

AAT GAG GAT GAC TGT GTC GTC AGA TTC CAG TAC TAT GAA GAT TCT AGT         2116
Asn Glu Asp Asp Cys Val Val Arg Phe Gln Tyr Tyr Glu Asp Ser Ser
685                 690                 695                 700

GGA AAG TCC ATC CTG TAT GTG GTA GAA GAG CCA GAG TGT CCC AAG GGC         2164
Gly Lys Ser Ile Leu Tyr Val Val Glu Glu Pro Glu Cys Pro Lys Gly
            705                 710                 715

CCT GAC ATC CTG GTG GTC CTG CTC TCA GTG ATG GGG GCC ATT CTG CTC         2212
Pro Asp Ile Leu Val Val Leu Leu Ser Val Met Gly Ala Ile Leu Leu
                720                 725                 730

ATT GGC CTT GCC GCC CTG CTC ATC TGG AAA CTC CTC ATC ACC ATC CAC         2260
Ile Gly Leu Ala Ala Leu Leu Ile Trp Lys Leu Leu Ile Thr Ile His
                    735                 740                 745

GAC CGA AAA GAA TTC GCT AAA TTT GAG GAA GAA CGC GCC AGA GCA AAA         2308
Asp Arg Lys Glu Phe Ala Lys Phe Glu Glu Glu Arg Ala Arg Ala Lys
750                 755                 760

TGG GAC ACA GCC AAC AAC CCA CTG TAT AAA GAG GCC ACG TCT ACC TTC         2356
Trp Asp Thr Ala Asn Asn Pro Leu Tyr Lys Glu Ala Thr Ser Thr Phe
765                 770                 775                 780

ACC AAT ATC ACG TAC CGG GGC ACT TAATGATAAG CAGTCATCCT CAGATCATTA       2410
Thr Asn Ile Thr Tyr Arg Gly Thr
                785

TCAGCCTGTG CCACGATTGC AGGAGTCCCT GCCATCATGT TTACAGAGGA CAGTATTTGT       2470

GGGGAGGGAT TTGGGCTCA GAGTGGGGTA GGTTGGGAGA ATGTCAGTAT GTGGAAGTGT        2530

GGGTCTGTGT GTGTGTATGT GGGGGTCTGT GTGTTTATGT GTGTGTGTTG TGTGTGGGAG       2590

TGTGTAATTT AAAATTGTGA TGTGTCCTGA TAAGCTGAGC TCCTTAGCCT TTGTCCCAGA       2650

ATGCCTCCTG CAGGGATTCT TCCTGCTTAG CTTGAGGGTG ACTATGGAGC TGAGCAGGTG       2710

TTCTTCATTA CCTCAGTGAG AAGCCAGCTT TCCTCATCAG GCCATTGTCC CTGAAGAGAA       2770

GGGCAGGGCT GAGGCCTCTC ATTCCAGAGG AAGGGACACC AAGCCTTGGC TCTACCCTGA       2830

GTTCATAAAT TTATGGTTCT CAGGCCTGAC TCTCAGCAGC TATGGTAGGA ACTGCTGGGC       2890

TTGGCAGCCC GGGTCATCTG TACCTCTGCC TCCTTTCCCC TCCCTCAGGC CGAAGGAGGA      2950

GTCAGGGAGA GCTGAACTAT TAGAGCTGCC TGTGCCTTTT GCCATCCCCT CAACCCAGCT       3010

ATGGTTCTCT CGCAAGGGAA GTCCTTGCAA GCTAATTCTT TGACCTGTTG GGAGTGAGGA       3070

TGTCTGGGCC ACTCAGGGGT CATTCATGGC CTGGGGGATG TACCAGCATC TCCCAGTTCA       3130
```

```
TAATCACAAC CCTTCAGATT TGCCTTATTG GCAGCTCTAC TCTGGAGGTT TGTTTAGAAG      3190

AAGTGTGTCA CCCTTAGGCC AGCACCATCT CTTTACCTCC TAATTCCACA CCCTCACTGC      3250

TGTAGACATT TGCTATGAGC TGGGGATGTC TCTCATGACC AAATGCTTTT CCTCAAAGGG      3310

AGAGAGTGCT ATTGTAGAGC CAGAGGTCTG GCCCTATGCT TCCGGCCTCC TGTCCCTCAT      3370

CCATAGCACC TCCACATACC TGGCCCTGAG CCTTGGTGTG CTGTATCCAT CCATGGGGCT      3430

GATTGTATTT ACCTTCTACC TCTTGGCTGC CTTGTGAAGG AATTATTCCC ATGAGTTGGC      3490

TGGGAATAAG TGCCAGGATG GAATGATGGG TCAGTTGTAT CAGCACGTGT GGCCTGTTCT      3550

TCTATGGGTT GGACAACCTC ATTTTAACTC AGTCTTTAAT CTGAGAGGCC ACAGTGCAAT      3610

TTTATTTTAT TTTTCTCATG ATGAGGTTTT CTTAACTTAA AAGAACATGT ATATAAACAT      3670

GCTTGCATTA TATTTGTAAA TTTATGTGTA TGGCAAAGAA GGAGAGCATA GGAAACCACA      3730

CAGACTTGGG CAGGGTACAG ACACTCCCAC TTGGCATCAT TCACAGCAAG TCACTGGCCA      3790

GTGGCTGGAT CTGTGAGGGG CTCTCTCATG ATAGAAGGCT ATGGGGATAG ATGTGTGGAC      3850

ACATTGGACC TTTCCTGAGG AAGAGGGACT GTTCTTTTGT CCCAGAAAAG CAGTGGCTCC      3910

ATTGGTGTTG ACATACATCC AACATTAAAA GCCACCCCCA AATGCCCAAG AAAAAAAGAA      3970

AGACTTATCA ACATTTGTTC CATGAGG                                         3997

(2) INFORMATION FOR SEQ ID NO:44:

(i) SEQUENCE CHARACTERISTICS:
        (A) LENGTH: 788 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:44:

Met Arg Ala Arg Pro Arg Pro Arg Pro Leu Trp Ala Thr Val Leu Ala
1               5                   10                  15

Leu Gly Ala Leu Ala Gly Val Gly Val Gly Gly Pro Asn Ile Cys Thr
            20                  25                  30

Thr Arg Gly Val Ser Ser Cys Gln Gln Cys Leu Ala Val Ser Pro Met
        35                  40                  45

Cys Ala Trp Cys Ser Asp Glu Ala Leu Pro Leu Gly Ser Pro Arg Cys
    50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
    130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
                165                 170                 175
```

```
Ile Gly Phe Gly Ala Phe Val Asp Lys Pro Val Ser Pro Tyr Met Tyr
            180                 185                 190

Ile Ser Pro Pro Glu Ala Leu Glu Asn Pro Cys Tyr Asp Met Lys Thr
            195                 200                 205

Thr Cys Leu Pro Met Phe Gly Tyr Lys His Val Leu Thr Leu Thr Asp
            210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
                245                 250                 255

Val Cys Asp Glu Lys Ile Gly Trp Arg Asn Asp Ala Ser His Leu Leu
            260                 265                 270

Val Phe Thr Thr Asp Ala Lys Thr His Ile Ala Leu Asp Gly Arg Leu
            275                 280                 285

Ala Gly Ile Val Gln Pro Asn Asp Gly Gln Cys His Val Gly Ser Asp
            290                 295                 300

Asn His Tyr Ser Ala Ser Thr Thr Met Asp Tyr Pro Ser Leu Gly Leu
305                 310                 315                 320

Met Thr Glu Lys Leu Ser Gln Lys Asn Ile Asn Leu Ile Phe Ala Val
                325                 330                 335

Thr Glu Asn Val Val Asn Leu Tyr Gln Asn Tyr Ser Glu Leu Ile Pro
            340                 345                 350

Gly Thr Thr Val Gly Val Leu Ser Met Asp Ser Ser Asn Val Leu Gln
            355                 360                 365

Leu Ile Val Asp Ala Tyr Gly Lys Ile Arg Ser Lys Val Glu Leu Glu
370                 375                 380

Val Arg Asp Leu Pro Glu Glu Leu Ser Leu Ser Phe Asn Ala Thr Cys
385                 390                 395                 400

Leu Asn Asn Glu Val Ile Pro Gly Leu Lys Ser Cys Met Gly Leu Lys
                405                 410                 415

Ile Gly Asp Thr Val Ser Phe Ser Ile Glu Ala Lys Val Arg Gly Cys
            420                 425                 430

Pro Gln Glu Lys Glu Lys Ser Phe Thr Ile Lys Pro Val Gly Phe Lys
            435                 440                 445

Asp Ser Leu Ile Val Gln Val Thr Phe Asp Cys Asp Cys Ala Cys Gln
450                 455                 460

Ala Gln Ala Glu Pro Asn Ser His Arg Cys Asn Asn Gly Asn Gly Thr
465                 470                 475                 480

Phe Glu Cys Gly Val Cys Arg Cys Gly Pro Gly Trp Leu Gly Ser Gln
                485                 490                 495

Cys Glu Cys Ser Glu Glu Asp Tyr Arg Pro Ser Gln Gln Asp Glu Cys
            500                 505                 510

Ser Pro Arg Glu Gly Gln Pro Val Cys Ser Gln Arg Gly Glu Cys Leu
            515                 520                 525

Cys Gly Gln Cys Val Cys His Ser Ser Asp Phe Gly Lys Ile Thr Gly
            530                 535                 540

Lys Tyr Cys Glu Cys Asp Asp Phe Ser Cys Val Arg Tyr Lys Gly Glu
545                 550                 555                 560

Met Cys Ser Gly His Gly Gln Cys Ser Cys Gly Asp Cys Leu Cys Asp
                565                 570                 575

Ser Asp Trp Thr Gly Tyr Tyr Cys Asn Cys Thr Thr Arg Thr Asp Thr
            580                 585                 590

Cys Met Ser Ser Asn Gly Leu Leu Cys Ser Gly Arg Gly Lys Cys Glu
```

```
                595                 600                      605
Cys Gly Ser Cys Val Cys Ile Gln Pro Gly Ser Tyr Gly Asp Thr Cys
            610             615                 620

Glu Lys Cys Pro Thr Cys Pro Asp Ala Cys Thr Phe Lys Lys Glu Cys
625                 630                 635                 640

Val Glu Cys Lys Lys Phe Asp Arg Glu Pro Tyr Met Thr Glu Asn Thr
                645                 650                 655

Cys Asn Arg Tyr Cys Arg Asp Glu Ile Glu Ser Val Lys Glu Leu Lys
                660                 665                 670

Asp Thr Gly Lys Asp Ala Val Asn Cys Thr Tyr Lys Asn Glu Asp Asp
            675                 680                 685

Cys Val Val Arg Phe Gln Tyr Tyr Glu Asp Ser Ser Gly Lys Ser Ile
690                 695                 700

Leu Tyr Val Val Glu Glu Pro Glu Cys Pro Lys Gly Pro Asp Ile Leu
705                 710                 715                 720

Val Val Leu Leu Ser Val Met Gly Ala Ile Leu Leu Ile Gly Leu Ala
                725                 730                 735

Ala Leu Leu Ile Trp Lys Leu Leu Ile Thr Ile His Asp Arg Lys Glu
            740                 745                 750

Phe Ala Lys Phe Glu Glu Glu Arg Ala Arg Ala Lys Trp Asp Thr Ala
            755                 760                 765

Asn Asn Pro Leu Tyr Lys Glu Ala Thr Ser Thr Phe Thr Asn Ile Thr
770                 775                 780

Tyr Arg Gly Thr
785
```

(2) INFORMATION FOR SEQ ID NO:45:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:45:

```
CTGCAGGTAA ATGAAGAAGG CAGTGAAGCA GCTGCAAGTA CCGCTGTTGT GATTGCTGGC      60

CGTTCGCTAA ACCCCAACAG GGTGACTTTC AAGGCCAACA GGCCTTTCCT GGTTTTTATA     120

AGAGAAGTTC CTCTGAACAC TATTATCTTC ATGGGCAGAG TAGCCAACCC TTGTGTTAAG     180

TAAAATGTTC TTATTCTTTG CACCTCTTCC TATTTTTGGT TTGTGAACAG AAGTAAAA      238
```

(2) INFORMATION FOR SEQ ID NO:46:

(i) SEQUENCE CHARACTERISTICS:
        (A) LENGTH: 623 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:46:

```
AAAACTCAGG AAGAAACAAA CCCACCAATC GTTCCAGGCA TATCTCAAAT GCAAAAGGCA      60

TCCATTGTGA GTACAGTGGG CTTTCATGTT CTGCGCTGGT CCAGGGAGGT GCTCATAGCT     120

ACTTCCTCAC ATGTGCTCTG GGGCCAGCAA ATCATCTGTA TACCCTGACC TTGGCCCCCG     180

TGTACCCCCA GGTCGGCTTC TTCAAGCGGA ACCGGCACAC CCTGGAAGAA GATGATGAAG     240
```

-continued

```
AGGGGGAGTG ATGGTGCAGC CTACACTATT CTAGCAGGAG GGTTGGGCGT GCTACCTGCA      300

CCGCCCCTTC TCCAACAAGT TGCCTCCAAG CTTTGGGTTG GAGCTGTTCC ATTGGGTCCT      360

CTTGGTGTCG TTTCCCTCCC AACAGAGCTG GGCTACCCCC CCTCCTGCTG CCTAATAAAG      420

AGACTGAGCC CTGATGCTGA GCATGCTGCC TCCTTTTGGG GCCAGAGAAG AGAGTACCGA      480

AGAATGTTTT GGACGGGGAC CTAGGGCTGG TGGAAGTATG AACGAGAGAG TCACTGCCAG      540

GGCGAAGTTT GCAAATCACT GTCTTTGGGG AGTGTCAGGG AGTACAGAGT TGGGGTGGTA      600

GGTGTAACAG AAGACGGAGA GCC                                             623
```

(2) INFORMATION FOR SEQ ID NO:47:

(i) SEQUENCE CHARACTERISTICS:
        (A) LENGTH: 1787 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 131...1609
        (D) OTHER INFORMATION:

(xi) SEQUENCE DESCRIPTION: SEQ ID NO:47:

```
GTGAATCTCT GGGGCCAGGA AGACCCTGCT GCCCGGAAGA GCCTCATGTT CCGTGGGGGC       60

TGGGCGGACA TACATATACG GGCTCCAGGC TGAACGGCTC GGGCCACTTA CACACCACTG      120

CCTGATAACC  ATG CTG GCT GCC ACA GTC CTG ACC CTG GCC CTG CTG GGC       169
            Met Leu Ala Ala Thr Val Leu Thr Leu Ala Leu Leu Gly
              1               5                  10

AAT GCC CAT GCC TGC TCC AAA GGC ACC TCG CAC GAG GCA GGC ATC GTG       217
Asn Ala His Ala Cys Ser Lys Gly Thr Ser His Glu Ala Gly Ile Val
         15                  20                  25

TGC CGC ATC ACC AAG CCT GCC CTC CTG GTG TTG AAC CAC GAG ACT GCC       265
Cys Arg Ile Thr Lys Pro Ala Leu Leu Val Leu Asn His Glu Thr Ala
 30                  35                  40                  45

AAG GTG ATC CAG ACC GCC TTC CAG CGA GCC AGC TAC CCA GAT ATC ACG       313
Lys Val Ile Gln Thr Ala Phe Gln Arg Ala Ser Tyr Pro Asp Ile Thr
                 50                  55                  60

GGC GAG AAG GCC ATG ATG CTC CTT GGC CAA GTC AAG TAT GGG TTG CAC       361
Gly Glu Lys Ala Met Met Leu Leu Gly Gln Val Lys Tyr Gly Leu His
             65                  70                  75

AAC ATC CAG ATC AGC CAC TTG TCC ATC GCC AGC AGC CAG GTG GAG CTG       409
Asn Ile Gln Ile Ser His Leu Ser Ile Ala Ser Ser Gln Val Glu Leu
         80                  85                  90

GTG GAA GCC AAG TCC ATT GAT GTC TCC ATT CAG AAC GTG TCT GTG GTC       457
Val Glu Ala Lys Ser Ile Asp Val Ser Ile Gln Asn Val Ser Val Val
     95                 100                 105

TTC AAG GGG ACC CTG AAG TAT GGC TAC ACC ACT GCC TGG TGG CTG GGT       505
Phe Lys Gly Thr Leu Lys Tyr Gly Tyr Thr Thr Ala Trp Trp Leu Gly
110                 115                 120                 125

ATT GAT CAG TCC ATT GAC TTC GAG ATC GAC TCT GCC ATT GAC CTC CAG       553
Ile Asp Gln Ser Ile Asp Phe Glu Ile Asp Ser Ala Ile Asp Leu Gln
                130                 135                 140

ATC AAC ACA CAG CTG ACC TGT GAC TCT GGT AGA GTG CGG ACC GAT GCC       601
Ile Asn Thr Gln Leu Thr Cys Asp Ser Gly Arg Val Arg Thr Asp Ala
            145                 150                 155

CCT GAC TGC TAC CTG TCT TTC CAT AAG CTG CTC CTG CAT CTC CAA GGG       649
Pro Asp Cys Tyr Leu Ser Phe His Lys Leu Leu Leu His Leu Gln Gly
```

|  |  |
|---|---|
| GAG CGA GAG CCT GGG TGG ATC AAG CAG CTG TTC ACA AAT TTC ATC TCC<br>Glu Arg Glu Pro Gly Trp Ile Lys Gln Leu Phe Thr Asn Phe Ile Ser<br>175                         180                        185 | 697 |
| TTC ACC CTG AAG CTG GTC CTG AAG GGA CAG ATC TGC AAA GAG ATC AAC<br>Phe Thr Leu Lys Leu Val Leu Lys Gly Gln Ile Cys Lys Glu Ile Asn<br>190                        195                       200                       205 | 745 |
| GTC ATC TCT AAC ATC ATG GCC GAT TTT GTC CAG ACA AGG GCT GCC AGC<br>Val Ile Ser Asn Ile Met Ala Asp Phe Val Gln Thr Arg Ala Ala Ser<br>                      210                       215                       220 | 793 |
| ATC CTT TCA GAT GGA GAC ATT GGG GTG GAC ATT TCC CTG ACA GGT GAT<br>Ile Leu Ser Asp Gly Asp Ile Gly Val Asp Ile Ser Leu Thr Gly Asp<br>           225                       230                       235 | 841 |
| CCC GTC ATC ACA GCC TCC TAC CTG GAG TCC CAT CAC AAG GGT CAT TTC<br>Pro Val Ile Thr Ala Ser Tyr Leu Glu Ser His His Lys Gly His Phe<br>              240                       245                       250 | 889 |
| ATC TAC AAG AAT GTC TCA GAG GAC CTC CCC CTC CCC ACC TTC TCG CCC<br>Ile Tyr Lys Asn Val Ser Glu Asp Leu Pro Leu Pro Thr Phe Ser Pro<br>255                         260                       265 | 937 |
| ACA CTG CTG GGG GAC TCC CGC ATG CTG TAC TTC TGG TTC TCT GAG CGA<br>Thr Leu Leu Gly Asp Ser Arg Met Leu Tyr Phe Trp Phe Ser Glu Arg<br>270                       275                       280                       285 | 985 |
| GTC TTC CAC TCG CTG GCC AAG GTA GCT TTC CAG GAT GGC CGC CTC ATG<br>Val Phe His Ser Leu Ala Lys Val Ala Phe Gln Asp Gly Arg Leu Met<br>              290                       295                       300 | 1033 |
| CTC AGC CTG ATG GGA GAC GAG TTC AAG GCA GTG CTG GAG ACC TGG GGC<br>Leu Ser Leu Met Gly Asp Glu Phe Lys Ala Val Leu Glu Thr Trp Gly<br>                  305                       310                       315 | 1081 |
| TTC AAC ACC AAC CAG GAA ATC TTC CAA GAG GTT GTC GGC GGC TTC CCC<br>Phe Asn Thr Asn Gln Glu Ile Phe Gln Glu Val Val Gly Gly Phe Pro<br>                     320                       325                       330 | 1129 |
| AGC CAG GCC CAA GTC ACC GTC CAC TGC CTC AAG ATG CCC AAG ATC TCC<br>Ser Gln Ala Gln Val Thr Val His Cys Leu Lys Met Pro Lys Ile Ser<br>335                         340                       345 | 1177 |
| TGC CAA AAC AAG GGA GTC GTG GTC AAT TCT TCA GTG ATG GTG AAA TTC<br>Cys Gln Asn Lys Gly Val Val Val Asn Ser Ser Val Met Val Lys Phe<br>350                         355                       360                       365 | 1225 |
| CTC TTT CCA CGC CCA GAC CAG CAA CAT TCT GTA GCT TAC ACA TTT GAA<br>Leu Phe Pro Arg Pro Asp Gln Gln His Ser Val Ala Tyr Thr Phe Glu<br>                     370                       375                       380 | 1273 |
| GAG GAT ATC GTG ACT ACC GTC CAG GCC TCC TAT TCT AAG AAA AAG CTC<br>Glu Asp Ile Val Thr Thr Val Gln Ala Ser Tyr Ser Lys Lys Lys Leu<br>                  385                       390                       395 | 1321 |
| TTC TTA AGC CTC TTG GAT TTC CAG ATT ACA CCA AAG ACT GTT TCC AAC<br>Phe Leu Ser Leu Leu Asp Phe Gln Ile Thr Pro Lys Thr Val Ser Asn<br>                     400                       405                       410 | 1369 |
| TTG ACT GAG AGC AGC TCC GAG TCC ATC CAG AGC TTC CTG CAG TCA ATG<br>Leu Thr Glu Ser Ser Ser Glu Ser Ile Gln Ser Phe Leu Gln Ser Met<br>415                         420                       425 | 1417 |
| ATC ACC GCT GTG GGC ATC CCT GAG GTC ATG TCT CGG CTC GAG GTA GTG<br>Ile Thr Ala Val Gly Ile Pro Glu Val Met Ser Arg Leu Glu Val Val<br>430                         435                       440                       445 | 1465 |
| TTT ACA GCC CTC ATG AAC AGC AAA GGC GTG AGC CTC TTC GAC ATC ATC<br>Phe Thr Ala Leu Met Asn Ser Lys Gly Val Ser Leu Phe Asp Ile Ile<br>              450                       455                       460 | 1513 |
| AAC CCT GAG ATT ATC ACT CGA GAT GGC TTC CTG CTG CTG CAG ATG GAC<br>Asn Pro Glu Ile Ile Thr Arg Asp Gly Phe Leu Leu Leu Gln Met Asp<br>                  465                       470                       475 | 1561 |
| TTT GGC TTC CCT GAG CAC CTG CTG GTG GAT TTC CTC CAG AGC TTG AGC | 1609 |

```
Phe Gly Phe Pro Glu His Leu Leu Val Asp Phe Leu Gln Ser Leu Ser
            480                 485                 490

TAGAAGTCTC CAAGGAGGTC GGGATGGGGC TTGTAGCAGA AGGCAAGCAC CAGGCTCACA    1669

GCTGGAACCC TGGTGTCTCC TCCAGCGTGG TGGAAGTTGG GTTAGGAGTA CGGAGATGGA    1729

GATTGGCTCC CAACTCCTCC CTATCCTAAA GGCCCACTGG CATTAAAGTG CTGTATCC     1787

(2) INFORMATION FOR SEQ ID NO:48:

(i) SEQUENCE CHARACTERISTICS:
        (A) LENGTH: 493 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:48:

Met Leu Ala Ala Thr Val Leu Thr Leu Ala Leu Leu Gly Asn Ala His
 1               5                  10                  15

Ala Cys Ser Lys Gly Thr Ser His Glu Ala Gly Ile Val Cys Arg Ile
            20                  25                  30

Thr Lys Pro Ala Leu Leu Val Leu Asn His Glu Thr Ala Lys Val Ile
        35                  40                  45

Gln Thr Ala Phe Gln Arg Ala Ser Tyr Pro Asp Ile Thr Gly Glu Lys
50                  55                  60

Ala Met Met Leu Leu Gly Gln Val Lys Tyr Gly Leu His Asn Ile Gln
65                  70                  75                  80

Ile Ser His Leu Ser Ile Ala Ser Ser Gln Val Glu Leu Val Glu Ala
                85                  90                  95

Lys Ser Ile Asp Val Ser Ile Gln Asn Val Ser Val Val Phe Lys Gly
            100                 105                 110

Thr Leu Lys Tyr Gly Tyr Thr Thr Ala Trp Trp Leu Gly Ile Asp Gln
        115                 120                 125

Ser Ile Asp Phe Glu Ile Asp Ser Ala Ile Asp Leu Gln Ile Asn Thr
130                 135                 140

Gln Leu Thr Cys Asp Ser Gly Arg Val Arg Thr Asp Ala Pro Asp Cys
145                 150                 155                 160

Tyr Leu Ser Phe His Lys Leu Leu His Leu Gln Gly Glu Arg Glu
                165                 170                 175

Pro Gly Trp Ile Lys Gln Leu Phe Thr Asn Phe Ile Ser Phe Thr Leu
            180                 185                 190

Lys Leu Val Leu Lys Gly Gln Ile Cys Lys Glu Ile Asn Val Ile Ser
        195                 200                 205

Asn Ile Met Ala Asp Phe Val Gln Thr Arg Ala Ala Ser Ile Leu Ser
210                 215                 220

Asp Gly Asp Ile Gly Val Asp Ile Ser Leu Thr Gly Asp Pro Val Ile
225                 230                 235                 240

Thr Ala Ser Tyr Leu Glu Ser His His Lys Gly His Phe Ile Tyr Lys
                245                 250                 255

Asn Val Ser Glu Asp Leu Pro Leu Pro Thr Phe Ser Pro Thr Leu Leu
            260                 265                 270

Gly Asp Ser Arg Met Leu Tyr Phe Trp Phe Ser Glu Arg Val Phe His
        275                 280                 285

Ser Leu Ala Lys Val Ala Phe Gln Asp Gly Arg Leu Met Leu Ser Leu
```

```
                     290                 295                 300
Met Gly Asp Glu Phe Lys Ala Val Leu Glu Thr Trp Gly Phe Asn Thr
305                 310                 315                 320

Asn Gln Glu Ile Phe Gln Glu Val Val Gly Gly Phe Pro Ser Gln Ala
                325                 330                 335

Gln Val Thr Val His Cys Leu Lys Met Pro Lys Ile Ser Cys Gln Asn
                340                 345                 350

Lys Gly Val Val Asn Ser Ser Val Met Val Lys Phe Leu Phe Pro
            355                 360                 365

Arg Pro Asp Gln Gln His Ser Val Ala Tyr Thr Phe Glu Glu Asp Ile
        370                 375                 380

Val Thr Thr Val Gln Ala Ser Tyr Ser Lys Lys Lys Leu Phe Leu Ser
385                 390                 395                 400

Leu Leu Asp Phe Gln Ile Thr Pro Lys Thr Val Ser Asn Leu Thr Glu
                405                 410                 415

Ser Ser Ser Glu Ser Ile Gln Ser Phe Leu Gln Ser Met Ile Thr Ala
                420                 425                 430

Val Gly Ile Pro Glu Val Met Ser Arg Leu Glu Val Val Phe Thr Ala
            435                 440                 445

Leu Met Asn Ser Lys Gly Val Ser Leu Phe Asp Ile Ile Asn Pro Glu
        450                 455                 460

Ile Ile Thr Arg Asp Gly Phe Leu Leu Leu Gln Met Asp Phe Gly Phe
465                 470                 475                 480

Pro Glu His Leu Leu Val Asp Phe Leu Gln Ser Leu Ser
                485                 490

(2) INFORMATION FOR SEQ ID NO:49:

(i) SEQUENCE CHARACTERISTICS:
        (A) LENGTH: 13204 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:49:

CTGCAGGTCA ACGGATCTGC TAGGGTCCTC CTATCAGCAC ACACACTCCA GCCCCACTTT      60

AGAGGTACCC GCTACCTTCC CTCATTAAAA CCAGCTCTCA AGAGGGGATC TGGTAACAGT     120

CTAGGCAGGC ATTCCAGGGA GCATGTGAAC CGCTGGTTCT TGTTGCGGGT GGAGGATGGA     180

GGTGTTGTAC AGAGTTTAGG TCTTTTTCAG CAAAGATCTC CAAACCCCGG GTGTTCAAAA     240

TCAAACCAAA GGGGATTATA GTCCCAGCTC TACTCACAAC TCACTGGTTA CTTTAGCCAC     300

GAGATTGCCC TCGCTGAGAG TCGGTTTCAC TGTCCATAAG ATGAAGAAGT ACATCACGGT     360

GGTCTGTGAG GTGTCATTGA GGAAAGATGG TCCAGTGCCC CCATGCCACA TGGCCTTCGG     420

GCAGTGCTCC CAGCGCCGGC GCCAGGGCCT GGGATACGCT GGAATCTGCG CGGCGCTCAC     480

CCAGCTTTCC TATGCAGAGT GGCCATCGTG GTGGGCGCCC CGCGGACCCT GGGCCCCAGC     540

CAGGAGGAGA CGGGCGGCGT GTTCCTGTGC CCCTGGAGGG CCGAGGGCGG CCAGTGCCCC     600

TCGCTGCTCT TTGACCTCCG TGAGTCCCAG GCAAGGAGAG CAAGGTTGGG GTCAGAGGGA     660

CGTGGACTGC CCGGGCTTCA GCGCCCCACC CCTTCTTGTG CCTTCCAGGT GATGAGACCC     720

GAAATGTAGG CTCCCAAACT TTACAAACCT TCAAGGCCCG CCAAGGACTG GGGGCGTCGG     780

TCGTCAGCTG GAGCGACGTC ATTGTGGTGG GCCCCGCGGT ACAGGGCACA GGGAACAATC     840
```

```
                                          -continued

GGGGGCAGGG ACACTGGGGC CAGGAGGAGC CCAAGTCTCG CGCCCCGTCC CCATCTGTGG     900

CCCTTTCTCA GGCCTGCGCC CCCTGGCAGC ACTGGAACGT CCTAGAAAAG ACTGAGGAGG     960

CTGAGAAGAC GCCCGTAGGT AGCTGCTTTT TGGCTCAGCC AGAGAGCGGC CGCCGCGCCG    1020

AGTACTCCCC CTGTCGCGGG AACACCCTGA GCCGCATTTA CGTGGAAAAT GATTTTAGTA    1080

AGCGCCAGCT ACGACCTGGC CCCGCCCACT CGCGACGGCT TGGCCCCGCC CCCCATCGGA    1140

TCCCGCCCCC AGCGCCGCAG CCCTTGCTTT GGATCTGGCC TCGCCCCAGG GCCCCGCCGA    1200

CTCAAGGCCC CGCCCCTGTC CCCCAGCCCT CCTCCGGGCT CGCGCGCGCC TCCCTTCACC    1260

CCTGGGCTGA CCCCTCCTCC TTGTCTCCTC AGGCTGGGAC AAGCGTTACT GTGAAGCGGG    1320

CTTCAGCTCC GTGGTCACTC AGGCGAGTAG GGAGCAAAAG CGCAGTGGGG GCGGCTCCCA    1380

AACAGGGCCC CCTCTCACCC TCAGGACTTC CCTTCCAGGC CGGAGAGCTG GTGCTTGGGG    1440

CTCCTGGCGG CTATTATTTC TTAGGTACGT GCCCATCCGT ACACCTCCCT CCCTTCTCGC    1500

GGCCGAAGGA GACCGCTTTG GCTTCACAC CCGCTGTCCC TCCCGCCCTA GGTCTCCTGG     1560

CCCAGGCTCC AGTTGCGGAT ATTTTCTCGA GTTACCGCCC AGGCATCCTT TTGTGGCACG    1620

TGTCCTCCCA GAGCCTCTCC TTTGACTCCA GCAACCCAGA GTACTTCGAC GGCTACTGGG    1680

GTAACACCGC CATTCCAGAC TTCCAGCACC CCGAGGGTCA CCGCCCACCG CAGACGGTCA    1740

GGTCCTGCCC CTGTGGGAGC CTCCATGGCC ACCCCTGCCG GCCAACCCAC CGCCTAAGCC    1800

GCTCCCGCCC TCCGCTCCTG CGCTTCCCCG CAGACCGCCC ACCTCCCATG CGCCCACCGC    1860

TCCCTTCCAC TGCGGACTCG TAGCGCAGCC TGGGCAGGG CTTGGCCCCT CGAAGGCCTC     1920

CGTTTTTCCA TCTGCACAAT GCAGGGCTGG GGCTGAGTGG CCTTAATCTC CTCCTTCTTT    1980

GCCCTCCGTC CCCTCTGTGC TTCCTCCCCT GGAAAAGACT AATTTGCGCC CTTGTCCTCA    2040

GGGTACTCGG TGGCCGTGGG CGAGTTCGAC GGGGATCTCA ACACTACAGG CAAGAAATCC    2100

ACTTAGGGCG GGAGTTGGGT AGCCCAGCCC GGGGAGGAGC GCCTTCCTGA AATCTCCCCT    2160

ATGTAGCTGG GTGCAGAACG GGGAGCGGGA AGTGGGTAGG TTCTAAGGCT CTCATTCCCT    2220

GAGCCTGGCT CTCCCTATCG CCAGAATATG TCGTCGTGCC CCCCACTTGG AGCTGGACCC    2280

TGGGAGCGGT AAGTGCCCCC ACCACTGGGC CTCCCGAAGC CCCTTATCCC AGTTCTCAGG    2340

CTGACAACTC CTGAGCGCCC CCCACCCCCG CCCCGCCTCC ACCAAACCAC CCTTTCTCAC    2400

CTGGAGTGGG AGGTTGCTTT GGGTACAAGA ATGATGCTCT CGCCTGCGCT GTCCGTGCAG    2460

GTGGAAATTT TGGATTCCTA CTACCAGAGG CTGCATCGGC TGCGCGGAGA GCAGGTGGGG    2520

GCCAGGTCCC AGTGGGCGTG GCTGGGTGGA GGGGAACTG AGACTTCAGA ATATTTCATG     2580

GGAGGTGAGG GCCCATTTCT TAAAGAGGAT GCTTGTCCAG CGGCGTGAAT GATGGTGCTC    2640

CTCATCTTGC AGATGGCGTC GTATTTTGGG CATTCAGTGG CTGTCACTGA CGTCAACGGG    2700

GATGGGTGAG GAGGGACATG CCCCCACCCC TACCCAGTTG GGTCCCAAAT TACCAGAGCT    2760

GCCCCTCTGT CTCCCTTTCC TAGCCCTAGT CTCACGTATC CACTGGAGGA ACAGGAGAGC    2820

AAGGGTCGAG GAGATTTGGC CCTAGCCCCA ATATACCCCT GGTCCAGTCC CATGTAACCA    2880

CTCATCTGGC CCACAGGAGG CATGATCTGC TGGTGGGCGC TCCACTGTAT ATGGAGAGCC    2940

GGGCAGACCA AAAACTGGCC GAAGTGGGGC GTGTGTATTT GTTCCTGCAG CCGCGAGGCC    3000

CCCACGCGCT GGGTGCCCCC AGCCTCCTGC TGACTGGCAC ACAGCTCTAT GGGCGATTCG    3060

GCTCTGCCAT CGCACCCCTG GGCGACCTCG ACCGGGATGG CTACAATGGT GAGGGAAGAG    3120

AGGAGCCCTA CTTGCTGCAG AGGGGTTAAC AGCCACTCAA AAAGCATGGA GTTGGCCTGA    3180

GGGCAGCCAG AACCAGGATG GGTTTTAAGC ATATAAGTAT GTGGCTTAGA CACATGGGGT    3240
```

```
GCTGAGTGGA GAGCAGATGG GAGAGTTGAA GACTAATTAG GAAGTGTTTG CCTTAATCCA   3300

AGCAAGAGAC AATGACCACC TGGATGTGGA TTTTGGCAGT GGAGTTAGAG ATGGGAGTGA   3360

CTTCACAGAT ATTTAGGACT CGGATTATTA GGACTTGGTG GGAGACTGGA TGTGGGGCCA   3420

GGGGAGAGGT TGGAGTTGGG TGCCTGTGAT GGCCTCCACT GCCTGGAACT CAGGCCGTGC   3480

AGCAGGTGCT GGGGAGAGGC GGGAGATCAG CAGTTCAGCT CTGGACCTGT TGAGCTTGAA   3540

GGGCTTGGGT GCTTTAGGCG GAAATATCCA AGAACAGTT GGGAGTGGCT CTCCCCGCTT    3600

CCACAAGAGA GATCTGAATG GGAGACAGGG GTTTGGGGAA AGTGGATGAG GTCCCGGGAC   3660

CTGTGAAATA AGAGGCCCAG GATAGAGCCC TAGGGAGCAA AAGCATTTAG GTGACTCCTA   3720

CAGGAGGTAA GTCTGAGAAG GAGACAGAGG AGTGTCCAGA GAGGGAGGAG GGAACCCAGG   3780

GGGTCTGATG GCCCGGGACT CAAGGAAGAG CATGCGTTAA AGAGCATGCA CAGGAGGAAG   3840

TGGGCGCTGC AGCTCCTGCT GCTGCTGCAA GATACAATTA GGTGGGGCTG GAGAAATATT   3900

CATGGGCTTT AGCAAGAAGA GGGTGCCAGG CATGGTGGCT CATACCTGTA ATCCCAGCTA   3960

CTTGGGAAAT TGAAGCAGGA GAATCTCTTG AACCCGGGAA GTGGAGGTTG CACTGAGCTG   4020

AGCTTGCGCC ACTACTGCAC TCCAGCCTGG GTGACAGAGC AAGACTCCAT CTCAACAAAA   4080

TAAAAAAAAA AATAGAGAAA GAAAGGAAGA AGAAAAAAG AAGGGGAGGT TATTGGTGAC     4140

AGTGACATAA ATTGATTCAG GCCAAGATAG GGTCAGAAGC CAGAATGCAA TGGGGTAAGG   4200

TATGAATGGA GATGAAAAAT TGGATGCAGC TAATGTAGAC AGCTCTTTCA ACAGGTTTGT   4260

GGTAAAAAGG AATTTGAGGA ATAGAAAGGA AAAAAAAAAA CATGTTTGAC TATAAGAGGA   4320

AAAAGAGAAA AGGTGATCAC AGAAAAGAGA TGAGGGTCAA GGGAAGATTA TTTCAATGTG   4380

GAAGAACATG TAGTAGGTTG AAAATGATGT TGTGGGGAAA TGGGGGGATG AGCCAGCAGA   4440

GAGTCCCTGT GATGCCTCAG GGGGTGGGAG GGTGACTGGC CCAGTGTCAG GGTGAAGGAA   4500

GGAAACCTCT TCCAGGGTCA AATGGGGAAA GGGAAAAAGA AAGTTGGTGT GGGATTATAG   4560

CATAACAGTG GGCTGCCTCT CTTCCTGAAG TAAGAGATTA CGTCACCTGC TGAAGGAAGT   4620

GTGGGGGGTC TGGGAGTTTG ATGGAATGGA GAAGGCTAGA AATAGATGCT AGATGGCCAG   4680

GCACGGTGGC TCACACCTGG AATCCCAGCA CTTTGGGAGG CCGAGGCAGG AGGATCACTG   4740

GAGCCTAGGA GTTTGACACC AGCCTGGCCA ACATAGGGAG ATCTCGTCTC CATAAAAATT   4800

TTTAAAAATT AGCTGGGCAT GGTGGCTATA GTCTCAACTG CTTGGGAAGC TGAGGTGGGA   4860

GGATTGCTTT AGTCCAGAAG GTTGAGGCTG CAGTAAGCCA TGGTTGCACC ACTGCACTTC   4920

AGCCTGAATG ACAAGTGCAA GACTGTCTTA AAATAAAAAA TTTAAAGGGC TTGGGCACGG   4980

TGGCTCACAC CTGTAATCCA GCACTTTGGG AGCCCAAGGT GGGCAGATCA CTTGAGGTCA   5040

GGAGTTCGAG ATCAGCCTGG CCAATGTGGT GAAACCCCGT CTCTACTGAA AATACAAAAA   5100

TTAGCCGGGC ATGGTGGTAG GCGCCTGTAA TCCCAGCTAC TGAAGAGGCT GAGGCACAAG   5160

AATCACTTTA ACGGGGAGG CAGAGGTTGC AGTGAGCCGA GATCGCACCA CTGCACTCCA    5220

GCCAGGACAA CAGAGCGAGA CTCCATCTCA AAAAAAAAA AATTTAGAAA AGGGAATAAT     5280

GATGCTTAAT TTTCAGGATA TATTTTCCTC AATAGACAGT GAGAGTTGTC ACTGTTTTTA   5340

TAACAATCCT ACTTGGCAGG TCCCTCTCCC ACCTGATTGT TAACTCCTGG AGGGTAGGGC   5400

AGTGCCTCCT TCACCCACAC TTTGCACCCC TTTCCTAGTC TCCTGGGATG TTCCCAGAGA   5460

AGCTCAGGAA AGTTTTACAG TCATCTAGGG AGGCTGAATA ACAATCAGCC ACTTCCTTTC   5520

TGTTACTCCT TCCAGACATT GCAGTGGCTG CCCCCTACGG GGGTCCCAGT GGCCGGGGCC   5580
```

```
AAGTGCTGGT GTTCCTGGGT CAGAGTGAGG GGCTGAGGTC ACGTCCCTCC CAGGTCCTGG    5640

ACAGCCCCTT CCCCACAGGC TCTGCCTTTG GCTTCTCCCT TCGAGGTGCC GTAGACATCG    5700

ATGACAACGG ATACCCAGGT GCCCTGGACT GCCTCCAGCT AGAAATGCCC AAGAAAGGCC    5760

CTTGGACATT CGCTGGAAGT GCCAAGAGAC ACGGCCAGGG CTCATGCCTG GCCTGGTGTC    5820

CCACTATGGA CTGCCAGAGG GGCTGGGTGA AACCTCCAGT GGGGGAGGTG GTGTGGGGAA    5880

CCCCTGGGAA GATGAGATGA GGATCCCCAT ACCCTAATCG CCAATTCTGA CCCATTCCTC    5940

GATGTCTATA GACCTGATCG TGGGAGCTTA CGGGGCCAAC CAGGTGGCTG TGTACAGGTG    6000

AGCACTGGCT CCAGGGGCGG GATGGGGAAG GTCCTGTGCC ATCAAGAGGA GGCCAGGCCA    6060

GGAGGAGCCA CAATGGCAAG CCTCCCCATC ACCCTATCCC ATCAGAGCTC AGCCAGTGGT    6120

GAAGGCCTCT GTCCAGCTAC TGGTGCAAGA TTCACTGAAT CCTGCTGTGA AGAGCTGTGT    6180

CCTACCTCAG ACCAAGACAC CCGTGAGCTG GTGAGGAGGC AGAGGGCATG GGCCTTAAAG    6240

GATCTGGGAC CTCAGAAAGG CTCCAACCCC TGAGCCCCAC TTACGTCTTT GCAGCTTCAA    6300

CATCCAGATG TGTGTTGGAG CCACTGGGCA CAACATTCCT CAGAAGCTAT GTGAGTGGCA    6360

TGAAGGGGGC AGGAGGGAGG TGGGCTTGGA CTCCCCCGGA GGCTGGCCAG GGAGGTCCTG    6420

ACTCTTCTGC TTGCCCTGCC AGCCCTAAAT GCCGAGCTGC AGCTGGACCG GCAGAAGCCC    6480

CGCCAGGGCC GGCGGGTGCT GCTGCTGGGC TCTCAACAGG CAGGCACCAC CCTGAACCTG    6540

GATCTGGGCG GAAAGCACAG CCCCATCTGC CACACCACCA TGGCCTTCCT TCGAGTACGC    6600

CCAGGCAGGG GATTGGCAGG GCTGGAGAG TAGAACTTAC CCACTGGACT TGTTCATCTA    6660

GCCCTGGGGC ACTGAGCTGG GTGCTGTGAG TCCGGGGGTG GTCAGGACAC AGGTGCCTAC    6720

TGGCCAGGAG AAGGTGGGAT GTGTATGGTA GCAAGATGGC CTGACTCTTG CCCCTGTCCT    6780

AGGATGAGGC AGACTTCCGG GACAAGCTGA GCCCCATTGT GCTCAGCCTC AATGTGTCCC    6840

TACCGCCCAC GGAGGCTGGA ATGGCCCCTG CTGTCGTGCT GCATGGAGAC ACCCATGTGC    6900

AGGAGCAGGT AGGGACAGGC AGGGACAGGC CAGGGAGGTG CAGGACCCCT GATAGCAAAT    6960

CAGGATTAGG GTTAGTGCCA AGTCACAATG TAACCCCAAA ACCTTGATGT CATTCCAAAC    7020

CCTAATGAAA ACCTCAAAAT CCAGCCAGTC ATGGTGGCTC ACACCTGTAA TCCCAGCACT    7080

TTGGGAGACC GAGGCAGGCA GATTGCCTGA GGTCAGGAGT TAGAGACCAA CCTGGCCAAC    7140

ATGGTGAAAA CCCATCTCTA CTAAAAATAC AAAAAAAATT AGCCGGGTGT GGTGACGCAT    7200

GCCTGTAATT CCAGCTACTC GGGAGGCTGA AGCAGGAGAA TCACTTGAAC CCAGGAGGCA    7260

GAGGTTGCAG TGAGCCAAGA GTGTGCCACA GCACTCCAGC CTGGGTGACA GAGCAAGACT    7320

CTGTCTCAAA AAAAAAAAAA AAAGCCAGGC GCAGTGGCCT CACGCCTGTA ATCCCAGCAC    7380

TTTGGGAGGC CAAGGCGGGT GGATCACGAG GTCAGGAGAT CAAGACCATC CTGGCTAACA    7440

CAGTGAAACC CCGTCTACTA AAAATACAAA AAAAAAAAA AAATTAGCTG GGCGTGGTGG    7500

CGGGTACCTG TAGTCCCAGC TACTTGGGAG GCTGAGGCAG GAGAATGGCG TGAACCCCGG    7560

GGGCGGACGT TGCAGTGAGC CGAGATAGTG CCACTGCACT CCAGCCTGGA CGACAGAGCG    7620

AGACTCCGTC TCCAAAAATA AAAAACACC TGAAAATCCC AGTATCCCCT AAGCTCTGAT    7680

GTAAATTGAC AAACCCTGAC ATTGTCCCAA ACCTCCAAAT ATAACCCGAG CCCCGATACC    7740

ATCTACAAAC TCCTTTTCGT CCTCAGATCT TCTTACTCCC TAAGCCCCTA TGTGAACCCC    7800

AAGCCCACTG TTTTCCTAAC CCTGATGTAA TCCCTAAACC TCACACATCC CCAACTTACC    7860

CGCACACCCC AATGTGCCCC TCTAGACACG AATCGTCCTG GACTGTGGGG AAGATGACGT    7920

ATGTGTGCCC CAGCTTCAGC TCACTGCCAG CGTGTGAGGA GGCCTCCCAT TCTGCCCGAC    7980
```

```
CCTGGCCCTT TCTGCCTATC ATACCTGCTC CACACCTTAG TCCCCTCTTT TCCCACATCC   8040

TGGGCCCAGA CCCAGGCTCC CTGGCTTCAC TCCTCTTTCC CCACAGGACG GGCTCCCCGC   8100

TCCTAGTTGG GGCAGATAAT GTCCTGGAGC TGCAGATGGA CGCAGCCAAC GAGGGCGAGG   8160

GGGCCTATGA AGCAGAGCTG GCCGTGCACC TGCCCCAGGG CGCCCACTAC ATGCGGGCCC   8220

TAAGCAATGT CGAGGTATGG CCCCCACCCT GGGAACAGTA CCCGGGACCT GGGAGGCACT   8280

GGAGCCTTGG CTCTCTCATC TCCCTCCCTG AGAGTCCCTC TTCTCTTCTG CTTTGCTGTC   8340

AAAGATGTAA TTTTTTTTTT AATTTGGAGG AGGATACTTG CTAATGGTCA GTCAGAATTC   8400

CAAAACTCTA TTACAAAAAC CAGAAAAACA AAAAGGTTT AGGAACCAAA TGTTAACAGG    8460

AACCTCTGTT AACATTTGGT GGATTTCCTT CCAGTCTTTT TTTCAATATT GACTCACACT   8520

CACATAAGTA TATATTTATT TTTTATGTTG TTAATATAGT TTATAATAAT GGGGTCATA    8580

CTCTAATGTT TTGTGTTTTT TATTTCCAAA ATGAAAATGC CTAAAAAGTA GTAGTGCTAC   8640

AGCAATACAC ACACTAGCAT GTGACAGTCC CTTGAGCGAC CCCACCCCAA GAAACCCCCC   8700

CCTCCCTACC TTGGCACACA AATCTTTCCA GACCTTCCAA GGGAGCTTAA ATATATATAT   8760

ATGATGCTCT GTAATTTCTT TCTTGGAACT GCCTTCCTGA AGGGCTTTGA GAGACTCATC   8820

TGTAATCAGA AGAAGGAGAA TGAGACCAGG GTGGTGCTGT GTGAGCTGGG CAACCCCATG   8880

AAGAAGAACG CCCAGGTGAG GCTGCTGGGT CGTGGTACCG GGTCTCCACC AGGGGCTCAT   8940

GAATAACCAG ATTTTAGGGG TGAGGTTTTA GAGCCACATA GTTCTGGGCC AGAATCTTGG   9000

TCCTCACACT CCCTTTGCCA ACATTGTCCT TGGGTGAGTG ACTTTCCCTC TCTGAGCCCC   9060

TTTACCAGTG GGCTTCCAGG TAAAATAGAA ATAATAATGG TGGCCTGGTG CGGTCGTCAC   9120

GCCTGTAATC CCAGCACTCT GGGAGGCCAG AGCGGGTGGA TCACGAGGTC AGGAGTTCAA   9180

GACCAGCCTG GCCAACATAG CAAAACCCCG TCTCTACTAA AAATACAAAA ATTACCCGGG   9240

CATGGTGGCG CACGCCTATA GTCAGAGCTA CTCGGGAGGT TGAGGCAGAA AAATCACTTG   9300

AACCTGGGAG GTGGAGGTTG CAGTGAGCCG AGATCATGCC ACTGCACTCC AGCCTGGGTG   9360

ACAGAGTGAG ACTCCGTCTC GGAAAAAAAA AAAAAGAAAA AGAATAGTGG TGATCTTGGA   9420

GGGTGAAGAC TGGAGGCCAC ATTCAGGGCA GGGCTGTCCT AAGTGGGGCA CTTGGGCAGT   9480

GACCTTGGCC CTCCTCATCT CCCAGATAGG AATCGCGATG TTGGTGAGCG TGGGGAATCT   9540

GGAAGAGGCT GGGGAGTCTG TGTCCTTCCA GCTGCAGATA CGGAGGTACT GACCTGGCGA   9600

GCGTGCCTAC CCACCACCCT TCCCCCGTCT GACCCCCGTG CAGAGCCCCT CAGGTCCCTT   9660

CCATACAGAA GGGTCTTTCG AGGCCAGGCG CAGTGGCTCA CACCTGTAAT CCCAGCACGT   9720

TGCGAGGCCA AGGCAGAAGG ATCACTGGAG GTCAGGAGTT GGAGACCAGC CTGGCCAACA   9780

TGGTGAAACC CCATCTCTAC TAAAAATATAA AATTAGCTGG GCATGGTGGT GCGCACCTAC   9840

AATCCCAGCT ACTCGGGAGG CTGAGGCAGG AGAATAGCTT GAACCGAACC TGGGAGGTGG   9900

AGGTTGCAGT GAGCTGAGAT TGGGCCACTG CACTCCAGCC TTCCAGCCTG GGCGACAGTG   9960

CGAGATTCTA TCTCAAAAGA AAAAAAAAAA AAGGTCTTGA AGAAGCCTGG TTCCCTTTCT   10020

TCCTCAGAGA TTTAGCGAGT CTTGGAGCCC TAGAGGAAGT TCTTTCCCAG GTCTAACTTC   10080

AGTGTGGCAT GCTCTTTGTA TAATTAGCTC TCTCTGAACT CTCTAAAATT CTGGCCTCAC   10140

CCCCAGAAAG TCACTGGGCT GGTGTCCCTG GCCCTGTTTC TCCTCATCCC CTCCCCTCTA   10200

GCAAGAACAG CCAGAATCCA AACAGCAAGA TTGTGCTGCT GGACGTGCCG GTCCGGGCAG   10260

AGGCCCAAGT GGAGCTGCGA GGGTGAGAGG CCAGGGGTGG AGAAGGGAGA TGGCATTCAG   10320
```

-continued

```
GGCTCTAAAC TCCAGGGGGC GCTGGGGAAA CCTCACAGGC CAATCAGGGC ATCACACTCT   10380
CTCTGGGGGT CTTGGGCACC TGCAGGAACT CCTTTCCAGC CTCCCTGGTG GTGGCAGCAG   10440
AAGAAGGTGA GAGGGAGCAG AACAGCTTGG ACAGCTGGGG ACCCAAAGTG GAGCACACCT   10500
ATGAGGTATT GGGGAGCCTC GCGTCCCTGG CTGGGGTGAG CGGGTCCTCA GAACTCCGGG   10560
TGAGGCGCTA AGCTCCCCAC ACCCTGCCAC CACCACCCCT TCAGCTCCAC AACAATGGCC   10620
CTGGGACTGT GAATGGTCTT CACCTCAGCA TCCACCTTCC GGGACAGTCC CAGCCCTCCG   10680
ACCTGCTCTA CATCCTGGAT ATACAGCCCC AGGGGGGCCT TCAGTGCTTC CCACAGCCTC   10740
CTGTCAACCC TCTCAAGGTA AGAGCTGGGT GGAAGAAAGA CCTGGGAAGG CGGCCCCAGA   10800
CCAACCACCG GGGCACCTCT GTGGGCTGGG GTTCGGGGGA GACCTGGGCC TGACCACTCC   10860
TTTGCCCCCC CAGGTGGACT GGGGGCTGCC CATCCCCAGC CCCTCCCCCA TTCACCCGGC   10920
CCATCACAAG CGGGATCGCA GACAGATCTT CCTGCCAGAG CCCGAGCAGC CCTCGAGGCT   10980
TCAGGATCCA GTTCTCGTAG TGAGCAGGCT CTCTGGTCTC GGGCCCGGCC TCCCCGGGAC   11040
CCACGGGGCA GAGGGGATGG GAGGAGGGAG AGGGGTCCGG GTGTGCTGTG GGCCTCTGTG   11100
GGCCACGCTT GGTCCCTGGG AGCACTTCAA GTGAACATGG AGGAGCATGC TGGCTTGTGT   11160
CTGGGGTGAG CTGAAAGACA CTTGCACTTT TTAAAAGCTT CCCAGTACGT TAAGGAGCAT   11220
AAAACAATGC CAAAGCAAGG TTATCATAGA TCTGAGCATT GTGCGCTGGG GGATGACCCT   11280
CCCTGCATCT CTGGGACTAT GTGAGCAAGC CCGTGGAAAG ACAGCATCCG AAGCTTGGAT   11340
CCAAGGCCCT TCCTGATGGG AAGGCCACCG CTTCCTGAAC CCCCGGCCCC TTCTGCGTTG   11400
GGTCCTGGGG GTAAGGGGGT GGGGGATGAT GGGGTGATGG GCCGGACGG CTGGGGACTG    11460
ACGATGCTTC CCCTCAGAGC TGCGACTCGG CGCCCTGTAC TGTGGTGCAG TGTGACCTGC   11520
AGGAGATGGC GCGCGGGCAG CGGGCCATGG TCACGGTGCT GGCCTTCCTG TGGCTGCCCA   11580
GCCTCTACCA GGTGGGGTGG GCCGTGGTGG GGCGGGCCG GGCCTTCTGG GCCGGGACCA    11640
CTTTGCTCTG GGAGGGCGG GGTTTGGTGT GGGAGGGCAG GAAGAGAGGG AAGGCAAGGT    11700
TTACTTTGGG GGATTGCAGT GGGATTAGGT CAGAGGCAGG GCTTCCCCGC CGGGTGTGGG   11760
ACCTGGACTC CGTGCAACCA ATAGGCCTCT TGTGGGTGTA AACGGCTTTC AACCCCAACC   11820
TGTCCAGAGG CCTCTGGATC AGTTTGTGCT GCAGTCGCAC GCATGGTTCA ACGTGTCCTC   11880
CCTCCCCTAT GCGGTGGCCC CGCTCAGCCT GCCCCGAGGG GAAGCTCAGG TGAGTGTGGG   11940
GGGATGGAGC AGAGACCAGT CCTGCAGGAC CCATTGTCCC CCAGTCAGTG CCCAGCCAGA   12000
AAAGTCTGAG GGGTGGTACG GGTGGGTGGC ATGGCTGGAG GTCACCAGCC TGAGGTTTGA   12060
GTCTTTGTGA AAGGCAGGTG TCAAGGTGAC TGAGGAGACA CGTGGGTTTG CCCCAGGTGT   12120
GGACACAGCT GCTCCGGGCC TTGGAGGAGA GGGCCATTCC AATCTGGTGG GTGCTGGTGG   12180
GTGTGCTGGG TGGCCTGCTG CTGCTCACCA TCCTGGTCCT GGCCATGTGG AAGGTGAGGT   12240
GTGAAGGACG GTGGAGTCCC CAGCGGGGCA CAGGCTTGGC TCTGCCCTGC CTCACAGGGA   12300
GTCAAGGAGA GATGGTGGCC CACCCAAGTG GGTAATCCAG GGACCAGGGG TCTATGTCTC   12360
CACTATTAGA ATGTCATTCT CGTCCAGGGG GGTGGCTCAC ACCTGTAATC CCAGCACTTT   12420
GGCAGGCAAA GCGTTTAGAT CACCTGAGGT CAAGAGTTCG AGACCAGCCT GGCCAACATG   12480
GTGAAACCCC ATCTCTACTA AAAATACCAA ATTAGCCGGG CGTGTTGACA CATGCCTGTA   12540
ATCTCAGCTA CTCGGGAGGC TGAGGCAGTA GAATTGCATG AACCCAGGAG GCGGAGGTTG   12600
CAGTGAGCCG AGATCACACC ACTGCACTCC AGCTTGGGCA ACAGAGCGAG CCTCCATCTC   12660
AAAAAAAAAA CAAAAAAATA GAATGTCTTT CTCTAGTAGA GCAAAAGGCA AACAAACAC    12720
```

| | | | | |
|---|---|---|---|---|
|AAAAATGTCA|TTCTCCTGGG|AACCCTTCCA|GACACATACC|ACTGGAAAGG ATAGCACCTG|12780
|AAATTCTGAG|GCCTTTAGAC|ACCCCTGCCA|CCAAAAAGAT|TCAGAGGATA TAGAGGGTAT|12840
|AGAGGGTGTA|AGTCCTGCCT|TCAGGAATTC|CTGGCTGGTC|TCAAGGACAA GATGCACTTC|12900
|TTCCTAGCCC|TGCCCTTCCC|CTTGAGTGAG|GAAGAGGCCA|AGGATTGGTC TAGACCCTAT|12960
|TCCATACCTT|CCTATGTGGC|CCTGGAGGGT|CACTCGCTCC|TCTGCACCTG GAGGAGTCTC|13020
|AAGCACACTG|AAGGGAAGAC|ATGGTGCTTT|TAGGGAAAAC|CACGCACTAG ACCCACAATA|13080
|ATCAAATACA|TATCATCATA|TGCTCGAGTC|ATGCAGACAC|AAACTTCAGT ATAAGAAAAA|13140
|TTCCAGGCTG|GCGTTGGTG|GCTCACACCG|GTAAAATCCC|AGCACTTTGG GAGGCCGAGG|13200
|TGGG| | | | |13204

(2) INFORMATION FOR SEQ ID NO:50:

(i) SEQUENCE CHARACTERISTICS:
        (A) LENGTH: 15849 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:50:

| | | | | |
|---|---|---|---|---|
|GGGCTTTGCA|TGTGTGAGAA|CAAGACAGAG|AATGAGGGAG|GTGGGCCCCA CGAGGAGTGT|60
|GGGCACAGAC|AGCAGCCTCT|GCCTGTGGTG|CCACGCTGAA|GACTCAGTAT TGTATGTGAC|120
|AGATGAAGGC|TCTAAGAAGA|CAGCTCTGAC|AAAAGCTAGA|GTGCAAAATC AGACTCAGAC|180
|ACAACCACCG|GTCTGTGTCC|TGAACACAAT|GGACCTTTAC|ACTCTGGAAT TTCTCAAACG|240
|GAGCAATGCA|CAGACACCCC|CATGGGCCCC|TTGCACACCC|GCAGATTCTC CTAGGAGTCA|300
|CATTCTCTCT|TCAGATAGAC|TCTGGGTGCC|GACACTCCCA|AACATGCTCT TGAGGAGCAG|360
|TCTCTGTGAT|AAGCTGATCT|TCCAGACAAT|CCAGAATATT|CTTAAAACTT TTTAGATCAT|420
|AAAATTTAAA|ACACAAATTA|AAAACAAAT|TATCATAAGG|CCGGGCACAG TGACTCATGC|480
|CTGTAATCCC|AGCACTTTGC|AAGGCTGAAG|CAGGAGGATC|ACTTGAGCCC AAGAGTTCAA|540
|GACCAGCCTA|GGCAACATAG|TGAGACCCTG|TCTCTACAAA|AAAGTCAAAA GTTAGCTAGA|600
|CATGGTGGTG|TGCACCTGTA|TTCCCAGCTA|CTTGCAGGGC|TGAGGTGAGG AGGATTGCTT|660
|CAGCTCGGGA|GGTTGAGGCT|GCAGTGAGCC|AAGATCACGC|CACTGCACTC CAGCCTGGGT|720
|AACAGAGTGA|GACCCTGTCT|CAAAAAACAC|ATAGGGCCAG|GCGTGGTGGC TCACGCATGT|780
|AATCCCAGCA|CTTTGGGAGG|CCGAGACGGG|AGGATCACTT|CACTCCAGGA GTTCAACACC|840
|AGCCTGGCCA|ACATAGTGAA|ACCCCGTCTC|TACTAAAAAT|ACAAAAAATT AGTTGGACAT|900
|GGTGGTGTGC|GCCTGTAATC|TCAGCCACTC|AGGAGGCTGA|GGCAGGAGAA CGCTTGAACT|960
|TGGGAGACAG|AGGTTGCAGT|GAGCTGAGAT|CGCACCACTG|CACTCCAGCA TGGGCAGCAG|1020
|CGCGAAACTC|TGTCTCAAAA|CAAACAAACA|AACAAACAAA|CACCCATAAA CACAAAATGT|1080
|ATCACAGCCT|CAGAGATCCC|CACGAATGCC|TAAGTGGCCC|TGAATTTGGG AGGCACTGCT|1140
|CAGTAATAGT|CCTATCTGTC|CCACAACAGA|CAGGAGTGCT|GGGCTGCACC TACTGGCAAC|1200
|AAACACAGCA|ACCCTTGACT|GAAGAAAGGT|CCATGCCACA|ATCCCCTTAT TCTGTAAGCC|1260
|ACTAATTTTG|TCCTCTCTCC|TCCACCTTTC|ACTGAGGAAC|GAGCTCTTGG AAGGACAGGG|1320
|ACACCCGCCT|AGTAGCTGAG|CCAGCCACAT|CAGTCCTGGA|GAGCAGGTGG AGGGCAGATG|1380
|CTGTGATCAT|CCCAGAAGAG|AGGACACAGT|TGGAGGCAGA|TGCATGGTCT CTACTTTCAG|1440

```
CTACCCTCAA TGCAGCCTGG TCCCCAGAGG CCTGAAGAGC GCCTTGTTTA TGTGGTGACC    1500

TCAAGAGGGG CTGCTCCTGC ACCAAGGCTA TGTGTGCATG CTAACACAGT AACCGTCATA    1560

TACTCAAAGT GTCAGCTCTA AGAACTGGAG ATGAGGAGCT GCAAGCCACT CTACAGTTAT    1620

CAAAGGCACA GCTGAGGGGG TTTGTGCTGA CCAAGCTGGT TGCCTGGTGT TTGGATTGGG    1680

ACTTATTTAC TTTGGAAAAT ATGCAGCAAC AGCCCAGCAC CAAAGTTCAC ATCAAAATCC    1740

CACTGATGAC CTTGGCTGCT TTCATCTCTG AAGCGCCACT TCTCAGAAAC ACAGAGGTAA    1800

GTTGGGTTTC TAATGTTTCT GCTGATTATA AATTATTTTT GGTGTTTACG GATAGGCAAC    1860

TGGTTCATTT TTCTAGCAAA CTAAGAATTC AGAAGCTTTC TACACTGTTT TAGAAGTGGG    1920

AAATGGTTTC ATTTTTCAGT GTGCCTATTA TAAAATTGTG TCAGTTCCAT TGTTGGGAGA    1980

GTTGACAAAC TTAGAATAGG AGCTGTGGAA TAGATGAAAA TATTGTACTT ATATTAAATT    2040

AATCGAATTG GATAACTGTC CTGTGATTAT GTATGAGAAT ATCCTTGCTC TTGGGTATTT    2100

TCCCTGAAGT ATTAGTATTA AAGGTTAGAG GGGCCGGGTG CAGTGGCTCA CGCCTGTAAT    2160

CCCAACACTT TGGGAGGCCG AGGCGGGTGG ATCACGAGGT CAGGAGTTCA AGACCAGCCT    2220

GACCAACATG GTGAAGCCAA GTCTCTACTA AAAATACAAA AATTAGCTGG GCGTGGTGGC    2280

ACGCGCCTGT AATCCCAGCT ACTCAGGAGG CTGAGGCAGG AGAATCGCTT AAACCCGGGA    2340

GGCAGAGGTT GCAGTGAGCG GAGATCGTGC CACTGCACTC CAGCCTGGAC AACAGAGTTA    2400

GACTCCGTCA AAAAAAAAA AAAAAGAAG AAAAAGAAA AATGTTAGA GGAACAAGAT        2460

ATAGGAGACC TACTCTCAAA TGGTCTAGAA GAAAAAATGT GTATGTGCAT GCCTGTGAGA    2520

ACACACACGT ACGTACACAC ACACACAGAT AATGACAGGG CAAAGGTTCC AAAATTTTAA    2580

ACCTGGTAAA TCTCGGTACG GGTATACAGG AGTTGTTCTA CTACACTATT CTTTCAACAT    2640

TTTTGGAAGT TTGAACTTAC TTCAAAATAA AAAGTTTTCC AAACTTTAGG CAGTTACTTC    2700

TCTCCCATTC TGCCTGCTCT GTTGGGCCTG GAGACCATAC ACCAGGAGGG ATGACGGTTT    2760

ATCAAGTGTT ATGCTCTGAT GCGTGACTGA AAAGGCCAAC CCAGCTCTGG CAATTAGCAA    2820

GAAAGCACAA TATGAAGTTC CCAGGAAAAA AAAAAAGCAA ACAAACTTT TGAATGATTT     2880

ATCTTTAAAA TATATTGTTT CTCTTCAAAC AGTAATCTGG ATTTAATCAC AACCTAGTGA    2940

TAGTTTTTAA ACGTCTTCTA CAATGTTTGT TATACTAAAT AGCAAAACAT CAGGAAGATT    3000

TACCTTCAGA TCTTTAATTT CAATCCATAA AAGATATCAG AGATATTTTC TCCTTCCTCT    3060

GGTAAGGGAA TGACGAAAAC TATTTTTGGC TTTTTATCAG ATAATGTGGG AACAGGGTAT    3120

AAGAAGTTTC CAAATATAAC TTCTGAATAC CGGGATAAAA CATGCATGTC TTTACTCTGC    3180

CACTCTATCT GGCCTCAGAT ACGTTTTCCT GAATGCTTAT TTATTCAAGT TGGTTTTTGT    3240

TTTGTTCTTT AACCTTATTT TTATCTGAGA AGAAAACATT TTCCCCCTTT GTTCCTTCTT    3300

CTTTTGGCTT TCTTTTTTAA AATAGAGATG AGGTCTTGCT ATGTTGCTCC AGCTGGTCTT    3360

GAACTCCTGG GCTCAAGCGA TCCTCCTGCC TTGGCCTCCC AAGATGCTAA GATTACAGGT    3420

GTGAGCCCCT ATGCCTGGTC TTCTTCTTCT TGATCTTAGC CAAAAGGCCA AGAAGTGATA    3480

AGAGGAGGAC ACTTGAAGTG TAGTTGGGCA AGGAGCCTTC TACCAGCTGC TTACTTTCTT    3540

TGTTCCTGAC TTTTAAAAGT GTGTTGCTAT TGATACACAG TCTCCTGATA TGTAAAATGC    3600

TGGGAGGATG AAGCTAAGTT ACTCAAAGTG CCATTCAGAA ACTGGGCCCA GTTCTATTTG    3660

CAGCTACATA CATTAGAAAT CATTTCTAGA GGCTGAGCAT GGTAACTCAT ACCTGTAATT    3720

CCAGCACTTT GGGAGGCCAA GGCAGGAGAA TTGCCTGAGC TCAGGAGTTT GAGACCTGTC    3780
```

```
TGGGCAACAT GGTAAAACCC CATCTTTACC AAAAACACAA AAAATTAACT GGGTTTGGTG    3840

GCACACACCT GTGGTCCCAG CTACTTCAAA AGGCTGAGGT GGGAGGGTCT CTTGAGCCTG    3900

AGAGGAACAG GTGGCAGTGA ACCAATATTG TGCCACTGCA CTCCAGCCTG GGTGACAGAG    3960

TGAGACCCCG CCGTCTCAAA ATAAAAATAA AAAGAAATCG TTTCTAGAAA CTGTTTTCCC    4020

GTGTGTAAAC TAGTGGCACT GCAGCCTGAG GCAGGTGCTG AGATGGGGAC CTGGAAAAGG    4080

CAACAGGCAT TTTGAGTCAG AAACAATGTG ACTTTCCTGC TCCAAAATGT GCAATTCAAA    4140

AGTCTTTCTT AGTTGTGACT AAAACAAACT TTGAACTTAC TATTTCAACA GTATTATAAG    4200

GGGAAGACCC AAGGAATGGG ACTGGCACTG GGAAAACAGC TAGGAAGCTG CTCTGCACGG    4260

CCAGGGAGTC TGGAAGCATC CTGGTACTCC AGAGCGAACA AGGCTGAGCG CTTGATGTGG    4320

GGCTTAGAGG CTTAACCAAC TTGGTTCGAA TCTAGCCACT GCCACTTATT AGTGACAGTG    4380

ACGAAAGGCT CAGTCTCCTG ATATATAAAA TGTTGGGAGG ATGAAACTAA GTTACACGAA    4440

GTGCCTTATA CAGCGTGTCA GGCATCCAAC AGAGGCCATT ATCAACATTA ACCACACTGA    4500

CAGCATTTCA AGCAGAGTAT CCGAACAGTT ACCCCATCTT CAGGCCTACT GAGTTCAAAT    4560

ATTTGCTTAA CAAGAGCAGC CAGTAACTCT TACCTGGCCT CAACTGGCAG CAGATATTCT    4620

GGGCCTCAAA TATCTATCTA ATAGGAAATG GTCACAGACA CAAAATAAGC TTAACAAAAG    4680

GCAGTTTTTT TTTGTTTTTT TTTTGTTTTC TGTTTTTTGA GATAAGGACT CACTCTATCC    4740

CCCAGGTTGG AGTGCAGTAG TGGCGTGATC ACGGCTCACT GCAGACTCAA GTGATCCTCC    4800

TACTTCAGCC TCTCAAGTAG ATGGGACCAC AGGCGTGTGC CATCACACCA GGCTAATTAT    4860

TTTTCTTTTC TTTTTTTTTT TTTTGAGACG GAGTTTCGCT CTTTTTGCCC AGGCTGGAGT    4920

GCAATGGTGC GATCTTGGCT CACCACAACC TCTGCCTCCT GAATTCAAAC GAATCTCCTG    4980

CCTCAGCCTC CTAAGTATCT GGGATTACAG GCATGCGCCA CCACGCCGGC TAATTTTTTT    5040

GTATTTTTTG TAGAGACAGG GTTTCTCCAT GTTGGCCAGG CTGGTCTCGA ACTCCCGACC    5100

TCAGATGATC CGCCCACCTC GGCCTCCCAA AGTGCTGGGA TTACTGACCT GAGCCACCGC    5160

ACCCAGCCTA TTTATTTAAT TTTTCACAGA GATGAGGTCT TGCTATGTTG CCCACACTGG    5220

TCTTGAGCTC CTGGGCTCAA GTGATCTTCC TGCCTTGGTC TCCCAGTGTT GGGATTATAG    5280

GCGTAAGCCA CAGCGCCTGG CCGGCAGTTC TTTCTGGGGT GATTAGAAGT TGGGACCATG    5340

TATTACCTGT CTGAGTCAGC ATTATAAACA CCTATGGTCA CTGTCCTGGC AAAACATGGA    5400

ATCATCAAAG CTCATCTAAC CAGAGTGCAG TTAATAACCA GGAAGTAAGC AAGAGAAAGA    5460

CAAAGGATTT GGCAGTCAAA ACAGATTTGA CAGGCCAAGT CAGATCCTCC TCTGAACGAG    5520

TCAGAGGAAC AAATAAAGAC AGGATTGCCA TAATGCCTCT GTGCTAAAAG CTTATCTTGT    5580

TTACTTAAAT AAAGGGAGTG CCCCTCAGGT CTTGAGTAAG AGCTTGCTGA CATCACCCTC    5640

ACACAGACTT TATCTCTTGT TTCTAACCCT GTGTTAGAAG CAGTAACACA GAAGATTTAG    5700

TTGCTCCTGA CAGCAGTGGG AGCTATTGTC TAAGAGATAC AAAGGAGAAA AAGTATACC    5760

TGCAGCAAGT GATATCACCT CTGGGGCTGC ACCACATCA CCTCACTACG CCCTGAGGGG    5820

GTCTCAGCAC TAGACAAGTT CCAAATCTTT TGCAAATTAA ACAACCCCAG GTCAGGCGTG    5880

GTGGCTTATG CCTGTAATCC CAGCACTTTG GGGGCTGAG GTGGGTGGAT CACCTGAGGT    5940

CAGGAGTTTG AGACCAGCCT GGCCAACAGA GCAAAACCCC ATCTCTACTA AACAAAATAC    6000

AAAAATTAAC CAGGCGTAGT GGTGTGCACC TGTAGTCCCA GCTACTTGGG AGGCTGAGGC    6060

AAGAGAATTG CTTGAGTCCA GGAGGCCGAA GTTGCAGTAA GCCGAGATCG CGCCACTGCA    6120

CTCCAGCCTG GGTGACAGAG TGAGACTCCA TTTCAAAAAA TAAAAACAAC AAAAGCCAAT    6180
```

```
TACAACAACA ACAACAAAAA AACAACGAAT TAAACAACCC CAAAGATTGC ACAAATTTCA    6240

AGTATCTTTA GAATATGTTT TCAGAAAGCC TGGCCCATGG ACATTTTTCA ACAGCATCTC    6300

CATTGCAAAG GTGGAATGGT GTGAGTCACA CAGGCATGGC TGAGTCCCAC TAATGCACAT    6360

CCCTTCTAGG TACTCTCCAA TCACCAGCCC CAGGTGCCCA CTCAAGCCCA GCTCTTAGTG    6420

AGGTTTCCCT GACTCTCTGG GCACTTCCAC TCCTACCACA CAGGGTAGAG CCACACCCCT    6480

TTCCGTACCC CCATGTGCTC TGGCAGCATT ATTTTGAGAG CCTTCGCTTT ACTGCACGTC    6540

TGTCCCATCT GTCCCCTGAC TGGTCCATGA GCCCCTGGTG GAACTTTGT CTCTGGTAAC     6600

TAAACACTGT CTGGAGGTGG TGGACAAGGT GTCTGGAGAA AAACAAACTC CTCCCTGGGA    6660

TGCCTGAGCT CCCAGGATTC TAGAAGGTTA GTTTTGCAAA CCTTTAAAGA AGGGATTTTC    6720

ATCAAGGGGC CCACAGATCC TTCATTGAGG TTTATGAGTC CCACATCAAA GGTTGGGTGT    6780

CTATCTACAT CAGATTCTCT TAAAGTCCAT GATCCTAAAA CAGTTAAGAA CTAATGCTGT    6840

GAGGGCCTCT TCCTGGGTCA AGCCACAGG GAACCTGCCA TGTGGATGCT GCAGCGGGGT     6900

GTGGATCAGC CAGGCCGCCT TTCACTGTGT TCTGTTTTCC CTCCCAGCTT TAGCTCCGCC    6960

AAAATGAAAC ACTCATTAAA CGCACTTCTC ATTTTCCTCA TCATAACATC TGCGTGGGGT    7020

GGGAGCAAAG GCCCGCTGGA TCAGCTAGAG AAAGGAGGGG AAACTGCTCA GTCTGCAGAT    7080

CCCCAGTGGG AGCAGTTAAA TAACAAAAAC CTGAGCATGC CTCTTCTCCC TGCCGACTTC    7140

CACAAGGAAA ACACCGTCAC CAACGACTGG ATTCCAGAGG GGAGGAGGA CGACGACTAT     7200

CTGGACCTGG AGAAGATATT CAGTGAAGAC GACGACTACA TCGACATCGT CGACAGTCTG    7260

TCAGTTTCCC CGACAGACTC TGATGTGAGT GCTGGGAACA TCCTCCAGCT TTTTCATGGC    7320

AAGAGCCGGA TCCAGCGTCT TAACATCCTC AACGCCAAGT TCGCTTTCAA CCTCTACCGA    7380

GTGCTGAAAG ACCAGGTCAA CACTTTCGAT AACATCTTCA TAGCACCCGT TGGCATTTCT    7440

ACTGCGATGG GTATGATTTC CTTAGGTCTG AAGGGAGAGA CCCATGAACA AGTGCACTCG    7500

ATTTTGCATT TTAAAGACTT TGTTAATGCC AGCAGCAAGT ATGAAATCAC GACCATTCAT    7560

AATCTCTTCC GTAAGCTGAC TCATCGCCTC TTCAGGAGGA ATTTTGGGTA CACACTGCGG    7620

TCAGTCAATG ACCTTTATAT CCAGAAGCAG TTTCCAATCC TGCTTGACTT CAAAACTAAA    7680

GTAAGAGAGT ATTACTTTGC TGAGGCCCAG ATAGCTGACT TCTCAGACCC TGCCTTCATA    7740

TCAAAAACCA ACAACCACAT CATGAAGCTC ACCAAGGGCC TCATAAAAGA TGCTCTGGAG    7800

AATATAGACC CTGCTACCCA GATGATGATT CTCAACTGCA TCTACTTCAA AGGTAAGAGG    7860

CACCTTTACA GTTCTCACAG CAAACCCACA ACATACTATT TTTGTATGTG GGTAGATTGA    7920

ATGCCAAGAA CTGTACTGTA GCTATAATTT ATCCAGGAAA ACTAGACACA AGATTGACTC    7980

TGGAACGGGG ACAGGGAAGG CCAAGCTGAA GTGACAGTAG CATCTGACAC TTACTGAGCC    8040

CTAACTCTGT GCTTTAACAC AGCCTTGTGA GGTCATCACT GTTATTAGCA TCCCCATTTT    8100

ACAGAGGAAG CCACCAACAC ATGAAGTAAA AGGATGGGCT GGGCGCGGTG GCTCACGCCT    8160

GTAATCCCAG CACTTTGGGA GGCCGAGGCA GGCAGATCAC TTGAGGTCAG GAGTTCGAGA    8220

TCAGCCTGAC CAACAGACCA ACATGGTGAA AACCTGGCTC TACTAAAAAT ACAAAAATTA    8280

GCTGGGCCTG GCGGTGGGTG CCTGTACTCC CAGCTACTTG GGAGGCTGAG GCAGGAGAAT    8340

CACTTGAACC TGGAAGGCAG AGATTGCAGT GAGCCGAGAC TGTGCCACTG CACTCTAGCC    8400

TGGACGACAG AGTGAGACTC CATCTCAAAA AAAAAAAAA AAGAAGTAAA ACGATGCTCC     8460

AAGGGCACCC AGTTATTAAG GGGCAGAGCC AAAGCTGAAC CCAGGGAGGC CAACCCTAGC    8520
```

```
AATCTGTTAA ATTGGAAGAA ATAATACAAA AACTGTTTTA GCATTTGGCC AGCCTGGATT      8580

TGAGTTTTCT CTTTTCCTTT CCCAATTATC AATAAGCAGG AATATAGACA AAAGGCTAAA      8640

GAAATGCACC TGTGAACTAT TCAGCTTGAG CAGCTGACAT TGACACCTAC AAGTGCTTTT      8700

CAGGATACTT TTGAACTACT GGGCAGGTGG GATGGAGAAA TAAATTACTA TTTCCCCAGC      8760

AACTGTTCTG GGCTGAGCAC AAGGGCACTT TTTAAGGAGG TCACCCCACA CCCATCACAC      8820

ACACATAGGA CCCCTGGAAT CCTAGGAATA AATAAGCATG GATTTGTAAA ATCCAAACCT      8880

CTCTTTTCAA ATATCCTCAC CTGGACCAGA CCAGAAGAAA CCTCTACTTT ACTCTCTAAG      8940

CTGAGAGTGT GGAAGGGGAA ACACGAGGAA TGGTTCGGCT TCAGGACTAA TTGCGGTGAC      9000

ACACAACCAC TTCTCTTTGC CACCAAGGAC TACCAGGTAC CTGCAAAGGG CAGTACTTGG      9060

AGGCCAGTGC TTTCTGCTAG TTAGCTCCCG TGGTTTTATA GCAGCCCAGG CGAAGGAAGG      9120

AGACCCCCCC CAGCTCCTGG CTTCTGTTCA GGGAAAGGGG GCCAGAGCCC CTCCTGATCT      9180

GTCCACACAC CTGCTCTGTG CCTTGGCTGA GGCCCCTGCA GCTCTACAAG GCAGGCATTC      9240

TGCTGGATAG GCCAAGCAGG GTCACTCTGA CACCCAGGTT TCCACCCCAA GGCATGGCAC      9300

AATGCTGGCC TCCTGTGGGT GGAATCAAAG GCTGAGTTCT AACAGGCTTG CGGCAGACAC      9360

ACACACAGAG ACCACATGTA CATGATGAAC ACACATATCC TTTTCATTAC AGGTTATTAG      9420

TACAAGTTTT GGAATTGAGC AAACAAGAGT CTAAGCGCTG GTTTCACCAC TTCTCGTTTG      9480

TGTGACCTCA GACAAGTCAT TCAACATCTC TATGACTCAG TTTCCTTATC TTTATCACAG      9540

AGATGACACC CACTCTGACA GGGCCGAGGG AAGAACCATA AGCGATGGCA ATGCAACAGA      9600

GTGGCACATG ACAAGAGCTC AGCGAATTTG AGGGAATGAA ACTGTAGATT ACAATACTAG      9660

TACAATATGA TAAACATATG ATATTGTTAG TGACATTTAT TTTACTTCTA CTAGCAAATA      9720

ACCTATGTTT AGGACTGACT TTAGAACAGG CTGGCAGAAG CATTTTTGGC AGCATCAAAG      9780

TCCTCCAACC TACTGGTCTG TTGGAGCCCC CCAAGTACAC CAAAGAGCCT CTGCATTAGC      9840

CCTGGCTGAG GGTTCAGGGA CAGGCAGAGA AGTACAGCAG TGAGCCATCC CTGCCTGCAT      9900

GGAGGTGGAG AAATGATCAG GCATGGTCAG TTGACAATCT CCTAAACACA GTAACCCGTG      9960

TCATACCACA GTGTAAACAC ACGTGCAAAT GCTTCTGCTT CCTTTCCCCA TCATGAGAAT     10020

AGTCACTCAA TGCCGGGCAT CACAAGGGAT CAAATGCTAG GAGTACCCAA TCATTCATGG     10080

ATGCTTCTCA AAGGGGACGA GTGTCTAGAA GTGTAATTTT AATTTCACTT AATTTCATAT     10140

GGAATCATCT CCATTACTAA TTTTGTTCTA ATTTTAATGT GATAATCACT TTGTAAAGCA     10200

CAATAAACAG AGGCAGGCTC TCATGAGGAA GTCAGAAGGA AAGAATCCCA AGAGACATGG     10260

GACAGCTCCA TCCAAACTGA AAGGGCCGTG ATTCCCAAAA GAGCAATTTT GTCCCCAAGG     10320

TCTGAAGACA CTTTTGGTTG TCACAACCTG GGGGGTTGGA GTAAGCATTA CTGGTATCTA     10380

GAAGGGGGAG GCTGGGGATG TTGCTAAACA CCCTACCATG CACAGGGCAG CCCACATTGC     10440

CACAAACTAT TATGTGGCCC AAATGTCAAA AATGCTGAGG TTGAGAAACC CTGGGTGAGG     10500

CAGACTCAGG GAGAAGGGAA TCGAGCTTCA CTCACAGGCA GGCAGGAGCT GTCTGGTACT     10560

TCAACCTCCA AGACACCTCC TGCTCATCTC ATCCTGGCTG CTCTACCCAC CAGCTAGAAA     10620

CCTTGAACAA GTTACTTCAC TTCTTTGTGC CTCTGTTTCC TCATATGTAA AAGAGGGATA     10680

ACAAAACGCA CACAACTTGC ATGTTGCTAG GAGCAGAAAT GAGATAATAC AGGAAAGGTG     10740

CTGAGAAGAA TGCCCGGCAC ATGGCCAGTT CTCAACTACT AGTCACCCAT TACTATTAGT     10800

TACTCACATC TTAGAGCTAA CATAGACATG GGCTTATTCC TGGATACACA GCACTGTCCC     10860

CATATCTACA GTGGTGATCC TAAGGGCAAC ATGGCATCAC CCAAATGTCT TGTTAGTCAC     10920
```

```
TACAGAATCA CAGTGTGAGG GATGAAGGCC ATCAAGACAG AGCTGAGGCT GGCAGGGTGG    10980

CTCATGCCTA TAATCCCAGT GCTTTGGAAG GCTGAGGCAG GAGGATTGCT TGAGGCCAAG    11040

GGTTTGAGAC CAGCCTAGGT AACATAGCAA GACCCCATCT ACAATTAAAA AAAAAAAAAA    11100

AAAGACAGAA AGAAAAAATA GCCAGGCGTG GCATGTGCTT GTAGTCCAAG CTACTGGGGA    11160

GGGAGGCTGA GGCAGGAGGA TTCCTTGAGC CTGGGAGTGT GAGGCTGCAG TGAGCTATGA    11220

TGGCATCGCC GCACTCCAGC CTGCATGACA CAGTGAGACC TGGTCTCAAA AACCAAATAA    11280

TAATAACAGT AATAAAAGCT GGAAAGAGCT CAAAGTTACT CATTTGACAG ATGTGACAGA    11340

TGAAGAAATA GAAGCGAGTT AGGTGCCTTA CCATGGTCAA ACAACTAGTT CGTATCAGAC    11400

CCTACTCCAG AAACTATTCC AGTCCGGGTA ACCTCTCGTT AACCTCTCTT GTTAGAAATG    11460

CAAATTTCTG CCCAAATCAG GCCTCAGGAA TCAAGAGACT GTGGGGTCGG CTCTGCAGGC    11520

TATCTGAATG AGGCCTCCAG GGAAATCAGA TTCACTCTCA AGGGTGAGAC GATTTCCCTA    11580

AAGGAACCTT CTCATAACAG CCTCTTCCTG TGGCCTTTAC AGGATCCTGG GTGAATAAAT    11640

TCCCAGTGGA AATGACACAC AACCACAACT TCCGGCTGAA TGAGAGAGAG GTAGTTAAGG    11700

TTTCCATGAT GCAGACCAAG GGGAACTTCC TCGCAGCAAA TGACCAGGAG CTGGACTGCG    11760

ACATCCTCCA GCTGGAATAC GTGGGGGGCA TCAGCATGCT AATTGTGGTC CCACACAAGA    11820

TGTCTGGGAT GAAGACCCTC GAAGCGCAAC TGACACCCCG GGTGGTGGAG AGATGGCAAA    11880

AAAGCATGAC AAACAGGTAT TCACACTGT GTGTTTGTTC TTTTGAGCTC CCAGATGCTG     11940

GGGGTGTCTG GGAATACTGG AAAATGGATC ATTTTTTTAA AAAGGGAGAA TTATGTACAA    12000

GTACCCAAGA ACTTCCATAC AGGGCCACTC TGTTAATTCA GCCCCAATTT GTTGCTTGAG    12060

ATAAGAGATG ATTAGAGAGC ATTCATAAGG GACACATCTG CCCTCTAGGG GCCAGTTTCA    12120

GAAGTTAGAG GCAGATGACT TAGAGACAGC TTGGTGCTTG CTTTGTGGCT TCGAGTCCCA    12180

GCTTCATCAT CCCTAAAATG GGTATAATTC CATTACTTCC CCGGGTCACT TGAGAAAATA    12240

ACAGAATCAG CGATGCTGAG CGCCCCTCCC AGTACTTGGA ACCTAGGAGG CACTCAAAAA    12300

AAGATTGGCT CAACTCTTCC CTGCCCAGGA AATTCCAAGG TCCTCTTAGC CTACCGAGGA    12360

CACATCATTC ATGATTTCCT CTATTATTAT TCGTTACTTT GTAGTTAAAA CTGCAGGTGT    12420

TAAGTACTTA TTGAGATTAT TATTGGGTCA TGGCAGAAAG AATGGAGAGG TCTTATTTCT    12480

GTCTTACTGG ATACTGGCTA GGCCCATATG AAGAAGTGAT TCTGGTTTGA ACCTCCTTAT    12540

AGGACAAGAA TACAAACATA TGCAACCAAA CTGAGAAAAG TAGGCTCTCA GAGGAAGGTA    12600

TTTGCCCGGG TAGCCAGTCA TCATGCTCTG TGAATTTTTC CTTAACAACG TCCCTTCTGT    12660

ACCTGCCTCC TTCCATTCCT CCCTGCAGCC CGGCAGCTCT TGAGAAAGGG ACTGCATCTT    12720

TTTTTTTTTT TTTTTTTTGA CAGGGTCT TGTTCTGTCA CCCAGGCTGG AGTGCAGTGG      12780

CATCATCATG GCTCACTGCA GCCTCAACCT CCTGAACTTA AGTGATCCTC TCACCTCAGC    12840

CTCCTGAATA GTTGAGACTA CAGGCGTGCA CCTTCATGCC CAGCTAATTA AACTTTTTTT    12900

GGTAGAGATG AGGTCTCGCT GTGTTGCCCA GGCTGGTCTT GAACTCCTGG CCTCAAGCAG    12960

TCCTCCTGCC TTGGCCTTCC AAAGTGCTGG GATTAACAGG CGTGAGCCGC TGTGCCTGGC    13020

CCATTTGACT TTTAATTGAG ATCTTACTTG GTGCAAGGTA TGAGCTAGGT AAAAGAGTGA    13080

AGAAGATCAA GCCTTCCTGC CCATCCAGCT GGGATTGCAC CTTAAATCTC TTTATCCCCT    13140

GCAAAGTGCC AGACTAACTC CACAGGCACT ACTGTTGCTA TCCGCCCCCT TAGGGATTGA    13200

GTAAGTTGAG GCAAAGATTG AGATATTCAG CATTGTCTAG TATATACAGG AAAGGTTCTT    13260
```

-continued

```
TTTAAAAGTA CACTACCAGA TATTCGACTC CTTAATTACA AAAAAAAAAC CAAATGCCTA   13320

AAATTGGGAA ACCAAACCAG AGAATTATTT TAGATGCCTT TTTAAACCAT AAACCAGGAA   13380

AAGTTCTGCT GCTAACCTTG AAGATAGGAA ACGAACCATA CAGTCTCAAG GAAATAATCA   13440

TGCAACAGAA AACACACCTC AGTTTTCAGT AGCGGAATTA CAAAGGAGTG TGCTTCCTAA   13500

AATCCTCAAC TGACAGTCCC GGAATATAAA TTTTAATAAG TGCTATATCA ATTCTGTGAT   13560

AAATATAACC CGTGGCCCTT TAAAGGGAAA ATCATGATTC TTTTGTAACT TGTGGTTCAA   13620

TAAAACTGGG CCCCCCTTTC CTTTTCTGTC TAGAACTCGA GAAGTGCTTC TGCCGAAATT   13680

CAAGCTGGAG AAGAACTACA ATCTAGTGGA GTCCCTGAAG TTGATGGGGA TCAGGATGCT   13740

GTTTGACAAA AATGGCAACA TGGCAGGCAT CTCAGACCAA AGGATCGCCA TCGACCTGGT   13800

AACCACTCCC TTGTCCACCC CCGACCCGTC CCCAGGGTCT GCCTCAGCAC AGCCCCACCT   13860

CCACTTGCCC TTCCTACCCA CCCCCCAATC TCATGTCCCA GCTTGGGGTG CTGAGTCTGC   13920

TCTTCGGCCT GGGTGGGATA CACAGAATGC CTAGTTTCAT GGATGCCAGC TGGAGAGCAC   13980

GGCACCTGGC AGACACTTAC TGGGCAGGGG GGATCCCAAG AGCAGCCATG GGGTGAGCCC   14040

CACTCCCGCT GACACCAGAG ACAGGGGAGA CATGTGCTGC GGTCTGGGAA ATAGCTACCC   14100

CCAGCCAAAT CATGAAAGAG CCATTAAACA CCGCACTATA CAACATACTT AACTTAAACC   14160

AATCGGGTCG CTCAGCAAAA GAGAGAGAAC ACCAGTCCAA ACAGTGCAGC AGACCCAGTT   14220

CCCCATCCCG GAGAAGTGCG CAGCAGTGTG GGGAGCTGGA GCTGGGGTGG CTGTCCTGCA   14280

CCAGCCCCCA CGACCCTCAG ACCACAGGCA CTGCCAAGAG GGAACATGAA CCTAGCCGGC   14340

CTCTAAGTGC AACGGCTGCC CCTGACAGGT GGTGACAGAT ATTTTCAAGA GTGACTCTGA   14400

CCAGCTGTGA TTTCCACCTT ACATGTTGTC TTTGGATCCT TTCCCTGAAT GATATGAGAT   14460

TGTGCTGGGA ACTCTAGCCC TCTGTGTGCT GACCTCCAGA ATCTGACAAC TTTCCTTTCC   14520

AAACAGTTCA AGCACCAAGG CACGATCACA GTGAACGAGG AAGGCACCCA AGCCACCACT   14580

GTGACCACGG TGGGGTTCAT GCCGCTGTCC ACCCAAGTCC GCTTCACTGT CGACCGCCCC   14640

TTTCTTTTCC TCATCTACGA GCATCGCACC AGCTGCCTGC TCTTCATGGG AAGAGTGGCC   14700

AACCCCAGCA GGTCCTAGAG GTGGAGGTCT AGGTGTCTGA AGTGCCTTGG GGGCACCCTC   14760

ATTTTGTTTC CATTCCAACA ACGAGAACAG AGATGTTCTG GCATCATTTA CGTAGTTTAC   14820

GCTACCAATC TGAATTCGAG GCCCATATGA GAGGAGCTTA GAAACGACCA AGAAGAGAGG   14880

CTTGTTGGAA TCAATTCTGC ACAATAGCCC ATGCTGTAAG CTCATAGAAG TCACTGTAAC   14940

TGTAGTGTGT CTGCTGTTAC CTAGAGGGTC TCACCTCCCC ACTCTTCACA GCAAACCTGA   15000

GCAGCGCGTC CTAAGCACCT CCCGCTCCGG TGACCCATC CTTGCACACC TGACTCTGTC   15060

ACTCAAGCCT TTCTCCACCA GGCCCCTCAT CTGAATACCA AGCACAGAAA TGAGTGGTGT   15120

GACTAATTCC TTACCTCTCC CAAGGAGGGT ACACAACTAG CACCATTCTT GATGTCCAGG   15180

GAAGAAGCCA CCTCAAGACA TATGAGGGGT GCCCTGGGCT AATGTTAGGG CTTAATTTTC   15240

TCAAAGCCTG ACCTTTCAAA TCCATGATGA ATGCCATCAG TCCCTCCTGC TGTTGCCTCC   15300

CTGTGACCTG GAGGACAGTG TGTGCCATGT CTCCCATACT AGAGATAAAT AAATGTAGCC   15360

ACATTTACTG TGTATCTGTT ATAATTCTCT ATTTTTTGAA GCTCAAATAT CAAAAGCCAA   15420

ATCCAAATTC CTGGATAACT CCAGGTATGA TAAAGGCTGA GAGGAAGTCA CTTGAGCACC   15480

ACAATGTGCC ACAGCAGGGC ATGTTCTCAG GACAGGACAG GTGTGTGCTG AATCCTGGGG   15540

AGGGTCTGTG CAGTACCCCA GAACTGTGGG GTGCTAAGTG GCACACAAGC CCCAGGGCTC   15600

CCACAGTCTA TGCCAGGCTG CTGCAGCTTT CATCCCTCAT ACCTGGTCCT GCAGTGGGTC   15660
```

```
TGGTTTGACA GAGCAGATGA CACCTGAGGA ATATGTTTCT GGATCCTTCA ATCCCTGGGT    15720

AAGACAAGTG AAATCCACAG AGGCTGTTCA GCACGCAAGA GTGCCAGTGC TCTTTCAGTG    15780

AGGGGATGAC TGACGGTCAC AGGTGCTGTG TGTGCAGGTG TCTAACTGTA ACCCCACAGC    15840

CTGGCAGAT                                                            15849
```

(2) INFORMATION FOR SEQ ID NO:51:

(i) SEQUENCE CHARACTERISTICS:
        (A) LENGTH: 499 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:51:

```
Met Lys His Ser Leu Asn Ala Leu Leu Ile Phe Leu Ile Ile Thr Ser
 1               5                  10                  15

Ala Trp Gly Gly Ser Lys Gly Pro Leu Asp Gln Leu Glu Lys Gly Gly
            20                  25                  30

Glu Thr Ala Gln Ser Ala Asp Pro Gln Trp Glu Gln Leu Asn Asn Lys
        35                  40                  45

Asn Leu Ser Met Pro Leu Leu Pro Ala Asp Phe His Lys Glu Asn Thr
 50                  55                  60

Val Thr Asn Asp Trp Ile Pro Glu Gly Glu Glu Asp Asp Asp Tyr Leu
65                  70                  75                  80

Asp Leu Glu Lys Ile Phe Ser Glu Asp Asp Tyr Ile Asp Ile Val
                85                  90                  95

Asp Ser Leu Ser Val Ser Pro Thr Asp Ser Asp Val Ser Ala Gly Asn
            100                 105                 110

Ile Leu Gln Leu Phe His Gly Lys Ser Arg Ile Gln Arg Leu Asn Ile
        115                 120                 125

Leu Asn Ala Lys Phe Ala Phe Asn Leu Tyr Arg Val Leu Lys Asp Gln
130                 135                 140

Val Asn Thr Phe Asp Asn Ile Phe Ile Ala Pro Val Gly Ile Ser Thr
145                 150                 155                 160

Ala Met Gly Met Ile Ser Leu Gly Leu Lys Gly Glu Thr His Glu Gln
                165                 170                 175

Val His Ser Ile Leu His Phe Lys Asp Phe Val Asn Ala Ser Ser Lys
            180                 185                 190

Tyr Glu Ile Thr Thr Ile His Asn Leu Phe Arg Lys Leu Thr His Arg
        195                 200                 205

Leu Phe Arg Arg Asn Phe Gly Tyr Thr Leu Arg Ser Val Asn Asp Leu
210                 215                 220

Tyr Ile Gln Lys Gln Phe Pro Ile Leu Leu Asp Phe Lys Thr Lys Val
225                 230                 235                 240

Arg Glu Tyr Tyr Phe Ala Glu Ala Gln Ile Ala Asp Phe Ser Asp Pro
                245                 250                 255

Ala Phe Ile Ser Lys Thr Asn Asn His Ile Met Lys Leu Thr Lys Gly
            260                 265                 270

Leu Ile Lys Asp Ala Leu Glu Asn Ile Asp Pro Ala Thr Gln Met Met
        275                 280                 285

Ile Leu Asn Cys Ile Tyr Phe Lys Gly Ser Trp Val Asn Lys Phe Pro
290                 295                 300
```

```
Val Glu Met Thr His Asn His Asn Phe Arg Leu Asn Glu Arg Glu Val
305                 310                 315                 320

Val Lys Val Ser Met Met Gln Thr Lys Gly Asn Phe Leu Ala Ala Asn
            325                 330                 335

Asp Gln Glu Leu Asp Cys Asp Ile Leu Gln Leu Glu Tyr Val Gly Gly
        340                 345                 350

Ile Ser Met Leu Ile Val Val Pro His Lys Met Ser Gly Met Lys Thr
    355                 360                 365

Leu Glu Ala Gln Leu Thr Pro Arg Val Val Glu Arg Trp Gln Lys Ser
370                 375                 380

Met Thr Asn Arg Thr Arg Glu Val Leu Leu Pro Lys Phe Lys Leu Glu
385                 390                 395                 400

Lys Asn Tyr Asn Leu Val Glu Ser Leu Lys Leu Met Gly Ile Arg Met
            405                 410                 415

Leu Phe Asp Lys Asn Gly Asn Met Ala Gly Ile Ser Asp Gln Arg Ile
        420                 425                 430

Ala Ile Asp Leu Phe Lys His Gln Gly Thr Ile Thr Val Asn Glu Glu
    435                 440                 445

Gly Thr Gln Ala Thr Thr Val Thr Thr Val Gly Phe Met Pro Leu Ser
450                 455                 460

Thr Gln Val Arg Phe Thr Val Asp Arg Pro Phe Leu Phe Leu Ile Tyr
465                 470                 475                 480

Glu His Arg Thr Ser Cys Leu Leu Phe Met Gly Arg Val Ala Asn Pro
            485                 490                 495

Ser Arg Ser
```

(2) INFORMATION FOR SEQ ID NO:52:

(i) SEQUENCE CHARACTERISTICS:
        (A) LENGTH: 3472 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 225...1499
        (D) OTHER INFORMATION:

(xi) SEQUENCE DESCRIPTION: SEQ ID NO:52:

```
GCGCCCGCGC GACCGCGCGC CCCAGTCCCG CCCCGCCCCG CTAACCGCCC CAGACACAGC        60

GCTCGCCGAG GGTCGCTTGG ACCCTGATCT TACCCGTGGG CACCCTGCGC TCTGCCTGCC       120

GCGAAGACCG GCTCCCCGAC CCGCAGAAGT CAGGAGAGAG GGTGAAGCGG AGCAGCCCGA       180

GGCGGGGCAG CCTCCCGGAG CAGCGCCGCG CAGAGCCCGG GACA ATG GGG CCG CGG       236
                                                Met Gly Pro Arg
                                                 1

CGG CTG CTG CTG GTG GCC GCC TGC TTC AGT CTG TGC GGC CCG CTG TTG       284
Arg Leu Leu Leu Val Ala Ala Cys Phe Ser Leu Cys Gly Pro Leu Leu
 5              10                  15                  20

TCT GCC CGC ACC CGG GCC CGC AGG CCA GAA TCA AAA GCA ACA AAT GCC       332
Ser Ala Arg Thr Arg Ala Arg Arg Pro Glu Ser Lys Ala Thr Asn Ala
            25                  30                  35

ACC TTA GAT CCC CGG TCA TTT CTT CTC AGG AAC CCC AAT GAT AAA TAT       380
Thr Leu Asp Pro Arg Ser Phe Leu Leu Arg Asn Pro Asn Asp Lys Tyr
        40                  45                  50

GAA CCA TTT TGG GAG GAT GAG GAG AAA AAT GAA AGT GGG TTA ACT GAA       428
```

```
                Glu Pro Phe Trp Glu Asp Glu Lys Asn Glu Ser Gly Leu Thr Glu
                            55                  60                  65

TAC AGA TTA GTC TCC ATC AAT AAA AGC AGT CCT CTT CAA AAA CAA CTT              476
Tyr Arg Leu Val Ser Ile Asn Lys Ser Ser Pro Leu Gln Lys Gln Leu
    70                  75                  80

CCT GCA TTC ATC TCA GAA GAT GCC TCC GGA TAT TTG ACC AGC TCC TGG              524
Pro Ala Phe Ile Ser Glu Asp Ala Ser Gly Tyr Leu Thr Ser Ser Trp
85                  90                  95                  100

CTG ACA CTC TTT GTC CCA TCT GTG TAC ACC GGA GTG TTT GTA GTC AGC              572
Leu Thr Leu Phe Val Pro Ser Val Tyr Thr Gly Val Phe Val Val Ser
                105                 110                 115

CTC CCA CTA AAC ATC ATG GCC ATC GTT GTG TTC ATC CTG AAA ATG AAG              620
Leu Pro Leu Asn Ile Met Ala Ile Val Val Phe Ile Leu Lys Met Lys
                120                 125                 130

GTC AAG AAG CCG GCG GTG GTG TAC ATG CTG CAC CTG GCC ACG GCA GAT              668
Val Lys Lys Pro Ala Val Val Tyr Met Leu His Leu Ala Thr Ala Asp
            135                 140                 145

GTG CTG TTT GTG TCT GTG CTC CCC TTT AAG ATC AGC TAT TAC TTT TCC              716
Val Leu Phe Val Ser Val Leu Pro Phe Lys Ile Ser Tyr Tyr Phe Ser
150                 155                 160

GGC AGT GAT TGG CAG TTT GGG TCT GAA TTG TGT CGC TTC GTC ACT GCA              764
Gly Ser Asp Trp Gln Phe Gly Ser Glu Leu Cys Arg Phe Val Thr Ala
165                 170                 175                 180

GCA TTT TAC TGT AAC ATG TAC GCC TCT ATC TTG CTC ATG ACA GTC ATA              812
Ala Phe Tyr Cys Asn Met Tyr Ala Ser Ile Leu Leu Met Thr Val Ile
                185                 190                 195

AGC ATT GAC CGG TTT CTG GCT GTG GTG TAT CCC ATG CAG TCC CTC TCC              860
Ser Ile Asp Arg Phe Leu Ala Val Val Tyr Pro Met Gln Ser Leu Ser
                200                 205                 210

TGG CGT ACT CTG GGA AGG GCT TCC TTC ACT TGT CTG GCC ATC TGG GCT              908
Trp Arg Thr Leu Gly Arg Ala Ser Phe Thr Cys Leu Ala Ile Trp Ala
            215                 220                 225

TTG GCC ATC GCA GGG GTA GTG CCT CTC GTC CTC AAG GAG CAA ACC ATC              956
Leu Ala Ile Ala Gly Val Val Pro Leu Val Leu Lys Glu Gln Thr Ile
230                 235                 240

CAG GTG CCC GGG CTC AAC ATC ACT ACC TGT CAT GAT GTG CTC AAT GAA             1004
Gln Val Pro Gly Leu Asn Ile Thr Thr Cys His Asp Val Leu Asn Glu
245                 250                 255                 260

ACC CTG CTC GAA GGC TAC TAT GCC TAC TAC TTC TCA GCC TTC TCT GCT             1052
Thr Leu Leu Glu Gly Tyr Tyr Ala Tyr Tyr Phe Ser Ala Phe Ser Ala
                265                 270                 275

GTC TTC TTT TTT GTG CCG CTG ATC ATT TCC ACG GTC TGT TAT GTG TCT             1100
Val Phe Phe Phe Val Pro Leu Ile Ile Ser Thr Val Cys Tyr Val Ser
                280                 285                 290

ATC ATT CGA TGT CTT AGC TCT TCC GCA GTT GCC AAC CGC AGC AAG AAG             1148
Ile Ile Arg Cys Leu Ser Ser Ser Ala Val Ala Asn Arg Ser Lys Lys
            295                 300                 305

TCC CGG GCT TTG TTC CTG TCA GCT GCT GTT TTC TGC ATC TTC ATC ATT             1196
Ser Arg Ala Leu Phe Leu Ser Ala Ala Val Phe Cys Ile Phe Ile Ile
        310                 315                 320

TGC TTC GGA CCC ACA AAC GTC CTC CTG ATT GCG CAT TAC TCA TTC CTT             1244
Cys Phe Gly Pro Thr Asn Val Leu Leu Ile Ala His Tyr Ser Phe Leu
325                 330                 335                 340

TCT CAC ACT TCC ACC ACA GAG GCT GCC TAC TTT GCC TAC CTC CTC TGT             1292
Ser His Thr Ser Thr Thr Glu Ala Ala Tyr Phe Ala Tyr Leu Leu Cys
                345                 350                 355

GTC TGT GTC AGC AGC ATA AGC TCG TGC ATC GAC CCC TTA ATT TAC TAT             1340
Val Cys Val Ser Ser Ile Ser Ser Cys Ile Asp Pro Leu Ile Tyr Tyr
                360                 365                 370
```

```
TAC GCT TCC TCT GAG TGC CAG AGG TAC GTC TAC AGT ATC TTA TGC TGC      1388
Tyr Ala Ser Ser Glu Cys Gln Arg Tyr Val Tyr Ser Ile Leu Cys Cys
        375                 380                 385

AAA GAA AGT TCC GAT CCC AGC AGT TAT AAC AGC AGT GGG CAG TTG ATG      1436
Lys Glu Ser Ser Asp Pro Ser Ser Tyr Asn Ser Ser Gly Gln Leu Met
        390                 395                 400

GCA AGT AAA ATG GAT ACC TGC TCT AGT AAC CTG AAT AAC AGC ATA TAC      1484
Ala Ser Lys Met Asp Thr Cys Ser Ser Asn Leu Asn Asn Ser Ile Tyr
405                 410                 415                 420

AAA AAG CTG TTA ACT TAGGAAAAGG GACTGCTGGG AGGTTAAAAA GAAAAGTTTA      1539
Lys Lys Leu Leu Thr
            425

TAAAAGTGAA TAACCTGAGG ATTCTATTAG TCCCCACCCA AACTTTATTG ATTCACCTCC    1599

TAAAACAACA GATGTACGAC TTGCATACCT GCTTTTTATG GGAGCTGTCA AGCATGTATT    1659

TTTGTCAATT ACCAGAAAGA TAACAGGACG AGATGACGGT GTTATTCCAA GGAATATTG     1719

CCAATGCTAC AGTAATAAAT GAATGTCACT TCTGGATATA GCTAGGTGAC ATATACATAC    1779

TTACATGTGT GTATATGTAG ATGTATGCAC ACACATATAT TATTTGCAGT GCAGTATAGA    1839

ATAGGCACTT TAAAACACTC TTTCCCCGCA CCCCAGCAAT TATGAAAATA ATCTCTGATT    1899

CCCTGATTTA ATATGCAAAG TCTAGGTTGG TAGAGTTTAG CCCTGAACAT TTCATGGTGT    1959

TCATCAACAG TGAGAGACTC CATAGTTTGG GCTTGTACCA CTTTTGCAAA TAAGTGTATT    2019

TTGAAATTGT TTGACGGCAA GGTTTAAGTT ATTAAGAGGT AAGACTTAGT ACTATCTGTG    2079

CGTAGAAGTT CTAGTGTTTT CAATTTTAAA CATATCCAAG TTTGAATTCC TAAAATTATG    2139

GAAACAGATG AAAAGCCTCT GTTTTGTATA TGGGTAGTATT TTTTACATTT TACACACTGT   2199

ACACATAAGC CAAAACTGAG CATAAGTCCT CTAGTGAATG TAGGCTGGCT TTCAGAGTAG    2259

GCTATTCCTG AGAGCTGCAT GTGTCCGCCC CCGATGGAGG ACTCCAGGCA GCAGACACAT    2319

GCCAGGGCCA TGTCAGACAC AGATTGGCCA GAAACCTTCC TGCTGAGCCT CACAGCAGTG    2379

AGACTGGGGC CACTACATTT GCTCCATCCT CCTGGGATTG GCTGTGAACT GATCATGTTT    2439

ATGAGAAACT GGCAAAGCAG AATGTGATAT CCTAGGAGGT AATGACCATG AAAGACTTCT    2499

CTACCCATCT TAAAAACAAC GAAAGAAGGC ATGGACTTCT GGATGCCCAT CCACTGGGTG    2559

TAAACACATC TAGTAGTTGT TCTGAAATGT CAGTTCTGAT ATGGAAGCAC CCATTATGCG    2619

CTGTGGCCAC TCCAATAGGT GCTGAGTGTA CAGAGTGGAA TAAGACAGAG ACCTGCCCTC    2679

AAGAGCAAAG TAGATCATGC ATAGAGTGTG ATGTATGTGT AATAAATATG TTTCACACAA    2739

ACAAGGCCTG TCAGCTAAAG AAGTTTGAAC ATTTGGGTTA CTATTTCTTG TGGTTATAAC    2799

TTAATGAAAA CAATGCAGTA CAGGACATAT ATTTTTTAAA ATAAGTCTGA TTTAATTGGG    2859

CACTATTTAT TTACAAATGT TTTGCTCAAT AGATTGCTCA AATCAGGTTT TCTTTTAAGA    2919

ATCAATCATG TCAGTCTGCT TAGAAATAAC AGAAGAAAAT AGAATTGACA TTGAAATCTA    2979

GGAAAATTAT TCTATAATTT CCATTTACTT AAGACTTAAT GAGACTTTAA AAGCATTTTT    3039

TAACCTCCTA AGTATCAAGT ATAGAAAATC TTCATGGAAT TCACAAAGTA ATTTGGAAAT    3099

TAGGTTGAAA CATATCTCTT ATCTTACGAA AAAATGGTAG CATTTTAAAC AAAATAGAAA    3159

GTTGCAAGGC AAATGTTTAT TTAAAAGAGC AGGCCAGGCG CGGTGGCTCA CGCCTGTAAT    3219

CCCAGCACTT TGGGAGGCTG AGGCGGGTGG ATCACGAGGT CAGGAGATCG AGACCATCCT    3279

GGCTAACACG GTGAAACCCG TCTCTACTAA AAATGCAAAA AAAATTAGCC GGGCGTGGTG    3339

GCAGGCACCT GTAGTCCCAG CTACTCGGGA GGCTGAGGCA GGAGACTGGC GTGAACCCAG    3399

GAGGCGGACC TTGTAGTGAG CCGAGATCGC GCCACTGTGC TCCAGCCTGG CAACAGAGC    3459
```

```
AAGACTCCAT CTC                                                          3472
```

(2) INFORMATION FOR SEQ ID NO:53:

(i) SEQUENCE CHARACTERISTICS:
        (A) LENGTH: 425 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:53:

```
Met Gly Pro Arg Arg Leu Leu Leu Val Ala Ala Cys Phe Ser Leu Cys
 1               5                  10                  15

Gly Pro Leu Leu Ser Ala Arg Thr Arg Ala Arg Arg Pro Glu Ser Lys
            20                  25                  30

Ala Thr Asn Ala Thr Leu Asp Pro Arg Ser Phe Leu Leu Arg Asn Pro
        35                  40                  45

Asn Asp Lys Tyr Glu Pro Phe Trp Glu Asp Glu Lys Asn Glu Ser
 50                  55                  60

Gly Leu Thr Glu Tyr Arg Leu Val Ser Ile Asn Lys Ser Ser Pro Leu
65                   70                  75                  80

Gln Lys Gln Leu Pro Ala Phe Ile Ser Glu Asp Ala Ser Gly Tyr Leu
                85                  90                  95

Thr Ser Ser Trp Leu Thr Leu Phe Val Pro Ser Val Tyr Thr Gly Val
            100                 105                 110

Phe Val Val Ser Leu Pro Leu Asn Ile Met Ala Ile Val Val Phe Ile
        115                 120                 125

Leu Lys Met Lys Val Lys Lys Pro Ala Val Val Tyr Met Leu His Leu
    130                 135                 140

Ala Thr Ala Asp Val Leu Phe Val Ser Val Leu Pro Phe Lys Ile Ser
145                 150                 155                 160

Tyr Tyr Phe Ser Gly Ser Asp Trp Gln Phe Gly Ser Glu Leu Cys Arg
                165                 170                 175

Phe Val Thr Ala Ala Phe Tyr Cys Asn Met Tyr Ala Ser Ile Leu Leu
            180                 185                 190

Met Thr Val Ile Ser Ile Asp Arg Phe Leu Ala Val Val Tyr Pro Met
        195                 200                 205

Gln Ser Leu Ser Trp Arg Thr Leu Gly Arg Ala Ser Phe Thr Cys Leu
    210                 215                 220

Ala Ile Trp Ala Leu Ala Ile Ala Gly Val Val Pro Leu Val Leu Lys
225                 230                 235                 240

Glu Gln Thr Ile Gln Val Pro Gly Leu Asn Ile Thr Thr Cys His Asp
                245                 250                 255

Val Leu Asn Glu Thr Leu Leu Glu Gly Tyr Tyr Ala Tyr Tyr Phe Ser
            260                 265                 270

Ala Phe Ser Ala Val Phe Phe Phe Val Pro Leu Ile Ile Ser Thr Val
        275                 280                 285

Cys Tyr Val Ser Ile Ile Arg Cys Leu Ser Ser Ser Ala Val Ala Asn
    290                 295                 300

Arg Ser Lys Lys Ser Arg Ala Leu Phe Leu Ser Ala Ala Val Phe Cys
305                 310                 315                 320

Ile Phe Ile Ile Cys Phe Gly Pro Thr Asn Val Leu Leu Ile Ala His
```

```
                    325                 330                 335
Tyr Ser Phe Leu Ser His Thr Ser Thr Thr Glu Ala Ala Tyr Phe Ala
                340                 345                 350
Tyr Leu Leu Cys Val Cys Val Ser Ser Ile Ser Ser Cys Ile Asp Pro
            355                 360                 365
Leu Ile Tyr Tyr Ala Ser Ser Glu Cys Gln Arg Tyr Val Tyr Ser
        370                 375                 380
Ile Leu Cys Cys Lys Glu Ser Ser Asp Pro Ser Ser Tyr Asn Ser Ser
385                 390                 395                 400
Gly Gln Leu Met Ala Ser Lys Met Asp Thr Cys Ser Ser Asn Leu Asn
                405                 410                 415
Asn Ser Ile Tyr Lys Lys Leu Leu Thr
                420                 425

(2) INFORMATION FOR SEQ ID NO:54:

(i) SEQUENCE CHARACTERISTICS:
        (A) LENGTH: 3877 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:54:

GAATTCAAGG TCTGCATTTT CTAGGTATGA ACACTGTGCA TGATGAAGTC TTTCCAAGCC      60

ACACCAGTGG TTCCATGTGT GTGCACTTCC GGTTTGAGTG CTAGTGAGAT ACTTCTGTGG     120

TTCTGAATTG CCTGACTATT TGGGGTTGTG ATATTTTCAT AAAGATTGAT CAACATGTTC     180

GAATTTCCTC CCCAACAGTC TTCCATTACC AAGTAAAGAT TCATTTTTCT GGGACTGAGA     240

GTGAAACCCA TACCAATCAG GCCTTTGAGA TTTCTCTGTA TGGCACCGTG GCCGAGAGTG     300

AGAACATCCC ATTCACTCTG TGAGTAGCAC AGGGGGGCGG TCATCATGGC ACCAGTCCCT     360

CTCCTGCCAT AACCCTTGGT CTGAGCAGCA GAAGCAGAGA GCGATGCCTA GAAAACAAGT     420

CTTTAGTTAA AAAAATCAGA ATTTCAAAAT TGAGGTCTTT CCTCTATTTG ATATTGAGAA     480

AAAAATGCTT CAAATTGGCC ATTTTATTTT CACTTACTAG TTATATTTTT TTATTTATCA     540

TCTTATATCT GTTTATTTCT TTTATAAAGC TGCTGTTAAA CAATATAATT AAACTATCTC     600

AAAAGGTTTG ACATTAAAGA AAATGAGCAA TGGTAACAGG AAACCACTCT ATAGATGTAC     660

ATATAATATG TACAGAAAAT ATAAGTAGTA AGAAGTCCAT GACAAAGTGT TAGCTCTTTT     720

TTTTTTTTTT TTTTTTTTTT TTTTTGAGAT GGAGTCTCTC TCTATTGCCC AGGCTGGAGT     780

GCAGTGATTC GATCTCAGCT CACTGCAACC TCTACCTCCC GAGTTCAAAC AATTCTTCTG     840

TCTCAGCCTC CCGAGTAGCT GGGGCTGCAG GTGCCCACCA CCATGCCCAG CTAATTTTTG     900

TATTTTTAGT AGCGACAGGG TCTCACCATG TTGGCCAAGC TGGTCTTGAA TTCCTGATCT     960

CAGGTGATCC ACCCGCCTCG GCCTCCCAAA GTGCTGGGAT TACAGGTGTG AGCCACCATG    1020

CCCAGCCTAC CCTTTACTAC TAATCAAAGA AATAAAAGTA AGGCAACTTG ATACTTTTAC    1080

AATTACTAGA TGAACAAATC TTTAAAAATA GCCAGTGCAG ACAAGGTGGT GAAGCAGAAC    1140

ATGCGAACCT ACCATGCATC ATTCACGGCT AGAACCCTCC AGGTGCGGAA GGTAGTATTT    1200

TAATAACTTT CCATAGCTAC AAAATATTAT TACATAGAAG GGAGTGATTT TTTTCTAATA    1260

TTTATCCTAA AGAAATAGTC AACAAACATT TTTAAAAACA TCAATTACAG TCGTACCTAT    1320

ACTAGCATAA ATTAGAAACC CAGTATCCAA CATTGAGGCA GTGGGTAAAT GAATCGTGGT    1380
```

-continued

```
TTATCAAGTC ATTAAAATCA ATCTAGCCTT TAAAAACTAT AATTGTAGGA AACCCAGGAA    1440

AACATAGTAA AAAATGGAAT ATAAAATCTG AAGAGAATAA AGAATAGAGA ATCGTATGTG    1500

TGCTATGATT GTAGCTAAAT AATGTTCAAG TATCAACACA AATTGAAAAG GAATACATGA    1560

AAATGAAAAT TATATTTCTG AATGATTGAC TTCAGGATTT TCTTTTAGAA TTGTATTAAA    1620

TAGTTCATGT CATTAGGATA AATGCTGGAA TGTGGATATA ATTTAAAATA TACTAAATGC    1680

CATCGACCTT CATTTTGAGT TCTTTGTTGG ACATTTTTGT GCATTTTTAA AATATCCCCT    1740

AAATAATAAA GCTATTTATA TTTGGAGAGG AGAAAAAAAA GTGGGGGGCA GGGAGAGCTG    1800

ATCTCTATAA CTAACCAAAT TTATTGCTTT TTTGTTTAGG CCTGAAGTTT CCACAAATAA    1860

GACCTACTCC TTCCTAATTT ACACAGAGGT AGATATTGGA GAACTACTCA TGTTGAAGCT    1920

CAAATGGAAG AGTGATTCAT ACTTTAGCTG GTCAGACTGG TGGAGCAGTC CCGGCTTCGC    1980

CATTCAGAAG ATCAGAGTAA AAGCAGGAGA GACTCAGAAA AAGTAATTAA ATGTATTTTT    2040

CTTCCTTCAC TTTAGACCCC CACCTGATGT CAGGACCTAG GGGCTGTATT TCAGGGGCCT    2100

TCACAATTCA GGGAGAGCTT TAGGAAACCT TGTATTTATT ACTGTATGAT GTAGATTTTC    2160

TTTAGGAGTC TTCTTTTATT TTCTTATTTT TGGGGGCGG GGGGGAAGT GACAGTATTT    2220

TTGTATTTCA TGTAAGGAAA ACATAAGCCC TGAATCGCTC ACAGTTATTC AGTGAGAGCT    2280

GGGATTAGAA GTCAGGAATC TCAGCTTCTC ATTTGGCACT GTTTCTTGTA AGTACAAAAT    2340

AGTTAGGGAA CAAACCTCCG AGATGCTACC TGGATAATCA AAGATTCAAA CCAACCTCTT    2400

CCAGAAGGGT GAGATTCCAA GATAATCTCA ACCTGTCTCC GCAGCCCCAC CCATGTGTAC    2460

CCATAAAATG AATTACACAG AGATCGCTAT AGGATTTAAA GCTTTTATAC TAAATGTGCT    2520

GGGATTTTGC AAACTATAGT GTGCTGTTAT TGTTAATTTA AAAAAACTCT AAGTTAGGAT    2580

TGACAAATTA TTTCTCTTTA GTCATTTGCT TGTATCACCA AAGAAGCAAA CAAACAAACA    2640

AAAAAAAAAA GAAAAAGATC TTGGGGATGG AAATGTTATA AAGAATCTTT TTTACACTAG    2700

CAATGTCTAG CTGAAGGCAG ATGCCCTAAT TCCTTAATGC AGATGCTAAG AGATGGCAGA    2760

GTTGATCTTT TATCATCTCT TGGTGAAAGC CCAGTAACAT AAGACTGCTC TAGGCTGTCT    2820

GCATGCCTGT CTATCTAAAT TAACTAGCTT GGTTGCTGAA CACCAGGTTA GGCTCTCAAA    2880

TTACCCTCTG ATTCTGATGT GGCCTGAGTG TGACAGTTAA TTATTGGGAA TATCAAAACA    2940

ATTACCCAGC ATGATCATGT ATTATTTAAA CAGTCCTGAC AGAACTGTAC CTTTGTGAAC    3000

AGTGCTTTTG ATTGTTCTAC ATGGCATATT CACATCCATT TTCTTCCACA GGGTGATCTT    3060

CTGTTCTAGG GAGAAAGTGT CTCATTTGCA GAAAGGAAAG GCACCTGCGG TATTTGTGAA    3120

ATGCCATGAC AAGTCTCTGA ATAAGAAGTC AGGCTGGTGA GCATTCTGGG CTAAAGCTGA    3180

CTGGGCATCC TGAGCTTGCA CCCTAAGGGA GGCAGCTTCA TGCATTCCTC TTCACCCCAT    3240

CACCAGCAGC TTGCCCTGAC TCATGTGATC AAAGCATTCA ATCAGTCTTT CTTAGTCCTT    3300

CTGCATATGT ATCAAATGGG TCTGTTGCTT TATGCAATAC TTCCTCTTTT TTTCTTTCTC    3360

CTCTTGTTTC TCCCAGCCCG GACCTTCAAC CCAGGCACAC ATTTTAGGTT TTATTTTACT    3420

CCTTGAACTA CCCCTGAATC TTCACTTCTC CTTTTTTCTC TACTGCGTCT CTGCTGACTT    3480

TGCAGATGCC ATCTGCAGAG CATGTAACAC AAGTTTAGTA GTTGCCGTTC TGGCTGTGGG    3540

TGCAGCTCTT CCCAGGATGT ATTCAGGGAA GTAAAAAGAT CTCACTGCAT CACCTGCAGC    3600

CACATAGTTC TTGATTCTCC AAGTGCCAGC ATACTCCGGG ACACACAGCC AACAGGGCTG    3660

CCCCAAGCAC CCATTCTCAA AACCCTCAAA GCTGCCAAGC AAACAGAATG AGAGTTATAG    3720

GAAACTGTTC TCTCTTCTAT CTCCAAACAA CTCTGTGCCT CTTTCCTACC TGACCTTTAG    3780
```

```
GGCTAATCCA TGTGGCAGCT GTTAGCTGCA TCTTTCCAGA GCGTCAGTAC TGAGAGGACA      3840

CTAAGCATGT GACCTTCACT ACTCCTGTTC TGAATTC                              3877
```

(2) INFORMATION FOR SEQ ID NO:55:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:55:

```
Phe His Tyr Gln Val Lys Ile His Phe Ser Gly Thr Glu Ser Glu Thr
 1               5                  10                  15

His Thr Asn Gln Ala Phe Glu Ile Ser Leu Tyr Gly Thr Val Ala Glu
            20                  25                  30

Ser Glu Asn Ile Pro Phe Thr Leu Pro Glu Val Ser Thr Asn Lys Thr
        35                  40                  45

Tyr Ser Phe Leu Ile Tyr Thr Glu Val Asp Ile Gly Glu Leu Leu Met
    50                  55                  60

Leu Lys Leu Lys Trp Lys Ser Asp Ser Tyr Phe Ser Trp Ser Asp Trp
65                  70                  75                  80

Trp Ser Ser Pro Gly Phe Ala Ile Gln Lys Ile Arg Val Lys Ala Gly
                85                  90                  95

Glu Thr Gln Lys Lys Val Ile Phe Cys Ser Arg Glu Lys Val Ser His
            100                 105                 110

Leu Gln Lys Gly Lys Ala Pro Ala Val Phe Val Lys Cys His Asp Lys
        115                 120                 125

Ser Leu Asn Lys Lys Ser Gly
    130                 135
```

(2) INFORMATION FOR SEQ ID NO:56:

(i) SEQUENCE CHARACTERISTICS:
        (A) LENGTH: 182 base pairs
        (B) TYPE: nucleic acid
        (C) STRANDEDNESS: single
        (D) TOPOLOGY: linear (xi) SEQUENCE DESCRIPTION: SEQ ID NO:56:

```
TCTCCTTATC CACTTGTGTG TCTAGATCTC CTCAGTGGCC GCCTCTACTG GGTTGACTCC        60

AAACTTCACT CCATCTCAAG CATCGATGTC AATGGGGGCA ACCGGAAGAC CATCTTGGAG       120

GATGAAAAGA GGCTGGCCCA CCCCTTCTCC TTGGCCGTCT TGAGGTGTG GCTTACGTAC        180

GA                                                                      182
```

(2) INFORMATION FOR SEQ ID NO:57:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:57:

```
Leu Leu Ser Gly Arg Leu Tyr Trp Val Asp Ser Lys Leu His Ser Ile
 1               5                  10                  15
```

```
Ser Ser Ile Asp Val Asn Gly Gly Asn Arg Lys Thr Ile Leu Glu Asp
         20                  25                  30

Glu Lys Arg Leu Ala His Pro Phe Ser Leu Ala Val Phe Glu
         35                  40                  45
```

(2) INFORMATION FOR SEQ ID NO:58:

(i) SEQUENCE CHARACTERISTICS:
        (A) LENGTH: 2566 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 70...1596
        (D) OTHER INFORMATION:

(xi) SEQUENCE DESCRIPTION: SEQ ID NO:58:

```
CGTCGCCGTC CCCGTCTCCT GCCAGGCGCG GAGCCCTGCG AGCCGCGGGT GGGCCCCAGG      60

CGCGCAGAC ATG GGC TGC TCC GCC AAA GCG CGC TGG GCT GCC GGG GCG CTG    111
          Met Gly Cys Ser Ala Lys Ala Arg Trp Ala Ala Gly Ala Leu
            1               5                  10

GGC GTC GCG GGG CTA CTG TGC GCT GTG CTG GGC GCT GTC ATG ATC GTG      159
Gly Val Ala Gly Leu Leu Cys Ala Val Leu Gly Ala Val Met Ile Val
 15              20                  25                  30

ATG GTG CCG TCG CTC ATC AAG CAG CAG GTC CTT AAG AAC GTG CGC ATC      207
Met Val Pro Ser Leu Ile Lys Gln Gln Val Leu Lys Asn Val Arg Ile
                 35                  40                  45

GAC CCC AGT AGC CTG TCC TTC AAC ATG TGG AAG GAG ATC CCT ATC CCC      255
Asp Pro Ser Ser Leu Ser Phe Asn Met Trp Lys Glu Ile Pro Ile Pro
                 50                  55                  60

TTC TAT CTC TCC GTC TAC TTC TTT GAC GTC ATG AAC CCC AGC GAG ATC      303
Phe Tyr Leu Ser Val Tyr Phe Phe Asp Val Met Asn Pro Ser Glu Ile
             65                  70                  75

CTG AAG GGC GAG AAG CCG CAG GTG CGG GAG CGC GGG CCC TAC GTG TAC      351
Leu Lys Gly Glu Lys Pro Gln Val Arg Glu Arg Gly Pro Tyr Val Tyr
     80                  85                  90

AGG GAG TCC AGG CAC AAA AGC AAC ATC ACC TTC AAC AAC AAC GAC ACC      399
Arg Glu Ser Arg His Lys Ser Asn Ile Thr Phe Asn Asn Asn Asp Thr
 95                 100                 105                 110

GTG TCC TTC CTC GAG TAC CGC ACC TTC CAG TTC CAG CCC TCC AAG TCC      447
Val Ser Phe Leu Glu Tyr Arg Thr Phe Gln Phe Gln Pro Ser Lys Ser
                115                 120                 125

CAC GGC TCG GAG AGC GAC TAC ATC GTC ATG CCC AAC ATC CTG GTC TTG      495
His Gly Ser Glu Ser Asp Tyr Ile Val Met Pro Asn Ile Leu Val Leu
            130                 135                 140

GGT GCG GCG GTG ATG ATG GAG AAT AAG CCC ATG ACC CTG AAG CTC ATC      543
Gly Ala Ala Val Met Met Glu Asn Lys Pro Met Thr Leu Lys Leu Ile
        145                 150                 155

ATG ACC TTG GCA TTC ACC ACC CTC GGC GAA CGT GCC TTC ATG AAC CGC      591
Met Thr Leu Ala Phe Thr Thr Leu Gly Glu Arg Ala Phe Met Asn Arg
    160                 165                 170

ACT GTG GGT GAG ATC ATG TGG GGC TAC AAG GAC CCC CTT GTG AAT CTC      639
Thr Val Gly Glu Ile Met Trp Gly Tyr Lys Asp Pro Leu Val Asn Leu
175                 180                 185                 190

ATC AAC AAG TAC TTT CCA GGC ATG TTC CCC TTC AAG GAC AAG TTC GGA      687
Ile Asn Lys Tyr Phe Pro Gly Met Phe Pro Phe Lys Asp Lys Phe Gly
                195                 200                 205
```

```
TTA TTT GCT GAG CTC AAC AAC TCC GAC TCT GGG CTC TTC ACG GTG TTC     735
Leu Phe Ala Glu Leu Asn Asn Ser Asp Ser Gly Leu Phe Thr Val Phe
        210                 215                 220

ACG GGG GTC CAG AAC ATC AGC AGG ATC CAC CTC GTG GAC AAG TGG AAC     783
Thr Gly Val Gln Asn Ile Ser Arg Ile His Leu Val Asp Lys Trp Asn
            225                 230                 235

GGG CTG AGC AAG GTT GAC TTC TGG CAT TCC GAT CAG TGC AAC ATG ATC     831
Gly Leu Ser Lys Val Asp Phe Trp His Ser Asp Gln Cys Asn Met Ile
    240                 245                 250

AAT GGA ACT TCT GGG CAA ATG TGG CCG CCC TTC ATG ACT CCT GAG TCC     879
Asn Gly Thr Ser Gly Gln Met Trp Pro Pro Phe Met Thr Pro Glu Ser
255                 260                 265                 270

TCG CTG GAG TTC TAC AGC CCG GAG GCC TGC CGA TCC ATG AAG CTA ATG     927
Ser Leu Glu Phe Tyr Ser Pro Glu Ala Cys Arg Ser Met Lys Leu Met
                275                 280                 285

TAC AAG GAG TCA GGG GTG TTT GAA GGC ATC CCC ACC TAT CGC TTC GTG     975
Tyr Lys Glu Ser Gly Val Phe Glu Gly Ile Pro Thr Tyr Arg Phe Val
            290                 295                 300

GCT CCC AAA ACC CTG TTT GCC AAC GGG TCC ATC TAC CCA CCC AAC GAA    1023
Ala Pro Lys Thr Leu Phe Ala Asn Gly Ser Ile Tyr Pro Pro Asn Glu
        305                 310                 315

GGC TTC TGC CCG TGC CTG GAG TCT GGA ATT CAG AAC GTC AGC ACC TGC    1071
Gly Phe Cys Pro Cys Leu Glu Ser Gly Ile Gln Asn Val Ser Thr Cys
    320                 325                 330

AGG TTC AGT GCC CCC TTG TTT CTC TCC CAT CCT CAC TTC CTC AAC GCC    1119
Arg Phe Ser Ala Pro Leu Phe Leu Ser His Pro His Phe Leu Asn Ala
335                 340                 345                 350

GAC CCG GTT CTG GCA GAA GCG GTG ACT GGC CTG CAC CCT AAC CAG GAG    1167
Asp Pro Val Leu Ala Glu Ala Val Thr Gly Leu His Pro Asn Gln Glu
                355                 360                 365

GCA CAC TCC TTG TTC CTG GAC ATC CAC CCG GTC ACG GGA ATC CCC ATG    1215
Ala His Ser Leu Phe Leu Asp Ile His Pro Val Thr Gly Ile Pro Met
            370                 375                 380

AAC TGC TCT GTG AAA CTG CAG CTG AGC CTC TAC ATG AAA TCT GTC GCA    1263
Asn Cys Ser Val Lys Leu Gln Leu Ser Leu Tyr Met Lys Ser Val Ala
        385                 390                 395

GGC ATT GGA CAA ACT GGG AAG ATT GAG CCT GTG GTC CTG CCG CTG CTC    1311
Gly Ile Gly Gln Thr Gly Lys Ile Glu Pro Val Val Leu Pro Leu Leu
    400                 405                 410

TGG TTT GCA GAG AGC GGG GCC ATG GAG GGG GAG ACT CTT CAC ACA TTC    1359
Trp Phe Ala Glu Ser Gly Ala Met Glu Gly Glu Thr Leu His Thr Phe
415                 420                 425                 430

TAC ACT CAG CTG GTG TTG ATG CCC AAG GTG ATG CAC TAT GCC CAG TAC    1407
Tyr Thr Gln Leu Val Leu Met Pro Lys Val Met His Tyr Ala Gln Tyr
                435                 440                 445

GTC CTC CTG GCG CTG GGC TGC GTC CTG CTG CTG GTC CCT GTC ATC TGC    1455
Val Leu Leu Ala Leu Gly Cys Val Leu Leu Leu Val Pro Val Ile Cys
            450                 455                 460

CAA ATC CGG AGC CAA GAG AAA TGC TAT TTA TTT TGG AGT AGT AGT AAA    1503
Gln Ile Arg Ser Gln Glu Lys Cys Tyr Leu Phe Trp Ser Ser Ser Lys
        465                 470                 475

AAG GGC TCA AAG GAT AAG GAG GCC ATT CAG GCC TAT TCT GAA TCC CTG    1551
Lys Gly Ser Lys Asp Lys Glu Ala Ile Gln Ala Tyr Ser Glu Ser Leu
    480                 485                 490

ATG ACA TCA GCT CCC AAG GGC TCT GTG CTG CAG GAA GCA AAA CTG        1596
Met Thr Ser Ala Pro Lys Gly Ser Val Leu Gln Glu Ala Lys Leu
495                 500                 505

TAGGGTCCTG AGGACACCGT GAGCCAGCCA GGCCTGGCCG CTGGGCCTGA CCGGCCCCCC    1656

AGCCCCTACA CCCCGCTTCT CCCGGACTCT CCCAGCAGAC AGCCCCCCAG CCCCACAGCC    1716
```

```
TGAGCCTCCC AGCTGCCATG TGCCTGTTGC ACACCTGCAC ACACGCCCTG GCACACATAC      1776

ACACATGCGT GCAGGCTTGT GCAGACACTC AGGGATGGAG CTGCTGCTGA AGGGACTTGT      1836

AGGGAGAGGC TCGTCAACAA GCACTGTTCT GGAACCTTCT CTCCACGTGG CCCACAGGCT      1896

GACCACAGGG GCTGTGGGTC CTGCGTCCCC TTCCTCGGGT GAGCCTGGCC TGTCCCGTTC      1956

AGCCGTTGGG CCAGGCTTCC TCCCCTCCAA GGTGAAACAC TGCAGTCCCG GTGTGGTGGC      2016

TCCCCATGCA GGACGGGCCA GGCTGGGAGT GCCGCCTTCC TGTGCCAAAT TCAGTGGGGA      2076

CTCAGTGCCC AGGCCCTGGC ACGAGCTTTG GCCTTGGTCT ACCTGCCAGG CCAGGCAAAG      2136

CGCCTTTACA CAGGCCTCGG AAAACAATGG AGTGAGCACA AGATGCCCTG TGCAGCTGCC      2196

CGAGGGTCTC CGCCCACCCC GGCCGGACTT TGATCCCCCC GAAGTCTTCA CAGGCACTGC      2256

ATCGGGTTGT CTGGCGCCCT TTTCCTCCAG CCTAAACTGA CATCATCCTA TGGACTGAGC      2316

CGGCCACTCT CTGGCCGAAG TGGCGCAGGC TGTGCCCCCG AGCTGCCCCC ACCCCCTCAC      2376

AGGGTCCCTC AGATTATAGG TGCCCAGGCT GAGGTGAAGA GGCCTGGGGG CCCTGCCTTC      2436

CGGGCGCTCC TGGACCCTGG GGCAAACCTG TGACCCTTTT CTACTGGAAT AGAAATGAGT      2496

TTTATCATCT TTGAAAAATA ATTCACTCTT GAAGTAATAA ACGTTAAAA AAATGGAAAA      2556

AAAAAAAAAA                                                            2566
```

(2) INFORMATION FOR SEQ ID NO:59:

(i) SEQUENCE CHARACTERISTICS:
        (A) LENGTH: 509 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:59:

```
Met Gly Cys Ser Ala Lys Ala Arg Trp Ala Ala Gly Ala Leu Gly Val
 1               5                  10                  15

Ala Gly Leu Leu Cys Ala Val Leu Gly Ala Val Met Ile Val Met Val
            20                  25                  30

Pro Ser Leu Ile Lys Gln Gln Val Leu Lys Asn Val Arg Ile Asp Pro
        35                  40                  45

Ser Ser Leu Ser Phe Asn Met Trp Lys Glu Ile Pro Ile Pro Phe Tyr
    50                  55                  60

Leu Ser Val Tyr Phe Phe Asp Val Met Asn Pro Ser Glu Ile Leu Lys
65                  70                  75                  80

Gly Glu Lys Pro Gln Val Arg Glu Arg Gly Pro Tyr Val Tyr Arg Glu
                85                  90                  95

Ser Arg His Lys Ser Asn Ile Thr Phe Asn Asn Asp Thr Val Ser
            100                 105                 110

Phe Leu Glu Tyr Arg Thr Phe Gln Phe Gln Pro Ser Lys Ser His Gly
        115                 120                 125

Ser Glu Ser Asp Tyr Ile Val Met Pro Asn Ile Leu Val Leu Gly Ala
    130                 135                 140

Ala Val Met Met Glu Asn Lys Pro Met Thr Leu Lys Leu Ile Met Thr
145                 150                 155                 160

Leu Ala Phe Thr Thr Leu Gly Glu Arg Ala Phe Met Asn Arg Thr Val
                165                 170                 175
```

```
-continued

Gly Glu Ile Met Trp Gly Tyr Lys Asp Pro Leu Val Asn Leu Ile Asn
            180                 185                 190

Lys Tyr Phe Pro Gly Met Phe Pro Phe Lys Asp Lys Phe Gly Leu Phe
        195                 200                 205

Ala Glu Leu Asn Asn Ser Asp Ser Gly Leu Phe Thr Val Phe Thr Gly
    210                 215                 220

Val Gln Asn Ile Ser Arg Ile His Leu Val Asp Lys Trp Asn Gly Leu
225                 230                 235                 240

Ser Lys Val Asp Phe Trp His Ser Asp Gln Cys Asn Met Ile Asn Gly
                245                 250                 255

Thr Ser Gly Gln Met Trp Pro Pro Phe Met Thr Pro Glu Ser Ser Leu
            260                 265                 270

Glu Phe Tyr Ser Pro Glu Ala Cys Arg Ser Met Lys Leu Met Tyr Lys
        275                 280                 285

Glu Ser Gly Val Phe Glu Gly Ile Pro Thr Tyr Arg Phe Val Ala Pro
    290                 295                 300

Lys Thr Leu Phe Ala Asn Gly Ser Ile Tyr Pro Pro Asn Glu Gly Phe
305                 310                 315                 320

Cys Pro Cys Leu Glu Ser Gly Ile Gln Asn Val Ser Thr Cys Arg Phe
                325                 330                 335

Ser Ala Pro Leu Phe Leu Ser His Pro His Phe Leu Asn Ala Asp Pro
            340                 345                 350

Val Leu Ala Glu Ala Val Thr Gly Leu His Pro Asn Gln Glu Ala His
        355                 360                 365

Ser Leu Phe Leu Asp Ile His Pro Val Thr Gly Ile Pro Met Asn Cys
    370                 375                 380

Ser Val Lys Leu Gln Leu Ser Leu Tyr Met Lys Ser Val Ala Gly Ile
385                 390                 395                 400

Gly Gln Thr Gly Lys Ile Glu Pro Val Val Leu Pro Leu Leu Trp Phe
                405                 410                 415

Ala Glu Ser Gly Ala Met Glu Gly Thr Leu His Thr Phe Tyr Thr
            420                 425                 430

Gln Leu Val Leu Met Pro Lys Val Met His Tyr Ala Gln Tyr Val Leu
        435                 440                 445

Leu Ala Leu Gly Cys Val Leu Leu Val Pro Val Ile Cys Gln Ile
    450                 455                 460

Arg Ser Gln Glu Lys Cys Tyr Leu Phe Trp Ser Ser Ser Lys Lys Gly
465                 470                 475                 480

Ser Lys Asp Lys Glu Ala Ile Gln Ala Tyr Ser Glu Ser Leu Met Thr
                485                 490                 495

Ser Ala Pro Lys Gly Ser Val Leu Gln Glu Ala Lys Leu
            500                 505
```